US011420966B2

(12) United States Patent
Jacobsen et al.

(10) Patent No.: US 11,420,966 B2
(45) Date of Patent: Aug. 23, 2022

(54) SUBSTITUTED PYRROLOPYRIDINES AS JAK INHIBITORS

(71) Applicant: ACLARIS THERAPEUTICS, INC., Wayne, PA (US)

(72) Inventors: Eric Jon Jacobsen, Chesterfield, MO (US); David Randolph Anderson, Salem, CT (US); James Robert Blinn, O'Fallon, MO (US); Paramita Mukherjee, Carbondale, IL (US); Paul Changelian, Framingham, MA (US); Canxin Xu, Ballwin, MO (US)

(*) Notice: Subject to any disclaimer, the term of this patent is extended or adjusted under 35 U.S.C. 154(b) by 58 days.

(21) Appl. No.: 16/866,182

(22) Filed: May 4, 2020

(65) Prior Publication Data

US 2020/0347053 A1    Nov. 5, 2020

Related U.S. Application Data

(60) Provisional application No. 62/842,197, filed on May 2, 2019.

(51) Int. Cl.
*C07D 471/04* (2006.01)
*A61K 45/06* (2006.01)
*A61P 1/00* (2006.01)

(52) U.S. Cl.
CPC ............. *C07D 471/04* (2013.01); *A61P 1/00* (2018.01); *A61K 45/06* (2013.01)

(58) Field of Classification Search
CPC ................................ C07D 471/04; A61P 1/00
USPC ........................................................ 514/269
See application file for complete search history.

(56) References Cited

U.S. PATENT DOCUMENTS

| | | | |
|---|---|---|---|
| 5,760,068 A | 6/1998 | Talley et al. | |
| 7,799,782 B2 | 9/2010 | Munson et al. | |
| 7,879,844 B2 | 2/2011 | Inoue et al. | |
| 8,163,767 B2 | 4/2012 | Inoue et al. | |
| 8,722,693 B2 | 5/2014 | Rodgers et al. | |
| 8,921,376 B2 | 12/2014 | Ledeboer et al. | |
| 9,556,187 B2 | 1/2017 | Hayashi et al. | |
| 9,617,258 B2 * | 4/2017 | Thorarensen | A61P 15/08 |

(Continued)

FOREIGN PATENT DOCUMENTS

| | | | |
|---|---|---|---|
| WO | 1999065909 A1 | 12/1999 | |
| WO | 2000000202 A1 | 1/2000 | |

(Continued)

OTHER PUBLICATIONS

PubChem CID 118115872, pp. 1-9, Feb. 23, 2016.
PubChem CID 59291875, pp. 1-10, Aug. 20, 2012.

Notification, International Search Report and Written Opinion for PCT/US2020/031332 dated Jul. 16, 2020.
Notification, International Search Report and Written Opinion for PCT/US2020/044542 dated Oct. 29, 2020.
Bundgaard "Design of Prodrugs" 1985, Elsevier (cover and TOC).

(Continued)

*Primary Examiner* — Niloofar Rahmani
(74) *Attorney, Agent, or Firm* — Gregory D. Frattini; DLP Piper LLP (US)

(57) ABSTRACT

The present invention relates to new pyrrolopyridine compounds having the structures of Formula (I)-(IV), wherein the R groups, A, B, C, D and n are as defined in the detailed description, and compositions and their application as pharmaceuticals for the treatment of disease.

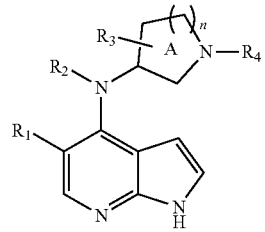

(I)

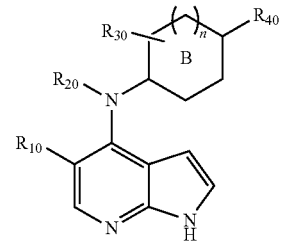

(II)

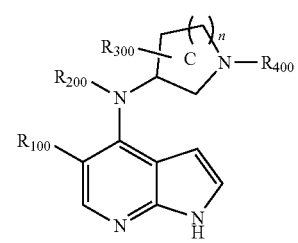

(III)

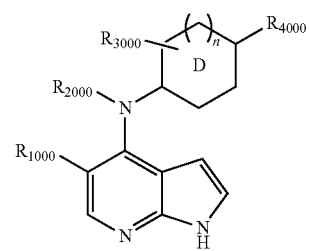

(IV)

Methods of inhibition of JAK kinase activity in a human or animal subject are also provided for the treatment diseases such as pruritus, alopecia, androgenetic alopecia, alopecia areata, vitiligo and psoriasis.

17 Claims, No Drawings

(56) References Cited

U.S. PATENT DOCUMENTS

| | | | |
|---|---|---|---|
| 2007/0135461 | A1 | 6/2007 | Rodgers et al. |
| 2007/0135466 | A1 | 6/2007 | Ledeboer et al. |
| 2009/0264399 | A1 | 10/2009 | Inoue et al. |
| 2010/0105661 | A1* | 4/2010 | Shirakami ............... A61P 35/00 514/217.07 |
| 2010/0113416 | A1 | 5/2010 | Friedman et al. |
| 2011/0039822 | A1 | 2/2011 | Inoue et al. |
| 2012/0149681 | A1 | 6/2012 | Rodgers et al. |
| 2014/0221379 | A1 | 8/2014 | Rodgers et al. |
| 2015/0158864 | A1 | 6/2015 | Thorarensen et al. |
| 2015/0329542 | A1 | 11/2015 | Coe et al. |
| 2016/0272648 | A1 | 9/2016 | Rodgers et al. |
| 2017/0349579 | A1 | 12/2017 | Rodgers et al. |
| 2018/0055846 | A1 | 3/2018 | Bates et al. |
| 2019/0135807 | A1 | 5/2019 | Anderson et al. |
| 2019/0135808 | A1 | 5/2019 | Anderson et al. |
| 2019/0135813 | A1 | 5/2019 | Rodgers et al. |
| 2020/0048262 | A1 | 2/2020 | Jacobsen et al. |

FOREIGN PATENT DOCUMENTS

| | | |
|---|---|---|
| WO | 2004099205 A1 | 11/2004 |
| WO | 2007007919 A2 | 1/2007 |
| WO | 2007077949 A1 | 7/2007 |
| WO | 2017097224 A1 | 6/2017 |
| WO | 2019090143 A1 | 5/2019 |
| WO | 2019090158 A1 | 5/2019 |
| WO | 2020033955 A1 | 2/2020 |

OTHER PUBLICATIONS

Eliel et al. "Stereochemistry of Organic Compounds" Sep. 1994, Wiley, New York, NY (cover and TOC).

Higuchi et al. "Pro-drugs as Novel Delivery Systems" ACS Symposium Series, 14:1-115.

Wortz et a; "Chemically Induced Mouse Models of Acute and Cronic Intestinal Inflammation" 2017, Nature Protocols 12(7):1295 (abstract).

International Search Report and Written Opinion for PCT/US2018/059050 dated Feb. 25, 2019.

International Search Report and Written Opinion for PCT/US2018/059071 dated Feb. 25, 2019.

International Search Report and Written Opinion for PCT/US2019/046182 dated Dec. 17, 2019.

Lam et al. "Vedolizumab for Ulcerative Colitis and Crohn's Disease: Results and Implications of GEMINI Studies" Oct. 23, 2014, Immunotherapy 6(9):963-971 (abstract).

McMahon "VEGF Receptor Signaling in Tumor Angiogenesis" 2000, The Oncologist 5(supp 1):3-10.

Mozaffari et al. "New Biologic Therapeutics for Ulcerative Colitis and Crohn's Disease" 2014, Expert Opin. Biol. Ther. 14(5):583-600.

Okayasu et al. "A Novel Method in the Induction of Reliable Experimental Acute and Chronic Ulcerative Colitis in Mice" 1990, Gastroenterology 98:694-702.

Papp et al. "Phase 2 Trial of Selective Tyrosine Kinase 2 Inhibition in Psoriasis" 2018, New England Journal of Medicine 379(14):1313-1321.

Pineda et al. "Translation Research: The Role of VEGF in Tumor Angiogenesis" 2000, The Oncologist 5(supp 1 ):1-2.

Roche "Bioreversible Carriers in Drug Design" 1987, American Pharmaceutical Association, Pergamon Press (Cover and TOC only).

Stahl "Pharmaceutical Salts: Properties, Selection, and Use" 2002, Wiley-VCHA, Zurich, Switzerland (abstract only).

Testa et al. "Hydrolysis in Drug and Prodrug Metabolism: Chemistry, Biochemistry and Enzymology" 2003, Wiley-VHCA, Zurich, Switzerland (Cover and TOC only).

\* cited by examiner

SUBSTITUTED PYRROLOPYRIDINES AS JAK INHIBITORS

SUMMARY

Embodiments herein are directed to having the structures of Formulas (I)-(IV), or a derivative thereof, where the R groups, ring labels, and n values are defined herein:

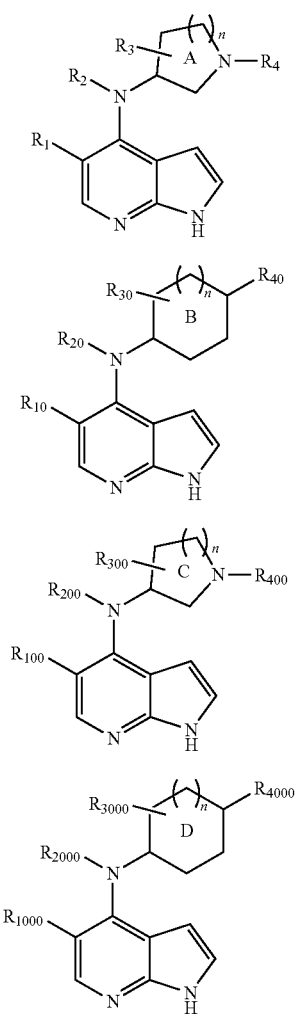

Disclosed herein are new pyrrolopyridine compounds and compositions and their application as pharmaceuticals for the treatment of disease. Methods of inhibition of JAK kinase activity in a human or animal subject are also provided for the treatment of JAK-mediated conditions.

The Janus Kinases (JAKs) are a subgroup of non-receptor tyrosine kinases that are essential to transducing signals originating from type I and type II cytokine receptors and whose enzymatic activity is essential for the biological activity of the cytokines. The JAK kinase family consists of four family members: JAK1, JAK2, JAK3 and Tyk2, and these kinases are central to the regulation of cytokine signaling in the immune system, as well as more broadly in other tissues. The kinase activity of JAKs is directed towards the JAKs themselves, the intracellular portion of the cytokine receptor, and several other substrates including the members of the STAT family of transcription factors. The STATs (STAT1 through STAT6) have specific and distinct effects on gene transcription in numerous cell types, including immune cells, and are critical in processes such as cell proliferation and differentiation. Due to the broad role these kinases have in immunity and inflammation, numerous small molecule drugs have been developed to intervene in diseases where JAK kinase signaling contributes to disease. Initially, these drugs were developed for systemic administration for the prevention of organ transplant rejection. Subsequently they have been developed as potential therapies for hematologic malignancies, and autoimmune and inflammatory diseases including rheumatoid arthritis, ulcerative colitis, inflammatory bowel disease, ankylosing spondylitis, psoriasis, atopic dermatitis, alopecia disorders, and vitiligo, to name a few. More recently, due to the hematologic, immunosuppressive and metabolic toxicities associated with systemic inhibition of the JAK kinases, local delivery of these inhibitors as topical agents has been described. These include alopecia areata, atopic dermatitis, vitiligo, psoriasis, inflammatory bowel diseases, and dry eye, among others. This document describes compounds that have excellent oral and topical bioavailability and are useful for systemic autoimmune disease, as well as compounds designed to have limited stability and hence limited systemic exposure, therefore, be best suited for local (e.g., topical) drug delivery.

Signal transduction of cytokine receptors activated by cytokines has been shown to occur through JAK kinases associated with receptor cytoplasmic domains. Receptor stimulation results in the activation of the JAKs and subsequent phosphorylation of the cytoplasmic domain of the associated receptor chains. This creates an SH2-binding domain, which serves to recruit the latent cytoplasmic transcription factors known as STATs (Signal Transducer and Activator of Transcription). While bound to the phosphorylated cytokine receptors, the STATs themselves become phosphorylated on tyrosine residues—which leads to SH2-domain mediated homo- and hetero-dimer formation and translocation to the nucleus. Once there, these proteins induce the transcription of genes associated with activation of the original cytokine receptor. This sequence of events (STAT protein phosphorylation in minutes, and STAT-induced gene transcription in hours) are both amenable to characterizing the cellular potency of compounds and informing structure-activity relationships.

DETAILED DESCRIPTION

Before the present compositions and methods are described, it is to be understood that this invention is not limited to the particular processes, formulations, compositions, or methodologies described, as these may vary. It is also to be understood that the terminology used in the description is for the purpose of describing the particular versions or embodiments only and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments herein, the preferred methods, devices, and materials are now described. All publications mentioned herein are incorporated by reference in their entirety. Nothing herein is to be construed as an admission that embodiments herein are not entitled to antedate such disclosure by virtue of prior invention.

Definitions

It must also be noted that as used herein and in the appended claims, the singular forms "a," "an," and "the" include plural reference unless the context clearly dictates otherwise. Thus, for example, reference to a "JAK inhibitor" is a reference to one or more JAK inhibitors and equivalents thereof known to those skilled in the art, and so forth.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean plus or minus 10% of the numerical value of the number with which it is being used. Therefore, about 50% means in the range of 45%-55%.

The transitional term "comprising," which is synonymous with "including," "containing," or "characterized by," is inclusive or open-ended and does not exclude additional, unrecited elements or method steps. In embodiments or claims where the term "comprising" is used as the transition phrase, such embodiments can also be envisioned with replacement of the term "comprising" with the terms "consisting of" or "consisting essentially of."

As used herein, the term "consists of" or "consisting of" means that the pharmaceutical composition, composition or the method includes only the elements, steps, or ingredients specifically recited in the particular claimed embodiment or claim.

As used herein, the term "consisting essentially of" or "consists essentially of" means that the pharmaceutical composition, or the method includes only the elements, steps or ingredients specifically recited in the particular claimed embodiment or claim and may optionally include additional elements, steps or ingredients that do not materially affect the basic and novel characteristics of the particular embodiment or claim. For example, the only active ingredient(s) in the composition or method that treats the specified condition (e.g., nutrient depletion) is the specifically recited therapeutic(s) in the particular embodiment or claim.

As used herein, two embodiments are "mutually exclusive" when one is defined to be something which is different from the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

As used herein, the term "a derivative thereof" refers to a salt thereof, a pharmaceutically acceptable salt thereof, an ester thereof, a free acid form thereof, a free base form thereof, a solvate thereof, a co-crystal thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

As used herein, the term "pharmaceutically acceptable salt" refers to a salt prepared from a base or acid which is acceptable for administration to a patient, such as a mammal. The term "pharmaceutically acceptable salts" embraces salts commonly used to form alkali metal salts and to form addition salts of free acids or free bases. The nature of the salt is not critical, provided that it is pharmaceutically-acceptable. Such salts can be derived from pharmaceutically-acceptable inorganic or organic bases and from pharmaceutically-acceptable inorganic or organic acids.

The term "gut-restricted" or "gut-restricted compound," as used herein, refers to a compound that preferentially acts within the intestinal lumen without reaching sufficient exposure in the systemic circulation to illicit a significant pharmacologic response. Without intending to be bound by theory, this results in enhanced safety of the molecule as a consequence of minimizing systemic exposure of the pharmacological agent, or its metabolites, to cells, tissues and organs/organ systems unrelated to disease treatment.

The term "improve" is used to convey that the compounds of embodiments herein change either the appearance, form, characteristics and/or the physical attributes of the tissue to which it is being provided, applied or administered.

The term "inhibit" means to limit, prevent or block the action or function of a target enzyme and/or, to prevent, alleviate or eliminate the onset of one or more symptoms associated with a disease, condition or disorder, or to prevent, alleviate or eliminate a disease, condition or disorder.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms.

In further embodiments, said alkyl will comprise from 1 to 8 carbon atoms. Alkyl groups may be optionally substituted as defined herein.

Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R-S-) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—).

Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)NH(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C$(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as in a carboxylic acid salt. An "O-carboxy" group refers to a RC(O)O— group, where R is as defined herein. A "C-carboxy" group refers to a —C(O)OR groups where R is as defined herein.

The term, "compound," as used herein is meant to include all stereoisomers, geometric isomers, tautomers, and isotopes (e.g., tritium, deuterium) of the structures depicted.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "halocycloalkyl" as used herein, alone or in combination, refers to a cycloalkyl radical having the meaning as defined above wherein one or more hydrogens are replaced with a halogen. Specifically embraced are monohalocycloalkyl, dihalocycloalkyl and polyhalochaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluorocyclopropyl, difluorocyclopropyl, fluorocyclobutyl, chlorocyclobutyl, and chlorocyclopentyl.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower alkyl," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between four and six ring members, of which between one and four may be heteroatoms chosen from N, O, and S (i.e., $C_3$-$C_6$ heterocycloalkyl). Examples of lower heterocycloalkyls include oxetane, azetidiene, pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —$NO_2$.

As used herein, an "N-oxide" is formed from the tertiary basic amines or imines present in the molecule, using a convenient oxidizing agent.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "substantially free" as used herein, alone or in combination, refers to a compound which is free from all other compounds within the limits of detection as measured by any means including nuclear magnetic resonance (NMR), gas chromatography/mass spectroscopy (GC/MS), or liquid chromatography/mass spectroscopy (LC/MS).

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3$CS(O)$_2$NR— group with X is a halogen and R as defined herein.

The term "trihalomethanesulfonyl" refers to a $X_3$CS(O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, C(O)$CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and Rn where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Stereogenic centers exist in the compounds disclosed herein. These centers are designated by the symbols "R" or "S," depending on the configuration of substituents around the stereogenic center. It should be understood that the invention encompasses all stereoisomeric forms, including diastereomeric, enantiomeric, and epimeric forms, as well as d-isomers and l-isomers, and mixtures thereof. Individual stereoisomers of compounds can be prepared synthetically from commercially available starting materials which contain defined stereochemical configurations or by separation of mixtures of stereoisomeric products by conversion to a mixture of diastereomers followed by separation or recrystallization, chromatographic techniques, direct separation of stereoisomers by chiral chromatographic columns, or any other appropriate method known in the art. Starting compounds of particular configurations are either commercially available or can be made and resolved by techniques known in the art. Additionally, the compounds disclosed herein may exist as geometric isomers. The present invention includes all cis, trans, syn, anti, endo, exo, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"JAK inhibitor" is used herein to refer to a compound that exhibits an IC$_{50}$ with respect to JAK1, JAK2, JAK3 and Tyk-2 activity of no more than about 100 µM and more typically not more than about 50 µM, as measured in the JAK1, JAK2, JAK3 and Tyk-2 enzyme assays described generally herein. In some embodiments, the compounds will exhibit an IC$_{50}$ with respect JAK1, JAK2, JAK3 and Tyk-2 of about 1 µM to about 50 µM. IC$_{50}$ is that concentration of inhibitor which reduces the activity of an enzyme (e.g., JAK1, JAK2, JAK3 and Tyk-2) to half-maximal level. Certain compounds disclosed herein have been discovered to exhibit inhibition against JAK1, JAK2, JAK3 and Tyk-2. In some embodiments, the compounds will exhibit an IC$_{50}$ with respect to JAK1, JAK2, JAK3 and Tyk-2 of no more than about 300 nM. In some embodiments, the compounds will exhibit an IC$_{50}$ with respect to JAK1, JAK2, JAK3 and Tyk-2 of no more than about 1 nM. In certain embodiments, compounds will exhibit an IC$_{50}$ with respect to JAK1, JAK2, JAK3 and Tyk-2 of no more than about 50 µM; in further embodiments, compounds will exhibit an IC$_{50}$ with respect to JAK1, JAK2, JAK3 and Tyk-2 of no more than about 10 µM; in yet further embodiments, compounds will exhibit an IC$_{50}$ with respect to JAK1, JAK2, JAK3 and Tyk-2 of not more than about 5 µM; in yet further embodiments, compounds will exhibit an IC$_{50}$ with respect to JAK1, JAK2, JAK3 and Tyk-2 of not more than about 1 µM, as measured in the JAK1, JAK2, JAK3 and Tyk-2 assays described herein.

The phrase "therapeutically effective" is intended to qualify the amount of active ingredients used in the treatment of a disease or disorder or on the effecting of a clinical endpoint.

As used herein, the term "therapeutic" or "therapeutic agent" or "pharmaceutically active agent" means an agent utilized to treat, combat, ameliorate, prevent or improve an unwanted condition or disease of a patient. In part, embodiments of the present invention are directed to the treatment of JAK-mediated diseases.

A "therapeutically effective amount" or "effective amount" of a composition is a predetermined amount calculated to achieve the desired effect, i.e., to inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from 0.001 to 10 mg/kg, more usually in the range of from 0.01 to 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The term "therapeutically acceptable" refers to those compounds, or a derivative thereof, which are suitable for use in contact with the tissues of patients without undue toxicity, irritation, and allergic response, are commensurate with a reasonable benefit/risk ratio, and are effective for their intended use.

The terms "treat," "treated," "treating", or "treatment" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total, whether induction of or maintenance of), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease and prolonging disease-free survival as compared to disease-free survival if not receiving treatment and prolonging disease-free survival as compared to disease-free survival if not receiving treatment.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with a compound of embodiments herein, can include, but is not limited to, providing the compound into or onto the target tissue; providing the compound systemically to a patient by, e.g., intravenous injection whereby the therapeutic reaches the target tissue; providing the compound in the form of the encoding sequence thereof to the target tissue (e.g., by so-called gene-therapy techniques). "Administering" a composition may be accomplished by injection, topically, orally, or by any of these methods in combination with other known techniques.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The terms "excipient" and "pharmaceutically acceptable excipient" as used herein are intended to be generally synonymous, and is used interchangeably with, the terms "carrier," "pharmaceutically acceptable carrier," "diluent," "pharmaceutically acceptable diluent."

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Embodiments of the present invention are directed to compounds and pharmaceutical compositions comprising such compounds, which have been found to inhibit JAK kinase have been discovered, together with methods of synthesizing and using the compounds including, without limitation, methods for the treatment of JAK mediated diseases in a patient by administering the compounds. In some embodiments the compounds and pharmaceutical compositions are administered topically.

Compounds of the present invention may be selective amongst the JAK isoforms in various ways. For example, compounds described herein may be selective for JAK1, JAK2, JAK3, and/or Tyk-2 over other isoforms, have equal potency agains all isoforms, or be selective for only one isoform. In certain embodiments, compounds of the present invention are selective for JAK over other isoforms. In some embodiments, the compounds disclosed herein are selective for JAK over JAK2 and Tyk-2. Selectivity may be determined using enzyme assays, cellular assays or both. In some embodiments, the compounds disclosed herein are at least about 10× more potent for JAK associated receptors compared to JAK2 associate receptors. In some embodiments, the compounds disclosed herein are at least about 10× selective for JAK1 associated receptors over Tyk-2 associated receptors.

Compounds

Embodiments herein are directed to compounds and pharmaceutical compositions comprising such compounds, which have been found to inhibit JAK kinases, together with methods of synthesizing and using the compounds. Some embodiments include methods for the treatment of diseases in a patient by administering the compounds of embodiments herein.

Certain compounds disclosed herein may possess useful JAK inhibiting activity and may be used in the treatment or prophylaxis of a disease or condition in which JAK kinases play an active role. Thus, embodiments are also directed to pharmaceutical compositions comprising one or more compounds disclosed herein together with a pharmaceutically acceptable carrier, as well as methods of making and using the compounds and compositions. Certain embodiments are directed to methods for inhibiting JAK kinases. Other embodiments are directed to methods for treating a JAK-mediated disorder in a patient in need of such treatment, comprising administering to said patient a therapeutically effective amount of a compound or composition according to the present invention. Also provided is the use of certain compounds disclosed herein in the manufacture of a medicament for the treatment of a disease or condition ameliorated by the inhibition of JAK kinase.

In some embodiments, the compounds disclosed herein have been designed to be poorly absorbed to minimize systemic exposure. In some embodiments, the compounds disclosed herein have been designed to be rapidly metabolized to minimize systemic exposure. In some embodiments, the compounds disclosed herein are designed to exert their effect at the desired site of action, for example in the gastrointestinal tract (e.g., the colon), to decrease the risk of significant systemic effects or adverse systemic effects. In some embodiments, the compounds disclosed herein are gut-restricted compounds.

Also provided are embodiments wherein any embodiment herein may be combined with any one or more of the other embodiments, unless otherwise stated and provided the combination is not mutually exclusive.

Also provided is a compound chosen from the Examples disclosed herein. The compounds of embodiments herein may also refer to a derivative thereof, or a combination of the foregoing of the compounds of embodiments herein.

Compounds described herein may contain one or more stereogenic centers and may thus exist as stereoisomers. Embodiments herein includes all such possible stereoisomers as substantially pure resolved stereoisomers, racemic mixtures thereof, as well as mixtures of diastereomers. In some embodiments, the formulas are shown without a definitive stereochemistry at certain positions. In other embodiments, the compounds are isolated as single stereoisomers, but the absolute configurations of the stereogenic centers are unknown or only the relative stereochemical configuration (i.e., cis or trans isomerism) is known. In such embodiments, the formulas are shown with provisionally assigned absolute assignments to denote that they are single stereoisomers and relative stereochemical configuration is likewise described. Embodiments herein include all stereoisomers of such formulas and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any stereoisomer of a compound of the general formula may be obtained by stereospecific or stereoselective synthesis using optically pure or enantioenriched starting materials or reagents of known configuration. The scope of embodiments herein as described and claimed encompasses the racemic forms of the compounds as well as the individual enantiomers, diastereomers, stereoisomers and stereoisomer-enriched mixtures.

Conventional techniques for the preparation/isolation of individual enantiomers include chiral synthesis from a suitable enantioenriched or optically pure precursors or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of embodiments herein (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomer conglomerates may be separated by conventional techniques known to those skilled in the art. See, e.g., "Stereochemistry of Organic Compounds" by Ernest L. Eliel (Wiley, New York, 1994).

Atropisomers are stereoisomers resulting from hindered rotation about single bonds where the steric strain barrier to rotation is high enough to allow for the isolation of the conformers. Oki (Oki, M; Topics in Stereochemistry 1983, 1) defined atropisomers as conformers that interconvert with a half-life of more than 1000 seconds at a given temperature. The scope of embodiments herein as described and claimed encompasses the racemic forms of the compounds as well as the individual atropisomers (an atropisomer "substantially free" of its corresponding enantiomer) and stereoisomer-enriched mixtures, i.e. mixtures of atropisomers. Separation of atropisomers is possibly by chiral resolution methods such as selective crystallization. In an atropo-enantioselective or atroposelective synthesis one atropisomer is formed at the expense of the other. Atroposelective synthesis may be carried out by use of chiral auxiliaries like a Corey-Bakshi-Shibata (CBS) catalyst (asymmetric catalyst derived from proline) in the total synthesis of knipholone or by approaches based on thermodynamic equilibration when an isomerization reaction favors one atropisomer over the other.

Suitable pharmaceutically acceptable acid addition salts of the compounds of embodiments herein may be prepared from an inorganic acid or an organic acid. All of these salts may be prepared by conventional means from the corresponding compound of embodiments herein by treating, for example, the compound with the appropriate acid or base.

Pharmaceutically acceptable acids include both inorganic acids, for example hydrochloric, hydrobromic, hydroiodic, nitric, carbonic, sulfuric, phosphoric and diphosphoric acid; and organic acids, for example formic, acetic, trifluoroacetic, propionic, succinic, glycolic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, O-hydroxybutyric, malonic, galactic, galacturonic, citric, fumaric, gluconic, glutamic, lactic, maleic, malic, mandelic, mucic, ascorbic, oxalic, pantothenic, succinic, tartaric, benzoic, acetic, xinafoic (1-hydroxy-2-naphthoic acid), napadisilic (1,5-naphthalenedisulfonic acid) and the like.

Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including alkyl amines, arylalkyl amines, heterocyclyl amines, cyclic amines, naturally-occurring amines and the like, such as arginine, betaine, caffeine, choline, chloroprocaine, diethanolamine, N-methylglucamine, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Other preferred salts according to embodiments herein are quaternary ammonium compounds wherein an equivalent of an anion (X−) is associated with the positive charge of the N atom. X− may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X− is preferably an anion selected from chloride, bromide, iodide, sulphate, nitrate, acetate, maleate, oxalate, succinate or trifluoroacetate. More preferably X− is chloride, bromide, trifluoroacetate or methanesulphonate.

The compounds of embodiments herein may exist in both unsolvated and solvated forms. The term solvate is used herein to describe a molecular complex comprising a compound of embodiments herein and an amount of one or more pharmaceutically acceptable solvent molecules. The term hydrate is employed when said solvent is water. Examples of solvate forms include, but are not limited to, compounds of embodiments herein in association with water, acetone, dichloromethane, 2-propanol, ethanol, methanol, dimethylsulfoxide (DMSO), ethyl acetate, acetic acid, ethanolamine, or mixtures thereof. It is specifically contemplated that in embodiments herein one solvent molecule can be associated with one molecule of the compounds of embodiments herein, such as a hydrate.

Furthermore, it is specifically contemplated that in embodiments herein, more than one solvent molecule may be associated with one molecule of the compounds of embodiments herein, such as a dihydrate. Additionally, it is specifically contemplated that in embodiments herein less than one solvent molecule may be associated with one molecule of the compounds of embodiments herein, such as a hemihydrate. Furthermore, solvates of embodiments herein are contemplated as solvates of compounds of embodiments herein that retain the biological effectiveness of the non-solvate form of the compounds.

Embodiments herein also include isotopically-labeled compounds of embodiments herein, wherein one or more atoms is replaced by an atom having the same atomic number, but an atomic mass or mass number different from the atomic mass or mass number usually found in nature. Examples of isotopes suitable for inclusion in the compounds of embodiments herein include isotopes of hydrogen, such as $^{2}H$ and $^{3}H$, carbon, such as $^{11}C$, $^{13}C$ and $^{14}C$, chlorine, such as $^{31}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labeled compounds of embodiments herein, for example, those incorporating a radioactive isotope, are useful in drug and/or substrate tissue distribution studies. The radioactive isotopes tritium, $^{3}H$, and carbon-14, $^{14}C$, are particularly useful for this purpose in view of their ease of incorporation and ready means of detection. Substitution with heavier isotopes such as deuterium, $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of embodiments herein can generally be prepared by conventional techniques known to those skilled in the art or by processes analogous to those described herein, using an appropriate isotopically-labeled reagent in place of the non-labeled reagent otherwise employed.

Preferred isotopically-labeled compounds include deuterated derivatives of the compounds of embodiments herein. As used herein, the term deuterated derivative embraces compounds of embodiments herein where in a particular position at least one hydrogen atom is replaced by deuterium. Deuterium (D or $^{2}H$) is a stable isotope of hydrogen which is present at a natural abundance of 0.015 molar %.

Hydrogen deuterium exchange (deuterium incorporation) is a chemical reaction in which a covalently bonded hydrogen atom is replaced by a deuterium atom. Said exchange (incorporation) reaction can be total or partial.

Typically, a deuterated derivative of a compound of embodiments herein has an isotopic enrichment factor (ratio between the isotopic abundance and the natural abundance of that isotope, i.e. the percentage of incorporation of deuterium at a given position in a molecule in the place of hydrogen) for each deuterium present at a site designated as a potential site of deuteration on the compound of at least 3500 (52.5% deuterium incorporation).

In some embodiments, the isotopic enrichment factor is at least 5000 (75% deuterium). In some embodiments, the isotopic enrichment factor is at least 6333.3 (95% deuterium incorporation). In some embodiments, the isotopic enrichment factor is at least 6633.3 (99.5% deuterium incorporation). It is understood that the isotopic enrichment factor of each deuterium present at a site designated as a site of deuteration is independent from the other deuteration sites.

The isotopic enrichment factor can be determined using conventional analytical methods known to one of ordinary skilled in the art, including mass spectrometry (MS) and nuclear magnetic resonance (NMR).

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Prodrugs of the compounds described herein are also within the scope of embodiments herein. Thus, certain derivatives of the compounds of embodiments herein, which derivatives may have little or no pharmacological activity themselves, when administered into or onto the body may be converted into compounds of embodiments herein having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with embodiments herein can, for example, be produced by replacing appropriate functionalities present in the compounds of embodiments herein with certain moieties known to those skilled in the art as 'promoieties' as described, for example, in Design of Prodrugs by H. Bundgaard (Elsevier, 1985).

In the case of compounds of embodiments herein that are solids, it is understood by those skilled in the art that the inventive compounds and salts may exist in different crystalline or polymorphic forms, or in an amorphous form, all of which are intended to be within the scope of embodiments herein.

The compounds disclosed herein can exist as and therefore include all stereoisomers, tautomers, conformational isomers and mixtures thereof in all proportions as well as isotopic forms such as deuterated compounds.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

In certain embodiments, compounds have structural Formula (I):

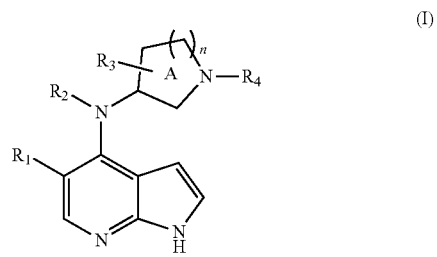

wherein:

$R_1$ is selected from CN or a heteroaryl group and is optionally substituted at the one or more available nitrogen atoms with a group independently selected from H or $C_1$-$C_5$alkyl and at one or more available carbon atoms with substituents wherein each substituent is independently selected from H, halogen, CN, —$C_1$-$C_4$alkyl, —$C_0$-$C_6$alkyl$C_3$-$C_6$cycloalkyl, —($C_0$-$C_6$alkyl)$C_3$-$C_6$heterocycle, —OH, —$SO_2R_9$, —$SOR_9$, —$SR_9$, —$NHSO_2R_9$, —$OSO_2R_9$, —$C_0$-$C_6$alkyl$SO_2R_9$, $C_0$-$C_6$alkylCOR$_9$, $C_0$-$C_6$alkylNR$_7$C(O)NR$_7$R$_8$, —$C_0$-$C_6$alkylOC(O)NR$_7$R$_8$, $C_0$-$C_6$alkylNR$_7$SO$_2$R$_9$, —$C_0$-$C_6$alkylNR$_7$COR$_9$ —OC$_1$-$C_6$alkyl, —OC$_0$-$C_6$alkylC$_3$-$C_6$cycloalkyl, —OC$_0$-$C_6$alkylC$_3$-$C_6$heterocycle, —OC$_0$-$C_6$alkylNR$_7$C(O)NR$_7$R$_8$, —OC$_0$-$C_6$alkylOC(O)NR$_7$R$_8$, —OC$_0$-$C_6$alkylNR$_7$SO$_2$R$_9$, —OC$_0$-$C_6$alkylNR$_7$COR$_9$, —NR$_7$R$_8$, —NR$_7$C$_0$-$C_6$alkylC$_1$-$C_6$alkyl, —NR$_7$C$_0$-$C_6$alkylC$_3$-$C_6$cycloalkyl, —NR$_7$C$_0$-$C_6$alkylNR$_7$C(O)NR$_7$R$_8$, —NR$_7$C$_0$-$C_6$alkylOC(O)NR$_7$R$_8$, —NR$_7$C$_0$-$C_6$alkylNR$_7$SO$_2$R$_9$, —NR$_7$C$_0$-$C_6$alkylNR$_7$COR$_9$, —NR$_7$C$_0$-$C_6$alkylC$_3$-$C_6$heterocycle, aryl and heteroaryl wherein each alkyl, cycloalkyl, aryl, heterocyclyl, or heteroaryl group is optionally substituted with one or more groups selected from: halogen, —OH, —C$_0$-$C_6$alkylNR$_7$R$_8$, —C$_0$-$C_6$alkylOH, —SO$_2$R$_9$, —SOR$_9$, —NHSO$_2$R$_9$, —C$_0$-$C_6$alkylNR$_7$R$_4$, CN, —C$_1$-$C_5$alkylalkoxy, C$_1$-$C_5$alkoxy or —O—C$_1$-C$_5$alkyl;

$R_2$ is selected from H, —$C_1$-$C_4$alkyl, —$C_3$-$C_6$cycloalkyl, or —$C_1$-$C_2$alkyl-$C_3$-$C_6$cycloalkyl, wherein the alkyl or cycloalkyl groups are optionally substituted with one or more groups selected from halogen, —OH, or —O—$C_1$-$C_5$alkyl;

n is 0, 1 or 2;

Ring A is substituted at one or more carbons with one, two, or three $R_3$ substituents wherein each $R_3$ substituent is independently selected from H, halogen, —$C_1$-$C_4$alkyl, —$C_3$-$C_6$cycloalkyl, —OH, or —O—$C_1$-$C_5$alkyl wherein each alkyl or cycloalkyl group is optionally substituted with one or more groups selected from: halogen, —OH, —$C_1$-$C_5$alkylalkoxy, or —O—$C_1$-$C_5$alkyl;

Two $R_3$ groups on the same or different carbon atoms of the ring A may be optionally joined to form a spirocyclic or bicyclic ring system with ring A;

$R_4$ is selected from —C(O)—$R_6$, —$CH_2R_6$, —C(O)—$C_1$-$C_5$alkyl, or —C(O)—$C_3$-$C_6$cycloalkyl, wherein the alkyl or cycloalkyl groups may be optionally substituted with one or more groups selected from —OH, halogen, alkyne, or —CN;

$R_5$ is selected from —$C_1$-$C_5$alkyl, or —$C_3$-$C_6$cycloalkyl wherein the alkyl or cycloalkyl groups may be optionally substituted by one or more groups selected from halogen, —OH, or —O—$C_1$-$C_5$alkyl;

$R_6$ is selected from —$C_1$-$C_5$alkyl, —$C_3$-$C_6$cycloalkyl, —$C_1$-$C_5$alkyl-$C_3$-$C_6$cycloalkyl, —$NR_7R_8$, —O-aryl, —O-heteroaryl, aryl, or heteroaryl wherein the alkyl, cycloalkyl, aryl or heteroaryl groups can be optionally substituted by one or more groups selected from halogen, —CN, alkyne, —OH, trifluoromethyl, —O—$C_1$-$C_5$alkyl, or —O—$C_3$-$C_6$cycloalkyl;

$R_7$ and $R_8$ are independently selected from H, —$C_1$-$C_5$ alkyl, —$C_1$-$C_5$ alkoxy, or —$C_3$-$C_5$ cycloalkyl wherein the alkyl groups may be optionally substituted by one or more groups selected from halogen, —OH, or —CN;

$R_7$ and $R_8$ may be optionally joined to form a ring to form a heterocycle such as piperidine, pyrrolidine, or with another heteroatom to form a ring such as morpholine wherein the heterocyclic ring may be optionally substituted by one or more groups selected from halogen, —OH, $NH_2$, NHMe, $NMe_2$, or —CN; and $R_9$ is selected from H, —$C_1$-$C_5$alkyl, —$OC_1$-$C_5$alkyl, —$C_3$-$C_6$cycloalkyl, and $NR_7R_8$ wherein the alkyl, heterocycle, or cycloalkyl groups may be optionally substituted by one or more groups selected from halogen, —OH, $NH_2$, NHMe, $NMe_2$, or —CN.

In certain embodiments, compounds have structural Formula (II):

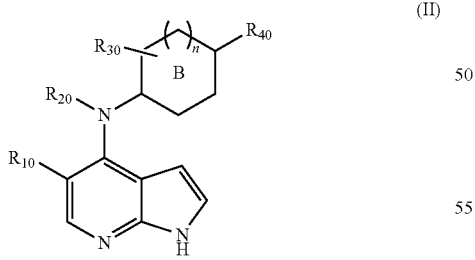

(II)

wherein:

$R_{10}$ is selected from CN or a heteroaryl group and is optionally substituted at the one or more available nitrogen atoms with a group independently selected from H or $C_1$-$C_5$alkyl and at one or more available carbon atoms with substituents wherein each substituent is independently selected from H, halogen, CN, —$C_1$-$C_4$alkyl, —$C_0$-$C_6$alkyl$C_3$-$C_6$cycloalkyl, —($C_0$-$C_6$alkyl)$C_3$-$C_6$heterocycle, —OH, —$SO_2R_{90}$, —$NHSO_2R_{90}$, —$OSO_2R_{90}$, —$C_0$-$C_6$alkyl$SO_2R_{90}$, $C_0$-$C_6$alkyl$COR_{90}$, $C_0$-$C_6$alkyl$NR_{70}C(O)NR_{70}R_{80}$, $C_0$-$C_6$alkylOC(O)$NR_{70}R_{80}$, $C_0$-$C_6$alkyl$NR_{70}SO_2R_{90}$, —$C_0$-$C_6$alkyl$NR_{70}COR_{90}$—$OC_1$-$C_6$alkyl, —$OC_0$-$C_6$alkyl$C_3$-$C_6$cycloalkyl, —$OC_0$-$C_6$alkyl$C_3$-$C_6$heterocycle, —$OC_0$-$C_6$alkyl$NR_{70}C(O)NR_{70}R_{80}$, —$OC_0$-$C_6$alkylOC(O)$NR_{70}R_{80}$, —$OC_0$-$C_6$alkyl$NR_{70}SO_2R_{90}$, —$OC_0$-$C_6$alkyl$NR_{70}COR_{90}$, —$NR_{70}R_{80}$, —$NR_{70}C_0$-$C_6$alkyl$C_1$-$C_6$alkyl, —$NR_{70}C_0$-$C_6$alkyl$C_3$-$C_6$cycloalkyl, —$NR_{70}C_0$-$C_6$alkyl$NR_7C(O)NR_{70}R_{80}$, —$NR_{70}C_0$-$C_6$alkylOC(O)$NR_{70}R_{80}$, —$NR_{70}C_0$-$C_6$alkyl$NR_{70}SO_2R_{90}$, —$NR_{70}C_0$-$C_6$alkyl$NR_{70}COR_{90}$, —$NR_{70}C_0$-$C_6$alkyl$C_3$-$C_6$heterocycle, aryl and heteroaryl wherein each alkyl, cycloalkyl, aryl, heterocyclyl, or heteroaryl group is optionally substituted with one or more groups selected from: halogen, —OH, —$C_0$-$C_6$alkyl$NR_{70}R_{80}$, —$C_0$-$C_6$alkylOH, —$SO_2R_9$, —$SOR_{90}$, —$NHSO_2R_{90}$, —$C_0$-$C_6$alkyl$NR_{70}R_{40}$, CN, —$C_1$-$C_5$alkylalkoxy, $C_1$-$C_5$alkoxy or —O—$C_1$-$C_5$alkyl;

$R_{20}$ is selected from H, —$C_1$-$C_4$alkyl, —$C_3$-$C_6$cycloalkyl, or —$C_1$-$C_2$alkyl-$C_3$-$C_6$cycloalkyl, wherein the alkyl or cycloalkyl groups are optionally substituted with one or more groups selected from halogen, —OH, or —O—$C_1$-$C_5$alkyl;

n is 0, 1 or 2;

Ring B is substituted at one or more carbons with one, two, or three $R_{30}$ substituents wherein each $R_{30}$ substituent is independently selected from H, halogen, —$C_1$-$C_4$alkyl, —$C_3$-$C_6$cycloalkyl, —OH, or —O—$C_1$-$C_5$alkyl wherein each alkyl or cycloalkyl group is optionally substituted with one or more groups selected from: halogen, —OH, —$C_1$-$C_5$alkylalkoxy, or —O—$C_1$-$C_5$alkyl;

Two $R_{30}$ groups on the same or different carbon atoms of the ring B may be optionally joined to form a spirocyclic or bicyclic ring system with ring B;

$R_{40}$ is selected from —C(O)—$R_{60}$, —$CH_2R_{60}$, —C(O)—$C_1$-$C_5$alkyl, or —C(O)—$C_3$-$C_6$cycloalkyl, wherein the alkyl or cycloalkyl groups may be optionally substituted with one or more groups selected from —OH, halogen, alkyne, or —CN;

$R_{50}$ is selected from —$C_1$-$C_5$alkyl, or —$C_3$-$C_6$cycloalkyl wherein the alkyl or cycloalkyl groups may be optionally substituted by one or more groups selected from halogen, —OH, or —O—$C_1$-$C_5$alkyl;

$R_{60}$ is selected from —$C_1$-$C_5$alkyl, —$C_3$-$C_6$cycloalkyl, —$C_1$-$C_5$alkyl-$C_3$-$C_6$cycloalkyl, —$NR_{70}R_{80}$, —O-aryl, —O-heteroaryl, aryl, or heteroaryl wherein the alkyl, cycloalkyl, aryl or heteroaryl groups can be optionally substituted by one or more groups selected from halogen, —CN, alkyne, —OH, trifluoromethyl, —O—$C_1$-$C_5$alkyl, or —O—$C_3$-$C_6$cycloalkyl;

$R_{70}$ and $R_{80}$ are independently selected from H, —$C_1$-$C_5$ alkyl, —$C_1$-$C_5$ alkoxy, or —$C_3$-$C_5$ cycloalkyl wherein the alkyl groups may be optionally substituted by one or more groups selected from halogen, —OH, or —CN;

$R_{70}$ and $R_{80}$ may be optionally joined to form a ring to form a heterocycle such as piperidine, pyrrolidine, or with another heteroatom to form a ring such as morpholine wherein the heterocyclic ring may be optionally substituted by one or more groups selected from halogen, —OH, $NH_2$, NHMe, $NMe_2$, or —CN; and $R_{90}$ is selected from H, —$C_1$-$C_5$alkyl, —$C_3$-$C_6$cycloalkyl, and $NR_{70}R_{80}$ wherein the alkyl, heterocycle, or cycloalkyl groups may be optionally substituted by one or more groups selected from halogen, —OH, NH$_2$, NHMe, NMe$_2$, or —CN.

In certain embodiments, compounds have structural Formula (III):

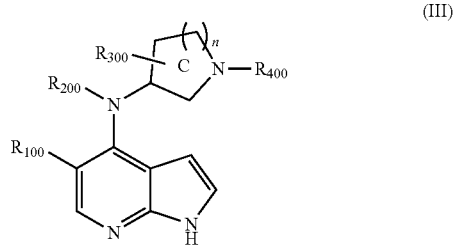

(III)

wherein:
- R$_{100}$ is selected from CN or a heteroaryl group and is substituted at the one or more available nitrogen atoms with a group independently selected from H or C$_1$-C$_5$alkyl and at one or more available carbon atoms with substituents wherein each substituent is independently selected from H, halogen, CN, —C$_1$-C$_4$alkyl, —C$_3$-C$_6$cycloalkyl, —OH, —O—C$_1$-C$_5$alkyl, —SO$_2$R$_{900}$, —NHSO$_2$R$_{900}$, —OSO$_2$R$_{900}$, —CH$_2$SO$_2$R$_{900}$, (CH$_2$)$_n$COR$_{900}$, aryl and heteroaryl wherein each alkyl, cycloalkyl, aryl or heteroaryl group is optionally substituted with one or more groups selected from: halogen, —OH, NH$_2$, NH—C$_1$-C$_5$alkyl, CN, —C$_1$-C$_5$alkylalkoxy, C$_1$-C$_5$alkoxy or —O—C$_1$-C$_5$alkyl;
- R$_{200}$ is selected from H, —C$_1$-C$_4$alkyl, —C$_3$-C$_6$cycloalkyl, or —C$_1$-C$_2$alkyl-C$_3$-C$_6$cycloalkyl, wherein the alkyl or cycloalkyl groups are optionally substituted with one or more groups selected from halogen, —OH, or —O—C$_1$-C$_5$alkyl;
- n is 0, 1 or 2;
- Ring C is substituted at one or more carbons with one, two, or three R$_{300}$ substituents wherein each R$_{300}$ substituent is independently selected from H, halogen, —C$_1$-C$_4$alkyl, —C$_3$-C$_6$cycloalkyl, —OH, or —O—C$_1$-C$_5$alkyl wherein each alkyl or cycloalkyl group is optionally substituted with one or more groups selected from: halogen, —OH, —C$_1$-C$_5$alkylalkoxy, or —O—C$_1$-C$_5$alkyl;
- Two R$_{300}$ groups on the same or different carbon atoms of the ring C may be optionally joined to form a spirocyclic or bicyclic ring system with ring C;
- R$_{400}$ is selected from —C(O)—R$_{600}$, —CH$_2$R$_{600}$, —C(O)—C$_1$-C$_5$alkyl, or —C(O)—C$_3$-C$_6$cycloalkyl, wherein the alkyl or cycloalkyl groups may be optionally substituted with one or more groups selected from —OH, halogen, alkyne, or —CN;
- R$_{500}$ is selected from —C$_1$-C$_5$alkyl, or —C$_3$-C$_6$cycloalkyl wherein the alkyl or cycloalkyl groups may be optionally substituted by one or more groups selected from halogen, —OH, or —O—C$_1$-C$_5$alkyl;
- R$_{600}$ is selected from —C$_1$-C$_5$alkyl, —C$_3$-C$_6$cycloalkyl, —C$_1$-C$_5$alkyl-C$_3$-C$_6$cycloalkyl, —NR$_{700}$R$_{800}$, —O-aryl, —O-heteroaryl, aryl, or heteroaryl wherein the alkyl, cycloalkyl, aryl or heteroaryl groups can be optionally substituted by one or more groups selected from halogen, —CN, alkyne, —OH, trifluoromethyl, —O—C$_1$-C$_5$alkyl, or —O—C$_3$-C$_6$cycloalkyl;
- R$_{700}$ and R$_{800}$ are independently selected from H, —C$_1$-C$_5$ alkyl, —C$_1$-C$_5$ alkoxy, or —C$_3$-C$_5$ cycloalkyl wherein the alkyl groups may be optionally substituted by one or more groups selected from halogen, —OH, or —CN;
- R$_{700}$ and R$_{800}$ may be optionally joined to form a ring to form a heterocycle such as piperidine, pyrrolidine, or with another heteroatom to form a ring such as morpholine; and
- R$_{900}$ is selected from H, —C$_1$-C$_5$alkyl, —C$_3$-C$_6$cycloalkyl, and NR$_{700}$R$_{800}$ wherein the alkyl groups may be optionally substituted by one or more groups selected from halogen, —OH, or —CN.

In certain embodiments, compounds have structural Formula (IV):

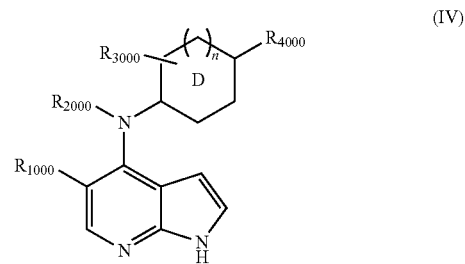

(IV)

wherein:
- R$_{1000}$ is selected from CN or a heteroaryl group and is substituted at the one or more available nitrogen atoms with a group independently selected from H or C$_1$-C$_5$alkyl and at one or more available carbon atoms with substituents wherein each substituent is independently selected from H, halogen, CN, —C$_1$-C$_4$alkyl, —C$_3$-C$_6$cycloalkyl, —OH, —O—C$_1$-C$_5$alkyl, —SO$_2$R$_{9000}$, —NHSO$_2$R$_{9000}$, —OSO$_2$R$_{9000}$, —CH$_2$SO$_2$R$_{9000}$, (CH$_2$), COR$_{9000}$, aryl and heteroaryl wherein each alkyl, cycloalkyl, aryl or heteroaryl group is optionally substituted with one or more groups selected from: halogen, —OH, NH$_2$, NH—C$_1$-C$_5$alkyl, CN, —C$_1$-C$_5$alkylalkoxy, C$_1$-C$_5$alkoxy or —O—C$_1$-C$_5$alkyl;
- R$_{2000}$ is selected from H, —C$_1$-C$_4$alkyl, —C$_3$-C$_6$cycloalkyl, or —C$_1$-C$_2$alkyl-C$_3$-C$_6$cycloalkyl, wherein the alkyl or cycloalkyl groups are optionally substituted with one or more groups selected from halogen, —OH, or —O—C$_1$-C$_5$alkyl;
- n is 0, 1 or 2;
- Ring D is substituted at one or more carbons with one, two, or three R$_{3000}$ substituents wherein each R$_{3000}$ substituent is independently selected from H, halogen, —C$_1$-C$_4$alkyl, —C$_3$-C$_6$cycloalkyl, —OH, or —O—C$_1$-C$_5$alkyl wherein each alkyl or cycloalkyl group is optionally substituted with one or more groups selected from: halogen, —OH, —C$_1$-C$_5$alkylalkoxy, or —O—C$_1$-C$_5$alkyl;
- Two R$_{3000}$ groups on the same or different carbon atoms of the ring D may be optionally joined to form a spirocyclic or bicyclic ring system with ring D;
- R$_{4000}$ is selected from —C(O)—R$_{6000}$, —CH$_2$R$_{6000}$, —C(O)—C$_1$-C$_5$alkyl, or —C(O)—C$_3$-C$_6$cycloalkyl, wherein the alkyl or cycloalkyl groups may be optionally substituted with one or more groups selected from —OH, halogen, alkyne, or —CN;

$R_{5000}$ is selected from —$C_1$-$C_5$alkyl, or —$C_3$-$C_6$cycloalkyl wherein the alkyl or cycloalkyl groups may be optionally substituted by one or more groups selected from halogen, —OH, or —O—$C_1$-$C_5$alkyl;

$R_{6000}$ is selected from —$C_1$-$C_5$alkyl, —$C_3$-$C_6$cycloalkyl, —$C_1$-$C_5$alkyl-$C_3$-$C_6$cycloalkyl, —$NR_{7000}R_{8000}$, —O-aryl, —O-heteroaryl, aryl, or heteroaryl wherein the alkyl, cycloalkyl, aryl or heteroaryl groups can be optionally substituted by one or more groups selected from halogen, —CN, alkyne, —OH, trifluoromethyl, —O—$C_1$-$C_5$alkyl, or —O—$C_3$-$C_6$cycloalkyl;

$R_{7000}$ and $R_{8000}$ are independently selected from H, —$C_1$-$C_5$ alkyl, —$C_1$-$C_5$ alkoxy, or —$C_3$-$C_5$ cycloalkyl wherein the alkyl groups may be optionally substituted by one or more groups selected from halogen, —OH, or —CN;

$R_{7000}$ and $R_{8000}$ may be optionally joined to form a ring to form a heterocycle such as piperidine, pyrrolidine, or with another heteroatom to form a ring such as morpholine; and $R_{9000}$ is selected from H, —$C_1$-$C_5$alkyl, —$C_3$-$C_6$cycloalkyl, and $NR_{7000}R_{8000}$ wherein the alkyl groups may be optionally substituted by one or more groups selected from halogen, —OH, or —CN.

The invention is further illustrated by the following examples of compounds of Formula (I)

| Example # | Structure | Name |
|---|---|---|
| 1 | 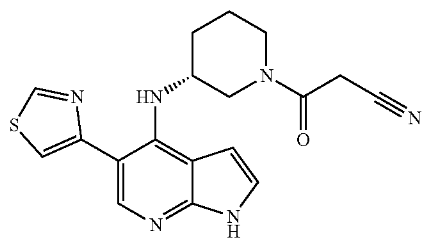 [SMILES: N#CCC(=O)N1CCC[C@@H](Nc2c(-c3cscn3)cnc3[nH]ccc23)C1] | (R)-3-oxo-3-(3-((5-(thiazol-4-yl)-1H-pyrrolo[2,3-b]pyridin-4-yl)amino)piperidin-1-yl)propanenitrile |
| 2 | 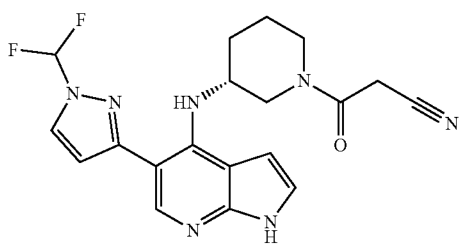 [SMILES: N#CCC(=O)N1CCC[C@@H](Nc2c(-c3ccn(C(F)F)n3)cnc3[nH]ccc23)C1] | (R)-3-(3-((5-(1-(difluoromethyl)-1H-pyrazol-3-yl)-1H-pyrrolo[2,3-b]pyridin-4-yl)amino)piperidin-1-yl)-3-oxopropanenitrile |
| 3 | 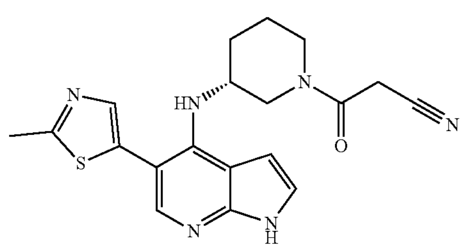 [SMILES: Cc1ncc(-c2cnc3[nH]ccc3c2N[C@@H]2CCCN(C(=O)CC#N)C2)s1] | (R)-3-(3-((5-(2-methylthiazol-5-yl)-1H-pyrrolo[2,3-b]pyridin-4-yl)amino)piperidin-1-yl)-3-oxopropanenitrile |
| 4 | 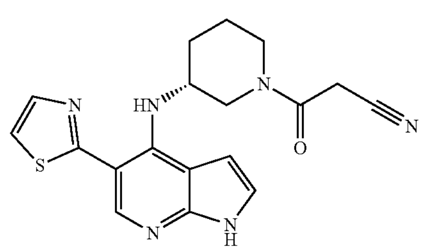 | (R)-3-oxo-3-(3-((5-(thiazol-2-yl)-1H-pyrrolo[2,3-b]pyridin-4-yl)amino)piperidin-1-yl)propanenitrile |
| 5 | 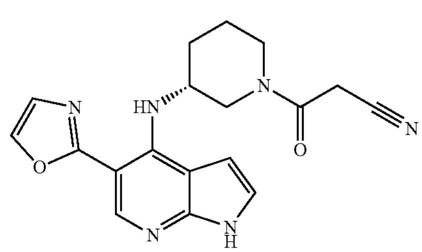 | (R)-3-(3-((5-(oxazol-2-yl)-1H-pyrrolo[2,3-b]pyridin-4-yl)amino)piperidin-1-yl)-3-oxopropanenitrile |

-continued

| Example # | Structure | Name |
|---|---|---|
| 6 | 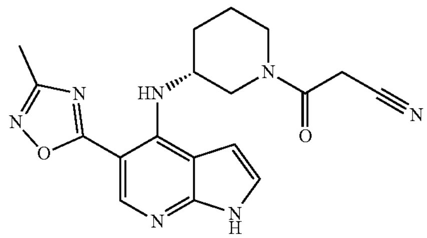 [SMILES: Cc1noc(-c2cnc3[nH]ccc3c2N[C@@H]2CCCN(C(=O)CC#N)C2)n1] | (R)-3-(3-((5-(3-methyl-1,2,4-oxadiazol-5-yl)-1H-pyrrolo[2,3-b]pyridin-4-yl)amino)piperidin-1-yl)-3-oxopropanenitrile |
| 7 | 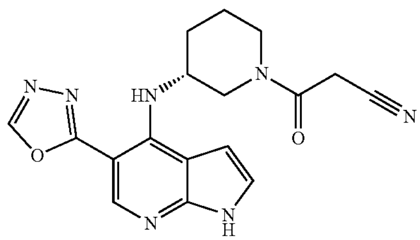 | (R)-3-(3-((5-(1,3,4-oxadiazol-2-yl)-1H-pyrrolo[2,3-b]pyridin-4-yl)amino)piperidin-1-yl)-3-oxopropanenitrile |
| 8 | 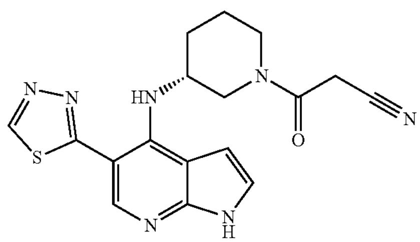 | rac-(R)-3-(3-((5-(1,3,4-thiadiazol-2-yl)-1H-pyrrolo[2,3-b]pyridin-4-yl)amino)piperidin-1-yl)-3-oxopropanenitrile |
| 9 | 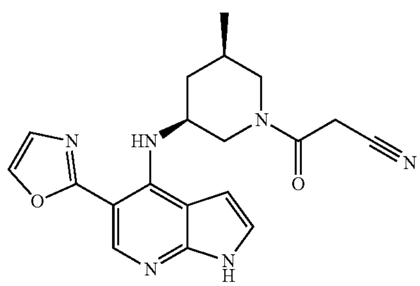 [SMILES: C[C@@H]1C[C@H](Nc2c(-c3ncco3)cnc3[nH]ccc23)CN(C(=O)CC#N)C1] | 3-((3R,5S)-3-methyl-5-((5-(oxazol-2-yl)-1H-pyrrolo[2,3-b]pyridin-4-yl)amino)piperidin-1-yl)-3-oxopropanenitrile |
| 10 | 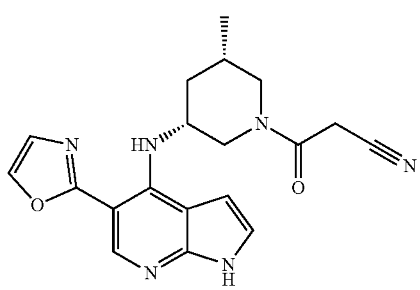 | 3-((3S,5R)-3-methyl-5-((5-(oxazol-2-yl)-1H-pyrrolo[2,3-b]pyridin-4-yl)amino)piperidin-1-yl)-3-oxopropanenitrile |
| 11 | 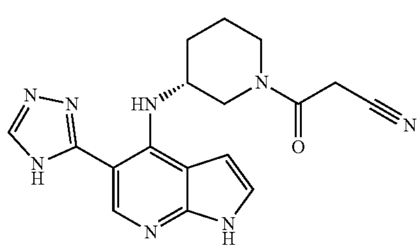 | (R)-3-(3-((5-(4H-1,2,4-triazol-3-yl)-1H-pyrrolo[2,3-b]pyridin-4-yl)amino)piperidin-1-yl)-3-oxopropanenitrile |

| Example # | Structure | Name |
|---|---|---|
| 14 | 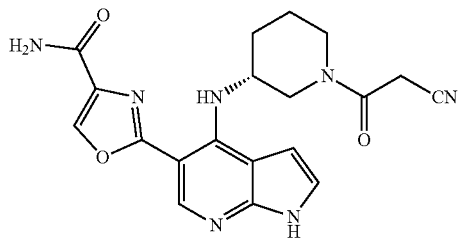 [SMILES: N#CCC(=O)N1CCC[C@@H](Nc2c(-c3nc(C(N)=O)co3)cnc3[nH]ccc23)C1] | (R)-2-(4-((1-(2-cyanoacetyl)piperidin-3-yl)amino)-1H-pyrrolo[2,3-b]pyridin-5-yl)oxazole-4-carboxamide |
| 15 | 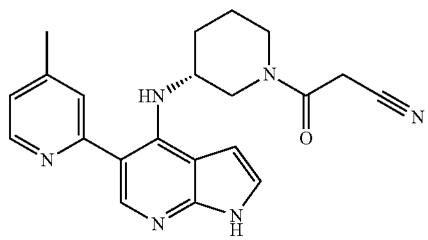 | (R)-3-(3-((5-(4-methylpyridin-2-yl)-1H-pyrrolo[2,3-b]pyridin-4-yl)amino)piperidin-1-yl)-3-oxopropanenitrile |
| 16 | 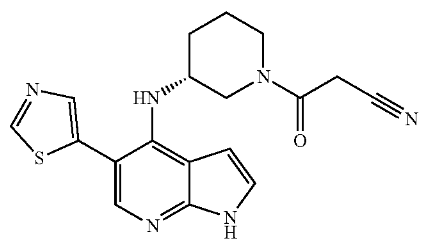 | (R)-3-oxo-3-(3-((5-(thiazol-5-yl)-1H-pyrrolo[2,3-b]pyridin-4-yl)amino)piperidin-1-yl)propanenitrile |
| 17 | 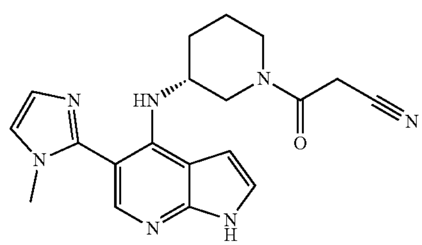 [SMILES: Cn1ccnc1-c1cnc2[nH]ccc2c1N[C@@H]1CCCN(C(=O)CC#N)C1] | (R)-3-(3-((5-(1-methyl-1H-imidazol-2-yl)-1H-pyrrolo[2,3-b]pyridin-4-yl)amino)piperidin-1-yl)-3-oxopropanenitrile |
| 18 | 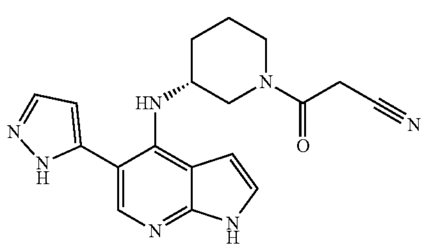 [SMILES: N#CCC(=O)N1CCC[C@@H](Nc2c(-c3ccn[nH]3)cnc3[nH]ccc23)C1] | (R)-3-(3-((5-(1H-pyrazol-5-yl)-1H-pyrrolo[2,3-b]pyridin-4-yl)amino)piperidin-1-yl)-3-oxopropanenitrile |
| 19 | 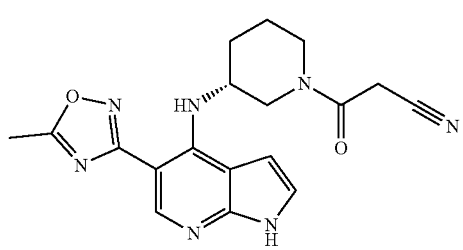 [SMILES: Cc1nc(-c2cnc3[nH]ccc3c2N[C@@H]2CCCN(C(=O)CC#N)C2)no1] | (R)-3-(3-((5-(5-methyl-1,2,4-oxadiazol-3-yl)-1H-pyrrolo[2,3-b]pyridin-4-yl)amino)piperidin-1-yl)-3-oxopropanenitrile |

-continued

| Example # | Structure | Name |
|---|---|---|
| 20 | 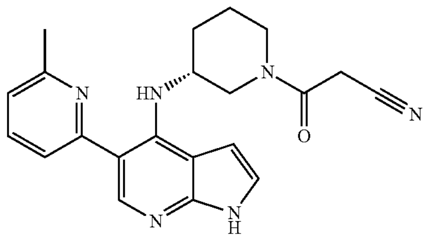 [SMILES: Cc1cccc(-c2cnc3[nH]ccc3c2N[C@@H]2CCCN(C(=O)CC#N)C2)n1] | (R)-3-(3-((5-(6-methylpyridin-2-yl)-1H-pyrrolo[2,3-b]pyridin-4-yl)amino)piperidin-1-yl)-3-oxopropanenitrile |
| 21 | 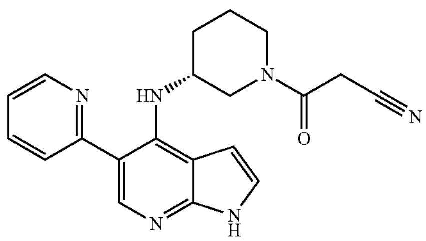 [SMILES: N#CCC(=O)N1CCC[C@@H](Nc2c(-c3ccccn3)cnc3[nH]ccc23)C1] | (R)-3-oxo-3-(3-((5-(pyridin-2-yl)-1H-pyrrolo[2,3-b]pyridin-4-yl)amino)piperidin-1-yl)propanenitrile |
| 22 | 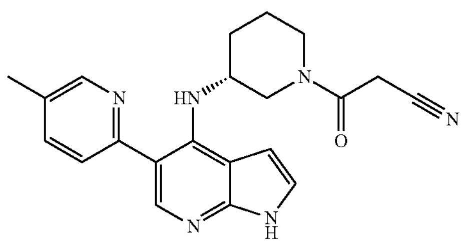 [SMILES: Cc1ccc(-c2cnc3[nH]ccc3c2N[C@@H]2CCCN(C(=O)CC#N)C2)nc1] | (R)-3-(3-((5-(5-methylpyridin-2-yl)-1H-pyrrolo[2,3-b]pyridin-4-yl)amino)piperidin-1-yl)-3-oxopropanenitrile |
| 23 | 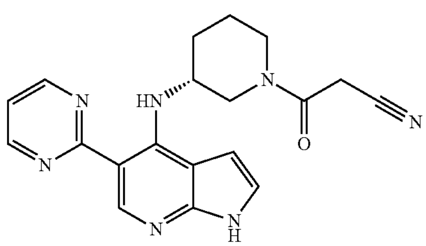 | (R)-3-oxo-3-(3-((5-(pyrimidin-2-yl)-1H-pyrrolo[2,3-b]pyridin-4-yl)amino)piperidin-1-yl)propanenitrile |
| 24 | 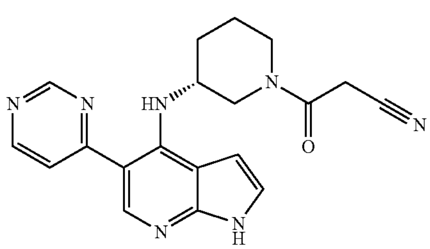 [SMILES: N#CCC(=O)N1CCC[C@@H](Nc2c(-c3ccncn3)cnc3[nH]ccc23)C1] | (R)-3-oxo-3-(3-((5-(pyrimidin-4-yl)-1H-pyrrolo[2,3-b]pyridin-4-yl)amino)piperidin-1-yl)propanenitrile |
| 25 | 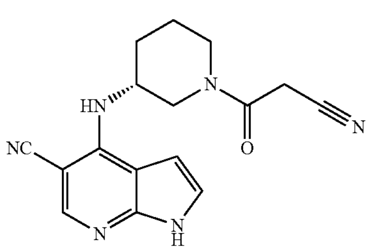 [SMILES: N#CCC(=O)N1CCC[C@@H](Nc2c(C#N)cnc3[nH]ccc23)C1] | (R)-4-((1-(2-cyanoacetyl)piperidin-3-yl)amino)-1H-pyrrolo[2,3-b]pyridine-5-carbonitrile |

| Example # | Structure | Name |
|---|---|---|
| 26 | 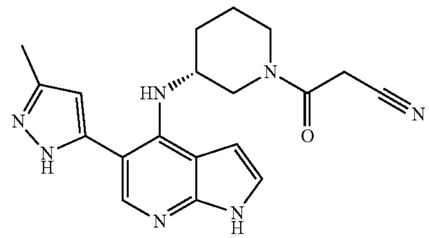 [SMILES: Cc1cc(-c2cnc3[nH]ccc3c2N[C@@H]2CCCN(C(=O)CC#N)C2)[nH]n1] | (R)-3-(3-((5-(3-methyl-1H-pyrazol-5-yl)-1H-pyrrolo[2,3-b]pyridin-4-yl)amino)piperidin-1-yl)-3-oxopropanenitrile |
| 27 | 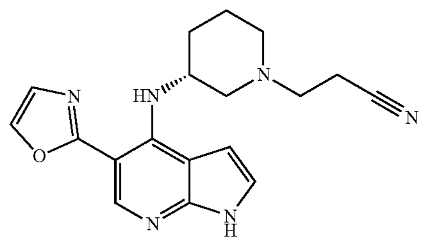 [SMILES: N#CCCN1CCC[C@@H](Nc2c(-c3ncco3)cnc3[nH]ccc23)C1] | (R)-3-(3-((5-(oxazol-2-yl)-1H-pyrrolo[2,3-b]pyridin-4-yl)amino)piperidin-1-yl)propanenitrile |
| 28 | 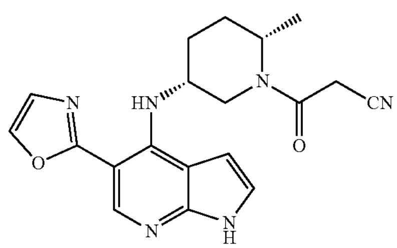 [SMILES: C[C@H]1CC[C@@H](Nc2c(-c3ncco3)cnc3[nH]ccc23)CN1C(=O)CC#N] | 3-((2S,5R)-2-methyl-5-((5-(oxazol-2-yl)-1H-pyrrolo[2,3-b]pyridin-4-yl)amino)piperidin-1-yl)-3-oxopropanenitrile |
| 30 | 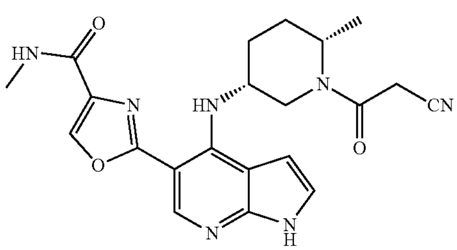 [SMILES: CNC(=O)c1coc(-c2cnc3[nH]ccc3c2N[C@@H]2CC[C@H](C)N(C(=O)CC#N)C2)n1] | 2-(4-(((3R,6S)-1-(2-cyanoacetyl)-6-methylpyridin-3-yl)amino)-1H-pyrrolo[2,3-b]pyridin-5-yl)-N-methyloxazole-4-carboxamide |
| 31 | 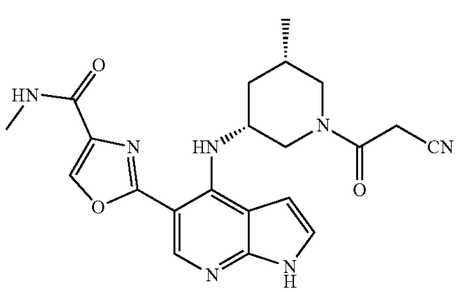 [SMILES: CNC(=O)c1coc(-c2cnc3[nH]ccc3c2N[C@@H]2C[C@H](C)CN(C(=O)CC#N)C2)n1] | 2-(4-(((3R,5S)-1-(2-cyanoacetyl)-5-methylpiperidin-3-yl)amino)-1H-pyrrolo[2,3-b]pyridin-5-yl)-N-methyloxazole-4-carboxamide |
| 32 | 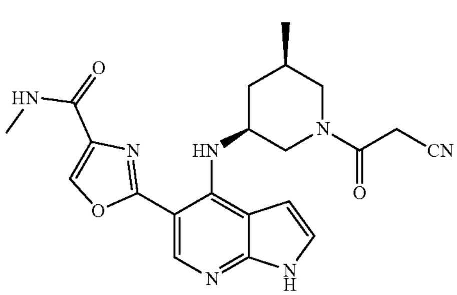 [SMILES: CNC(=O)c1coc(-c2cnc3[nH]ccc3c2N[C@H]2C[C@@H](C)CN(C(=O)CC#N)C2)n1] | 2-(4-(((3S,5R)-1-(2-cyanoacetyl)-5-methylpiperidin-3-yl)amino)-1H-pyrrolo[2,3-b]pyridin-5-yl)-N-methyloxazole-4-carboxamide |

-continued

| Example # | Structure | Name |
|---|---|---|
| 33 | 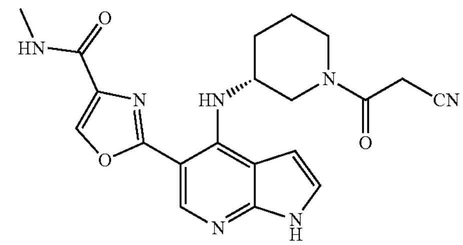 [SMILES: CNC(=O)c1coc(-c2cnc3[nH]ccc3c2N[C@@H]2CCCN(C(=O)CC#N)C2)n1] | (R)-2-(4-((1-(2-cyanoacetyl)piperidin-3-yl)amino)-1H-pyrrolo[2,3-b]pyridin-5-yl)-N-methyloxazole-4-carboxamide |
| 34 | 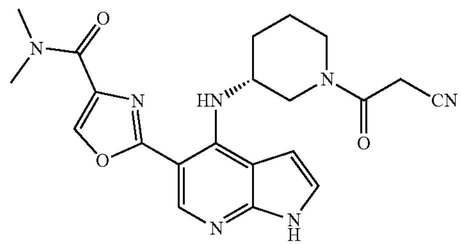 [SMILES: CN(C)C(=O)c1coc(-c2cnc3[nH]ccc3c2N[C@@H]2CCCN(C(=O)CC#N)C2)n1] | (R)-2-(4-((1-(2-cyanoacetyl)piperidin-3-yl)amino)-1H-pyrrolo[2,3-b]pyridin-5-yl)-N,N-dimethyl-oxazole-4-carboxamide |
| 35 | 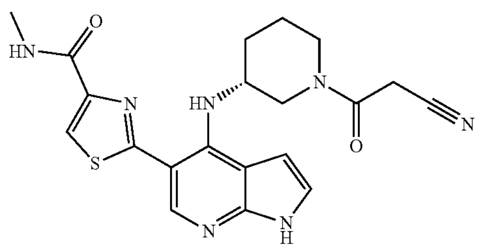 [SMILES: CNC(=O)c1csc(-c2cnc3[nH]ccc3c2N[C@@H]2CCCN(C(=O)CC#N)C2)n1] | (R)-2-(4-((1-(2-cyanoacetyl)piperidin-3-yl)amino)-1H-pyrrolo[2,3-b]pyridin-5-yl)-N-methylthiazole-4-carboxamide |
| 36 | 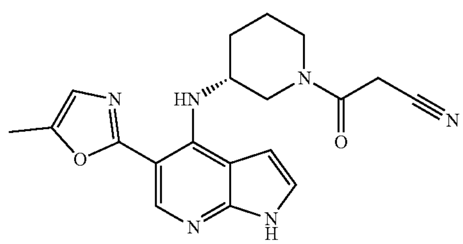 [SMILES: Cc1cnc(-c2cnc3[nH]ccc3c2N[C@@H]2CCCN(C(=O)CC#N)C2)o1] | (R)-3-(3-((5-(5-methyloxazol-2-yl)-1H-pyrrolo[2,3-b]pyridin-4-yl)amino)piperidin-1-yl)-3-oxopropanenitrile |
| 37 | 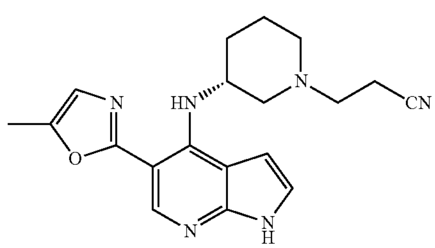 [SMILES: Cc1cnc(-c2cnc3[nH]ccc3c2N[C@@H]2CCCN(CCC#N)C2)o1] | (R)-3-(3-((5-(5-methyloxazol-2-yl)-1H-pyrrolo[2,3-b]pyridin-4-yl)amino)piperidin-1-yl)propanenitrile |
| 38 | 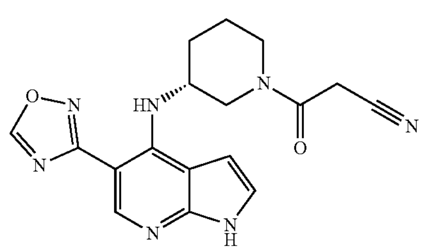 [SMILES: N#CCC(=O)N1CCC[C@@H](Nc2c(-c3ncon3)cnc3[nH]ccc23)C1] | (R)-3-(3-((5-(1,2,4-oxadiazol-3-yl)-1H-pyrrolo[2,3-b]pyridin-4-yl)amino)piperidin-1-yl)-3-oxopropanenitrile |

-continued

| Example # | Structure | Name |
|---|---|---|
| 39 | 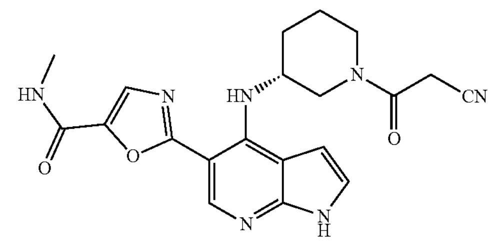 [SMILES: CNC(=O)c1cnc(-c2cnc3[nH]ccc3c2N[C@@H]2CCCN(C(=O)CC#N)C2)o1] | (R)-2-(4-((1-(2-cyanoacetyl)piperidin-3-yl)amino)-1H-pyrrolo[2,3-b]pyridin-5-yl)-N-methyloxazole-5-carboxamide |
| 40 | 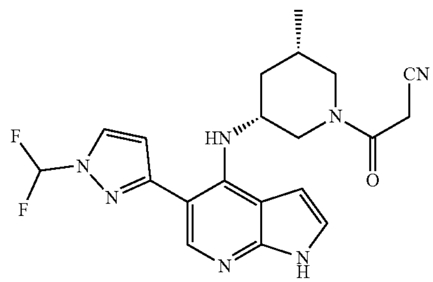 [SMILES: C[C@H]1C[C@@H](Nc2c(-c3ccn(C(F)F)n3)cnc3[nH]ccc23)CN(C(=O)CC#N)C1] | 3-((3R,5S)-3-((5-(1-(difluoromethyl)-1H-pyrazol-3-yl)-1H-pyrrolo[2,3-b]pyridin-4-yl)amino)-5-methylpiperidin-1-yl)-3-oxopropanenitrile |
| 41 | 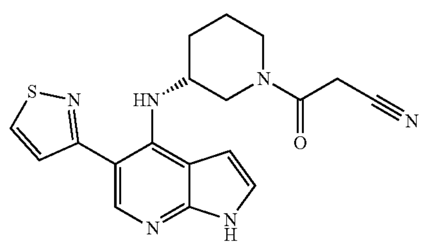 | (R)-3-(3-((5-(isothiazol-3-yl)-1H-pyrrolo[2,3-b]pyridin-4-yl)amino)piperidin-1-yl)-3-oxopropanenitrile |
| 42 | 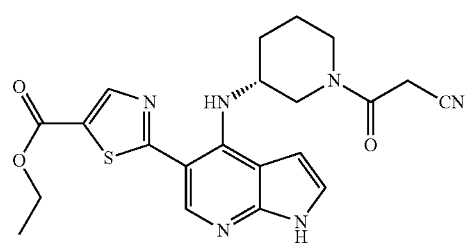 [SMILES: CCOC(=O)c1cnc(-c2cnc3[nH]ccc3c2N[C@@H]2CCCN(C(=O)CC#N)C2)s1] | (R)-2-(4-((1-(2-cyanoacetyl)piperidin-3-yl)amino)-1H-pyrrolo[2,3-b]pyridin-5-yl)thiazole-5-carboxylate |
| 43 | 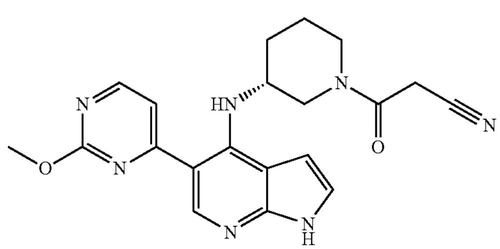 [SMILES: COc1nccc(-c2cnc3[nH]ccc3c2N[C@@H]2CCCN(C(=O)CC#N)C2)n1] | (R)-3-(3-((5-(2-methoxypyrimidin-4-yl)-1H-pyrrolo[2,3-b]pyridin-4-yl)amino)piperidin-1-yl)-3-oxopropanenitrile |
| 44 | 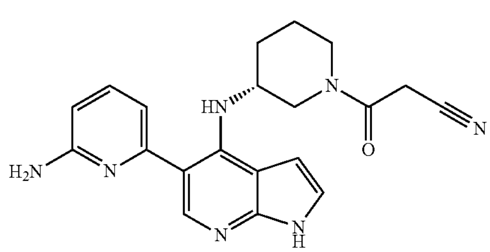 [SMILES: N#CCC(=O)N1CCC[C@@H](Nc2c(-c3cccc(N)n3)cnc3[nH]ccc23)C1] | (R)-3-(3-((5-(6-aminopyridin-2-yl)-1H-pyrrolo[2,3-b]pyridin-4-yl)amino)piperidin-1-yl)-3-oxopropanenitrile |

| Example # | Structure | Name |
|---|---|---|
| 45 | 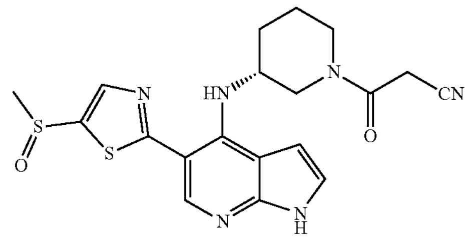 [SMILES: CS(=O)c1cnc(-c2cnc3[nH]ccc3c2N[C@@H]2CCCN(C(=O)CC#N)C2)s1] | 3-((3R)-3-((5-(5-(methylsulfinyl)thiazol-2-yl)-1H-pyrrolo[2,3-b]pyridin-4-yl)amino)piperidin-1-yl)-3-oxopropanenitrile |
| 46 | 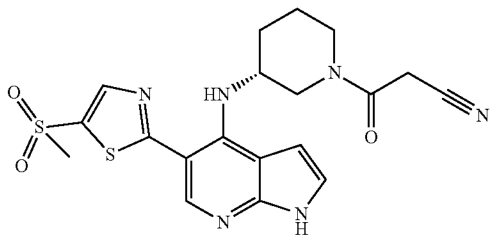 [SMILES: CS(=O)(=O)c1cnc(-c2cnc3[nH]ccc3c2N[C@@H]2CCCN(C(=O)CC#N)C2)s1] | (R)-3-(3-((5-(5-(methylsulfonyl)thiazol-2-yl)-1H-pyrrolo[2,3-b]pyridin-4-yl)amino)piperidin-1-yl)-3-oxopropanenitrile |
| 47 | 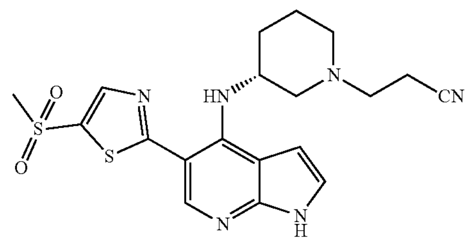 [SMILES: CS(=O)(=O)c1cnc(-c2cnc3[nH]ccc3c2N[C@@H]2CCCN(CCC#N)C2)s1] | (R)-3-(3-((5-(5-(methylsulfonyl)thiazol-2-yl)-1H-pyrrolo[2,3-b]pyridin-4-yl)amino)piperidin-1-yl)propanenitrile |
| 48 | 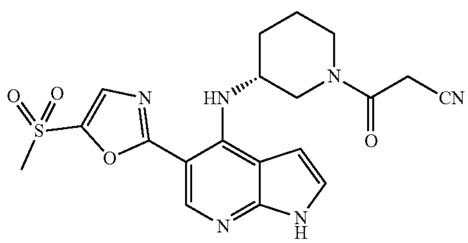 [SMILES: CS(=O)(=O)c1cnc(-c2cnc3[nH]ccc3c2N[C@@H]2CCCN(C(=O)CC#N)C2)o1] | (R)-3-(3-((5-(5-(methylsulfonyl)oxazol-2-yl)-1H-pyrrolo[2,3-b]pyridin-4-yl)amino)piperidin-1-yl)-3-oxopropanenitrile |
| 49 | 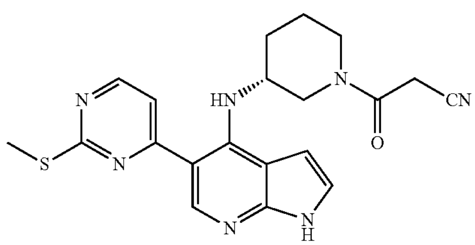 [SMILES: CSc1nccc(-c2cnc3[nH]ccc3c2N[C@@H]2CCCN(C(=O)CC#N)C2)n1] | (R)-3-(3-((5-(2-(methylthio)pyrimidin-4-yl)-1H-pyrrolo[2,3-b]pyridin-4-yl)amino)piperidin-1-yl)-3-oxopropanenitrile |
| 50 | 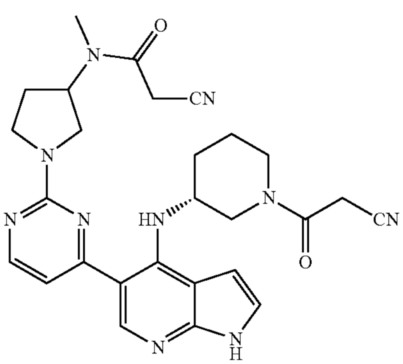 [SMILES: CN(C(=O)CC#N)C1CCN(c2nccc(-c3cnc4[nH]ccc4c3N[C@@H]3CCCN(C(=O)CC#N)C3)n2)C1] | 2-cyano-N-(1-(4-(4-(((R)-1-(2-cyanoacetyl)piperidin-3-yl)amino)-1H-pyrrolo[2,3-b]pyridin-5-yl)pyrimidin-2-yl)pyrrolidin-3-yl)-N-methylacetamide |

-continued

| Example # | Structure | Name |
|---|---|---|
| 51 | 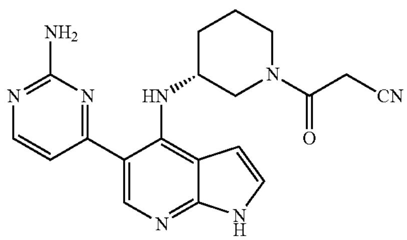 [SMILES: N#CCC(=O)N1CCC[C@@H](Nc2c(-c3ccnc(N)n3)cnc3[nH]ccc23)C1] | (R)-3-(3-((5-(2-aminopyrimidin-4-yl)-1H-pyrrolo[2,3-b]pyridin-4-yl)amino)piperidin-1-yl)-3-oxopropanenitrile |
| 52 | 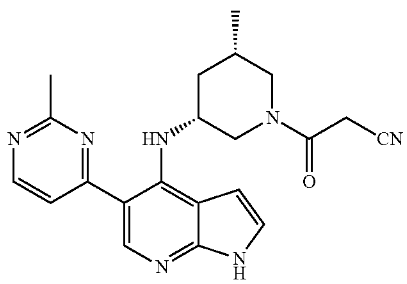 [SMILES: Cc1nccc(-c2cnc3[nH]ccc3c2N[C@@H]2C[C@H](C)CN(C(=O)CC#N)C2)n1] | 3-((3S,5R)-3-methyl-5-((5-(2-methylpyrimidin-4-yl)-1H-pyrrolo[2,3-b]pyridin-4-yl)amino)piperidin-1-yl)-3-oxopropanenitrile |
| 53 | 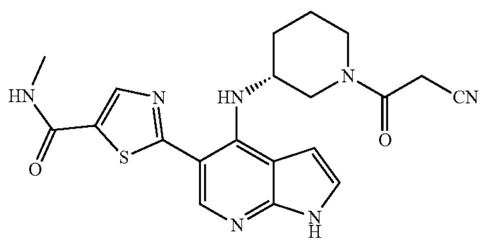 | (R)-2-(4-((1-(2-cyanoacetyl)piperidin-3-yl)amino)-1H-pyrrolo[2,3-b]pyridin-5-yl)-N-methylthiazole-5-carboxamide |
| 54 | 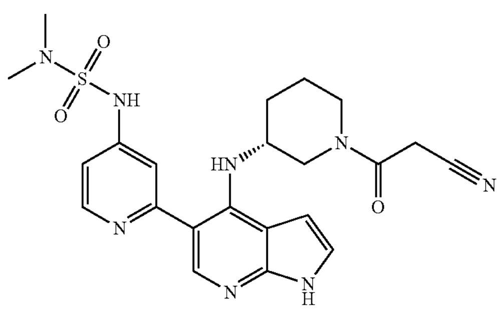 [SMILES: CN(C)S(=O)(=O)Nc1ccnc(-c2cnc3[nH]ccc3c2N[C@@H]2CCCN(C(=O)CC#N)C2)c1] | (R)-N-(2-(4-((1-(2-cyanoacetyl)piperidin-3-yl)amino)-1H-pyrrolo[2,3-b]pyridin-5-yl)pyridin-4-yl)N,N-dimethyl sulfuric diamide |
| 55 | 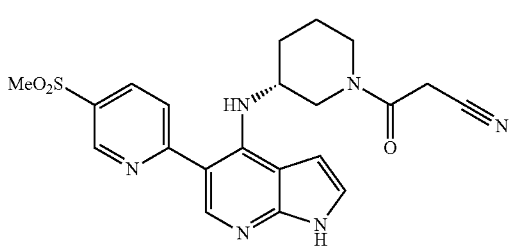 [SMILES: CS(=O)(=O)c1ccc(-c2cnc3[nH]ccc3c2N[C@@H]2CCCN(C(=O)CC#N)C2)nc1] | (R)-3-(3-((5-(5-(methylsulfonyl)pyridin-2-yl)-1H-pyrrolo[2,3-b]pyridin-4-yl)amino)piperidin-1-yl)-3-oxopropanenitrile |

| Example # | Structure | Name |
|---|---|---|
| 56 | 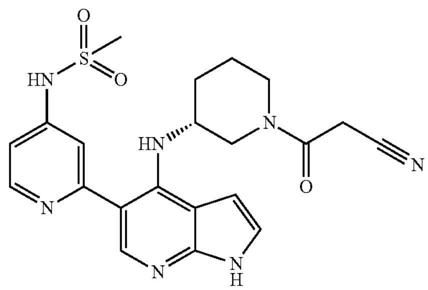 [SMILES: CS(=O)(=O)Nc1ccnc(-c2cnc3[nH]ccc3c2N[C@@H]2CCCN(C(=O)CC#N)C2)c1] | (R)-N-(2-(4-((1-(2-cyanoacetyl)piperidin-3-yl)amino)-1H-pyrrolo[2,3-b]pyridin-5-yl)pyridin-4-yl)methanesulfonamide |
| 57 | 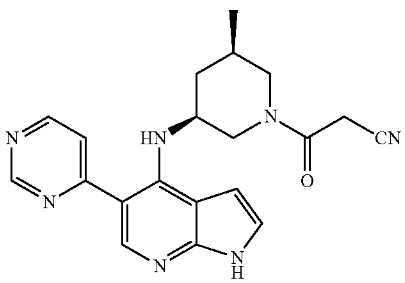 [SMILES: C[C@@H]1C[C@H](Nc2c(-c3ccncn3)cnc3[nH]ccc23)CN(C(=O)CC#N)C1] | 3-((3R,5S)-3-methyl-5-((5-(pyrimidin-4-yl)-1H-pyrrolo[2,3-b]pyridin-4-yl)amino)piperidin-1-yl)-3-oxopropanenitrile |
| 58 | 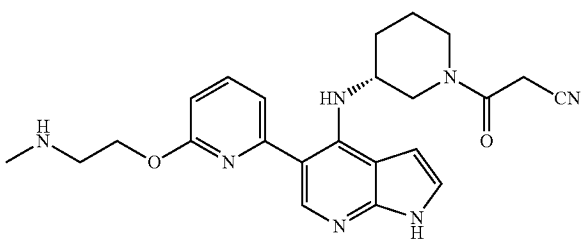 [SMILES: CNCCOc1cccc(-c2cnc3[nH]ccc3c2N[C@@H]2CCCN(C(=O)CC#N)C2)n1] | (R)-3-(3-((5-(1H-pyrazol-5-yl)-1H-pyrrolo[2,3-b]pyridin-4-yl)amino)piperidin-1-yl)-3-oxopropanenitrile |
| 59 | 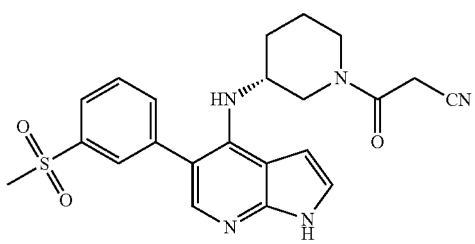 [SMILES: CS(=O)(=O)c1cccc(-c2cnc3[nH]ccc3c2N[C@@H]2CCCN(C(=O)CC#N)C2)c1] | (R)-3-(3-((5-(3-(methylsulfonyl)phenyl)-1H-pyrrolo[2,3-b]pyridin-4-yl)amino)piperidin-1-yl)-3-oxopropanenitrile |
| 60 | 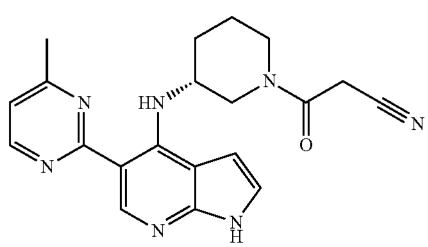 | (R)-3-(3-((5-(4-methylpyridin-2-yl)-1H-pyrrolo[2,3-b]pyridin-4-yl)amino)piperidin-1-yl)-3-oxopropanenitrile |
| 61 | 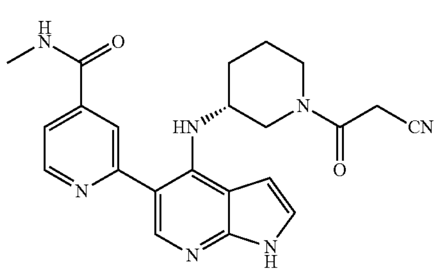 [SMILES: CNC(=O)c1ccnc(-c2cnc3[nH]ccc3c2N[C@@H]2CCCN(C(=O)CC#N)C2)c1] | (R)-2-(4-((1-(2-cyanoacetyl)piperidin-3-yl)amino)-1H-pyrrolo[2,3-b]pyridin-5-yl)-N-methylisonicotinamide |

-continued

| Example # | Structure | Name |
|---|---|---|
| 62 | 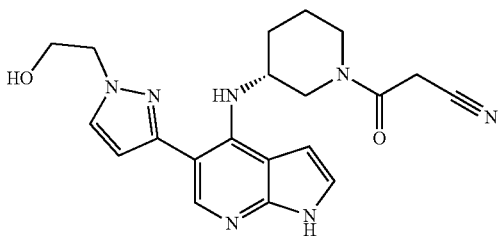 [SMILES: N#CCC(=O)N1CCC[C@@H](Nc2c(-c3ccn(CCO)n3)cnc3[nH]ccc23)C1] | (R)-3-(3-((5-(1-(2-hydroxyethyl)-1H-pyrazol-3-yl)-1H-pyrrolo[2,3-b]pyridin-4-yl)amino)piperidin-1-yl)-3-oxopropanenitrile |
| 63 | 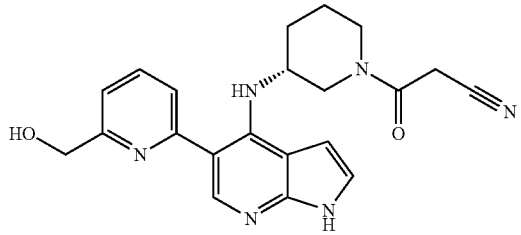 [SMILES: N#CCC(=O)N1CCC[C@@H](Nc2c(-c3cccc(CO)n3)cnc3[nH]ccc23)C1] | (R)-3-(3-((5-(3-(hydroxymethyl)phenyl)-1H-pyrrolo[2,3-b]pyridin-4-yl)amino)piperidin-1-yl)-3-oxopropanenitrile |
| 64 | 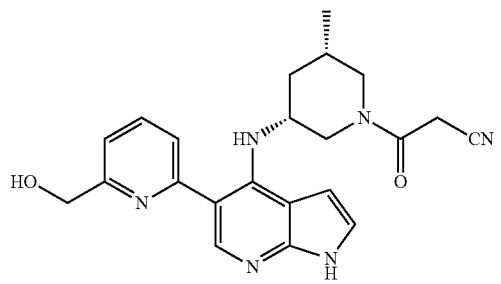 [SMILES: C[C@H]1C[C@@H](Nc2c(-c3cccc(CO)n3)cnc3[nH]ccc23)CN(C(=O)CC#N)C1] | 3-((3R,5S)-3-((5-(6-(hydroxymethyl)pyridin-2-yl)-1H-pyrrolo[2,3-b]pyridin-4-yl)amino)-5-methylpiperidin-1-yl)-3-oxopropanenitrile |
| 65 | 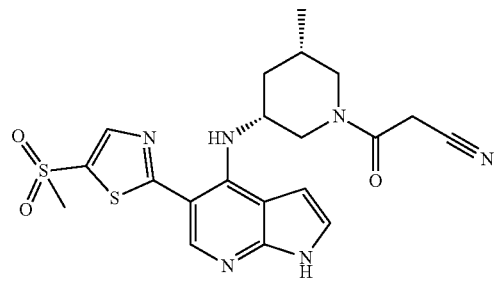 [SMILES: C[C@H]1C[C@@H](Nc2c(-c3ncc(S(C)(=O)=O)s3)cnc3[nH]ccc23)CN(C(=O)CC#N)C1] | 3-((3S,5R)-3-methyl-5-((5-(5-(methylsulfonyl)thiazol-2-yl)-1H-pyrrolo[2,3-b]pyridin-4-yl)amino)piperidin-1-yl)-3-oxopropanenitrile |
| 66 | 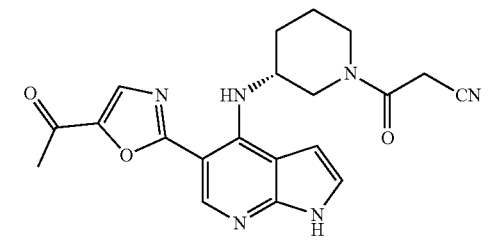 [SMILES: CC(=O)c1cnc(-c2cnc3[nH]ccc3c2N[C@@H]2CCCN(C(=O)CC#N)C2)o1] | (R)-3-(3-((5-(5-acetyloxazol-2-yl)-1H-pyrrolo[2,3-b]pyridin-4-yl)amino)piperidin-1-yl)-3-oxopropanenitrile |

-continued

| Example # | Structure | Name |
|---|---|---|
| 67 | 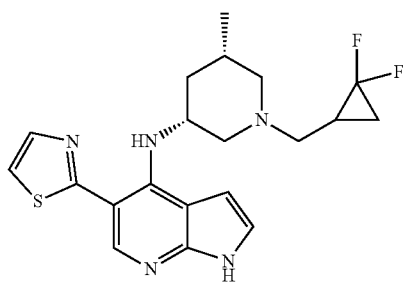 [SMILES: C[C@H]1C[C@@H](Nc2c(-c3nccs3)cnc3[nH]ccc23)CN(CC2CC2(F)F)C1] | N-((3R,5S)-1-((2,2-difluorocyclopropyl)methyl)-5-methylpiperidin-3-yl)-5-(thiazol-2-yl)-1H-pyrrolo[2,3-b]pyridin-4-amine |
| 68 | 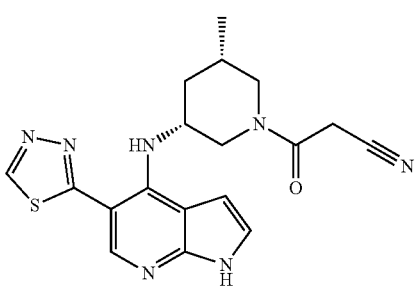 [SMILES: C[C@H]1C[C@@H](Nc2c(-c3nncs3)cnc3[nH]ccc23)CN(C(=O)CC#N)C1] | 3-((3R,5S)-3-((5-(1,3,4-thiadiazol-2-yl)-1H-pyrrolo[2,3-b]pyridin-4-yl)amino)-5-methylpyridin-1-yl)-3-oxopropanenitrile |
| 69 | 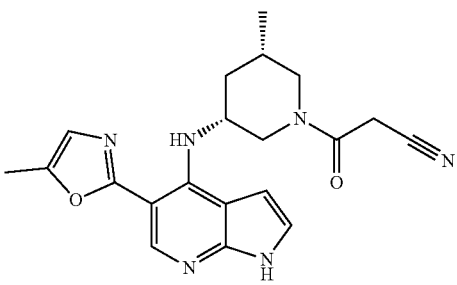 [SMILES: Cc1cnc(-c2cnc3[nH]ccc3c2N[C@@H]2C[C@H](C)CN(C(=O)CC#N)C2)o1] | 3-((3S,5R)-3-methyl-5-((5-(5-methyloxazol-2-yl)-1H-pyrrolo[2,3-b]pyridin-4-yl)amino)piperidin-1-yl)-3-oxopropanenitrile |
| 70 | 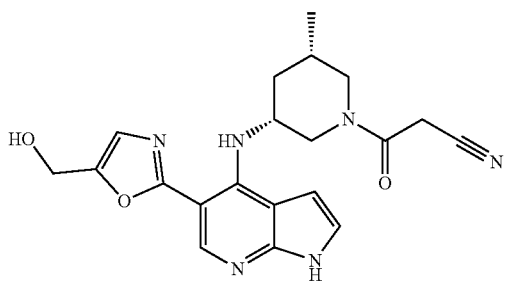 [SMILES: C[C@H]1C[C@@H](Nc2c(-c3ncc(CO)o3)cnc3[nH]ccc23)CN(C(=O)CC#N)C1] | 3-((3R,5S)-3-((5-(5-(hydroxymethyl)oxazol-2-yl)-1H-pyrrolo[2,3-b]pyridin-4-yl)amino)-5-methylpiperidin-1-yl)-3-oxopropanenitrile |
| 71 | 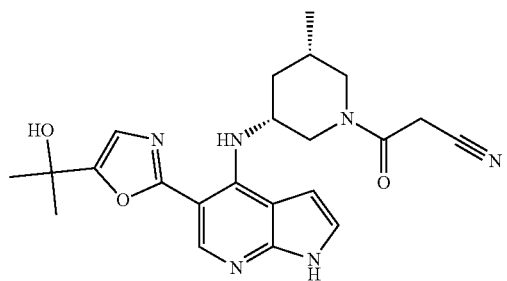 [SMILES: C[C@H]1C[C@@H](Nc2c(-c3ncc(C(C)(C)O)o3)cnc3[nH]ccc23)CN(C(=O)CC#N)C1] | 3-((3R,5S)-3-((5-(5-(2-hydroxypropan-2-yl)oxazol-2-yl)-1H-pyrrolo[2,3-b]pyridin-4-yl)amino)-5-methylpiperidin-1-yl)-3-oxopropanenitrile |

-continued

| Example # | Structure | Name |
|---|---|---|
| 72 | 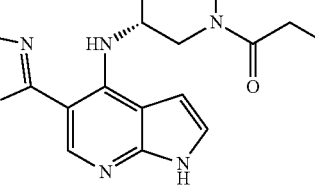 | 3-((3R,5S)-3-((5-(5-(fluoromethyl)oxazol-2-yl)-1H-pyrrolo[2,3-b]pyridin-4-yl)amino)-5-methylpiperidin-1-yl)-3-oxopropanenitrile |
| 73 | 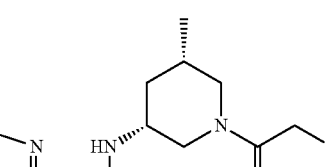 | 3-((3R,5S)-3-((5-(5-acetyloxazol-2-yl)-1H-pyrrolo[2,3-b]pyridin-4-yl)amino)-5-methylpiperidin-1-yl)-3-oxopropanenitrile |
| 74 | 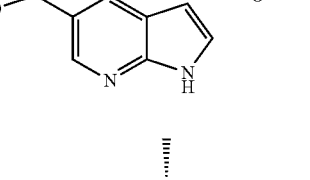 | 3-((3R,5S)-3-((5-(4-acetyloxazol-2-yl)-1H-pyrrolo[2,3-b]pyridin-4-yl)amino)-5-methylpiperidin-1-yl)-3-oxopropanenitrile |
| 75 | 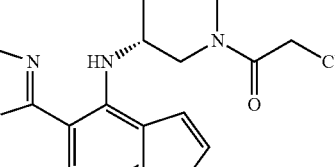 | 3-((3S,5R)-3-methyl-5-((5-(5-(methylsulfonyl)oxazol-2-yl)-1H-pyrrolo[2,3-b]pyridin-4-yl)amino)piperidin-1-yl)-3-oxopropanenitrile |
| 76 | 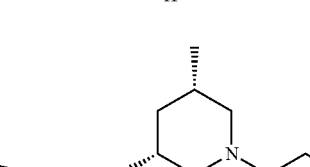 | 3-((3S,5R)-3-methyl-5-((5-(4-methyloxazol-2-yl)-1H-pyrrolo[2,3-b]pyridin-4-yl)amino)piperidin-1-yl)-3-oxopropanenitrile |

| Example # | Structure | Name |
|---|---|---|
| 77 | 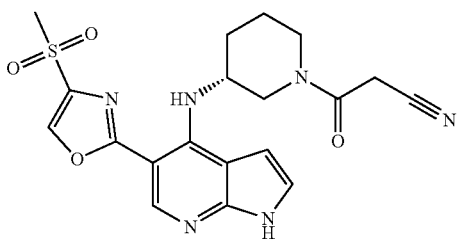 [SMILES: CS(=O)(=O)c1coc(-c2cnc3[nH]ccc3c2N[C@@H]2CCCN(C(=O)CC#N)C2)n1] | (R)-3-(3-((5-(4-(methylsulfonyl)oxazol-2-yl)-1H-pyrrolo[2,3-b]pyridin-4-yl)amino)piperidin-1-yl)-3-oxopropanenitrile |
| 78 | 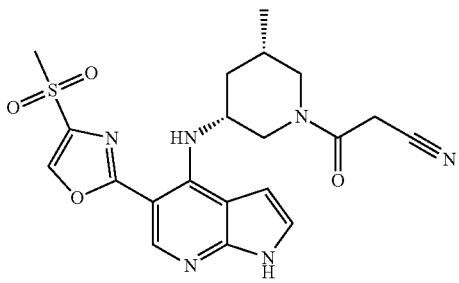 [SMILES: C[C@H]1C[C@@H](Nc2c(-c3nc(S(C)(=O)=O)co3)cnc3[nH]ccc23)CN(C(=O)CC#N)C1] | 3-((3S,5R)-3-methyl-5-((5-(4-(methylsulfonyl)oxazol-2-yl)-1H-pyrrolo[2,3-b]pyridin-4-yl)amino)piperidin-1-yl)-3-oxopropanenitrile |
| 79 | 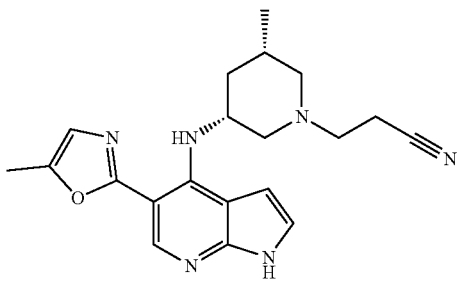 | 3-((3S,5R)-3-methyl-5-((5-(5-methyloxazol-2-yl)-1H-pyrrolo[2,3-b]pyridin-4-yl)amino)piperidin-1-yl)propanenitrile |
| 80 | 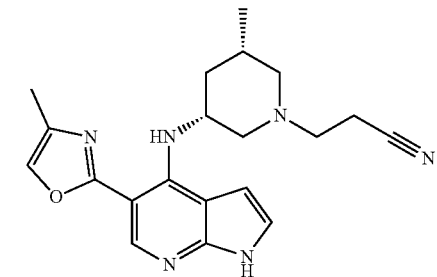 [SMILES: Cc1coc(-c2cnc3[nH]ccc3c2N[C@@H]2C[C@H](C)CN(CCC#N)C2)n1] | 3-((3S,5R)-3-methyl-5-((5-(4-methyloxazol-2-yl)-1H-pyrrolo[2,3-b]pyridin-4-yl)amino)piperidin-1-yl)propanenitrile |
| 81 | 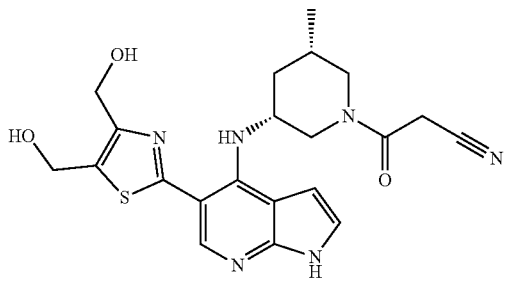 [SMILES: C[C@H]1C[C@@H](Nc2c(-c3nc(CO)c(CO)s3)cnc3[nH]ccc23)CN(C(=O)CC#N)C1] | 3-((3R,5S)-3-((5-(4,5-bis(hydroxymethyl)thiazol-2-yl)-1H-pyrrolo[2,3-b]pyridin-4-yl)amino)-5-methylpiperidin-1-yl)-3-oxopropanenitrile |

-continued

| Example # | Structure | Name |
|---|---|---|
| 82 | 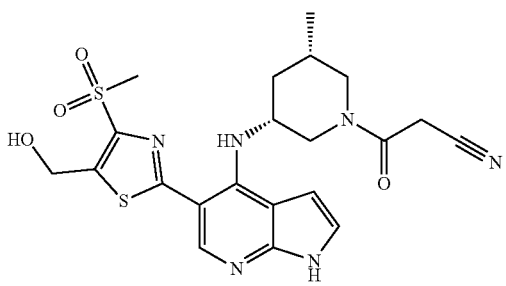 [SMILES: C[C@H]1C[C@@H](Nc2c(-c3nc(S(C)(=O)=O)c(CO)s3)cnc3[nH]ccc23)CN(C(=O)CC#N)C1] | 3-((3R,5S)-3-((5-(5-(hydroxymethyl)-4-(methylsulfonyl)thiazol-2-yl)-1H-pyrrolo[2,3-b]pyridin-4-yl)amino)-5-methylpiperidin-1-yl)-3-oxopropanenitrile |
| 83 | 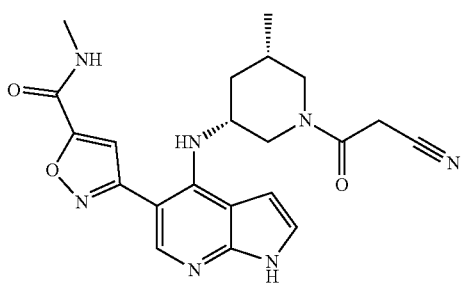 [SMILES: CNC(=O)c1cc(-c2cnc3[nH]ccc3c2N[C@@H]2C[C@H](C)CN(C(=O)CC#N)C2)no1] | 3-(4-(((1R,5R)-3-(2-cyanoacetyl)-5-methylcyclohexyl)amino)-1H-pyrrolo[2,3-b]pyridin-5-yl)-N-methylisoxazole-5-carboxamide |
| 84 | 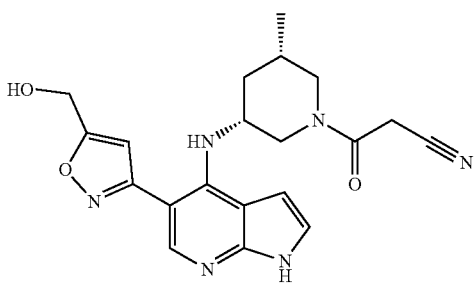 [SMILES: C[C@H]1C[C@@H](Nc2c(-c3cc(CO)on3)cnc3[nH]ccc23)CN(C(=O)CC#N)C1] | 3-((3R,5S)-3-((5-(5-(hydroxymethyl)isoxazol-3-yl)-1H-pyrrolo[2,3-b]pyridin-4-yl)amino)-5-methylpiperidin-1-yl)-3-oxopropanenitrile |
| 85 | 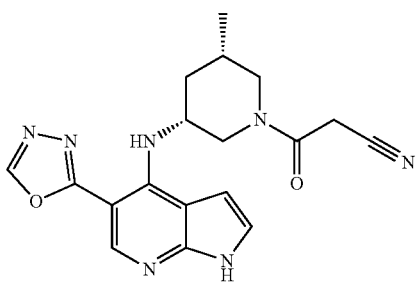 | 3-((3R,5S)-3-((5-(1,3,4-oxadiazol-2-yl)-1H-pyrrolo[2,3-b]pyridin-4-yl)amino)-5-methylpiperidin-1-yl)-3-oxopropanenitrile |
| 86 | 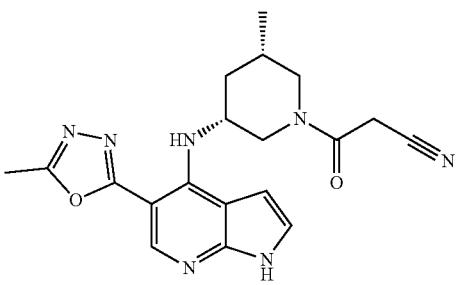 | 3-((3S,5R)-3-methyl-5-((5-(5-methyl-1,3,4-oxadiazol-2-yl)-1H-pyrrolo[2,3-b]pyridin-4-yl)amino)piperidin-1-yl)-3-oxopropanenitrile |

| Example # | Structure | Name |
|---|---|---|
| 87 | 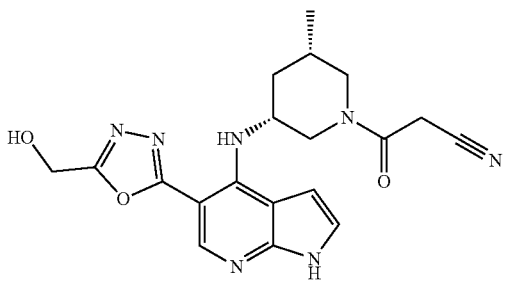 [SMILES: C[C@H]1C[C@@H](Nc2c(-c3nnc(CO)o3)cnc3[nH]ccc23)CN(C(=O)CC#N)C1] | 3-((3R,5S)-3-((5-(5-(hydroxymethyl)-1,3,4-oxadiazol-2-yl)-1H-pyrrolo[2,3-b]pyridin-4-yl)amino)-5-methylpiperidin-1-yl)-3-oxopropanenitrile |
| 88 | 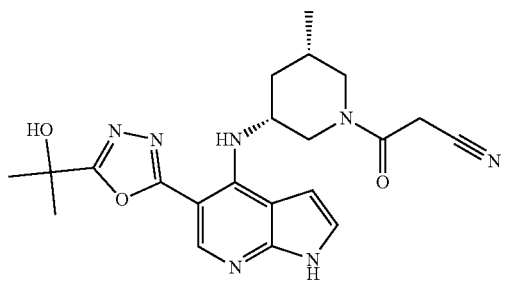 | 3-((3R,5S)-3-((5-(5-(2-hydroxypropan-2-yl)-1,3,4-oxadiazol-2-yl)-1H-pyrrolo[2,3-b]pyridin-4-yl)amino)-5-methylpiperidin-1-yl)-3-oxopropanenitrile |
| 89 | 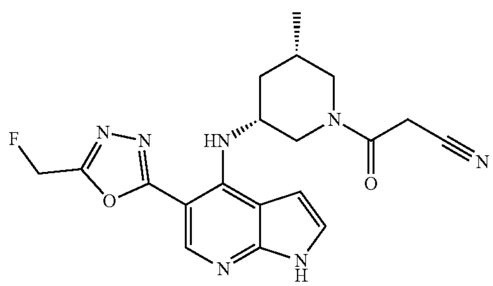 [SMILES: C[C@H]1C[C@@H](Nc2c(-c3nnc(CF)o3)cnc3[nH]ccc23)CN(C(=O)CC#N)C1] | 3-((3R,5S)-3-((5-(5-(fluoromethyl)-1,3,4-oxadiazol-2-yl)-1H-pyrrolo[2,3-b]pyridin-4-yl)amino)-5-methylpiperidin-1-yl)-3-oxopropanenitrile |
| 90 | 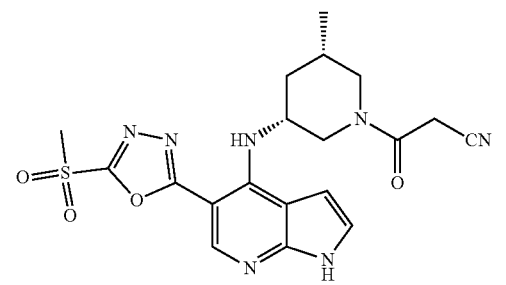 [SMILES: C[C@H]1C[C@@H](Nc2c(-c3nnc(S(C)(=O)=O)o3)cnc3[nH]ccc23)CN(C(=O)CC#N)C1] | 3-((3S,5R)-3-methyl-5-((5-(5-(methylsulfonyl)-1,3,4-oxadiazol-2-yl)-1H-pyrrolo[2,3-b]pyridin-4-yl)amino)piperidin-1-yl)-3-oxopropanenitrile |
| 91 | 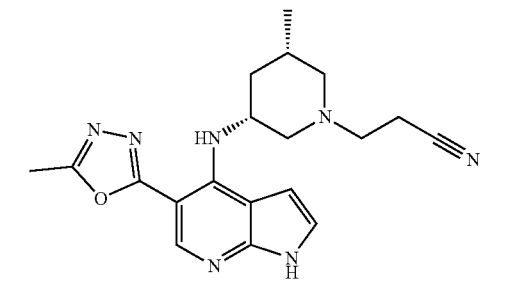 [SMILES: Cc1nnc(-c2cnc3[nH]ccc3c2N[C@@H]2C[C@H](C)CN(CCC#N)C2)o1] | 3-((3S,5R)-3-methyl-5-((5-(5-methyl-1,3,4-oxadiazol-2-yl)-1H-pyrrolo[2,3-b]pyridin-4-yl)amino)piperidin-1-yl)propanenitrile |

-continued

| Example # | Structure | Name |
|---|---|---|
| 92 | 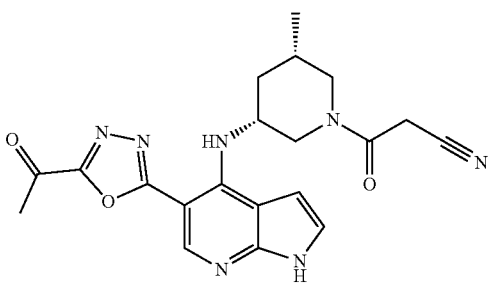 [SMILES: CC(=O)c1nnc(-c2cnc3[nH]ccc3c2N[C@@H]2C[C@H](C)CN(C(=O)CC#N)C2)o1] | 3-((3R,5S)-3-((5-(5-acetyl-1,3,4-oxadiazol-2-yl)-1H-pyrrolo[2,3-b]pyridin-4-yl)amino)-5-methylpiperidin-1-yl)-3-oxopropanenitrile |
| 93 | 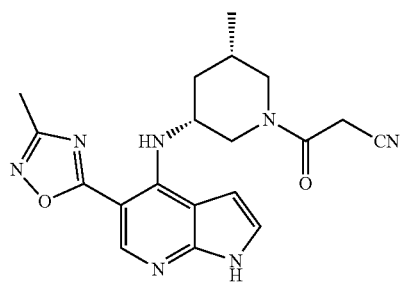 | 3-((3S,5R)-3-methyl-5-((5-(3-methyl-1,2,4-oxadiazol-5-yl)-1H-pyrrolo[2,3-b]pyridin-4-yl)amino)piperidin-1-yl)-3-oxopropanenitrile |
| 94 | 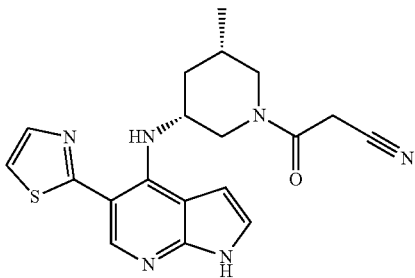 | 3-((3S,5R)-3-methyl-5-((5-(thiazol-2-yl)-1H-pyrrolo[2,3-b]pyridin-4-yl)amino)piperidin-1-yl)-3-oxopropanenitrile |
| 95 | 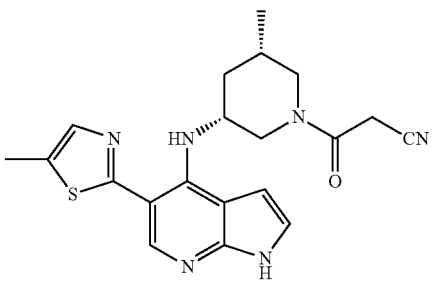 [SMILES: Cc1cnc(-c2cnc3[nH]ccc3c2N[C@@H]2C[C@H](C)CN(C(=O)CC#N)C2)s1] | 3-((3S,5R)-3-methyl-5-((5-(5-methylthiazol-2-yl)-1H-pyrrolo[2,3-b]pyridin-4-yl)amino)piperidin-1-yl)-3-oxopropanenitrile |
| 96 | 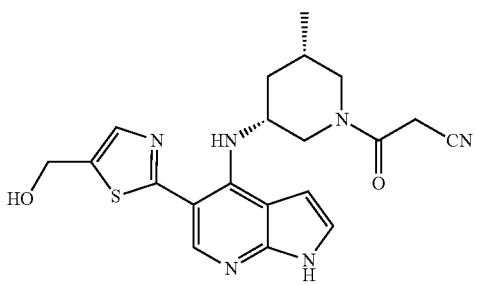 [SMILES: C[C@H]1C[C@@H](Nc2c(-c3ncc(CO)s3)cnc3[nH]ccc23)CN(C(=O)CC#N)C1] | 3-((3R,5S)-3-((5-(5-(hydroxymethyl)thiazol-2-yl)-1H-pyrrolo[2,3-b]pyridin-4-yl)amino)-5-methylpiperidin-1-yl)-3-oxopropanenitrile |

| Example # | Structure | Name |
|---|---|---|
| 97 | 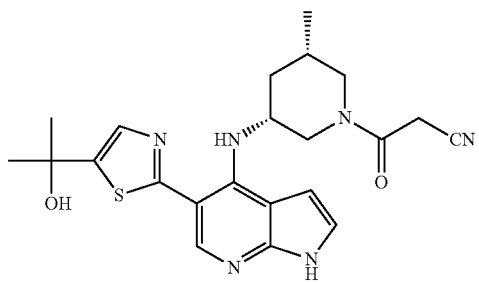 [SMILES: C[C@H]1C[C@@H](Nc2c(-c3ncc(C(C)(C)O)s3)cnc3[nH]ccc23)CN(C(=O)CC#N)C1] | 3-((3R,5S)-3-((5-(5-(2-hydroxypropan-2-yl)thiazol-2-yl)-1H-pyrrolo[2,3-b]pyridin-4-yl)amino)-5-methylpiperidin-1-yl)-3-oxopropanenitrile |
| 98 | 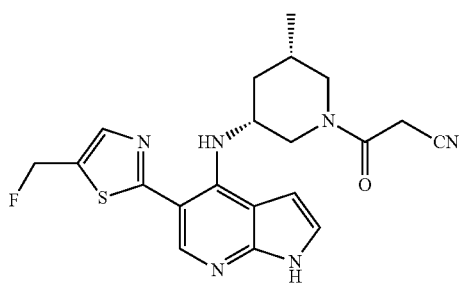 [SMILES: C[C@H]1C[C@@H](Nc2c(-c3ncc(CF)s3)cnc3[nH]ccc23)CN(C(=O)CC#N)C1] | 3-((3R,5S)-3-((5-(5-(fluoromethyl)thiazol-2-yl)-1H-pyrrolo[2,3-b]pyridin-4-yl)amino)-5-methylpiperidin-1-yl)-3-oxopropanenitrile |
| 99 | 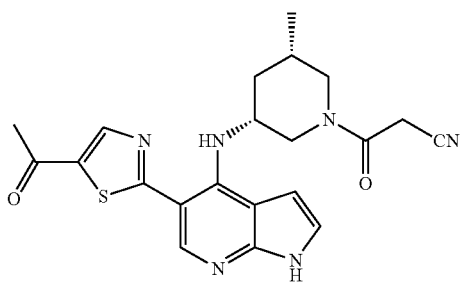 | 3-((3R,5S)-3-((5-(5-acetylthiazol-2-yl)-1H-pyrrolo[2,3-b]pyridin-4-yl)amino)-5-methylpiperidin-1-yl)-3-oxopropanenitrile |
| 100 | 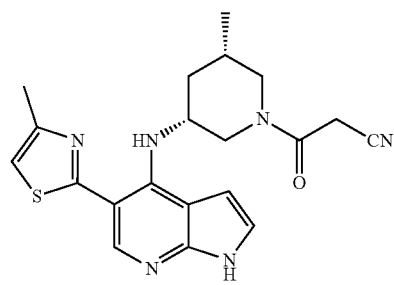 [SMILES: Cc1csc(-c2cnc3[nH]ccc3c2N[C@@H]2C[C@H](C)CN(C(=O)CC#N)C2)n1] | 3-((3S,5R)-3-methyl-5-((5-(4-methylthiazol-2-yl)-1H-pyrrolo[2,3-b]pyridin-4-yl)amino)piperidin-1-yl)-3-oxopropanenitrile |
| 101 | 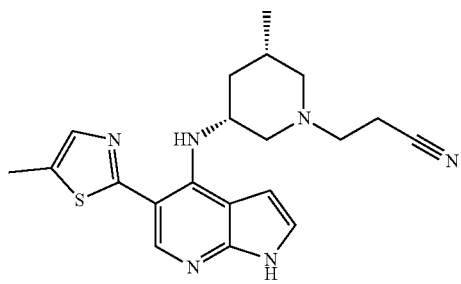 | 3-((3S,5R)-3-methyl-5-((5-(5-methylthiazol-2-yl)-1H-pyrrolo[2,3-b]pyridin-4-yl)amino)piperidin-1-yl)propanenitrile |

-continued

| Example # | Structure | Name |
|---|---|---|
| 102 | 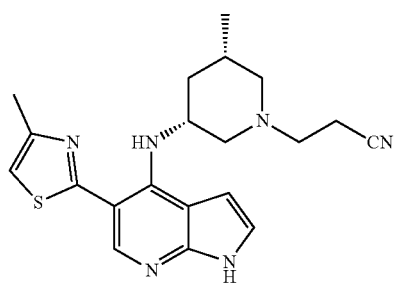 [SMILES: Cc1csc(-c2cnc3[nH]ccc3c2N[C@@H]2C[C@H](C)CN(CCC#N)C2)n1] | 3-((3S,5R)-3-methyl-5-((5-(4-methylthiazol-2-yl)-1H-pyrrolo[2,3-b]pyridin-4-yl)amino)piperidin-1-yl)propanenitrile |
| 103 | 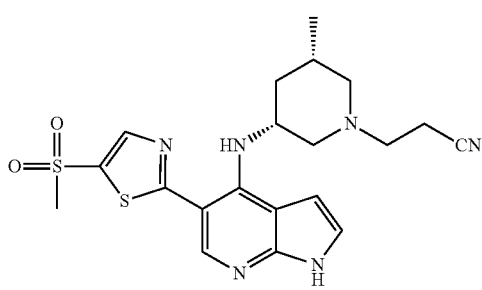 [SMILES: C[C@H]1C[C@@H](Nc2c(-c3ncc(S(C)(=O)=O)s3)cnc3[nH]ccc23)CN(CCC#N)C1] | 3-((3S,5R)-3-methyl-5-((5-(5-(methylsulfonyl)thiazol-2-yl)-1H-pyrrolo[2,3-b]pyridin-4-yl)amino)piperidin-1-yl)propanenitrile |
| 104 | 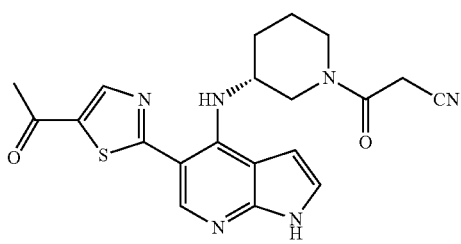 [SMILES: CC(=O)c1cnc(-c2cnc3[nH]ccc3c2N[C@@H]2CCCN(C(=O)CC#N)C2)s1] | (R)-3-(3-((5-(5-acetylthiazol-2-yl)-1H-pyrrolo[2,3-b]pyridin-4-yl)amino)piperidin-1-yl)-3-oxopropanenitrile |
| 105 | 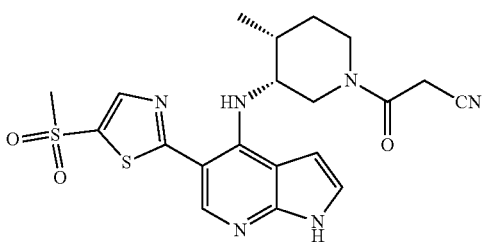 [SMILES: C[C@@H]1CCN(C(=O)CC#N)C[C@@H]1Nc1c(-c2ncc(S(C)(=O)=O)s2)cnc2[nH]ccc12] | 3-((3R,4R)-4-methyl-3-((5-(5-(methylsulfonyl)thiazol-2-yl)-1H-pyrrolo[2,3-b]pyridin-4-yl)amino)piperidin-1-yl)-3-oxopropanenitrile |
| 106 | 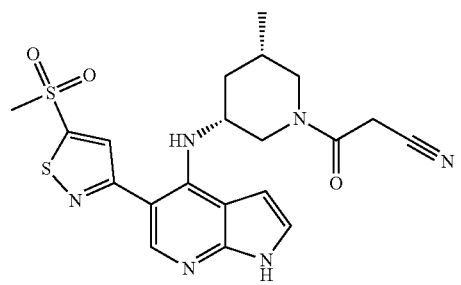 [SMILES: C[C@H]1C[C@@H](Nc2c(-c3cc(S(C)(=O)=O)sn3)cnc3[nH]ccc23)CN(C(=O)CC#N)C1] | 3-((3S,5R)-3-methyl-5-((5-(5-(methylsulfonyl)isothiazol-3-yl)-1H-pyrrolo[2,3-b]pyridin-4-yl)amino)piperidin-1-yl)-3-oxopropanenitrile |

| Example # | Structure | Name |
|---|---|---|
| 107 | 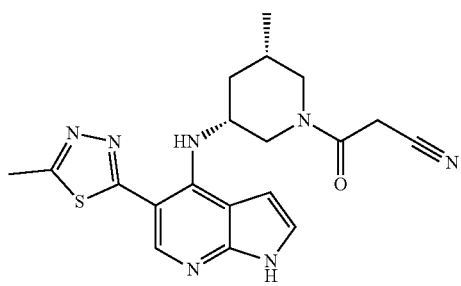 [SMILES: Cc1nnc(-c2cnc3[nH]ccc3c2N[C@@H]2C[C@H](C)CN(C(=O)CC#N)C2)s1] | 3-((3S,5R)-3-methyl-5-((5-(5-methyl-1,3,4-thiadiazol-2-yl)-1H-pyrrolo[2,3-b]pyridin-4-yl)amino)piperidin-1-yl)-3-oxopropanenitrile |
| 108 | 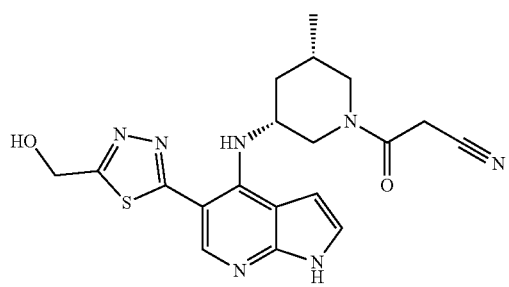 [SMILES: C[C@H]1C[C@@H](Nc2c(-c3nnc(CO)s3)cnc3[nH]ccc23)CN(C(=O)CC#N)C1] | 3-((3R,5S)-3-((5-(5-(hydroxymethyl)-1,3,4-thiadiazol-2-yl)-1H-pyrrolo[2,3-b]pyridin-4-yl)amino)-5-methylpiperidin-1-yl)-3-oxopropanenitrile |
| 109 | 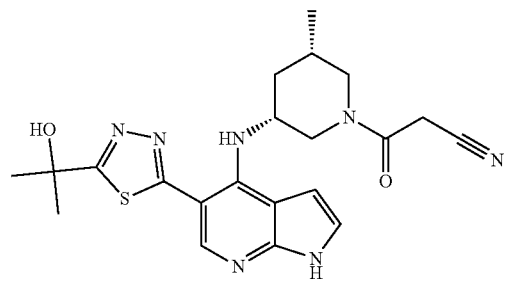 [SMILES: C[C@H]1C[C@@H](Nc2c(-c3nnc(C(C)(C)O)s3)cnc3[nH]ccc23)CN(C(=O)CC#N)C1] | 3-((3R,5S)-3-((5-(5-(2-hydroxypropan-2-yl)-1,3,4-thiadiazol-2-yl)-1H-pyrrolo[2,3-b]pyridin-4-yl)amino)-5-methylpiperidin-1-yl)-3-oxopropanenitrile |
| 110 | 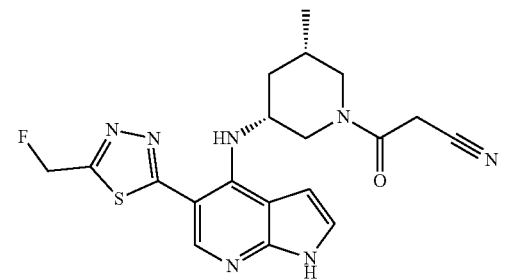 | 3-((3R,5S)-3-((5-(5-(fluoromethyl)-1,3,4-thiadiazol-2-yl)-1H-pyrrolo[2,3-b]pyridin-4-yl)amino)-5-methylpiperidin-1-yl)-3-oxopropanenitrile |
| 111 | 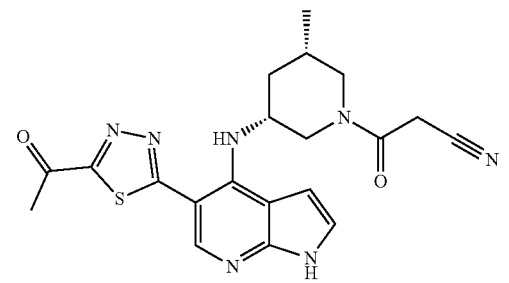 [SMILES: CC(=O)c1nnc(-c2cnc3[nH]ccc3c2N[C@@H]2C[C@H](C)CN(C(=O)CC#N)C2)s1] | 3-((3R,5S)-3-((5-(5-acetyl-1,3,4-thiadiazol-2-yl)-1H-pyrrolo[2,3-b]pyridin-4-yl)amino)-5-methylpiperidin-1-yl)-3-oxopropanenitrile |

| Example # | Structure | Name |
|---|---|---|
| 112 | 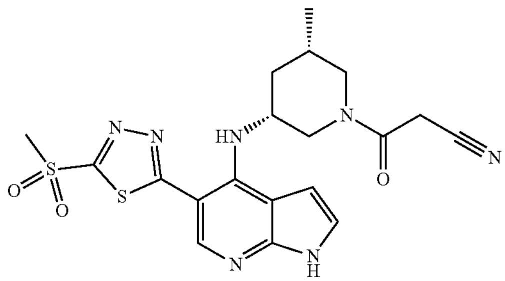 [SMILES: C[C@H]1C[C@@H](Nc2c(-c3nnc(S(C)(=O)=O)s3)cnc3[nH]ccc23)CN(C(=O)CC#N)C1] | 3-((3S,5R)-3-methyl-5-((5-(5-(methylsulfonyl)-1,3,4-thiadiazol-2-yl)-1H-pyrrolo[2,3-b]pyridin-4-yl)amino)piperidin-1-yl)-3-oxopropanenitrile |
| 113 | 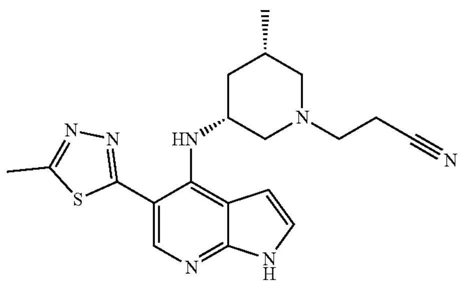 | 3-((3S,5R)-3-methyl-5-((5-(5-methyl-1,3,4-thiadiazol-2-yl)-1H-pyrrolo[2,3-b]pyridin-4-yl)amino)piperidin-1-yl)propanenitrile |
| 114 | 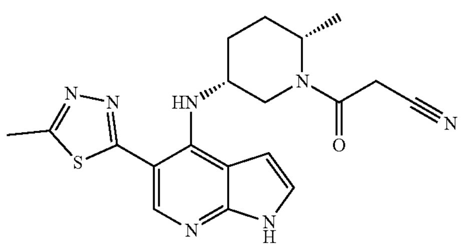 [SMILES: Cc1nnc(-c2cnc3[nH]ccc3c2N[C@@H]2CC[C@H](C)N(C(=O)CC#N)C2)s1] | 3-((2S,5R)-2-methyl-5-((5-(5-methyl-1,3,4-thiadiazol-2-yl)-1H-pyrrolo[2,3-b]pyridin-4-yl)amino)piperidin-1-yl)-3-oxopropanenitrile |
| 115 | 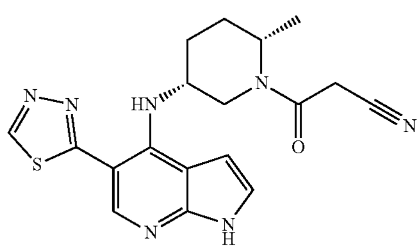 [SMILES: C[C@H]1CC[C@@H](Nc2c(-c3nncs3)cnc3[nH]ccc23)CN1C(=O)CC#N] | 3-((2S,5R)-5-((5-(1,3,4-thiadiazol-2-yl)-1H-pyrrolo[2,3-b]pyridin-4-yl)amino)-2-methylpiperidin-1-yl)-3-oxopropanenitrile |
| 116 | 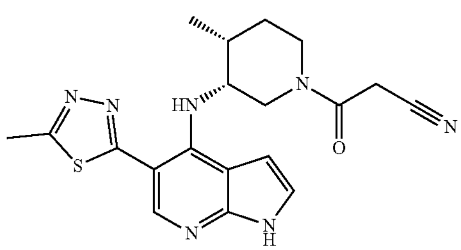 [SMILES: Cc1nnc(-c2cnc3[nH]ccc3c2N[C@H]2CN(C(=O)CC#N)CC[C@H]2C)s1] | 3-((3R,4R)-4-methyl-3-((5-(5-methyl-1,3,4-thiadiazol-2-yl)-1H-pyrrolo[2,3-b]pyridin-4-yl)amino)piperidin-1-yl)-3-oxopropanenitrile |
| 117 | 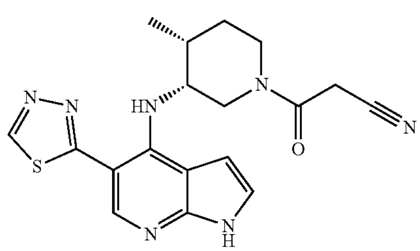 [SMILES: C[C@@H]1CCN(C(=O)CC#N)C[C@@H]1Nc1c(-c2nncs2)cnc2[nH]ccc12] | 3-((3R,4R)-3-((5-(1,3,4-thiadiazol-2-yl)-1H-pyrrolo[2,3-b]pyridin-4-yl)amino)-4-methylpiperidin-1-yl)-3-oxopropanenitrile |

| Example # | Structure | Name |
|---|---|---|
| 118 | 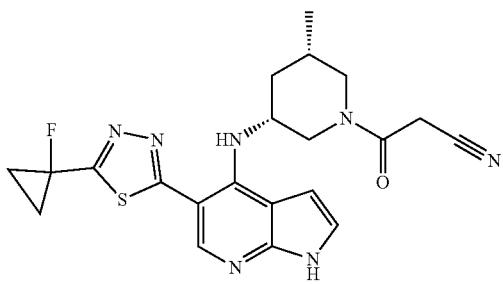 [SMILES: C[C@H]1C[C@@H](Nc2c(-c3nnc(C4(F)CC4)s3)cnc3[nH]ccc23)CN(C(=O)CC#N)C1] | 3-((3R,5S)-3-((5-(5-(1-fluorocyclopropyl)-1,3,4-thiadiazol-2-yl)-1H-pyrrolo[2,3-b]pyridin-4-yl)amino)-5-methylpiperidin-1-yl)-3-oxopropanenitrile |
| 119 | 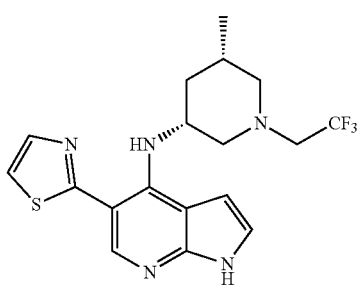 [SMILES: C[C@H]1C[C@@H](Nc2c(-c3nccs3)cnc3[nH]ccc23)CN(CC(F)(F)F)C1] | N-((3R,5S)-5-methyl-1-(2,2,2-trifluoroethyl)piperidin-3-yl)-5-(thiazol-2-yl)-1H-pyrrolo[2,3-b]pyridin-4-amine |
| 120 | 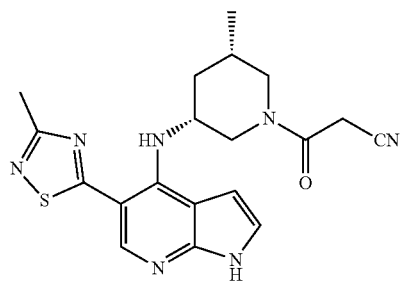 | 3-((3S,5R)-3-methyl-5-((5-(3-methyl-1,2,4-thiadiazol-5-yl)-1H-pyrrolo[2,3-b]pyridin-4-yl)amino)piperidin-1-yl)-3-oxopropanenitrile |
| 121 | 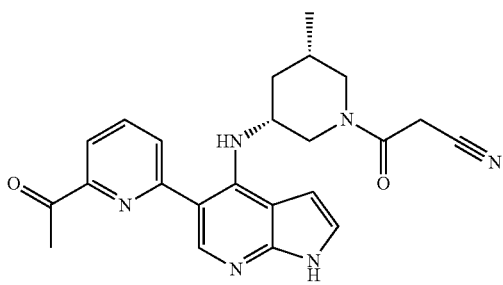 [SMILES: CC(=O)c1cccc(-c2cnc3[nH]ccc3c2N[C@@H]2C[C@H](C)CN(C(=O)CC#N)C2)n1] | 3-((3R,5S)-3-((5-(6-acetylpyridin-2-yl)-1H-pyrrolo[2,3-b]pyridin-4-yl)amino)-5-methylpiperidin-1-yl)-3-oxopropanenitrile |
| 122 | 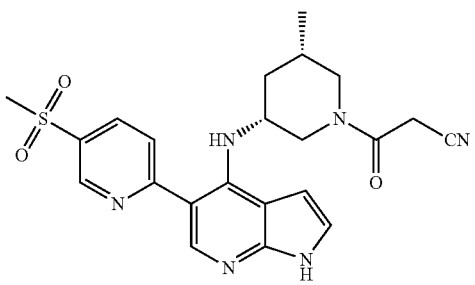 [SMILES: C[C@H]1C[C@@H](Nc2c(-c3ccc(S(C)(=O)=O)cn3)cnc3[nH]ccc23)CN(C(=O)CC#N)C1] | 3-((3S,5R)-3-methyl-5-((5-(5-(methylsulfonyl)pyridin-2-yl)-1H-pyrrolo[2,3-b]pyridin-4-yl)amino)piperidin-1-yl)-3-oxopropanenitrile |

-continued

| Example # | Structure | Name |
|---|---|---|
| 123 | 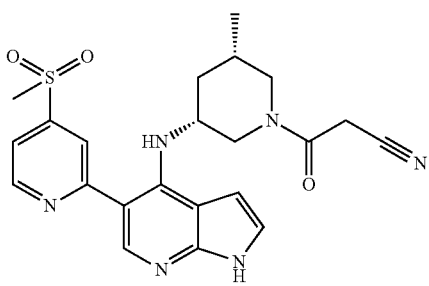 [SMILES: C[C@H]1C[C@@H](Nc2c(-c3cc(S(C)(=O)=O)ccn3)cnc3[nH]ccc23)CN(C(=O)CC#N)C1] | 3-((3S,5R)-3-methyl-5-((5-(4-(methylsulfonyl)pyridin-2-yl)-1H-pyrrolo[2,3-b]pyridin-4-yl)amino)piperidin-1-yl)-3-oxopropanenitrile |
| 124 | 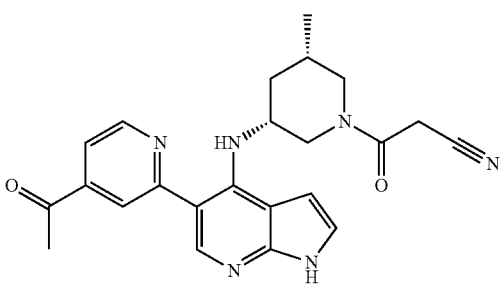 [SMILES: CC(=O)c1ccnc(-c2cnc3[nH]ccc3c2N[C@@H]2C[C@H](C)CN(C(=O)CC#N)C2)c1] | 3-((3R,5S)-3-((5-(4-acetylpyridin-2-yl)-1H-pyrrolo[2,3-b]pyridin-4-yl)amino)-5-methylpiperidin-1-yl)-3-oxopropanenitrile |
| 125 | 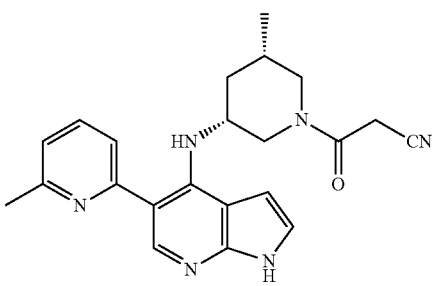 [SMILES: Cc1cccc(-c2cnc3[nH]ccc3c2N[C@@H]2C[C@H](C)CN(C(=O)CC#N)C2)n1] | 3-((3S,5R)-3-methyl-5-((5-(6-methylpyridin-2-yl)-1H-pyrrolo[2,3-b]pyridin-4-yl)amino)piperidin-1-yl)-3-oxopropanenitrile |
| 126 | 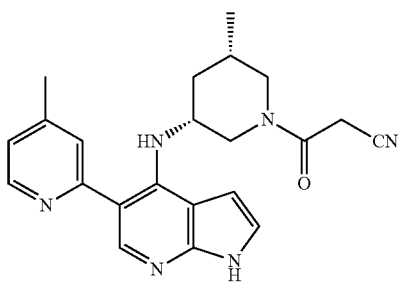 [SMILES: Cc1ccnc(-c2cnc3[nH]ccc3c2N[C@@H]2C[C@H](C)CN(C(=O)CC#N)C2)c1] | 3-((3S,5R)-3-methyl-5-((5-(4-methylpyridin-2-yl)-1H-pyrrolo[2,3-b]pyridin-4-yl)amino)piperidin-1-yl)-3-oxopropanenitrile |
| 127 | 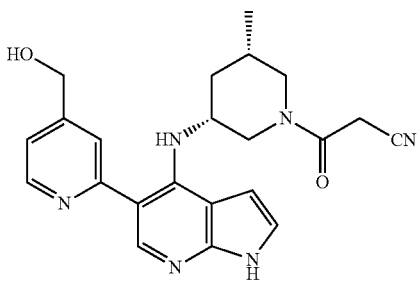 [SMILES: C[C@H]1C[C@@H](Nc2c(-c3cc(CO)ccn3)cnc3[nH]ccc23)CN(C(=O)CC#N)C1] | 3-((3R,5S)-3-((5-(4-(hydroxymethyl)pyridin-2-yl)-1H-pyrrolo[2,3-b]pyridin-4-yl)amino)-5-methylpiperidin-1-yl)-3-oxopropanenitrile |

-continued

| Example # | Structure | Name |
|---|---|---|
| 128 | 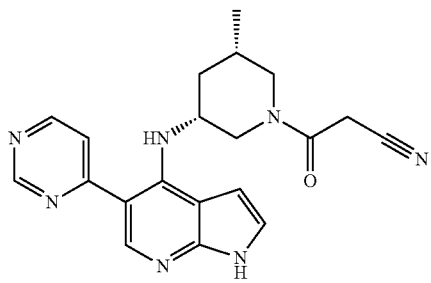 | 3-((3S,5R)-3-methyl-5-((5-(pyrimidin-4-yl)-1H-pyrrolo[2,3-b]pyridin-4-yl)amino)piperidin-1-yl)-3-oxopropanenitrile |
| 129 | 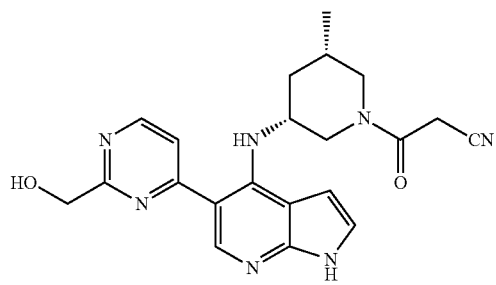 [SMILES: C[C@H]1C[C@@H](Nc2c(-c3ccnc(CO)n3)cnc3[nH]ccc23)CN(C(=O)CC#N)C1] | 3-((3R,5S)-3-((5-(2-(hydroxymethyl)pyrimidin-4-yl)-1H-pyrrolo[2,3-b]pyridin-4-yl)amino)-5-methylpiperidin-1-yl)-3-oxopropanenitrile |
| 130 | 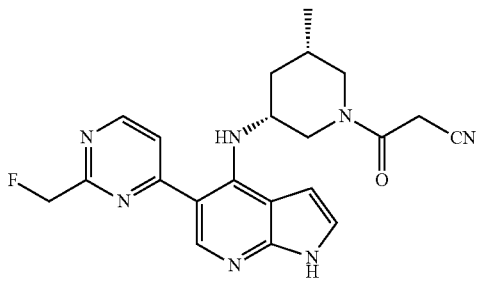 [SMILES: C[C@H]1C[C@@H](Nc2c(-c3ccnc(CF)n3)cnc3[nH]ccc23)CN(C(=O)CC#N)C1] | 3-((3R,5S)-3-((5-(2-(fluoromethyl)pyrimidin-4-yl)-1H-pyrrolo[2,3-b]pyridin-4-yl)amino)-5-methylpiperidin-1-yl)-3-oxopropanenitrile |
| 131 | 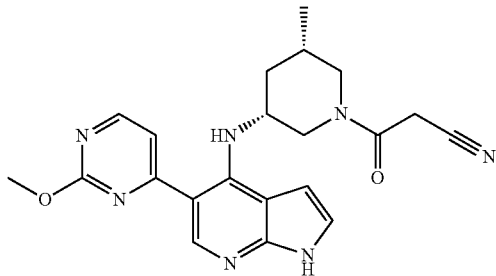 [SMILES: COc1nccc(-c2cnc3[nH]ccc3c2N[C@@H]2C[C@H](C)CN(C(=O)CC#N)C2)n1] | 3-((3R,5S)-3-((5-(2-methoxypyrimidin-4-yl)-1H-pyrrolo[2,3-b]pyridin-4-yl)amino)-5-methylpiperidin-1-yl)-3-oxopropanenitrile |
| 132 | 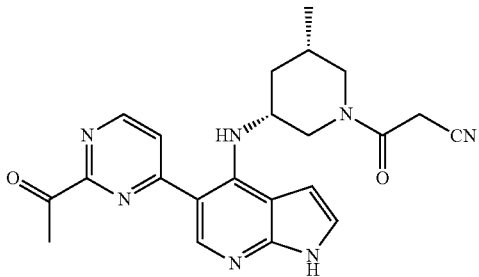 [SMILES: CC(=O)c1nccc(-c2cnc3[nH]ccc3c2N[C@@H]2C[C@H](C)CN(C(=O)CC#N)C2)n1] | 3-((3R,5S)-3-((5-(2-acetylpyrimidin-4-yl)-1H-pyrrolo[2,3-b]pyridin-4-yl)amino)-5-methylpiperidin-1-yl)-3-oxopropanenitrile |

-continued

| Example # | Structure | Name |
|---|---|---|
| 133 | 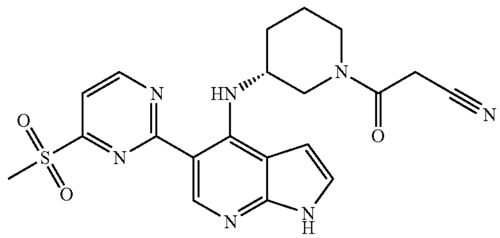 [SMILES: CS(=O)(=O)c1ccnc(-c2cnc3[nH]ccc3c2N[C@@H]2CCCN(C(=O)CC#N)C2)n1] | (R)-3-(3-((5-(4-(methylsulfonyl)pyrimidin-2-yl)-1H-pyrrolo[2,3-b]pyridin-4-yl)amino)piperidin-1-yl)-3-oxopropanenitrile |
| 134 | 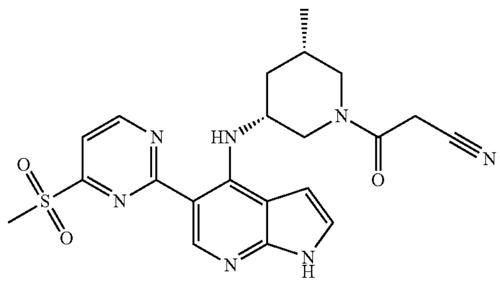 [SMILES: C[C@H]1C[C@@H](Nc2c(-c3nccc(S(C)(=O)=O)n3)cnc3[nH]ccc23)CN(C(=O)CC#N)C1] | 3-((3S,5R)-3-methyl-5-((5-(4-(methylsulfonyl)pyrimidin-2-yl)-1H-pyrrolo[2,3-b]pyridin-4-yl)amino)piperidin-1-yl)-3-oxopropanenitrile |
| 135 | 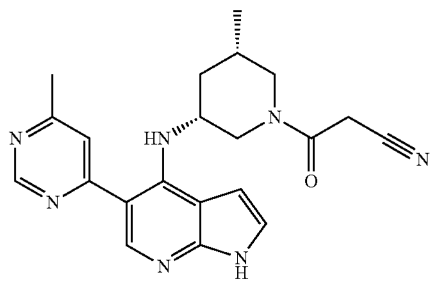 [SMILES: Cc1cc(-c2cnc3[nH]ccc3c2N[C@@H]2C[C@H](C)CN(C(=O)CC#N)C2)ncn1] | 3-((3S,5R)-3-methyl-5-((5-(6-methylpyrimidin-4-yl)-1H-pyrrolo[2,3-b]pyridin-4-yl)amino)piperidin-1-yl)-3-oxopropanenitrile |
| 136 | 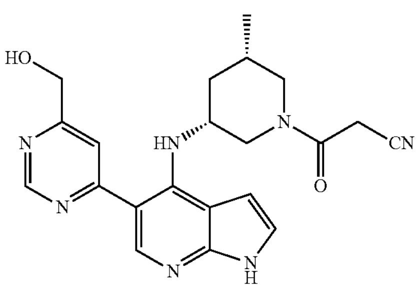 [SMILES: C[C@H]1C[C@@H](Nc2c(-c3cc(CO)ncn3)cnc3[nH]ccc23)CN(C(=O)CC#N)C1] | 3-((3R,5S)-3-((5-(6-(hydroxymethyl)pyrimidin-4-yl)-1H-pyrrolo[2,3-b]pyridin-4-yl)amino)-5-methylpiperidin-1-yl)-3-oxopropanenitrile |

The invention is further illustrated by the following examples of compounds of Formula (II)

| Example # | Structure | Name |
|---|---|---|
| 12 | 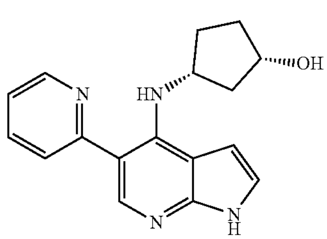 [SMILES: O[C@H]1CC[C@@H](Nc2c(-c3ccccn3)cnc3[nH]ccc23)C1] | (1S,3R)-3-((5-(pyridin-2-yl)-1H-pyrrolo[2,3-b]pyridin-4-yl)amino)cyclopentan-1-ol |

-continued

| Example # | Structure | Name |
|---|---|---|
| 13 | 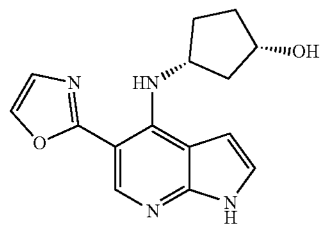 [SMILES: O[C@H]1CC[C@@H](Nc2c(-c3ncco3)cnc3[nH]ccc23)C1] | (1S,3R)-3-((5-(oxazol-2-yl)-1H-pyrrolo[2,3-b]pyridin-4-yl)amino)cyclopentan-1-ol |
| 29 | 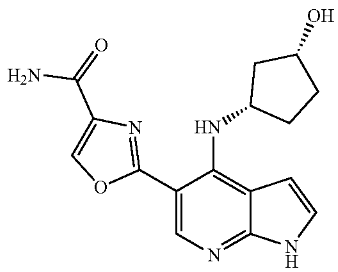 [SMILES: NC(=O)c1coc(-c2cnc3[nH]ccc3c2N[C@H]2CC[C@@H](O)C2)n1] | 2-(4-(((1S,3R)-3-hydroxycyclopentyl)amino)-1H-pyrrolo[2,3-b]pyridin-5-yl)oxazole-4-carboxamide |

In some embodiments, the compounds disclosed herein are gut-restricted compounds.

Pharmaceutical Compositions

Some embodiments herein are directed to a pharmaceutical composition comprising a compound of embodiments herein and a pharmaceutically acceptable excipient.

Also provided is a pharmaceutical composition comprising a compound as disclosed herein, together with a pharmaceutically acceptable excipient.

In some embodiments, the pharmaceutical compositions disclosed herein are gut-restricted compounds.

While it may be possible for the compounds described herein to be administered as the raw chemical, it is also possible to present them as a pharmaceutical composition. Accordingly, provided herein are pharmaceutical compositions which comprise one or more of certain compounds disclosed herein, or a derivative thereof, together with one or more pharmaceutically acceptable excipients thereof and optionally one or more other therapeutic ingredients. The excipient(s) must be "acceptable" in the sense of being compatible with the other ingredients of the formulation and not deleterious to the recipient thereof. Proper formulation of the pharmaceutical composition is dependent upon the route of administration chosen. Any of the well-known techniques and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

In some embodiments, the pharmaceutical compositions for use in accordance with embodiments herein can be formulated in conventional manner using one or more physiologically acceptable excipients.

The compositions include those suitable for oral, parenteral (including subcutaneous, intradermal, intramuscular, intravenous, intraarticular, and intramedullary), intraperitoneal, intrathecal, intradural, transmucosal, transdermal, rectal, intranasal, topical (including, for example, dermal, buccal, sublingual and intraocular), intravitreal, or intravaginal administration although the most suitable route may depend upon for example the condition and disorder of the recipient. The composition could include those suitable for administration by depot injections or by implants. The composition could include those suitable for administration by inhalation, such as, for example, a gas, vapor, or powder. The composition could include those suitable for administration, e.g., as an aerosol via a nebulizer, humidifier, inhaler and vaporizer or the like. The compositions may conveniently be presented in unit dosage form and may be prepared by any of the methods well known in the art of pharmacy. Typically, these methods include the step of bringing into association a compound disclosed herein or a derivative thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired composition.

Compositions of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All compositions for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Compositions for injection may be presented in unit dosage form, e.g., in ampoules or in multi-dose containers, with an added preservative. The pharmaceutical compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the composition isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the pharmaceutical compositions described previously, the compounds may also be formulated as a depot preparation. Such long acting compositions may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the pharmaceutical compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose. In contrast, systemic administration refers to oral, intravenous, intraperitoneal and intramuscular administration.

In some embodiments, the compounds disclosed herein may be administered ophthalmically. In some embodiments, the compounds disclosed herein may be administered as an ophthalmic composition. The compounds of embodiments herein may be administered as, for example, liquid preparations, including eye lotions, spray, or eye drops for topical administration. In some embodiments, the compounds disclosed herein may be administered as semi-solid preparations, for example, applied to the eyelid, such as cream, lotion, gel, ointment, or paste. In some embodiments, the compounds disclosed herein may be administered as solid dosage forms, for example, applied to the eye surface to produce modified release, such as a powder. In some embodiments, the compounds of embodiments herein are administered through devices for surgical implantation, parenteral products, (e.g., intracorneal or intravitreous products), liquids for irrigation, or the like. In some embodiments, the pharmaceutical composition comprising the compounds disclosed herein are sterile and free from particulate matters. In some embodiments, the compounds disclosed herein may be administered by intraocular injection, intraorbital injection, or an intravitreal injection. In some embodiments, the intraocular injection may be to the anterior chamber of the eye, posterior chamber of the eye, or a combination thereof. For example, the compounds disclosed herein may be administered to the posterior intraorbital region of the eye.

In some embodiments, pharmaceutical compositions suitable for topical administration include liquid or semi-liquid preparations suitable for penetration through the skin to the site of inflammation such as a solution, powder, fluid emulsion, fluid suspension, semi-solid, ointment, paste, cream, gel, jelly, foam, liniment, lotion, and drops suitable for administration to the eye, ear or nose. The active ingredient for topical administration may comprise, for example, from 0.001% to 10% w/w (by weight) of the composition. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the composition.

Gels for topical or transdermal administration may comprise, generally, a mixture of volatile solvents, nonvolatile solvents, and water. In certain embodiments, the volatile solvent component of the buffered solvent system may include lower ($C_1$-$C_6$) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes are semi-solid pharmaceutical compositions of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The pharmaceutical composition may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Pharmaceutical compositions for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage pharmaceutical compositions are those containing an effective dose, as herein below recited, or an appropriate fraction thereof, of the active ingredient.

It should be understood that in addition to the ingredients particularly mentioned above, the pharmaceutical compositions described above may include other agents conventional in the art having regard to the type of pharmaceutical composition in question, for example those suitable for oral administration may include flavoring agents.

Compounds may be administered at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

When employed as pharmaceuticals, the compounds can be administered in the form of pharmaceutical compositions. These compositions can be prepared in a manner well known in the pharmaceutical arts, and can be administered by a variety of routes, depending upon whether local or systemic treatment is desired and upon the area to be treated. Administration of the disclosed compounds or compositions may be oral, parenteral (including subcutaneous, intradermal, intramuscular, intravenous, intraarticular, and intramedullary), pulmonary (e.g., by inhalation or insufflation of powders or aerosols, including by nebulizer; intratracheal or intranasal), intraperitoneal, intrathecal, intradural, transmucosal, transdermal, rectal, topical (including dermal, buccal, sublingual and intraocular), or intravaginal administration. Parenteral administration includes intravenous, intraarterial, subcutaneous, intraperitoneal, intramuscular or injection or infusion; or intracranial, e.g., intrathecal or intraventricular, administration. Parenteral administration can be in the form of a single bolus dose, or may be, for example, by a continuous perfusion pump. Pharmaceutical compositions for topical administration may include foams, transdermal patches, ointments, lotions, creams, gels, solutions, fluid emulsions, fluid suspensions, semi-solids, pastes, drops, suppositories, sprays, liquids and powders. Conventional pharmaceutical carriers, aqueous, powder or oily bases, thickeners and the like may be necessary or desirable. Coated condoms, gloves and the like may also be useful. In some embodiments, the compounds can be contained in such pharmaceutical compositions with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The artisan can refer to various pharmacologic references for guidance. For example, Modem Pharmaceutics, 5th Edition, Banker & Rhodes, CRC Press (2009); and Goodman & Gilman's The Pharmaceutical Basis of Therapeutics, 13th Edition, McGraw Hill, New York (2018) can be consulted.

In some embodiments, a method of treating a JAK kinase-mediated disease by administering a pharmaceutical composition of embodiments disclosed herein. In some embodiments, the compound is in a therapeutically effective amount. In some embodiments, the therapeutically effective amount is an amount disclosed herein.

Some embodiments disclosed herein also include pharmaceutical compositions which contain, as the active ingredient, one or more of the compounds disclosed herein in combination with one or more pharmaceutically acceptable carriers (excipients).

In some embodiments, a method of making a pharmaceutical composition comprises mixing the active ingredient with an excipient, diluting the active ingredient using an excipient, or enclosing the active ingredient within a carrier in the form of, for example, a capsule, sachet, paper, or other container. When the excipient serves as a diluent, it can be a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose, including eutectic solvents, eutectic-based ionic liquids, or ionic liquids. The pharmaceutical compositions can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

The pharmaceutical compositions can be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and can be generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, the pharmaceutical composition may comprise about 0.01% to about 50% of one or more compounds disclosed herein. In some embodiments, the one or more compounds is in an amount of about 0.01% to about 50%, about 0.01% to about 45%, about 0.01% to about 40%, about 0.01% to about 30%, about 0.01% to about 20%, about 0.01% to about 10%, about 0.01% to about 5%, about 0.05% to about 50%, about 0.05% to about 45%, about 0.05% to about 40%, about 0.05% to about 30%, about 0.05% to about 20%, about 0.05% to about 10%, about 0.1% to about 50%, about 0.1% to about 45%, about 0.1% to about 40%, about 0.1% to about 30%, about 0.1% to about 20%, about 0.1% to about 10%, about 0.1% to about 5%, about 0.5% to about 50%, about 0.5% to about 45%, about 0.5% to about 40%, about 0.5% to about 30%, about 0.5% to about 20%, about 0.5% to about 10%, about 0.5% to about 5%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 45%, about 5% to about 40%, about 5% to about 35%, about 5% to about 30%, about 5% to about 25%, about 5% to about 20%, about 5% to about 15%, about 5% to about 10%, about 10% to about 45%, about 10% to about 40%, about 10% to about 35%, about 10% to about 30%, about 10% to about 25%, about 10% to about 20%, about 10% to about 15%, or a value within one of these ranges. Specific examples may include about 0.01%, about 0.05%, about 0.1%, about 0.25%, about 0.5%, about 0.75%, about 1%, about 5%, about 10%, about 15%, about 20%, about 25%, about 30%, about 35%, about 40%, about 45%, about 50%, about 60%, about 70%, about 80%, about 90%, or a range between any two of these values. The foregoing all representing weight percentages of the pharmaceutical composition. In some embodiments, the pharmaceutical composition is suitable for topical administration. In some embodiments, the pharmaceutical composition is suitable for oral, parenteral (including subcutaneous, intradermal, intramuscular, intravenous, intraarticular, and intramedullary), intraperitoneal, intrathecal, intradural, transmucosal, transdermal, rectal, intranasal, topical (including, for example, dermal, buccal, sublingual and intraocular), intravitreal, or intravaginal administration.

In some embodiments, the compound is in a therapeutically effective amount. In some embodiments, the therapeutically effective amount may be about 1 mg to about 1000 mg, about 1 mg to about 900 mg, about 1 mg to about 800 mg, about 1 mg to about 700 mg, about 1 mg to about 600 mg, about 1 mg to about 500 mg, about 1 mg to about 400 mg, about 1 mg to about 300 mg, about 1 mg to about 200 mg, about 1 mg to about 100 mg, about 10 mg to about 1000 mg, about 50 mg to about 1000 mg, about 100 mg to about 1000 mg, about 200 mg to about 1000 mg, about 300 mg to about 1000 mg, about 400 mg to about 1000 mg, about 500 mg to about 1000 mg, about 10 mg to about 500 mg, about 50 mg to about 500 mg, about 100 mg to about 500 mg, about 10 mg to about 300 mg, about 50 mg to about 300 mg, from about 100 mg to about 300 mg, about 10 mg to about 150 mg, about 50 mg to about 150 mg, about 60 mg to about 120 mg, about 50 mg to about 120 mg or a range between any two of these values. Specific examples include, for example, about 1000 mg, about 900 mg, about 800 mg, about 700 mg, about 750 mg, about 600 mg, about 500 mg, about 400 mg, about 450 mg, about 300 mg, about 250 mg, about 200 mg, about 175 mg, about 150 mg, about 125 mg, about 120 mg, about 110 mg, about 100 mg, about 90 mg, about 80 mg, about 70 mg, about 60 mg, about 50 mg, about 30 mg, about 20 mg, or any value between the ranges disclosed above.

In some embodiments, the therapeutically effective amount can vary according to, for example, the particular use for which the treatment is made, the manner of administration of the compound, the health and condition of the patient, and the judgment of the prescribing physician. The proportion or concentration of a compound in a pharmaceutical composition can vary depending upon a number of factors including dosage, chemical characteristics (e.g., hydrophobicity), and the route of administration. For example, the compounds can be provided in an aqueous physiological buffer solution containing about 0.1 to about 10% w/v of the compound for parenteral administration. Some typical dose ranges for the compounds are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, composition of the excipient, and its route of administration. Effective doses can be extrapolated from dose-response curves derived from in vitro or animal model test systems.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications.

For preparing solid compositions such as tablets, the principal active ingredient can be mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the pharmaceutical composition so that the pharmaceutical composition can be readily subdivided into equally therapeutically effective unit dosage forms such as tablets, pills and capsules. This solid pre-formulation is then subdivided into unit dosage forms of the type described above containing from, for example, about 0.1 to about 1000 mg of the active ingredient.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the pharmaceutical compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the composition in an appropriate manner.

In some embodiments, the pharmaceutical compositions administered to a patient can be in the form of pharmaceutical compositions described above. In some embodiments, these compositions can be sterilized by conventional sterilization techniques, or may be sterile filtered. Aqueous solutions can be packaged for use as is, or lyophilized, the lyophilized preparation being combined with a sterile aqueous carrier prior to administration. In some embodiments, the pH of the compound preparations is about 3 to about 11, about 5 to about 9, about 5.5 to about 6.5, or about 5.5 to about 7.5. It will be understood that use of certain of the foregoing excipients, carriers, or stabilizers will result in the formation of pharmaceutical salts.

Methods of Use

The present invention relates to a method of modulating JAK-mediated function in a subject comprising the administration of a therapeutically effective amount of a compound or a pharmaceutical composition containing a compound as disclosed herein.

The present invention also relates to a method of inhibiting a JAK-mediated disease through the interaction between a compound described herein and at least one JAK kinase isoform. This interaction may result in changes in biochemical output produced by JAK kinases, expression of JAK kinases, binding of JAK kinases with normal binding partners, cell phenotype or cell proliferation. These changes may be monitored to determine the extent of modulation acheived by the compounds described herein. Such methods may be modes of treatment of disease, biological assays, cellular assays, biochemical assays or the like.

Also provided herein is a method of treating a JAK-mediated disease comprising administering to a patient in need thereof a therapeutically effective amount of a compound as disclosed herein, a derivative thereof, or a combination thereof. In certain embodiments, the therapeutically effective amount of a compound as disclosed herein, a derivative thereof, or a combination thereof, may be in the form of a pharmaceutical composition. In embodiments, the pharmaceutical composition may include a pharmaceutically acceptable excipient.

In embodiments, diseases or disorders associated with a JAK kinase are treated by compounds of the present invention include autoimmune disorders, chronic inflammatory disorders, acute inflammatory disorders, auto-inflammatory disorders, fibrotic disorders, metabolic disorders, neoplasias, or cardiovascular or cerebrovascular disorders. Thus, in some embodiments, the present invention provides a method for treating a JAK-mediated disease or disorder in a patient in need thereof, wherein said method comprises administering to said patient a therapeutically effective amount of a provided compound, or composition thereof. Such JAK-mediated diseases or disorders include, but are not limited to, those described herein.

Some embodiments herein are directed to a method of modulation of an JAK-mediated function in a subject comprising the administration of a therapeutically effective amount of a gut-restricted compound as disclosed herein. In some embodiments, a method of inhibiting JAK in a subject comprises administering to the subject a gut-restricted compound of embodiments herein.

The present invention also relates to a method of inhibiting at least one JAK function comprising the step of contacting JAK kinases with a gut-restricted compound as described herein. The cell phenotype, cell proliferation, activity of JAK kinases, change in biochemical output produced by active JAK kinases, expression of JAK kinases, or binding of JAK kinases with a natural binding partner may be monitored. Such methods may be modes of treatment of disease, biological assays, cellular assays, biochemical assays, or the like.

Also provided herein is a method of treating a JAK-mediated disease comprising administering to a patient in need thereof a therapeutically effective amount of a gut-restricted compound as disclosed herein. In some embodiments the administering is gut-restricted. In certain embodiments, the therapeutically effective amount of a gut-restricted compound as disclosed herein may be in the form of a pharmaceutical composition. In embodiments, the pharmaceutical composition may further include a pharmaceutically acceptable excipient.

In some embodiments, said JAK-mediated disease or disorder is chosen from a skin disorder, pruritus, a hair loss disorder, a cancer, a neoplasm, Alzheimer's disease, an inflammatory condition, connective tissue diseases and an autoimmune condition.

In certain embodiments, said JAK-mediated disease or disorder is a neoplasm, a malignancy, a myeloproliferative disorder, a hematopoietic neoplasm, a myeloid neoplasm, a lymphoid neoplasm, including myelofibrosis, primary myelofibrosis, polycythemia vera, essential thrombocythemia, acute and chronic leukemias, lymphomas, cutaneous lymphomas including mycosis fungoides, other myeloid malignancies, and myelodysplastic syndrome.

In certain embodiments, said JAK-mediated disease is selected from the group consisting of an autoimmune disorders or responses, broad activation of the immune responses, bacterial infection, viral infection, inflammation, a chronic and/or acute inflammatory disorder or condition, and/or auto-inflammatory disorder, fibrotic disorders, metabolic disorders, a neoplasm, or cardiovascular or cerebrovascular disorders, a skin disorder, pruritus, a hair loss disorder, a cancer or malignancy, autoimmune connective tissue diseases and an autoimmune condition; Still's disease, adult-onset Still's disease, Th17-associated inflammation, polychondritis (e.g. relapsing polychondritis); myositis, polymyositis, autoimmune myositis, dermatomyositis, juvenile dermatomyositis; myasthenia gravis; Arthritis (e.g. rheumatoid arthritis, juvenile rheumatoid arthritis, systemic-onset juvenile rheumatoid arthritis, osteoarthritis, infectious arthritis, inflammatory arthritis, inflammatory bowel disease-associated arthritis, idiopathic arthritis, juvenile idiopathic arthritis, systemic juvenile idiopathic arthritis, psoriatic arthritis), spondylitis/spondyloarthritis/spondyloarthropathy (ankylosing spondylitis), gout, scleroderma (systemic scleroderma, juvenile scleroderma), Reiter's syndrome/reactive arthritis, Lyme disease, lupus/systemic lupus erythematosus (SLE) (lupus erythematosus, pediatric systemic lupus erythematosus, cutaneous lupus (subacute cutaneous lupus, chronic cutaneous lupus/discoid lupus, chilblain lupus erythematosus), polymyalgia rheumatica, enthesitis, mixed connective tissue disease, enthesopathy; carditis, myocarditis, angiogenesis disorders, myelodysplastic syndrome, atherosclerosis, restenosis (restenosis of an atherosclerotic coronary artery), acute coronary syndrome, myocardial infarction, cardiac-allograft vasculopathy, transplant arteriopathy; vasculitis (large vessel vasculitis, small vessel vasculitis, giant-cell arteritis, polyarteritis nodosa, vasculitis syndromes including: Takayasu's arteritis, Wegener's granulomatosis, Behcet's Disease), stimulator of interferon genes (STING) associated vasculopathy with onset in infancy (SAVI); gastrointestinal disorders, enterocolitis, colitis, inflammatory bowel disease (ulcerative colitis, Crohn's disease), irritable bowel syndrome, enteritis syndrome/spastic colon, celiac disease; acute and chronic pancreatitis; primary biliary cirrhosis, primary sclerosing cholangitis, jaundice, cirrhosis (for example, primary biliary cirrhosis or cirrhosis due to fatty liver disease (for example, alcoholic and nonalcoholic steatosis); esophagitis, gastritis, gastric and duodenal ulcers, peritonitis; Nephropathies: immunologically mediated glomerulonephropathy, autoimmune nephropathy, membranous glomerulopathy, chronic progressive nephropathies, diabetic kidney disease/diabetic nephropathy, renal fibrosis, renal ischemic/reperfusion injury, HIV associated nephropathy, ureteral obstructive nephropathy, glomerulosclerosis, proteinuria, nephrotic syndrome, polycystic kidney disease, autosomal dominant polycystic kidney disease, a nephropathy is an immunologically mediated nephropathy, autoimmune nephropathy, chronic progressive nephropathies, diabetic nephropathy, renal fibrosis, ischemic/reperfusion injury associated, HIV associated nephropathy, ureteral obstructive nephropathy, glomerulonephritis, chronic kidney disease (for example, diabetic nephropathy), hypertension induced nephropathy, glomerulosclerosis, proteinuria, nephrotic syndrome, polycystic kidney disease, autosomal dominant polycystic kidney disease, diabetic kidney disease, lupus nephritis; interstitial cystitis; periodontitis, gingivitis; pulmonary inflammation, sinusitis, pneumonia, bronchitis, asthma, bronchial asthma, allergic asthma, non-allergic asthma, allergic bronchopulmonary mycosis, aspirin-induced asthma, adult-onset asthma, asthma with fixed airflow obstruction, exercise-induced asthma, cough-variant asthma, work-related asthma, nighttime (nocturnal) asthma, asthma with obesity, eosinophilic asthma, steroid-resistant asthma/severe asthma, extrinsic asthma, intrinsic/cryptogenic asthma, Churg-Strauss syndrome, bronchiolitis, bronchiolitis obliterans, chronic obstructive pulmonary disease (COPD), interstitial lung disease (pulmonary fibrosis, idiopathic pulmonary fibrosis), acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury; Meniere's disease; ocular disorders including, (e.g.), ocular inflammation, uveitis, dry eye/keratoconjunctivitis sicca, scleritis, episcleritis, keratitis/keratopathy, choroiditis, retinal vasculitis, optic neuritis, retinopathy (diabetic retinopathy, immune mediated retinopathy, macular degeneration, wet macular degeneration, dry (age related) macular degeneration); Mastocytosis, iron deficiency anemia, uremia, hypereosinophilic syndrome (HES), systemic mast cell disease (SMCD), myelodysplastic syndrome, idiopathic thrombocytic purpura; bone resorption diseases; Neurodegenerative disorders, neurological/neuromuscular disorders (e.g.), multiple sclerosis, Parkinson's disease, Huntington's disease, amyotrophic lateral sclerosis (ALS) (familial ALS, sporadic ALS), Alzheimer's disease, myasthenia gravis, Lambert-Eaton myasthenic syndrome (LEMS), Guillain-Barret syndrome, meningitis, encephalitis, traumatic brain injury; nervous system damage, delusional parasitosis, dysregulation of neuronal processes and sensory perception, stroke/neuronal ischemia, spinal cord injury, peripheral neuropathy, tactile hallucinations, spinal cord injury, psychiatric disease; pain (acute pain, chronic pain, neuropathic pain, or fibromyalgia) paresthetica, nerve irritation, peripheral neuropathy; pruritus/itch (atopic pruritus, xerotic pruritus, pruritus associated with psoriasis/psoriatic itch/psoriasis-associated itch), acute pruritus, chronic pruritus, idiopathic pruritus, chronic idiopathic itch, biliary itch, hepatobiliary-associated itch, renal associated itch/renal itch, uremic itch, cholestasis, intrahepatic cholestasis of pregnancy, lichen simplex chronicus associated pruritus, lymphoma-associated itch, leukemia-associated itch, prurigo nodularis, atopic dermatitis-associated itch, atopic itch/atopic pruritus, bullous itch, brachioradial pruritus) neurogenic itch, neuropathic itch, notalgia paresthetica, pruritic popular eruption of HIV, psychogenic itch, swimmer's itch, pruritus or uremic itch, urticarial itch; dermatologic disorders (e.g.), dermatologic drug reactions/drug eruptions, xerosis/dry skin, skin rash, skin sensitization, skin irritation, sunburn, shaving, body louse, head lice/pediculosis, pubic lice, cutaneous larva migrans, scabies, parasitic infection, insect infestation, urticaria/hives, papular uriticaria, insect bites, insect stings, dandruff, foreign objects or devices on skin, fungal infection, herpes, varicella/chicken pox, eosinophilic folliculitis, dermatosis of pregnancy/pruritic urticarial papules and plaques of pregnancy (PUPP), inflammatory dermatoses, neutrophilic dermatoses, histiocytoid neutrophilic dermatosis, bowel-bypass syndrome dermatosis, psoriasis/psoriasis vulgaris, lichen planus, lichen sclerosus, acne (acne vulgaris, comedonal acne, inflammatory acne, nodulo-cystic acne, scarring acne, acne keloidalis nuchae), atopies (allergic contact sensitization, allergic dermatitis) dermatitis (atopic dermatitis/eczema, contact dermatitis, photodermatitis, seborrheic dermatitis, stasis dermatitis, acute febrile neutrophilic dermatosis (Sweet's syndrome), chronic atypical neutrophilic dermatosis with lipodystrophy and elevated temperature syndrome (CANDLE Syndrome), hidradenitis suppurativa, hives, pyoderma gangrenosum, alopecia (eyebrow alopecia, intranasal hair alopecia, scarring alopecia (e.g., cicatricial alopecia, central centrifugal cicatricial alopecia, lichen planopilaris, frontal fibrosing alopecia, folliculitis decalvans), nonscarring alopecia (alopecia areata (AA) (patchy AA, alopecia totalis (AT), alopecia universalis (AU), ophiasis pattern alopecia areata, sisaihpo pattern alopecia areata)), androgenetic/androgenic alopecia (AGA)/male and female pattern AGA), telogen effluvium, tinea capitis, hypotrichosis (hereditary hypotrichosis simplex), lichen planopilaris (frontal fibrosing alopecia), punctate palmoplantar keratoderma, erythema elevatinum diutinum (EED), neutrophilic eccrine hidradenitis, palisading neutrophilic granulomatous dermatitis, neutrophilic urticarial dermatosis, vitiligo including segmental vitiligo (unisegmental vitiligo, bisegmental vitiligo, multisegmental vitiligo) nonsegmental vitiligo (acral, facial, or acrofacial vitiligo, centrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, generalized vitiligo, universal vitiligo), mixed vitiligo/nonsegmental associated with segmental vitiligo, focal vitiligo, solitary mucosal vitiligo or vitiligo with or without leukotricia (involvement of body hair); bullous diseases, immunobullous diseases (bullous pemphigoid, cicatricial pemphigoid, pemphigus vulgaris, linear IgA disease), gestational pemphigoid, xeroderma pigmentosum; disorders of fibrosis and scarring: fibroids, hepatic fibrosis, pulmonary fibrosis, idiopathic pulmonary fibrosis, low grade scarring such as, scleroderma, increased fibrosis, keloids, post-surgical scars; wound healing, surgical scarring, radiation induced fibrosis (for example, head and neck, gastrointestinal or pulmonary), CNS scarring, alimentary track or gastrointestinal fibrosis, renal fibrosis, hepatic or biliary fibrosis, liver fibrosis (for example, nonalcoholic steatohepatitis, hepatitis C, or hepatocellular carcinoma), cardiac fibrosis (for example, endomyocardial fibrosis or atrial fibrosis), ophthalmic scarring, fibrosclerosis, scar growth, wound or scab healing, keloid, mediastinal fibrosis, myelofibrosis, retroperitoneal fibrosis/Ormond's disease, progressive massive fibrosis, nephrogenic systemic fibrosis; Sjorgren's syndrome, sarcoidosis, familial Mediterranean fever, Cryopyrin associated periodic syndrome (Muckle-Wells syndrome, familial cold auto-inflammatory syndrome/familial cold uticaria/TNF receptor associated periodic syndrome, neonatal-onset multisystem inflammatory disease), hyperoxia induced inflammations, reperfusion injury, post-surgical trauma, tissue injury, elevated temperature syndrome; diabetes (Type I diabetes, Type II diabetes)/diabetes mellitus, Hashimoto's thyroiditis, Graves' disease, Addison's disease, Castleman's disease, hyperparathyroidism, menopause, obesity, steroid-resistance, glucose intolerance, metabolic syndrome, thyroid illness, hypophysitis; systemic immune senescence; autoimmune atrophic gastritis, autoimmune atrophic gastritis of pernicious anemia, autoimmune encephalomyelitis, autoimmune orchitis, Goodpasture's disease, Sjogren's syndrome, autoimmune thrombocytopenia, sympathetic ophthalmia; secondary hematologic manifestations of autoimmune diseases (for example, anemias), autoimmune hemolytic syndromes (autoimmune hemolytic anemia), autoimmune and inflammatory hepatitis, autoimmune ovarian failure, autoimmune thrombocytopenia, silicone implant associated autoimmune disease, drug-induced autoimmunity, HIV-related autoimmune syndromes, metal-induced autoimmunity, autoimmune deafness, autoimmune thyroid disorders; allergy and allergic reactions including hypersensitivity reactions such as Type I hypersensitivity reactions, (e.g. including anaphylaxis), Type II hypersensitivity reactions (e.g. Goodpasture's Disease, autoimmune hemolytic anemia), Type III hypersensitivity reaction diseases (e.g. the Arthus reaction, serum sickness), and Type IV hypersensitivity reactions (e.g. contact dermatitis, allograft rejection); acute and chronic infection, sepsis syndromes (sepsis, septic shock, endotoxic shock, exotoxin-induced toxic shock, gram negative sepsis, gram positive sepsis, fungal sepsis, toxic shock syndrome); acute and chronic infection, sepsis syndromes (sepsis, septic shock, endotoxic shock, exotoxin-induced toxic shock, gram negative sepsis, gram positive sepsis, fungal sepsis, toxic shock syndrome); a rejection: graft vs. host reaction/graft vs. host disease, allograft rejections (for example, acute allograft rejection or chronic allograft rejection), early transplantation rejection; Malignancy, cancer, lymphoma, leukemia, multiple myeloma, a solid tumor, teratoma, metastatic and bone disorders, internal cancers, cancer of the: bone, mouth/pharynx, esophagus, larynx, stomach, intestine, colon, rectum, lung (for example, non-small cell lung cancer or small cell lung cancer), liver (hepatic), pancreas, nerve, brain (for example, glioma, glioblastoma multiforme, astrocytoma, neuroblastoma, and schwannomas), head and neck, throat, ovary, uterus, prostate, testis, bladder, kidney (renal), breast, gall bladder, cervix, thyroid, prostate, eye (ocular malignancies), and skin (melanoma, keratoacanthoma); as well as fibrotic cancers, fibroma, fibroadenomas, fibrosarcomas, a myeloproliferative disorder, neoplasm (hematopoietic neoplasm, a myeloid neoplasm, a lymphoid neoplasm (myelofibrosis, primary myelofibrosis, polycythemia vera, essential thrombocythemia)), leukemias (acute lymphocytic leukemia, acute and chronic myelogenous leukemia, chronic lymphocytic leukemia, acute lymphoblastic leukemia, chronic myelomonocytic leukemia (CMML), or promyelocytic leukemia), multiple myeloma and other myeloid malignancies (myeloid metaplasia with myelofibrosis (MMM), primary myelofibrosis (PMF), idiopathic myelofibrosis (IMF)), lymphomas (Hodgkin's disease, cutaneous lymphomas (cutaneous T-cell lymphoma, mycosis fungoides), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease); Kaposi's sarcoma, rhabdomyosarcoma, seminoma, teratocarcinoma, osteosarcoma, thyroid follicular cancer; increased accumulation of exogenous opioids or synthetic opioids, notalgia paraesthetica, obsessive-compulsive disorders, nostalgia associated with obsessive-compulsive disorders, and a combination thereof.

In some embodiments, additional exemplary disorders include, but are not limited to: complications from organ transplants (including xenotransplantation) such as graft vs. host reaction (for example, graft vs. host disease), allograft rejections (for example, acute allograft rejection or chronic allograft rejection), early transplantation, diabetes, a myeloproliferative disorder, a rejection (for example, acute allograft rejection); bone resorption diseases, asthma (e.g., bronchial asthma), atopy, autoimmune thyroid disorders, chronic atypical neutrophilic dermatosis with lipodystrophy and elevated temperature syndrome (CANDLE Syndrome), SAVI (stimulator of interferon genes (STING) associated vasculopathy with onset in infancy), ulcerative colitis, inflammatory bowel disease, Crohn's disease, celiac disease, ulcerative colitis, Behcet's disease, myasthenia gravis, nephropathies, and myocarditis, secondary hematologic manifestations of autoimmune diseases (for example, anemias), autoimmune hemolytic syndromes, autoimmune and inflammatory hepatitis, autoimmune ovarian failure, autoimmune orchitis, autoimmune thrombocytopenia, silicone implant associated autoimmune disease, drug-induced autoimmunity, HIV-related autoimmune syndromes; acute and chronic infection, sepsis syndromes (e.g.) sepsis, septic shock, endotoxic shock, exotoxin-induced toxic shock, gram negative sepsis, gram positive sepsis, fungal sepsis, toxic shock syndrome; hyperoxia induced inflammations, reperfusion injury, post-surgical trauma, tissue injury, pain (e.g.) acute pain, chronic pain, neuropathic pain, or fibromyalgia.

In an embodiment, said asthma is allergic asthma, non-allergic asthma, allergic bronchopulmonary mycosis, aspirin-induced asthma, adult-onset asthma, asthma with fixed airflow obstruction, exercise-induced asthma, cough-variant asthma, work-related asthma, nighttime (nocturnal) asthma, asthma with obesity, eosinophilic asthma, steroid-resistant asthma/severe asthma, extrinsic asthma, or intrinsic/cryptogenic asthma.

In an embodiment, said vitiligo is segmental vitiligo including unisegmental, bisegmental or multisegmental vitiligo, non-segmental vitiligo including acral, facial, or acrofacial vitiligo, centrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, generalized vitiligo, universal vitiligo, mixed vitiligo (nonsegmental associated with segmental vitiligo), focal vitiligo, solitary mucosal vitiligo or vitiligo with or without leukotricia (involvement of body hair) or any type of vitiligo set forth in Table 1 below:

TABLE 1

Classification of vitiligo.

| NOMENCLATURE | SUBSET | NOTES |
| --- | --- | --- |
| Non-segmental vitiligo | Acrofacial | Usually limited to face, head, hands, and feet |
| | Generalized | Symmetrical macules, mainly hands, fingers, face, and trauma-exposed areas |
| | Mucosal (at least two sites involved) | Involvement of the oral and/or genital mucosae with other sites of skin involvement |
| | Universal | Depigmentation affects 80%-90% of body surface. |
| Segmental vitiligo | Unisegmental | One or more depigmented macules distributed on one side of the body |
| | Bisegmental | Two segmental lesions distributed either unilaterally or bilaterally |
| | Plurisegmental | Multiple segmental lesions distributed either unilaterally or bi-laterally |
| Mixed vitiligo | Occurrence of SV and NSV | SV followed by NSV with a delay of at least 6 months. At least 20% of a dermatomal segment affected by SV. |
| Unclassified vitiligo | Focal vitiligo | Isolated macules that do not have a segmental distribution. No evolution into NSV after at least 2 years |
| | Mucosal vitiligo (only one site involved) | Exclusive involvement of the oral or genital mucosae |

In an embodiment, said skin disorder is atopic dermatitis, psoriasis, psoriasis vulgaris, skin sensitization, skin irritation, skin rash, contact dermatitis, allergic contact sensitization, allergic dermatitis, inflammatory dermatoses, or neutrophilic dermatoses.

"Pruritus", as used herein, is interchangeable with "itch." In some embodiments, pruritus includes chronic idiopathic pruritus, as well as pruritic components of other pruritic disorders. In some embodiments, pruritus may be a symptom of a disease or condition selected from the group consisting of: allergic reaction, arthropod bites, athlete's foot, atopic dermatitis (AD), atopic itch, atopic dermatitis-associated itch, autoimmune responses, autoimmune connective tissue disease, bacterial infection, biliary itch, broad activation of the immune responses, body louse, bullous diseases, brachioradial pruritus, brain tumors, chronic idiopathic pruritus, contact dermatitis, cholestasis, cutaneous larva migrans, cutaneous T-cell lymphoma, nervous system damage, dandruff, delusional parasitosis, dermatomyositis, dermatosis of pregnancy, diabetes mellitus, drug eruptions, dysregulation of neuronal processes and sensory perception, eczema, eosinophilic folliculitis, foreign objects or devices on skin, fungal infection, gestational pemphigoid, head lice, herpes, hidradenitis suppurativa, hives, Hodgkin's disease, hyperparathyroidism, idiopathic chronic itch, inflammation, insect infestation, insect bites, insect stings, intrahepatic cholestasis of pregnancy, iron deficiency anemia, increased accumulation of exogenous opioids or synthetic opioids, internal cancer, jaundice, lichen planus, lichen sclerosus, lupus erythematosus, lymphoma, lymphoma-associated itch, leukemia-associated itch, malignancy, mastocytosis, menopause, multiple sclerosis, neoplasm, nerve irritation, neurogenic itch, neuropathic itch, notalgia paresthetica, notalgia obsessive-compulsive disorders, paresthetica, parasitic infection, popular urticaria, pediculosis, peripheral neuropathy, photodermatitis, polycythemia vera, psychiatric disease, psychogenic itch, pruritic popular eruption of HIV, pruritic urticarial papules and plaques of pregnancy (PUPPP), psoriasis, psoriasis-associated itch, psoriatic itch, pubic lice, punctate palmoplantar keratoderma, renal itch, rheumatoid arthritis, scabies, scar growth, shaving, seborrheic dermatitis, stasis dermatitis, sunburn, swimmer's itch, systemic immune senescence, tactile hallucinations, Th17-associated inflammation, thyroid illness, uremia, pruritus or uremic itch, urticaria, urticarial itch, varicella, viral infection, wound or scab healing, and xerosis.

In an embodiment, the hair loss disorder is selected from alopecia, alopecia areata, patchy alopecia areata, alopecia totalis, alopecia universalis, ophiasis pattern alopecia areata, sisaihpo pattern alopecia areata, androgenetic alopecia (male and female pattern hair loss), telogen effluvium, tinea capitis, hypotrichosis, hereditary hypotrichosis simplex, scarring alopecia, lichen planopilaris, central centrifugal cicatricial alopecia, folliculitis decalvans, or frontal fibrosing alopecia.

In an embodiment, the connective tissue disease is selected from SLE (systemic lupus erythematosus), cutaneous lupus (e.g. SCLE, discoid lupus), chilblain lupus erythematosus, myositis, polymyositis, dermatomyositis, scleroderma, Sjogren's syndrome, polychondritis (relapsing polychondritis), vasculitis, or large vessel vasculitis.

In an embodiment, the nephropathy is selected from an immunologically mediated nephropathy, autoimmune nephropathy, chronic progressive nephropathies, diabetic nephropathy, renal fibrosis, ischemic/reperfusion injury associated, HIV associated nephropathy, ureteral obstructive nephropathy, glomerulosclerosis, proteinuria, nephrotic syndrome, polycystic kidney disease, autosomal dominant polycystic kidney disease or diabetic kidney disease.

In an embodiment, said cancer is a solid tumor.

In an embodiment, said cancer is prostate cancer, renal cancer, hepatic cancer, breast cancer, lung cancer, thyroid cancer, Kaposi's sarcoma, Castleman's disease or pancreatic cancer.

In an embodiment, said cancer is lymphoma, leukemia, or multiple myeloma.

In an embodiment, said myeloproliferative disorder (MPD) is polycythemia vera (PV), essential thrombocythemia (ET), myeloid metaplasia with myelofibrosis (MMM), primary myelofibrosis (PMF), chronic myelogenous leukemia (CML), chronic myelomonocytic leukemia (CMML), hypereosinophilic syndrome (HES), idiopathic myelofibrosis (IMF), or systemic mast cell disease (SMCD).

In an embodiment, said myeloproliferative disorder is myelofibrosis.

In an embodiment, said myeloproliferative disorder is primary myelofibrosis (PMF).

In some embodiments, the JAK-mediated disease or disorder is a cancer, prostate cancer, renal cancer, hepatic cancer, breast cancer, lung cancer, thyroid cancer, Kaposi's sarcoma, Castleman's disease, pancreatic cancer, lymphoma, leukemia, multiple myeloma, neoplasia, primary malignancies, secondary or recurrent malignancies, metastatic malignancies, angiogenesis disorders, acute lymphocytic leukemia, acute and chronic myelogenous leukemia, chronic lymphocytic leukemia, acute lymphoblastic leukemia, promyelocytic leukemia, B-cell lymphoma, T-cell lymphoma, mantle cell lymphoma, hairy cell lymphoma, Burkitt's lymphoma, mast cell tumors, Hodgkin's disease or non-Hodgkin's disease, myelodysplastic syndrome, sarcoma, fibrosarcoma, rhabdomyosarcoma; astrocytoma, neuroblastoma, glioma, schwannoma, non-melanoma skin cancers, squamous cell carcinoma, basal cell carcinoma, Merkel cell carcinoma, seminoma, teratocarcinoma, osteosarcoma, xeroderma pigmentosum, keratoacanthoma, thyroid follicular cancer, melanoma, teratoma, rhabdomyosarcoma, metastatic and bone disorders, glioblastoma multiforme, a malignancy, a myeloproliferative disorder, a hematopoietic neoplasm, a myeloid neoplasm, a lymphoid neoplasm, myelofibrosis, primary myelofibrosis, polycythemia vera, essential thrombocythemia, acute and chronic leukemias, lymphomas, cutaneous lymphomas, mycosis fungoides, other myeloid malignancies, myelodysplastic syndrome, myeloproliferative disorder, polycythemia vera, essential thrombocythemia, myeloid metaplasia with myelofibrosis, primary myelofibrosis, chronic myelogenous leukemia (CML), chronic myelomonocytic leukemia, hypereosinophilic syndrome, idiopathic myelofibrosis (IMF), systemic mast cell disease, and a combination thereof.

In an embodiment, said bone resorption disease is osteoporosis, osteoarthritis, bone resorption associated with hormonal imbalance, bone resorption associated with hormonal therapy, bone resorption associated with autoimmune disease, or bone resorption associated with cancer.

In some embodiments, the JAK-mediated disease or disorder is a fibrotic disorder. Exemplary fibrotic disorders include systemic sclerosis/scleroderma, lupus nephritis, connective tissue disease, wound healing, surgical scarring, spinal cord injury, CNS scarring, acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury, glomerulonephritis, chronic kidney disease (for example, diabetic nephropathy), hypertension induced nephropathy, alimentary track or gastrointestinal fibrosis, renal fibrosis, hepatic or biliary fibrosis, liver fibrosis (for example, nonalcoholic steatohepatitis, hepatitis C, or hepatocellular carcinoma), cirrhosis (for example, primary biliary cirrhosis or cirrhosis due to fatty liver disease (for example, alcoholic and nonalcoholic steatosis), radiation induced fibrosis (for example, head and neck, gastrointestinal or pulmonary), primary sclerosing cholangitis, restenosis, cardiac fibrosis (for example, endomyocardial fibrosis or atrial fibrosis), ophthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

In some embodiments, the JAKmediated disease or disorder is a metabolic disorder. Exemplary metabolic disorders include obesity, steroid-resistance, glucose intolerance, and metabolic syndrome. In some embodiments, the JAK-mediated disease or disorder is a neoplasia. Exemplary neoplasias include cancers. In some embodiments the neoplasms include primary malignancies, secondary or recurrent malignancies, or metastatic malignancies. In some embodiments, exemplary neoplasias include angiogenesis disorders, multiple myeloma, leukemias (for example, acute lymphocytic leukemia, acute and chronic myelogenous leukemia, chronic lymphocytic leukemia, acute lymphoblastic leukemia, or promyelocytic leukemia), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease), myelodysplastic syndrome, sarcoma, fibrosarcoma, rhabdomyosarcoma; astrocytoma, neuroblastoma, glioma and schwannomas; melanoma, non-melanoma skin cancers, (e.g. squamous cell carcinoma, basal cell carcinoma, Merkel cell carcinoma), seminoma, teratocarcinoma, osteosarcoma, xeroderma pigmentosum, keratoacanthoma, thyroid follicular cancer, Kaposi's sarcoma, melanoma, teratoma, rhabdomyosarcoma, metastatic and bone disorders, as well as cancer of the bone, mouth/pharynx, esophagus, larynx, stomach, intestine, colon, rectum, lung (for example, non-small cell lung cancer or small cell lung cancer), liver, pancreas, nerve, brain (for example, glioma or glioblastoma multiforme), head and neck, throat, ovary, uterus, prostate, testis, bladder, kidney, breast, gall bladder, cervix, thyroid, prostate, and skin.

In some embodiments, the JAK-mediated disorder is a cardiovascular or cerebrovascular disorder. Exemplary cardiovascular disorders include atherosclerosis, restenosis of an atherosclerotic coronary artery, acute coronary syndrome, myocardial infarction, cardiac-allograft vasculopathy and stroke. Exemplary cerebrovascular diseases include central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

In some embodiments, the JAK-mediated disorder is a gastrointestinal disorder including, but not limited to, inflammatory bowel disease, Crohn's disease, ulcerative colitis, (e.g., proctosigmoiditis, pancolitis, ulcerative proctitis, left-sided colitis), collagenous colitis, lymphocytic colitis, immune checkpoint inhibitor induced colitis, ileitis, eosinophilic esophagitis, graft vs. host disease, graft versus host disease-related colitis, infectious colitis, indeterminant colitis, atypical colitis, autoimmune enteropathy, irritable bowel syndrome, spastic colitis, acute and chronic pancreatitis, Celiac disease, Behcet's disease, primary biliary cirrhosis, primary sclerosing cholangitis, periodontitis, gingivitis, esophagitis, gastritis, gastric and duodenal ulcers, peritonitis, periodontitis, enteritis, colitis, stomatitis, and stomal/peristomal pyoderma gangrenosum.

In some embodiments, the JAK-mediated disorder is inflammatory bowel disease.

Also provided herein is a compound as disclosed herein for use as a medicament.

Also provided herein is a compound as disclosed herein for use as a medicament for the treatment of a JAK-mediated disease.

Also provided is the use of a compound as disclosed herein as a medicament.

Also provided is the use of a compound as disclosed herein as a medicament for the treatment of a JAK-mediated disease.

Also provided is a compound as disclosed herein for use in the manufacture of a medicament for the treatment of a JAK-mediated disease.

Also provided is the use of a compound as disclosed herein for the treatment of a JAK-mediated disease.

Also provided herein is a method of inhibition of JAK comprising contacting JAK enzyme with a compound as disclosed herein, or a derivative thereof.

In some embodiments, the compound is a gut-restricted compound.

Also provided herein is a method for achieving an effect in a patient comprising the administration of a therapeutically effective amount of a compound as disclosed herein, or a salt thereof, to a patient, wherein the effect is chosen from cognition enhancement.

In certain embodiments, the JAK-mediated disease is chosen from pruritus, alopecia, alopecia areata, vitiligo, male pattern androgenetic alopecia, female pattern androgenetic alopecia, atopic dermatitis, rheumatoid arthritis, psoriatic arthritis, and psoriasis.

The compounds can be administered in various modes, e.g. oral, parenteral (including subcutaneous, intradermal, intramuscular, intravenous, intraarticular, and intramedullary), intraperitoneal, intrathecal, intradural, transmucosal, transdermal, rectal, intranasal, topical (including, for example, dermal, buccal, sublingual and intraocular), intravitreal, or intravaginal administration. The specific dose level for any particular patient will depend upon a variety of factors including the activity of the specific compound employed, the age, body weight, general health, sex, diet, time of administration, route of administration, rate of excretion, drug combination, the precise disorder being treated, and the severity of the indication or condition being treated. Also, the route of administration may vary depending on the condition and its severity.

In certain embodiments, a topically or orally administered JAK inhibitor/antagonist described herein for the treatment of alopecia areata (e.g., patchy alopecia areata, alopecia totalis, alopecia universalis) alone or in combination with topical or intralesional corticosteroids, topical minoxidil, oral minoxidil, topical or systemic antiandrogens, oral finasteride, oral dutasteride, topical or oral cortexolone 17α-propionate, ketoconazole, spionolactone, prostaglandin F2 analogues (e.g. bimatoprost or latanoprost), contact sensitization therapy such as with squaric acid dibutyl ester, dinitrochlorobenzene, diphencyprone, topical or oral methoxalen and ultraviolet a (PUVA), topical anthralin, hair transplantation procedures, microneedling, low level laser light therapy, low level non-laser light therapy, platelet-rich plasma (PRP) therapy or other therapies known to have beneficial effects in the condition.

In certain embodiments, a topically or orally administered JAK inhibitor/antagonist disclosed herein the treatment of male or female-pattern baldness (androgenetic alopecia) alone or in combination with topical minoxidil, oral minoxidil, topical or systemic antiandrogens, oral finasteride, oral dutasteride, topical or oral cortexolone 17α-propionate, ketoconazole, spionolactone, prostaglandin F2 analogues (e.g. bimatoprost or latanoprost), contact sensitization therapy such as with squaric acid dibutyl ester, dinitrochlorobenzene, diphencyprone, topical or oral methoxalen and ultraviolet a (PUVA), topical anthralin, hair transplantation procedures, microneedling, low level laser light therapy, low level non-laser light therapy, platelet-rich plasma (PRP) therapy or other therapies known to have beneficial effects in the condition.

In certain embodiments, a topically or orally administered JAK inhibitor/antagonist disclosed herein can be used for the treatment of scarring alopecia (e.g., cicatricial alopecia, central centrifugal cicatricial alopecia, lichen planopilaris, frontal fibrosing alopecia, folliculitis decalvans) alone or in combination with topical minoxidil, oral minoxidil, topical or systemic antiandrogens, oral finasteride, oral dutasteride, topical or oral cortexolone 17α-propionate, ketoconazole, spionolactone, prostaglandin F2 analogues (e.g. bimatoprost or latanoprost), contact sensitization therapy such as with squaric acid dibutyl ester, dinitrochlorobenzene, diphencyprone, topical or oral methoxalen and ultraviolet a (PUVA), topical anthralin, hair transplantation procedures, microneedling, low level laser light therapy, low level non-laser light therapy, platelet-rich plasma (PRP) therapy or other therapies known to have beneficial effects in the condition.

In certain embodiments, the compounds may be used for the treatment of vitiligo (e.g., localized vitiligo, focal vitiligo, generalized vitiligo, segmental vitiligo, acral vitiligo, facial vitiligo, acrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, mixed acrofacial and vulgaris vitiligo, or universal vitiligo) alone or in combination with topical corticosteroids, topical tacrolimus, topical pimecrolimus, phototherapy such as ultraviolet light therapy with UVB, narrow-band UVB, oral or topical psoralen plus ultraviolet A (PUVA), calcipotriene or other topical vitamin D analogs, excimer laser phototherapy, systemic immunosuppressive agents, surgical treatments such as skin minigrafting, transplantation of autologous epidermal suspension, camouflage such as with make-up or dihydroxyacetone and such, or other therapies known to have beneficial effects in the condition.

Specific JAK-mediated diseases to be treated by the compounds, compositions, and methods disclosed herein include a skin disorder, pruritus, cancer, Alzheimer's disease, an inflammatory condition, and an autoimmune condition.

In an embodiment, said skin disorder is pruritus, atopic dermatitis, psoriasis, acne vulgaris, comedonal acne, inflammatory acne, nodulo-cystic acne, scarring acne, hidradenitis suppurativa, pyoderma gangrenosum, skin sensitization, skin irritation, skin rash, contact dermatitis or allergic contact sensitization.

Besides being useful for human treatment, certain compounds and compositions disclosed herein may also be useful for veterinary treatment of companion animals, exotic animals and farm animals, including mammals, rodents, and the like. More preferred animals include horses, dogs, and cats.

Combination Therapy

The compounds and pharmaceutical compositions of the present disclosure may be used to prevent or treat an JAK-mediated disorder by the sequential or co-administration of another pharmaceutical agent.

The compounds of the present invention can be used, alone or in combination with other pharmaceutically active compounds, to treat conditions such as those previously described above. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In certain instances, it may be appropriate to administer at least one of the compounds described herein, or a derivative thereof, in combination with another pharmaceutical agent. By way of example only, if one of the side effects experienced by a patient upon receiving one of the compounds herein is hypertension, then it may be appropriate to administer an anti-hypertensive agent in combination with the initial pharmaceutical agent. Or, by way of example only, the therapeutic effectiveness of one of the compounds described herein may be enhanced by administration of an adjuvant (i.e., by itself the adjuvant may only have minimal therapeutic benefit, but in combination with another pharmaceutical agent, the overall therapeutic benefit to the patient is enhanced). Or, by way of example only, the benefit of experienced by a patient may be increased by administering one of the compounds described herein with another pharmaceutical agent (which also includes a therapeutic regimen) that also has therapeutic benefit. By way of example only, in a treatment for diabetes involving administration of one of the compounds described herein, increased therapeutic benefit may result by also providing the patient with another pharmaceutical agent for diabetes. In any case, regardless of the disease, disorder or condition being treated, the overall benefit experienced by the patient may simply be additive of the two pharmaceutical agents or the patient may experience a synergistic benefit.

Specific, non-limiting examples of possible combination therapies include use of compounds of embodiments herein with: chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

Specific, non-limiting examples of possible combination therapies for inflammation include use of certain compounds of the disclosure with: (1) corticosteroids, including but not limited to cortisone, dexamethasone, and methylprednisolone; (2) nonsteroidal anti-inflammatory drugs (NSAIDs), including but not limited to ibuprofen, naproxen, acetaminophen, aspirin, fenoprofen (NALFON™), flurbiprofen (ANSAID™), ketoprofen, oxaprozin (DAYPRO™) diclofenac sodium (VOLTAREN™), diclofenac potassium (CATAFLAM™), etodolac (LODINE™), indomethacin (INDOCIN™), ketorolac (TORADOL™), sulindac (CLINORIL™) tolmetin (TOLECTIN™), meclofenamate (MECLOMEN™), mefenamic acid (PONSTEL™) nabumetone (RELAFEN™) and piroxicam (FELDENE™); (3) immunosuppressants, including but not limited to methotrexate (RHEUMATREX™), leflunomide (ARAVA™), azathioprine (IMURAN™), cyclosporine (NEORAL™, SANDIMMUNE™), tacrolimus and cyclophosphamide (CYTOXAN™); (4) CD20 blockers, including but not limited to rituximab (RITUXAN™); (5) Tumor Necrosis Factor (TNF) blockers, including but not limited to etanercept (ENBREL™), infliximab (REMICADE™) and adalimumab (HUMIRA™)(6) interleukin-1 receptor antagonists, including but not limited to anakinra (KINERET™)(7) interleukin-6 inhibitors, including but not limited to tocilizumab (ACTEMRA™); (8) interleukin-17 inhibitors, including but not limited to AIN457; (9) Janus kinase inhibitors, including but not limited to tasocitinib; and (10) syk inhibitors, including but not limited to fostamatinib.

Specific, non-limiting examples of possible combination therapies for the treatment of cancer include use of certain compounds of the disclosure with: (1) alkylating agents, including but not limited to cisplatin (PLATIN™), carboplatin (PARAPLATIN™), oxaliplatin (ELOXATIN™), streptozocin (ZANOSAR™), busulfan (MYLERAN™) and cyclophosphamide (ENDOXAN™); (2) anti-metabolites, including but not limited to mercaptopurine (PURINETHOL™), thioguanine, pentostatin (NIPENT™), cytosine arabinoside (ARA-C™) gemcitabine (GEMZAR™), fluorouracil (CARAC™), leucovorin (FUSILEV™) and methotrexate (RHEUMATREX™); (3) plant alkaloids and terpenoids, includingbut not limited to vincristine (ONCOVIN™), vinblastine and paclitaxel (TAXOL™); (4) topoisomerase inhibitors, including but not limited to irinotecan (CAMPTOSAR™), topotecan (HYCAMTIN™) and etoposide (EPOSIN™); (5) cytotoxic antibiotics, including but not limited to actinomycin D (COSMEGEN™), doxorubicin (ADRIAMYCIN™), bleomycin (BLENOXANE™) and mitomycin (MITOSOL™); (6) angiogenesis inhibitors, including but not limited to sunitinib (SUTENT™) and bevacizumab (AVASTIN™); (7) tyrosine kinase inhibitors, including but not limited to imatinib (GLEEVEC™), erlotinib (TARCEVA™) lapatininb (TYKERB™) and axitinib (INLYTA™); and (8) immune checkpoint inhibitors, including but not limited to atezolizumab (TECENTRIQ™), avelumab (BAVENCIO™) durvalumab (IMFINZI™), ipilimumab (YERVOY™), pembrolizumab (KEYTRUDA™) nivolumab (OPDIVO™), and tremelimumab.

The compounds and pharmaceutical compositions of the present disclosure may be used to prevent or treat a JAK-mediated disease by the sequential or co-administration of another pharmaceutical agent.

In some embodiments, the compounds disclosed in embodiments herein can also be co-administered (concurrently or sequentially) with a variety of other pharmaceutical agents or treatments, for example, pharmaceutical agents or treatments that are administered systemically, such as orally or parenterally. Examples of such systemic treatments include topical or systemic corticosteroids (such as prednisone), antibiotics (such as erythromycin, tetracycline, and dicloxacillin), antifungal agents (such as ketoconazole and fluconazole sold under the tradename Diflucan™), antiviral agents (such as valacyclovir sold under the tradename Valtrex™ acyclovir, and famciclovir sold under the tradename Famvir™), corticosteroids, immunosuppressants (such as cyclophosphamide sold under the tradename Cytoxan™ azathioprine, methotrexate, mycophenolate), biologics (such as rituximab sold under the tradename Rituxan™, etanercept sold under the tradename Enbrel™, adalimumab sold under the tradename Humira™, infliximab sold under the tradename Remicade™, ustekinumab sold under the tradename Stelara™, and alefacept sold under the tradename Amevive™), and/or thyroid hormone replacement.

In some embodiments, other therapies that can be used in combination with the compounds disclosed herein include, for example, mercaptopurine, topical or systemic corticosteroids such as prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil, azathioprine, various antibodies, for example, anti-lymphocyte globulin (ALG), antithymocyte globulin (ATG), monoclonal anti-T-cell antibodies (OKT3), and irradiation. These various agents can be used in accordance with their standard or common dosages, as specified in the prescribing information accompanying commercially available forms of the drugs (see also, the prescribing information in the 2006 Edition of The Physician's Desk Reference). In some embodiments, standard dosages of these agents may be reduced when used in combination with the compounds of embodiments herein. Without limiting the scope of this disclosure, it is believed the such combination may result in synergistic results with better efficacy, less toxicity, longer duration of action, or quicker response to therapy. In some embodiments, the combination therapies in embodiments herein may be administered in sub-therapeutic amounts of either the compounds of embodiments herein or the additional pharmaceutical agents, or both. Azathioprine is currently available from Salix Pharmaceuticals, Inc. under the brand name Azasan™; mercaptopurine is currently available from Gate Pharmaceuticals, Inc. under the brand name Purinethol™; prednisone and prednisolone are currently available from Roxane Laboratories, Inc.; methyl prednisolone is currently available from Pfizer; sirolimus (rapamycin) is currently available from Wyeth-Ayerst under the brand name Rapamune™; tacrolimus is currently available from Fujisawa under the brand name Prograf™; cyclosporine is current available from Novartis under the brand name Sandimmune™ and Abbott under the brand name Gengraf™; IMPDH inhibitors such as mycophenolate mofetil and mycophenolic acid are currently available from Roche under the brand name Cellcept™ and Novartis under the brand name Myfortic™; azathioprine is currently available from Glaxo Smith Kline under the brand name Imuran™; and antibodies are currently available from Ortho Biotech under the brand name Orthoclone™, Novartis under the brand name Simulect™ (basiliximab) and Roche under the brand name Zenapax™ (daclizumab).

In some embodiments, the compounds of embodiments herein are administered in conjunction, concomitantly or adjunctively, with the pharmaceutical agents or therapies above and/or with a pharmaceutical agent or therapy for another disease. For example, the compounds of embodiments herein may be combined with thyroid hormone replacement therapy or with anti-inflammatory or immunomodulatory therapies.

In some embodiments, the combination therapies in embodiments herein may be administered in sub-therapeutic amounts of either the compounds of embodiments herein or the additional pharmaceutical agents, or both.

In any case, the multiple pharmaceutical agents (at least one of which is a compound disclosed herein) may be administered in any order or even simultaneously. If simultaneously, the multiple pharmaceutical agents may be provided in a single, unified form, or in multiple forms (by way of example only, either as a single pill or as two separate pills). One of the pharmaceutical agents may be given in multiple doses, or both may be given as multiple doses. If not simultaneous, the timing between the multiple doses may be any duration of time ranging from a few minutes to eight weeks or at any interval appropriate to maintain the desired therapeutic efficacy. In some embodiments, the timing between the multiple doses may be a minute, an hour, six hours, a day, two days, three days, four days, five days, six days, a week, two weeks, three weeks, four weeks, five weeks, six weeks, seven weeks or eight weeks.

Thus, in another aspect, certain embodiments provide methods for treating JAK-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of JAK-mediated disorders.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-inflammatory drugs, anti-atherosclerotic drugs, immunosuppressive drugs, immunomodulatory drugs, cytostatic drugs, anti-proliferative agents, angiogenesis inhibitors, kinase inhibitors, cytokine blockers and inhibitors of cell adhesion molecules.

In another embodiment, the pharmaceutical compositions can further include one or more additional pharmaceutical agents such as a chemotherapeutic, steroid, anti-inflammatory compound, or immunosuppressant.

JAK inhibitor compositions described herein are also optionally used in combination with other therapeutic reagents that are selected for their therapeutic value for the condition to be treated. In general, the pharmaceutical compositions described herein and, in embodiments where combinational therapy is employed, other agents do not have to be administered in the same pharmaceutical composition, and, because of different physical and chemical characteristics, are optionally administered by different routes. The initial administration is generally made according to established protocols, and then, based upon the observed effects, the dosage, modes of administration and times of administration subsequently modified. In certain instances, it is appropriate to administer a JAK inhibitor composition as described herein in combination with another therapeutic agent. By way of example only, if one of the side effects experienced by a patient upon receiving a JAK inhibitor composition as described herein is rash, then it is appropriate to administer an anti-histamine agent in combination with the initial therapeutic agent. Or, by way of example only, the therapeutic effectiveness of a JAK inhibitor is enhanced by administration of another therapeutic agent (which also includes a therapeutic regimen) that also has therapeutic benefit. In any case, regardless of the disease, disorder or condition being treated, the overall benefit experienced by the patient is either simply additive of the two therapeutic agents or the patient experiences a synergistic benefit.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a JAK inhibitor as described herein) are administered in any order, or even simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods and compositions are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time period between the multiple administration steps ranges from, a few minutes to several hours, depending upon the properties of each pharmaceutical agent, such as potency, solubility, bioavailability, plasma half-life and kinetic profile of the pharmaceutical agent. Circadian variation of the target molecule concentration is optionally used to determine the optimal dose interval.

In another embodiment, a JAK inhibitor is optionally used in combination with procedures that provide additional or synergistic benefit to the patient. A JAK inhibitor and the additional therapy(ies) are optionally administered before, during or after the occurrence of a disease or condition, and the timing of administering the pharmaceutical composition containing a JAK inhibitor varies in some embodiments. Thus, for example, a JAK inhibitor is used as a prophylactic and is administered continuously to subjects with a propensity to develop conditions or diseases in order to prevent the occurrence of the disease or condition. A JAK inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A JAK inhibitor may be used in combination with drugs from the following classes: NSAIDs, immunosuppressive drugs, immunomodulatory drugs, cytostatic drugs, antiproliferative agents, angiogenesis inhibitors, biological agents, steroids, vitamin D3 analogs, retinoids, other kinase inhibitors, cytokine blockers, corticosteroids and inhibitors of cell adhesion molecules. Where a subject is suffering from or at risk of suffering from atherosclerosis or a condition that is associated with atherosclerosis, a JAK inhibitor composition described herein is optionally used together with one or more agents or methods for treating atherosclerosis or a condition that is associated with atherosclerosis in any combination. Examples of therapeutic agents/treatments for treating atherosclerosis or a condition that is associated with atherosclerosis include, but are not limited to any of the following: torcetrapib, aspirin, niacin, HMG CoA reductase inhibitors (e.g., atorvastatin, fluvastatin, lovastatin, pravastatin, rosuvastatin and simvastatin), colesevelam, cholestyramine, colestipol, gemfibrozil, probucol and clofibrate.)

Where a subject is suffering from or at risk of suffering from an inflammatory condition, a JAK inhibitor composition described herein is optionally used together with one or more agents or methods for treating an inflammatory condition in any combination.

One or more additional pharmaceutical agents such as, for example, anti-inflammatory agents, steroids, immunosuppressants, as well as one or more other ITK kinase inhibitors and/or other kinase inhibitors, such as JAK3 kinase, JAK kinase, JAK1/2 kinase, or JAK2 kinase inhibitors, such as, for example, those described in WO 99/65909, WO 00/00202, and/or WO/2004/099205, or other agents can be used in combination with the compounds of the present invention for treatment of JAK-associated diseases, disorders or conditions.

In certain embodiments, the additional pharmaceutical agent is selected from taxanes, inhibitors of bcr-abl, inhibitors of EGFR, DNA damaging agents, antimetabolites, paclitaxel, imatinib, dasatinib, nilotinib, erlotinib, gefitinib, cisplatin, oxaliplatin, carboplatin, anthracyclines, AraC, 5-FU, camptothecin, doxorubicin, idarubicin, paclitaxel, docetaxel, vincristine, a MEK inhibitor, U0126, a KSP inhibitor, vorinostat, pembrolizumab, nivolumab, atezolizumab, avelumab, tremelimumab, and durvalumab.

In some embodiments, said composition further comprises an additional pharmaceutical agent selected from a chemotherapeutic or anti-proliferative agent, antiviral, antibiotic, antihistamine, an emollient, systemic phototherapy, psoralen photochemotherapy, laser therapy, hormone replacement therapy, an anti-inflammatory agent, an immunomodulatory or immunosuppressive agent, a neurotrophic factor, an agent for treating cardiovascular disease, an agent for treating diabetes, and an agent for treating immunodeficiency disorders.

In some embodiments, one or more compounds of the embodiments herein can be used in combination with one or more other therapeutics used in the treatment of ITK-mediated disorders, and may improve the treatment response as compared to the response to the other therapeutics alone, without exacerbation of its toxic effects. In some embodiments, compounds of embodiments herein can be used in combination with one or more other ITK inhibitors and/or JAK inhibitors for the treatment of ITK-mediated disorders. Additive or synergistic effects are desirable outcomes of such combinations. The additional agents can be combined with the present compounds in a single or continuous dosage form, or the agents can be administered simultaneously or sequentially as separate dosage forms. In some embodiments, one or more additional agents can be administered to a patient in combination with at least one JAK inhibitor/antagonist described herein where the additional agents are administered intermittently as opposed to continuously.

For example, in certain embodiments, a topically or orally administered JAK inhibitor/antagonist described herein can be used for the treatment of alopecia areata (e.g. patchy alopecia areata, alopecia totalis, alopecia universalis) alone or in combination with topical or intralesional corticosteroids, topical minoxidil, oral finasteride, oral dutasteride, contact sensitization therapy such as with squaric acid dibutyl ester, dinitrochlorobenzene, diphencyprone, topical or oral methoxalen and ultraviolet a (PUVA), topical anthralin, hair transplantation procedures, or other therapies known to have beneficial effects in the condition.

For example, in certain embodiments, a topically or orally administered JAK inhibitor/antagonist disclosed herein can be used for the treatment of male or female-pattern baldness (androgenetic alopecia) alone or in combination with topical minoxidil, oral finasteride (in male), oral dutasteride (in male), topical antiandrogens, hair transplantation procedures, or other therapies known to have beneficial effects in the condition.

For example, in certain embodiments, the compounds can be used for the treatment of vitiligo (e.g. localized vitiligo, focal vitiligo, generalized vitiligo, segmental vitiligo, acral vitiligo, facial vitiligo, acrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, mixed acrofacial and vulgaris vitiligo, or universal vitiligo) alone or in combination with topical corticosteroids, topical tacrolimus, topical pimecrolimus, phototherapy such as ultraviolet light therapy with UVB, narrow-band UVB, oral or topical psoralen plus ultraviolet A (PUVA), calcipotriene or other topical vitamin D analogs, excimer laser phototherapy, systemic immunosuppressive agents, surgical treatments such as skin minigrafting, transplantation of autologous epidermal suspension, camouflage such as with make-up or dihydroxyacetone and such, or other therapies known to have beneficial effects in the condition.

In certain embodiments the compounds of the disclosure may be used in combination with one or more agents which act by the same mechanism or by different mechanisms to effect treatment of gastrointestinal disorders. The different agents may be administered sequentially or simultaneously (in separate compositions or in the same composition). Useful classes of agents for combination therapy include, but are not limited to, aminosalicylates, steroids, systemic immunosuppressants, anti-TNFα antibodies, TNF alpha ligand inhibitor, TNF binding agent, anti-VLA-4 antibodies, anti-integrin Cv37 antibodies, anti-bacterial agents, Glucocorticoid agonists, Nuclear factor kappa B inhibitors, 5-Lipoxygenase inhibitors, integrin alpha-4/beta-7 antagonist, Cyclooxygenase inhibitors, IL-23 antagonists, Leukotriene BLT receptor antagonist, IL-6 antagonists, IL-8 antagonists, integrin antagonists, nicotinic acetylcholine receptor agonists, PPAR gamma agonists, sphingosine-1-phosphate receptor-1 modulators, B-lymphocyte antigen CD20 inhibitors, calcineurin inhibitors, CD3 antagonist, cell adhesion molecule inhibitors, eosinophil peroxidase inhibitors, heparin agonists, ICAM1 gene inhibitors, IL-13 antagonists, IL-2 receptor alpha subunit inhibitors, insulin sensitizers, interferon beta ligands, interferon gamma receptor antagonists, interleukin-1 beta ligand modulators, MAdCAM inhibitors, PDE 4 inhibitors, sphingosine-1-phosphate receptor-1 agonists, TLR-9 agonists, acetylcholinesterase inhibitors, ACTH receptor agonists, activin receptor antagonists, CCR5 chemokine antagonists, CCR9 chemokine antagonists, and anti-diarrheal medicines.

Aminosalicylates that may be used in combination with the presently disclosed compounds include, but are not limited to, mesalamine, osalazine and sulfasalazine. Examples of steroids include, but are not limited to, prednisone, prednisolone, hydrocortisone, budesonide, beclomethasone, and fluticasone. Systemic immunosuppressants useful for treatment of inflammatory disorders include, but are not limited to cyclosporine, azathioprine, methotrexate, 6-mercaptopurine, and tacrolimus. Further, anti-TNFα antibodies, which include, but are not limited to, infliximab, adalimumab, golimumab, and certolizumab, may be used in combination therapy. Useful compounds acting by other mechanisms include anti-VLA-4 antibodies, such as natalizumab, anti-integrin $α_4β_7$ antibodies, such as vedolizumab, anti-bacterial agents, such as rifaximin, and anti-diarrheal medicines, such as loperamide. (Mozaffari et al. *Expert Opin. Biol. Ther.* 2014, 14, 583-600; Danese, Gut, 2012, 61, 918-932; Lam et al., *Immunotherapy*, 2014, 6, 963-971.)

Other compounds that may be used in combination with the presently disclosed compounds include, but are not limited to opaganib, abatacept, mongersen, filgotinib, LYC-30937, BI-655130, mirikizumab, adalimumab, tacrolimus, rituximab, GSK-2982772, andecaliximab, naltrexone, risankizumab, QBECO, alicaforsen, etrolizumab, foralumab, ocrelizumab, vedolizumab, amiselimod, ozanimod, dolcanatide, catridecacog, budesonide, STNM-01, cannabidiol, telotristat etiprate, SHP-647, carotegrast methyl, peg-ilodecakin, TOP-1288, iberogast N, PF-06480605, peficitinib, beclomethasone, recombinant interferon beta-1a, infliximab, golimumab, tralokinumab, ustekinumab, certolizumab pegol, thalidomide, upadacitinib, apremilast, natalizumab, interferon beta-1a, rifaximin, RBX-2660, etrasimod, zileuton, fingolimod, cobitolimod, ropivacaine, ABX-464, PF-06700841, prednisolone, GLPG-0974, valganciclovir, ciclosporin, VB-201, tulinercept, MDGN-002, PTG-100, dexamethasone, GED-0507-34-Levo, bertilimumab, brazikumab, KHK-4083, rosiglitazone, mocravimod, sotrastaurin, KAG-308, PUR-0110, E-6007, balsalazide, basiliximab, LP-02, ASP-3291, *Trichuris suis* ova, K(D)PT, midismase, DNVX-078, vatelizumab, alequel, low molecular weight heparin, metenkefalin, tridecactide, HMPL-004, SB-012, olsalazine, balsalazide, propionyl-L-camitine, *Clostridium butyricum*, beclomethasone and acemannan.

General Synthetic Methods for Preparing Compounds

Compounds of the present invention can be prepared using methods illustrated in general synthetic schemes and experimental procedures detailed below. General synthetic schemes and experimental procedures are presented for purposes of illustration and are not intended to be limiting. Starting materials used to prepare compounds of the present invention are commercially available or can be prepared using routine methods known in the art. Representative procedures for the preparation of compounds of the invention are outlined in Schemes 1-4 below. Solvents and reagents, whose synthetic preparations are not described below, can be purchased at Sigma-Aldrich or Fisher Scientific.

Scheme 1 depicts the general synthesis of compounds of Formula (I) where $R_1$, $R_2$, $R_3$, and $R_4$ are defined as above, n is 0, 1 or 2, and X is a bromo or iodo. $PG_1$ is an indole protecting group such as benzenesulfonyl, toluenesulfonyl, mesitylenesulfonyl, t-butylcarbamate (Boc), allyl, benzyl, triisopropylsilyl (TIPS), 2-(trimethylsilyl)ethoxymethyl (SEM), or p-methoxybenzyl. $PG_2$ is a secondary amine protecting group such as t-butylcarbamate (Boc), benzyl carbamate (Cbz), benzyl (Bn), p-methoxybenzyl (PMB), or N-acetyl (Ac). Compound 1b is formed by protecting 1a with an appropriate indole protecting group following methods known to those in the art. Coupling of amine 1c with 1b under thermal conditions in a solvent such as N-methyl-2-pyrrolidinone (NMP) in the presence of triethylamine provides id. Alternatively, Buchwald conditions may be used for the coupling of 1b with 1c. Aryl 1e is formed by treating 1d with an arylboronate or heteroarylboronate under Suzuki conditions using a palladium catalyst in the presence of a base such as cesium carbonate in a dioxane/water solvent mixture. Deprotection of 1e under standard conditions for the appropriate protecting group ($PG_2$) provides 1f. Coupling of 1f with a compound of formula $HOR_4$ using peptide coupling conditions such as EDC and HOBT or halo-$R_4$ in the presence of an amine base yields compound 1g. Finally, removal of indole protecting group $PG_1$ of 1g provides 1h. Alternatively, one could remove both protecting groups of 1e and couple the intermediate with a compound of formula $HOR_4$ to yield compound 1h.

Scheme 1. General Synthesis of Pyrrolopyridine Heterocyclic-amine Analogs of Formula (I)

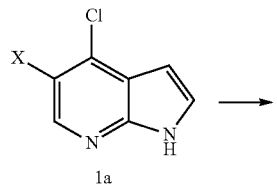

1a

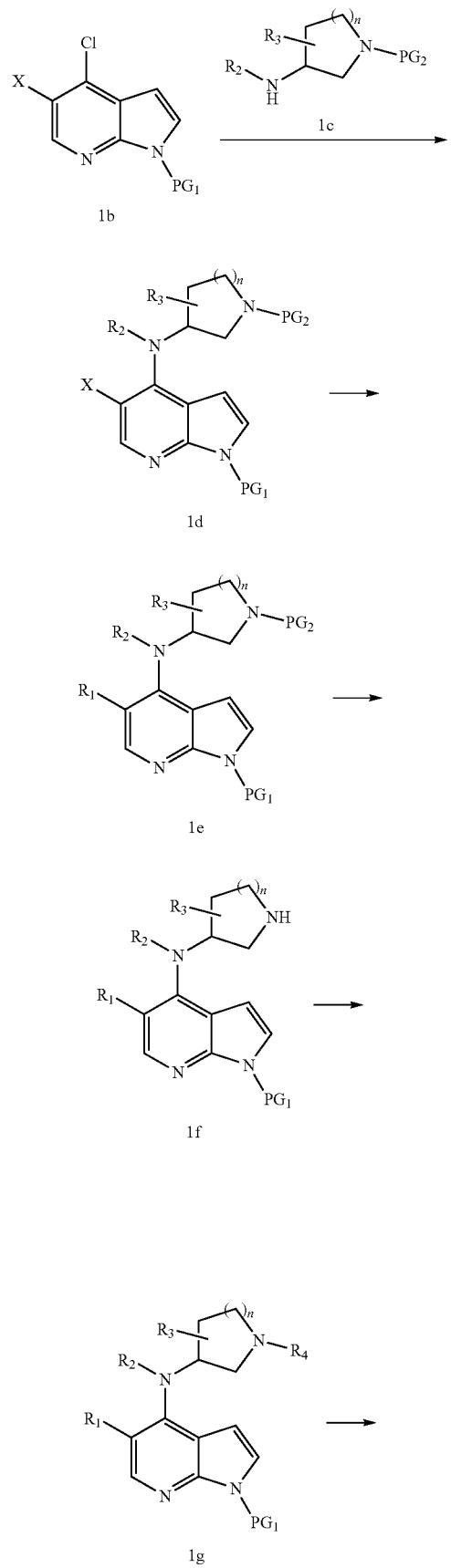

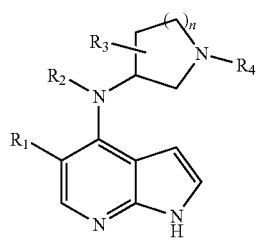

1h

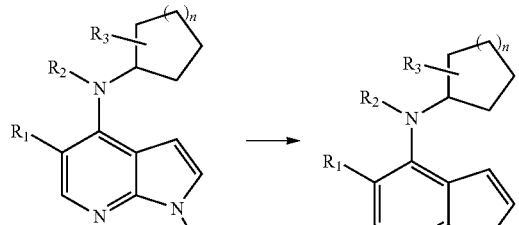

2e  2f

Scheme 2 depicts the general synthesis of compounds of Formula (I) where $R_1$, $R_2$, $R_3$, and $R_4$ are defined as above, n is 0, 1 or 2, and X is a bromo or iodo. Compound 2b is formed by protecting 2a with an appropriate indole protecting group. Coupling of amine 2c with 2b under thermal conditions in a solvent such as NMP in the presence of triethylamine provides 2d. Alternatively, Buchwald conditions may be used for the coupling of 1b with 1c. Aryl 2e is formed by treating 2d with an arylboronate or heteroarylboronate under Suzuki conditions using a palladium catalyst in the presence of a base such as cesium carbonate in a dioxane/water solvent mixture. Deprotection of 2e under standard conditions for the appropriate protecting group ($PG_1$) provides 2f. In some cases the $R_3$ substituent on 2d, 2e, or 2f may be modified to provide a different $R_3$ group by methods known to those skilled in the art.

Scheme 3 depicts the general synthesis of compounds of Formula (I) where $R_1$, $R_2$, $R_3$, and $R_4$ are defined as above, n is 0, 1 or 2, and X is a bromo or iodo. Boronate 3a is formed by reacting 1d with bis(pinacolato)diboron (B-Pin) in the presence of a palladium catalyst and a ligand such as X-Phos. Aryl 3b is formed by treating 3a with an arylbromide or heteroarylbromide under Suzuki conditions using a palladium catalyst in the presence of a base such as cesium carbonate in a dioxane/water solvent mixture. Deprotection of 3b under standard conditions for the appropriate protecting group ($PG_2$) provides 3c. Coupling of 3c with a compound of formula $HOR_4$ using peptide coupling conditions such as EDC and HOBT or halo-$R_4$ in the presence of an amine base yields compound 3d. Removal of indole protecting group $PG_1$ of 3d provides 3e. Alternatively, one could remove both protecting groups of 3b and couple the intermediate with a compound of formula $HOR_4$ to yield compound 3e.

Scheme 2. General Synthesis of Pyrrolopyridine Cycloalkylamine Analogs of Formula (II)

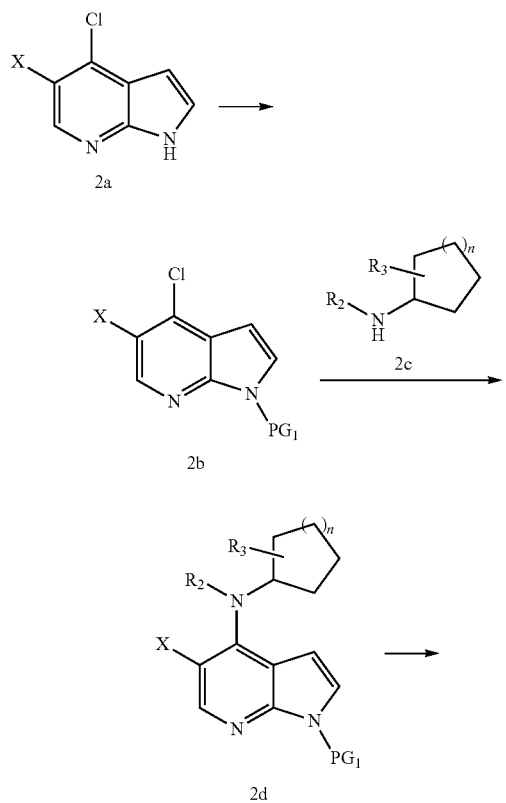

Scheme 3. General Synthesis of Pyrrolopyridine Heterocyclic-amine Analogs of Formula (I) by a Reversed Suzuki Coupling

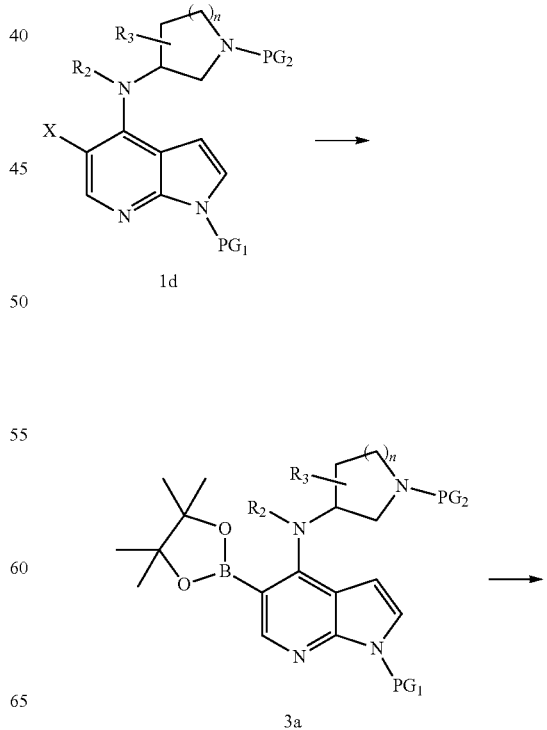

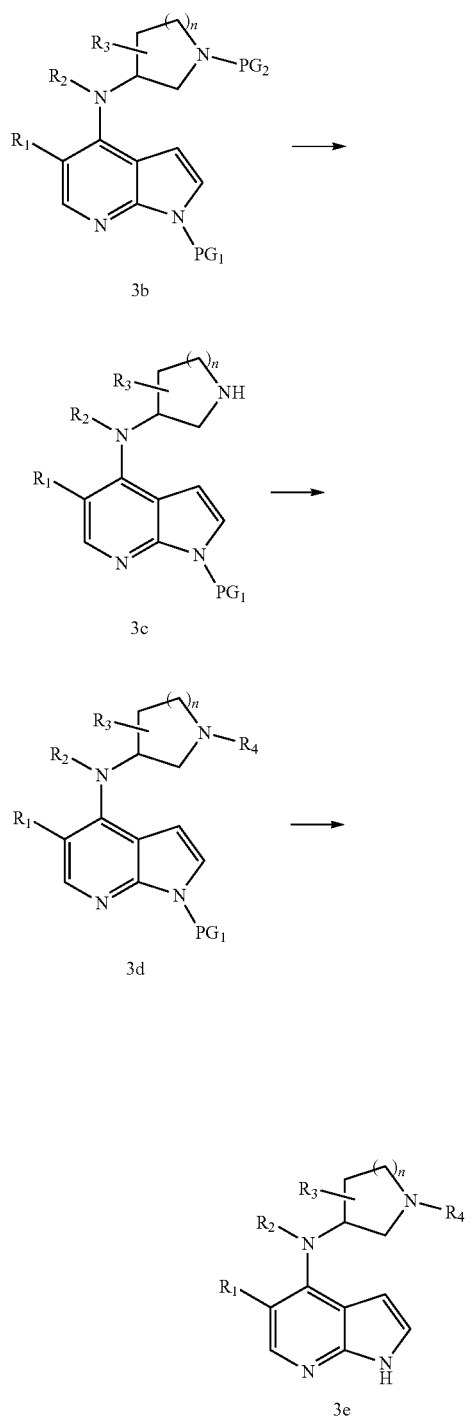

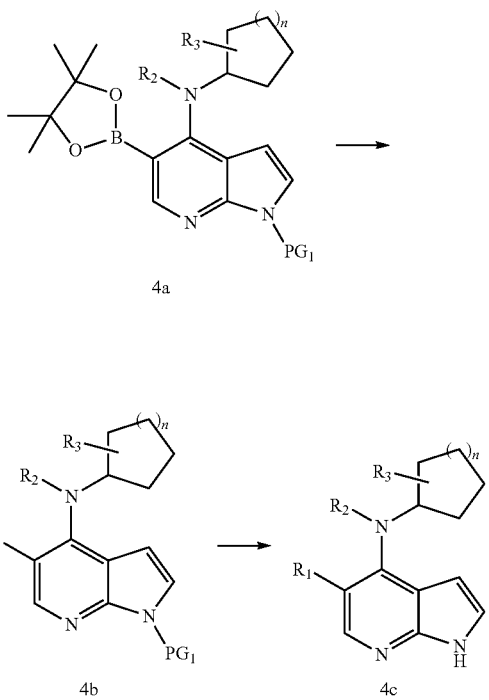

Exemplary synthetic methods for certain compounds detailed in the example section are further illustrated by the following.

Example 1: Preparation of (R)-3-oxo-3-(3-((5-(thiazol-4-yl)-1H-pyrrolo[2,3-b]pyridin-4-yl)amino)piperidin-1-yl)propanenitrile

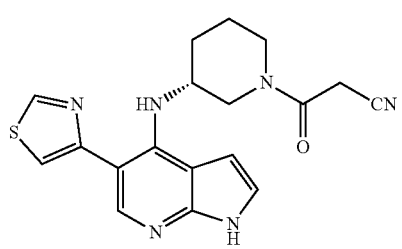 [SMILES: N#CCC(=O)N1CCC[C@@H](Nc2c(-c3cscn3)cnc3[nH]ccc23)C1]

Scheme 4 depicts the general synthesis of compounds of Formula (I) where $R_1$, $R_2$, $R_3$, and $R_4$ are defined as above, n is 0, 1 or 2, and X is a bromo or iodo. Boronate 4a is formed by reacting 1d with B-Pin in the presence of a palladium catalyst and a ligand such as X-Phos. Aryl 4b is formed by treating 4a with an arylbromide or heteroarylbromide under Suzuki conditions using a palladium catalyst in the presence of a base such as cesium carbonate in a dioxane/water solvent mixture. Removal of indole protecting group $PG_1$ of 4b provides 4c.

Scheme 5: Preparation of (R)-3-oxo-3-(3-((5-(thiazol-4-yl)-1H-pyrrolo[2,3-b]pyridin-4-yl)amino)piperidin-1-yl)propanenitrile

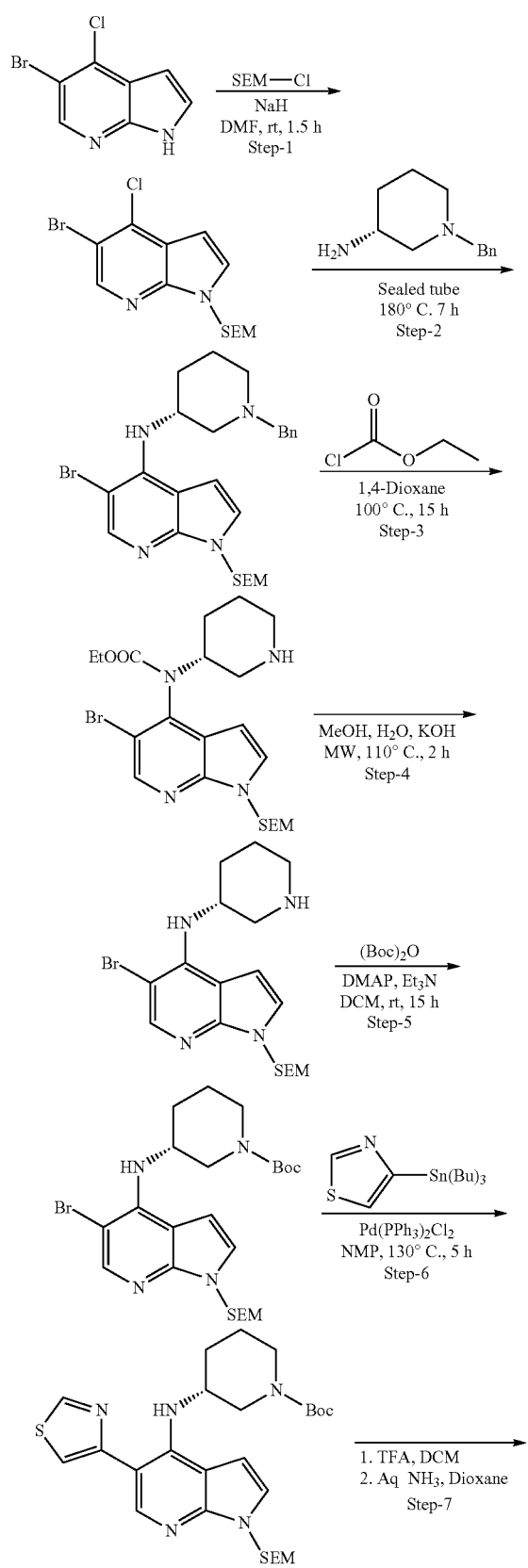

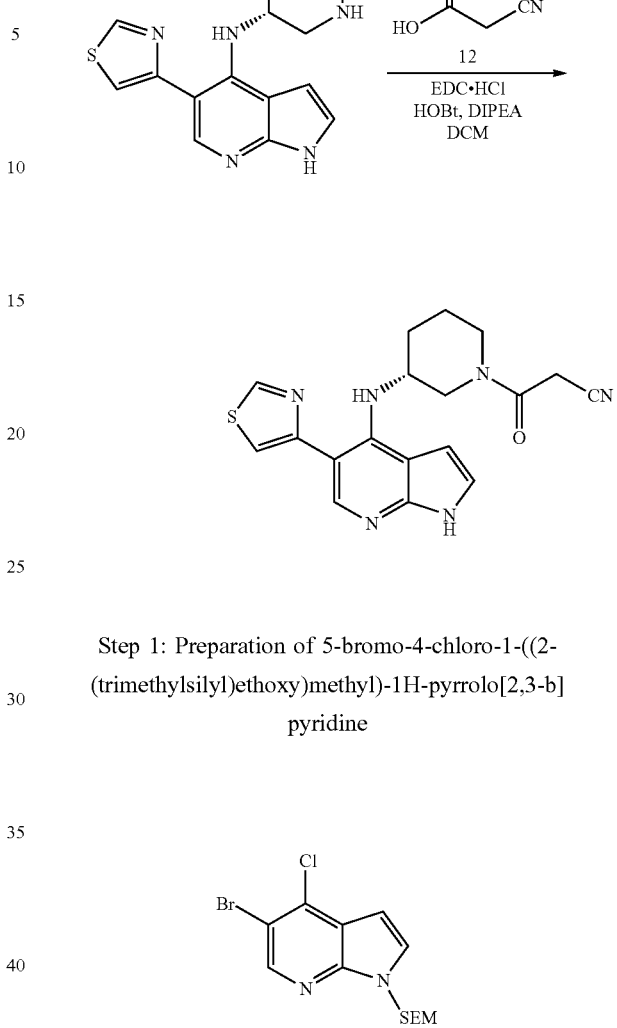

Step 1: Preparation of 5-bromo-4-chloro-1-((2-(trimethylsilyl)ethoxy)methyl)-1H-pyrrolo[2,3-b]pyridine A solution of 5-bromo-4-chloro-1H-pyrrolo[2,3-b]pyridine (6 g, 25.92 mmol) in dry dimethylformamide (60 mL) at 0° C. was treated with sodium hydride (1.65 g, 41.47 mmol, 60% suspension in mineral oil) and the suspension was stirred for 30 minutes. Then 2-(trimethylsilyl)ethoxymethyl chloride (9.56 mL, 53.91 mmol) was added and the mixture stirred at ambient temperature for 1.5 hours. The reaction mixture was quenched with saturated ammonium chloride solution and extracted with ethyl acetate. The combined organic extract was washed with brine, dried over anhydrous sodium sulfate, the solution was filtered and concentrated in vacuo. The crude material was purified by column chromatography (ethyl acetate/hexane) to provide 5-bromo-4-chloro-1-((2-(trimethylsilyl)ethoxy)methyl)-1H-pyrrolo[2,3-b]pyridine as a yellow oil (8.6 g, 92% yield): MS (ES) m/z 361.0 (M+H).

Step 2: Preparation of (R)-N-(1-benzylpiperidin-3-yl)-5-bromo-1-((2-(trimethylsilyl)ethoxy)methyl)-1H-pyrrolo[2,3-b]pyridin-4-amine

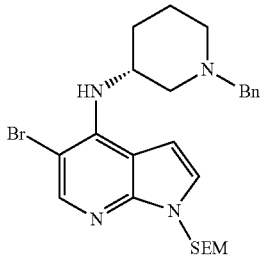 [SMILES: C[Si](C)(C)CCOCn1ccc2c(N[C@@H]3CCCN(Cc4ccccc4)C3)c(Br)cnc21]

A mixture of 5-bromo-4-chloro-1-((2-(trimethylsilyl)ethoxy)methyl)-1H-pyrrolo[2,3-b]pyridine (3 g, 8.29 mmol) and (R)-1-benzylpiperidin-3-amine (3.15 g, 16.58 mmol) was heated in a sealed tube to 180° C. After 7 hours the reaction was cooled to room temperature and the crude material was purified by column chromatography (ethyl acetate/hexane) to provide (R)-N-(1-benzylpiperidin-3-yl)-5-bromo-1-((2-(trimethylsilyl)ethoxy)methyl)-1H-pyrrolo[2,3-b]pyridin-4-amine as a yellow oil (3.7 g, 45% yield): MS (ES) m/z 517.1 (M+2H).

Step 3: Preparation of ethyl (R)-(5-bromo-1-((2-(trimethylsilyl)ethoxy)methyl)-1H-pyrrolo[2,3-b]pyridin-4-yl)(piperidin-3-yl)carbamate

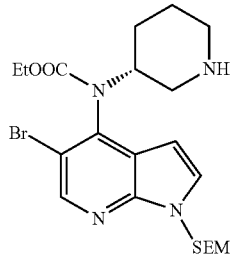 [SMILES: CCOC(=O)N(c1c(Br)cnc2c1ccn2COCC[Si](C)(C)C)[C@@H]1CCCNC1]

To a stirred solution of (R)-N-(1-benzylpiperidin-3-yl)-5-bromo-1-((2-(trimethylsilyl)ethoxy)methyl)-1H-pyrrolo[2,3-b]pyridin-4-amine (3.7 g, 7.17 mmol) in dry 1,4-dioxane (50 mL) was added ethyl chloroformate (1.03 mL, 10.76 mmol) at room temperature and the resulting mixture was heated at 100° C. After 15 hours the reaction was cooled to room temperature and concentrated in vacuo to remove volatiles. The crude material was purified by column chromatography (ethyl acetate/hexane) to provide ethyl (R)-(5-bromo-1-((2-(trimethylsilyl)ethoxy)methyl)-1H-pyrrolo[2,3-b]pyridin-4-yl)(piperidin-3-yl)carbamate as a yellow oil (2.7 g, 76% yield): MS (ES) m/z 496.9 (M+H).

Step 4: Preparation of (R)-5-bromo-N-(piperidin-3-yl)-1-((2-(trimethylsilyl)ethoxy)methyl)-1H-pyrrolo[2,3-b]pyridin-4-amine

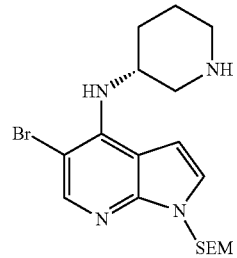 [SMILES: C[Si](C)(C)CCOCn1ccc2c(N[C@@H]3CCCNC3)c(Br)cnc21]

To a stirred solution of ethyl (R)-(5-bromo-1-((2-(trimethylsilyl)ethoxy)methyl)-1H-pyrrolo[2,3-b]pyridin-4-yl)(piperidin-3-yl)carbamate (0.5 g, 1.0 mmol) in methanol:water (12 mL:4 mL) was added potassium hydroxide (2.81 g, 50.25 mmol) and the resulting mixture was subjected to microwave irradiation at 110° C. for 2 hours. The reaction was cooled to room temperature and diluted with dichloromethane and washed with water. The organic layer was washed with brine, dried over anhydrous sodium sulfate, filtered and concentrated in vacuo to provide (R)-5-bromo-N-(piperidin-3-yl)-1-((2-(trimethylsilyl)ethoxy)methyl)-1H-pyrrolo[2,3-b]pyridin-4-amine as a yellow semisolid (2 g, 94% yield): MS (ES) m/z 424.9 (M+H).

Step 5: Preparation of tert-butyl (R)-3-((5-bromo-1-((2-(trimethylsilyl)ethoxy)methyl)-1H-pyrrolo[2,3-b]pyridin-4-yl)amino)piperidine-1-carboxylate

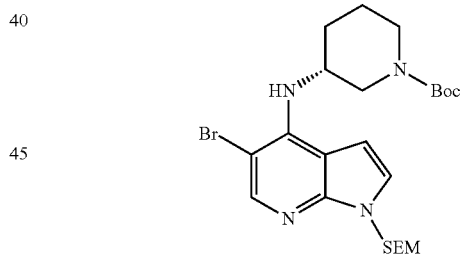

To a stirred solution of (R)-5-bromo-N-(piperidin-3-yl)-1-((2-(trimethylsilyl)ethoxy)methyl)-1H-pyrrolo[2,3-b]pyridin-4-amine (2 g, 4.70 mmol) in dry dichloromethane (30 mL) at 0° C. were added 4-dimethylaminopyridine (0.11 g, 0.94 mmol) and triethylamine (1.32 mL, 9.4 mmol) followed by di-tert-butyl dicarbonate (1.23 mL, 5.64 mmol). The resulting mixture was stirred at ambient temperature for 15 hours. The reaction mixture was diluted with dichloromethane, washed with water and brine. The organic layer was dried over anhydrous sodium sulfate, filtered and concentrated in vacuo. The crude material was purified by column chromatography (ethyl acetate/hexane) to provide tert-butyl (R)-3-((5-bromo-1-((2-(trimethylsilyl)ethoxy)methyl)-1H-pyrrolo[2,3-b]pyridin-4-yl)amino)piperidine-1-carboxylate as a yellow oil (1.9 g, 77% yield): MS (ES) m/z 524.9 (M+H).

Step 6: Preparation of tert-butyl (R)-3-((5-(thiazol-4-yl)-1-((2-(trimethylsilyl)ethoxy)methyl)-1H-pyrrolo[2,3-b]pyridin-4-yl)amino)piperidine-1-carboxylate

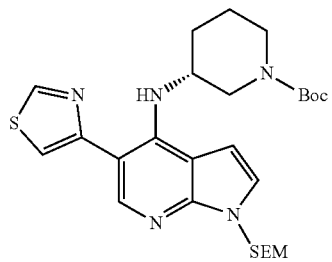 [SMILES: CC(C)(C)OC(=O)N1CCC[C@@H](Nc2c(-c3cscn3)cnc3c2ccn3COCC[Si](C)(C)C)C1]

A solution of tert-butyl (R)-3-((5-bromo-1-((2-(trimethylsilyl)ethoxy)methyl)-1H-pyrrolo[2,3-b]pyridin-4-yl)amino)piperidine-1-carboxylate (0.5 g, 0.94 mmol), 4-(tributylstannyl)thiazole (0.46 g, 1.23 mmol) and bis(triphenylphosphine)palladium(II) dichloride (0.13 g, 0.18 mmol) in N-methyl-2-pyrrolidone (10 mL) was heated at 130° C. under a nitrogen atmosphere in sealed tube. After 4 hours the reaction was cooled to ambient temperature, diluted with ethyl acetate and filtered through celite. The filtrate was washed with water, brine, dried over anhydrous sodium sulfate, filtered and concentrated in vacuo. The crude material was purified by using flash chromatography (50% ethyl acetate/hexane) to provide tert-butyl (R)-3-((5-(thiazol-4-yl)-1-((2-(trimethylsilyl)ethoxy)methyl)-1H-pyrrolo[2,3-b]pyridin-4-yl)amino)piperidine-1-carboxylate as a pink gummy solid (0.22 g, 44% yield): MS (ES) m/z 529.9 (M+H).

Step 7: Preparation of (R)-N-(piperidin-3-yl)-5-(thiazol-4-yl)-1H-pyrrolo[2,3-b]pyridin-4-amine

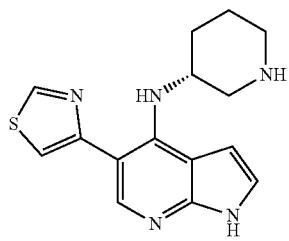 [SMILES: c1cc2c(N[C@@H]3CCCNC3)c(-c3cscn3)cnc2[nH]1]

A solution of tert-butyl (R)-3-((5-(thiazol-4-yl)-1-((2-(trimethylsilyl)ethoxy)methyl)-1H-pyrrolo[2,3-b]pyridin-4-yl)amino)piperidine-1-carboxylate (0.21 g, 0.39 mmol) in dichloromethane:trifluoroacetic acid (3.0 mL:3.0 mL) was stirred at ambient temperature for 2 hours. The reaction mixture was concentrated in vacuo, the obtained residue was dissolved in 1,4-dioxane:aqueous ammonia (3.0 mL:3.0 mL) and was then stirred at ambient temperature overnight. The reaction mixture was concentrated in vacuo to provide (R)-N-(piperidin-3-yl)-5-(thiazol-4-yl)-1H-pyrrolo[2,3-b]pyridin-4-amine as an off-white solid (0.08 g, 66% yield): MS (ES) m/z 300.0 (M+H).

Step 8: Preparation of (R)-3-oxo-3-(3-((5-(thiazol-4-yl)-1H-pyrrolo[2,3-b]pyridin-4-yl)amino)piperidin-1-yl)propanenitrile

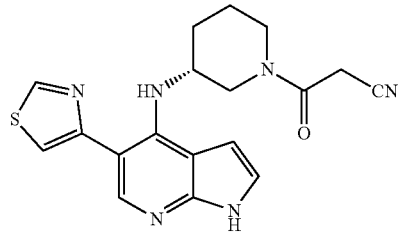 [SMILES: N#CCC(=O)N1CCC[C@@H](Nc2c(-c3cscn3)cnc3[nH]ccc23)C1]

A solution of cyanoacetic acid (0.024 g, 0.28 mmol), N-(3-dimethylaminopropyl)-N'-ethylcarbodiimide hydrochloride (0.07 g, 0.34 mmol), 1-hydroxybenzotriazole (0.04 g, 0.26 mmol) and N,N-diisopropylethylamine (0.13 mL, 0.68 mmol) in dichloromethane (4 mL) was stirred at ambient temperature for 5 minutes. Then (R)-N-(piperidin-3-yl)-5-(thiazol-4-yl)-1H-pyrrolo[2,3-b]pyridin-4-amine (0.07 g, 0.23 mmol) was added and the resulting mixture was stirred at ambient temperature for 18 hours. The reaction mixture was quenched with water and extracted with dichloromethane. The organic layer was washed with water, brine, dried over anhydrous sodium sulfate, filtered and concentrated in vacuo. The crude material was purified by flash chromatography (5% methanol/dichloromethane) to provide (R)-3-oxo-3-(3-((5-(thiazol-4-yl)-1H-pyrrolo[2,3-b]pyridin-4-yl)amino)piperidin-1-yl)propanenitrile as an off-white solid (0.01 g, 12% yield): $^1$H NMR (400 MHz, DMSO-$d_6$) δ 11.37 (br s, 1H), 9.20 (br s, 1H), 8.30-8.57 (m, 1H), 7.96 (d, J=14.8 Hz, 1H), 7.16 (br s, 1H), 6.60 (s, 1H), 3.92-4.48 (m, 3H), 3.55-3.70 (m, 1H), 3.05-3.27 (m, 3H), 1.92-2.33 (m, 2H), 1.46-1.75 (m, 3H); MS (ES) m/z 366.9 (M+H).

Example 2: Preparation of (R)-3-(3-((5-(1-(difluoromethyl)-1H-pyrazol-3-yl)-1H-pyrrolo[2,3-b]pyridin-4-yl)amino)piperidin-1-yl)-3-oxopropanenitrile

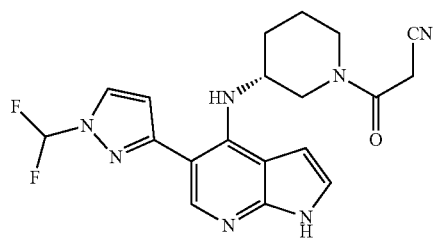 [SMILES: N#CCC(=O)N1CCC[C@@H](Nc2c(-c3ccn(C(F)F)n3)cnc3[nH]ccc23)C1]

Scheme 6: Preparation of (R)-3-(3-((5-(1-(difluoromethyl)-1H-pyrazol-3-yl)-1H-pyrrolo[2,3-b]pyridin-4-yl)amino)piperidin-1-yl)-3-oxopropanenitrile

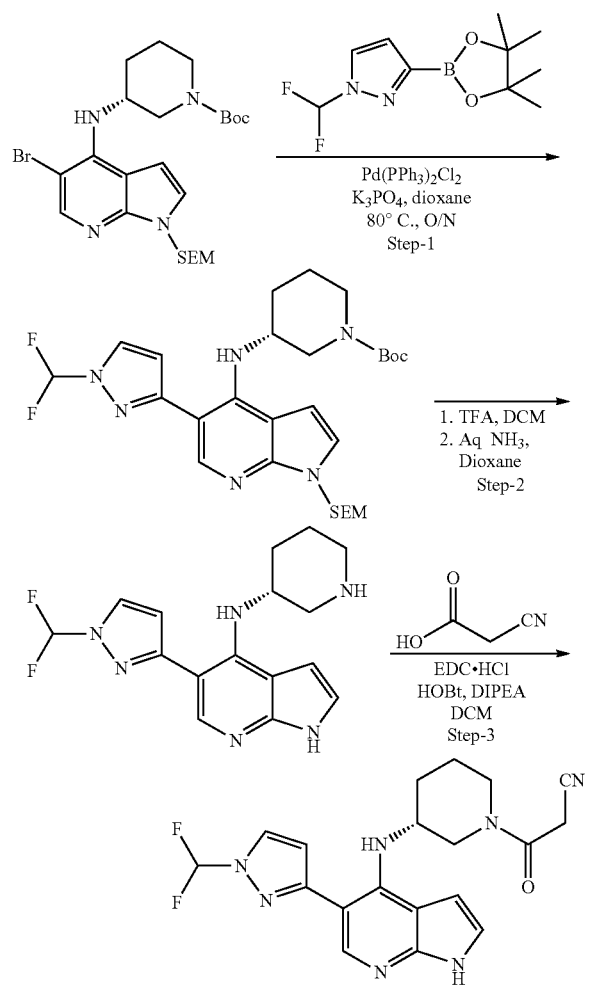

Step 1: Preparation of tert-butyl (R)-3-((5-(1-(difluoromethyl)-1H-pyrazol-3-yl)-1-((2-(trimethylsilyl)ethoxy)methyl)-1H-pyrrolo[2,3-b]pyridin-4-yl)amino)piperidine-1-carboxylate

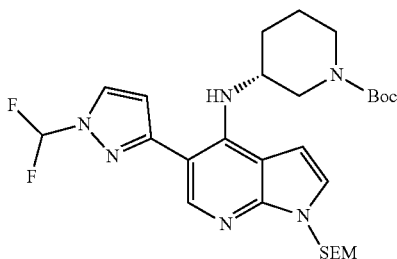 [SMILES: CC(C)(C)OC(=O)N1CCC[C@@H](Nc2c(-c3ccn(C(F)F)n3)cnc3c2ccn3COCC[Si](C)(C)C)C1]

A mixture of tert-butyl (R)-3-((5-bromo-1-((2-(trimethylsilyl)ethoxy)methyl)-1H-pyrrolo[2,3-b]pyridin-4-yl)amino)piperidine-1-carboxylate (0.4 g, 0.76 mmol, as prepared by the method described in Scheme 5, step-5), 1-(difluoromethyl)-3-(4,4,5,5-tetramethyl-1,3,2-dioxaborolan-2-yl)-1H-pyrazole (0.24 g, 0.10 mmol), bis-(triphenylphosphine)palladium(II) dichloride (0.11 g, 0.15 mmol) and 2M aqueous solution of potassium phosphate tribasic (0.48 g. 2.28 mmol) in 1,4-dioxane (20 mL) was heated at 80° C. overnight under a nitrogen atmosphere. The reaction mixture was cooled to ambient temperature, diluted with ethyl acetate and filtered through celite. The filtrate was washed with water, brine, dried over anhydrous sodium sulfate, filtered and concentrated in vacuo. The crude material was purified by using flash chromatography (50% ethyl acetate in hexane) to provide tert-butyl (R)-3-((5-(1-(difluoromethyl)-1H-pyrazol-3-yl)-1-((2-(trimethyl-silyl)ethoxy)methyl)-1H-pyrrolo[2,3-b]pyridin-4-yl)amino)piperidine-1-carboxylate as an orange-colored gummy solid (0.34 g, 80% yield): MS (ES) m/z 562.9 (M+H).

Step 2: Preparation of (R)-5-(1-(difluoromethyl)-1H-pyrazol-3-yl)-N-(piperidin-3-yl)-1H-pyrrolo[2,3-b]pyridin-4-amine

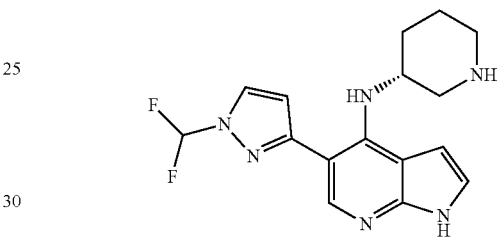

(R)-5-(1-(Difluoromethyl)-1H-pyrazol-3-yl)-N-(piperidin-3-yl)-1H-pyrrolo[2,3-b]pyridin-4-amine was prepared by the method described in Example 1, step-7 and isolated as a pale yellow gum (0.23 g, 98%): MS (ES) m/z 333.0 (M+H)+.

Step 3: Preparation of (R)-3-(3-((5-(1-(difluoromethyl)-1H-pyrazol-3-yl)-1H-pyrrolo[2,3-b]pyridin-4-yl)amino)piperidin-1-yl)-3-oxopropanenitrile

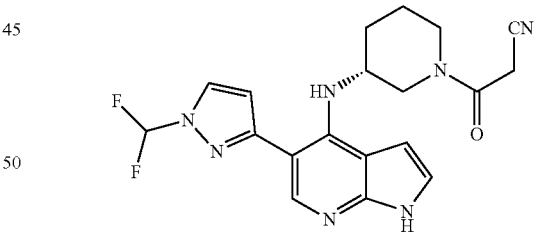

(R)-3-(3-((5-(1-(difluoromethyl)-1H-pyrazol-3-yl)-1H-pyrrolo[2,3-b]pyridin-4-yl)amino)piperidin-1-yl)-3-oxopropanenitrile was prepared by the method described in Example 1, Step-8 to give an off-white solid (0.05 g, 18% yield): $^1$H NMR (400 MHz, DMSO-$d_6$) δ 11.46 (br s, 1H), 8.41-8.46 (m, 2H), 8.28-8.31 (m, 1H), 7.60-7.91 (m, 1H), 7.10-7.20 (m, 2H), 6.65 (s, 1H), 4.40 (s, 1H), 3.91-4.18 (m, 3H), 3.43-3.68 (m, 2H), 3.18-3.26 (m, 1H), 2.06-2.07 (m, 1H), 1.57-1.77 (m, 3H); MS (ES) m/z 399.9 (M+H).

Analytical Conditions:
Column: Kinetex C18 (100 mm×4.6 mm×2.6 μm)
Mobile phase (A): 0.1% TFA acid in Water
Mobile phase (B): ACN
Flow rate: 0.75 mL/min

Example 3: Preparation of (R)-3-(3-((5-(2-methyl-thiazol-5-yl)-1H-pyrrolo[2,3-b]pyridin-4-yl)amino)piperidin-1-yl)-3-oxopropanenitrile

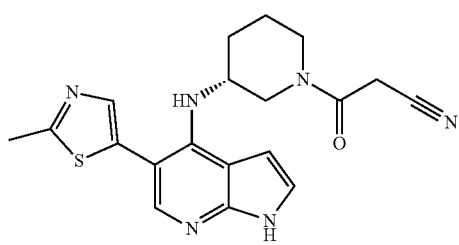 [SMILES: Cc1ncc(-c2cnc3[nH]ccc3c2N[C@@H]2CCCN(C(=O)CC#N)C2)s1]

Scheme 7: Preparation of (R)-3-(3-((5-(2-methylthiazol-5-yl)-1H-pyrrolo[2,3-b]pyridin-4-yl)amino)piperidin-1-yl)-3-oxopropanenitrile

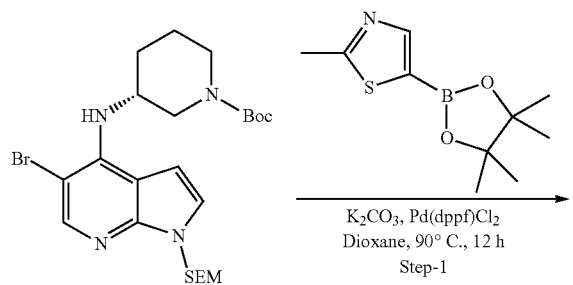

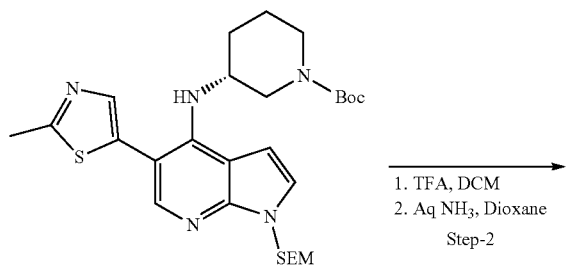

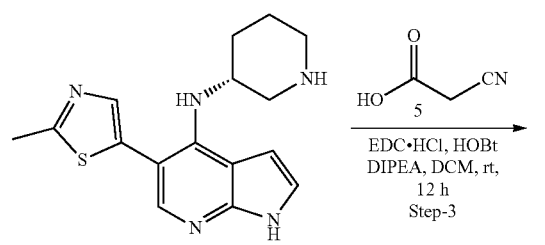

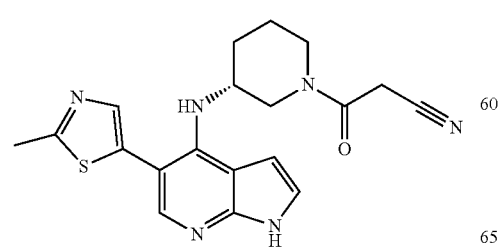

Step 1: Preparation of tert-butyl (R)-3-((5-(2-methylthiazol-5-yl)-1-((2-(trimethylsilyl)ethoxy)methyl)-1H-pyrrolo[2,3b]pyridin-4-yl)amino)piperidine-1-carboxylate

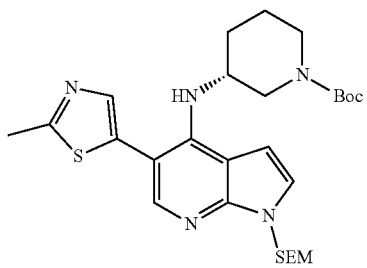 [SMILES: Cc1ncc(-c2cnc3c(ccn3COCC[Si](C)(C)C)c2N[C@@H]2CCCN(C(=O)OC(C)(C)C)C2)s1]

A solution of tert-butyl (R)-3-((5-bromo-1-((2-(trimethylsilyl)ethoxy)methyl)-1H-pyrrolo[2,3-b]pyridin-4-yl)amino)piperidine-1-carboxylate (0.2 g, 0.38 mmol, as prepared by the method described in Scheme-1, step-5), in 1,4-dioxane: water (4.5 mL:0.5 mL) was treated with potassium carbonate (0.16 g, 0.76 mmol) followed by 2-methyl-5-(4,4,5,5-tetramethyl-1,3,2-dioxaborolan-2-yl)thiazole (0.17 g, 0.76 mmol) and [1,1'-bis(diphenyl phosphino)-ferrocene]dichloropalladium(II) complex with dichloromethane (0.03 g, 0.04 mmol). The resulting mixture was heated in a sealed tube at 100° C. for 16 hours under a nitrogen atmosphere. The reaction was cooled to ambient temperature, diluted with ethyl acetate and water. The organic layer was separated, washed with brine, dried over anhydrous sodium sulfate, filtered and concentrated in vacuo. The crude material was purified by flash chromatography (40% ethyl acetate/hexane) to provide tert-butyl (R)-3-((5-(2-methylthiazol-5-yl)-1-((2-(trimethylsilyl)ethoxy)methyl)-1H-pyrrolo[2,3-b]pyridin-4-yl)amino)piperidine-1-carboxylate as a brown liquid (0.15 g, 36% yield): MS (ES) m/z 543.9 (M+H).

Step 2: Preparation of (R)-5-(2-methylthiazol-5-yl)-N-(piperidin-3-yl)-1H-pyrrolo[2,3-b]pyridin-4-amine

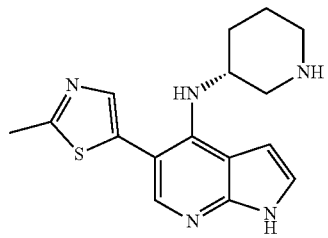 [SMILES: Cc1ncc(-c2cnc3[nH]ccc3c2N[C@@H]2CCCNC2)s1]

(R)-5-(2-Methylthiazol-5-yl)-N-(piperidin-3-yl)-1H-pyrrolo[2,3-b]pyridin-4-amine was prepared by the method described in Example-1, Step-7 which was isolated as a pale yellow gum (0.13 g, 94% yield): MS (ES) m/z 314.0 (M+H)$^+$.

119

Step 3: (R)-3-(3-((5-(2-methylthiazol-5-yl)-1H-pyrrolo[2,3-b]pyridin-4-yl)amino)piperidin-1-yl)-3-oxopropanenitrile

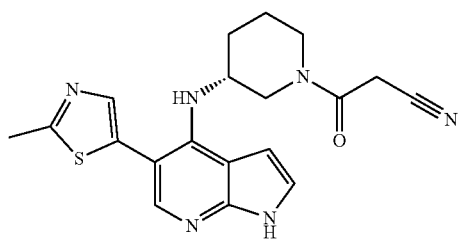 [SMILES: Cc1ncc(-c2cnc3[nH]ccc3c2N[C@@H]2CCCN(C(=O)CC#N)C2)s1]

(R)-3-(3-((5-(2-methylthiazol-5-yl)-1H-pyrrolo[2,3-b]pyridin-4-yl)amino)piperidin-1-yl)-3-oxopropanenitrile was prepared by the method as described in Example 1, Step-8 to give an off-white solid (0.01 g, 5% yield): $^1$H NMR (400 MHz, DMSO-$d_6$) δ 11.43 (s, 1H), 7.77-7.75 (m, 1H), 7.59-7.57 (m, 1H), 7.22 (s, 1H), 6.61-6.57 (m, 1H), 5.16-5.14 (m, 1H), 4.16-4.13 (m, 1H), 4.03 (s, 2H), 3.89-3.77 (m, 3H), 2.67-2.65 (m, 3H), 1.96 (s, 2H), 1.60-1.57 (m, 3H); MS (ES) m/z 381.3 (M+H). HPLC purity: 98.58%

Analytical Conditions:
Column: X bridge (250 mm×4.6 mm×5 mic)
Mobile phase (A): 0.1% Ammonia in water
Mobile phase (B): Methanol
Flow rate: 1.0 mL/min Example 4: Preparation of (R)-3-oxo-3-(3-((5-(thiazol-2-yl)-1H-pyrrolo[2,3-b]pyridin-4-yl)amino)piperidin-1-yl)propanenitrile

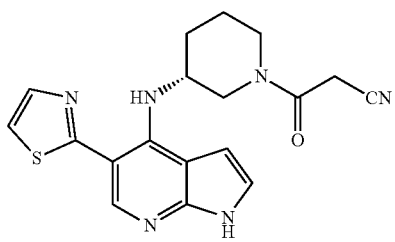 [SMILES: N#CCC(=O)N1CCC[C@@H](Nc2c(-c3nccs3)cnc3[nH]ccc23)C1]

Scheme 8: Preparation of (R)-3-oxo-3-(3-((5-(thiazol-2-yl)-1H-pyrrolo[2,3-b]pyridin-4-yl)amino)piperidin-1-yl)propanenitrile

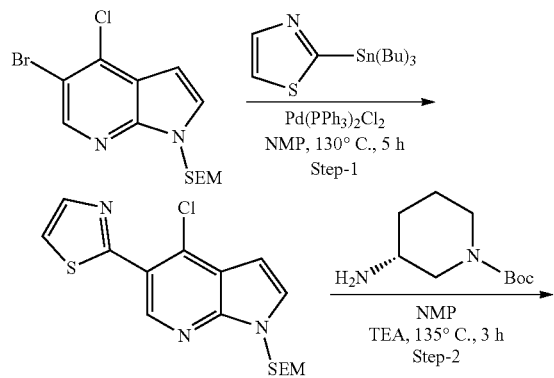

120

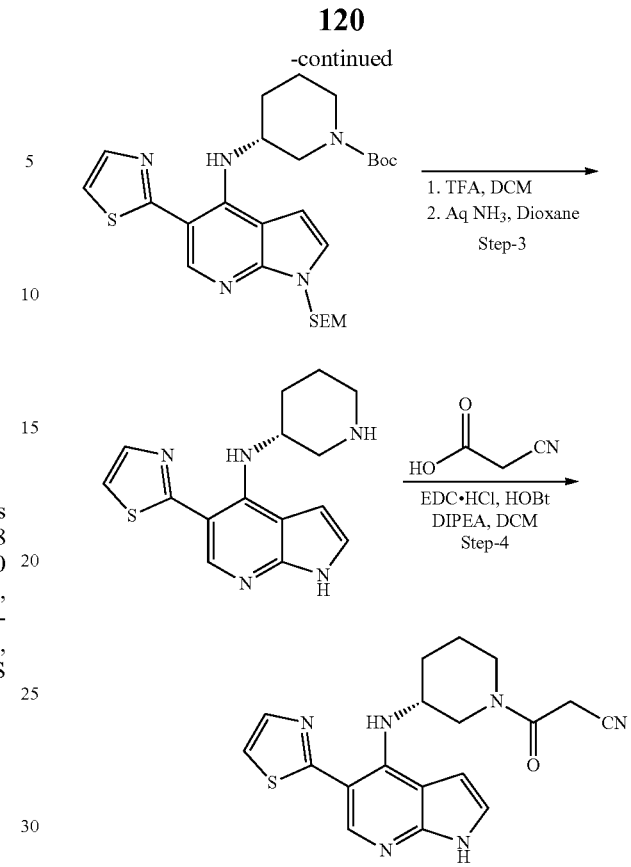

Step 1: Preparation of 2-(4-chloro-1-((2-(trimethylsilyl)ethoxy)methyl)-1H-pyrrolo[2,3-b]pyridin-5-yl)thiazole

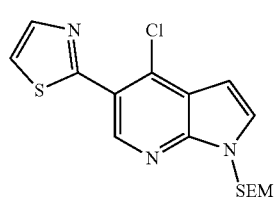 [SMILES: C[Si](C)(C)CCOCn1ccc2c(Cl)c(-c3nccs3)cnc21]

A solution of 5-bromo-4-chloro-1-((2-(trimethylsilyl)ethoxy)methyl)-1H-pyrrolo[2,3-b]pyridine (1.5 g, 4.15 mmol, prepared by the method described in Scheme 1, step-1), 2-(tributylstannyl)thiazole (1.7 g, 4.57 mmol) and bis(triphenylphosphine)palladium(II) dichloride (0.58 g, 0.83 mmol) in N-methyl-2-pyrrolidone (15 mL) was heated at 130° C. in a sealed tube under a nitrogen atmosphere. After 4 hours the reaction mixture was cooled to ambient temperature, diluted with ethyl acetate and filtered through celite. The filtrate was washed with water, brine, dried over anhydrous sodium sulfate, filtered and concentrated in vacuo. The crude material was purified by using flash chromatography (10% ethyl acetate in hexane) to provide 2-(4-chloro-1-((2-(trimethylsilyl)ethoxy)methyl)-1H-pyrrolo[2,3-b]pyridin-5-yl)thiazole as a colorless oil (0.75 g, 49% yield): MS (ES) m/z 365.8 (M+H).

Step 2: Preparation of tert-butyl (R)-3-((5-(thiazol-2-yl)-1-((2-(trimethylsilyl)ethoxy)methyl)-1H-pyrrolo[2,3-b]pyridin-4-yl)amino)piperidine-1-carboxylate

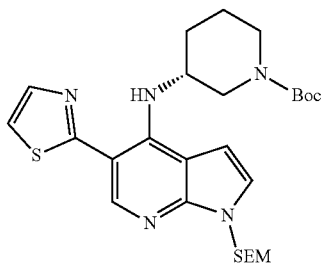 [SMILES: CC(C)(C)OC(=O)N1CCC[C@@H](Nc2c(-c3nccs3)cnc3c2ccn3COCC[Si](C)(C)C)C1]

A solution of 2-(4-chloro-1-((2-(trimethylsilyl)ethoxy)methyl)-1H-pyrrolo[2,3-b]pyridin-5-yl)thiazole (0.7 g, 1.92 mmol), tert-butyl (R)-3-aminopiperidine-1-carboxylate (0.57 g, 2.87 mmol) and triethylamine (0.27 mL, 1.92 mmol) in N-methyl-2-pyrrolidone (10 mL) was subjected to microwave irradiation at 130° C. for 3 hours. The reaction was cooled to ambient temperature, diluted with ethyl acetate, washed with water, brine, dried over anhydrous sodium sulfate, filtered and concentrated in vacuo. The crude material was purified by using flash chromatography (50% ethyl acetate in hexane) to provide tert-butyl (R)-3-((5-(thiazol-2-yl)-1-((2-(trimethylsilyl)ethoxy)methyl)-1H-pyrrolo[2,3-b]pyridin-4-yl)amino)piperidine-1-carboxylate as a pale yellow solid (0.24 g, 24% yield): MS (ES) m/z 529.9 (M+H).

Step 3: Preparation of (R)-N-(piperidin-3-yl)-5-(thiazol-2-yl)-1H-pyrrolo[2,3-b]pyridin-4-amine

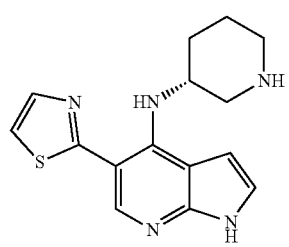

(R)-N-(Piperidin-3-yl)-5-(thiazol-2-yl)-1H-pyrrolo[2,3-b]pyridin-4-amine was prepared by the method described in Example 1, step-7 which was isolated as an off-white solid (0.11 g, 81% yield): MS (ES) m/z 300.0 (M+H)⁺.

Step 4: Preparation of (R)-3-oxo-3-(3-((5-(thiazol-2-yl)-1H-pyrrolo[2,3-b]pyridin-4-yl)amino)piperidin-1-yl)propanenitrile

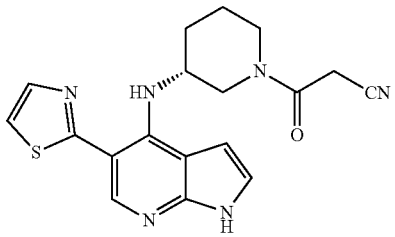 [SMILES: N#CCC(=O)N1CCC[C@@H](Nc2c(-c3nccs3)cnc3[nH]ccc23)C1]

(R)-3-Oxo-3-(3-((5-(thiazol-2-yl)-1H-pyrrolo[2,3-b]pyridin-4-yl)amino)piperidin-1-yl)propanenitrile was prepared by the method described in Example 1, Step-8 to give a yellow solid (0.05 g, 38% yield): $^1$H NMR (400 MHz, DMSO-$d_6$) δ 11.44 (br s, 1H), 9.75 (br s, 1H), 7.41 (d, J=10.4 Hz, 1H), 7.74-7.80 (m, 1H), 7.59 (s, 1H), 7.22 (s, 1H), 6.69 (s, 1H), 4.15-4.45 (m, 1H), 3.90-4.10 (m, 2H), 3.61-3.82 (m, 1H), 3.25-3.55 (m, 2H), 1.95-2.20 (m, 2H), 1.45-1.85 (m, 3H); MS (ES) m/z 366.9 (M+H).

Example 5: Preparation of (R)-3-(3-((5-(oxazol-2-yl)-1H-pyrrolo[2,3-b]pyridin-4-yl)amino)piperidin-1-yl)-3-oxopropanenitrile

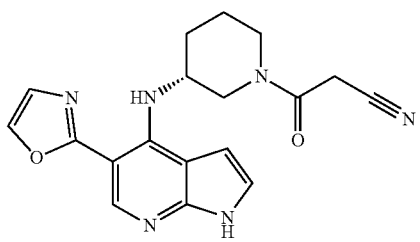 [SMILES: N#CCC(=O)N1CCC[C@@H](Nc2c(-c3ncco3)cnc3[nH]ccc23)C1]

Scheme 9: Preparation of (R)-3-(3-((5-(oxazol-2-yl)-1H-pyrrolo[2,3-b]pyridin-4-yl)amino(piperidin-1-yl)-3-oxopropanenitrile

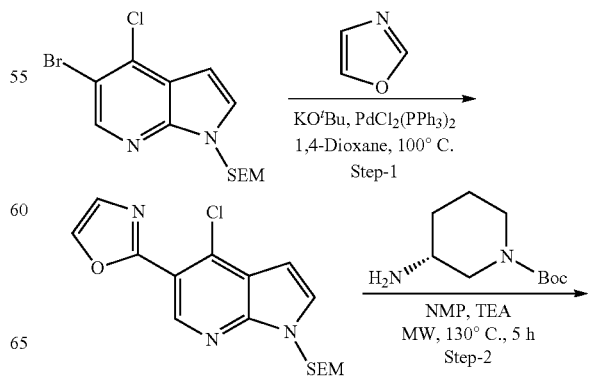

123

-continued

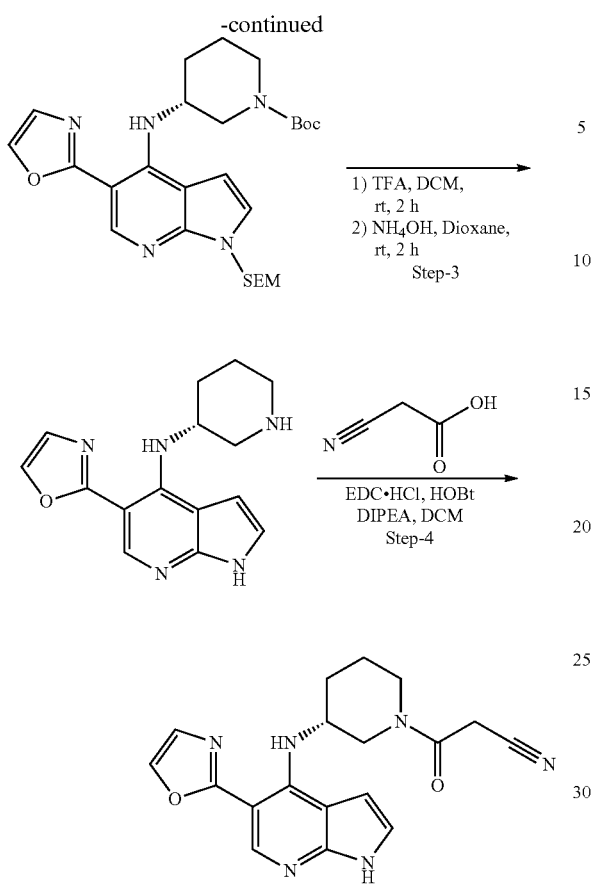

Step 1: Preparation of 2-(4-chloro-1-((2-(trimethyl-silyl)ethoxy)methyl)-1H-pyrrolo[2,3-b]pyridin-5-yl)oxazole

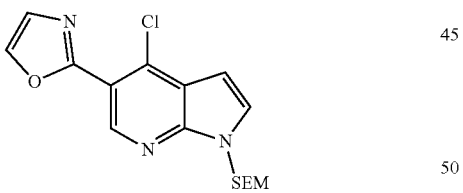

A mixture of 5-bromo-4-chloro-1-((2-(trimethylsilyl)ethoxy)methyl)-1H-pyrrolo[2,3-b]pyridine (2 g, 5.54 mmol, prepared by the method described in Scheme 5, step-1), potassium tert-butoxide (1.24 g, 11.08 mmol) bis(triphenylphosphine)palladium(II) dichloride (0.19 g, 0.27 mmol) and oxazole (0.68 g, 9.97 mmol) in 1,4-dioxane (20 mL) was heated in a sealed tube to 110° C. under nitrogen. After 5 hours the reaction was cooled to ambient temperature, diluted with water and extracted with ethyl acetate. The organic layer was washed with brine, dried over sodium sulfate, filtered and concentrated in vacuo. The crude material was purified by flash chromatography (ethyl acetate/hexane) to provide 2-(4-chloro-1-((2-(trimethylsilyl)ethoxy)methyl)-1H-pyrrolo[2,3-b]pyridin-5-yl)oxazole as an off-white solid (0.43 g, 22% yield): MS (ES) m/z 349.9 (M+H).

124

Step 2: Preparation of tert-butyl (R)-3-((5-(oxazol-2-yl)-1-((2-(trimethylsilyl)ethoxy)methyl)-1H-pyrrolo[2,3-b]pyridin-4-yl)amino)piperidine-1-carboxylate

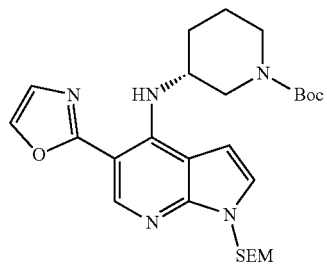 [SMILES: CC(C)(C)OC(=O)N1CCC[C@@H](Nc2c(-c3ncco3)cnc3c2ccn3COCC[Si](C)(C)C)C1]

To a stirred solution of 2-(4-chloro-1-((2-(trimethylsilyl)ethoxy)methyl)-1H-pyrrolo[2,3-b]pyridin-5-yl)oxazole (0.43 g, 1.28 mmol), triethylamine (0.03 mL, 0.24 mmol) and tert-butyl (R)-3-aminopiperidine-1-carboxylate (0.464 g, 2.32 mmol) in N-methylpyrrolidone (4 mL) was subjected to microwave irradiation at 130° C. for 5 hours. The reaction was cooled to ambient temperature, diluted with water and extracted with ethyl acetate. The organic layer was washed with brine, dried over sodium sulfate, filtered and concentrated in vacuo. The crude material was purified by flash chromatography (50% ethyl acetate/hexane) to provide tert-butyl (R)-3-((5-(oxazol-2-yl)-1-((2-(trimethylsilyl)ethoxy)methyl)-1H-pyrrolo[2,3-b]pyridin-4-yl)amino)piperidine-1-carboxylate as an off-white solid (0.35 g, 53%): MS (ES) m/z 514.0 (M+H).

Step 3: Preparation of (R)-5-(oxazol-2-yl)-N-(piperidin-3-yl)-1H-pyrrolo[2,3-b]pyridin-4-amine

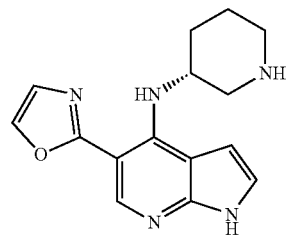 [SMILES: c1coc(-c2cnc3[nH]ccc3c2N[C@@H]2CCCNC2)n1]

(R)-5-(Oxazol-2-yl)-N-(piperidin-3-yl)-1H-pyrrolo[2,3-b]pyridin-4-amine was prepared by the method as described in Example 1, step-7: MS (ES) m/z 284.1 (M+H).

Step 4: Preparation of (R)-3-(3-((5-(oxazol-2-yl)-1H-pyrrolo[2,3-b]pyridin-4-yl)amino)piperidin-1-yl)-3-oxopropanenitrile

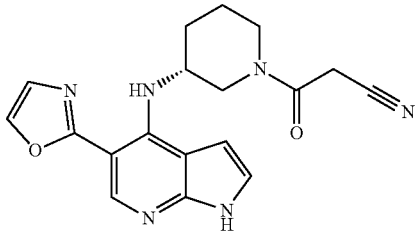 [SMILES: N#CCC(=O)N1CCC[C@@H](Nc2c(-c3ncco3)cnc3[nH]ccc23)C1]

(R)-3-(3-((5-(Oxazol-2-yl)-1H-pyrrolo[2,3-b]pyridin-4-yl)amino)piperidin-1-yl)-3-oxopropanenitrile was prepared by the method as described in Example 1, Step-8 to give an off-white solid (0.05 g, 27% yield): $^1$H NMR (400 MHz, DMSO-$d_6$) δ 11.61 (br s, J=8.8 Hz, 1H), 9.11-9.05 (m, 1H), 8.53 (d, J=6.8 Hz, 1H), 8.10 (s, 1H), 7.33-7.22 (m, 2H), 6.69 (s, 1H), 4.37 (br s, 1H), 4.17-3.58 (m, 6H), 2.04 (s, 1H), 1.73-1.54 (m, 3H); MS (ES) m/z 351.1 (M+H).

Example 6: Preparation of (R)-3-(3-((5-(3-methyl-1,2,4-oxadiazol-5-yl)-1H-pyrrolo[2,3-b]pyridin-4-yl)amino)piperidin-1-yl)-3-oxopropanenitrile

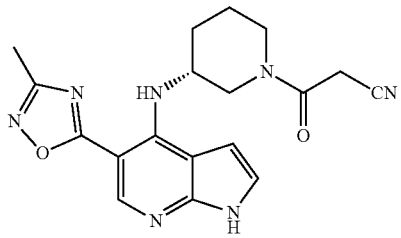 [SMILES: Cc1noc(-c2cnc3[nH]ccc3c2N[C@@H]2CCCN(C(=O)CC#N)C2)n1]

Scheme 10: Preparation of (R)-3-(3-((5-(3-methyl-1,2,4-oxadiazol-5-yl)-1H-pyrrolo[2,3-b]pyridin-4-yl)amino)piperidin-1-yl)-3-oxopropanenitrile

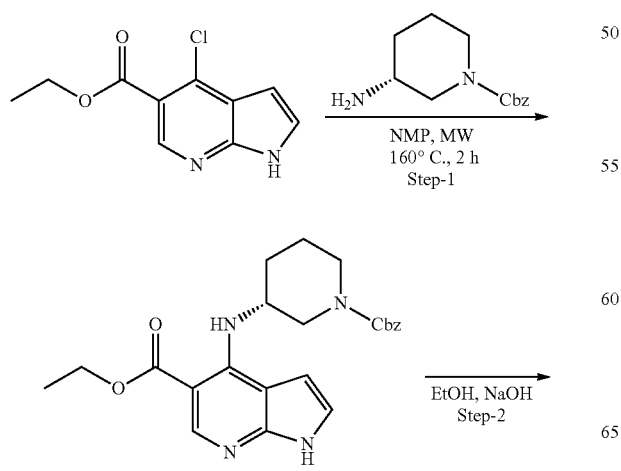

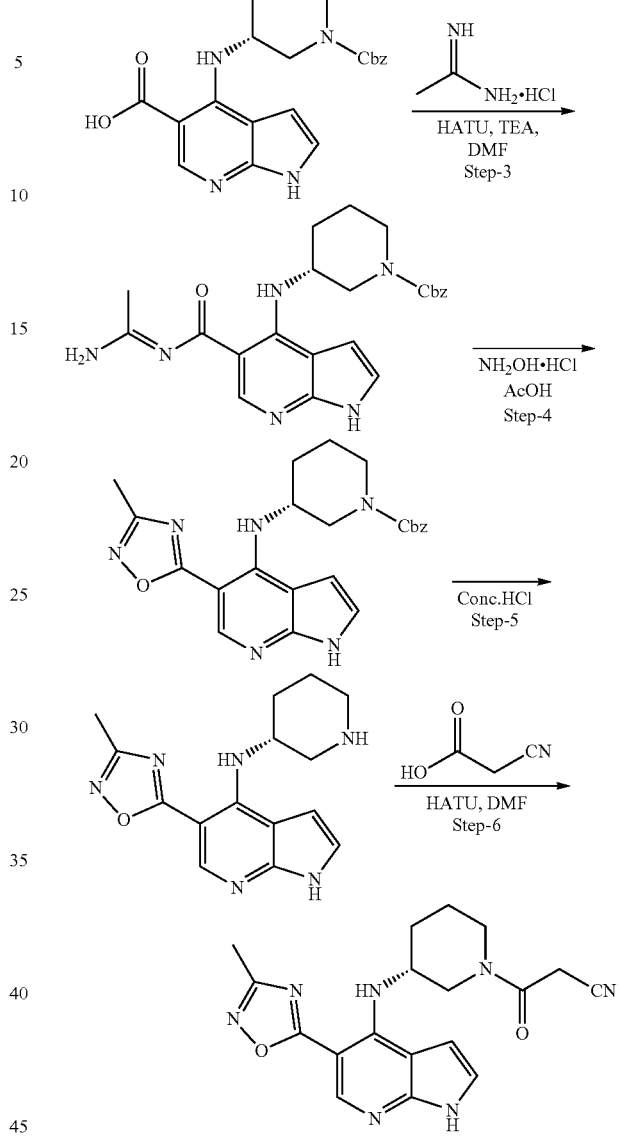

Step 1: Preparation of ethyl (R)-4-((1-((benzyloxy)carbonyl)piperidin-3-yl)amino)-1H-pyrrolo[2,3-b]pyridine-5-carboxylate

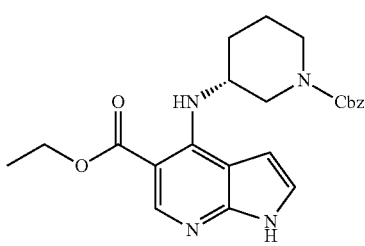 [SMILES: CCOC(=O)c1cnc2[nH]ccc2c1N[C@@H]1CCCN(C(=O)OCc2ccccc2)C1]

To a stirred solution ethyl 4-chloro-1H-pyrrolo[2,3-b]pyridine-5-carboxylate (0.2 g, 0.89 mmol), triethylamine (0.06 mL, 0.44 mmol) and benzyl (R)-3-aminopiperidine- 1-carboxylate (0.31 g, 1.33 mmol) in N-methylpyrrolidone (1 mL) was subjected to microwave irradiation at 165° C. for 2 hours. The reaction was cooled to ambient temperature, diluted with water and extracted with ethyl acetate. The organic layer was washed with brine, dried over sodium sulfate, filtered and concentrated in vacuo. The crude material was purified by flash chromatography (40% ethyl acetate/hexane) to give ethyl (R)-4-((1-((benzyloxy)carbonyl)piperidin-3-yl)amino)-1H-pyrrolo[2,3-b]pyridine-5-carboxylate as a pale yellow solid (0.25 g, 67%): MS (ES) m/z 422.9 [M+H]+.

Step 2: Preparation of (R)-4-((1-((benzyloxy)carbonyl)piperidin-3-yl)amino)-1H-pyrrolo[2,3-b]pyridine-5-carboxylicacid

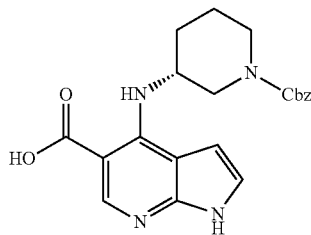 [SMILES: O=C(O)c1cnc2[nH]ccc2c1N[C@@H]1CCCN(C(=O)OCc2ccccc2)C1]

To a stirred solution of propyl ethyl (R)-4-((1-((benzyloxy)carbonyl)piperidin-3-yl)amino)-1H-pyrrolo[2,3-b]pyridine-5-carboxylate (1.5 g, 3.55 mmol) in ethanol (20 mL) at 0° C. was added sodium hydroxide (5N, 10 mL) and the mixture was stirred at ambient temperature for 12 hours. The reaction mixture was concentrated in vacuo and the residue was dissolved in water and washed with diethyl ether. The aqueous layer was acidified to pH2.0 with saturated potassium bisulfate solution at 0° C. and then extracted with 5% methanol/dichloromethane. The organic layer was dried over anhydrous sodium sulfate, filtered and concentrated in vacuo. The obtained crude product was triturated with n-pentane to provide (R)-4-((1-((benzyloxy)carbonyl)piperidin-3-yl)amino)-1H-pyrrolo[2,3-b]pyridine-5-carboxylic acid as an off-white solid (1.10 g, crude): MS (ES) m/z 394.9 (M+H).

Step 3: Preparation of benzyl (R,E)-3-((5-((1-aminoethylidene)carbamoyl)-1H-pyrrolo[2,3-b]pyridin-4-yl)amino)piperidine-1-carboxylate

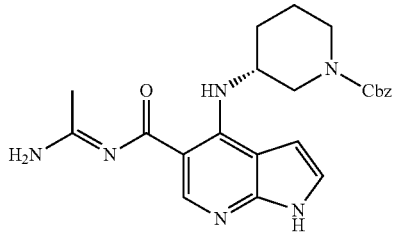 [SMILES: C/C(N)=N\C(=O)c1cnc2[nH]ccc2c1N[C@@H]1CCCN(C(=O)OCc2ccccc2)C1]

To a stirred solution of (R)-4-((1-((benzyloxy)carbonyl) piperidin-3-yl)amino)-1H-pyrrolo[2,3-b]pyridine-5-carboxylic (0.5 g, 1.26 mmol) in N,N-dimethylformamide (10 mL) was added 1-bis(dimethylamino)methylene]-1H-1,2,3-triazolo[4,5-b]pyridinium 3-oxid hexafluorophosphate (0.53 g, 1.39 mmol), N,N-diisopropylethylamine (1.2 g, 1.73 mmol) and acetamidine hydrochloride (0.178 g, 1.90 mmol). The mixture was stirred at ambient temperature for 18 hours. The reaction mixture was filtered and concentrated in vacuo to provide benzyl (R,E)-3-((5-((1-aminoethylidene)carbamoyl)-1H-pyrrolo[2,3-b]pyridin-4-yl)amino)piperidine-1-carboxylate as a white solid (0.4 g, crude): MS (ES) m/z 435.0 (M+H).

Step 4: Preparation of benzyl (R)-3-((5-(3-methyl-1,2,4-oxadiazol-5-yl)-1H-pyrrolo[2,3-b]pyridin-4-yl)amino)piperidine-1-carboxylate

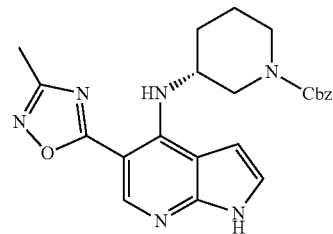 [SMILES: Cc1noc(-c2cnc3[nH]ccc3c2N[C@@H]2CCCN(C(=O)OCc3ccccc3)C2)n1]

A stirred solution of benzyl (R,E)-3-((5-((1-aminoethylidene)carbamoyl)-1H-pyrrolo[2,3-b]pyridin-4-yl)amino)piperidine-1-carboxylate (0.1 g, 0.23 mmol) and hydroxylamine hydrochloride (0.024 g, 0.345 mmol), in acetic acid (0.2 mL) was heated to 90° C. After 3 hours the reaction mixture was cooled to ambient temperature, quenched with water and extracted with ethyl acetate. The organic layer was washed with brine, dried over anhydrous sodium sulfate, filtered and concentrated in vacuo. The crude material was purified by flash chromatography (5% methanol/dichloromethane) to provide benzyl (R)-3-((5-(3-methyl-1,2,4-oxadiazol-5-yl)-1H-pyrrolo[2,3-b]pyridin-4-yl)amino)piperidine-1-carboxylate as a white solid (0.01 g, 10% yield): MS (ES) m/z 433.3 (M+H).

Step 5: Preparation of (R)-5-(3-methyl-1,2,4-oxadiazol-5-yl)-N-(piperidin-3-yl)-1H-pyrrolo[2,3-b]pyridin-4-amine hydrochloride

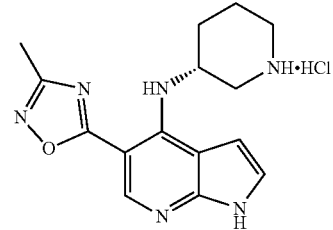

A stirred solution of benzyl (R)-3-((5-(3-methyl-1,2,4-oxadiazol-5-yl)-1H-pyrrolo[2,3-b]pyridin-4-yl)amino)piperidine-1-carboxylate (0.34 g, 0.78 mmol) and conc.HCl (3 mL) in a sealed tube was heated at 70° C. After 3 hours the reaction was cooled to room temperature and concentrated in vacuo to provide ((R)-5-(3-methyl-1,2,4-oxadiazol-5-yl)-N-(piperidin-3-yl)-H-pyrrolo[2,3-b]pyridin-4-amine as an off-white solid (0.25 g, crude): MS (ES) m/z 299.0 (M+H).

Step 6: Preparation of (R)-3-(3-((5-(3-methyl-1,2,4-oxadiazol-5-yl)-H-pyrrolo[2,3-b]pyridin-4-yl)amino)piperidin-1-yl)-3-oxopropanenitrile

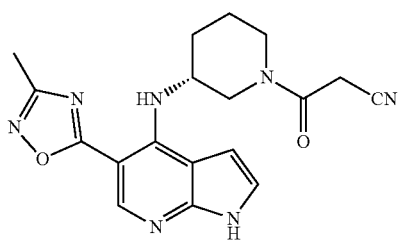 [SMILES: Cc1noc(-c2cnc3[nH]ccc3c2N[C@@H]2CCCN(C(=O)CC#N)C2)n1]

To a stirred solution ((R)-5-(3-methyl-1,2,4-oxadiazol-5-yl)-N-(piperidin-3-yl)-H-pyrrolo[2,3-b]pyridin-4-amine (0.25 g, 0.83 mmol) in N,N-dimethylformamide (0.5 mL) was added 1-[bis(dimethylamino)methylene]-1H-1,2,3-triazolo[4,5-b]pyridinium 3-oxid hexafluorophosphate (0.34 g, 0.91 mmol), N,N-diisopropylethylamine (1.2 g, 1.73 mmol) and cyanoacetic acid (0.118 g, 1.25 mmol). The mixture was stirred at ambient temperature for 18 hours. The reaction mixture was concentrated in vacuo and the crude material was purified by flash chromatography (5% methanol/dichloromethane) to provide (R)-3-(3-((5-(3-methyl-1,2,4-oxadiazol-5-yl)-1H-pyrrolo[2,3-b]pyridin-4-yl)amino)piperidin-1-yl)-3-oxopropanenitrile as an off-white solid (0.04 g, 13% yield): $^1$H NMR (400 MHz, DMSO-$d_6$) δ 11.82 (br s, 1H), 8.71-8.76 (m, 1H), 8.56-8.57 (m, 1H), 7.28 (s, 1H), 6.74 (s, 1H), 4.50 (br s, 1H), 4.28 (m, 1H), 4.03-4.14 (m, 1H), 3.82-3.91 (m, 1H), 3.57-3.60 (m, 1H), 3.39 (m, 2H), 3.29 (m, 1H), 2.39-2.41 (m, 3H), 2.04 (m, 1H), 1.56-1.78 (m, 2H); MS (ES) m/z 365.9 (M+H).

Example 7: Preparation of (R)-3-(3-((5-(1,3,4-oxadiazol-2-yl)-1H-pyrrolo[2,3-b]pyridin-4-yl)amino)piperidin-1-yl)-3-oxopropanenitrile

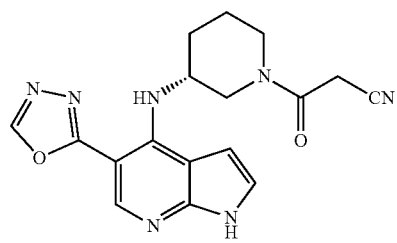 [SMILES: N#CCC(=O)N1CCC[C@@H](Nc2c(-c3nnco3)cnc3[nH]ccc23)C1]

Scheme 11: Preparation of (R)-3-(3-((5-(1,3,4-oxadiazol-2-yl)-1H-pyrrolo[2,3-b]pyridin-4-yl)amino)piperidin-1-yl)-3-oxopropanenitrile

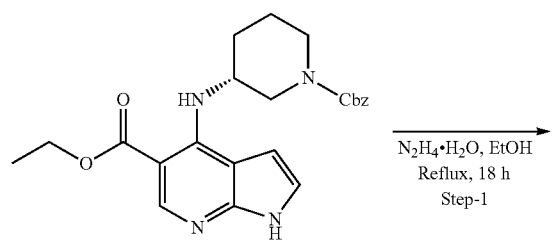

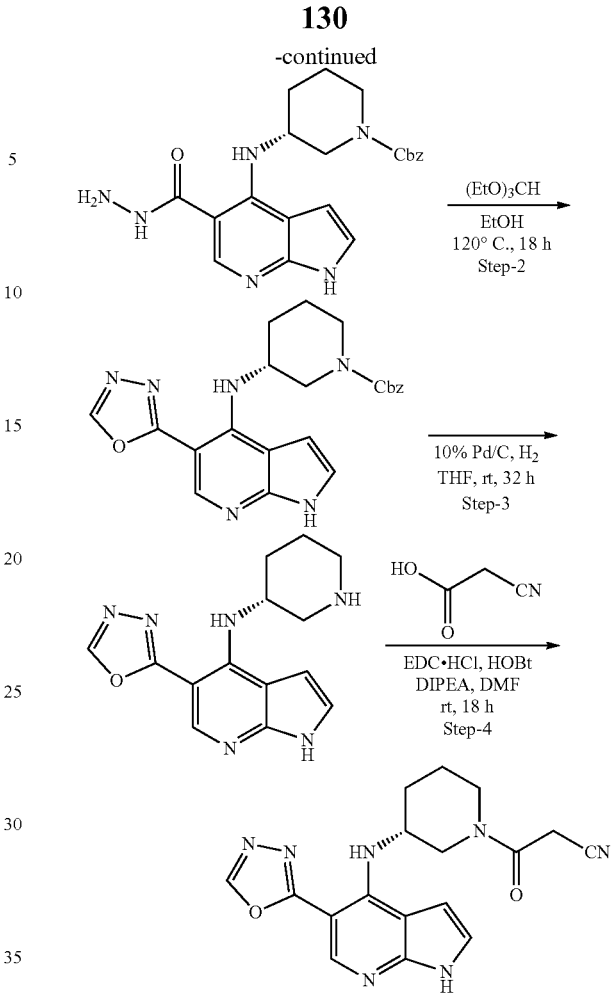

Step 1: Preparation of benzyl (R)-3-((5-(hydrazinecarbonyl)-1H-pyrrolo[2,3-b]pyridin-4-yl)amino)piperidine-1-carboxylate

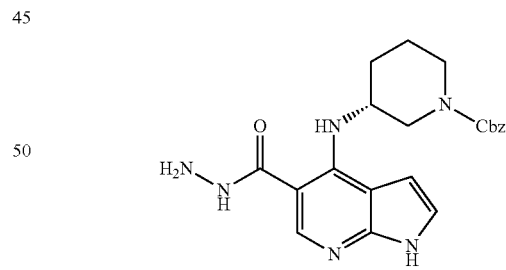

To a stirred solution of ethyl (R)-4-((1-((benzyloxy)carbonyl)piperidin-3-yl)amino)-1H-pyrrolo[2,3-b]pyridine-5-carboxylate (0.5 g, 1.18 mmol, prepared by the method as described in Example 6, step-1) and hydrazine hydrate (32 mL) in ethanol (8 mL) was heated at 110° C. for 18 hours. After cooling to room temperature the mixture was concentrated in vacuo to remove volatiles and the residue was triturated with 10% methanol in diethyl ether to provide benzyl (R)-3-((5-(hydrazinecarbonyl)-1H-pyrrolo[2,3-b]pyridin-4-yl)amino)piperidine-1-carboxylate as a yellow solid (0.3 g, 62% yield): MS (ES) m/z 409.2 (M+H).

Step 2: Preparation of benzyl (R)-3-((5-(1,3,4-oxadiazol-2-yl)-1H-pyrrolo[2,3-b]pyridin-4-yl)amino)piperidine-1-carboxylate

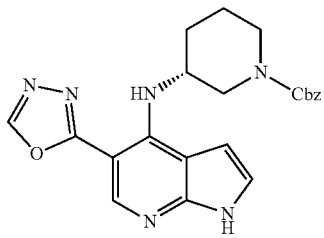 [SMILES: O=C(OCc1ccccc1)N1CCC[C@@H](Nc2c(-c3nnco3)cnc3[nH]ccc23)C1]

To a stirred solution of benzyl (R)-3-((5-(hydrazinecarbonyl)-1H-pyrrolo[2,3-b]pyridin-4-yl)amino)piperidine-1-carboxylate (0.1 g, 0.24 mmol) and triethylorthoformate (2 mL, 12.0 mmol) in ethanol (8 mL) was heated in a sealed tube to 120° C. After 18 hours the reaction was cooled to room temperature and the mixture was concentrated in vacuo to remove volatiles. The crude material was purified by column chromatography (methanol/dichloromethane) to provide benzyl (R)-3-((5-(1,3,4-oxadiazol-2-yl)-1H-pyrrolo[2,3-b]pyridin-4-yl)amino)piperidine-1-carboxylate as a pale yellow solid (0.16 g, 40% yield): MS (ES) m/z 419.2 (M+H).

Step 3: Preparation of (R)-5-(1,3,4-oxadiazol-2-yl)-N-(piperidin-3-yl)-1H-pyrrolo[2,3-b]pyridin-4-amine

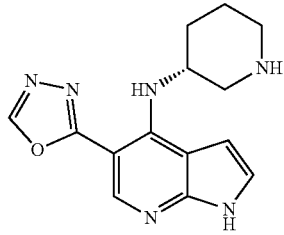 [SMILES: c1cc2c(N[C@@H]3CCCNC3)c(-c3nnco3)cnc2[nH]1]

To a solution of benzyl (R)-3-((5-(1,3,4-oxadiazol-2-yl)-1H-pyrrolo[2,3-b]pyridin-4-yl)amino)piperidine-1-carboxylate (0.16 g, 0.38 mmol) in tetrahydrofuran:ethanol (8 mL:5 mL) was added 10% palladium on carbon (0.03 g) and the heterogeneous mixture was stirred at ambient temperature under hydrogen atmosphere for 32 hours. The reaction mixture was filtered through celite and washed with methanol. The filtrate was concentrated in vacuo to provide crude material which was triturated with diethyl ether to provide (R)-5-(1,3,4-oxadiazol-2-yl)-N-(piperidin-3-yl)-1H-pyrrolo[2,3-b]pyridin-4-amine as a yellow solid (0.05 g, 52% yield): MS (ES) m/z 285.2 (M+H).

Step 4: Preparation of (R)-3-(3-((5-(1,3,4-oxadiazol-2-yl)-1H-pyrrolo[2,3-b]pyridin-4-yl)amino)piperidin-1-yl)-3-oxopropanenitrile

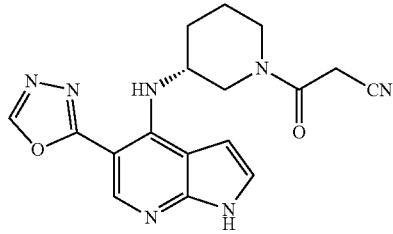 [SMILES: N#CCC(=O)N1CCC[C@@H](Nc2c(-c3nnco3)cnc3[nH]ccc23)C1]

(R)-3-(3-((5-(1,3,4-Oxadiazol-2-yl)-1H-pyrrolo[2,3-b]pyridin-4-yl)amino)piperidin-1-yl)-3-oxopropanenitrile was prepared by the method as described in Example 1, Step-8 to give a pale brown solid (0.01 g, 14% yield): $^1$H NMR (400 MHz, DMSO-d$_6$) δ 11.77 (s, 1H), 9.24 (s, 1H), 8.40-8.47 (m, 2H), 7.28 (s, 1H), 6.75 (s, 1H), 4.20 (d, J=10.0 Hz, 1H), 4.04 (q, J1=18.8 Hz, J2=18.4 Hz, 2H), 3.73-3.84 (m, 2H), 3.47 (d, J=10.0 Hz, 1H), 3.14 (d, J=4.8 Hz, 1H), 2.11 (bs, 1H), 1.98 (t, J=8.0 Hz, 1H), 1.70-1.75 (m, 2H); MS (ES) m/z 352.0 (M+H).

Analytical Conditions:

Column: Inertsil ODS 3V (250 mm×4.6 mm×5 mic)

Mobile phase (A): 0.1% Ammonia in water

Mobile phase (B): ACN

Flow rate: 1.0 mL/min

Composition of B: 0/10, 12/70, 25/90, 27/10, 30/10

Example 8: Preparation of (R)-3-(3-((5-(1,3,4-thiadiazol-2-yl)-1H-pyrrolo[2,3-b]pyridin-4-yl)amino)piperidin-1-yl)-3-oxopropanenitrile

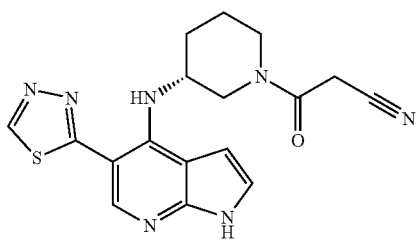

Scheme 12: Preparation of (R)-3-(3-((5-(1,3,4-thiadiazol-2-yl)-1H-pyrrolo[2,3-b]pyridin-4-yl)amino)piperidin-1-yl)-3-oxopropanenitrile

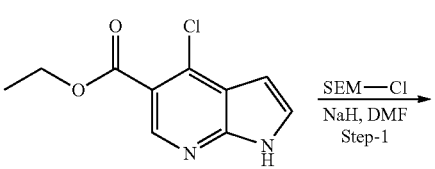

133
-continued

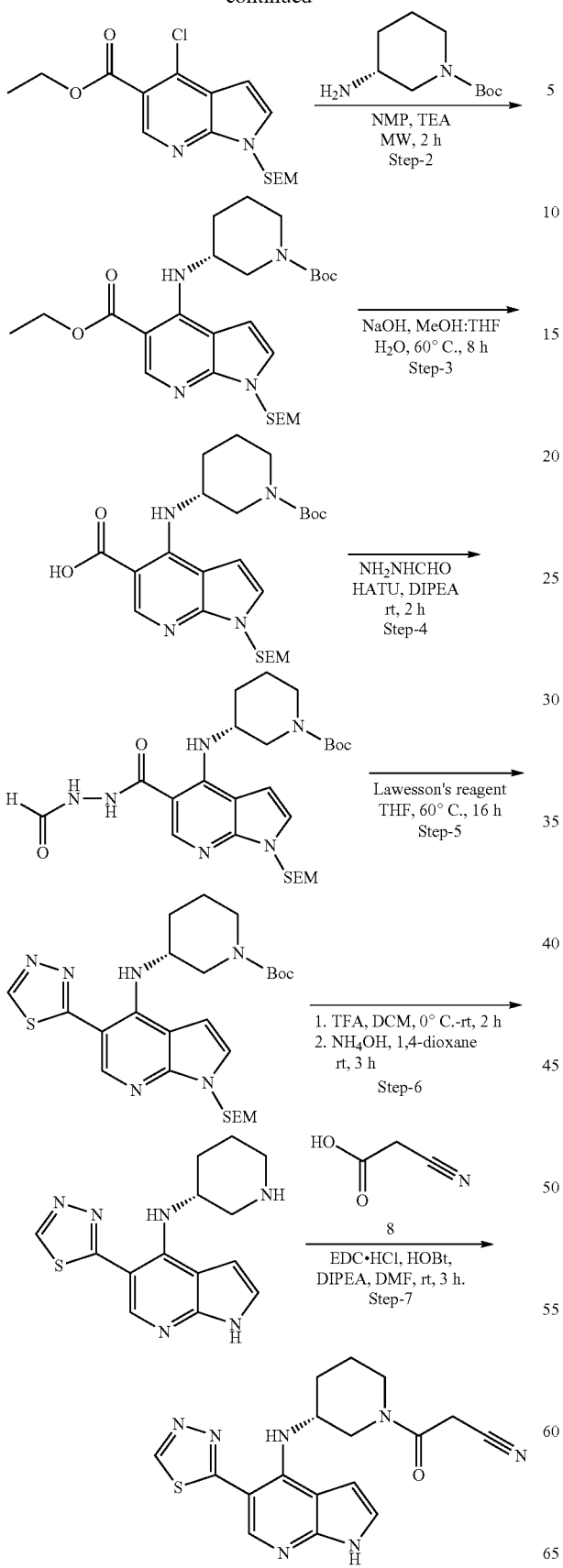

134

Step 1: Preparation of ethyl 4-chloro-1-((2-(trimethylsilyl)ethoxy)methyl)-1H-pyrrolo[2,3-b]pyridine-5-carboxylate

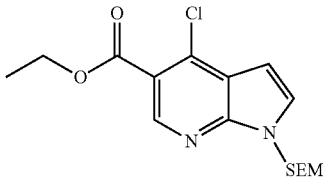 [SMILES: CCOC(=O)c1cnc2c(ccn2COCC[Si](C)(C)C)c1Cl]

To a stirred solution of ethyl 4-chloro-1H-pyrrolo[2,3-b]pyridine-5-carboxylate (5 g, 22.2 mol) in dry dimethylformamide (20 mL) at 0° C. was added sodium hydride (1.42 g, 35.6 mol, 60% suspension in mineral oil) and the suspension was stirred for 30 minutes. Then 2-(trimethylsilyl)ethoxymethyl chloride (7.88 mL, 44.5 mol) was added and the resulting mixture was stirred at ambient temperature for 1.5 hours. The reaction mixture was quenched with saturated ammonium chloride solution and extracted with ethyl acetate. The combined organic extract was washed with brine, dried over anhydrous sodium sulfate, the solution was filtered, and concentrated in vacuo. The crude material was purified by column chromatography (ethyl acetate/hexane) to provide ethyl 4-chloro-1-((2-(trimethylsilyl)ethoxy)methyl)-1H-pyrrolo[2,3-b]pyridine-5-carboxylate as a yellow oil (5.5 g, 70% yield): MS (ES) m/z 354.9 (M+H).

Step 2: Preparation of ethyl (R)-4-((1-(tert-butoxycarbonyl)piperidin-3-yl)amino)-1-((2-(trimethylsilyl)ethoxy)methyl)-1H-pyrrolo[2,3-b]pyridine-5-carboxylate

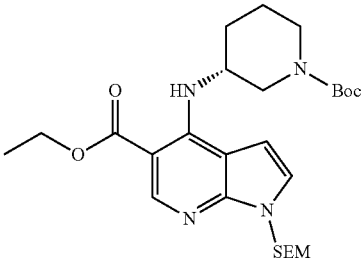 [SMILES: CCOC(=O)c1cnc2c(ccn2COCC[Si](C)(C)C)c1N[C@@H]1CCCN(C(=O)OC(C)(C)C)C1]

To a solution of ethyl 4-chloro-1-((2-(trimethylsilyl)ethoxy)methyl)-1H-pyrrolo[2,3-b]pyridine-5-carboxylate (2.0 g, 5.64 mmol) in N-methyl-2-pyrrolidone (20 mL) was added tert-butyl (R)-3-aminopiperidine-1-carboxylate (1.7 g, 2.11 mmol) followed by triethylamine (0.8 mL) in a sealed tube. The mixture was heated to 135° C. for 3 hours. After cooling to ambient temperature, the reaction mixture was quenched with water and extracted with ethyl acetate. The organic layer was washed with brine, dried over anhydrous sodium sulfate, filtered and concentrated in vacuo. The crude material was purified by flash chromatography (17% ethyl acetate/hexane) to provide ethyl (R)-4-((1-(tert-butoxycarbonyl)piperidin-3-yl)amino)-1-((2-(trimethylsilyl)ethoxy)methyl)-1H-pyrrolo[2,3-b]pyridine-5-carboxylate as a colorless oil (1.0 g, 35% yield): MS (ES) m/z 519.0 [M+H]$^+$.

Step 3: Preparation of (R)-4-((1-(tert-butoxycarbonyl)piperidin-3-yl)amino)-1-((2-(trimethylsilyl)ethoxy)methyl)-1H-pyrrolo[2,3-b]pyridine-5-carboxylic acid

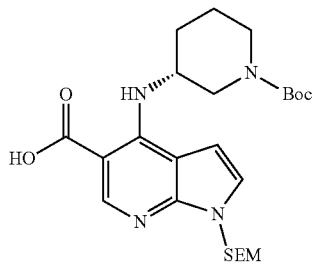 [SMILES: CC(C)(C)OC(=O)N1CCC[C@@H](Nc2c(C(=O)O)cnc3c2ccn3COCC[Si](C)(C)C)C1]

To a stirred solution of ethyl (R)-4-((1-(tert-butoxycarbonyl)piperidin-3-yl)amino)-1-((2-(trimethylsilyl) ethoxy)methyl)-1H-pyrrolo[2,3-b]pyridine-5-carboxylate (1.0 g, 1.93 mmol) in methanol (3 mL), tetrahydrofuran:water (3 mL:3 mL) was added sodium hydroxide (0.15 g, 3.85 mmol) at ambient temperature. The mixture was stirred at 60° C. for 8 hours. The reaction was cooled to ambient temperature and concentrated in vacuo to remove volatiles. The residue was dissolved in water and acidified with 1N HCl and extracted with ethyl acetate. The organic layer was washed with brine, dried over anhydrous sodium sulfate, filtered and concentrated in vacuo. The crude material was triturated with n-pentane to provide (R)-4-((1-(tert-butoxycarbonyl)piperidin-3-yl)amino)-1-((2-(trimethylsilyl)ethoxy)methyl)-1H-pyrrolo[2,3-b]pyridine-5-carboxylic acid as an off-white solid (0.8 g, 84% yield): MS (ES) m/z 490.9 [M+H]$^+$.

Step 4: Preparation of tert-butyl (R)-3-((5-(2-formylhydrazine-1-carbonyl)-1-((2-(trimethylsilyl)ethoxy)methyl)-1H-pyrrolo[2,3-b]pyridin-4-yl)amino)piperidine-1-carboxylate

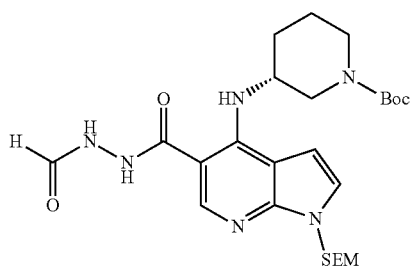 [SMILES: CC(C)(C)OC(=O)N1CCC[C@@H](Nc2c(C(=O)NNC=O)cnc3c2ccn3COCC[Si](C)(C)C)C1]

To a solution of (R)-4-((1-(tert-butoxycarbonyl)piperidin-3-yl)amino)-1-((2-(trimethylsilyl)ethoxy)methyl)-1H-pyrrolo[2,3-b]pyridine-5-carboxylic acid (0.4 g, 0.752 mmol) in dimethylformamide (5 mL) was added formic acid hydrazide (0.07 g, 1.13 mmol), 1-[bis(dimethylamino)methylene]-1H-1,2,3-triazolo[4,5-b]pyridinium 3-oxid hexafluorophosphate (0.15 g, 0.37 mmol) and N,N-disopropylethylamine (0.07 mL, 0.376 mmol) and the mixture was stirred at ambient temperature for 3 hours. The reaction was quenched with water and extracted with ethyl acetate. The organic layer was washed with sodium bicarbonate solution, brine, dried over anhydrous sodium sulfate. The solution was filtered and concentrated in vacuo to provide tert-butyl (R)-3-((5-(2-formylhydrazine-1-carbonyl)-1-((2-(trimethylsilyl)ethoxy)methyl)-1H-pyrrolo[2,3-b]pyridin-4-yl)amino)piperidine-1-carboxylate as a pale yellow liquid (0.4 g, 90% yield): MS (ES) m/z 533.0 [M+H]$^+$.

Step 5: Preparation of tert-butyl (R)-3-((5-(1,3,4-thiadiazol-2-yl)-1-((2-(trimethylsilyl)ethoxy)methyl)-1H-pyrrolo[2,3-b]pyridin-4-yl)amino)piperidine-1-carboxylate

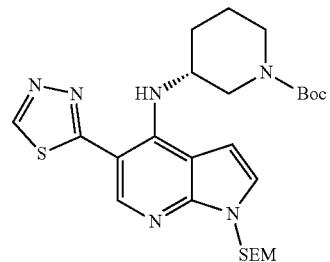 [SMILES: CC(C)(C)OC(=O)N1CCC[C@@H](Nc2c(-c3nncs3)cnc3c2ccn3COCC[Si](C)(C)C)C1]

To a solution of tert-butyl (R)-3-((5-(2-formylhydrazine-1-carbonyl)-1-((2-(trimethylsilyl)ethoxy)methyl)-1H-pyrrolo[2,3-b]pyridin-4-yl)amino)piperidine-1-carboxylate (0.37 g, 0.695 mmol) in tetrahydrofuran (20 mL) was added Lawesson's reagent (0.84 g, 2.08 mmol) at ambient temperature and the mixture was stirred at 70° C. for 16 hours. The reaction was cooled to ambient temperature quenched with 10% citric acid and the solution was stirred for 5 minutes followed by the addition of sodium bicarbonate solution and stirred for another 10 minutes. The aqueous layer was extracted with ethyl acetate, washed with saturated sodium bicarbonate and brine. The organic layer was dried over anhydrous sodium sulfate, filtered and concentrated in vacuo. The crude material was purified by flash chromatography (35% ethyl acetate/hexane) to provide tert-butyl (R)-3-((5-(1,3,4-thiadiazol-2-yl)-1-((2-(trimethylsilyl)ethoxy)methyl)-1H-pyrrolo[2,3-b]pyridin-4-yl)amino)piperidine-1-carboxylate as a pale yellow liquid (0.28 g, 78% yield): MS (ES) m/z 530.9 [M+H]$^+$.

Step 6: Preparation of (R)-N-(piperidin-3-yl)-5-(1,3,4-thiadiazol-2-yl)-1H-pyrrolo[2,3-b]pyridin-4-amine

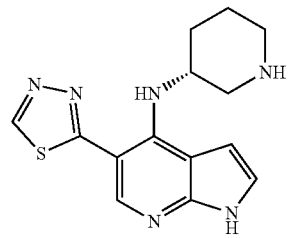 [SMILES: c1cc2c(N[C@@H]3CCCNC3)c(-c3nncs3)cnc2[nH]1]

(R)-N-(Piperidin-3-yl)-5-(1,3,4-thiadiazol-2-yl)-1H-pyrrolo[2,3-b]pyridin-4-amine was prepared by the method as described in Example 1, Step-7 to give a yellow liquid (0.2 g, % yield): MS (ES) m/z 301.2 [M+H]$^+$.

Step 7: (R)-3-(3-((5-(1,3,4-thiadiazol-2-yl)-1H-pyrrolo[2,3-b]pyridin-4-yl)amino)piperidin-1-yl)-3-oxopropanenitrile

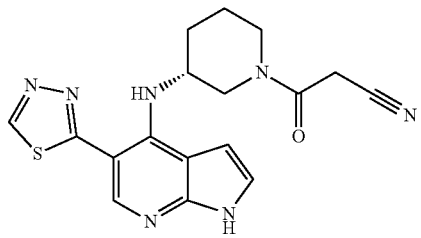

(R)-3-(3-((5-(1,3,4-Thiadiazol-2-yl)-1H-pyrrolo[2,3-b]pyridin-4-yl)amino)piperidin-1-yl)-3-oxopropanenitrile was prepared by the method as described in Example 1, Step-8 to give an off-white solid (0.05 g, 20% yield): $^1$H NMR (400 MHz, DMSO-$d_6$) δ 11.71 (s, 1H), 9.4-9.5 (m, 2H), 8.35 (d, J=6.4 Hz, 1H), 7.25 (s, 1H), 6.78 (s, 1H), 4.39 (s, 1H), 3.60-4.21 (m, 6H), 2.09 (s, 1H), 1.65-1.74 (m, 3H); MS (ES) m/z 351.3 (M+H).

Example 9 and 10: Preparation of 3-((3R,5S)-3-methyl-5-((5-(oxazol-2-yl)-1H-pyrrolo[2,3-b]pyridin-4-yl)amino)piperidin-1-yl)-3-oxopropanenitrile and 3-((3S,5R)-3-methyl-5-((5-(oxazol-2-yl)-1H-pyrrolo[2,3-b]pyridin-4-yl)amino)piperidin-1-yl)-3-oxopropanenitrile

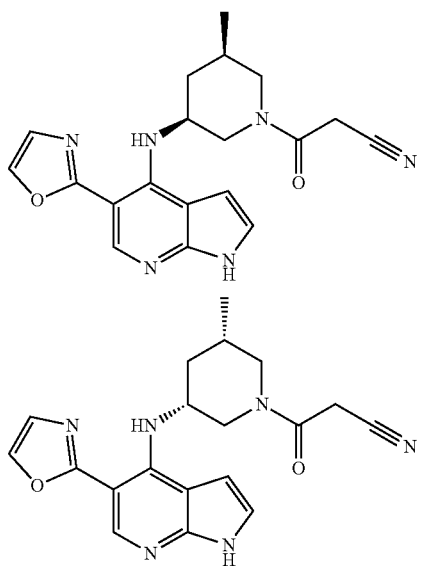

Benzyl 3-amino-5-methylpiperidine-1-carboxylate hydrochloride was prepared by the method described below.

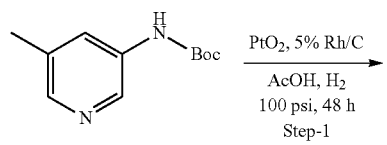

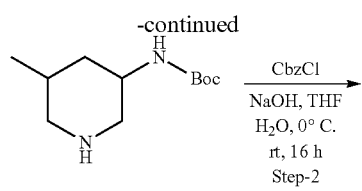

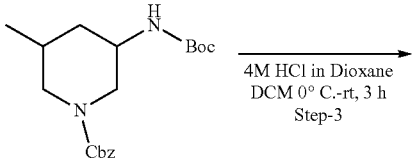

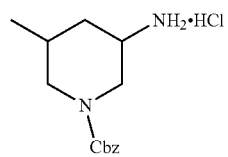

Step 1: Preparation of tert-butyl (5-methylpiperidin-3-yl)carbamate

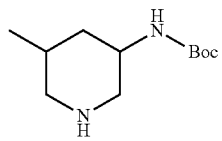

In a Parr shaker vessel, a stirred solution of tert-butyl (5-methylpyridin-3-yl)carbamate (0.8 g) in acetic acid (30 mL) was added platinum dioxide (0.2 g) and rhodium on carbon (0.2 g) under a nitrogen atmosphere. The reaction mixture was stirred under hydrogen (100 psi) at ambient temperature for 24 hours. The mixture was filtered through celite and the filtration concentrated in vacuo to provide tert-butyl (5-methylpiperidin-3-yl)carbamate as a glassy liquid (0.74 g, 90% yield): MS (ES) m/z 215.1 [M+H]$^+$.

Step 2: Preparation of benzyl 3-((tert-butoxycarbonyl)amino)-5-methylpiperidine-1-carboxylate

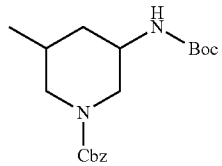 [SMILES: CC1CC(NC(=O)OC(C)(C)C)CN(C(=O)OCc2ccccc2)C1]

To a stirred solution of tert-butyl (5-methylpiperidin-3-yl)carbamate (1.5 g, 6.99 mmol) in tetrahydrofuran (12 mL) and water (3 mL), was added sodium hydroxide (1.4 g, 34.99 mmol) and benzyl chloroformate, (2.4 mL, 13.99) at 0° C. The mixture was stirred at ambient temperature for 16 hours. The reaction mixture was diluted with ethyl acetate, washed with brine, dried over sodium sulfate, filtered and concentrated in vacuo. The crude material was purified by flash chromatography (23% ethyl acetate/hexane) to provide benzyl 3-((tert-butoxycarbonyl)amino)-5-methylpiperidine-1-carboxylate as a white solid (0.8 g, 33% yield): MS (ES) m/z 293.2 [M−56]$^+$.

Step 3: Preparation of benzyl 3-amino-5-methylpiperidine-1-carboxylate hydrochloride

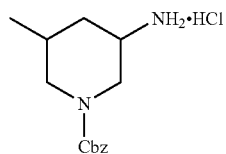

To a stirred solution of benzyl 3-((tert-butoxycarbonyl)amino)-5-methylpiperidine-1-carboxylate (0.8 g) in dichloromethane (20 mL), was added 4M hydrochloric acid in 1,4-dioxane (8 mL) at 0° C. The reaction mixture was stirred for 3 hours at ambient temperature then concentrated in vacuo to provide benzyl 3-amino-5-methylpiperidine-1-carboxylate hydrochloride as a white solid (0.54 g, 95% yield): MS (ES) m/z 249.0 [M+H]$^+$.

Scheme 13: Preparation of 3-((3S,5R)-3-methyl-5-((5-(oxazol-2-yl)-1H-pyrrolo[2,3-b]pyridin-4-yl)amino)piperidin-1-yl)-3-oxopropanenitrile and 3-((3S,5S)-3-methyl-5-((5-(oxazol-2-yl)-1H-pyrrolo[2,3-b]pyridin-4-yl)amino)piperidin-1-yl)-3-oxopropanenitrile

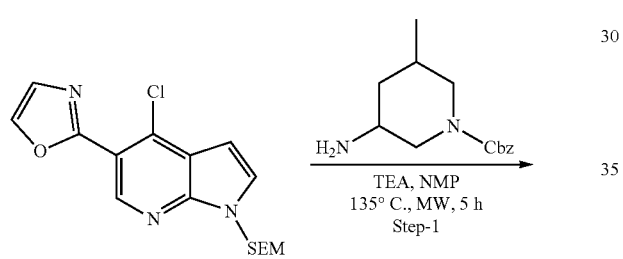

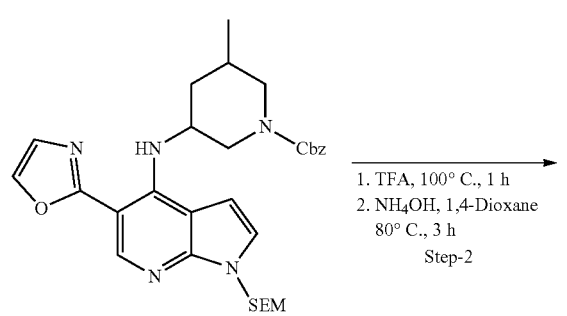

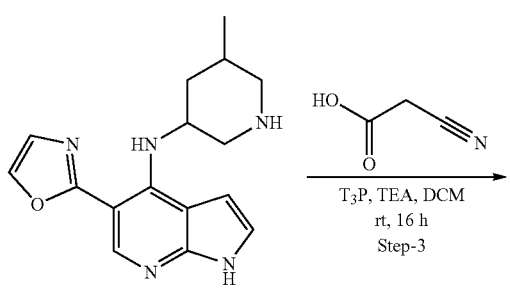

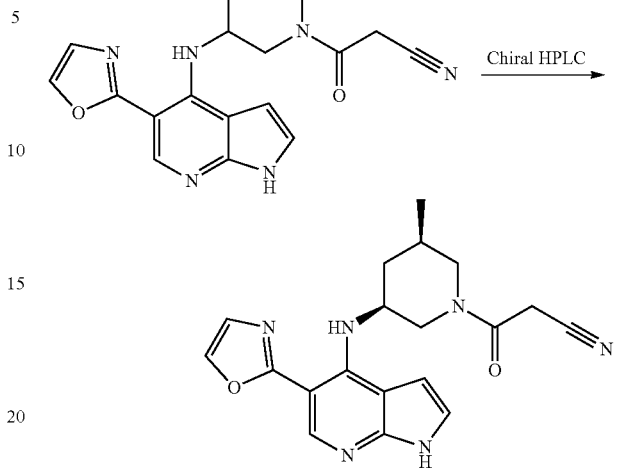

Example-9

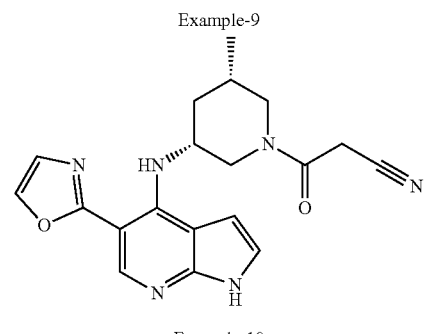

Example-10

Step 1: Preparation of benzyl 3-methyl-5-((5-(oxazol-2-yl)-1-((2-(trimethylsilyl)ethoxy)methyl)-1H-pyrrolo[2,3-b]pyridin-4-yl)amino)piperidine-1-carboxylate

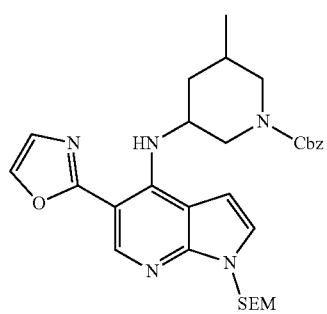 [SMILES: CC1CC(Nc2c(-c3ncco3)cnc3c2ccn3COCC[Si](C)(C)C)CN(C(=O)OCc2ccccc2)C1]

To a stirred solution of 2-(4-chloro-1-((2-(trimethylsilyl)ethoxy)methyl)-1H-pyrrolo[2,3-b]pyridin-5-yl)oxazole (0.35 g, 1.00 mmol, prepared by the method described in Example 5, Step-1), triethylamine (0.4 mL, 3.00 mmol) benzyl 3-amino-5-methylpiperidine-1-carboxylate hydrochloride (0.43 g, 1.50 mmol) in N-methylpyrrolidone (10 mL) was subjected to microwave irradiation at 135° C. for 5 hours. The reaction was cooled to ambient temperature, diluted with water, and extracted with ethyl acetate. The organic layer was washed with brine, dried over sodium sulfate, filtered and concentrated in vacuo. The crude material was purified by flash chromatography (21% ethyl acetate/hexane) to provide benzyl 3-methyl-5-((5-(oxazol-2-yl)-1-((2-(trimethylsilyl)ethoxy)methyl)-1H-pyrrolo[2,3-b]pyridin-4-yl)amino)piperidine-1-carboxylate as a thick brown liquid (0.13 g, 23%): MS (ES) m/z=561.9 [M+H]⁺.

Step 2: Preparation of N-(5-methylpiperidin-3-yl)-5-(oxazol-2-yl)-1H-pyrrolo[2,3-b]pyridin-4-amine

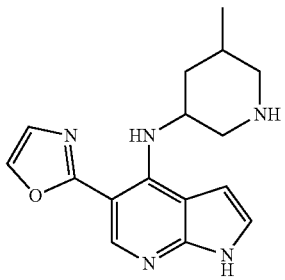 [SMILES: CC1CNCC(Nc2c(-c3ncco3)cnc3[nH]ccc23)C1]

A solution of benzyl 3-methyl-5-((5-(oxazol-2-yl)-1-((2-(trimethylsilyl)ethoxy)methyl)-1H-pyrrolo[2,3-b]pyridin-4-yl)amino)piperidine-1-carboxylate (0.13 g, 0.23 mmol) in trifluoroacetic acid (3.0 mL) was stirred at 100° C. for 1 hour. After cooling the reaction mixture was concentrated in vacuo, the obtained residue was dissolved in 1,4-dioxane: aqueous ammonia (5.0 mL:5.0 mL) and was then stirred at ambient temperature overnight. The reaction mixture was concentrated in vacuo to provide N-(5-methylpiperidin-3-yl)-5-(oxazol-2-yl)-1H-pyrrolo[2,3-b]pyridin-4-amine as thick liquid (0.08 g, crude): MS (ES) m/z 298.0 [M+H]⁺.

Step 3: Preparation of 3-(3-methyl-5-((5-(oxazol-2-yl)-1H-pyrrolo[2,3-b]pyridin-4-yl)amino)piperidin-1-yl)-3-oxopropanenitrile

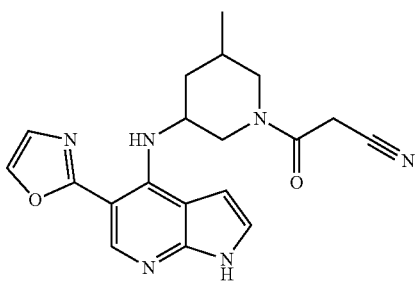 [SMILES: CC1CC(Nc2c(-c3ncco3)cnc3[nH]ccc23)CN(C(=O)CC#N)C1]

To a solution of N-(5-methylpiperidin-3-yl)-5-(oxazol-2-yl)-1H-pyrrolo[2,3-b]pyridin-4-amine (0.07 g, 0.235 mmol) in dichloromethane (10 mL) was added triethylamine (0.1 mL, 0.706 mmol), propanephosphonic acid anhydride (0.4 mL, 0.706 mmol) and cyanoacetic acid (0.03 g, 0.353 mmol) at 0° C. The reaction mixture was stirred at ambient temperature for 3 hours. The reaction mixture was quenched with water and extracted with dichloromethane. The organic layer was washed with water, brine, dried over anhydrous sodium sulfate, filtered and concentrated in vacuo. The crude material was purified by flash chromatography (70% ethyl acetate/hexane) to provide racemic 3-(3-methyl-5-((5-(oxazol-2-yl)-1H-pyrrolo[2,3-b]pyridin-4-yl)amino)piperidin-1-yl)-3-oxopropanenitrile as an off-white solid (0.025 g, 31% yield): MS (ES) m/z 351.1 [M+H]⁺.

The racemic compound was further purified by chiral preparative HPLC to separate the enantiomers.

Chiral HPLC

Analytical Conditions:

Column: CHIRALPAC IC (10 mm×4.6 mm×3 mic)

Mobile phase (A): n-hexane:ethanol with 0.1% DEA (80:20)

Flow rate: 1.0 mL/min

Example 9: 3-((3R,5S)-3-methyl-5-((5-(oxazol-2-yl)-1H-pyrrolo[2,3-b]pyridin-4-yl)amino)piperidin-1-yl)-3-oxopropanenitrile (stereochemistry has been provisionally assigned)

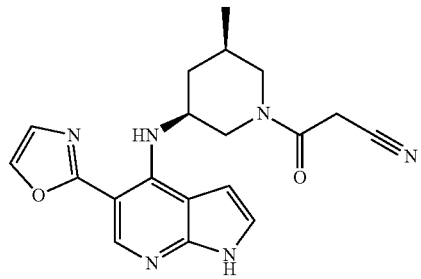 [SMILES: C[C@@H]1C[C@H](Nc2c(-c3ncco3)cnc3[nH]ccc23)CN(C(=O)CC#N)C1]

Isolated as a white solid, (0.028 g, 11% yield): ¹H NMR (400 MHz, CDCl₃) δ 11.84 (s, 1H), 10.37-10.35 (m, 1H), 8.56 (m, 2H), 7.75 (s, 1H), 6.975 (m, 2H), 5.12 (d, J=12.4 Hz, 1H), 4.2 (br s, 1H), 3.75-2.00 (m, 7H), 1.49 (s, 1H), 0.96 (d, 3H); MS (ES) m/z=365.2 [M+H]⁺; HPLC Purity: 99.45%. Retention time 11.4 min.

Example 10: 3-((3S,5R)-3-methyl-5-((5-(oxazol-2-yl)-1H-pyrrolo[2,3-b]pyridin-4-yl)amino)piperidin-1-yl)-3-oxopropanenitrile (stereochemistry has been provisionally assigned)

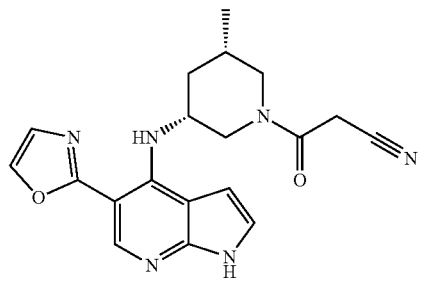 [SMILES: C[C@H]1C[C@@H](Nc2c(-c3ncco3)cnc3[nH]ccc23)CN(C(=O)CC#N)C1]

Isolated as a white solid, (0.003 g, 13% yield): ¹H NMR (400 MHz, CDCl₃) δ 11.86 (s, 1H), 10.37-10.35 (m, 1H), 8.56 (m, 2H), 7.75 (s, 1H), 6.98 (m, 2H), 5.12 (d, J=12.4 Hz, 1H), 4.18 (br s, 1H), 3.8-2.20 (m, 7H), 2.00 (s, 1H), 0.9 (d, 3H); MS (ES) m/z=365.1 [M+H]⁺; HPLC purity: 98.16%. Retention time 16.22 min.

Example 11: Preparation of (R)-3-(3-((5-(4H-1,2,4-triazol-3-yl)-1H-pyrrolo[2,3-b]pyridin-4-yl)amino)piperidin-1-yl)-3-oxopropanenitrile

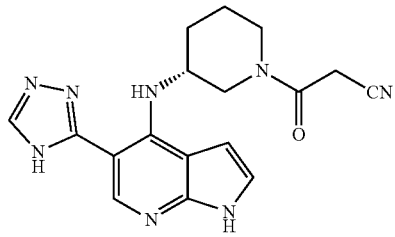

Scheme 14: Preparation of (R)-3-(3-((5-(4H-1,2,4-triazol-3-yl)-1H-pyrrolo[2,3-b]pyridin-4-yl)amino)piperidin-1-yl)-3-oxopropanenitrile

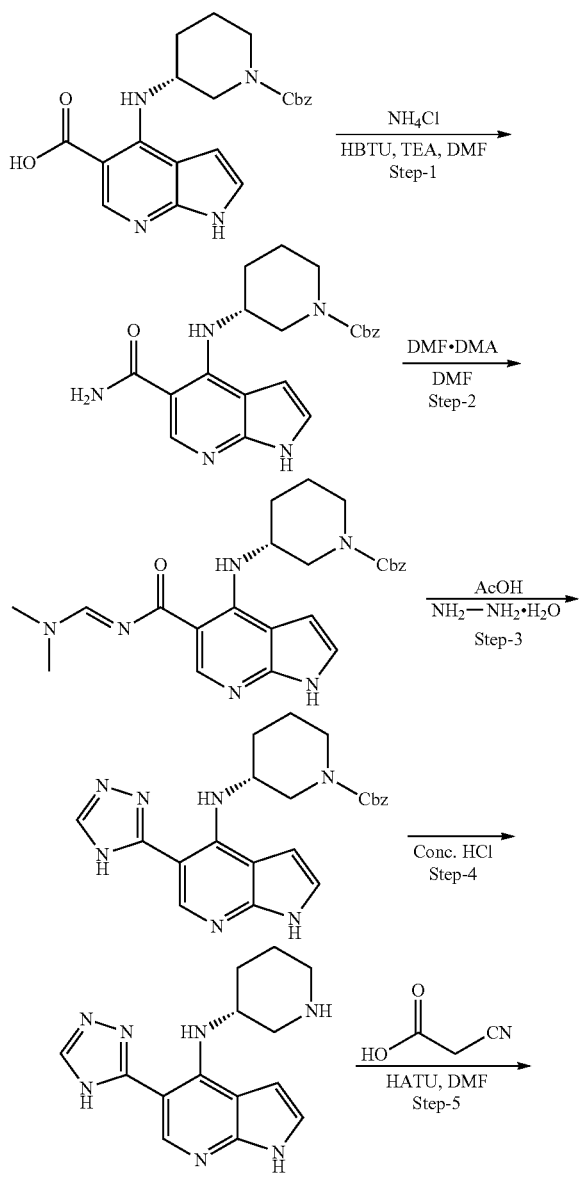

Step 1: Preparation of benzyl (R)-3-((5-carbamoyl-1H-pyrrolo[2,3-b]pyridin-4-yl)amino)piperidine-1-carboxylate

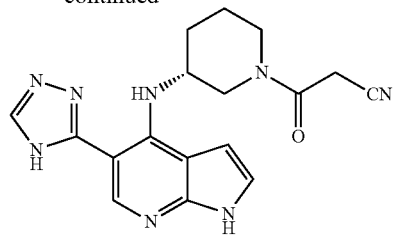

To a stirred solution (R)-4-((1-((benzyloxy)carbonyl)piperidin-3-yl)amino)-1H-pyrrolo[2,3-b]pyridine-5-carboxylic acid (0.1 g, 0.25 mmol, prepared by the method described in Example 9, Step-1) in N,N-dimethylformamide (1 mL) was added 1-[bis(dimethylamino)methylene]-1H-1,2,3-triazolo[4,5-b]pyridinium 3-oxid hexafluorophosphate (0.19 g, 0.508 mmol), triethylamine (0.08 g, 0.76 mmol) and ammonium chloride (0.07 g, 1.27 mmol). The mixture was stirred at ambient temperature for 18 hours. The reaction mixture was quenched with water and extracted with ethyl acetate. The organic layer was washed with brine, dried over anhydrous sodium sulfate, filtered and concentrated in vacuo to provide benzyl (R)-3-((5-carbamoyl-1H-pyrrolo[2,3-b]pyridin-4-yl)amino)piperidine-1-carboxylate as an off-white solid (0.1 g, crude): MS (ES) m/z 394.1 (M+H).

Step 2: Preparation of benzyl (R,E)-3-((5-(((dimethylamino)methylene)carbamoyl)-1H-pyrrolo[2,3-b]pyridin-4-yl)amino)piperidine-1-carboxylate

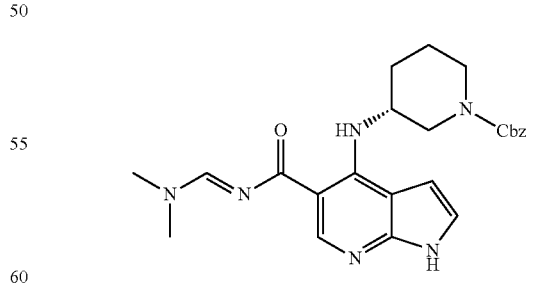

A stirred solution benzyl (R)-3-((5-carbamoyl-1H-pyrrolo[2,3-b]pyridin-4-yl)amino)piperidine-1-carboxylate (0.3 g, 0.76 mmol), N,N-dimethylformamide dimethyl acetal (5 mL) and N,N-dimethylformamide (0.3 mL) was heated at 90° C. for 3 hours. The reaction mixture was concentrated in vacuo to provide benzyl (R,E)-3-((5-(((dimethylamino)

methylene)carbamoyl)-1H-pyrrolo[2,3-b]pyridin-4-yl) amino)piperidine-1-carboxylate as an off-white solid (0.25 g, crude): MS (ES) m/z 448.9 (M+H).

Step 3: Preparation of benzyl (R)-3-((5-(4H-1,2,4-triazol-3-yl)-1H-pyrrolo[2,3-b]pyridin-4-yl)amino) piperidine-1-carboxylate

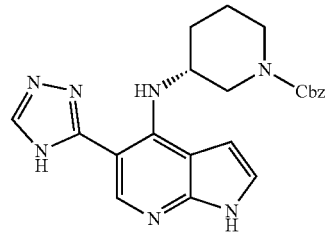

A stirred solution of benzyl (R,E)-3-((5-(((dimethyl-amino)methylene)carbamoyl)-1H-pyrrolo[2,3-b]pyridin-4-yl)amino)piperidine-1-carboxylate (0.25 g, 0.55 mmol) and hydrazine hydrate (1.2 mL) in acetic acid (2.5 mL) was stirred at 90° C. After 3 hours the reaction was cooled to ambient temperature, quenched with water and extracted with ethyl acetate. The organic layer was washed with water, brine, dried over anhydrous sodium sulfate, filtered and concentrated in vacuo. The crude material was purified by flash chromatography (5% methanol/dichloromethane) to provide benzyl (R)-3-((5-(4H-1,2,4-triazol-3-yl)-1H-pyrrolo[2,3-b]pyridin-4-yl)amino)piperidine-1-carboxylate as an off-white solid (0.25 g, crude): MS (ES) m/z 417.9 (M+H).

Step 4: Preparation of (R)-N-(piperidin-3-yl)-5-(4H-1,2,4-triazol-3-yl)-1H-pyrrolo[2,3-b]pyridin-4-amine hydrochloride

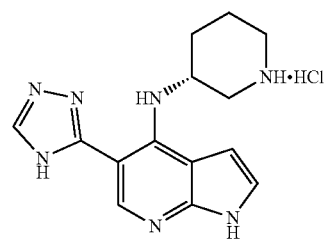

(R)-N-(Piperidin-3-yl)-5-(4H-1,2,4-triazol-3-yl)-1H-pyrrolo[2,3-b]pyridin-4-amine hydrochloride was prepared by the method described in Example 6, Step 5 which provided an off-white solid (0.15 g, 98% yield): MS (ES) m/z 284.0 (M+H)+.

Step 5: Preparation of (R)-3-(3-((5-(4H-1,2,4-triazol-3-yl)-1H-pyrrolo[2,3-b]pyridin-4-yl)amino) piperidin-1-yl)-3-oxopropanenitrile

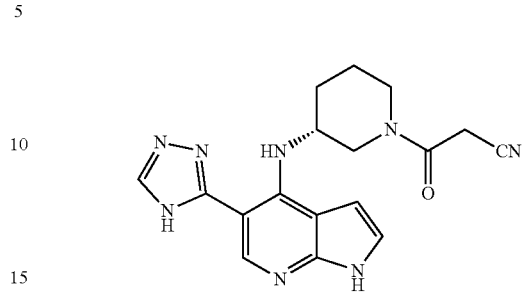

(R)-3-(3-((5-(4H-1,2,4-Triazol-3-yl)-1H-pyrrolo[2,3-b] pyridin-4-yl)amino)piperidin-1-yl)-3-oxopropanenitrile was prepared by the method described in Example 9, Step-5 to give an off-white solid (0.09 g, 7.5% yield): $^1$H NMR (400 MHz, DMSO-$d_6$) 14.13 (br s, 1H), 11.49 (br s, 1H), 9.2 (br s, 1H), 8.58-8.61 (br s, 2H), 7.2 (s, 1H), 6.66 (s, 1H), 4.35 (br s, 1H), 3.96-4.12 (m, 3H), 3.32-3.69 (m, 2H), 2.06 (m, 1H), 1.53-1.76 (m, 3H), 1.21 (s, 1H); MS (ES) m/z 351.2 (M+H).

Example 12: Preparation of (1S,3R)-3-((5-(pyridin-2-yl)-1H-pyrrolo[2,3-b]pyridin-4-yl)amino)cyclopentan-1-ol

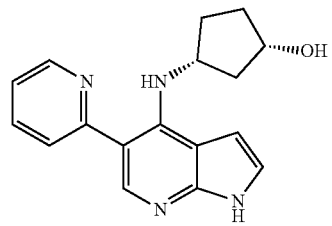 [SMILES: O[C@H]1CC[C@@H](Nc2c(-c3ccccn3)cnc3[nH]ccc23)C1]

(1S,3R)-3-Aminocyclopentan-1-ol hydrochloride was prepared by the following method

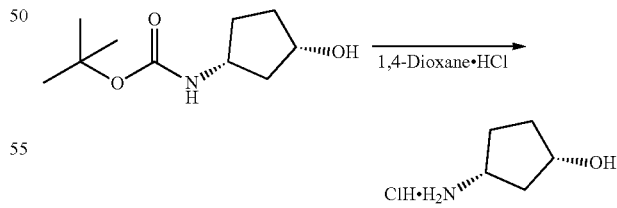

A solution of tert-butyl ((1R,3S)-3-hydroxycyclopentyl) carbamate (0.5 g, 2.48 mmol) in 1,4-dioxane (1 mL) was treated with (4M) hydrochloride acid in 1,4-dioxane (2.5 mL) and stirred under a nitrogen atmosphere at ambient temperature for 12 hours. The reaction mixture was concentrated in vacuo to provide (1S,3R)-3-aminocyclopentan-1-ol hydrochloride as an off-white solid (0.25 g, crude): MS (ES) m/z 102.1 (M+H).

Scheme 15: Preparation of (1S,3R)-3-((5-(pyridin-2-yl)-1H-pyrrolo[2,3-b]pyridin-4-yl)amino)cyclopentan-1-ol

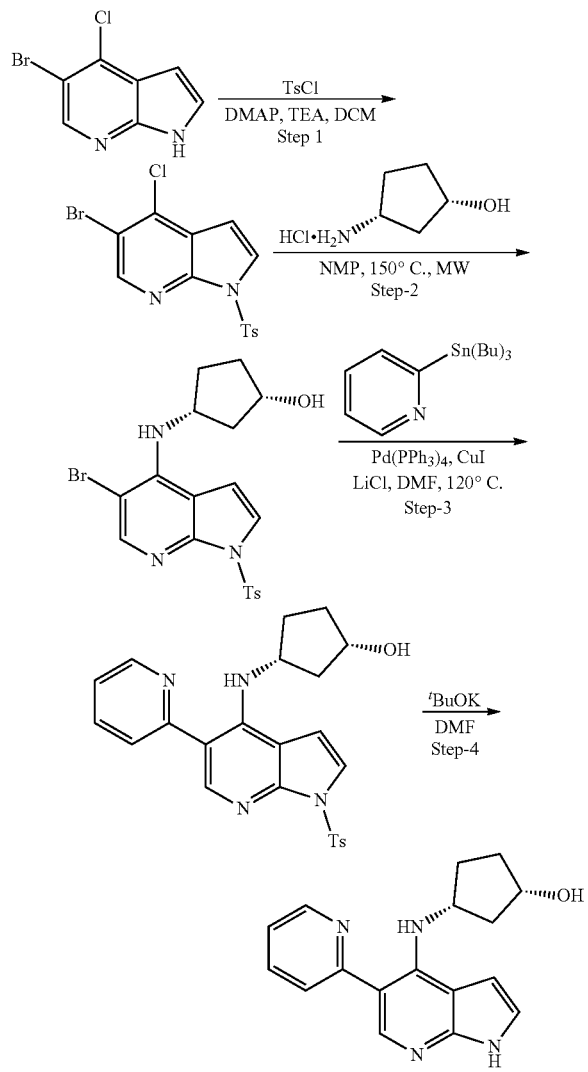

Step 1: Preparation of 5-bromo-4-chloro-1-tosyl-1H-pyrrolo[2,3-b]pyridine

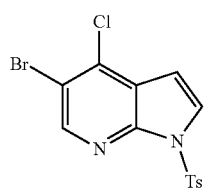

To a solution 5-bromo-4-chloro-1H-pyrrolo[2,3-b]pyridine (5 g, 21.7 mmol) in dicholoromethane (40 mL) was added 4-dimethylaminopyridine (0.26 g, 2.17 mmol), p-toulenesufonyl chloride (5.3 g, 28.2 mmol) and triethylamine (4.3 g, 43.4 mmol) and the mixture stirred at room temperature for 12 hours. The reaction was quenched with water and extracted with ethyl acetate. The organic layer was washed with water, brine, dried over anhydrous sodium sulfate, filtered and concentrated in vacuo to provide 5-bromo-4-chloro-1-tosyl-1H-pyrrolo[2,3-b]pyridine as an off-white solid (7 g, 96% yield): MS (ES) m/z 384.7 (M+H).

Step 2: Preparation of (1S,3R)-3-((5-bromo-1-tosyl-1H-pyrrolo[2,3-b]pyridin-4-yl)amino)cyclopentan-1-ol

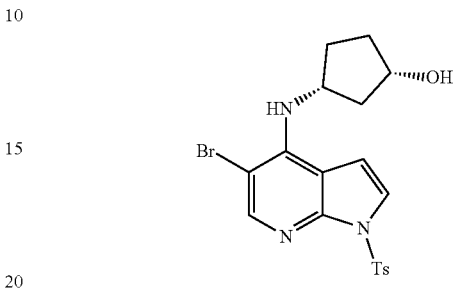

To a stirred solution of 5-bromo-4-chloro-1-tosyl-1H-pyrrolo[2,3-b]pyridine (0.1 g, 0.260 mmol) in N-methyl-2-pyrrolidone (0.6 mL) was added (1S,3R)-3-aminocyclopentan-1-ol hydrochloride (0.03 g, 0.33 mmol) and triethylamine (0.1 mL) and the mixture was subjected to microwave irradiation at 150° C. for 2.5 hours. The reaction was cooled to room temperature, quenched with water and extracted with ethyl acetate. The organic layer was washed with brine, dried over anhydrous sodium sulfate, filtered and concentrated in vacuo. The crude material was purified by flash chromatography (50% ethyl acetate/hexane) to provide (1S,3R)-3-((5-bromo-1-tosyl-1H-pyrrolo[2,3-b]pyridin-4-yl)amino)cyclopentan-1-ol as a colorless oil (0.15 g, crude): MS (ES) m/z 449.0 (M+H).

Step 3: Preparation of (1S,3R)-3-((5-(pyridin-2-yl)-1-tosyl-1H-pyrrolo[2,3-b]pyridin-4-yl)amino)cyclopentan-1-ol

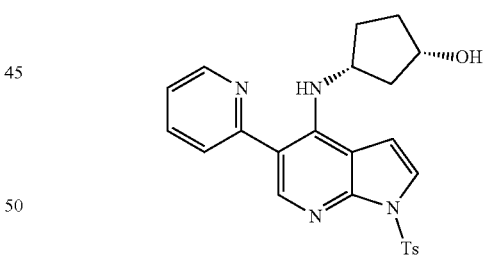

A mixture of (1S,3R)-3-((5-bromo-1-tosyl-1H-pyrrolo[2,3-b]pyridin-4-yl)amino)cyclopentan-1-ol (0.3 g, 0.66 mmol), 2-(tributylstannyl)pyridine (0.32 g, 0.86 mmol), lithium chloride (0.002 g, 0.06 mmol), copper iodide (0.01 g, 0.06 mmol) and tetrakis(triphenylphosphine)platinum(0) (0.03 g, 0.033 mmol) in N,N-dimethylformamide (0.5 mL) was degassed with nitrogen for 5 minutes. The reaction mixture was heated in a sealed tube at 120° C. for 2 hours. The reaction mixture was cooled to ambient temperature and filtered through celite. The filtrate was diluted with ethyl acetate and washed with water. The organic phase was washed with brine, dried over sodium sulfate, filtered and concentrated in vacuo. The crude product was purified by flash chromatography (40% ethyl acetate/hexane) to provide (1S,3R)-3-((5-(pyridin-2-yl)-1-tosyl-1H-pyrrolo[2,3-b]pyridin-4-yl)amino)cyclopentan-1-ol as an off-white solid (0.17 g, 56% yield): MS (ES) m/z 449.3 (M+H).

Step 4: Preparation of (1S,3R)-3-((5-(pyridin-2-yl)-1H-pyrrolo[2,3-b]pyridin-4-yl)amino)cyclopentan-1-ol

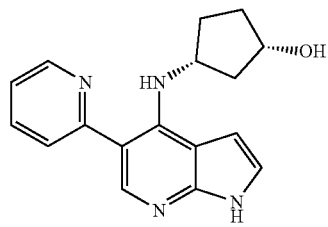 [SMILES: O[C@H]1CC[C@@H](Nc2c(-c3ccccn3)cnc3[nH]ccc23)C1]

To a solution of (1S,3R)-3-((5-(pyridin-2-yl)-1-tosyl-1H-pyrrolo[2,3-b]pyridin-4-yl)amino)cyclopentan-1-ol (0.17 g, 0.3 8 mmol) in N-methyl-2-pyrrolidone (1.5 mL) was added potassium tert-butoxide (0.09 g, 0.83 mmol) and the mixture was stirred at room temperature for 3 hours. The reaction mixture was quenched with water and extracted with ethyl acetate. The organic layer was washed with brine, dried over anhydrous sodium sulfate, filtered and concentrated in vacuo. The crude material was purified by flash chromatography (50% ethyl acetate/hexane) to provide (1S,3R)-3-((5-(pyridin-2-yl)-1H-pyrrolo[2,3-b]pyridin-4-yl)amino)cyclopentan-1-ol as an off-white solid (0.02 g, 10% yield): $^1$H NMR (400 MHz, DMSO-$d_6$) 11.28 (br s, 1H), 9.99 (d, J=8.0 Hz, 1H), 8.52-8.54 (m, 1H), 8.31 (m, 1H), 7.81-7.82 (m, 2H), 7.20-7.22 (m, 1H), 7.09 (s, 1H), 6.60 (s, 1H), 4.62 (s, 1H), 4.59-4.61 (m, 1H), 4.18-4.19 (m, 1H), 2.24-2.31 (m, 1H), 1.95-2.04 (m, 1H), 1.62-1.83 (m, 2H), 1.48-1.52 (m, 1H), 1.22 (s, 1H); MS (ES) m/z 295.0 (M+H).

Example 13: Preparation of (1S,3R)-3-((5-(oxazol-2-yl)-1H-pyrrolo[2,3-b]pyridin-4-yl)amino)cyclopentan-1-ol

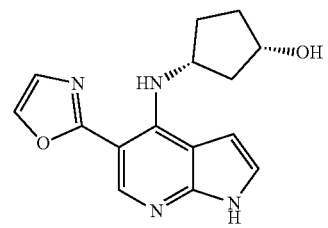 [SMILES: O[C@H]1CC[C@@H](Nc2c(-c3ncco3)cnc3[nH]ccc23)C1]

Scheme 16: Preparation of (1S,3R)-3-((5-(oxazol-2-yl)-1H-pyrrolo[2,3-b]pyridin-4-yl)amino)cyclpentan-1-ol

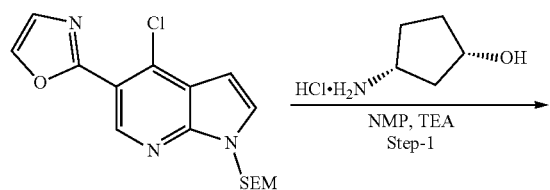

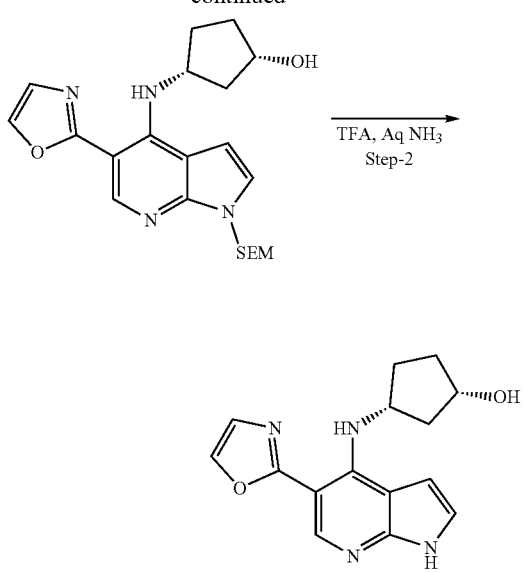

Step 1: Preparation of (1S,3R)-3-((5-(oxazol-2-yl)-1-((2-(trimethylsilyl)ethoxy)methyl)-1H-pyrrolo[2,3-b]pyridin-4-yl)amino)cyclopentan-1-ol

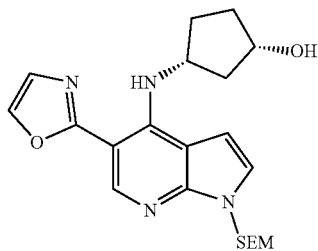 [SMILES: C[Si](C)(C)CCOCn1ccc2c(N[C@@H]3CC[C@H](O)C3)c(-c3ncco3)cnc21]

To a stirred solution of 2-(4-chloro-1-((2-(trimethylsilyl)ethoxy)methyl)-1H-pyrrolo[2,3-b]pyridin-5-yl)oxazole (0.2 g, 0.573 mmol as prepared by the method described in Example 5, Step-1) in N-methyl-2-pyrrolidone (0.5 mL) was added (1S,3R)-3-aminocyclopentan-1-ol hydrochloride (0.09 g, 0.86 mmol) and triethylamine (0.1 mL) and the mixture was subjected to microwave irradiation at 140° C. for 6 hours. The reaction mixture was cooled to room temperature, quenched with water and extracted with ethyl acetate. The organic layer was washed with brine, dried over anhydrous sodium sulfate, filtered and concentrated in vacuo. The crude material was purified by flash chromatography (40% ethyl acetate/hexane) to provide (1S,3R)-3-((5-(oxazol-2-yl)-1-((2-(trimethylsilyl)ethoxy)methyl)-1H-pyrrolo[2,3-b]pyridin-4-yl)amino)cyclopentan-1-ol as a colorless oil (0.19 g, 80% yield): MS (ES) m/z 415.0 (M+H).

Step 2: Preparation of (1S,3R)-3-((5-(oxazol-2-yl)-1H-pyrrolo[2,3-b]pyridin-4-yl)amino)cyclopentan-1-ol

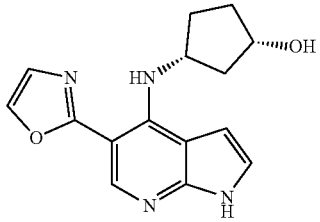 [SMILES: O[C@H]1CC[C@@H](Nc2c(-c3ncco3)cnc3[nH]ccc23)C1]

A solution of (1S,3R)-3-((5-(oxazol-2-yl)-1-((2-(trimethylsilyl)ethoxy)methyl)-1H-pyrrolo[2,3-b]pyridin-4-yl)amino)cyclopentan-1-ol (0.19 g, 0.46 mmol) in dichloromethane:trifluoroacetic acid (2 ml:2 mL) was stirred at ambient temperature for 3 hours. The volatiles were removed in vacuo and the residue was dissolved dioxane: aqueous ammonia (5 mL:5 mL) and the mixture was stirred at ambient temperature for 12 hours. The reaction was quenched with water and extracted with ethyl acetate. The organic layer was washed with brine, dried over anhydrous sodium sulfate, filtered and concentrated in vacuo to provide (1S,3R)-3-((5-(oxazol-2-yl)-1H-pyrrolo[2,3-b]pyridin-4-yl)amino)cyclopentan-1-ol as an off-white solid (0.06 g, 50% yield): 1H NMR (400 MHz, DMSO-$d_6$) 11.52 (br s, 1H), 9.13 (d, J=8.0 Hz, 1H), 8.50 (s, 1H), 8.08 (s, 1H), 7.36 (s, 1H), 7.16 (s, 1H), 6.65 (s, 1H), 4.65-4.66 (m, 1H), 4.52 (m, 1H), 4.18-4.19 (m, 1H), 2.31-2.48 (m, 1H), 2.09-2.18 (m, 1H), 1.66-1.81 (m, 3H), 1.48-1.53 (m, 1H); MS (ES) m/z 285.3 (M+H).

Example 14: Preparation of (R)-2-(4-((1-(2-cyanoacetyl)piperidin-3-yl)amino)-1H-pyrrolo[2,3-b]pyridin-5-yl)oxazole-4-carboxamide

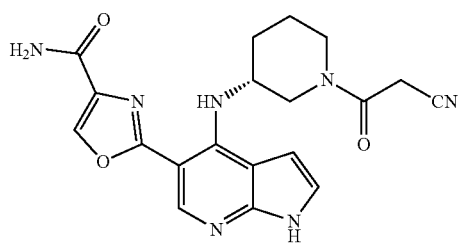

Scheme 17: Preparation of (R)-2-(4-((1-(2-cyanoacetyl)piperidin-3-yl)amino)-1H-pyrrolo[2,3-b]pyridin-5-yl)oxazole-4-carboxamide

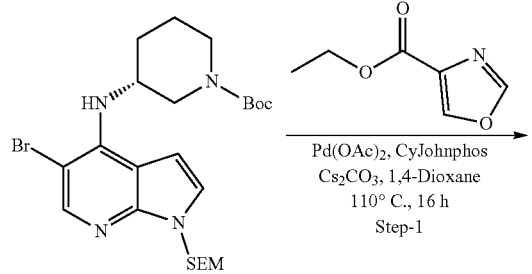

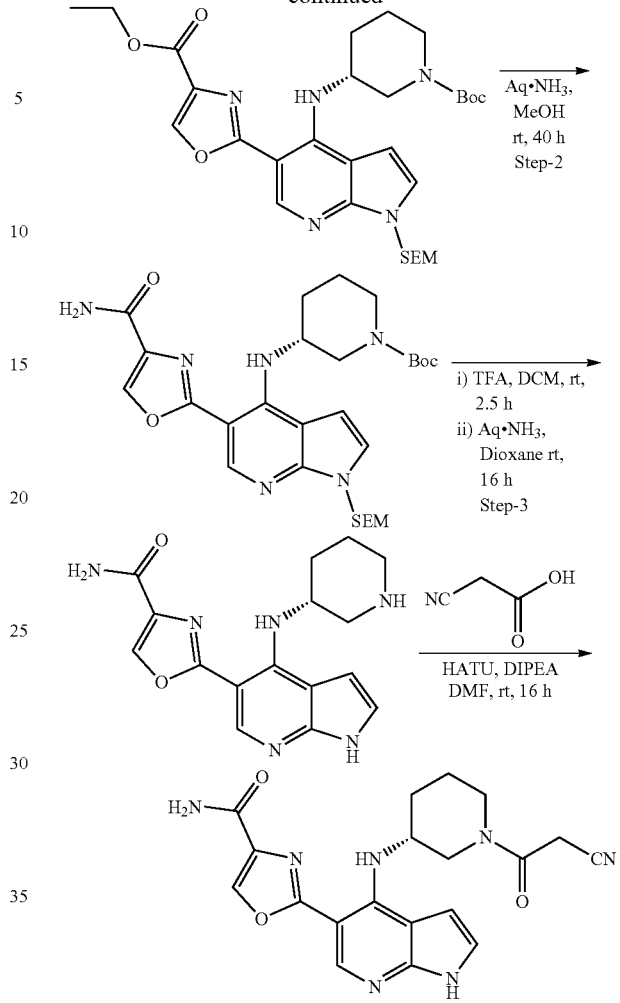

Step 1: Preparation of ethyl (R)-2-(4-((1-(tert-butoxycarbonyl)piperidin-3-yl)amino)-1-((2-(trimethylsilyl)ethoxy)methyl)-1H-pyrrolo[2,3-b]pyridin-5-yl)oxazole-4-carboxylate

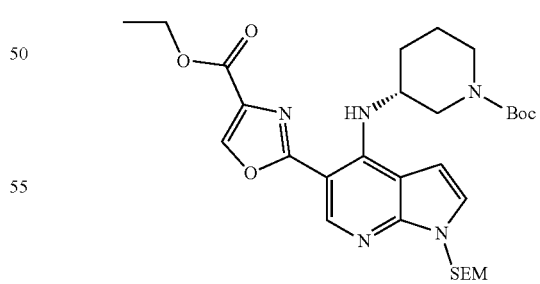

To a stirred solution of tert-butyl (R)-3-((5-bromo-1-((2-(trimethylsilyl)ethoxy)methyl)-1H-pyrrolo[2,3-b]pyridin-4-yl)amino)piperidine-1-carboxylate (0.8 g, 1.522 mmol, as prepared by the method described in Scheme 1, Step 5) in 1,4-dioxane (8 mL) was added ethyl oxazole-4-carboxylate (0.03 g, 1.83 mmol) and cesium carbonate (0.99 g, 3.044 mmol) at room temperature and the solution was degassed with nitrogen for 15 minutes. Palladium acetate (0.017 g, 0.0761 mmol) and CyJohnphos (0.053 g, 0.1522 mmol) were added and the resulting mixture was heated in a sealed tube to 110° C. for 16 hours. The reaction was cooled to ambient temperature, filtered through celite and the filtrate was concentrated in vacuo. The crude was purified by column chromatography (ethyl acetate/hexane) to provide ethyl (R)-2-(4-((1-(tert-butoxycarbonyl)piperidin-3-yl)amino)-1-((2-(trimethylsilyl)ethoxy)methyl)-1H-pyrrolo[2,3-b]pyridin-5-yl)oxazole-4-carboxylate as a yellow solid (0.35 g, 39% yield): MS (ES) m/z 585.9 (M+H).

Step 2: Preparation of tert-butyl (R)-3-((5-(4-carbamoyloxazol-2-yl)-1-((2-(trimethylsilyl)ethoxy)methyl)-1H-pyrrolo[2,3-b]pyridin-4-yl)amino)piperidine-1-carboxylate

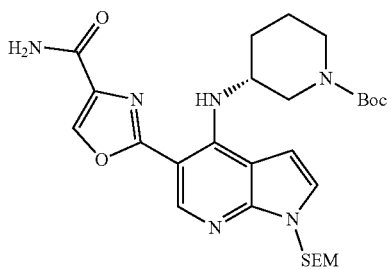 [SMILES: CC(C)(C)OC(=O)N1CCC[C@@H](Nc2c(-c3nc(C(N)=O)co3)cnc3c2ccn3COCC[Si](C)(C)C)C1]

A solution of ethyl (R)-2-(4-((1-(tert-butoxycarbonyl)piperidin-3-yl)amino)-1-((2-(trimethylsilyl)-ethoxy)methyl)-1H-pyrrolo[2,3-b]pyridin-5-yl)oxazole-4-carboxylate (0.35 g, 0.597 mmol) and 23% aqueous ammonia (16 mL) in methanol (5 mL) was stirred in a sealed tube for 40 hours. The reaction mixture was concentrated in vacuo and the aqueous portion was extracted with dichloromethane. The organic extract was washed with brine, dried over anhydrous sodium sulfate, filtered and concentrated in vacuo. The crude was purified by column chromatography (ethyl acetate/hexane) to provide tert-butyl (R)-3-((5-(4-carbamoyloxazol-2-yl)-1-((2-(trimethylsilyl)ethoxy)methyl)-1H-pyrrolo[2,3-b]pyridin-4-yl)amino)piperidine-1-carboxylate as a yellow solid (0.12 g, 36% yield): MS (ES) m/z 556.9 (M+H).

Step 3: Preparation of (R)-2-(4-(piperidin-3-ylamino)-1H-pyrrolo[2,3-b]pyridin-5-yl)oxazole-4-carboxamide

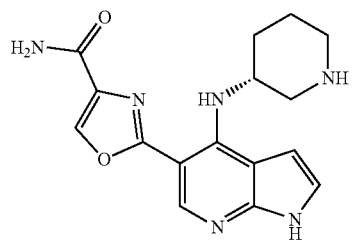 [SMILES: NC(=O)c1coc(-c2cnc3[nH]ccc3c2N[C@@H]2CCCNC2)n1]

(R)-2-(4-(Piperidin-3-ylamino)-1H-pyrrolo[2,3-b]pyridin-5-yl)oxazole-4-carboxamide was prepared by the method described in Example 1, Step-7 to give title compound (0.1 g crude): MS (ES) m/z 327.0 (M+H).

Step 4: Preparation of (R)-2-(4-((1-(2-cyanoacetyl)piperidin-3-yl)amino)-1H-pyrrolo[2,3-b]pyridin-5-yl)oxazole-4-carboxamide

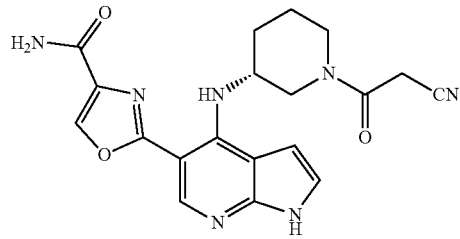 [SMILES: N#CCC(=O)N1CCC[C@@H](Nc2c(-c3nc(C(N)=O)co3)cnc3[nH]ccc23)C1]

(R)-2-(4-((1-(2-Cyanoacetyl)piperidin-3-yl)amino)-1H-pyrrolo[2,3-b]pyridin-5-yl)oxazole-4-carboxamide was prepared by the method described in Example 9, Step-5 to give a pale brown solid (0.01 g, 13% yield): $^1$H NMR (400 MHz, DMSO-$d_6$) δ 11.66 (d, J=12.0 Hz, 1H), 8.71 (d, J=8.4 Hz, 1H), 8.52-8.53 (m, 2H), 7.56-7.67 (m, 2H), 7.24 (s, 1H), 6.72 (s, 1H), 4.14-4.29 (m, 2H), 4.07 (s, 1H), 3.77-3.94 (m, 2H), 3.52 (d, J=14.4 Hz, 1H), 3.00-3.25 (m, 1H), 2.08 (bs, 1H), 1.85 (bs, 2H), 1.50-1.70 (m, 1H); MS (ES) m/z 394.1 (M+H).

Analytical Conditions:
Column: X Bridge C18 (250 mm×4.6 mm×5 mic)
Mobile phase (A): 0.1% Ammonia in water
Mobile phase (B): ACN
Flow rate: 1.0 mL/min
Composition of B: 0/10, 12/60, 25/90, 27/10, 30/10

Example 15: Preparation of (R)-3-(3-((5-(4-methylpyridin-2-yl)-1H-pyrrolo[2,3-b]pyridin-4-yl)amino)piperidin-1-yl)-3-oxopropanenitrile

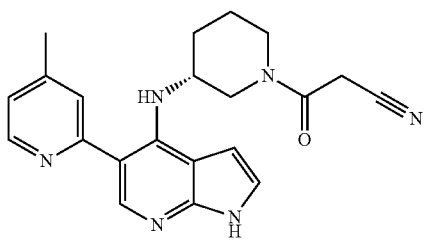 [SMILES: Cc1ccnc(-c2cnc3[nH]ccc3c2N[C@@H]2CCCN(C(=O)CC#N)C2)c1]

Scheme 18: Preparation of (R)-3-(3-((5-(4-methylpyridin-2-yl)-1H-pyrrolo[2,3-b]pyridin-4-yl)amino)piperidin-1-yl)-3-oxopropanenitrile

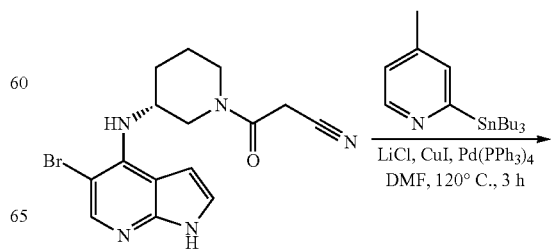

155 / 156
-continued

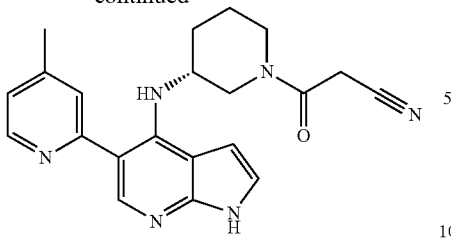

To a solution of (R)-3-(3-((5-bromo-1H-pyrrolo[2,3-b]pyridin-4-yl)amino)piperidin-1-yl)-3-oxopropanenitrile (0.2 g, 0.55 mmol, prepared by the method as described in Scheme 23, Step-4) in N,N-dimethylformamide (5 mL) was added lithium chloride (0.048 g, 1.1 mmol), 4-methyl-2-(tributylstannyl)pyridine (0.25 g, 0.66 mmol), copper iodide (0.011 g, 0.05 mmol), and tetrakis(triphenyl-phosphine)palladium (0) (0.03 g, 0.02 mmol). The mixture was stirred in a sealed tube at 120° C. for 3 hours under a nitrogen atmosphere. The reaction was cooled to ambient temperature, diluted with ethyl acetate and water. The organic layer was separated, washed with brine, dried over anhydrous sodium sulfate, filtered and concentrated in vacuo. The crude material was purified by reverse phase chromatography to provide (R)-3-(3-((5-(4-methylpyridin-2-yl)-1H-pyrrolo[2,3-b]pyridin-4-yl)amino)piperidin-1-yl)-3-oxopropanenitrile as an off-white solid (0.02 g, 8% yield): $^1$H NMR (400 MHz, DMSO-$d_6$) δ 11.42-11.37 (m, 1H), 10.13-10.02 (m, 1H), 8.42-8.32 (m, 2H), 7.75-7.72 (m, 1H), 7.15-7.08 (m, 2H), 6.61 (s, 1H), 4.38 (m, 1H), 4.12-3.94 (m, 3H), 3.73-3.55 (m, 3H), 2.31 (s, 3H), 1.97 (s, 1H), 1.69-1.52 (s, 3H); MS (ES) m/z 375.1 (M+H). HPLC purity: 99.38%.

Analytical Conditions:

Column: Inertsil ODS 3V (150 mm×4.6 mm×5 mic)

Mobile phase (A): 0.1% Ammonia in water

Mobile phase (B): ACN

Flow rate: 1.0 mL/min

Example 16: Preparation of (R)-3-oxo-3-(3-((5-(thiazol-5-yl)-1H-pyrrolo[2,3-b]pyridin-4-yl)amino)piperidin-1-yl)propanenitrile

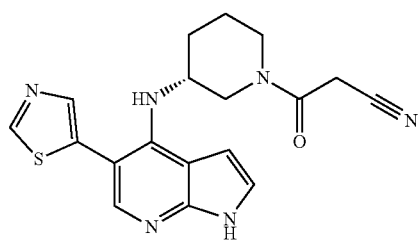

Scheme 19: Preparation of (R)-3-oxo-3-(3-((5-(thiazol-5-yl)-1H-pyrrolo[2,3-b]pyridin-4-yl)amino)piperidin-1-yl)propanenitrile

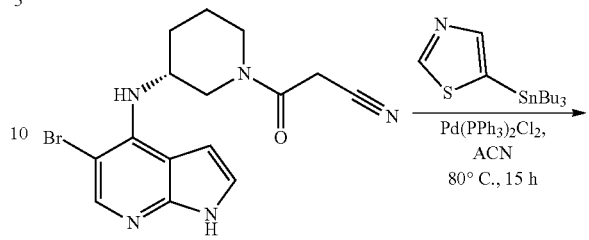

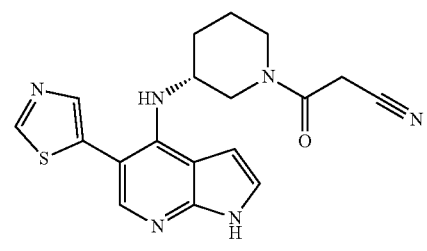

Example-16

A solution of (R)-3-(3-((5-bromo-1H-pyrrolo [2,3-b]pyridin-4-yl)amino)piperidin-1-yl)-3-oxopropanenitrile (0.2 g, 0.55 mmol, prepared by the method as described in Scheme 23, Step 4), 5-(tributylstannyl)thiazole (0.24 g, 0.66 mmol) and bis(triphenylphosphine)palladium(II) dichloride (0.09 g, 0.027 mmol) in acetonitrile (5 mL) was heated in a sealed tube to 80° C. for 15 hours. The reaction mixture was cooled to ambient temperature and quenched with water and extracted with ethyl acetate. The organic layer was washed with brine, dried over anhydrous sodium sulfate, filtered and concentrated in vacuo. The crude material was purified by flash chromatography (5% methanol/dichloromethane) to provide (R)-3-oxo-3-(3-((5-(thiazol-5-yl)-1H-pyrrolo[2,3-b]pyridin-4-yl)amino)piperidin-1-yl)propanenitrile as an off-white solid (0.04 g, 22% yield): $^1$H NMR (400 MHz, DMSO-$d_6$, at 70° C.) δ 11.29 (s, 1H), 9.10 (s, 1H), 7.86 (s, 1H), 7.79 (s, 1H), 7.20 (s, 1H), 6.58 (s, 1H), 5.04 (s, 1H), 4.13 (br s, 1H), 3.82-3.99 (m, 3H), 3.53-3.65 (m, 1H), 3.35-3.44 (m, 1H), 1.94 (br s, 1H), 1.40-1.65 (m, 3H), 1.29-1.30 (m, 1H); MS (ES) m/z 367.2 (M+1).

Example 17: Preparation of (R)-3-(3-((5-(1-methyl-1H-imidazol-2-yl)-1H-pyrrolo[2,3-b]pyridin-4-yl)amino)piperidin-1-yl)-3-oxopropanenitrile

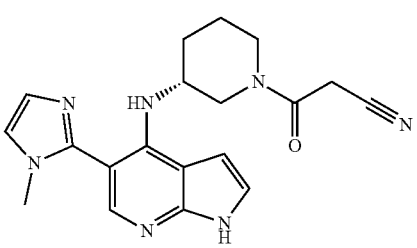

Scheme 20: (R)-3-(3-((5-(1-methyl-1H-imidazol-2-yl)-1H-pyrrolo[2,3-b]pyridin-4-yl)amino)piperidin-1-yl)-3-oxopropanenitrile

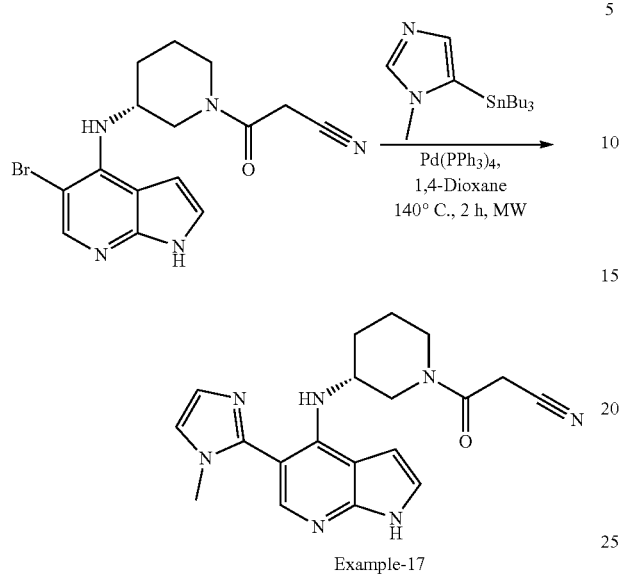

Example-17

Scheme 21: Preparation of (R)-3-(3-((5-(1H-pyrazol-5-yl)-1H-pyrrolo[2,3-b]pyridin-4-yl)amino)piperidin-1-yl)-3-oxopropanenitrile

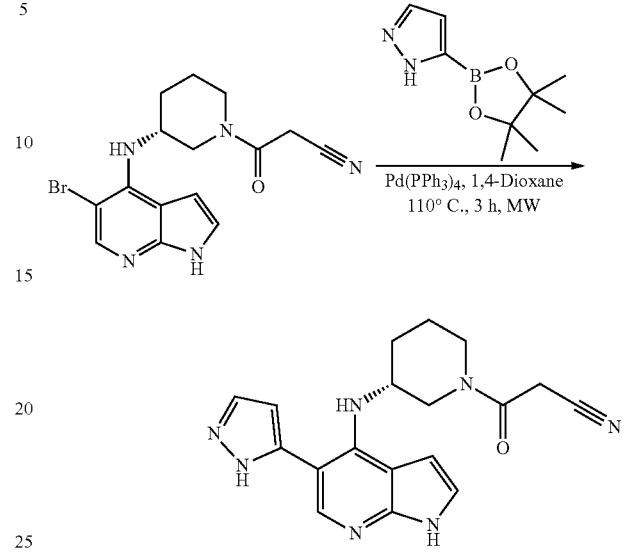

A solution of (R)-3-(3-((5-bromo-1H-pyrrolo [2,3-b]pyridin-4-yl)amino)piperidin-1-yl)-3-oxopropanenitrile (0.3 g, 0.82 mmol, prepared by the method as described in Scheme 23, Step 4), 1-methyl-2-(tributylstannyl)-1H-imidazole (0.46 g, 1.24 mmol) and tetrakis(triphenylphosphine)palladium (0) (0.09 g, 0.08 mmol) in 1,4-dioxane (4 mL) was subjected to microwave irradiation at 140° C. for 2 hours. The reaction mixture was cooled to ambient temperature, diluted with ethyl acetate. The organic layer was washed with water, brine, dried over anhydrous sodium sulfate, filtered and concentrated in vacuo. The crude material was purified by flash chromatography (5% methanol/dichloromethane) to provide (R)-3-(3-((5-(1-methyl-1H-imidazol-2-yl)-1H-pyrrolo[2,3-b]pyridin-4-yl)amino)piperidin-1-yl)-3-oxopropanenitrile as an off-white solid (0.04 g, 15% yield): $^1$H NMR (400 MHz, DMSO-$d_6$, at 70° C.) δ 11.41 (s, 1H), 7.72-7.74 (m, 1H), 7.63-7.64 (m, 1H), 7.21 (s, 1H), 6.88 (s, 1H), 6.59-6.64 (m, 1H), 4.85-4.99 (m, 2H), 3.79-4.20 (m, 5H), 2.68-3.07 (m, 3H), 1.91 (bs, 2H), 1.49-1.56 (m, 3H); MS (ES) m/z 364.1 (M+1).

Example 18: Preparation of (R)-3-(3-((5-(1H-pyrazol-5-yl)-1H-pyrrolo[2,3-b]pyridin-4-yl)amino)piperidin-1-yl)-3-oxopropanenitrile A mixture of (R)-3-(3-((5-bromo-1H-pyrrolo [2,3-b]pyridin-4-yl)amino)piperidin-1-yl)-3-oxopropanenitrile (0.2 g, 0.55 mmol, prepared by the method as described in Scheme 23, Step 4), 5-(4,4,5,5-tetramethyl-1,3,2-dioxaborolan-2-yl)-1H-pyrazole (0.16 g, 0.83 mmol), sodium carbonate (0.17 g, 1.65 mmol) and tetrakis(triphenylphosphine)palladium(0) (0.032 g, 0.03 mmol) in 1,4-dioxane (4 mL)/water (1 mL) was subjected to microwave irradiation at 100° C. for 3 hours. The reaction mixture was cooled to ambient temperature and diluted with ethyl acetate. The organic layer was washed with water, brine, dried over anhydrous sodium sulfate, filtered and concentrated in vacuo. The crude material was purified by flash chromatography (5% methanol/dichloromethane) to provide (R)-3-(3-((5-(1H-pyrazol-5-yl)-1H-pyrrolo[2,3-b]pyridin-4-yl)amino)piperidin-1-yl)-3-oxopropanenitrile as an off-white solid (0.045 g, 15% yield): $^1$H NMR (400 MHz, DMSO-$d_6$, at 70° C.) δ 12.67 (s, 1H), 11.11 (s, 1H), 8.63 (s, 1H), 8.31 (s, 1H), 7.75 (s, 1H), 7.12 (s, 1H), 6.70 (s, 1H), 6.60 (s, 1H), 4.41 (br s, 1H), 3.81-4.09 (m, 3H), 3.51 (br s, 1H), 3.22 (s, 1H), 2.99 (s, 1H), 2.11 (br s, 1H), 1.61-1.81 (m, 3H); MS (ES) m/z 350.3 (M+1).

Example 19: Preparation of (R)-3-(3-((5-(5-methyl-1,2,4-oxadiazol-3-yl)-1H-pyrrolo[2,3-b]pyridin-4-yl)amino)piperidin-1-yl)-3-oxopropanenitrile

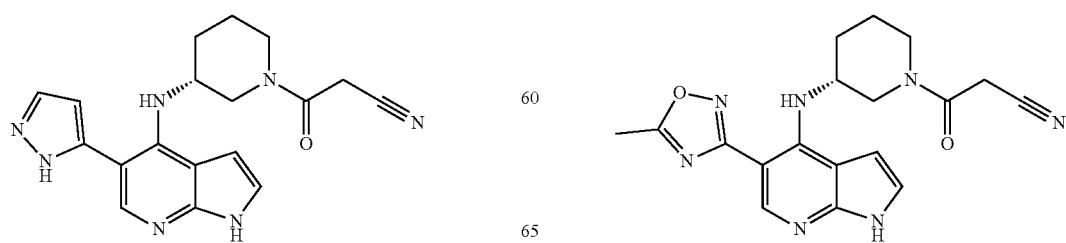

Scheme 22: Preparation of (R)-3-((5-(5-methyl-1,2,4-oxadiazol-3-yl)-1H-pyrrolo[2,3-b]pyridin-4-yl)amino)piperidin-1-yl)-3-oxopropanenitrile

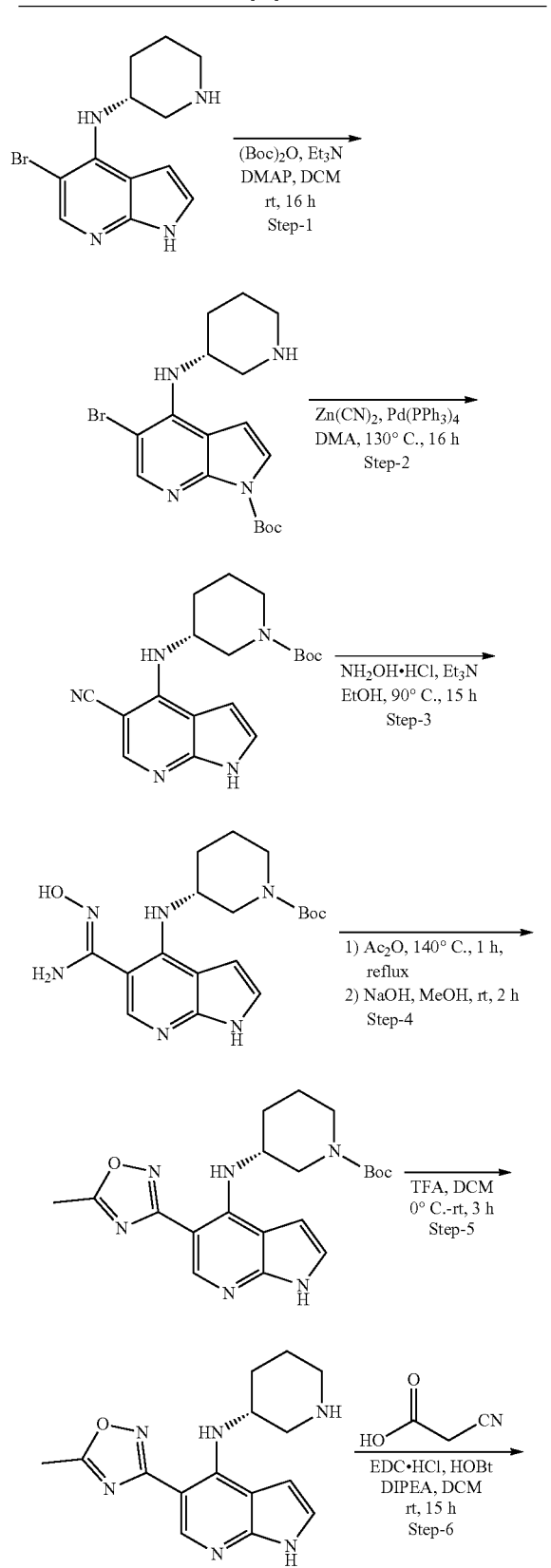

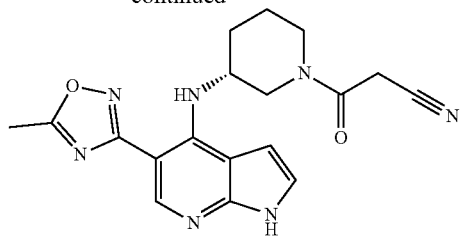

Step 1: Preparation of tert-butyl (R)-5-bromo-4-((1-(tert-butoxycarbonyl)piperidin-3-yl)amino)-1H-pyrrolo[2,3-b]pyridine-1-carboxylate

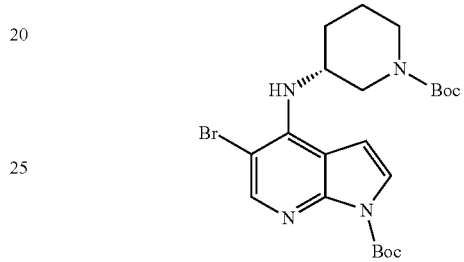

To a solution of (R)-5-bromo-N-(piperidin-3-yl)-1H-pyrrolo[2,3-b]pyridin-4-amine (crude) (5.0 g, 17.0 mmol, prepared by the method as described in Scheme 23, Step 3) in dichloromethane (70 mL) was added di-tert-butyl dicarbonate (3.9 mL, 17.0 mmol), triethylamine (4.7 mL, 34 mmol) and 4-dimethylaminopyridine (0.02 g, 0.17 mmol) and the mixture was stirred at ambient temperature for 16 hours. The reaction mixture was diluted with dichloromethane and washed with water, brine, dried over anhydrous sodium sulfate, filtered and concentrated in vacuo. The crude material was purified by flash chromatography (30% ethyl acetate/hexane) to provide tert-butyl (R)-5-bromo-4-((1-(tert-butoxycarbonyl)-piperidin-3-yl)amino)-1H-pyrrolo[2,3-b]pyridine-1-carboxylate as an off-white solid (1.2 g, 14% yield): MS (ES) m/z 496.8 (M+2).

Step 2: Preparation of tert-butyl (R)-3-((5-cyano-1H-pyrrolo[2,3-b]pyridin-4-yl)amino)piperidine-1-carboxylate

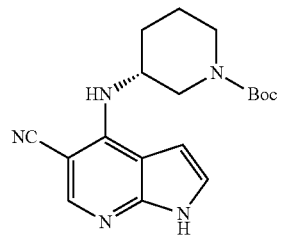 [SMILES: CC(C)(C)OC(=O)N1CCC[C@@H](Nc2c(C#N)cnc3[nH]ccc23)C1]

A suspension of tert-butyl (R)-5-bromo-4-((1-(tert-butoxycarbonyl)piperidin-3-yl)amino)-1H-pyrrolo[2,3-b]pyridine-1-carboxylate (1.5 g, 3.02 mmol), zinc cyanide (0.53 g, 4.54 mmol) and tetrakis(triphenyl-phosphine)palladium(0) (0.87 g, 0.75 mmol) in dimethylacetamide (15 mL) was heated in a sealed tube at 130° C. for 16 hours under argon atmosphere. The reaction mixture was cooled to ambient temperature and diluted with ethyl acetate. The organic layer was washed with water, brine, dried over anhydrous sodium sulfate, filtered and concentrated in vacuo. The crude material was purified by flash chromatography (30% ethyl acetate/hexane) to provide tert-butyl (R)-3-((5-cyano-1H-pyrrolo[2,3-b]pyridin-4-yl)amino)piperidine-1-carboxylate as an off-white solid (0.7 g, crude): MS (ES) m/z 342.2 (M+H).

Step 3: Preparation of tert-butyl (R,Z)-3-((5-(N'-hydroxycarbamimidoyl)-1H-pyrrolo[2,3-b]pyridin-4-yl)amino)piperidine-1-carboxylate

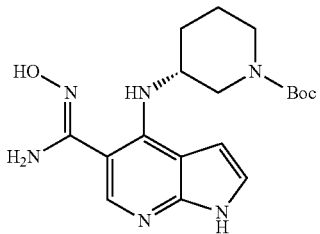 [SMILES: CC(C)(C)OC(=O)N1CCC[C@@H](Nc2c(/C(N)=N/O)cnc3[nH]ccc23)C1]

A suspension of tert-butyl (R)-3-((5-cyano-1H-pyrrolo[2,3-b]pyridin-4-yl)amino)piperidine-1-carboxylate (0.2 g, 0.58 mmol), hydroxylamine hydrochloride (0.06 g, 0.88 mmol) and triethylamine (0.16 mL, 1.17 mmol) in ethanol (5 mL) was heated under an argon atmosphere at 90° C. for 15 hours. The reaction mixture was cooled to ambient temperature and concentrated in vacuo to remove volatiles. The residue was dissolved in dichloromethane and washed with water, brine solution, dried over anhydrous sodium sulfate, filtered and concentrated in vacuo to provide tert-butyl (R,Z)-3-((5-(N-hydroxycarbamimidoyl)-1H-pyrrolo[2,3-b]pyridin-4-yl)amino)piperidine-1-carboxylate as a viscous solid (0.21 g, 95% yield): MS (ES) m/z 375.2 (M+1).

Step 4: Preparation of tert-butyl (R)-3-((5-(5-methyl-1,2,4-oxadiazol-3-yl)-1H-pyrrolo[2,3-b]pyridin-4-yl)amino)piperidine-1-carboxylate

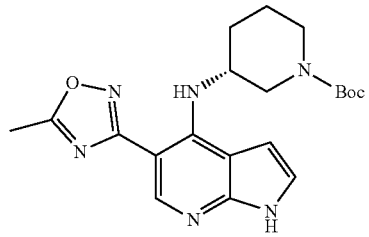 [SMILES: Cc1nc(-c2cnc3[nH]ccc3c2N[C@@H]2CCCN(C(=O)OC(C)(C)C)C2)no1]

A solution of tert-butyl (R,Z)-3-((5-(N-hydroxycarbamimidoyl)-1H-pyrrolo[2,3-b]pyridin-4-yl)amino) piperidine-1-carboxylate (0.1 g, 0.27 mmol) in acetic anhydride (2 mL) was heated at 140° C. for 45 minutes. The reaction mixture was cooled to ambient temperature, neutralized using aqueous ammonia and extracted with dichloromethane (30 ml). The organic layer was washed with water, brine, dried over anhydrous sodium sulfate, filtered and concentrated in vacuo. The crude mass was dissolved in methanol (4 mL) and 3M aqueous sodium hydroxide solution (2 mL) was added and then the solution stirred at ambient temperature for 2 hours. The reaction mixture was concentrated in vacuo to remove volatiles; the residue was dissolved in dichloromethane, washed with water, brine, dried over anhydrous sodium sulfate. The solution was filtered and concentrated in vacuo to provide tert-butyl (R)-3-((5-(5-methyl-1,2,4-oxadiazol-3-yl)-1H-pyrrolo[2,3-b]pyridin-4-yl)amino)piperidine-1-carboxylate as an off-white solid (0.12 g, crude): MS (ES) m/z 399.0 (M+H).

Step 5: Preparation of (R)-5-(5-methyl-1,2,4-oxadiazol-3-yl)-N-(piperidin-3-yl)-1H-pyrrolo[2,3-b]pyridin-4-amine

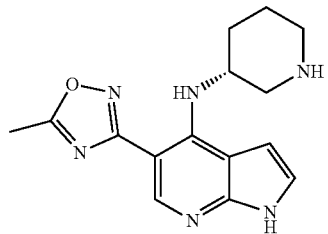 [SMILES: Cc1nc(-c2cnc3[nH]ccc3c2N[C@@H]2CCCNC2)no1]

A solution of tert-butyl (R)-3-((5-(5-methyl-1,2,4-oxadiazol-3-yl)-1H-pyrrolo[2,3-b]pyridin-4-yl)amino)piperidine-1-carboxylate (0.12 g, 0.3 mmol) in dichloromethane:trifluoroacetic acid (3 mL:0.5 mL) was stirred for 3 hours at ambient temperature. The reaction mixture was concentrated in vacuo to remove volatiles, neutralized by using aqueous ammonia and extracted with dichloromethane (30 mL). The organic layer was washed with water, brine, dried over anhydrous sodium sulfate, filtered and concentrated in vacuo to provide (R)-5-(5-methyl-1,2,4-oxadiazol-3-yl)-N-(piperidin-3-yl)-1H-pyrrolo[2,3-b]pyridin-4-amine as an off-white solid (0.1 g, crude): MS (ES) m/z 299.0 (M+1).

Step 5: Preparation of (R)-3-(3-((5-(5-methyl-1,2,4-oxadiazol-3-yl)-1H-pyrrolo[2,3-b]pyridin-4-yl)amino)piperidin-1-yl)-3-oxopropanenitrile

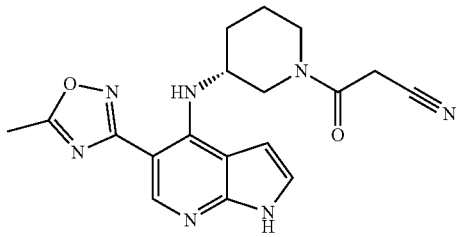 [SMILES: Cc1nc(-c2cnc3[nH]ccc3c2N[C@@H]2CCCN(C(=O)CC#N)C2)no1]

(R)-3-(3-((5-(5-Methyl-1,2,4-oxadiazol-3-yl)-1H-pyrrolo[2,3-b]pyridin-4-yl)amino)piperidin-1-yl)-3-oxopropanenitrile was prepared by the method described in Example 1, Step 8 to give an off-white solid (0.01 g, 9% yield): $^1$H NMR (400 MHz, DMSO-$d_6$, at 60° C.) δ 11.64 (s, 1H), 8.67 (s, 1H), 7.49-7.57 (m, 1H), 7.25 (s, 1H), 6.70 (s, 1H), 4.21 (br s, 1H), 4.03-4.12 (m, 2H), 3.66-3.84 (m, 1H), 3.42-3.53 (m, 2H), 2.65 (s, 3H), 2.06 (br s, 2H), 1.65-1.73 (m, 3H); MS (ES) m/z 366.1 (M+H).

Examples 20-25: Preparation of 5-aryl substituted pyrrolopyridines

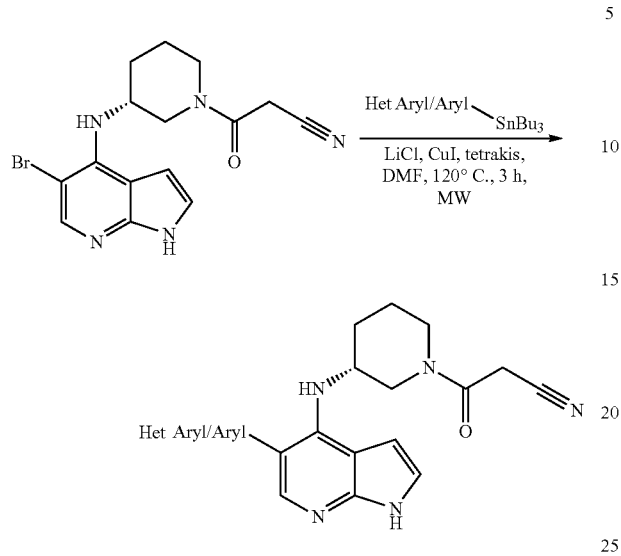

Scheme 23: Preparation of (R)-3-(3-((5-bromo-1H-pyrrolo[2,3-b]pyridin-4-yl)amino)piperidin-1-yl)-3-oxopropanenitrile

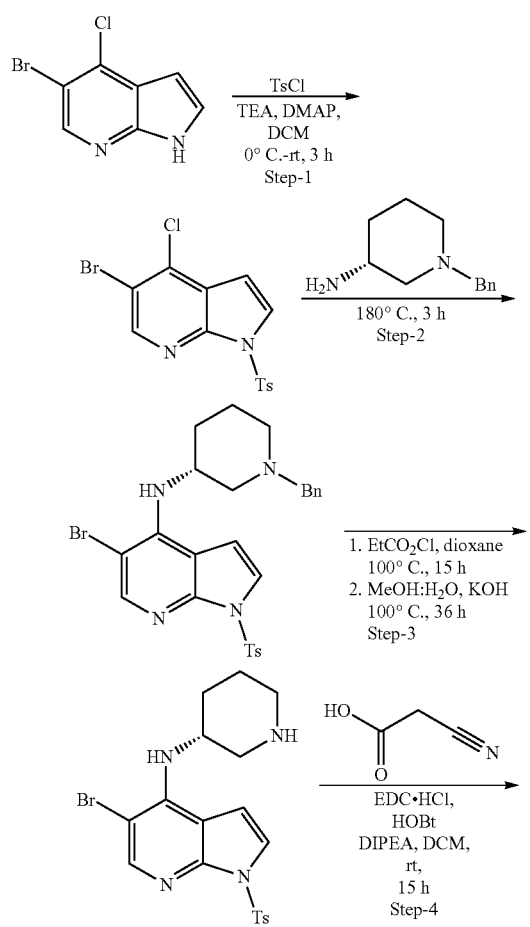

Step 1: Preparation of 5-bromo-4-chloro-1-tosyl-1H-pyrrolo[2,3-b]pyridine

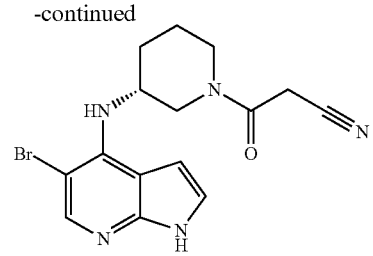

To a solution of 5-bromo-4-chloro-1H-pyrrolo[2,3-b]pyridine (15 g, 65.0 mmol) in dichloromethane (200 mL) was added triethylamine (18.2 mL, 130 mmol), p-toluenesulfonyl chloride (18.5 g, 97 mmol) and 4-dimethylaminopyridine (0.79 g, 6.0 mmol) at 0° C. The solution was stirred at ambient temperature for 16 hours. The reaction mixture was diluted with dichloromethane, washed with water, brine, dried over anhydrous sodium sulfate, filtered and concentrated in vacuo. The crude product was triturated with n-pentane and dried to provide 5-bromo-4-chloro-1-tosyl-1H-pyrrolo[2,3-b]pyridine as an off-white solid (23.0 g, 92% yield): MS (ES) m/z 386.7 (M+2).

Step 2: Preparation of (R)-N-(1-benzylpiperidin-3-yl)-5-bromo-1-tosyl-1H-pyrrolo[2,3-b]pyridin-4-amine

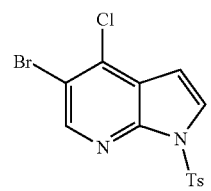

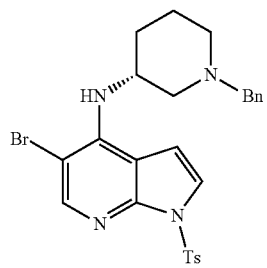 [SMILES: Cc1ccc(S(=O)(=O)n2ccc3c(N[C@@H]4CCCN(Cc5ccccc5)C4)c(Br)cnc32)cc1]

A mixture of 5-bromo-4-chloro-1-tosyl-1H-pyrrolo[2,3-b]pyridine (10.0 g, 25.0 mmol) and (R)-1-benzylpiperidin-3-amine (9.88 g, 52 mmol) was heated in a sealed tube to 180° C. for 3 hours. The reaction mixture was cooled to ambient temperature and the crude material was purified by flash chromatography (30% ethyl acetate/hexane) to provide (R)-N-(1-benzylpiperidin-3-yl)-5-bromo-1-tosyl-1H-pyrrolo[2,3-b]pyridin-4-amine as a pale yellow sticky solid (9.1 g, 66% yield): MS (ES) m/z 541.1 (M+2).

Step 3: Preparation of (R)-5-bromo-N-(piperidin-3-yl)-1H-pyrrolo[2,3-b]pyridin-4-amine

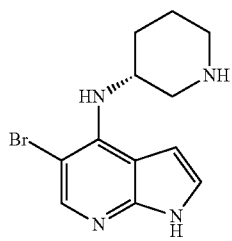 [SMILES: Brc1cnc2[nH]ccc2c1N[C@@H]1CCCNC1]

To a solution of (R)-N-(1-benzylpiperidin-3-yl)-5-bromo-1-tosyl-1H-pyrrolo[2,3-b]pyridin-4-amine (10.0 g, 18.5 mmol) in 1,4-dioxane (200 mL) was added ethyl chloroformate (2.1 mL, 22.6 mmol) and the resulting mixture was heated to 100° C. After 16 hours the reaction mixture was cooled to ambient temperature and was concentrated in vacuo. The crude intermediate was dissolved in methanol:water (150 mL:70 mL) and potassium hydroxide (20.75 g, 370 mmol) was added and the mixture heated at 90° C. for 16 hours. The reaction mixture was cooled to ambient temperature and concentrated in vacuo to remove volatiles. The residue was dissolved in dichloromethane and washed with water, brine, dried over anhydrous sodium sulfate, filtered and concentrated in vacuo to provide (R)-5-bromo-N-(piperidin-3-yl)-1H-pyrrolo[2,3-b]pyridin-4-amine as a brown oil (8.4 g, crude): MS (ES) m/z 297.0 (M+2).

Step-4: Preparation of (R)-3-(3-((5-bromo-1H-pyrrolo[2,3-b]pyridin-4-yl)amino)piperidin-1-yl)-3-oxopropanenitrile

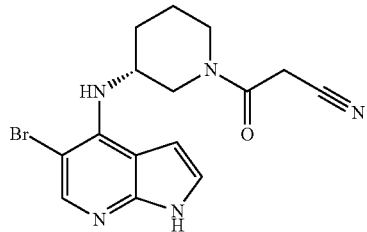 [SMILES: N#CCC(=O)N1CCC[C@@H](Nc2c(Br)cnc3[nH]ccc23)C1]

To a solution of (R)-5-bromo-N-(piperidin-3-yl)-1H-pyrrolo[2,3-b]pyridin-4-amine (8.4 g, 28.4 mmol) in dichloromethane (150 mL) was added cyanoacetic acid (4.84 g, 56.9 mmol), 1-ethyl-3-(3-dimethylaminopropyl) carbodiimide.hydrochloride (10.94 g, 56.9 mmol), hydroxybenzotriazole (7.68 g, 56.9 mmol) and N,N-disopropylethylamine (14.7 mL, 85.4 mmol). The reaction mixture was stirred for 16 hours at ambient temperature. The reaction mixture was diluted with dichloromethane (150 mL) and washed with water, brine solution, dried over anhydrous sodium sulfate, filtered and concentrated in vacuo. The crude material was purified by flash chromatography (5% methanol/dichloromethane) to provide (R)-3-(3-((5-bromo-1H-pyrrolo[2,3-b]pyridin-4-yl)amino)piperidin-1-yl)-3-oxopropanenitrile as an off-white solid (2.8 g, 27% yield): $^1$H NMR (400 MHz, DMSO-$d_6$, at 60° C.) δ 11.37 (b, 1H), 7.96 (s, 1H), 7.20 (s, 1H), 6.57 (s, 1H), 5.19 (d, J=8.8 Hz, 1H), 4.20 (br s, 1H), 3.80-4.10 (m, 4H), 3.52-3.54 (m, 1H), 3.01 (br s, 1H), 2.02 (br s, 1H), 1.51-1.75 (m, 3H); MS (ES) m/z 364.2 (M+2).

General procedure for cross coupling reaction

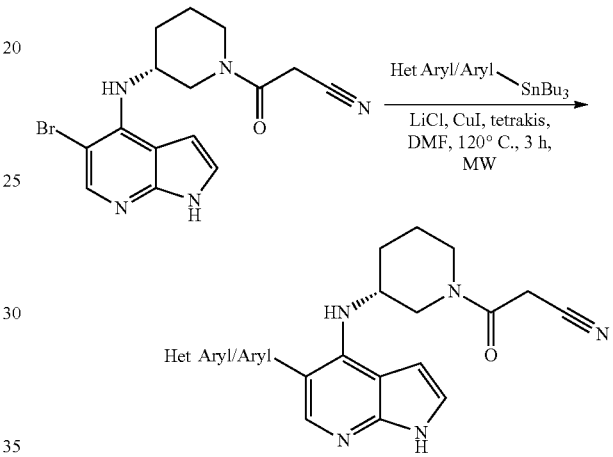

A mixture of (R)-3-(3-((5-bromo-1H-pyrrolo[2,3-b]pyridin-4-yl)amino)piperidin-1-yl)-3-oxopropanenitrile (1.0 equiv), Aryl/Heteroaryl(tributyl or stannyl) (1.2 eq), lithium chloride (2.0 eq), copper iodide (0.1 eq) and tetrakis(triphenylphosphine)palladium (0) in N,N-dimethylformamide (5 mL) was heated to 120° C. for 3 hours under argon atmosphere. The reaction mixture was cooled to ambient temperature and diluted with ethyl acetate. The ethyl acetate layer washed with water, brine, dried over anhydrous sodium sulfate, filtered and concentrated in vacuo. The crude material was purified by flash chromatography (5% methanol/dichloromethane) to provide the desired products as indicated in Table 2.

TABLE 2

The following compounds were prepared by the method described above:

| Example # | Structure | IUPAC Name | Analytical Data |
|---|---|---|---|
| 20 | (structure) | (R)-3-(3-((5-(6-methylpyridin-2-yl)-1H-pyrrolo[2,3-b]pyridin-4-yl)amino)piperidin-1-yl)-3-oxopropanenitrile | $^1$H NMR (400 MHz, DMSO-$d_6$ at 70° C.) δ 11.21 (br s, 1H), 9.96-10.07 (m, 2H), 8.36 (s, 1H), 7.72 (m, 1H), 7.64 (d, J = 8.0 Hz, 1H), 7.09-7.14 (m, 1H), 6.63 (s, 1H), 4.28-4.43 (m, 1H), 3.90-4.15 (m, 1H), 3.62-3.88 (m, 1H), 3.42-3.58 (m, 2H), 2.95-3.08 (m, 1H), 2.52 (s, 3H), 2.10-2.18 (m, 2H), 1.52-1.82 (m, 3H); MS (ES) m/z 375.1 (M + H). |

TABLE 2-continued

The following compounds were prepared by the method described above:

| Example # | Structure | IUPAC Name | Analytical Data |
|---|---|---|---|
| 21 | 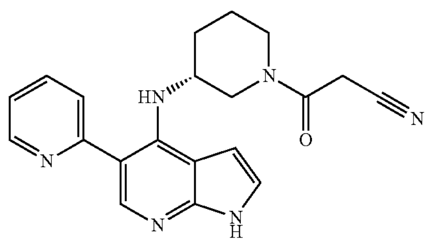 [SMILES: N#CCC(=O)N1CCC[C@@H](Nc2c(-c3ccccn3)cnc3[nH]ccc23)C1] | (R)-3-oxo-3-(3-((5-(pyridin-2-yl)-1H-pyrrolo[2,3-b]pyridin-4-yl)amino)piperidin-1-yl)propanenitrile | $^1$H NMR (400 MHz, DMSO-$d_6$ at 70° C.) δ 11.2 (bs, 1H), 9.82-9.98 (m, 1H), 8.55 (bs, 1H), 8.37 (bs, 1H), 7.85 (s, 2H), 7.23 (s, 1H), 7.14 (s, 1H), 6.62 (s, 1H), 4.17-4.38 (m, 1H), 3.97 (bs, 3H), 3.60-3.72 (m, 1H), 3.20-3.69 (m, 2H), 2.00 (bs, 2H), 1.62-1.71 (m, 2H); MS (ES) m/z 361.3 (M+). |
| 22 | 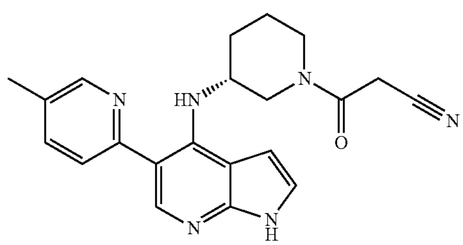 [SMILES: Cc1ccc(-c2cnc3[nH]ccc3c2N[C@@H]2CCCN(C(=O)CC#N)C2)nc1] | (R)-3-(3-((5-(5-methylpyridin-2-yl)-1H-pyrrolo[2,3-b]pyridin-4-yl)amino)piperidin-1-yl)-3-oxopropanenitrile | $^1$H NMR (400 MHz, DMSO-$d_6$ at 70° C.) 11.24 (s, 1H), 9.90 (s, 1H), 8.38-8.39 (m, 2H), 7.68-7.75 (m, 2H), 7.14 (s, 1H), 6.62 (s, 1H), 4.32-4.42 (m, 1H), 4.12-4.25 (m, 1H), 3.90-3.98 (m, 2H), 3.44-3.65 (m, 2H), 2.32 (s, 3H), 1.99-2.07 (m, 2H), 1.58-1.72 (m, 3H); MS (ES) m/z 375.3 (M + H). |
| 23 | 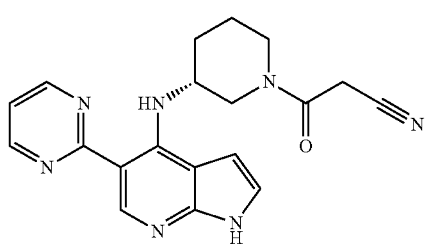 [SMILES: N#CCC(=O)N1CCC[C@@H](Nc2c(-c3ncccn3)cnc3[nH]ccc23)C1] | (R)-3-oxo-3-(3-((5-(pyrimidin-2-yl)-1H-pyrrolo[2,3-b]pyridin-4-yl)amino)piperidin-1-yl)propanenitrile | $^1$H NMR (400 MHz, DMSO-$d_6$ at 70° C.) 11.23 (s, 1H), 10.27-10.29 (m, 1H), 9.18 (s, 1H), 8.77 (d, J = 4.8 Hz, 1H), 7.25 (s, 1H), 7.13 (s, 1H), 6.64-6.65 (d, J = 1.6 Hz, 1H), 4.38-4.51 (m, 1H), 4.10-4.36 (m, 1H), 3.91-4.10 (m, 2H), 3.58-3.80 (m, 1H), 3.47-3.57 (m, 1H), 3.36-3.41 (m, 1H), 2.01-2.09 (m, 1H), 1.71-1.89 (m, 1H), 1.58 (s, 2H), 1.33 (s, 1H); MS (ES) m/z 362.3 (M + H). |
| 24 | 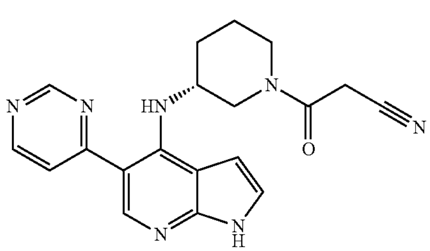 [SMILES: N#CCC(=O)N1CCC[C@@H](Nc2c(-c3ccncn3)cnc3[nH]ccc23)C1] | (R)-3-oxo-3-(3-((5-(pyrimidin-4-yl)-1H-pyrrolo[2,3-b]pyridin-4-yl)amino)piperidin-1-yl)propanenitrile | $^1$H NMR (400 MHz, DMSO-$d_6$ at 70° C.) 11.42 (s, 1H), 10.34 (s, 1H), 9.05 (s, 1H), 8.65-8.57 (m, 2H), 8.00 (s, 1H), 7.17 (s, 1H), 6.66 (s, 1H), 4.24-4.43 (m, 1H), 3.9-4.02 (m, 1H), 3.52-3.71 (m, 2H), 3.40 (s, 2H), 2.04 (s, 1H), 1.68-1.75 (m, 3H); MS (ES) m/z 362.0 (M + H). |

Example 25: Preparation of (R)-4-((1-(2-cyanoacetyl)piperidin-3-yl)amino)-1H-pyrrolo[2,3-b]pyridine-5-carbonitrile

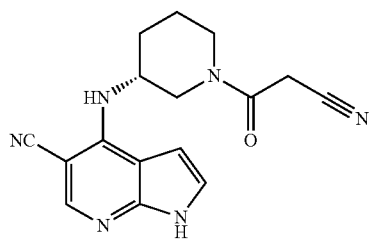 [SMILES: N#CCC(=O)N1CCC[C@@H](Nc2c(C#N)cnc3[nH]ccc23)C1]

Scheme 24: Preparation of (R)-4-((1-(2-cyanoacetyl)piperidin-3-yl)amino)-1H-pyrrolo[2,3-b]pyridine-5-carbonitrile

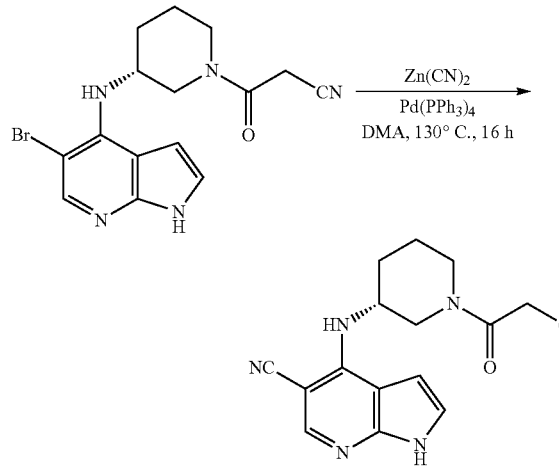

A suspension of (R)-3-(3-((5-bromo-1H-pyrrolo[2,3-b]pyridin-4-yl)amino)piperidin-1-yl)-3-oxopropanenitrile (0.2 g, 0.55 mmol as prepared by the method described in Scheme 23, Step 4), zinc cyanide (0.01 mg, 0.83 mmol) and tetrakis(triphenylphosphine)palladium(0) (0.16 g, 0.14 mmol) in dimethylformamide (5 mL) was heated in a sealed tube at 130° C. for 16 hours under argon atmosphere. The reaction mixture was cooled to room temperature and diluted with ethyl acetate. The organic layer was washed with water, brine, dried over anhydrous sodium sulfate, filtered and concentrated in vacuo. The crude product was purified by reverse phase chromatography to provide (R)-4-((1-(2-cyanoacetyl)piperidin-3-yl)amino)-1H-pyrrolo[2,3-b]pyridine-5-carbonitrile as an off-white solid (0.04 g, 26% yield): $^1$H NMR (400 MHz, DMSO-$d_6$ at 70° C.) 11.67 (s, 1H), 8.07 (s, 1H), 7.23 (s, 1H), 6.71 (s, 1H), 6.21-6.66 (m, 1H), 4.05-4.29 (m, 2H), 3.99 (s, 2H), 3.53-3.91 (m, 1H), 2.85-3.02 (m, 1H), 2.03-2.10 (m, 2H), 1.68-1.78 (m, 3H); MS (ES) m/z 309.2 (M+H). HPLC purity: 99.58%

Prep. HPLC Conditions:

Column: Kinetex C18 (100 mm×4.6 mm×2.6 μm)

Mobile phase A: 0.1% TFA in Water

Mobile phase B: ACN

Flow rate: 0.75 mL/min

Example 26: Preparation of (R)-3-(3-((5-(3-methyl-1H-pyrazol-5-yl)-1H-pyrrolo[2,3-b]pyridin-4-yl)amino)piperidin-1-yl)-3-oxopropanenitrile

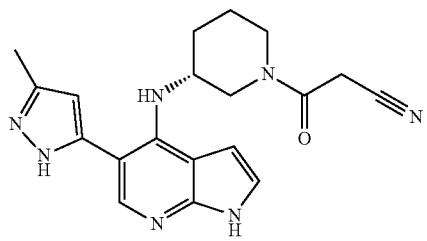 [SMILES: Cc1cc(-c2cnc3[nH]ccc3c2N[C@@H]2CCCN(C(=O)CC#N)C2)[nH]n1]

Scheme 25: Preparation of (R)-3-(3-((5-(3-methyl-1H-pyrazol-5-yl)-1H-pyrrolo[2,3-b]pyridin-4-yl)amino)piperidin-1-yl)-3-oxopropanenitrile

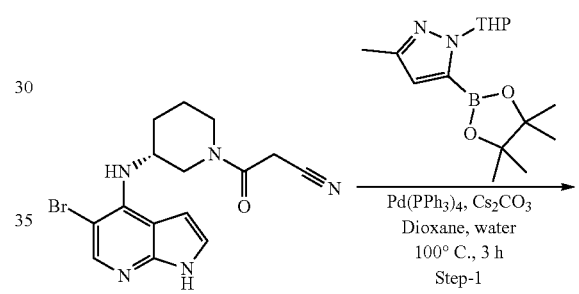

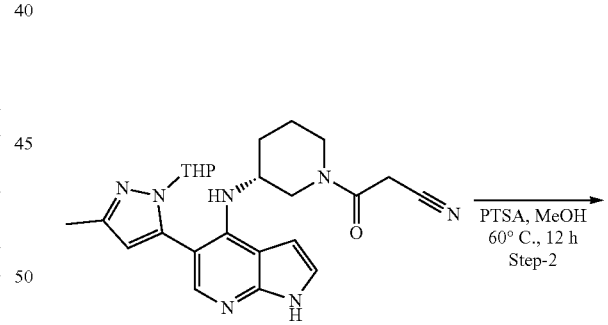

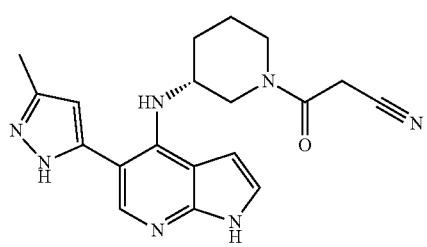

Step 1: Preparation of 3-((3R)-3-((5-(3-methyl-1-(tetrahydro-2H-pyran-2-yl)-1H-pyrazol-5-yl)-1H-pyrrolo[2,3-b]pyridin-4-yl)amino)piperidin-1-yl)-3-oxopropanenitrile

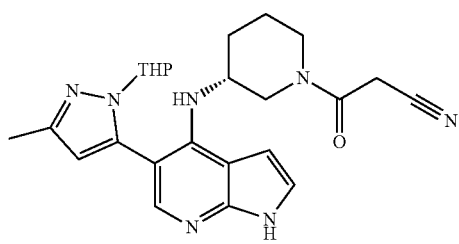

A mixture of (R)-3-(3-((5-bromo-1H-pyrrolo[2,3-b]pyridin-4-yl)amino)piperidin-1-yl)-3-oxopropanenitrile (0.5 g, 1.38 mmol, as prepared by the method described in Scheme 23, Step 4), 3-methyl-1-(tetrahydro-2H-pyran-2-yl)-5-(4,4,5,5-tetramethyl-1,3,2-dioxaborolan-2-yl)-1H-pyrazole (0.6 g, 2.07 mmol), cesium carbonate (1.35 g, 4.14 mmol) and tetrakis(triphenylphosphine)palladium (0) (0.08 g, 0.07 mmol) in 1,4-dioxane:water (4 mL:1 mL) was heated in a sealed tube at 100° C. for 5 hours under an argon atmosphere. The reaction mixture was cooled to ambient temperature and diluted with ethyl acetate and water. The organic layer was washed with brine, dried over anhydrous sodium sulfate, filtered and concentrated in vacuo. The crude material was purified by flash chromatography (80% ethyl acetate/hexane) to provide 3-((3R)-3-((5-(3-methyl-1-(tetrahydro-2H-pyran-2-yl)-1H-pyrazol-5-yl)-1H-pyrrolo[2,3-b]pyridin-4-yl)amino)piperidin-1-yl)-3-oxopropanenitrile as a brown solid (0.2 g, 32% yield): MS (ES) m/z 448 (M+H).

Step 2: Preparation of (R)-3-(3-((5-(3-methyl-1H-pyrazol-5-yl)-1H-pyrrolo[2,3-b]pyridin-4-yl)amino)piperidin-1-yl)-3-oxopropanenitrile

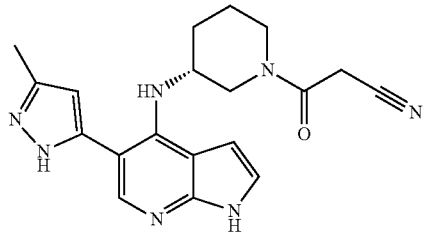 [SMILES: Cc1cc(-c2cnc3[nH]ccc3c2N[C@@H]2CCCN(C(=O)CC#N)C2)[nH]n1]

A stirred solution of 3-((3R)-3-((5-(3-methyl-1-(tetrahydro-2H-pyran-2-yl)-1H-pyrazol-5-yl)-1H-pyrrolo[2,3-b]pyridin-4-yl)amino)piperidin-1-yl)-3-oxopropanenitrile (0.2 g, 0.44 mmol) and p-toluenesulfonic acid (0.15 g, 0.89 mmol) in methanol (5 mL) was heated at 60° C. for 12 hours. The reaction mixture was cooled to room temperature and concentrated in vacuo. The crude material was purified by reverse phase chromatograpy to provide (R)-3-(3-((5-(3-methyl-1H-pyrazol-5-yl)-1H-pyrrolo[2,3-b]pyridin-4-yl)amino)piperidin-1-yl)-3-oxopropanenitrile as an off-white solid (0.01 g, 6% yield): $^1$H NMR (400 MHz, DMSO-$d_6$) δ 12.52 (s, 1H), 11.35 (s, 1H), 8.24-8.27 (m, 1H), 7.44-7.46 (m, 1H), 7.08-7.16 (m, 2H), 6.47-6.50 (m, 1H), 4.31 (s, 1H), 3.89-4.11 (m, 2H), 3.49-3.69 (m, 2H), 3.20 (s, 3H), 2.94 (s, 2H), 2.27 (m, 3H), 2.05-2.10 (m, 1H); MS (ES) m/z 364.1 (M+).

Analytical conditions: Flow rate: 0.3 mL/min

Column: BEH C18 (100 mm×2.1 mm×1.7 μm)

Mobile Phase (A): 0.1% Formic acid in water

Mobile Phase (B): ACN

Example 27: Preparation of (R)-3-(3-((5-(oxazol-2-yl)-1H-pyrrolo[2,3-b]pyridin-4-yl)amino)piperidin-1-yl)propanenitrile

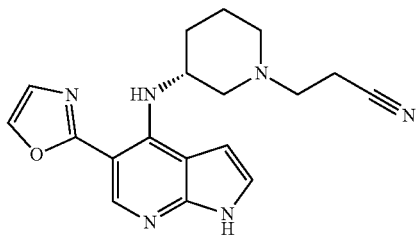 [SMILES: N#CCCN1CCC[C@@H](Nc2c(-c3ncco3)cnc3[nH]ccc23)C1]

Scheme 26: Preparation of (R)-3-(3-((5-(oxazol-2-yl)-1H-pyrrolo[2,3-b]pyridin-4-yl)amino)piperidin-1-yl)propanenitrile

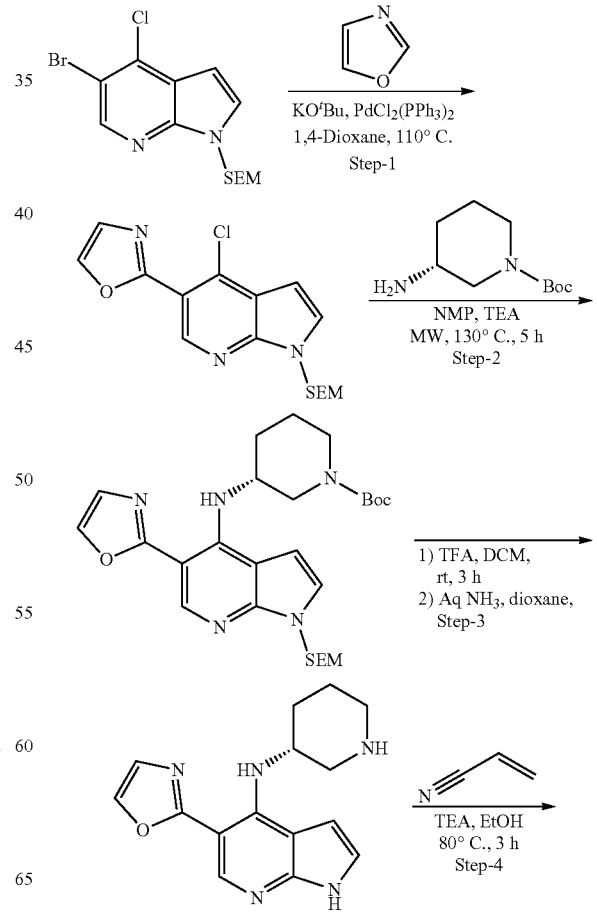

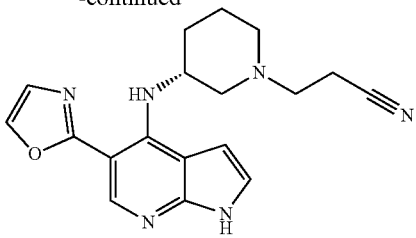

Step 1: Preparation of 2-(4-chloro-1-((2-(trimethylsilyl)ethoxy)methyl)-1H-pyrrolo[2,3-b]pyridin-5-yl)oxazole

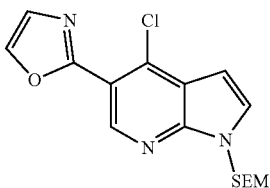

A mixture of 5-bromo-4-chloro-1-((2-(trimethylsilyl)ethoxy)methyl)-1H-pyrrolo[2,3-b]pyridine (2.00 g, 5.54 mmol), oxazole (0.68 g, 9.97 mmol), potassium tert-butoxide (1.24 g, 11.1 mmol) and bis(triphenyl phosphine)palladium(II) dichloride (0.19 g, 0.27 mmol) in 1,4-dioxane (20 mL) was heated in a sealed tube at 110° C. under nitrogen. After 5 hours the reaction was cooled to ambient temperature, diluted with water and extracted with ethyl acetate. The organic layer was washed with brine, dried over sodium sulfate, filtered and concentrated in vacuo. The crude material was purified by flash chromatography (10% ethyl acetate/hexane) to provide 2-(4-chloro-1-((2-(trimethylsilyl)ethoxy)methyl)-1H-pyrrolo[2,3-b]pyridin-5-yl)oxazole as an off-white solid (0.43 g, 22% yield): MS (ES) m/z 349.9 (M+H).

Step 2: Preparation of tert-butyl (R)-3-((5-(oxazol-2-yl)-1-((2-(trimethylsilyl)ethoxy)methyl)-1H-pyrrolo[2,3-b]pyridin-4-yl)amino)piperidine-1-carboxylate

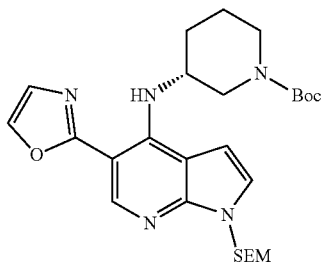 [SMILES: CC(C)(C)OC(=O)N1CCC[C@@H](Nc2c(-c3ncco3)cnc3c2ccn3COCC[Si](C)(C)C)C1]

A stirred solution of 2-(4-chloro-1-((2-(trimethylsilyl)ethoxy)methyl)-1H-pyrrolo[2,3-b]pyridin-5-yl)oxazole (0.43 g, 1.28 mmol), triethylamine (0.03 mL, 0.24 mmol) and tert-butyl (R)-3-aminopiperidine-1-carboxylate (0.46 g, 2.32 mmol) in N-methylpyrrolidone (4 mL) was subjected to microwave irradiation at 130° C. for 5 hours. The reaction was cooled to ambient temperature, diluted with water and extracted with ethyl acetate. The organic layer was washed with brine, dried over sodium sulfate, filtered and concentrated in vacuo. The crude material was purified using flash chromatography (50% ethyl acetate/hexane) to provide tert-butyl (R)-3-((5-(oxazol-2-yl)-1-((2-(trimethylsilyl)ethoxy)methyl)-1H-pyrrolo[2,3-b]pyridin-4-yl)amino)piperidine-1-carboxylate as an off-white solid (0.35 g, 53% yield): MS (ES) m/z 514.0 (M+H).

Step 3: Preparation of (R)-5-(oxazol-2-yl)-N-(piperidin-3-yl)-1H-pyrrolo[2,3-b]pyridin-4-amine

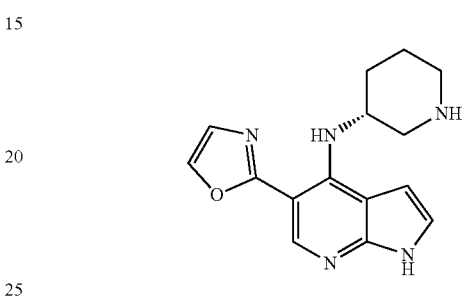

A solution of tert-butyl (R)-3-((5-(oxazol-2-yl)-1-((2-(trimethylsilyl)ethoxy)methyl)-1H-pyrrolo[2,3-b]pyridin-4-yl)amino)piperidine-1-carboxylate (0.12 g, 0.23 mmol) in dichloromethane:trifluoroacetic acid (3 mL:3 mL) was stirred at ambient temperature for 3 hours. The reaction mixture was concentrated in vacuo, the residue was dissolved in 1,4-dioxane:aqueous ammonia (3 mL:3 mL, 23% in water) and the mixture was stirred at ambient temperature for 16 hours. The reaction mixture was concentrated in vacuo to provide (R)-5-(oxazol-2-yl)-N-(piperidin-3-yl)-1H-pyrrolo[2,3-b]pyridin-4-amine as an off-white solid (0.05 g, crude): MS (ES) m/z 284.2 (M+H).

Step 4: Preparation of (R)-3-(3-((5-(oxazol-2-yl)-1H-pyrrolo[2,3-b]pyridin-4-yl)amino)piperidin-1-yl)propanenitrile

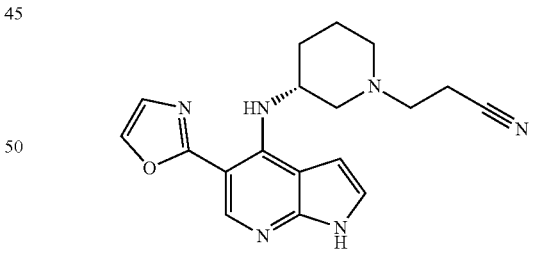

To a stirred solution of (R)-5-(oxazol-2-yl)-N-(piperidin-3-yl)-1H-pyrrolo[2,3-b]pyridin-4-amine (0.05 g, 0.17 mmol) in ethanol (3 mL), was added acrylonitrile (0.09 g, 1.7 mmol) followed by trimethylamine (0.05 mL, 0.34 mmol) and the solution was stirred at 80° C. for 3 hours. The reaction was cooled to ambient temperature and concentrated in vacuo. The crude material was purified using flash chromatography (5% methanol/dichloromethane) to provide (R)-3-(3-((5-(oxazol-2-yl)-1H-pyrrolo[2,3-b]pyridin-4-yl)amino)piperidin-1-yl)propanenitrile as an off-white solid (0.03 g, 45% yield): $^1$H NMR (400 MHz, DMSO-$d_6$) δ 11.53 (br s, 1H), 9.17 (br s, 1H), 8.50 (s, 1H), 8.06 (s, 1H), 7.36

(s, 1H), 7.17 (s, 1H), 6.56 (s, 1H), 4.14-4.27 (m, 1H), 2.85-2.98 (m, 1H), 2.55-2.66 (m, 2H), 2.83-2.97 (m, 2H), 1.52-1.69 (m, 2H), 1.42-1.60 (m, 3H), 1.21 (s, 2H); MS (ES) m/z 337.2 (M+H).

Example 28: Preparation of 3-((2S,5R)-2-methyl-5-((5-(oxazol-2-yl)-1H-pyrrolo[2,3-b]pyridin-4-yl)amino)piperidin-1-yl)-3-oxopropanenitrile

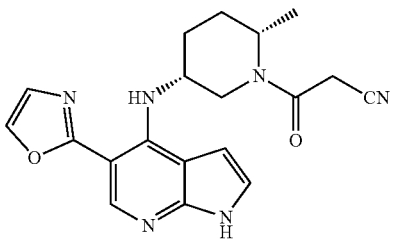 [SMILES: C[C@H]1CC[C@@H](Nc2c(-c3ncco3)cnc3[nH]ccc23)CN1C(=O)CC#N]

Scheme 27. Preparation of 3-((2S,5R)-2-methyl-5-((5-oxazol-2-yl)-1H-pyrrolo[2,3-b]pyridin-4-yl) amino) piperidin-1-yl)-3-oxopropanenitrile

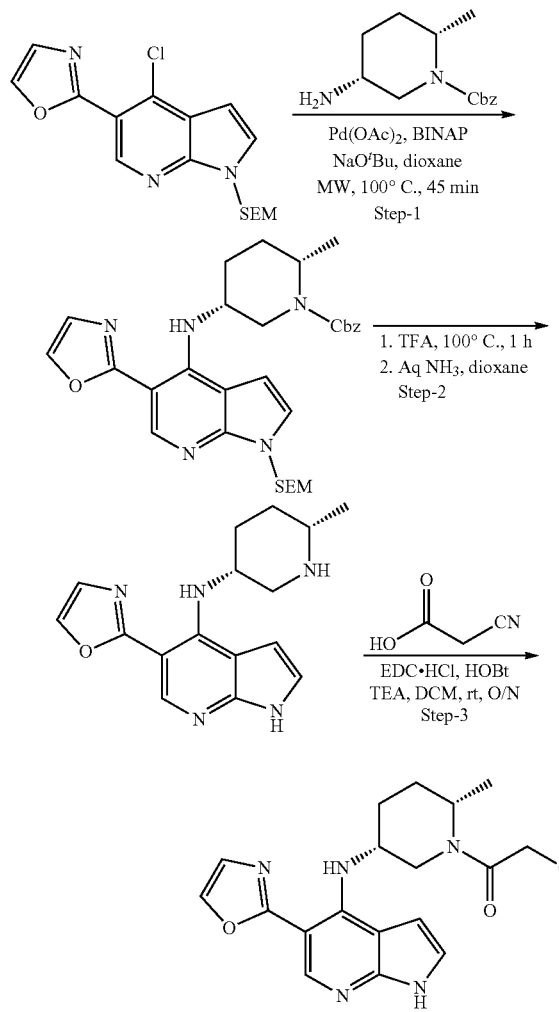

Step 1: Preparation of benzyl (2S,5R)-2-methyl-5-((5-(oxazol-2-yl)-1-((2-(trimethylsilyl)ethoxy)methyl)-1H-pyrrolo[2,3-b]pyridin-4-yl)amino)piperidine-1-carboxylate

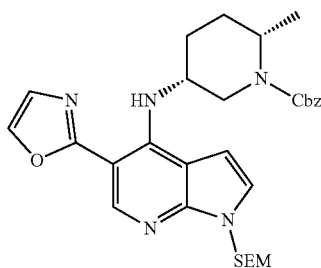 [SMILES: C[C@H]1CC[C@@H](Nc2c(-c3ncco3)cnc3c2ccn3COCC[Si](C)(C)C)CN1C(=O)OCc1ccccc1]

To a stirred solution of 2-(4-chloro-1-((2-(trimethylsilyl)ethoxy)methyl)-1H-pyrrolo[2,3-b]pyridin-5-yl)oxazole (0.2 g, 0.57 mmol) (obtained from Example 27, Step 1) and benzyl (2S,5R)-5-amino-2-methylpiperidine-1-carboxylate (0.21 g, 0.85 mmol) in 1,4-dioxane (5 mL), was added potassium tert-butoxide (0.16 g, 1.71 mmol), palladium(II) acetate (0.02 g, 0.08 mmol) and (R)-(+)-2,2'-bis(diphenylphosphino)-1,1'-binaphthyl (0.05 g, 0.08 mmol) and the resulting mixture was subjected to MW irradiation at 100° C. for 45 minutes. The reaction was cooled to ambient temperature, diluted with water and extracted with ethyl acetate. The organic layer was washed with brine, dried over sodium sulfate, filtered and concentrated in vacuo. The crude material was purified by flash chromatography (40% ethyl acetate/hexane) to provide benzyl (2S,5R)-2-methyl-5-((5-(oxazol-2-yl)-1-((2-(trimethylsilyl)ethoxy)methyl)-1H-pyrrolo[2,3-b]pyridin-4-yl)amino)piperidine-1-carboxylate as a colorless gummy liquid (0.12 g, 37% yield); MS (ES) m/z 561.9 (M+H).

Step 2: Preparation of N-((3R,6S)-6-methylpiperidin-3-yl)-5-(oxazol-2-yl)-1H-pyrrolo[2,3-b]pyridin-4-amine

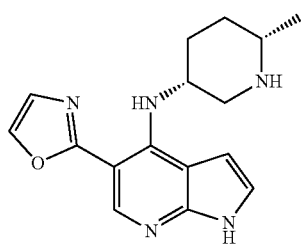 [SMILES: C[C@H]1CC[C@@H](Nc2c(-c3ncco3)cnc3[nH]ccc23)CN1]

A solution of benzyl(2S,5R)-2-methyl-5-((5-(oxazol-2-yl)-1-((2-(trimethylsilyl)ethoxy)methyl)-1H-pyrrolo[2,3-b]pyridin-4-yl)amino)piperidine-1-carboxylate (2.0 g, 0.35 mmol) in trifluoroacetic acid (2.0 mL) was stirred at 100° C. for 1 hour. The reaction was cooled to ambient temperature and the mixture was concentrated in vacuo, the residue was dissolved in 1,4-dioxane:aqueous ammonia (2 mL:2 mL) and was stirred at ambient temperature for 16 hours. The reaction mixture was concentrated in vacuo to provide N-((3R,6S)-6-methylpiperidin-3-yl)-5-(oxazol-2-yl)-1H-pyrrolo[2,3-b]pyridin-4-amine as a pale yellow gummy liquid (0.1 g, crude): MS (ES) m/z 298.0 (M+H).

Step 3: Preparation of 3-((2S,5R)-2-methyl-5-((5-(oxazol-2-yl)-1H-pyrrolo[2,3-b]pyridin-4-yl)amino)piperidin-1-yl)-3-oxopropanenitrile

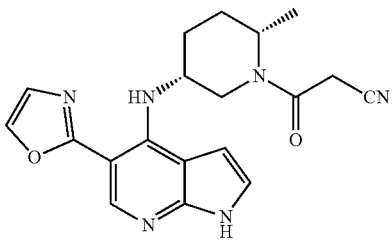 [SMILES: C[C@H]1CC[C@@H](Nc2c(-c3ncco3)cnc3[nH]ccc23)CN1C(=O)CC#N]

To a solution of cyanoacetic acid (0.03 g, 0.4 mmol) and 1-hydroxybenzotriazole (0.055 g, 0.4 mmol) in dichloromethane (5 mL), was added N-(3-dimethylaminopropyl)-N'-ethylcarbodiimide hydrochloride (0.1 g, 0.51 mmol) and the mixture stirred at ambient temperature for 5 minutes. At this time N-((3R,6S)-6-methylpiperidin-3-yl)-5-(oxazol-2-yl)-1H-pyrrolo[2,3-b]pyridin-4-amine (0.1 g, 0.34 mmol) was added followed by N,N-diisopropylethylamine (0.18 mL, 1.02 mmol) and then the resulting mixture was stirred at ambient temperature for 18 hours. The reaction was quenched with water and extracted with dichloromethane. The organic layer was washed with water, brine, dried over anhydrous sodium sulfate, filtered and concentrated in vacuo. The crude material was purified by flash chromatography (5% methanol/dichloromethane) and further purified by reverse phase chromatograpy to provide 3-((2S,5R)-2-methyl-5-((5-(oxazol-2-yl)-1H-pyrrolo[2,3-b]pyridin-4-yl)amino)piperidin-1-yl)-3-oxopropanenitrile as an off-white solid (0.04 g, 33% yield): $^1$H NMR (400 MHz, DMSO-$d_6$, VT at 70° C.) δ 11.43 (br s, 1H), 8.92 (d, J=7.6 Hz, 1H), 8.55 (s, 1H), 8.05 (s, 1H), 7.36 (s, 1H), 7.20 (s, 1H), 6.68 (s, 1H), 3.93-4.02 (m, 3H), 3.56 (s, 2H), 1.80-2.12 (m, 2H), 1.60-1.79 (m, 2H), 1.24 (s, 4H); MS (ES) m/z 365.1 (M+H).

Analytical Conditions: Flow rate: 0.3 mL/min
Column: BEH C18 (50 mm×2.1 mm×1.7 μm)
Mobile Phase (A): 0.1% Formic acid in water
Mobile Phase (B): MeCN Example 29: Preparation of 2-(4-(((1S,3R)-3-hydroxycyclopentyl)amino)-1H-pyrrolo[2,3-b]pyridin-5-yl)oxazole-4-carboxamide

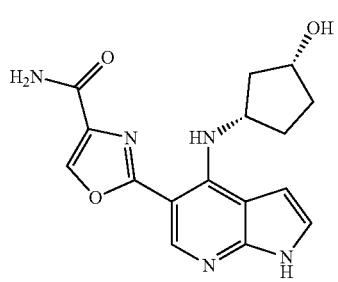 [SMILES: NC(=O)c1coc(-c2cnc3[nH]ccc3c2N[C@H]2CC[C@@H](O)C2)n1]

Scheme 28. Preparation of 2-(4-(((1S,3R)-3-hydroxycyclopental)amino)-1H-pyrrolo[2,3-b]pyridin-5-yl)oxazole-4-carboxamide

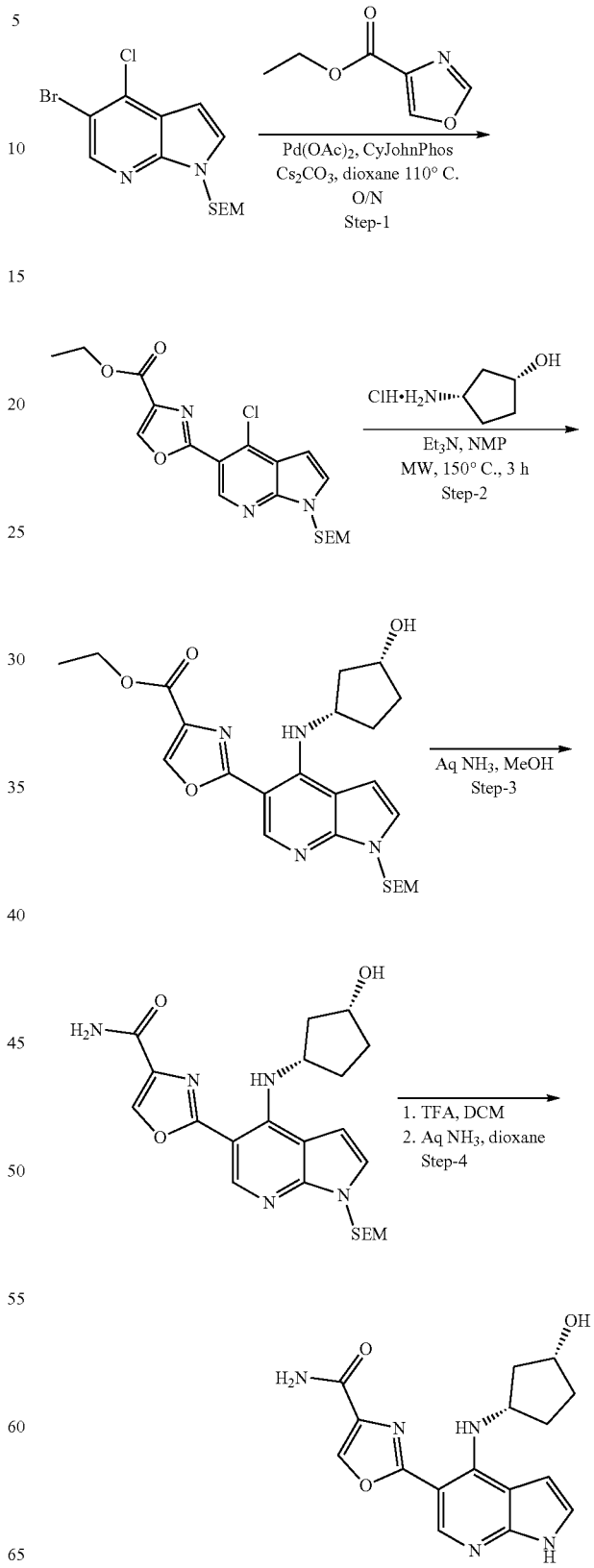

Step 1: Preparation of ethyl 2-(4-chloro-1-((2-(trimethylsilyl)ethoxy)methyl)-1H-pyrrolo[2,3-b]pyridin-5-yl)oxazole-4-carboxylate

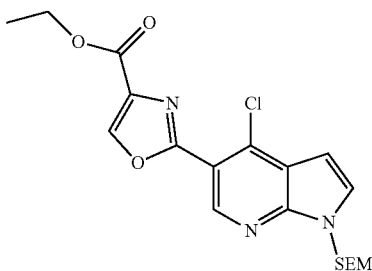 [SMILES: CCOC(=O)c1coc(-c2cnc3c(ccn3COCC[Si](C)(C)C)c2Cl)n1]

To a stirred solution of 5-bromo-4-chloro-1-((2-(trimethylsilyl)ethoxy)methyl)-1H-pyrrolo[2,3-b]pyridine (0.8 g, 2.22 mmol) and ethyl oxazole-4-carboxylate (0.37 g, 2.66 mmol) in 1,4-dioxane (30 mL), was added palladium acetate (0.024 g, 0.11 mmol), CyJohnphos (0.08 g, 0.22 mmol) and cesium carbonate (1.44 g, 4.44 mmol) and the mixture was heated in a sealed tube at 110° C. for 16 hours. The reaction was cooled to room temperature, filtered through celite and the filtrate was concentrated in vacuo. The crude was purified using flash chromatography (30% ethyl acetate/hexane) to provide ethyl 2-(4-chloro-1-((2-(trimethylsilyl)ethoxy)methyl)-1H-pyrrolo[2,3-b]pyridin-5-yl)oxazole-4-carboxylate as a brown liquid (0.41 g, 44% yield): MS (ES) m/z 421.9 (M+H).

Step 2: Preparation of ethyl 2-(4-(((1S,3R)-3-hydroxycyclopentyl)amino)-1-((2-(trimethylsilyl)ethoxy)methyl)-1H-pyrrolo[2,3-b]pyridin-5-yl)oxazole-4-carboxylate

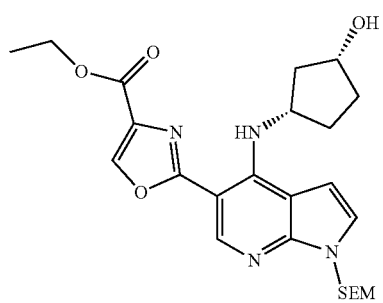 [SMILES: CCOC(=O)c1coc(-c2cnc3c(ccn3COCC[Si](C)(C)C)c2N[C@H]2CC[C@@H](O)C2)n1]

To a stirred solution of ethyl 2-(4-chloro-1-((2-(trimethylsilyl)ethoxy)methyl)-1H-pyrrolo[2,3-b]pyridin-5-yl)oxazole-4-carboxylate (0.4 g, 0.95 mmol) in N-methylpyrrolidone (5 mL) was added (1R,3S)-3-aminocyclopentan-1-ol hydrochloride (0.13 g, 0.95 mmol) followed by trimethylamine (0.17 mL, 1.23 mmol). The resulting mixture was subjected to microwave irradiation at 150° C. for 45 minutes. The reaction was cooled to ambient temperature, diluted with water and extracted with ethyl acetate. The organic layer was washed with brine, dried over sodium sulfate, filtered and concentrated in vacuo. The crude material was purified by flash chromatography (50% ethyl acetate/hexane) to provide ethyl 2-(4-(((1S,3R)-3-hydroxycyclopentyl)amino)-1-((2-(trimethylsilyl)ethoxy)methyl)-1H-pyrrolo[2,3-b]pyridin-5-yl)oxazole-4-carboxylate as a colorless thick liquid (0.31 g, 67% yield): MS (ES) m/z 486.9 (M+H).

Step 3: Preparation of 2-(4-(((1S,3R)-3-hydroxycyclopentyl)amino)-1-((2-(trimethylsilyl)ethoxy)methyl)-1H-pyrrolo[2,3-b]pyridin-5-yl)oxazole-4-carboxamide

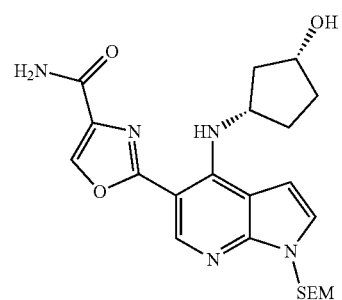 [SMILES: C[Si](C)(C)CCOCn1ccc2c(N[C@H]3CC[C@@H](O)C3)c(-c3nc(C(N)=O)co3)cnc21]

A stirred solution of ethyl 2-(4-(((1S,3R)-3-hydroxycyclopentyl)amino)-1-((2-(trimethylsilyl)ethoxy)methyl)-1H-pyrrolo[2,3-b]pyridin-5-yl)oxazole-4-carboxylate (0.30 g, 0.62 mmol), methanol (5 mL) and aqueous ammonia (5 mL, 23% in water) was stirred at ambient temperature for 20 hours. The reaction mixture was concentrated in vacuo to provide 2-(4-(((1S,3R)-3-hydroxycyclopentyl)amino)-1-((2-(trimethylsilyl)ethoxy)methyl)-1H-pyrrolo[2,3-b]pyridin-5-yl)oxazole-4-carboxamide as a white solid (0.28 g, 99% yield): MS (ES) m/z 457.9 (M+H).

Step 4: Preparation of 2-(4-(((1S,3R)-3-hydroxycyclopentyl)amino)-1H-pyrrolo[2,3-b]pyridin-5-yl)oxazole-4-carboxamide

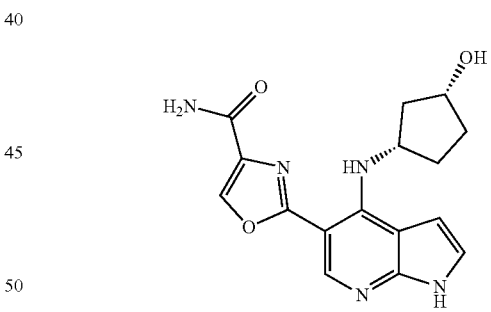

A solution of 2-(4-(((1S,3R)-3-hydroxycyclopentyl)amino)-1-((2-(trimethylsilyl)ethoxy)methyl)-1H-pyrrolo[2,3-b]pyridin-5-yl)oxazole-4-carboxamide (0.25 g, 0.55 mmol) in dichloromethane:trifluoroacetic acid (3 mL:3 mL) was stirred at ambient temperature for 3 hours. The mixture was concentrated in vacuo, the residue was dissolved in 1,4-dioxane:aqueous ammonia (3 mL:5 mL, 23% in water) and the solution was stirred at ambient temperature for 16 hours. The reaction mixture was concentrated in vacuo and the crude material was purified using flash chromatography (5% methanol/dichloromethane) to provide 2-(4-(((1S,3R)-3-hydroxycyclopentyl)amino)-1H-pyrrolo[2,3-b]pyridin-5-yl)oxazole-4-carboxamide as an off-white solid (0.05 g, 35% yield): $^1$H NMR (400 MHz, DMSO-$d_6$) δ 11.56 (br s, 1H), 9.35 (d, J=8.4 Hz, 1H), 8.48 (d, J=8.4 Hz, 1H), 7.58 (s, 1H), 7.17 (s, 1H), 6.71 (s, 1H), 5.13 (s, 1H), 4.63 (s, 1H), 4.35 (s, 1H), 2.05-2.19 (m, 2H), 1.82-2.00 (m, 2H), 1.75-1.80 (m, 1H), 1.15-1.30 (m, 3H); MS (ES) m/z 328.1 (M+H).
Intermediate

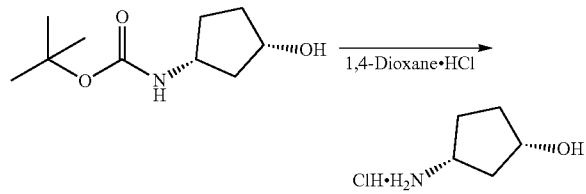

Preparation of (1S,3R)-3-aminocyclopentan-1-ol hydrochloride

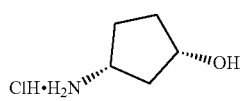

To a solution of tert-butyl ((1R,3S)-3-hydroxycyclopentyl)carbamate (0.5 g, 2.48 mmol) in 1,4-dioxane (1 mL) was added 4N hydrochloric acid in 1,4-dioxane (2.5 mL) and stirred at ambient temperature for 12 hours. The reaction mixture was concentrated in vacuo to provide ethyl (S)-4-(piperidin-3-ylamino)-1H-pyrrolo[2,3-b]pyridine-5-carboxylate hydrochloride as an off-white solid (0.25 g, crude): MS (ES) m/z 102.1 (M+H).

Example 30: Preparation of 2-(4-(((3R,6S)-1-(2-cyanoacetyl)-6-methylpiperidin-3-yl)amino)-1H-pyrrolo[2,3-b]pyridin-5-yl)-N-methyloxazole-4-carboxamide

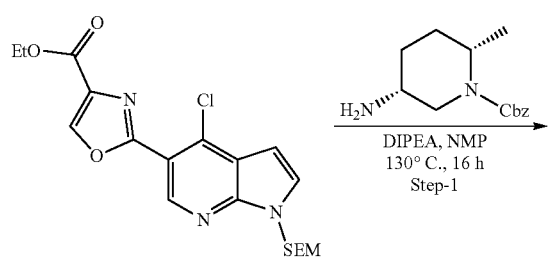

Scheme 29. Preparaion of 2-(4-(((3R,6S)-1-(2-cyanoacetyl)-6-methylpiperidin-3-yl)amino)-1H-pyrrolo[2,3-b]pyridin-5-yl)-N-methyloxazole-4-carboxyamide

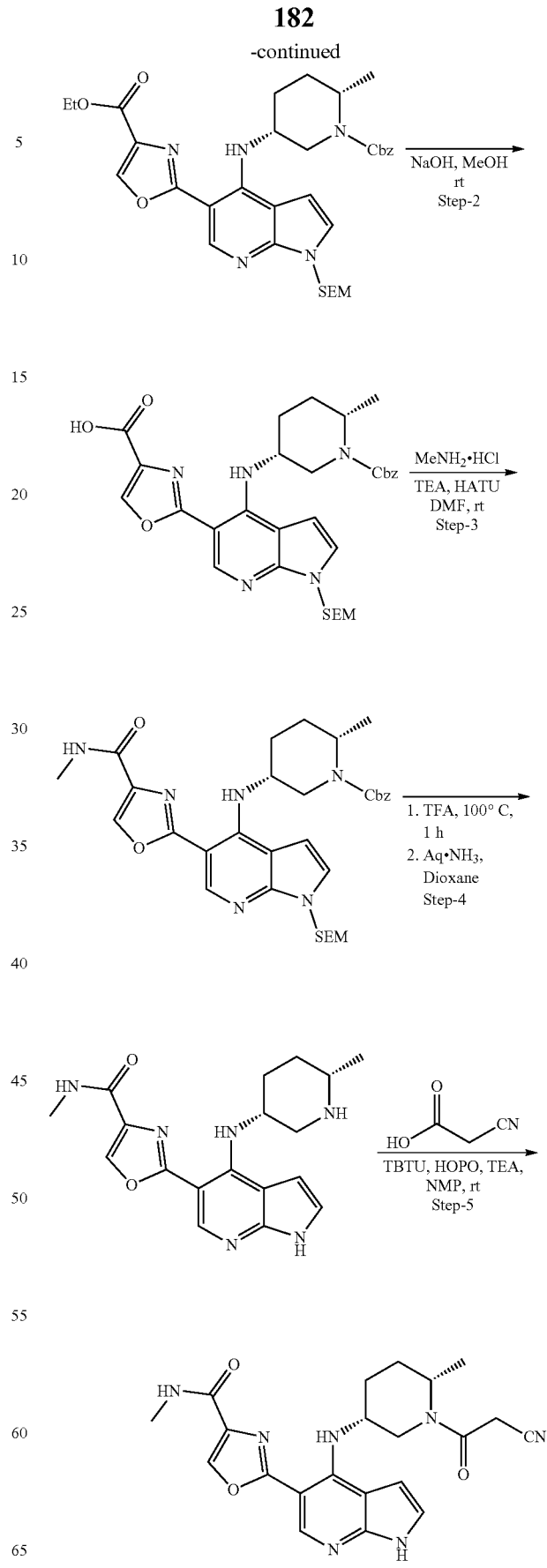

Step 1: Preparation of ethyl 2-(4-(((3R,6S)-1-((benzyloxy)carbonyl)-6-methylpiperidin-3-yl)amino)-1-((2-(trimethylsilyl)ethoxy)methyl)-1H-pyrrolo[2,3-b]pyridin-5-yl)oxazole-4-carboxylate

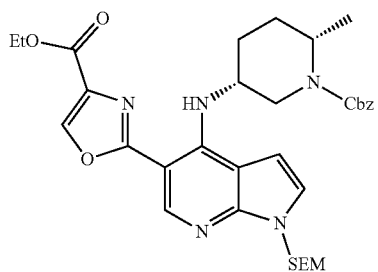 [SMILES: CCOC(=O)c1coc(-c2cnc3c(ccn3COCC[Si](C)(C)C)c2N[C@@H]2CC[C@H](C)N(C(=O)OCc3ccccc3)C2)n1]

In a 10 mL vial, a solution of ethyl 2-(4-chloro-1-{[2-(trimethylsilyl)ethoxy]methyl}-1H-pyrrolo[2,3-b]pyridin-5-yl)-1,3-oxazole-4-carboxylate (2.0 g, 4.74 mmol) (obtained from Example 29, Step 1), benzyl (2S,5R)-5-amino-2-methylpiperidine-1-carboxylate (2.35 g, 9.48 mmol) and diisopropylethylamine (1.29 mL, 14.2 mmol) in N-methylpyrrolidone (15 mL) was heated at 130° C. for 16 h. The reaction mixture was cooled to ambient temperature, diluted with ethyl acetate, washed with water, brine, dried over anhydrous sodium sulfate, filtered and concentrated in vacuo. The crude material was purified using flash chromatography (30% ethyl acetate/hexane) to provide benzyl (2S,5R)-5-({5-[4-(ethoxycarbonyl)-1,3-oxazol-2-yl]-1-{[2-(trimethylsilyl)ethoxy]methyl}-1H-pyrrolo[2,3-b]pyridin-4-yl}amino)-2-methylpiperidine-1-carboxylate as a pale yellow gummy liquid (0.71 g, 24% yield): MS (ES) m/z 634.3 (M+H).

Step 2: Preparation of 2-(4-(((3R,6S)-1-((benzyloxy)carbonyl)-6-methylpiperidin-3-yl)amino)-1-((2-(trimethylsilyl)ethoxy)methyl)-1H-pyrrolo[2,3-b]pyridin-5-yl)oxazole-4-carboxylic acid

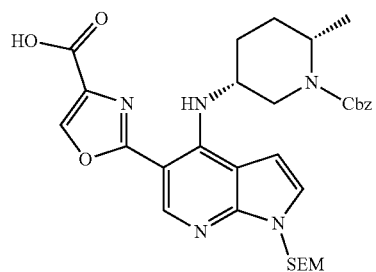 [SMILES: C[C@H]1CC[C@@H](Nc2c(-c3nc(C(=O)O)co3)cnc3c2ccn3COCC[Si](C)(C)C)CN1C(=O)OCc1ccccc1]

A solution of benzyl (2S,5R)-5-({5-[4-(ethoxycarbonyl)-1,3-oxazol-2-yl]-1-{[2-(trimethylsilyl) ethoxy]methyl}-1H-pyrrolo[2,3-b]pyridin-4-yl}amino)-2-methylpiperidine-1-carboxylate (0.60 g, 0.95 mmol), methanol (20 mL), and a 2M aqueous solution of sodium hydroxide (0.2 g, 4.73 mmol) was stirred at ambient temperature for 5 hours. Volatiles were removed in vacuo, the residue was dissolved in water and acidified with 1N hydrochloric acid and adjusted pH3. The aqueous layer was extracted with dichloromethane, washed with brine, dried over anhydrous sodium sulfate, filtered and concentrated in vacuo to provide 2-(4-{[(3R,6S)-1-[(benzyloxy)carbonyl]-6-methylpiperidin-3-yl]amino}-1-{[2-(trimethylsilyl)ethoxy]methyl}-1H-pyrrolo[2,3-b]pyridin-5-yl)-1,3-oxazole-4-carboxylic acid as a colorless thick liquid (0.51 g, 89% yield): MS (ES) m/z 606.3 (M+H).

Step 3: Preparation of benzyl (2S,5R)-2-methyl-5-({5-[4-(methylcarbamoyl)-1,3-oxazol-2-yl]-1-{[2-(trimethylsilyl)ethoxy]methyl}-1H-pyrrolo[2,3-b]pyridin-4-yl}amino)piperidine-1-carboxylate

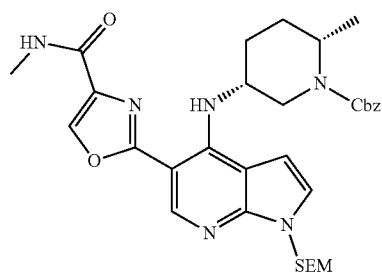 [SMILES: CNC(=O)c1coc(-c2cnc3c(ccn3COCC[Si](C)(C)C)c2N[C@@H]2CC[C@H](C)N(C(=O)OCc3ccccc3)C2)n1]

To a stirred solution of 2-(4-{[(3R,6S)-1-[(benzyloxy)carbonyl]-6-methylpiperidin-3-yl]amino}-1-{[2-(trimethylsilyl)ethoxy]methyl}-1H-pyrrolo[2,3-b]pyridin-5-yl)-1,3-oxazole-4-carboxylic acid (0.5 g, 0.82 mmol) and 1-[bis(dimethylamino)methylene]-1H-1,2,3-triazolo[4,5-b]pyridinium 3-oxid hexafluorophosphate (0.48 g, 1.24 mmol) in N,N-dimethylformamide (8 mL) at ambient temperature was added methylamine hydrochloride (0.13 g, 4.13 mmol) followed by triethylamine (0.6 mL, 4.13 mmol) and the mixture stirred at ambient temperature for 10 hours. The reaction mixture was diluted with ethyl acetate, washed with water and brine. The organic layer was dried over anhydrous sodium sulfate, filtered and concentrated in vacuo. The crude material was purified by flash chromatography (30% ethyl acetate/hexane) to provide benzyl (2S,5R)-2-methyl-5-({5-[4-(methylcarbamoyl)-1,3-oxazol-2-yl]-1-{[2-(trimethylsilyl)ethoxy]methyl}-1H-pyrrolo[2,3-b]pyridin-4-yl}amino)piperidine-1-carboxylate as a pale yellow sticky solid (0.32 g, 63% yield): MS (ES) m/z 619.3 (M+H).

Step 4: Preparation of N-methyl-2-(4-{[(3R,6S)-6-methylpiperidin-3-yl]amino}-1H-pyrrolo[2,3-b]pyridin-5-yl)-1,3-oxazole-4-carboxamide

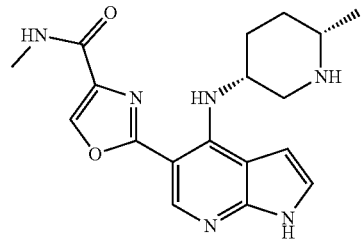

A solution of benzyl (2S,5R)-2-methyl-5-({5-[4-(methylcarbamoyl)-1,3-oxazol-2-yl]-1-{[2-(trimethylsilyl) ethoxy]methyl}-1H-pyrrolo[2,3-b]pyridin-4-yl}amino)piperidine-1-carboxylate (0.32 g, 0.51 mmol) in trifluoroacetic acid (5.0 mL) was stirred at 100° C. for 1 hour. The reaction was cooled to ambient temperature and the mixture was concentrated in vacuo. The obtained residue was dissolved in 1,4-dioxane:aqueous ammonia (5 mL:5 mL, 23% in water) and then stirred at ambient temperature for 16 hours. The reaction mixture was concentrated in vacuo to provide N-methyl-2-(4-{[(3R,6S)-6-methylpiperidin-3-yl]amino}-1H-pyrrolo[2,3-b]pyridin-5-yl)-1,3-oxazole-4-carboxamide as a pale yellow gummy liquid (0.15 g, crude): MS (ES) m/z 355.2 (M+H).

Step 5: Preparation of 2-(4-(((3R,6S)-1-(2-cyanoacetyl)-6-methylpiperidin-3-yl)amino)-1H-pyrrolo[2,3-b]pyridin-5-yl)-N-methyloxazole-4-carboxamide

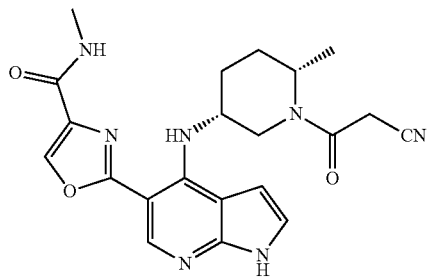 [SMILES: CNC(=O)c1coc(-c2cnc3[nH]ccc3c2N[C@@H]2CC[C@H](C)N(C(=O)CC#N)C2)n1]

A solution of 2-cyanoacetic acid (0.3 g, 0.27 mmol), 1-hydroxy-1,2-dihydropyridin-2-one (0.03 g, 0.27 mmol) and 2-(1H-benzotriazole-1-yl)-1,1,3,3-tetramethylaminium tetrafluoroborate (TBTU) (0.11 g, 0.34 mmol) in N-methylpyrrolidone (3.0 mL) was stirred at ambient temperature for 2 minutes. N-Methyl-2-(4-{[(3R,6S)-6-methylpiperidin-3-yl]amino}-1H-pyrrolo[2,3-b]pyridin-5-yl)-1,3-oxazole-4-carboxamide (0.08 g, 0.23 mmol) was added followed by triethylamine (0.1 mL, 0.70 mmol) and the mixture was stirred at ambient temperature for 16 hours. The reaction mixture was diluted with ethyl acetate, washed with water and brine. The organic layer was dried over anhydrous sodium sulfate, filtered and concentrated in vacuo. The crude was purified by reverse phase purification to obtain 2-(4-(((3R,6S)-1-(2-cyanoacetyl)-6-methylpiperidin-3-yl)amino)-1H-pyrrolo[2,3-b]pyridin-5-yl)-N-methyloxazole-4-carboxamide as a white solid (0.03 g, 30% yield): $^1$H NMR (400 MHz, DMSO-$d_6$, VT at 80° C.) δ 11.46 (br s, 1H), 8.46-8.53 (m, 3H), 8.03 (br s, 1H), 7.21 (s, 1H), 6.68 (s, 1H), 4.40-4.70 (m, 1H), 3.92-4.01 (m, 5H), 2.84 (d, J=4.0 Hz, 3H), 1.80-2.10 (m, 3H), 1.20-1.35 (m, 4H); MS (ES) m/z 422.4 (M+H).

Analytical Conditions:
Mobile phase A: 0.1% NH$_4$OH in H$_2$O
Mobile phase B: MeCN
Column: X-Bridge, C18 19*100*5 micron
Flow rate: 20 mL/min Example 31: Preparation of 2-(4-(((3R,5S)-1-(2-cyanoacetyl)-5-methylpiperidin-3-yl)amino)-1H-pyrrolo[2,3-b]pyridin-5-yl)-N-methyloxazole-4-carboxamide Scheme 30. Preparation of 2-(4-(((3R,5S)-1-(2-cyanoacetyl)-5-methylpiperidin-3-yl)amino)-1H-pyrrolo[2,3-b]pyridin-5-yl)-N-methyloxazole-4-carboxamide

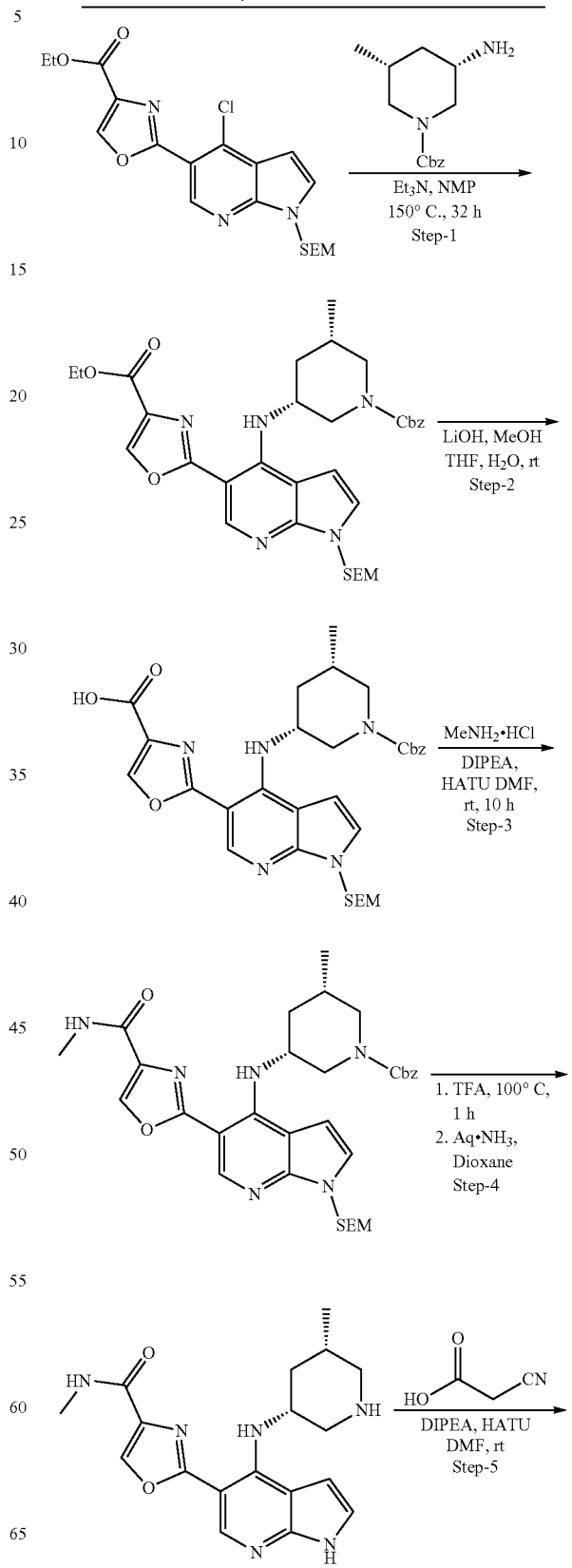

-continued

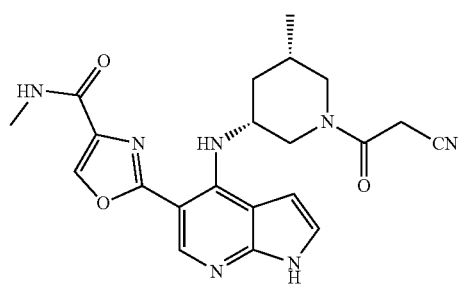 [SMILES: CNC(=O)c1coc(-c2cnc3[nH]ccc3c2N[C@@H]2C[C@H](C)CN(C(=O)CC#N)C2)n1]

Step 1: Preparation of ethyl 2-(4-(((3R,5S)-1-((benzyloxy)carbonyl)-5-methylpiperidin-3-yl) amino)-1-((2-(trimethylsilyl)ethoxy)methyl)-1H-pyrrolo[2,3-b]pyridin-5-yl)oxazole-4-carboxylate

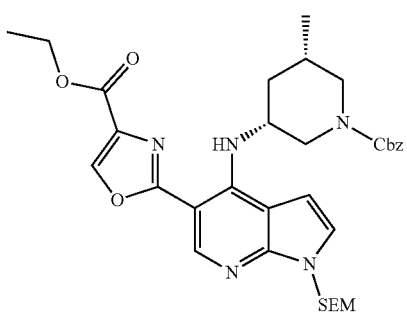 [SMILES: CCOC(=O)c1coc(-c2cnc3c(ccn3COCC[Si](C)(C)C)c2N[C@@H]2C[C@H](C)CN(C(=O)OCc3ccccc3)C2)n1]

A stirred solution of ethyl 2-(4-chloro-1-{[2-(trimethylsilyl)ethoxy]methyl}-1H-pyrrolo[2,3-b]pyridin-5-yl)-1,3-oxazole-4-carboxylate (7.0 g, 16.6 mmol) (obtained from Example 29, Step 1), N-methylpyrrolidone (42 mL), benzyl (3S,5R)-3-amino-5-methylpiperidine-1-carboxylate (5.36 g, 21.6 mmol) and triethylamine (11.7 mL, 82.9 mmol) in a sealed tube was heated to 150° C. for 32 hours. The reaction mixture was cooled to ambient temperature, quenched with water and extracted with ethyl acetate. The organic layer was washed with brine, dried over annhydrous sodium sulfate, filtered and concentrated in vacuo. The crude was purified using flash chromatography (ethyl acetate/hexane) to provide ethyl 2-(4-(((3R,5S)-1-((benzyloxy)carbonyl)-5-methylpiperidin-3-yl)amino)-1-((2-(trimethylsilyl)ethoxy)methyl)-1H-pyrrolo[2,3-b]pyridin-5-yl)oxazole-4-carboxylate as a pale yellow semi solid (5.8 g, 55% yield): MS (ES) m/z 634.3 (M+H).

Step 2: Preparation of 2-(4-(((3R,5S)-1-((benzyloxy)carbonyl)-5-methylpiperidin-3-yl)amino)-1-((2-(trimethylsilyl)ethoxy)methyl)-1H-pyrrolo[2,3-b]pyridin-5-yl)oxazole-4-carboxylic acid

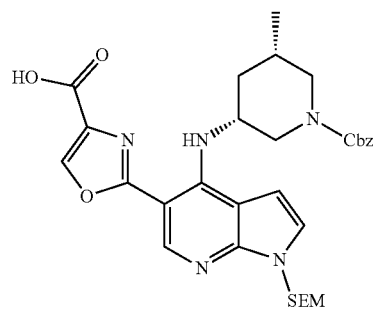 [SMILES: C[C@H]1C[C@@H](Nc2c(-c3nc(C(=O)O)co3)cnc3c2ccn3COCC[Si](C)(C)C)CN(C(=O)OCc2ccccc2)C1]

To a stirred solution of benzyl (3R,5S)-3-({5-[4-(ethoxycarbonyl)-1,3-oxazol-2-yl]-1-{[2-(trimethylsilyl)ethoxy]methyl}-1H-pyrrolo[2,3-b]pyridin-4-yl}amino)-5-methylpiperidine-1-carboxylate (5.8 g, 9.15 mmol) in methanol: tetrahydrofuran (20 mL:20 mL), was added 2M aqueous solution of lithium hydroxide monohydrate (0.8 g, 18.3 mmol) and the mixture was stirred at ambient temperature for 5 hours. Volatiles were removed in vacuo, the residue was dissolved in water and acidified with 10% NaHSO₄ solution and adjusted pH2. The aqueous layer was extracted with dichloromethane, washed with brine, dried over anhydrous sodium sulfate, filtered and concentrated in vacuo to provide 2-(4-(((3R,5S)-1-((benzyloxy)carbonyl)-5-methylpiperidin-3-yl)amino)-1-((2-(trimethylsilyl)ethoxy)methyl)-1H-pyrrolo[2,3-b]pyridin-5-yl)oxazole-4-carboxylic acid as an off-white solid (5.7 g, crude): MS (ES) m/z 606.3 (M+H).

Step 3: Preparation of benzyl (3S,5R)-3-methyl-5-((5-(4-(methylcarbamoyl)oxazol-2-yl)-1-((2-(trimethylsilyl)ethoxy)methyl)-1H-pyrrolo[2,3-b]pyridin-4-yl)amino)piperidine-1-carboxylate

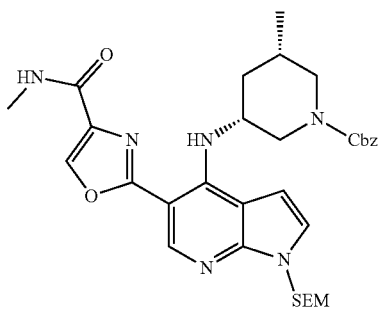 [SMILES: CNC(=O)c1coc(-c2cnc3c(ccn3COCC[Si](C)(C)C)c2N[C@@H]2C[C@H](C)CN(C(=O)OCc3ccccc3)C2)n1]

A solution of 2-(4-{[(3R,5S)-1-[(benzyloxy)carbonyl]-5-methylpiperidin-3-yl]amino}-1-{[2-(trimethylsilyl)ethoxy]methyl}-1H-pyrrolo[2,3-b]pyridin-5-yl)-1,3-oxazole-4-carboxylic acid (5.7 g, 9.41 mmol) and 1-[bis(dimethylamino)methylene]-1H-1,2,3-triazolo[4,5-b]pyridinium 3-oxid hexafluorophosphate (0.29 g, 0.74 mmol) in N,N-dimethylformamide (60 mL) was stirred at ambient temperature for 3 minutes. Methylamine hydrochloride (1.27 g, 18.8 mmol) was added followed by N,N-diisopropylethylamine (8.22 mL, 47.0 mmol) and the mixture was stirred at ambient temperature for 10 hours. The reaction mixture was diluted with ethyl acetate, washed with water and brine. The organic layer was dried over anhydrous sodium sulfate, filtered and concentrated in vacuo. The crude material was purified by flash chromatography (30% ethyl acetate/hexane) to provide benzyl (3S,5R)-3-methyl-5-((5-(4-(methylcarbamoyl)oxazol-2-yl)-1-((2-(trimethylsilyl)ethoxy)methyl)-1H-pyrrolo[2,3-b]pyridin-4-yl)amino)piperidine-1-carboxylate as a pale yellow sticky solid (5.7 g, 97% yield): MS (ES) m/z 619.3 (M+H).

Step 4: Preparation of N-methyl-2-(4-(((3R,5S)-5-methylpiperidin-3-yl)amino)-1H-pyrrolo[2,3-b]pyridin-5-yl)oxazole-4-carboxamide

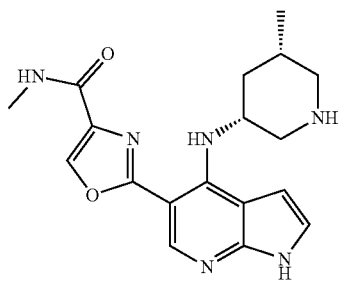 [SMILES: CNC(=O)c1coc(-c2cnc3[nH]ccc3c2N[C@H]2CNC[C@@H](C)C2)n1]

A stirred solution of benzyl (3S,5R)-3-methyl-5-((5-(4-(methylcarbamoyl)oxazol-2-yl)-1-((2-(trimethylsilyl)ethoxy)methyl)-1H-pyrrolo[2,3-b]pyridin-4-yl)amino)piperidine-1-carboxylate (5.7 g, 9.21 mmol) in trifluoroacetic acid (15 mL) was heated at 100° C. for 1 hour in a sealed tube. After cooling, the reaction mixture was concentrated to dryness, the residue was dissolved in 1,4-dioxane:aq ammonia (10 mL:20 mL, 23% in water) and the reaction mixture stirred at ambient temperature for 15 hours. The reaction was concentrated to dryness in vacuo to provide N-methyl-2-(4-(((3R,5S)-5-methylpiperidin-3-yl)amino)-1H-pyrrolo[2,3-b]pyridin-5-yl) oxazole-4-carboxamide as an off-white solid. (9.2 g, crude): MS (ES) m/z 355.4 (M+H).

Step 5: Preparation of 2-(4-(((3R,5S)-1-(2-cyanoacetyl)-5-methylpiperidin-3-yl)amino)-1H-pyrrolo[2,3-b]pyridin-5-yl)-N-methyloxazole-4-carboxamide

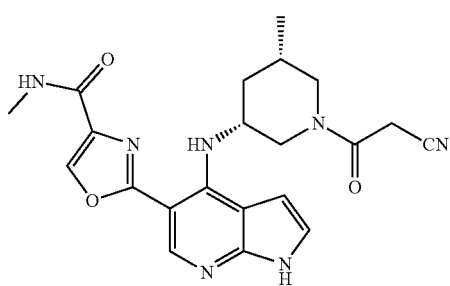 [SMILES: CNC(=O)c1coc(-c2cnc3[nH]ccc3c2N[C@@H]2C[C@H](C)CN(C(=O)CC#N)C2)n1]

A solution of cyanoacetic acid (1.48 g, 17.4 mmol) and 1-[bis(dimethylamino)methylene]-1H-1,2,3-triazolo[4,5-b]pyridinium 3-oxid hexafluorophosphate (11 g, 28.9 mmol) in N,N-dimethylformamide (45 mL) was stirred at ambient temperature for 10 minutes. Then N-methyl-2-(4-(((3R,5S)-5-methylpiperidin-3-yl)amino)-1H-pyrrolo[2,3-b]pyridin-5-yl)oxazole-4-carboxamide (4.1 g, 11.6 mmol) was added followed by N,N-diisopropylethylamine (10 mL, 57.8 mmol) and the resulting mixture was stirred at ambient temperature for 12 hours. The reaction was quenched with ice water and extracted with ethyl acetate and the combined organic portion was washed with water and brine, and dried over anhydrous sodium sulfate. The solution was filtered and concentrated in vacuo. The crude material was purified using reverse phase chromatography to give a white solid (0.67 g, 13% yield): $^1$H NMR (400 MHz, DMSO-$d_6$, VT at 90° C.) δ 11.40 (s, 1H), 8.54 (s, 1H), 8.47-8.43 (m, 2H), 7.85 (br s, 1H), 7.21 (s, 1H), 6.72 (s, 1H), 4.80 (br s, 1H), 4.15 (s, 1H), 3.98 (s, 2H), 3.75 (br s, 1H), 2.85 (s, 3H), 2.65 (s, 1H), 2.30-2.27 (m, 2H), 1.86 (br s, 1H), 1.41 (d, J=11.2 Hz, 1H), 0.95 (d, J=5.6 Hz, 3H); MS (ES) m/z 422.3 (M+H).

Analytical Conditions:

Column: X-BridgeC-18 (250 mm×4.6 mm×5 mic)

Mobile phase (A): 0.1% Ammonia in water

Mobile phase (B): MeCN

Flow rate: 1.0 mL/min

Example 32: Preparation of 2-(4-(((3S,5R)-1-(2-cyanoacetyl)-5-methylpiperidin-3-yl)amino)-1H-pyrrolo[2,3-b]pyridin-5-yl)-N-methyloxazole-4-carboxamide

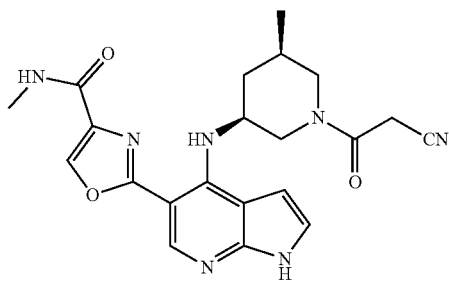 [SMILES: CNC(=O)c1coc(-c2cnc3[nH]ccc3c2N[C@H]2C[C@@H](C)CN(C(=O)CC#N)C2)n1]

2-(4-(((3S,5R)-1-(2-cyanoacetyl)-5-methylpiperidin-3-yl)amino)-1H-pyrrolo[2,3-b]pyridin-5-yl)-N-methyloxazole-4-carboxamide was prepared following the same method as Example 31 and using benzyl (3R,5S)-3-amino-5-methylpiperidine-1-carboxylate in Step 1 to give a white solid (0.6 g, 11% yield): $^1$H NMR (400 MHz, DMSO-$d_6$, VT at 80° C.) δ 11.45 (s, 1H), 8.45-8.43 (m, 3H), 7.91 (br s, 1H), 7.21 (s, 1H), 6.72 (s, 1H), 4.80 (br s, 1H), 4.15 (s, 1H), 3.98 (s, 2H), 3.75 (br s, 1H), 2.85 (s, 3H), 2.65 (s, 1H), 2.30-2.27 (m, 2H), 1.86 (br s, 1H), 1.41 (d, J=11.2 Hz, 1H), 0.95 (d, J=5.6 Hz, 3H); MS (ES) m/z 422.3 (M+H).

Analytical Conditions:

Column: X-BridgeC-18 (250 mm×4.6 mm×5 mic)

Mobile phase (A): 0.1% Ammonia in water

Mobile phase (B): MeCN

Flow rate: 1.0 mL/min

Example 33: Preparation of (R)-2-(4-((1-(2-cyanoacetyl)piperidin-3-yl)amino)-1H-pyrrolo[2,3-b]pyridin-5-yl)-N-methyloxazole-4-carboxamide

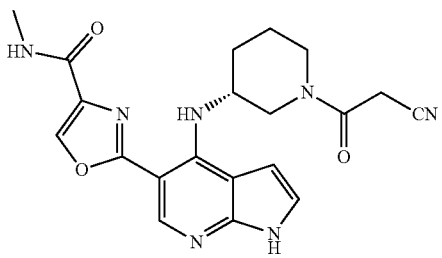 [SMILES: CNC(=O)c1coc(-c2cnc3[nH]ccc3c2N[C@@H]2CCCN(C(=O)CC#N)C2)n1]

Scheme 31. Preparation of (R)-2-(4-((1-(2-cyanoacetyl)piperidin-3-yl)amino)-1H-pyrrolo[2,3-b]pyridin-5-yl)-N-methyloxazole-4-carboxamide

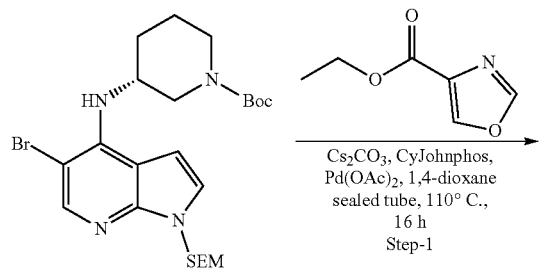

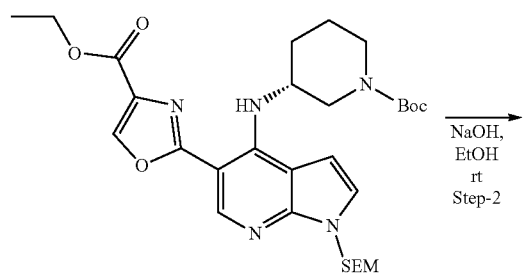

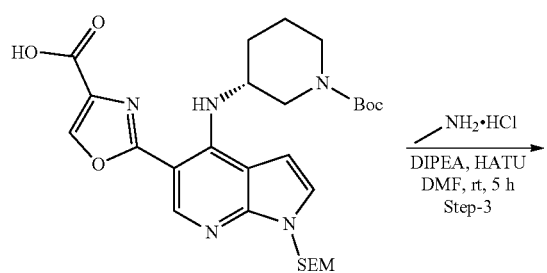

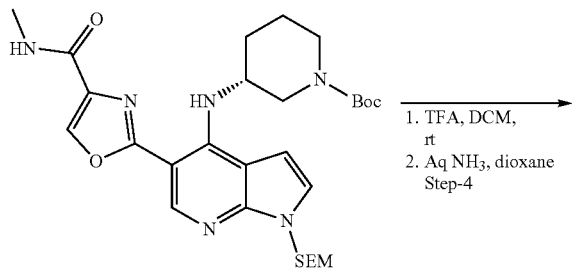

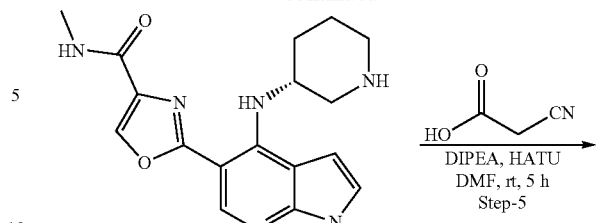

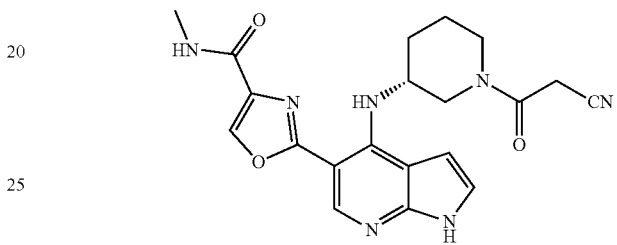

Step 1: Preparation of ethyl (R)-2-(4-((1-(tert-butoxycarbonyl)piperidin-3-yl)amino)-1-((2-(trimethylsilyl)ethoxy)methyl)-1H-pyrrolo[2,3-b]pyridin-5-yl)oxazole-4-carboxylate

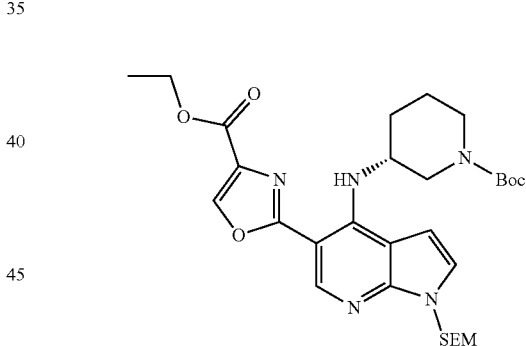

To a stirred solution of tert-butyl (R)-3-((5-bromo-1-((2-(trimethylsilyl)ethoxy)methyl)-1H-pyrrolo[2,3-b]pyridin-4-yl)amino)piperidine-1-carboxylate (1.2 g, 2.28 mmol) and ethyl oxazole-4-carboxylate (0.38 g, 2.74 mmol) in 1,4-dioxane (18 mL), was added palladium acetate (0.03 g, 0.12 mmol), CyJohnphos (0.08 g, 0.23 mmol) and cesium carbonate (1.48 g, 4.56 mmol) and the resulting mixture was heated in a sealed tube at 110° C. for 16 hours under a nitrogen atmosphere. The reaction mixture was cooled to ambient temperature, filtered through celite, washed with ethyl acetate and the filtrate concentrated in vacuo. The crude material was purified using flash chromatography (40% ethyl acetate/hexane) to provide ethyl (R)-2-(4-((1-(tert-butoxycarbonyl)piperidin-3-yl)amino)-1-((2-(trimethylsilyl)ethoxy)methyl)-1H-pyrrolo[2,3-b]pyridin-5-yl)oxazole-4-carboxylate as an off-white solid (1.1 g, 41% yield): MS (ES) m/z 585.9 (M+H).

Step 2: Preparation of (R)-4-((1-(tert-butoxycarbonyl)piperidin-3-yl)amino)-1-((2-(trimethylsilyl)ethoxy)methyl)-1H-pyrrolo[2,3-b]pyridine-5-carboxylic acid

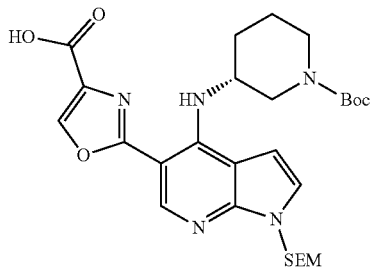

To a stirred solution of ethyl (R)-2-(4-((1-(tert-butoxycarbonyl)piperidin-3-yl)amino)-1-((2-(trimethylsilyl) ethoxy)methyl)-1H-pyrrolo[2,3-b]pyridin-5-yl)oxazole-4-carboxylate (0.5 g, 0.85 mmol) in ethanol (12 mL) was added a 2M aqueous solution of sodium hydroxide (0.1 g, 2.56 mmol) and the resulting mixture was stirred at ambient temperature for 3 hours. Volatiles were removed in vacuo, the residue was dissolved in water and acidified with 10% solution of potassium bisulphate and adjusted to pH3. The aqueous layer was extracted with dichloromethane and washed with brine. The organic layer was dried over anhydrous magnesium sulfate, filtered and concentrated in vacuo to provide (R)-4-((1-(tert-butoxycarbonyl)piperidin-3-yl)amino)-1-((2-(trimethylsilyl)ethoxy)methyl)-1H-pyrrolo[2,3-b]pyridine-5-carboxylic acid as an off-white solid. (0.3 g, 64% yield): MS (ES) m/z 557.9 (M+H).

Step 3: Preparation of tert-butyl (R)-3-((5-(4-(methylcarbamoyl)oxazol-2-yl)-1-((2-(trimethylsilyl)ethoxy)methyl)-1H-pyrrolo[2,3-b]pyridin-4-yl)amino)piperidine-1-carboxylate

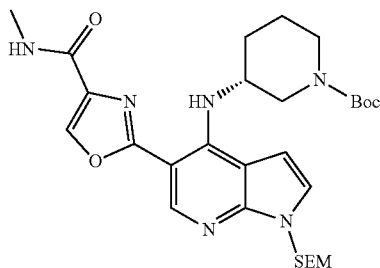 [SMILES: CNC(=O)c1coc(-c2cnc3c(ccn3COCC[Si](C)(C)C)c2N[C@@H]2CCCN(C(=O)OC(C)(C)C)C2)n1]

A solution of (R)-2-(4-((1-(tert-butoxycarbonyl)piperidin-3-yl)amino)-1-((2-(trimethylsilyl)ethoxy)methyl)-1H-pyrrolo[2,3-b]pyridin-5-yl)oxazole-4-carboxylic acid (0.27 g, 0.48 mmol) and 1-[bis(dimethylamino)methylene]-1H-1,2,3-triazolo[4,5-b]pyridinium 3-oxid hexafluorophosphate (0.24 g, 0.63 mmol) in N,N-dimethylformamide (10 mL) was stirred for 5 minutes. Methylamine hydrochloride (0.05 g, 0.726 mmol) was added followed by N,N-diisopropylethylamine (0.25 mL, 1.45 mmol) and the resulting mixture was stirred at ambient temperature for 3 hours. The reaction was quenched with ice water, extracted with ethyl acetate, and the organic portion washed with water and brine, and then dried over anhydrous sodium sulfate. The solution was filtered and concentrated in vacuo. The crude material was purified using flash chromatography (5% methanol/dichloromethane) to provide tert-butyl (R)-3-((5-(4-(methylcarbamoyl)oxazol-2-yl)-1-((2-(trimethylsilyl)ethoxy)methyl)-1H-pyrrolo[2,3-b]pyridin-4-yl)amino)piperidine-1-carboxylate as a yellow oil (0.27 g, 99% yield): MS (ES) m/z 571.3 (M+H).

Step 4: Preparation of (R)-N-methyl-2-(4-(piperidin-3-ylamino)-1H-pyrrolo[2,3-b]pyridin-5-yl)oxazole-4-carboxamide

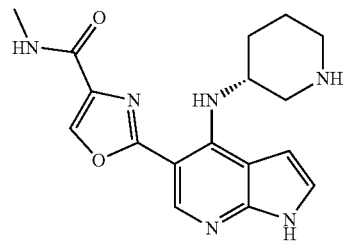 [SMILES: CNC(=O)c1coc(-c2cnc3[nH]ccc3c2N[C@@H]2CCCNC2)n1]

A solution of tert-butyl (R)-3-((5-(4-(methylcarbamoyl)oxazol-2-yl)-1-((2-(trimethylsilyl)ethoxy)methyl)-1H-pyrrolo[2,3-b]pyridin-4-yl)amino)piperidine-1-carboxylate (0.30 g, 0.52 mmol) in dichloromethane:trifluoroacetic acid (5 mL:4 mL) was stirred at ambient temperature for 3 hours. The reaction mixture was concentrated in vacuo and the residue was dissolved in 1,4-dioxane:aqueous ammonia (4 mL:5 mL, 23% in water). The reaction mixture was stirred at ambient temperature for 16 hours. The reaction was concentrated in vacuo to provide a residue which was dissolved in 5% methanol/dichloromethane. The organic layer was washed with water, brine and dried over anhydrous sodium sulfate. The solution was filtered and concentrated in vacuo to provide (R)-N-methyl-2-(4-(piperidin-3-ylamino)-1H-pyrrolo[2,3-b]pyridin-5-yl)oxazole-4-carboxamide as a gummy liquid (0.12 g, 70% yield): MS (ES) m/z 341.2 (M+H).

Step 5: Preparation of (R)-2-(4-((1-(2-cyanoacetyl)piperidin-3-yl)amino)-1H-pyrrolo[2,3-b]pyridin-5-yl)-N-methyloxazole-4-carboxamide

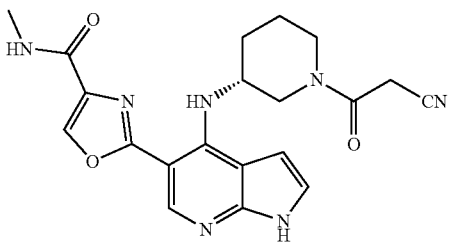 [SMILES: CNC(=O)c1coc(-c2cnc3[nH]ccc3c2N[C@@H]2CCCN(C(=O)CC#N)C2)n1]

A solution of cyanoacetic acid (0.05 g, 0.55 mmol) and 1-[bis(dimethylamino)methylene]-1H-1,2,3-triazolo[4,5-b]pyridinium 3-oxid hexafluorophosphate (0.17 g, 0.45 mmol) in N,N-dimethylformamide (5 mL) was stirred for 10 minutes. (R)-N-Methyl-2-(4-(piperidin-3-ylamino)-1H-pyrrolo[2,3-b]pyridin-5-yl)oxazole-4-carboxamide (0.12 g, 0.35 mmol) was added followed by N,N-diisopropylethylamine (0.18 mL, 1.05 mmol) and the resulting mixture was stirred at ambient temperature for 6 hours. The reaction was quenched with ice water and extracted with ethyl acetate. The organic layer was washed with brine, dried over anhydrous sodium sulfate, filtered and concentrated in vacuo. The crude material was purified by reverse phase chromatography to provide (R)-2-(4-((1-(2-cyanoacetyl)piperidin-3-yl)amino)-1H-pyrrolo[2,3-b]pyridin-5-yl)-N-methyloxazole-4-carboxamide as a white solid (0.01 g, 8% yield): $^1$H NMR (400 MHz, DMSO-$d_6$) δ 11.68-11.64 (br s, 1H), 8.63 (d, J=7.2 Hz, 1H), 8.55-8.52 (m, 2H), 8.13 (s, 1H), 7.24 (s, 1H), 6.72 (s, 1H), 4.38 (br s, 1H), 4.22-4.19 (m, 1H), 4.08 (s, 1H), 3.96 (s, 1H), 3.82-3.77 (m, 1H), 3.48 (s, 1H), 3.36 (s, 1H), 2.83 (d, J=3.6 Hz, 3H), 2.07 (br s, 2H), 1.85 (br s, 2H); MS (ES) m/z 408.5 (M+H).

Analytical Conditions:

Column: X-Bridge C-18 (250 mm×4.6 mm×5 mic)

Mobile phase (A): 0.1% Ammonia in water

Mobile phase (B): MeCN

Flow rate: 1.0 mL/min.

Example 34: Preparation of (R)-2-(4-((1-(2-cyanoacetyl)piperidin-3-yl)amino)-1H-pyrrolo[2,3-b]pyridin-5-yl)-N,N-dimethyl-oxazole-4-carboxamide

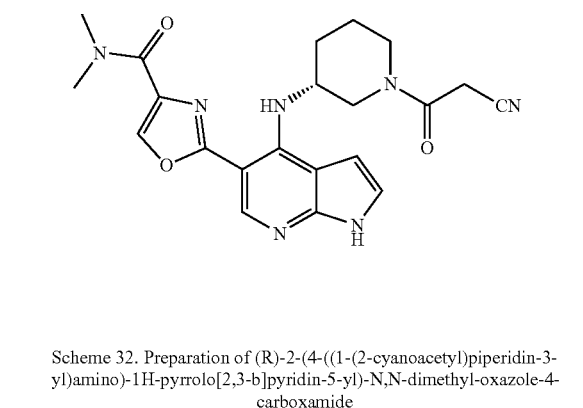

Scheme 32. Preparation of (R)-2-(4-((1-(2-cyanoacetyl)piperidin-3-yl)amino)-1H-pyrrolo[2,3-b]pyridin-5-yl)-N,N-dimethyl-oxazole-4-carboxamide

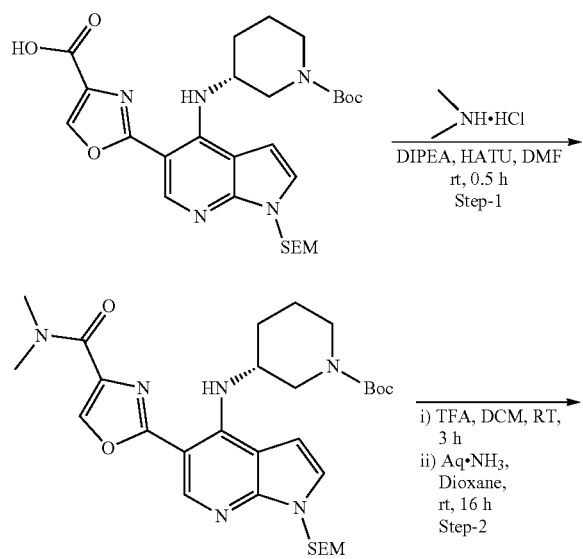

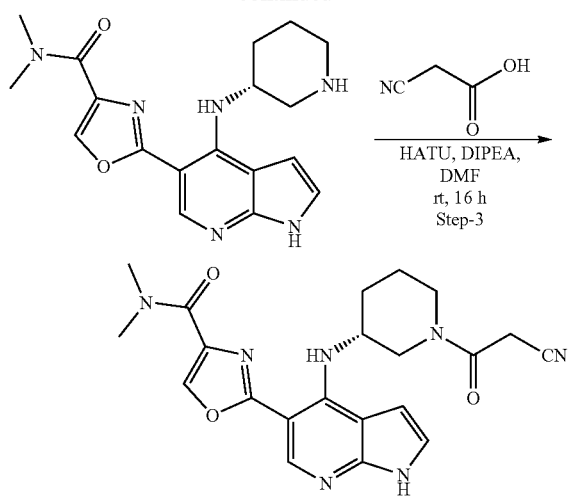

Step 1: Preparation of tert-butyl (R)-3-((5-(4-(dimethylcarbamoyl)oxazol-2-yl)-1-((2-(trimethylsilyl)ethoxy)methyl)-1H-pyrrolo[2,3-b]pyridin-4-yl)amino)piperidine-1-carboxylate To a stirred solution of (R)-2-(4-((1-(tert-butoxycarbonyl)piperidin-3-yl)amino)-1-((2-(trimethylsilyl)ethoxy)methyl)-1H-pyrrolo[2,3-b]pyridin-5-yl)oxazole-4-carboxylic acid (0.25 g, 0.44 mmol) (obtained from Example 32, Step 2) and 1-[bis(dimethylamino)methylene]-1H-1,2,3-triazolo[4,5-b]pyridinium 3-oxid hexafluorophosphate (0.22 g, 0.58 mmol) in N,N-dimethylformamide (10 mL), was added dimethylamine hydrochloride (0.05 g, 0.67 mmol) followed by N,N-diisopropylethylamine (0.23 ml, 1.34 mmol) and the mixture stirred at ambient temperature for 30 minutes. The reaction mixture was diluted with water and extracted with ethyl acetate. The organic layer was washed with brine, dried over sodium sulfate, filtered and concentrated in vacuo. The crude was purified by column chromatography (50% ethyl acetate/hexane) to provide the titled product as yellow oil (0.23 g, 88% yield): MS (ES) m/z 585.3 (M+H).

Step 2: Preparation of (R)-N,N-dimethyl-2-(4-(piperidin-3-ylamino)-1H-pyrrolo[2,3-b]pyridin-5-yl)oxazole-4-carboxamide

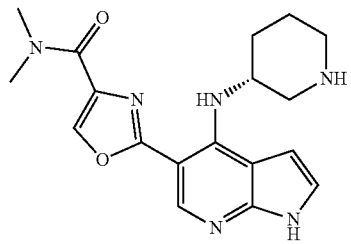 [SMILES: CN(C)C(=O)c1coc(-c2cnc3[nH]ccc3c2N[C@@H]2CCCNC2)n1]

A solution of tert-butyl (R)-3-((5-(4-(dimethylcarbamoyl)oxazol-2-yl)-1-((2-(trimethylsilyl)ethoxy)methyl)-1H-pyrrolo[2,3-b]pyridin-4-yl)amino)piperidine-1-carboxylate (0.23 g, 0.39 mmol) in dichloromethane:trifluoroacetic acid (3 mL:3 mL) was stirred at ambient temperature for 3 hours. The reaction mixture was concentrated in vacuo, the residue was dissolved in 1,4-dioxane:aqueous ammonia (3 mL:3 mL, 23% in water) and stirred at ambient temperature for 16 hours. The reaction mixture was concentrated in vacuo to provide (R)-N,N-dimethyl-2-(4-(piperidin-3-ylamino)-1H-pyrrolo[2,3-b]pyridin-5-yl)oxazole-4-carboxamide (0.1 g crude): MS (ES) m/z 355.2 (M+H).

Step 3: Preparation of (R)-2-(4-((1-(2-cyanoacetyl)piperidin-3-yl)amino)-1H-pyrrolo[2,3-b]pyridin-5-yl)-N,N-dimethyl-oxazole-4-carboxamide

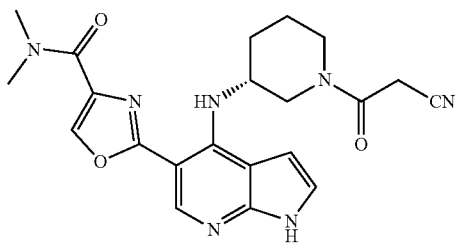 [SMILES: CN(C)C(=O)c1coc(-c2cnc3[nH]ccc3c2N[C@@H]2CCCN(C(=O)CC#N)C2)n1]

To a stirred solution of cyanoacetic acid (0.03 g, 0.33 mmol), 1-hydroxy-2-pyridone (0.03 g, 0.27 mmol) and 2-(1H-benzotriazole-1-yl)-1,1,3,3-tetramethylaminium tetrafluoroborate (0.09 g, 0.27 mmol) in N-methylpyrrolidone (5 mL) was added (R)-2-(4-(piperidin-3-ylamino)-1H-pyrrolo[2,3-b]pyridin-5-yl)oxazole-4-carboxamide (0.08 g, 0.22 mmol) followed by triethylamine (0.1 mL, 0.7 mmol) and the resulting mixture was stirred at ambient temperature for 2 hours. The reaction mixture was diluted with water and extracted with ethyl acetate. The organic layer was washed with brine, dried over anhydrous sodium sulfate, filtered and concentrated in vacuo. The crude was purified using flash chromatography (10% methanol/hexane) to provide (R)-2-(4-((1-(2-cyanoacetyl)piperidin-3-yl)amino)-1H-pyrrolo[2,3-b]pyridin-5-yl)-N,N-dimethyloxazole-4-carboxamide as an off-white solid (0.05 g, 52% yield): $^1$H NMR (400 MHz, DMSO-$d_6$) δ 11.4 (br s, 1H), 8.73 (br s, 1H), 8.55 (s, 1H), 8.42 (s, 1H), 7.22 (s, 1H), 6.72 (s, 1H), 4.20 (m, 2H), 3.51-3.99 (m, 4H), 3.09-3.29 (m, 6H), 1.67-2.15 (m, 5H); MS (ES) m/z 422.1 (M+H).

Example 35: Preparation of (R)-2-(4-((1-(2-cyanoacetyl)piperidin-3-yl)amino)-1H-pyrrolo[2,3-b]pyridin-5-yl)-N-methylthiazole-4-carboxamide

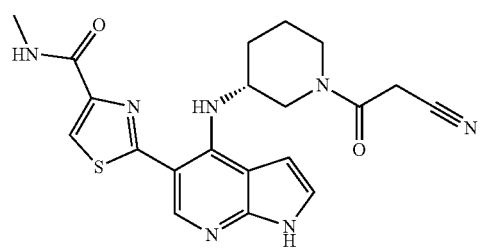 [SMILES: CNC(=O)c1csc(-c2cnc3[nH]ccc3c2N[C@@H]2CCCN(C(=O)CC#N)C2)n1]

Scheme 33. Preparation of (R)-2-(4-((1-(2-cyanoacetyl)piperidin-3-yl)amino)-1H-pyrrolo[2,3-b]pyridin-5-yl)-N-methylthiazole-4-carboxamide

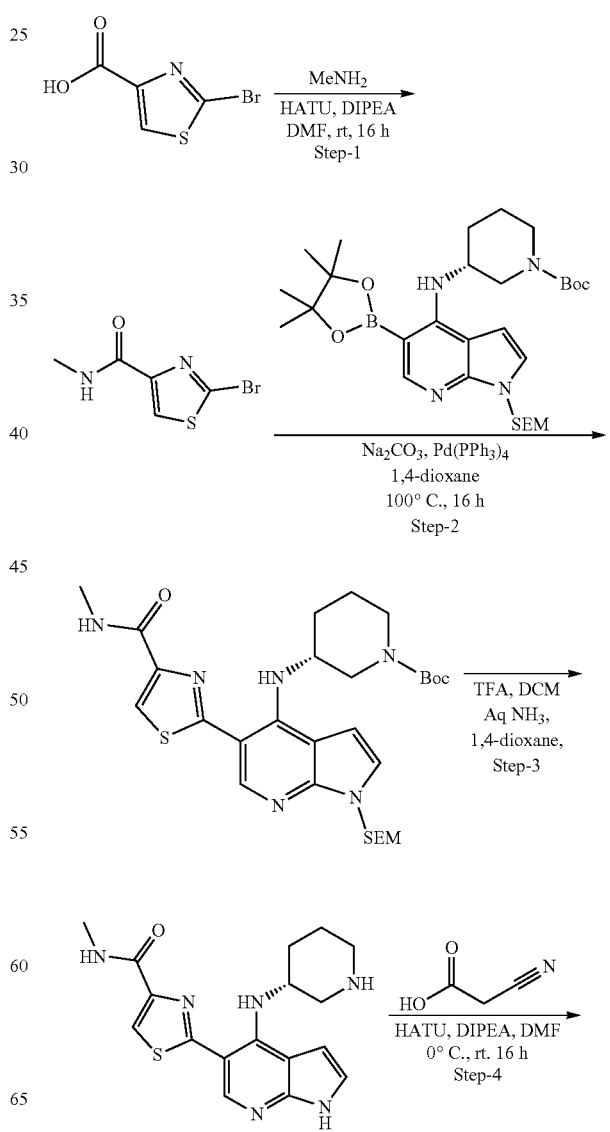

-continued

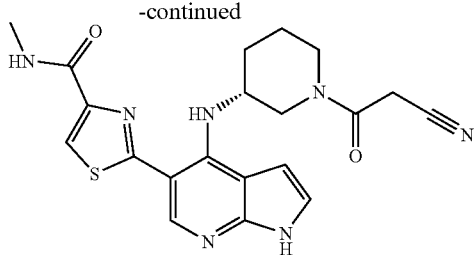

Step 1: Preparation of 2-bromo-N-methylthiazole-4-carboxamide

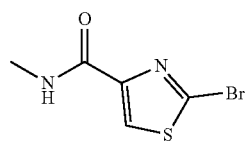

To a stirred solution of 2-bromothiazole-4-carboxylic acid (1.0 g, 4.8 mmol) and 1-[bis(dimethylamino)-methylene]-1H-1,2,3-triazolo[4,5-b]pyridinium 3-oxid hexafluorophosphate (4.5 g, 12.0 mmol) in N,N-dimethylformamide (20 mL) was added methylamine (3.6 mL, 7.2 mmol, 2M in tetrahydrofuran) followed by diisopropylethylamine (4.2 mL, 24.0 mmol) and the resulting mixture was stirred at ambient temperature for 16 hours. The reaction mixture was quenched with ice cold water and extracted twice with ethyl acetate. The organic layer was washed with brine solution, dried over anhydrous sodium sulfate and concentrated in vacuo. The crude material was purified by flash chromatography (13% ethyl acetate/hexane) to provide 2-bromo-N-methylthiazole-4-carboxamide as a white solid (0.7 g, 70% yield): MS (ES) m/z 221.0 (M+H).

Step 2: Preparation of tert-butyl (R)-3-((5-(4-(methylcarbamoyl)thiazol-2-yl)-1-((2-(trimethylsilyl)ethoxy)methyl)-1H-pyrrolo[2,3-b]pyridin-4-yl)amino)piperidine-1-carboxylate

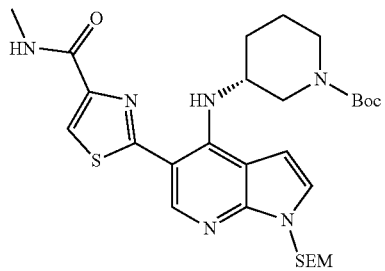 [SMILES: CNC(=O)c1csc(-c2cnc3c(ccn3COCC[Si](C)(C)C)c2N[C@@H]2CCCN(C(=O)OC(C)(C)C)C2)n1]

To a stirred solution of 2-bromo-N-methylthiazole-4-carboxamide (0.7 g, 1.22 mmol), tert-butyl (R)-3-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate (0.4 g, 1.83 mmol, intermediate 7) in 1,4-dioxane (25 mL) was added tetrakis(triphenylphosphine) palladium(0) (0.14 g, 0.12 mmol) and aqueous solution of 2M sodium carbonate (0.39 g, 3.66 mmol) and the reaction mixture stirred at 100° C. for 16 hours. After cooling, the reaction mixture was diluted with ethyl acetate and filtered through celite. The filtrate was washed with water, brine, dried over anhydrous sodium sulfate, filtered and concentrated in vacuo. The crude material was purified by flash chromatography (35% ethyl acetate/hexane) to provide tert-butyl (R)-3-((5-(4-(methylcarbamoyl)thiazol-2-yl)-1-((2-(trimethylsilyl)ethoxy)methyl)-1H-pyrrolo[2,3-b]pyridin-4-yl)amino)piperidine-1-carboxylate as a pale brown liquid (0.55 g, 79% yield): MS (ES) m/z 587.6 (M+H).

Step 3: Preparation of (R)-N-methyl-2-(4-(piperidin-3-ylamino)-1H-pyrrolo[2,3-b]pyridin-5-yl)thiazole-4-carboxamide

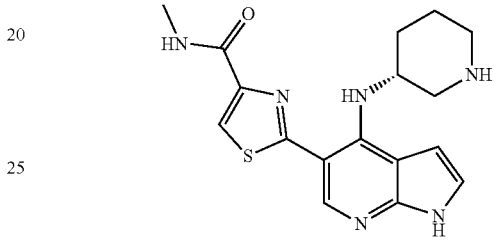

A solution of tert-butyl (R)-3-((5-(4-(methylcarbamoyl)thiazol-2-yl)-1-((2-(trimethylsilyl)ethoxy)methyl)-1H-pyrrolo[2,3-b]pyridin-4-yl)amino)piperidine-1-carboxylate (0.55 g, 0.94 mmol) in dichloromethane:trifluoroacetic acid (2.0 mL:3.0 mL) was stirred at ambient temperature for 3 hours. The reaction mixture was concentrated in vacuo, the obtained residue was dissolved in 1,4-dioxane:aqueous ammonia (2.0 mL:5.0 mL, 23% in water) and was then stirred at ambient temperature for 16 hours. The reaction mixture was concentrated in vacuo to provide (R)-N-methyl-2-(4-(piperidin-3-ylamino)-1H-pyrrolo[2,3-b]pyridin-5-yl)thiazole-4-carboxamide as a yellow liquid (0.36 g, crude): MS (ES) m/z 357.2 (M+H).

Step 4: Preparation of (R)-2-(4-((1-(2-cyanoacetyl)piperidin-3-yl)amino)-1H-pyrrolo[2,3-b]pyridin-5-yl)-N-methylthiazole-4-carboxamide

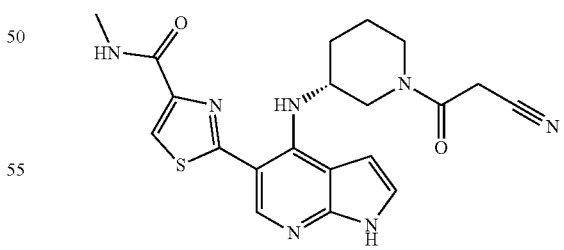

A solution of cyanoacetic acid (0.1 g, 1.2 mmol) and 1-[bis(dimethylamino)methylene]-1H-1,2,3-triazolo[4,5-b]pyridinium 3-oxid hexafluorophosphate (0.9 g, 2.5 mmol) in N,N-dimethylformamide (10 mL) was stirred for 3 minutes. At that time (R)-N-methyl-2-(4-(piperidin-3-ylamino)-1H-pyrrolo[2,3-b]pyridin-5-yl)thiazole-4-carboxamide (0.36 g, 1.0 mmol) was added followed by N,N-diisopropylethylamine (0.72 mL, 5.0 mmol) and the mixture stirred at ambient temperature for 16 hours. The reaction mixture was quenched with ice cold water and extracted with ethyl acetate. The organic layer was washed with brine solution, dried over anhydrous sodium sulfate and concentrated in vacuo. The crude material was purified by reverse phase chromatography to provide (R)-2-(4-((1-(2-cyanoacetyl)piperidin-3-yl)amino)-1H-pyrrolo[2,3-b]pyridin-5-yl)-N-methylthiazole-4-carboxamide as an off-white solid (0.01 g, 3% yield): $^1$HNMR (400 MHz, DMSO-$d_6$) δ 11.65 (br s, 1H), 9.32 (d, J=7.6 Hz, 1H), 8.37 (s, 1H), 8.30 (s, 1H), 8.09 (s, 1H), 7.23 (s, 1H), 6.72 (d, J=8.8 Hz, 1H), 4.27 (s, 1H), 4.11 (s, 1H), 4.05 (s, 1H), 3.89 (s, 1H), 3.78 (d, J=12.4 Hz, 1H), 3.64 (s, 1H), 3.51 (s, 1H), 3.20-3.23 (m, 3H), 3.00 (s, 1H), 2.83 (s, 3H); MS (ES) m/z 424.2 (M+H).

Analytical Conditions:

Column: X Bridge C18 (100 mm×4.6 mm×3.5 μm)

Mobile phase (A): 0.1% Ammonia in water

Mobile phase (B): MeCN

Flow rate: 0.8 mL/min.

Example 36: Preparation of (R)-3-(3-((5-(5-methyloxazol-2-yl)-1H-pyrrolo[2,3-b]pyridin-4-yl)amino)piperidin-1-yl)-3-oxopropanenitrile

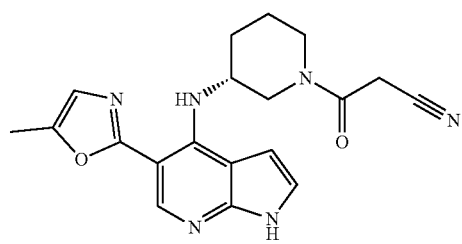 [SMILES: Cc1cnc(-c2cnc3[nH]ccc3c2N[C@@H]2CCCN(C(=O)CC#N)C2)o1]

Scheme 34. Preparation of (R)-3-(3-((5-(5-methyloxazol-2-yl)-1H-pyrrolo[2,3-b]pyridin-4-yl)amino)piperidin-1-yl)-3-oxopropanenitrile

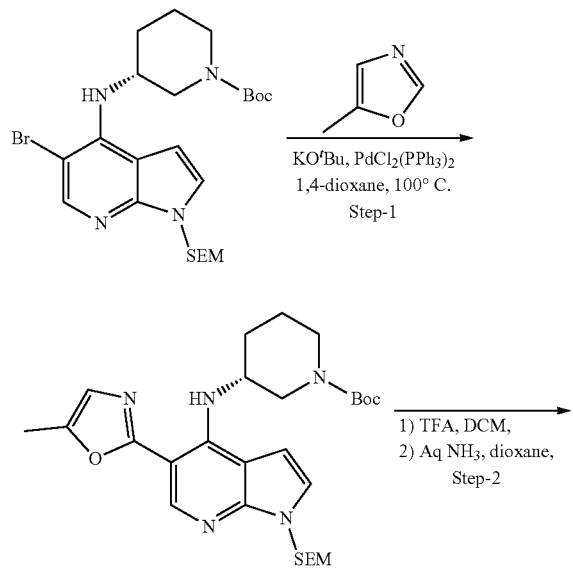

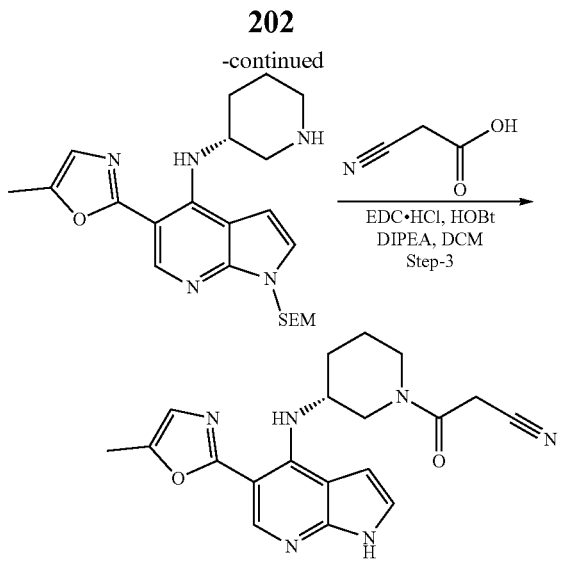

Step 1: Preparation of tert-butyl (R)-3-((5-(5-methyloxazol-2-yl)-1-((2-(trimethylsilyl)ethoxy)methyl)-1H-pyrrolo[2,3-b]pyridin-4-yl)amino)piperidine-1-carboxylate A mixture of tert-butyl (R)-3-((5-bromo-1-((2-(trimethylsilyl)ethoxy)methyl)-1H-pyrrolo[2,3-b]pyridin-4-yl)amino)piperidine-1-carboxylate (0.30 g, 5.57 mmol), potassium tert-butoxide (0.13 g, 1.14 mmol) bis(triphenylphosphine) palladium(II) dichloride (0.02 g, 0.03 mmol) and 5-methyloxazole (0.09 g, 1.14 mmol) in 1,4-dioxane (5 mL) was heated in a sealed tube at 100° C. under nitrogen atmosphere. After 6 hours the reaction was cooled to ambient temperature, diluted with water and extracted with ethyl acetate. The organic layer was washed with brine, dried over anhydrous sodium sulfate, filtered and concentrated in vacuo. The crude material was purified by flash chromatography (40% ethyl acetate/hexane) to provide tert-butyl (R)-3-((5-(5-methyloxazol-2-yl)-1-((2-(trimethylsilyl)ethoxy)methyl)-1H-pyrrolo[2,3-b]pyridin-4-yl)amino)piperidine-1-carboxylate as a thick yellow oil (0.2 g, 66% yield): MS (ES) m/z 528.0 (M+H).

Step 2: Preparation of (R)-5-(5-methyloxazol-2-yl)-N-(piperidin-3-yl)-1H-pyrrolo[2,3-b]pyridin-4-amine

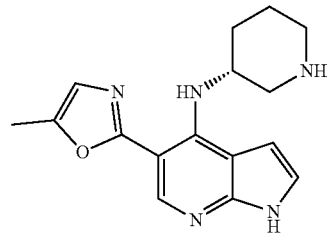 [SMILES: Cc1cnc(-c2cnc3[nH]ccc3c2N[C@@H]2CCCNC2)o1]

A solution of tert-butyl (R)-3-((5-(5-methyloxazol-2-yl)-1-((2-(trimethylsilyl)ethoxy)methyl)-1H-pyrrolo[2,3-b]pyridin-4-yl)amino)piperidine-1-carboxylate (0.20 g, 0.37 mmol) in dichloromethane:trifluoroacetic acid (2.0 mL:2.0 mL) was stirred at ambient temperature for 3 hours. The reaction mixture was concentrated in vacuo, the residue was dissolved in 1,4-dioxane:aqueous ammonia (3.0 mL:3.0 mL, 23% in water) and stirred at ambient temperature for 16 hours. The reaction was concentrated in vacuo to provide (R)-5-(5-methyloxazol-2-yl)-N-(piperidin-3-yl)-1H-pyrrolo[2,3-b]pyridin-4-amine as a yellow solid (0.17 g, crude): MS (ES) m/z 298.2 (M+H).

Step 3: Preparation of (R)-3-(3-((5-(5-methyloxazol-2-yl)-1H-pyrrolo[2,3-b]pyridin-4-yl)amino)piperidin-1-yl)-3-oxopropanenitrile

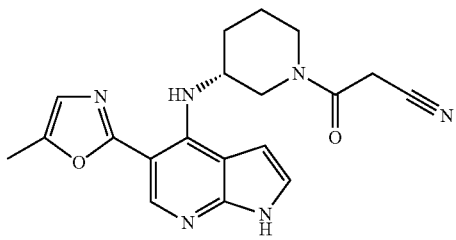 [SMILES: Cc1cnc(-c2cnc3[nH]ccc3c2N[C@@H]2CCCN(C(=O)CC#N)C2)o1]

A solution of cyanoacetic acid (0.02 g, 0.24 mmol), N-(3-dimethylaminopropyl)-N'-ethylcarbodiimide hydrochloride (0.58 g, 0.30 mmol), 1-hydroxybenzotriazole (0.03 g, 0.22 mmol) and N,N-diisopropylethylamine (0.1 mL, 0.6 mmol) in dichloromethane (5 mL) was stirred at ambient temperature for 5 minutes. Then (R)-5-(5-methyloxazol-2-yl)-N-(piperidin-3-yl)-1H-pyrrolo[2,3-b]pyridin-4-amine (0.06 g, 0.20 mmol) was added and the resulting mixture was stirred at ambient temperature for 18 hours. The reaction mixture was quenched with water and extracted with dichloromethane. The organic layer was washed with water, brine, dried over anhydrous sodium sulfate, filtered and concentrated in vacuo. The crude material was purified by flash chromatography (5% methanol/dichloromethane) to provide (R)-3-(3-((5-(5-methyloxazol-2-yl)-1H-pyrrolo[2,3-b]pyridin-4-yl)amino)piperidin-1-yl)-3-oxopropanenitrile an off-white solid (0.01 g, 27% yield): $^1$H NMR (400 MHz, DMSO-d$_6$, VT at 100° C.) 11.38 (br s, J=9.2 Hz, 1H), 8.98 (br s, 1H), 8.50 (s, 1H), 7.19 (s, 1H), 6.91 (s, 1H), 6.66 (s, 1H), 3.90-4.40 (m, 3H), 3.52-3.91 (m, 1H), 3.20-3.40 (m, 2H), 2.31 (s, 3H), 1.95-2.10 (m, 2H), 1.50-1.90 (m, 3H); MS (ES) m/z 365.1 (M+H).

Example 37: Preparation of (R)-3-(3-((5-(5-methyloxazol-2-yl)-1H-pyrrolo[2,3-b]pyridin-4-yl)amino)piperidin-1-yl)propanenitrile

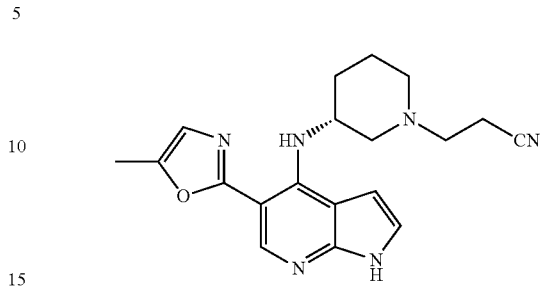

Scheme 35. Preparation of (R)-3-(3-((5-(5-methyloxazol-2-yl)-1H-pyrrolo[2,3-b]pyridin-4-yl)amino)piperidin-1-yl)propanenitrile

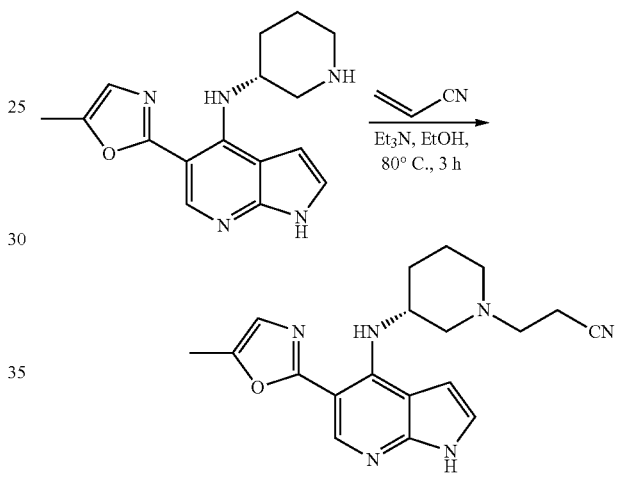

Preparation of (R)-3-(3-((5-(5-methyloxazol-2-yl)-1H-pyrrolo[2,3-b]pyridin-4-yl)amino)piperidin-1-yl)propanenitrile

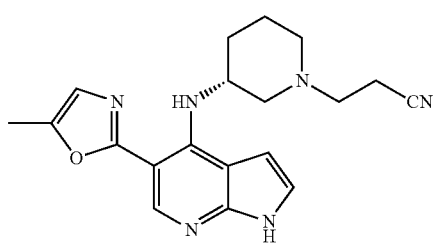 [SMILES: Cc1cnc(-c2cnc3[nH]ccc3c2N[C@@H]2CCCN(CCC#N)C2)o1]

A solution of (R)-5-(5-methyloxazol-2-yl)-N-(piperidin-3-yl)-1H-pyrrolo[2,3-b]pyridin-4-amine (0.08 g, 0.26 mmol, Example 36, step 2) and acrylonitrile (0.04 g, 0.60 mmol), triethylamine (0.1 mL, 0.80 mmol) in ethanol (10 mL) was heated to 80° C. for 3 hours. The reaction was cooled to ambient temperature and concentrated in vacuo. The crude was purified by flash chromatography (10% methanol/dichloromethane) to provide (R)-3-(3-((5-(5-methyloxazol-2-yl)-1H-pyrrolo[2,3-b]pyridin-4-yl)amino)piperidin-1-yl)propanenitrile as a white solid (0.02 g, 30% yield): $^1$H NMR (400 MHz, DMSO-d₆,) δ 11.49 (s, 1H), 9.10 (d, J=8 Hz, 1H), 8.46 (s, 1H), 7.16 (s, 1H), 6.96 (s, 1H), 6.55 (s, 1H), 4.18-4.20 (m, 1H), 2.92-2.95 (m, 1H), 2.56-2.64 (m, 5H), 2.30-2.47 (m, 5H), 1.91-1.20 (m, 1H), 1.60-1.69 (m, 1H), 1.49-1.53 (m, 2H); MS (ES) m/z 351.1 (M+H).

Example 38: Preparation of (R)-3-(3-((5-(1,2,4-oxadiazol-3-yl)-1H-pyrrolo[2,3-b]pyridin-4-yl)amino)piperidin-1-yl)-3-oxopropanenitrile

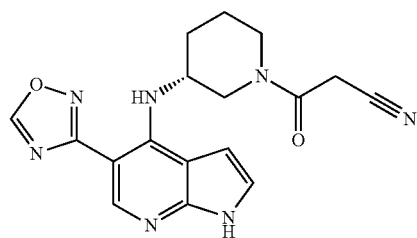 [SMILES: N#CCC(=O)N1CCC[C@@H](Nc2c(-c3ncon3)cnc3[nH]ccc23)C1]

Scheme 36. Preparation of (R)-3-(3-((5-(1,2,4-oxadiazol-3-yl)-1H-pyrrolo[2,3-b]pyridin-4-yl)amino)piperidin-1-yl)-3-oxopropanenitrile

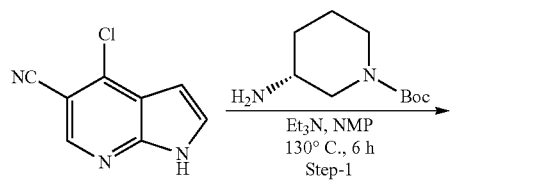

Et₃N, NMP
130° C., 6 h
Step-1

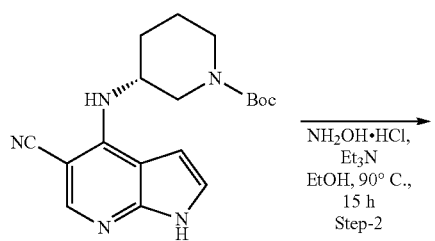

NH₂OH·HCl,
Et₃N
EtOH, 90° C.,
15 h
Step-2

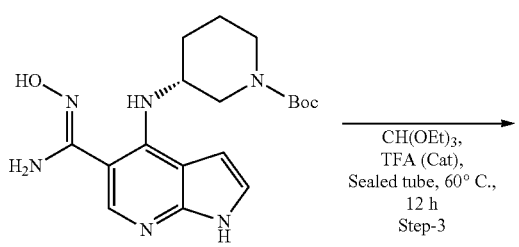

CH(OEt)₃,
TFA (Cat),
Sealed tube, 60° C.,
12 h
Step-3

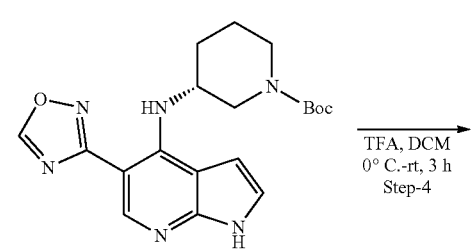

TFA, DCM
0° C.-rt, 3 h
Step-4

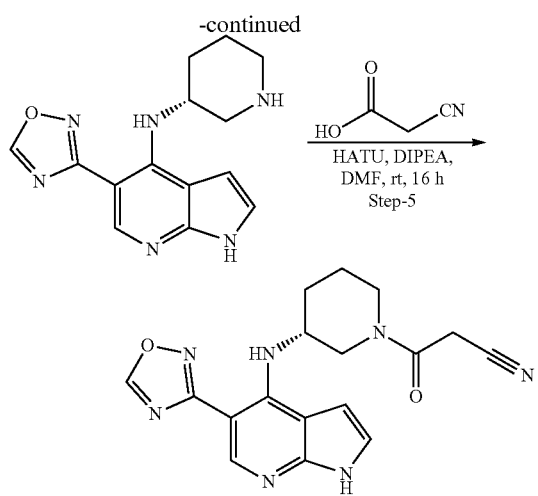

HATU, DIPEA,
DMF, rt, 16 h
Step-5

Step 1: Preparation of tert-butyl(R)-3-((5-cyano-1H-pyrrolo[2,3-b]pyridin-4-yl)amino)piperidine-1-carboxylate

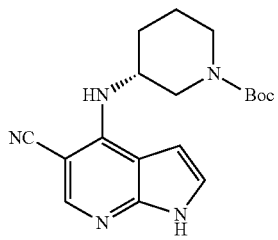 [SMILES: CC(C)(C)OC(=O)N1CCC[C@@H](Nc2c(C#N)cnc3[nH]ccc23)C1]

In a sealed tube a stirred solution of 4-chloro-1H-pyrrolo[2,3-b]pyridine-5-carbonitrile (1.0 g, 5.64 mmol), tert-butyl (R)-3-aminopiperidine-1-carboxylate (1.69 g, 8.4 mmol) and triethylamine (2.37 mL, 16.9 mmol) in N-methyl-2-pyrrolidone (15 mL) was heated at 130° C. for 6 hours. The reaction mixture was cooled to room temperature, quenched with water and extracted with ethyl acetate. The organic layer was washed with brine, dried over anhydrous sodium sulfate, filtered and concentrated in vacuo to obtain the crude tert-butyl (R)-3-((5-cyano-1H-pyrrolo[2,3-b]pyridin-4-yl)amino)piperidine-1-carboxylate as an off-white solid (2.3 g, crude): MS (ES) m/z 342.2 (M+H).

Step 2: Preparation of tert-butyl (R,Z)-3-((5-(N'-hydroxycarbamimidoyl)-1H-pyrrolo[2,3-b]pyridin-4-yl)amino)piperidine-1-carboxylate

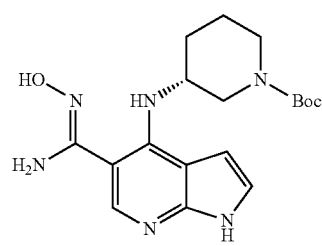

A suspension of tert-butyl (R)-3-((5-cyano-1H-pyrrolo[2,3-b]pyridin-4-yl)amino)piperidine-1-carboxylate (2.3 g, 6.74 mmol), hydroxylamine hydrochloride (0.70 g, 10.1 mmol) and triethylamine (1.89 mL, 13.4 mmol) in ethanol (10 mL) was heated at 90° C. for 15 hours under an argon atmosphere. The reaction mixture was cooled to ambient temperature and concentrated in vacuo to remove volatiles. The residue was dissolved in dichloromethane and washed with water, brine, dried over anhydrous sodium sulfate, filtered and concentrated in vacuo to provide crude tert-butyl (R,Z)-3-((5-(N'-hydroxycarbamimidoyl)-1H-pyrrolo[2,3-b]pyridin-4-yl)amino)piperidine-1-carboxylate as a semi solid (1.2 g, crude): MS (ES) m/z 375.0 (M+H).

Step 3: Preparation of tert-butyl (R)-3-((5-(1,2,4-oxadiazol-3-yl)-1H-pyrrolo[2,3-b]pyridin-4-yl)amino)piperidine-1-carboxylate

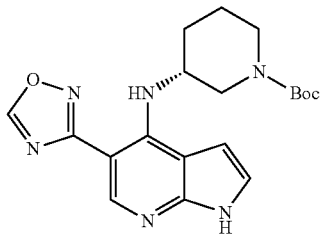 [SMILES: CC(C)(C)OC(=O)N1CCC[C@@H](Nc2c(-c3ncon3)cnc3[nH]ccc23)C1]

A stirred solution of tert-butyl (R,Z)-3-((5-(N'-hydroxycarbamimidoyl)-1H-pyrrolo[2,3-b]pyridin-4-yl) amino)piperidine-1-carboxylate (0.5 g, 1.3 mmol), trifluoroacetic acid (0.05 mL) and triethylorthoformate (0.5 mL) was heated at 60° C. for 12 hours in a sealed tube. The reaction was cooled to ambient temperature, diluted with dichloromethane and washed with water and brine. The organic layer was dried over anhydrous sodium sulfate, filtered and concentrated in vacuo to provide tert-butyl (R)-3-((5-(1,2,4-oxadiazol-3-yl)-1H-pyrrolo[2,3-b]pyridin-4-yl)amino) piperidine-1-carboxylate as an off-white solid (0.25 g, crude): MS (ES) m/z 385.0 (M+H).

Step 4: Preparation of (R)-5-(1,2,4-oxadiazol-3-yl)-N-(piperidin-3-yl)-1H-pyrrolo[2,3-b]pyridin-4-amine

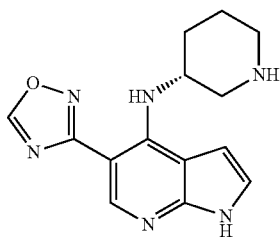 [SMILES: c1cc2c(N[C@@H]3CCCNC3)c(-c3ncon3)cnc2[nH]1]

A solution of tert-butyl (R)-3-((5-(1,2,4-oxadiazol-3-yl)-1H-pyrrolo[2,3-b]pyridin-4-yl)amino) piperidine-1-carboxylate (0.25 g, 0.6 mmol) in dichloromethane:trifluoroacetic acid (5 mL:2 mL) was stirred at ambient temperature for 3 hours. The reaction mixture was concentrated in vacuo to remove volatiles and neutralized with aqueous ammonia and extracted with dichloromethane (30 mL). The organic layer was washed with water, brine, dried over anhydrous sodium sulfate, filtered and concentrated in vacuo to provide (R)-5-(1,2,4-oxadiazol-3-yl)-N-(piperidin-3-yl)-1H-pyrrolo[2,3-b]pyridin-4-amine as a colorless liquid (0.11 g, crude): MS (ES) m/z 285.0 (M+H).

Step 5: Preparation of (R)-3-(3-((5-(1,2,4-oxadiazol-3-yl)-1H-pyrrolo[2,3-b]pyridin-4-yl)amino)piperidin-1-yl)-3-oxopropanenitrile

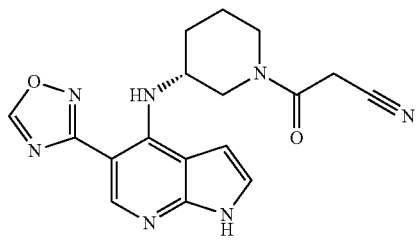 [SMILES: N#CCC(=O)N1CCC[C@@H](Nc2c(-c3ncon3)cnc3[nH]ccc23)C1]

To a stirred solution of cyanoacetic acid (0.044 g, 0.52 mmol), 1-[bis(dimethylamino)methylene]-1H-1,2,3-triazolo[4,5-b]pyridinium 3-oxid hexafluorophosphate (0.17 g, 0.45 mmol) in N,N-dimethylformamide (15 mL) was added (R)-5-(1,2,4-oxadiazol-3-yl)-N-(piperidin-3-yl)-1H-pyrrolo[2,3-b]pyridin-4-amine (0.1 g, 0.35 mmol) followed by N,N-diisopropylethylamine (0.19 mL, 1.05 mmol) and then the resulting mixture was stirred at ambient temperature for 16 hours. The reaction mixture was quenched with water and extracted with dichloromethane. The organic layer was washed with water, brine, dried over anhydrous sodium sulfate, filtered and concentrated in vacuo. The crude material was purified by reverse phase chromatography to provide (R)-3-(3-((5-(1,2,4-oxadiazol-3-yl)-1H-pyrrolo[2,3-b]pyridin-4-yl)amino)piperidin-1-yl)-3-oxopropanenitrile as an off-white solid (0.01 g, 9% yield): $^1$H NMR (400 MHz, DMSO-$d_6$ VT at 70° C.) δ 11.51 (br s, 1H), 9.56 (s, 1H), 8.73 (s, 1H), 8.34 (s, 1H), 7.46 (s, 1H), 7.23 (s, 1H), 6.70 (d, J=3.2 Hz, 1H), 4.05-4.29 (m, 2H), 3.89-4.02 (m, 2H), 3.49-3.75 (m, 2H), 3.40-3.51 (m, 2H), 2.10 (br s, 1H), 1.64-1.82 (m, 1H); MS (ES) m/z 352.2 (M+H).

Analytical Conditions:
Column: X-BridgeC-18 (250 mm×4.6 mm×5 mic)
Mobile phase (A): 0.1% Ammonia in water
Mobile phase (B): MeCN
Flow rate: 1.0 mL/min Example 39: Preparation of (R)-2-(4-((1-(2-cyanoacetyl)piperidin-3-yl)amino)-1H-pyrrolo[2,3-b]pyridin-5-yl)-N-methyloxazole-5-carboxamide

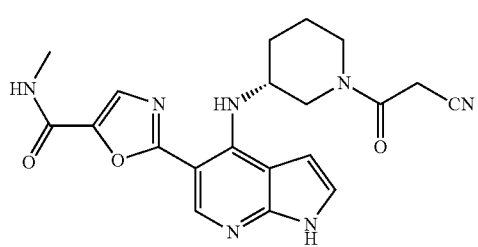 [SMILES: CNC(=O)c1cnc(-c2cnc3[nH]ccc3c2N[C@@H]2CCCN(C(=O)CC#N)C2)o1]

209

Scheme 37. Preparation of (R)-2-(4-((1-(2-cyanoacetyl)piperidin-3-yl)amino)-1H-pyrrolo[2,3-b]pyridin-5-yl)-N-methyloxazole-5-carboxamide

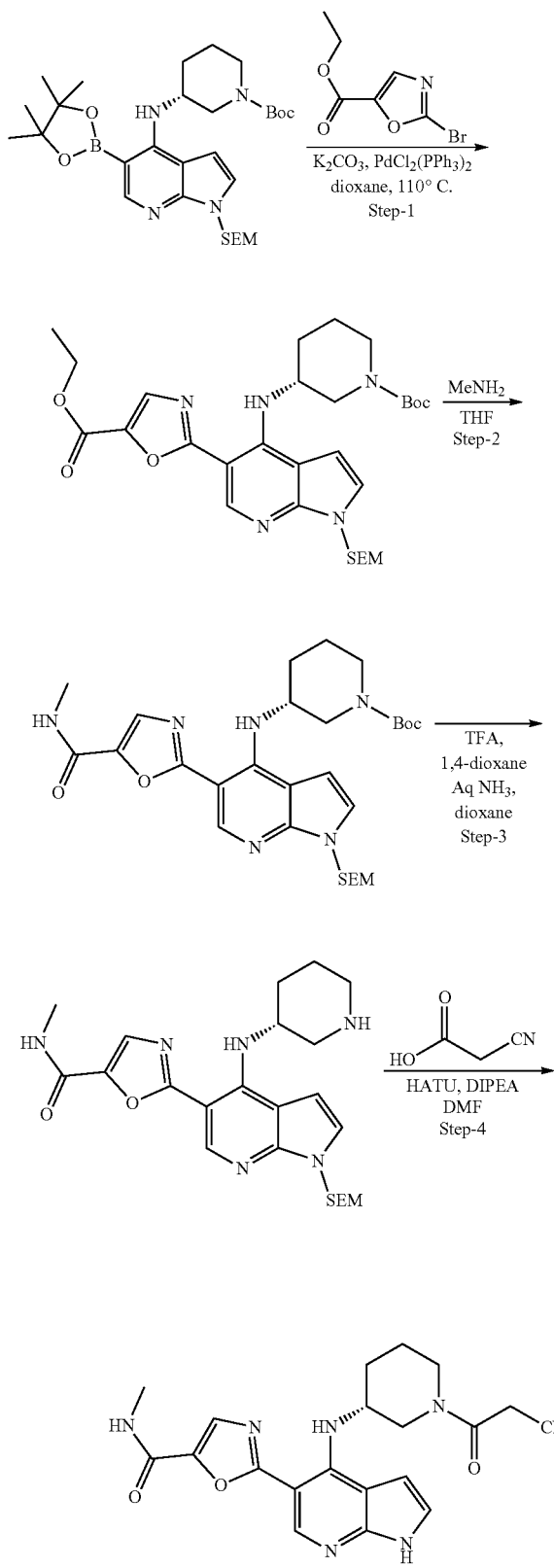

210

Step 1: Preparation of ethyl (R)-2-(4-((1-(tert-butoxycarbonyl)piperidin-3-yl)amino)-1-((2-(trimethylsilyl)ethoxy)methyl)-1H-pyrrolo[2,3-b]pyridin-5-yl)oxazole-5-carboxylate

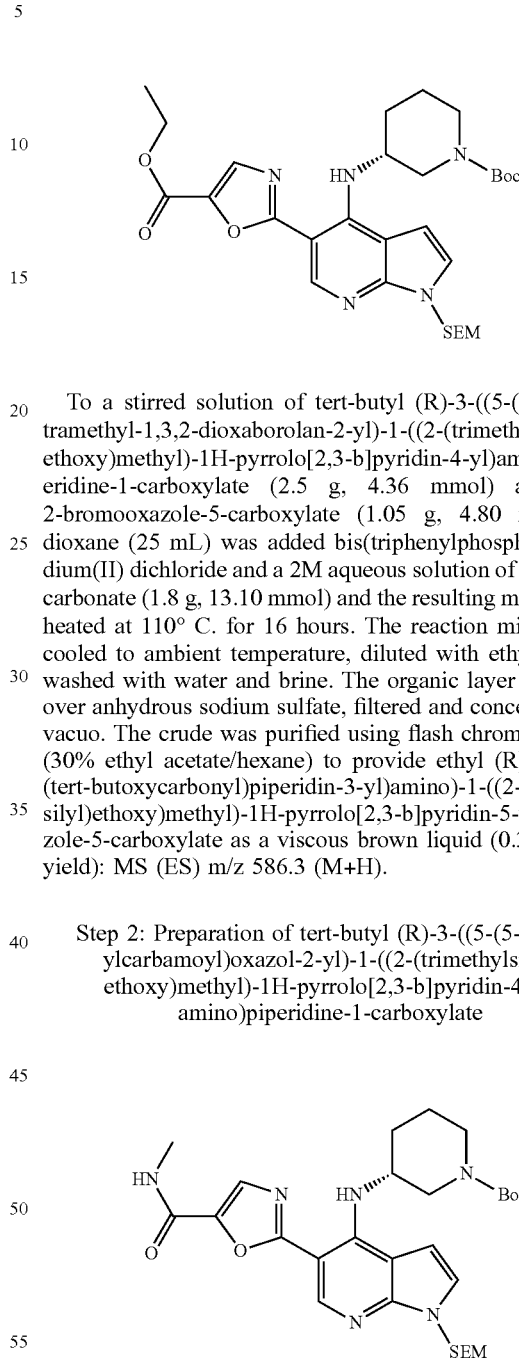

To a stirred solution of tert-butyl (R)-3-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate (2.5 g, 4.36 mmol) and ethyl 2-bromooxazole-5-carboxylate (1.05 g, 4.80 mmol) in dioxane (25 mL) was added bis(triphenylphosphine)palladium(II) dichloride and a 2M aqueous solution of potassium carbonate (1.8 g, 13.10 mmol) and the resulting mixture was heated at 110° C. for 16 hours. The reaction mixture was cooled to ambient temperature, diluted with ethyl acetate, washed with water and brine. The organic layer was dried over anhydrous sodium sulfate, filtered and concentrated in vacuo. The crude was purified using flash chromatography (30% ethyl acetate/hexane) to provide ethyl (R)-2-(4-((1-(tert-butoxycarbonyl)piperidin-3-yl)amino)-1-((2-(trimethylsilyl)ethoxy)methyl)-1H-pyrrolo[2,3-b]pyridin-5-yl)oxazole-5-carboxylate as a viscous brown liquid (0.35 g, 14% yield): MS (ES) m/z 586.3 (M+H).

Step 2: Preparation of tert-butyl (R)-3-((5-(5-(methylcarbamoyl)oxazol-2-yl)-1-((2-(trimethylsilyl)ethoxy)methyl)-1H-pyrrolo[2,3-b]pyridin-4-yl)amino)piperidine-1-carboxylate A solution of ethyl (R)-2-(4-((1-(tert-butoxycarbonyl)piperidin-3-yl)amino)-1-((2-(trimethylsilyl)ethoxy) methyl)-1H-pyrrolo[2,3-b]pyridin-5-yl)oxazole-5-carboxylate (0.5 g, 0.85 mmol) and methylamine (5 mL, 2M in tetrahydrofuran) was stirred at ambient temperature for 48 hours. The reaction mixture was concentrated in vacuo to provide tert-butyl (R)-3-((5-(5-(methylcarbamoyl)oxazol-2-yl)-1-((2-(trimethylsilyl)ethoxy)methyl)-1H-pyrrolo[2,3-b]pyridin-4-yl)amino)piperidine-1-carboxylate as a viscous brown liquid (0.1 g, crude): MS (ES) m/z 571.3 (M+H).

Step 3: Preparation of (R)-N-methyl-2-(4-(piperidin-3-ylamino)-1H-pyrrolo[2,3-b]pyridin-5-yl)oxazole-5-carboxamide

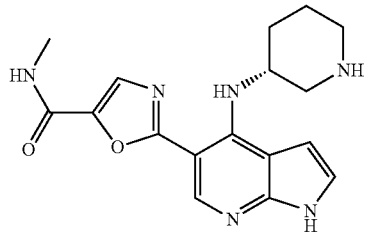 [SMILES: CNC(=O)c1cnc(-c2cnc3[nH]ccc3c2N[C@@H]2CCCNC2)o1]

A solution of tert-butyl (R)-3-((5-(5-(methylcarbamoyl)oxazol-2-yl)-1-((2-(trimethylsilyl)ethoxy)methyl)-1H-pyrrolo[2,3-b]pyridin-4-yl)amino)piperidine-1-carboxylate (0.17 g, 0.29 mmol) in dichloromethane:trifluoroacetic acid (2 mL:2 mL) was stirred at ambient temperature for 3 hours. The reaction mixture was concentrated in vacuo, the residue was dissolved in 1,4-dioxane:aqueous ammonia (3 mL:3 mL, 23% in water) and stirred at ambient temperature for 16 hours. The reaction mixture was concentrated in vacuo to provide (R)-N-methyl-2-(4-(piperidin-3-ylamino)-1H-pyrrolo[2,3-b]pyridin-5-yl)oxazole-5-carboxamide as a gummy liquid (0.2 g, crude): MS (ES) m/z 341.1 (M+H).

Step 4: Preparation of (R)-2-(4-((1-(2-cyanoacetyl)piperidin-3-yl)amino)-1H-pyrrolo[2,3-b]pyridin-5-yl)-N-methyloxazole-5-carboxamide

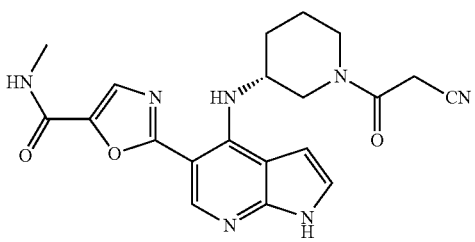 [SMILES: CNC(=O)c1cnc(-c2cnc3[nH]ccc3c2N[C@@H]2CCCN(C(=O)CC#N)C2)o1]

A solution of cyanoacetic acid (0.07 g, 0.83 mmol) and 1-[bis(dimethylamino)methylene]-1H-1,2,3-triazolo[4,5-b]pyridinium 3-oxide hexafluorophosphate (0.32 g, 0.83 mmol) in N,N-dimethylformamide (5 mL) was stirred for 5 minutes. Then (R)-N-methyl-2-(4-(piperidin-3-ylamino)-1H-pyrrolo[2,3-b]pyridin-5-yl)oxazole-5-carboxamide (0.19 g, 0.56 mmol) was added followed by N,N-diisopropylethylamine (0.21 mL, 1.67 mmol) and the mixture stirred at ambient temperature for 16 hours. The reaction was quenched with water and extracted with dichloromethane. The organic layer was washed with water, brine and dried over anhydrous sodium sulfate. The solution was filtered and concentrated in vacuo. The crude material was purified by using flash chromatography (6% methanol/dichloromethane) to provide (R)-2-(4-((1-(2-cyanoacetyl)piperidin-3-yl)amino)-1H-pyrrolo[2,3-b]pyridin-5-yl)-N-methyloxazole-5-carboxamide as an off-white solid (0.03 g, 12% yield): $^1$H NMR (400 MHz, DMSO-$d_6$, 80° C., VT at 80° C.) δ 11.493 (s, 1H), 8.90 (br s, 1H), 8.80 (s, 1H), 8.40 (s, 1H), 7.72 (s, 1H) 7.22 (s, 1H), 6.69 (s, 1H), 3.97 (m, 4H), 3.45 (m, 5H), 2.80-2.81 (m, 3H), 2.07 (m, 1H), 1.77 (s, 1H); MS (ES) m/z 408.4 (M+H).

Example 40: Preparation of 3-((3R,5S)-3-((5-(1-(difluoromethyl)-1H-pyrazol-3-yl)-1H-pyrrolo[2,3-b]pyridin-4-yl)amino)-5-methylpiperidin-1-yl)-3-oxopropanenitrile

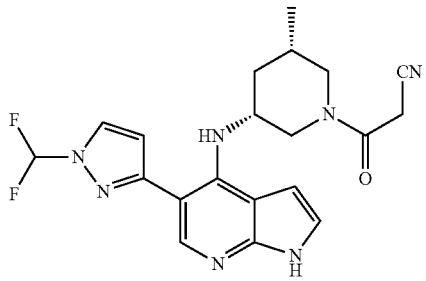 [SMILES: C[C@H]1C[C@@H](Nc2c(-c3ccn(C(F)F)n3)cnc3[nH]ccc23)CN(C(=O)CC#N)C1]

Scheme 38. Preparation of 3-((3R,5S)-3-((5-(1-(difluoromethyl)-1H-pyrazol-3-yl)-1H-pyrrolo[2,3-b]pyridin-4-yl)amino)-5-methylpiperidin-1-yl)-3-oxopropanenitrile

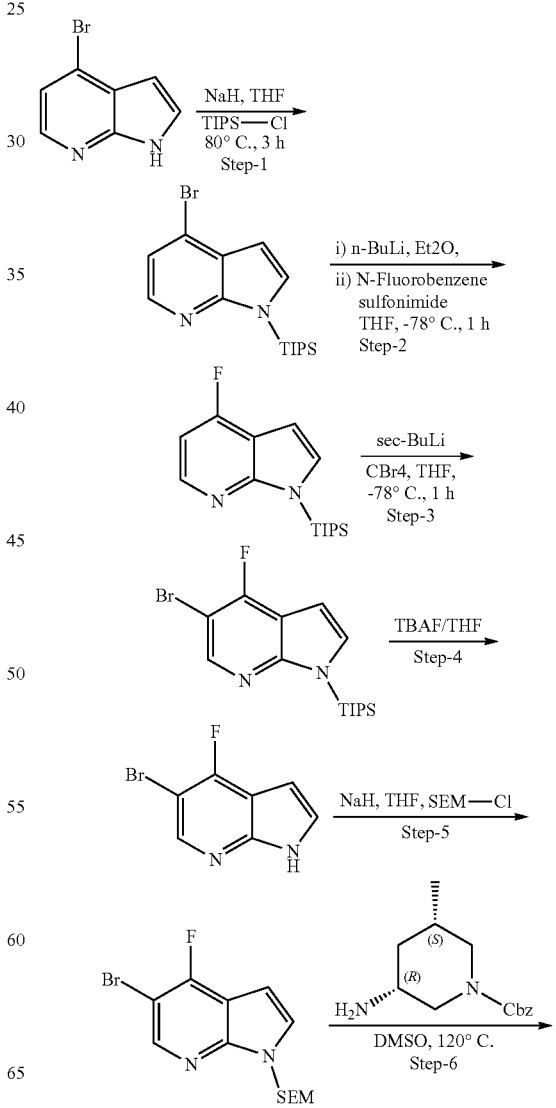

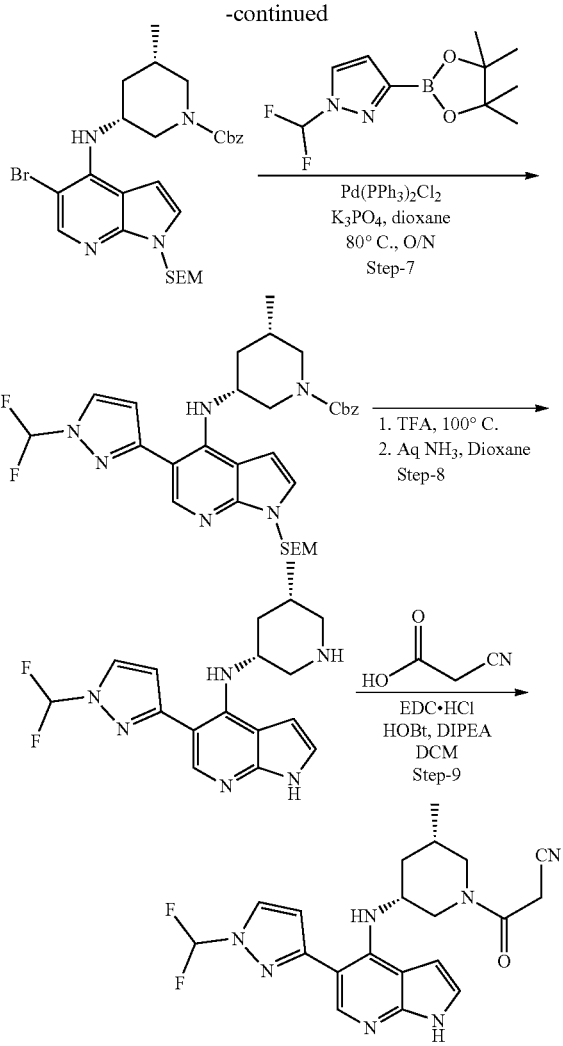

Step 1: Preparation of 4-bromo-1-(triisopropylsilyl)-1H-pyrrolo[2,3-b]pyridine

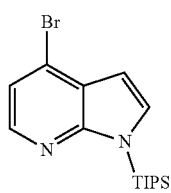

To a suspension of sodium hydride (10.55 g, 263 mmol, 60% in mineral oil) in THF (400 ml) cooled to 0-5° C. was added 4-bromo-1H-pyrrolo[2,3-b]pyridine (40 g, 203 mmol) portion wise for about 20 minutes. The reaction was stirred for 30 minutes at 0-5° C. Then triisopropylsilyl chloride (64.7 mL, 304 mmol) was added dropwise over 20 minutes and the reaction was heated to 70° C. for 3 hours. The reaction was cooled to ambient temperature, diluted with water and extracted with ethyl acetate. The layers were separated and the aqueous layer re-extracted with ethyl acetate. The combined organic layers were dried over anhydrous sodium sulfate, filtered and concentrated in vacuo.

The crude compound was purified by flash chromatography over 230-400 mesh silica gel using pet-ether as eluent to afford 4-bromo-1-(triisopropylsilyl)-1H-pyrrolo[2,3-b]pyridine (70 g, 97% yield) as a colorless liquid: MS (ES) m/z 355.2 (M+H).

Step 2: Preparation of 4-fluoro-1-(triisopropylsilyl)-1H-pyrrolo[2,3-b]pyridine

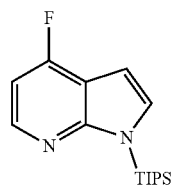

A solution of 4-bromo-1-(triisopropylsilyl)-1H-pyrrolo[2,3-b]pyridine (46 g, 133 mmol) in THF (800 ml) was cooled to −78° C. Then n-butyllithium (1.2 M in hexanes, titrated by diphenylacetic acid method) (167 mL, 200 mmol) was added slowly using a syringe over ~1 hour. The reaction mixture was stirred for 15 minutes at the same temperature. Then a solution of N-fluorobenzenesulfonamide (84 g, 266 mmol) in THF (235 ml) was added slowly, and the reaction stirred for 1 hour at the same temperature. The reaction was quenched with aqueous saturated NH$_4$Cl solution and diluted with MTBE (235 mL). The reaction was slowly raised to ambient temperature, the two layers were seperated, and aqueous layer was extracted with MTBE (235 mL). The combined organic layers were dried over anhydrous sodium sulfate, filtered and concentrated in vacuo. The crude compound was purified by flash column chromatography using 230-400 mesh silica gel and pet-ether to afford 4-fluoro-1-(triisopropylsilyl)-1H-pyrrolo[2,3-b]pyridine (15.5 g, 40.6% yield) as a pale yellow liquid: MS (ES) m/z 293.4 (M+H).

Step 3: Preparation of 5-bromo-4-fluoro-1-(triisopropylsilyl)-1H-pyrrolo[2,3-b]pyridine

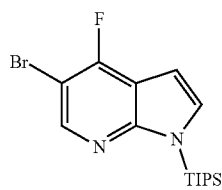

A solution of 4-fluoro-1-(triisopropylsilyl)-1H-pyrrolo[2,3-b]pyridine (15 g, 51.31 mmol) in THF (600 mL) was cooled to −78° C. Then sec-butyllithium (1.2 M in cyclohexane, 64 mL, 76.97 mmol) was added slowly over 30 minutes and the mixture stirred for 1 hour. A solution of carbon tetrabromide (30.57 g, 92.36 mmol) in THF (45 mL) was added slowly and the reaction mass stirred for 1 hour at −78° C. The reaction mixture was quenched by slow addition of aqueous saturated NH$_4$Cl solution, followed by addition of MTBE (150 ml, 10 vol) and warming to ambient temperature. The two layers were separated and the aqueous layer extracted with MTBE (150 mL). The combined organic layers were dried over anhydrous sodium sulfate, filtered and concentrated in vacuo. The crude compound was purified by flash column chromatography using 230-400 mesh silica gel and pet-ether to afford 5-bromo-4-fluoro-1-(triisopropylsilyl)-1H-pyrrolo[2,3-b]pyridine (15.6 g, 82% yield) as pale yellow liquid: MS (ES) m/z 371.3; 373.3 (1:1; M+H).

Step 4: Preparation of 5-bromo-4-fluoro-1H-pyrrolo[2,3-b]pyridine

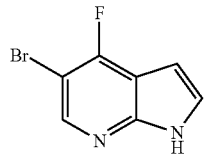

A solution of 5-bromo-4-fluoro-1-(triisopropylsilyl)-1H-pyrrolo[2,3-b]pyridine (26 g, 70.08 mmol) in THF (260 mL) was cooled to 0-5° C. using an ice bath. Then tetrabutylammonium fluoride (1.0 M in THF; 84 ml) was added slowly over 30 minutes and the reaction mass stirred for 4 hours. The reaction mixture was diluted with water (260 mL) and extracted with ethyl acetate (2×130 mL) The combined organic layers were dried over anhydrous sodium sulfate, filtered and concentrated in vacuo. The crude compound was purified by flash column using 230-400 mesh silica gel and 15-20% ethyl acetate in pet-ether to afford 5-bromo-4-fluoro-1H-pyrrolo[2,3-b]pyridine (11 g, 73% yield) as a pale yellow solid: MS (ES) m/z 215.1; 217.1 (1:1; M+H).

Step 5: Preparation of 5-bromo-4-fluoro-1-((2-(trimethylsilyl)ethoxy)methyl)-1H-pyrrolo[2,3-b]pyridine

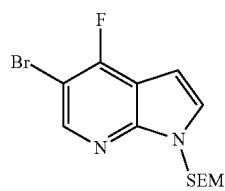 [SMILES: C[Si](C)(C)CCOCn1ccc2c(F)c(Br)cnc21]

A suspension of sodium hydride (2.94 g, 73.6 mmol, 60% in mineral oil) in DMF (110 mL) was cooled to 0-5° C. using an ice salt mixture. To the above suspension was added 5-bromo-4-fluoro-1H-pyrrolo[2,3-b]pyridine (11 g, 51.1 mmol) portion wise and the reaction mixture stirred for 30 minutes at the same temperature. Then 2-(trimethylsilyl)ethoxymethyl chloride (13.83 g, 82 mmol) was added dropwise using an additional funnel over 30 minutes and the reaction stirred at ambient temperature for 4 hours. The reaction mixture was poured into cold water and extracted with ethyl acetate (2×). The combined organic layers were dried over anhydrous sodium sulfate, filtered and concentrated in vacuo. The crude compound was purified by flash chromatography using 100-200 mesh silica gel using pet-ether as eluent to afford 5-bromo-4-fluoro-1-((2-(trimethylsilyl)ethoxy)methyl)-1H-pyrrolo[2,3-b]pyridine (16 g, 91% yield) as a pale yellow liquid: MS (ES) m/z 345.1; 347.1 (1:1; M+H).

Step 6: Preparation of benzyl (3R,5S)-3-((5-bromo-1-((2-(trimethylsilyl)ethoxy)methyl)-1H-pyrrolo[2,3-b]pyridin-4-yl)amino)-5-methylpiperidine-1-carboxylate

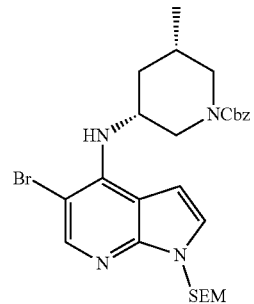 [SMILES: C[C@H]1C[C@@H](Nc2c(Br)cnc3c2ccn3COCC[Si](C)(C)C)CN(C(=O)OCc2ccccc2)C1]

Benzyl (3R,5S)-3-amino-5-methylpiperidine-1-carboxylate (13.85 g, 55.8 mmol) was added to a stirred solution of 5-bromo-4-fluoro-1-((2-(trimethylsilyl)ethoxy)methyl)-1H-pyrrolo[2,3-b]pyridine (16 g, 46.5 mmol) in dimethyl sulfoxide (96 mL) under a nitrogen atmosphere. The reaction mass was stirred for 10 min at ambient temperature followed by the addition of N, N-diisopropylethylamine (20.7 mL, 116.2 mmol). The reaction mixture was slowly heated to 125-130° C. and maintained for 24 hours under a nitrogen atmosphere. The reaction mixture was cooled to room temperature and poured in chilled water (240 mL), stirred for 15 minutes and ethyl acetate (160 mL) added. The organic layer was separated and the aqueous layer extracted with ethyl acetate (100 mL). The combined organic layers were washed with water (2×100 mL), dried over anhydrous sodium sulfate, filtered and concentrated under vacuum to provide crude product as very thick syrupy mass. The crude product was purified by column chromatography using 100-200 mesh silica gel to obtain benzyl (3R,5S)-3-((5-bromo-1-((2-(trimethylsilyl)ethoxy)methyl)-1H-pyrrolo[2,3-b]pyridin-4-yl)amino)-5-methylpiperidine-1-carboxylate (19.5 g, 73.3% yield) as a pale yellow viscous mass: MS (ES) m/z 573.3; 575.4 (1:1; M+H).

Step 7: Preparation of benzyl (3R,5S)-3-((5-(1-(difluoromethyl)-1H-pyrazol-3-yl)-1-((2-(trimethylsilyl)ethoxy)methyl)-1H-pyrrolo[2,3-b]pyridin-4-yl)amino)-5-methylpiperidine-1-carboxylate

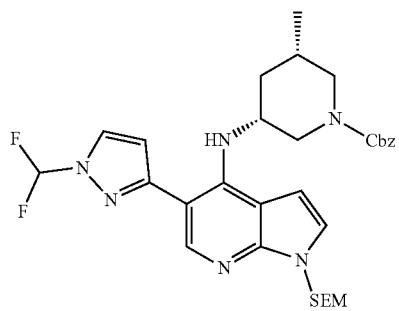 [SMILES: C[C@H]1C[C@@H](Nc2c(-c3ccn(C(F)F)n3)cnc3c2ccn3COCC[Si](C)(C)C)CN(C(=O)OCc2ccccc2)C1]

To a stirred solution of benzyl (3R,5S)-3-((5-bromo-1-((2-(trimethylsilyl)ethoxy)methyl)-1H-pyrrolo[2,3-b]pyridin-4-yl)amino)-5-methylpiperidine-1-carboxylate (0.6 g, 1.05 mmol) and 1-(difluoromethyl)-3-(4,4,5,5-tetramethyl-1,3,2-dioxaborolan-2-yl)-1H-pyrazole (0.38 g, 1.57 mmol) in 1,4-dioxane (35 mL) was added bis-(triphenylphosphine) palladium(II) dichloride (0.15 g, 0.21 mmol) and 2M aqueous solution of potassium phosphate tribasic (0.90 g, 4.18 mmol) and the mixture heated at 80° C. for 16 hours under a nitrogen atmosphere. The reaction mixture was cooled to ambient temperature, diluted with ethyl acetate and filtered through celite. The filtrate was washed with water, brine, dried over anhydrous sodium sulfate, filtered and concentrated in vacuo. The crude material was purified by using flash chromatography (50% ethyl acetate/hexane) to provide benzyl (3R,5S)-3-({5-[1-(difluoromethyl)-1H-pyrazol-3-yl]-1-{[2-(trimethylsilyl)ethoxy]methyl}-1H-pyrrolo[2,3-b]pyridin-4-yl}amino)-5-methylpiperidine-1-carboxylate as a viscous pale yellow liquid (0.52 g, 81% yield): MS (ES) m/z 611.3 (M+H).

Step 8: Preparation of 5-(1-(difluoromethyl)-1H-pyrazol-3-yl)-N-((3R,5S)-5-methylpiperidin-3-yl)-1H-pyrrolo[2,3-b]pyridin-4-amine

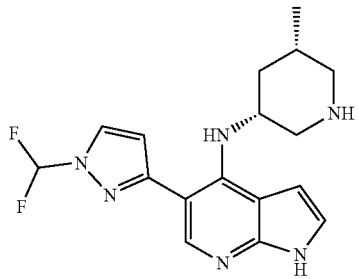 [SMILES: C[C@@H]1CNC[C@H](Nc2c(-c3ccn(C(F)F)n3)cnc3[nH]ccc23)C1]

A solution of benzyl(3R,5S)-3-({5-[1-(difluoromethyl)-1H-pyrazol-3-yl]-1-{[2-(trimethylsilyl) ethoxy]methyl}-1H-pyrrolo[2,3-b]pyridin-4-yl}amino)-5-methylpiperidine-1-carboxylate (0.56 g, 0.90 mmol) in trifluoroacetic acid (5 mL) was stirred at 100° C. for 1 hour. The reaction was cooled to ambient temperature and the mixture was concentrated in vacuo. The residue was dissolved in 1,4-dioxane: aqueous ammonia (5 mL:5 mL) and stirred at ambient temperature for 16 hours. The reaction mixture was concentrated in vacuo to provide 5-(1-(difluoromethyl)-1H-pyrazol-3-yl)-N-((3R,5S)-5-methylpiperidin-3-yl)-1H-pyrrolo[2,3-b]pyridin-4-amine as a gum (0.53 g, crude): MS (ES) m/z 347.2 (M+H).

Step 9: Preparation of 3-((3R,5S)-3-((5-(1-(difluoromethyl)-1H-pyrazol-3-yl)-1H-pyrrolo[2,3-b]pyridin-4-yl)amino)-5-methylpiperidin-1-yl)-3-oxopropanenitrile

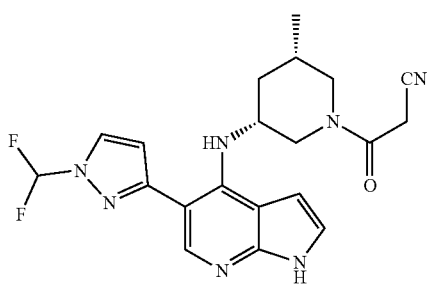 [SMILES: C[C@H]1C[C@@H](Nc2c(-c3ccn(C(F)F)n3)cnc3[nH]ccc23)CN(C(=O)CC#N)C1]

A solution of cyanoacetic acid (0.11 g, 1.3 mmol), 1-hydroxybenzotriazole (0.16 g, 1.04 mmol) and N-(3-dimethylaminopropyl)-N'-ethylcarbodiimide hydrochloride (0.25 g, 1.30 mmol) in dichloromethane (10 mL) was stirred at ambient temperature for 5 minutes. Then 5-(1-(difluoromethyl)-1H-pyrazol-3-yl)-N-((3R,5S)-5-methylpiperidin-3-yl)-1H-pyrrolo[2,3-b]pyridin-4-amine (0.23 g, 0.86 mmol) was added followed by triethylamine (0.36 mL 2.60 mmol) and then the resulting mixture was stirred at ambient temperature for 16 hours. The reaction mixture was quenched with water and extracted with dichloromethane. The organic layer was washed with water, brine, dried over anhydrous sodium sulfate, filtered and concentrated in vacuo. The crude material was purified using reverse phase chromatography to obtain 3-[(3R,5S)-3-({5-[1-(difluoromethyl)-1H-pyrazol-3-yl]-1H-pyrrolo[2,3-b]pyridin-4-yl}amino)-5-methylpiperidin-1-yl]-3-oxopropanenitrile as a white solid (0.04 g, 11% yield); 1H NMR (400 MHz, DMSO-d$_6$, VT at 90° C.) δ 11.17 (br s, 1H), 8.14-8.37 (m, 3H), 7.63-7.94 (m, 1H), 7.16 (s, 1H), 7.01 (s, 1H), 6.67 (s, 1H), 4.80-4.83 (m, 1H), 3.60-4.36 (m, 3H), 2.66-2.83 (m, 1H), 2.18-2.39 (m, 2H), 1.65-1.93 (m, 1H), 1.11-1.26 (m, 2H), 0.91 (d, J=6.4 Hz, 3H); MS (ES) m/z 414.4 (M+H).

Analytical Conditions:
Flow rate: 20.0 mL/min
Column: Sunfire C18 19*150*5 micron
Mobile Phase (A): 0.1% TFA in water
Mobile Phase (B): MeCN Example 41: Preparation of (R)-3-(3-((5-(isothiazol-3-yl)-1H-pyrrolo[2,3-b]pyridin-4-yl)amino)piperidin-1-yl)-3-oxopropanenitrile

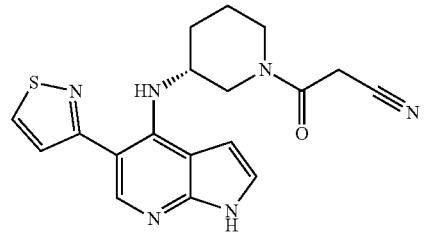 [SMILES: N#CCC(=O)N1CCC[C@@H](Nc2c(-c3ccsn3)cnc3[nH]ccc23)C1]

Scheme 39. Preparation of (R)-3-(3-((5-(isothiazol-3-yl)-1H-pyrrolo[2,3-b]pyridin-4-yl)amino)piperidin-1-yl)-3-oxopropanenitrile

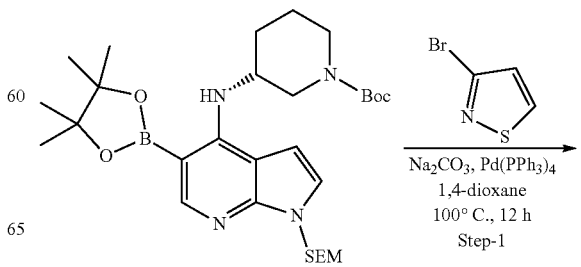

-continued

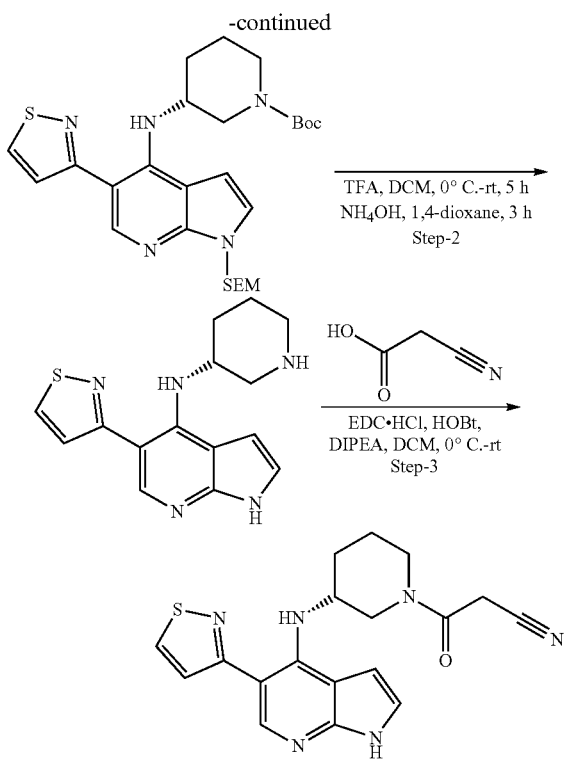

Step 1: Preparation of tert-butyl (R)-3-((5-(isothiazol-3-yl)-1-((2-(trimethylsilyl)ethoxy)methyl)-1H-pyrrolo[2,3-b]pyridin-4-yl)amino)piperidine-1-carboxylate

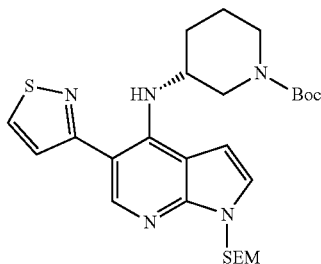

To a stirred solution of tert-butyl (R)-3-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate (0.72 g, 1.25 mmol) and 3-bromoisothiazole (0.3 g, 1.63 mmol) in 1,4-dioxane (20 mL) was added tetrakis(triphenyl phosphine)palladium(0) (0.18 g, 0.25 mmol) followed by 2M aqueous solution of sodium carbonate (0.4 g, 3.77 mmol) and the reaction mixture heated at 100° C. for 16 hours. After cooling the reaction mixture was diluted with ethyl acetate and filtered through celite. The filtrate was washed with water, brine, dried over anhydrous sodium sulfate, filtered and concentrated in vacuo. The crude material was purified by flash chromatography (25% ethyl acetate/hexane) to provide tert-butyl (R)-3-((5-(isothiazol-3-yl)-1-((2-(trimethylsilyl)ethoxy)methyl)-1H-pyrrolo[2,3-b]pyridin-4-yl)amino)piperidine-1-carboxylate as a pale yellow liquid (0.23 g, 35% yield): MS (ES) m/z 529.9 (M+H).

Step 2: Preparation of (R)-5-(isothiazol-3-yl)-N-(piperidin-3-yl)-1H-pyrrolo[2,3-b]pyridin-4-amine

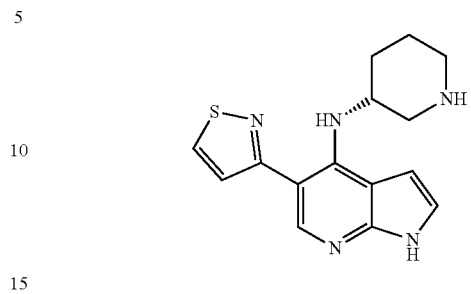

A stirred solution of tert-butyl (R)-3-((5-(isothiazol-3-yl)-1-((2-(trimethylsilyl)ethoxy)methyl)-1H-pyrrolo[2,3-b]pyridin-4-yl)amino)piperidine-1-carboxylate (0.3 g, 0.56 mmol) in dichloromethane:trifluoroacetic acid (3.0 mL:3.0 mL) was stirred at ambient temperature for 5 hours. The reaction mixture was concentrated in vacuo, the residue was dissolved in 1,4-dioxane:ammonia (3.0 mL:3.0 mL, 23% in water) and stirred at ambient temperature for 16 hours. The reaction mixture was concentrated to dryness to provide (R)-5-(isothiazol-3-yl)-N-(piperidin-3-yl)-1H-pyrrolo[2,3-b]pyridin-4-amine as a viscous brown liquid (0.22 g, crude): MS (ES) m/z 300.0 (M+H).

Step 3: Preparation of (R)-3-(3-((5-(isothiazol-3-yl)-1H-pyrrolo[2,3-b]pyridin-4-yl)amino)piperidin-1-yl)-3-oxopropanenitrile

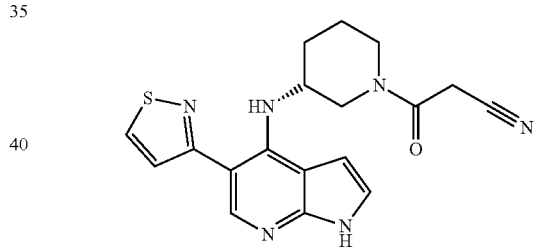

A solution of cyanoacetic acid (0.1 g, 1.00 mmol), 1-hydroxybenzotriazole (0.15 g, 1.10 mmol) and N-(3-dimethylaminopropyl)-N'-ethylcarbodiimide hydrochloride (0.21 g, 1.10 mmol) in dichloromethane (20 mL) was stirred at ambient temperature for 5 minutes. Then (R)-5-(isothiazol-3-yl)-N-(piperidin-3-yl)-1H-pyrrolo[2,3-b]pyridin-4-amine (0.22 g, 0.73 mmol) was added followed by N,N-diisopropylethylamine (0.4 mL, 2.20 mmol) and the resulting mixture stirred at ambient temperature for 16 hours. The reaction mixture was quenched with water and extracted with dichloromethane. The organic layer was washed with water, brine, dried over anhydrous sodium sulfate, filtered and concentrated in vacuo. The crude material was purified by flash chromatography (3% methanol/dichloromethane) to provide (R)-3-(3-((5-(isothiazol-3-yl)-1H-pyrrolo[2,3-b]pyridin-4-yl)amino)piperidin-1-yl)-3-oxopropanenitrile as an off-white solid (0.04 g, 16% yield): $^1$H NMR (400 MHz, DMSO-$d_6$) δ 11.48 (br s, 1H), 9.58 (d, J=6.0 Hz, 1H), 9.08 (d, J=4.4 Hz, 1H), 8.6 (d, J=12.0 Hz, 1H), 7.99 (d, J=4.8 Hz, 1H), 7.19 (s, 1H), 6.67 (s, 1H), 4.39 (s, 1H), 4.02-3.95 (m, 6H), 2.02 (s, 1H), 1.72-1.60 (m, 3H); MS (ES) m/z 367.1 (M+H).

Example 42: Preparation of ethyl (R)-2-(4-((1-(2-cyanoacetyl)piperidin-3-yl)amino)-1H-pyrrolo[2,3-b]pyridin-5-yl)thiazole-5-carboxylate

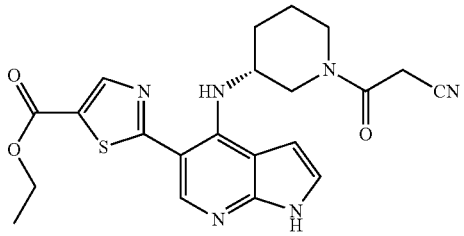 [SMILES: CCOC(=O)c1cnc(-c2cnc3[nH]ccc3c2N[C@@H]2CCCN(C(=O)CC#N)C2)s1]

Scheme 40. Preparation of ethyl (R)-2-(4-((1-(2-cyanoacetyl)piperidin-3-yl)amino)-1H-pyrrolo[2,3-b]pyridin-5-yl)thiazole-5-carboxylate

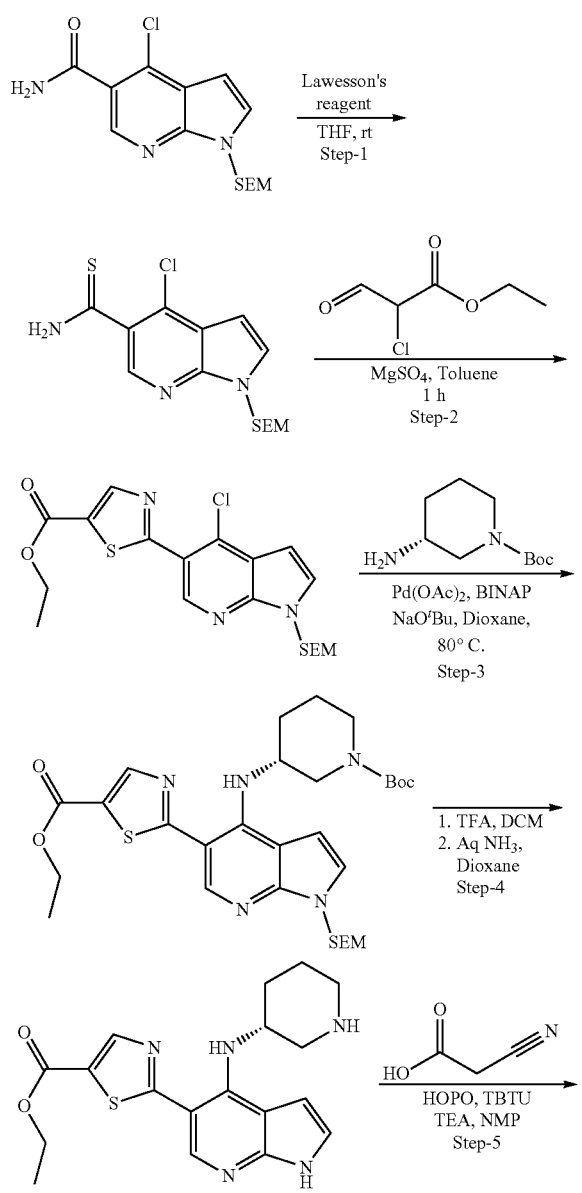

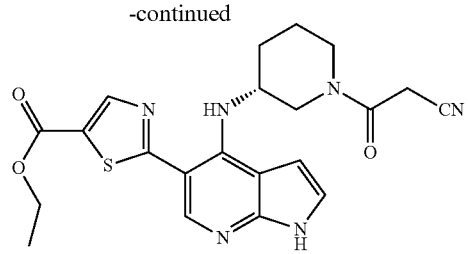

Step 1: Preparation of 4-chloro-1-((2-(trimethylsilyl)ethoxy)methyl)-1H-pyrrolo[2,3-b]pyridine-5-carbothioamide

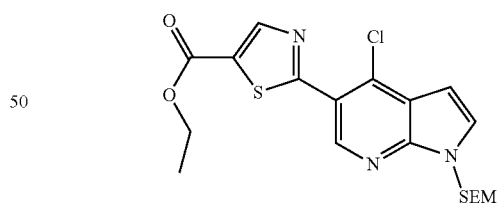

A suspension of 4-chloro-1-((2-(trimethylsilyl)ethoxy)methyl)-1H-pyrrolo[2,3-b]pyridine-5-carboxamide (2.0 g, 6.1 mmol) and Lawesson's reagent (3.73 g, 9.20 mmol) in tetrahydrofuran (20 mL) was stirred at ambient temperature for 30 minutes. The reaction mixture was diluted with water and extracted with ethyl acetate. The organic layer was washed with brine, dried over sodium sulfate, filtered and concentrated in vacuo. The crude was purified by flash chromatography to provide 4-chloro-1-((2-(trimethylsilyl)ethoxy)methyl)-1H-pyrrolo[2,3-b]pyridine-5-carbothioamide as a yellow solid (1 g, 50% yield): MS (ES) m/z 342.1 (M+H).

Step 2: Preparation of ethyl 2-(4-chloro-1-((2-(trimethylsilyl)ethoxy)methyl)-1H-pyrrolo[2,3-b]pyridin-5-yl)thiazole-5-carboxylate To a stirred solution of 4-chloro-1-((2-(trimethylsilyl)ethoxy)methyl)-1H-pyrrolo[2,3-b]pyridine-5-carbothioamide (0.9 g, 2.63 mmol) and ethyl 2-chloro-3-oxopropanoate (0.39 g, 2.63 mmol) in toluene (10 mL) was added magnesium sulfate (0.317 g, 2.63 mmol) and the mixture was heated to 110° C. for 1 hour under a nitrogen atmosphere. The reaction was cooled to ambient temperature, diluted with water and extracted with ethyl acetate. The organic layer was washed with brine, dried over sodium sulfate, filtered and concentrated in vacuo. The crude material was purified by flash chromatography (20% ethyl acetate/hexane) to provide ethyl 2-(4-chloro-1-((2-(trimethylsilyl)

ethoxy)methyl)-1H-pyrrolo[2,3-b]pyridin-5-yl)thiazole-5-carboxylate as a yellow solid (0.8 g, 70% yield): MS (ES) m/z 438.1 (M+H).

Step 3: Preparation of ethyl (R)-2-(4-((1-(tert-butoxycarbonyl)piperidin-3-yl)amino)-1-((2-(trimethylsilyl)ethoxy)methyl)-1H-pyrrolo[2,3-b]pyridin-5-yl)thiazole-5-carboxylate

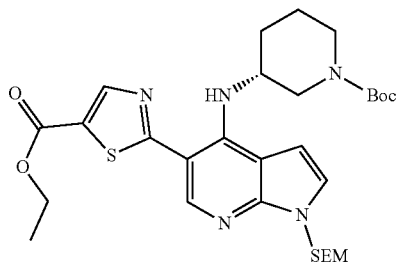 [SMILES: CCOC(=O)c1cnc(-c2cnc3c(ccn3COCC[Si](C)(C)C)c2N[C@@H]2CCCN(C(=O)OC(C)(C)C)C2)s1]

In a 20 mL microwave vial, ethyl 2-(4-chloro-1-((2-(trimethylsilyl)ethoxy)methyl)-1H-pyrrolo[2,3-b]pyridin-5-yl)thiazole-5-carboxylate (0.60 g, 1.37 mmol), tert-butyl (R)-3-aminopiperidine-1-carboxylate (0.411 g, 2.05 mmol), palladium(II) acetate (0.05 g, 0.20 mmol), (2,2'-bis(diphenylphosphino)-1,1'-binaphthyl) (0.13 g, 0.20 mmol), sodium tert-butoxide (0.39 g, 4.11 mmol) and 1,4-dioxine (7 mL) were combined and the resulting mixture subjected to microwave irradiation at 80° C. for 1 hour. The reaction was cooled to ambient temperature, diluted with water and extracted with ethyl acetate. The organic layer was washed with brine, dried over sodium sulfate, filtered and concentrated in vacuo. The crude was purified using flash chromatography (40% ethyl acetate/hexane) to provide ethyl (R)-2-(4-((1-(tert-butoxycarbonyl)piperidin-3-yl)amino)-1-((2-(trimethylsilyl)ethoxy)methyl)-1H-pyrrolo[2,3-b]pyridin-5-yl)thiazole-5-carboxylate as a viscous brown liquid (0.23 g, 28% yield): MS (ES) m/z 602.3 (M+H).

Step 4: Preparation of ethyl (R)-2-(4-(piperidin-3-ylamino)-1H-pyrrolo[2,3-b]pyridin-5-yl)thiazole-5-carboxylate

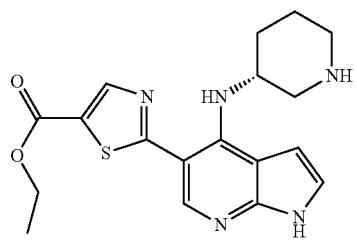 [SMILES: CCOC(=O)c1cnc(-c2cnc3[nH]ccc3c2N[C@@H]2CCCNC2)s1]

A solution of ethyl 2-(4-((1-(tert-butoxycarbonyl)piperidin-3-yl)amino)-1-((2-(trimethylsilyl)ethoxy)methyl)-1H-pyrrolo[2,3-b]pyridin-5-yl)thiazole-5-carboxylate (0.15 g, 0.24 mmol) in dichloromethane:trifluoroacetic acid (3.0 mL:3.0 mL) was stirred at ambient temperature for 3 hours. The reaction mixture was concentrated in vacuo, the residue was dissolved in 1,4-dioxane:aqueous ammonia (5.0 mL:4.0 mL, 23% in water) and stirred at ambient temperature for 16 hours. The reaction was concentrated in vacuo to provide ethyl (R)-2-(4-(piperidin-3-ylamino)-1H-pyrrolo[2,3-b]pyridin-5-yl)thiazole-5-carboxylate as a brown solid (0.15 g, crude): MS (ES) m/z 372.1 (M+H).

Step 5: Preparation of ethyl (R)-2-(4-((1-(2-cyanoacetyl)piperidin-3-yl)amino)-1H-pyrrolo[2,3-b]pyridin-5-yl)thiazole-5-carboxylate

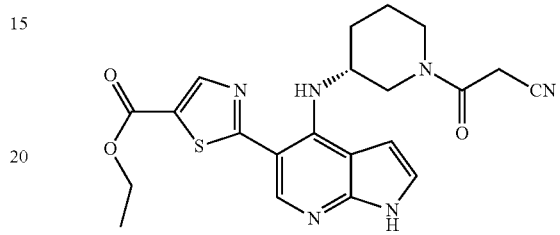

To a stirred solution of cyanoacetic acid (g, 0.60 mmol), 1-hydroxy-2-pyridone (0.05 g, 0.48 mmol) and 2-(1H-benzotriazole-1-yl)-1,1,3,3-tetramethylaminium tetrafluoroborate (0.15 g, 0.48 mmol) in N-methylpyrrolidone (5 mL), was added ethyl 2-(4-(piperidin-3-ylamino)-1H-pyrrolo[2,3-b]pyridin-5-yl)thiazole-5-carboxylate (0.15 g, 0.40 mmol) followed by triethylamine (0.16 mL, 1.21 mmol) and the stirring continued at ambient temperature for 2 hours. The reaction mixture was diluted with water and extracted with ethyl acetate. The organic layer was washed with brine, dried over sodium sulfate, filtered and concentrated in vacuo. The crude was purified by flash chromatography (10% methanol/dichloromethane) to provide ethyl (R)-2-(4-((1-(2-cyanoacetyl)piperidin-3-yl)amino)-1H-pyrrolo[2,3-b]pyridin-5-yl)thiazole-5-carboxylate as a pale yellow solid (0.02 g, 10% yield): $^1$H NMR (400 MHz, DMSO-$d_6$) δ 11.57 (s, 1H), 9.71 (m, 1H), 8.43-8.34 (m, 2H), 7.20 (s, 1H), 6.69 (s, 1H), 4.30-4.35 (q, J=6.4 Hz, 2H), 4.02 (m, 1H), 3.79-3.87 (m, 2H), 3.56 (m, 1H), 3.39 (m, 1H), 2.03 (m, 2H), 1.77 (m, 2H), 1.62 (m, 2H), 1.29-1.33 (t, J=7.2 Hz, 3H); MS (ES) m/z 439.1 (M+H).

Example 43: Preparation of (R)-3-(3-((5-(2-methoxypyrimidin-4-yl)-1H-pyrrolo[2,3-b]pyridin-4-yl)amino)piperidin-1-yl)-3-oxopropanenitrile

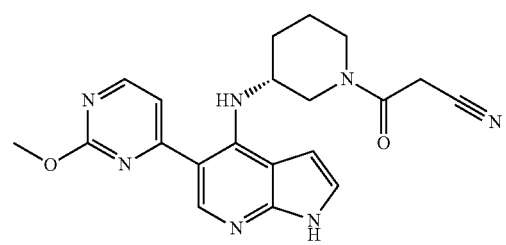 [SMILES: COc1nccc(-c2cnc3[nH]ccc3c2N[C@@H]2CCCN(C(=O)CC#N)C2)n1]

Scheme 41. Preparation of (R)-3-(3-((5-(2-methoxypyrimidin-4-yl)-1H-pyrrolo[2,3-b]pyridin-4-yl) amino) piperidin-1-yl)-3-oxopropanenitrile

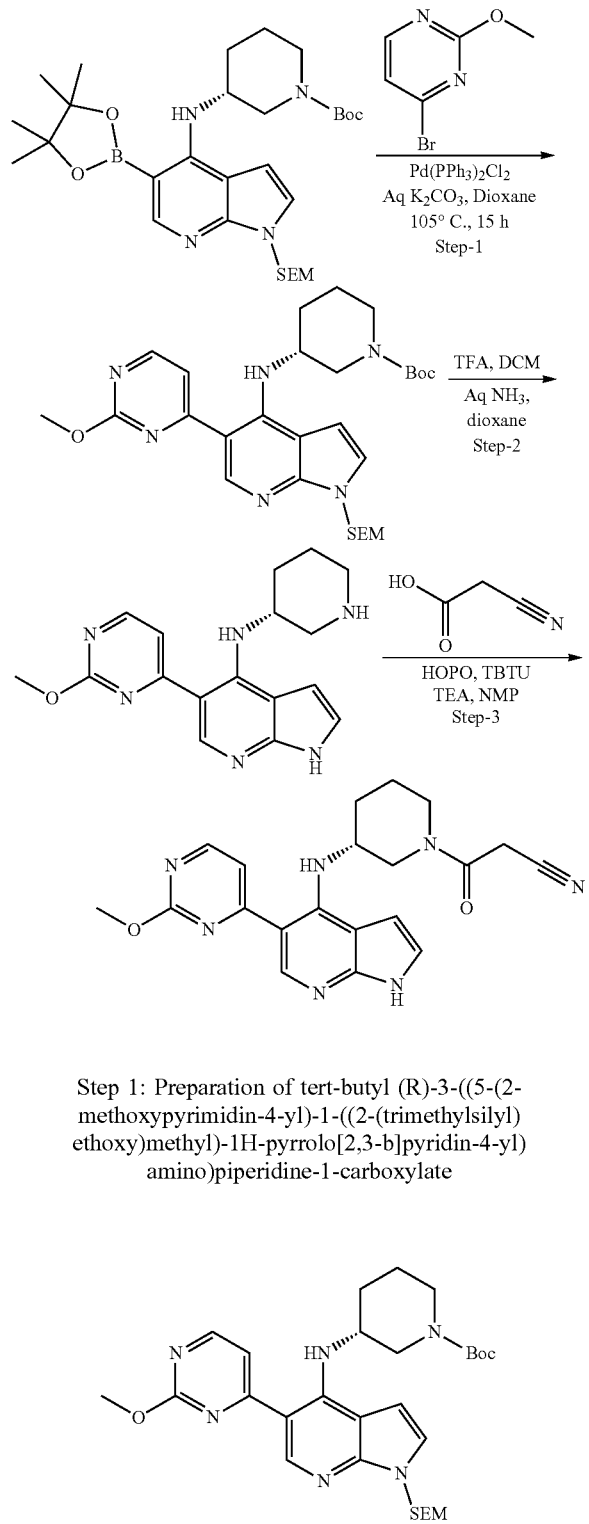

Step 1: Preparation of tert-butyl (R)-3-((5-(2-methoxypyrimidin-4-yl)-1-((2-(trimethylsilyl)ethoxy)methyl)-1H-pyrrolo[2,3-b]pyridin-4-yl)amino)piperidine-1-carboxylate To a stirred solution of tert-butyl (R)-3-((5-(4,4,5,5-tetramethyl-1,3,2-dioxaborolan-2-yl)-1-((2-(trimethyl silyl) ethoxy)methyl)-1H-pyrrolo[2,3-b]pyridin-4-yl)amino)piperidine-1-carboxylate (1.36 g, 2.38 mmol) and 4-bromo-2-methoxypyrimidine (0.30 g, 1.58 mmol) in 1,4-dioxane (15 mL) was added bis(triphenylphosphine) palladium(II) dichloride (0.22 g, 0.32 mmol) and 2M aqueous solution of potassium carbonate (0.87 g, 6.32 mmol) and the mixture stirred at 105° C. for 15 hours. The reaction mixture was cooled to ambient temperature, diluted with ethyl acetate, washed with water, brine, dried over anhydrous sodium sulfate, filtered and concentrated in vacuo. The crude material was purified by flash chromatography (30% ethyl acetate/hexane) to provide tert-butyl (R)-3-((5-(2-methoxypyrimidin-4-yl)-1-((2-(trimethylsilyl)ethoxy)methyl)-1H-pyrrolo[2,3-b]pyridin-4-yl)amino)piperidine-1-carboxylate as a viscous pale yellow liquid (0.62 g, 70% yield): MS (ES) m/z 555.5 (M+H).

Step 2: Preparation of (R)-5-(2-methoxypyrimidin-4-yl)-N-(piperidin-3-yl)-1H-pyrrolo[2,3-b]pyridin-4-amine

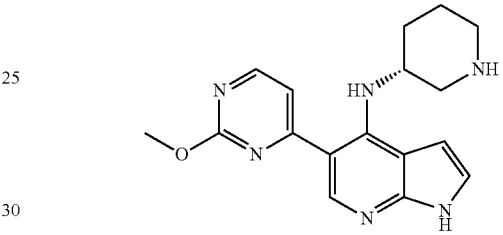

A solution of tert-butyl (R)-3-((5-(2-methoxypyrimidin-4-yl)-1-((2-(trimethylsilyl)ethoxy)methyl)-1H-pyrrolo[2,3-b]pyridin-4-yl)amino)piperidine-1-carboxylate (0.3 g, 0.54 mmol) in dichloromethane:trifluoroacetic acid (3 mL:3 mL) was stirred at ambient temperature for 3 hours. The reaction mixture was concentrated in vacuo, the obtained residue was dissolved in 1,4-dioxane:aqueous ammonia (3 mL:3 mL, 23% in water) and then stirred at ambient temperature for 16 hours. The reaction mixture was concentrated in vacuo to provide (R)-5-(2-methoxypyrimidin-4-yl)-N-(piperidin-3-yl)-1H-pyrrolo[2,3-b]pyridin-4-amine as a gummy brown liquid (0.18 g, crude): MS (ES) m/z 325.2 (M+H).

Step 3: Preparation of (R)-3-(3-((5-(2-methoxypyrimidin-4-yl)-1H-pyrrolo[2,3-b]pyridin-4-yl)amino)piperidin-1-yl)-3-oxopropanenitrile

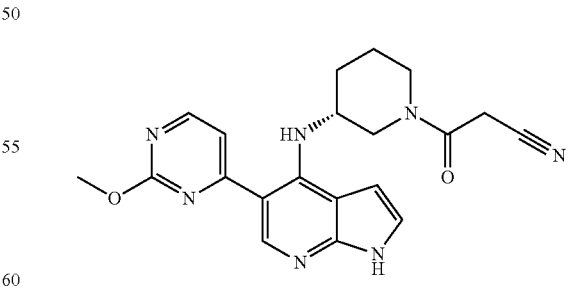

A solution of cyanoacetic acid (0.03 g, 0.32 mmol), 2-hydroxypyridine-N-oxide (0.03 g, 0.32 mmol) and O-(benzotriazol-1-yl)-N,N,N',N'-tetramethyluronium tetrafluoroborate (0.11 g, 0.32 mmol) in N-methylpyrrolidone (4 mL) was stirred at ambient temperature for 5 minutes. Then (R)-5-(2-methoxypyrimidin-4-yl)-N-(piperidin-3-yl)-

1H-pyrrolo[2,3-b]pyridin-4-amine (0.08 g, 0.25 mmol) was added followed by triethylamine (0.1 mL, 0.74 mmol). The resulting mixture was stirred at ambient temperature for 16 hours, quenched with water and extracted with dichloromethane. The organic layer was washed with water, brine, dried over anhydrous sodium sulfate, filtered and concentrated in vacuo. The crude material was purified by flash chromatography (5% methanol/dichloromethane) to provide (R)-3-(3-((5-(2-methoxypyrimidin-4-yl)-1H-pyrrolo[2,3-b]pyridin-4-yl)amino)piperidin-1-yl)-3-oxopropanenitrile as an off-white solid (0.04 g, 15% yield): $^1$H NMR (400 MHz, DMSO-$d_6$, VT at 100° C.) 11.27 (br s, 1H), 9.89 (br s, 1H), 8.44-8.59 (m, 2H), 7.55 (s, 1H), 7.15 (s, 1H), 6.66 (s, 1H), 4.16-4.27 (m, 2H), 4.39 (s, 2H), 3.83-3.87 (m, 2H), 3.45-3.55 (m, 2H), 2.05-2.10 (m, 2H), 1.58-1.95 (m, 4H); MS (ES) m/z 392.2 (M+H).

Example 44: Preparation of (R)-3-(3-((5-(6-aminopyridin-2-yl)-1H-pyrrolo[2,3-b]pyridin-4-yl)amino)piperidin-1-yl)-3-oxopropanenitrile

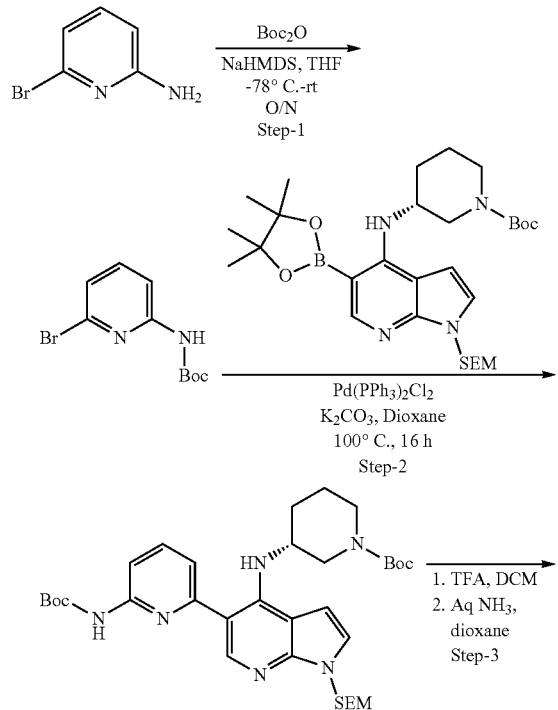

Scheme 42. Preparation of (R)-3-(3-((5-(6-aminopyridin-2-yl)-1H-pyrrolo[2,3-b]pyridin-4-yl)amino)piperidin-1-yl)-3-oxopropanenitrile

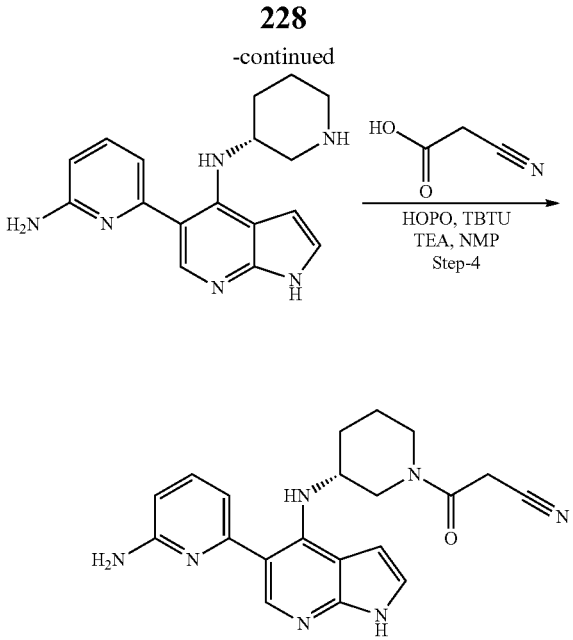

Step 1: Preparation of tert-butyl (6-bromopyridin-2-yl)carbamate

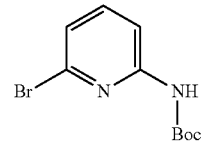

Sodium bis(trimethylsilyl)amide (6.1 mL, 6.13 mmol, 1.0 M in THF) was added to a solution of 6-bromopyridin-2-amine (0.70 g, 4.09 mmol) in tetrahydrofuran (15 mL) at −78° C. and the mixture stirred for 0.5 hours. A solution of di-tert-butyl dicarbonate (0.98 g, 4.50 mmol) dissolved in tetrahydrofuran (5 mL) was added at −78° C. and then the mixture was slowly warmed to ambient temperature and stirred for 16 hours. The reaction mixture was quenched with saturated ammonium chloride and extracted with ethyl acetate. The organic layer was washed with water, brine, dried over anhydrous sodium sulfate, filtered and concentrated in vacuo. The crude material was purified by flash chromatography (20% ethyl acetate/hexane) to provide tert-butyl (6-bromopyridin-2-yl)carbamate as a colorless semi solid: $^1$H NMR (400 MHz, DMSO-$d_6$) δ 10.07 (s, 1H), 7.76-7.78 (m, 1H), 7.62-7.66 (m, 1H), 7.20-7.22 (m, 1H), 1.44 (s, 9H); MS (ES) m/z 174.2 (M-Boc).

229

Step 2: Preparation of tert-butyl (R)-3-((5-(6-((tert-butoxycarbonyl)amino)pyridin-2-yl)-1-((2-(trimethylsilyl)ethoxy)methyl)-1H-pyrrolo[2,3-b]pyridin-4-yl)amino)piperidine-1-carboxylate

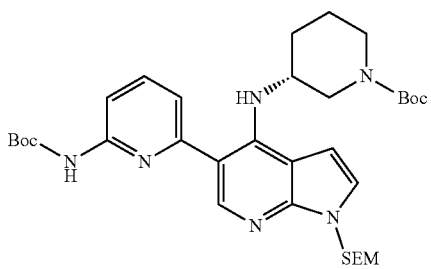 [SMILES: CC(C)(C)OC(=O)Nc1cccc(-c2cnc3c(ccn3COCC[Si](C)(C)C)c2N[C@@H]2CCCN(C(=O)OC(C)(C)C)C2)n1]

To a stirred solution of tert-butyl (R)-3-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate (1.2 g, 2.19 mmol) and tert-butyl (6-bromopyridin-2-yl)carbamate (0.4 g, 1.58 mmol) in 1,4-dioxane (40 mL) was added bis(triphenylphosphine) palladium(II) dichloride (0.2 g, 0.29 mmol) and 2M aqueous solution of potassium carbonate (0.81 g, 5.84 mmol) and the mixture was stirred at 100° C. for 16 hours. The reaction mixture was cooled to ambient temperature, diluted with ethyl acetate, washed with water, brine, dried over anhydrous sodium sulfate, filtered and concentrated in vacuo. The crude material was purified by flash chromatography (30% ethyl acetate/hexane) to provide tert-butyl (R)-3-((5-(6-((tert-butoxycarbonyl)amino)pyridin-2-yl)-1-((2-(trimethylsilyl)ethoxy)methyl)-1H-pyrrolo[2,3-b]pyridin-4-yl)amino)piperidine-1-carboxylate as a gummy pale liquid (0.42 g, 45% yield): MS (ES) m/z 639.4 (M+H).

Step 3: Preparation of (R)-5-(6-aminopyridin-2-yl)-N-(piperidin-3-yl)-1H-pyrrolo[2,3-b]pyridin-4-amine

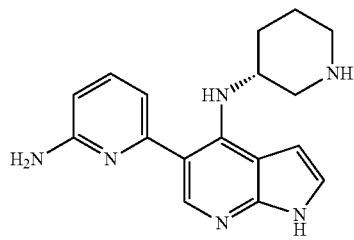 [SMILES: Nc1cccc(-c2cnc3[nH]ccc3c2N[C@@H]2CCCNC2)n1]

A solution of tert-butyl (R)-3-((5-(6-((tert-butoxycarbonyl)amino)pyridin-2-yl)-1-((2-(trimethylsilyl)ethoxy)methyl)-1H-pyrrolo[2,3-b]pyridin-4-yl)amino)piperidine-1-carboxylate (0.42 g, 0.66 mmol) in dichloromethane:trifluoroacetic acid (4 mL:4 mL) was stirred at ambient temperature for 3 hours. The reaction mixture was concentrated in vacuo, the residue was dissolved in 1,4-dioxane:aqueous ammonia (5 mL:5 mL, 23% in water) and the solution stirred at ambient temperature for 16 hours. The reaction mixture was concentrated in vacuo to provide (R)-5-(6-aminopyridin-2-yl)-N-(piperidin-3-yl)-1H-pyrrolo[2,3-b]pyridin-4-amine as an off-white solid (0.45 g, crude): MS (ES) m/z 309.2 (M+H).

230

Step 4: Preparation of (R)-3-(3-((5-(6-aminopyridin-2-yl)-1H-pyrrolo[2,3-b]pyridin-4-yl)amino)piperidin-1-yl)-3-oxopropanenitrile

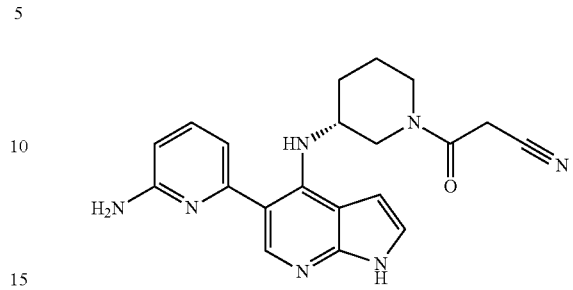

A solution of cyanoacetic acid (0.07 g, 0.84 mmol), 2-hydroxypyridine-N-oxide (0.08 g, 0.71 mmol) and 2-(1H-benzotriazole-1-yl)-1,1,3,3-tetramethylaminium tetrafluoroborate (0.27 g, 0.84 mmol) in N-methylpyrrolidone (5 mL) was stirred at ambient temperature for 5 minutes. Then (R)-5-(6-aminopyridin-2-yl)-N-(piperidin-3-yl)-1H-pyrrolo[2,3-b]pyridin-4-amine (0.08 g, 0.25 mmol) was added followed by triethylamine (0.27 mL, 1.95 mmol) and the resulting mixture stirred at ambient temperature for 18 hours. The reaction mixture was quenched with water and extracted with ethyl acetate. The organic layer was washed with water, brine, dried over anhydrous sodium sulfate, filtered and concentrated in vacuo. The crude material was purified by flash chromatography (10% methanol/dichloromethane) to provide (R)-3-(3-((5-(6-aminopyridin-2-yl)-1H-pyrrolo[2,3-b]pyridin-4-yl)amino)piperidin-1-yl)-3-oxopropanenitrile as an off-white solid (0.11 g, 45% yield): $^1$H NMR (400 MHz, DMSO-$d_6$, VT at 70° C.) 11.11 (br s, 1H), 9.58 (br s, 1H), 8.19 (s, 1H), 7.44 (s, 1H), 7.10 (s, 1H), 6.85 (s, 1H), 6.57 (s, 1H), 634-6.36 (m, 1H), 5.79 (s, 2H), 4.20-4.35 (m, 1H), 3.95-4.07 (m, 1H), 3.45-3.60 (m, 2H), 2.10-2.15 (m, 2H), 1.60-1.75 (m, 2H), 1.15-1.30 (m, 3H); MS (ES) m/z 376.2 (M+H).

Example 45: Preparation of 3-((3R)-3-((5-(5-(methylsulfinyl)thiazol-2-yl)-1H-pyrrolo[2,3-b]pyridin-4-yl)amino)piperidin-1-yl)-3-oxopropanenitrile

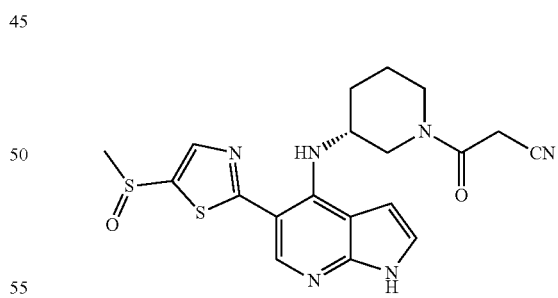

Scheme 43. Preparation of 3-((3R)-3-((5-(5-(methylsulfinyl)thiazol-2-yl)-1H-pyrrolo[2,3-b]pyridin-4-yl)amino)piperidin-1-yl)-3-oxopropanenitrile

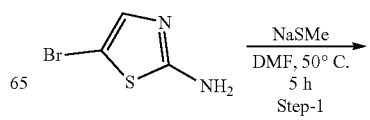

231

-continued

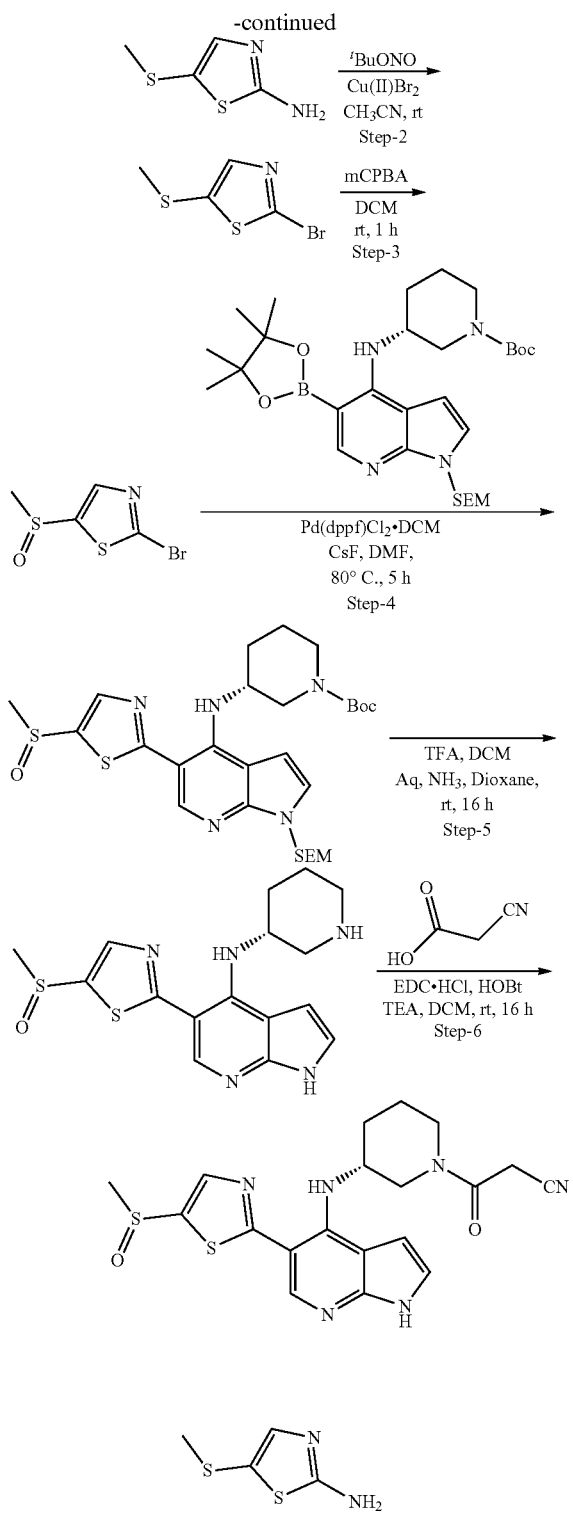

232 provide 5-(methylthio)thiazol-2-amine as a brown solid (1.5 g, 41% yield): $^1$H NMR (400 MHz, CDCl$_3$) δ 7.08 (s, 1H), 2.36 (s, 3H).

Step 2: Preparation of 2-bromo-5-(methylthio)thiazole

To a stirred solution of 5-(methylthio)thiazol-2-amine (1.5 g, 10.27 mmol) in acetonitrile (60 mL) was added tert-butyl nitrite (1.58 g, 15.40 mmol) at 0° C. and the mixture stirred for 15 minutes. Copper (II) bromide (6.87 g, 30.81 mmol) was added and the mixture stirred at 0° C. for 3 hours. The reaction mixture was diluted with ethyl acetate, washed with water and brine. The organic layer was dried over anhydrous sodium sulfate, filtered and concentrated in vacuo. The crude was purified using flash chromatography (5% ethyl acetate/hexane) to provide 2-bromo-5-(methylthio)thiazole as an orange oil (0.75 g, 34% yield): MS (ES) m/z 209.8; 211.0 (1:1; M+H).

Step 3: Preparation of 2-bromo-5-methanesulfinyl-1,3-thiazole

A solution of 2-bromo-5-(methylthio)-1,3-thiazole (0.59 g, 2.81 mmol) and meta-chloroperoxybenzoic acid (0.48 g, 2.81 mmol) in dichloromethane (20 mL) was stirred at ambient temperature for 1 hour. The reaction mixture was quenched with saturated bicarbonate solution and stirred for 30 minutes. The organic layer was separated, washed with water, brine, dried over sodium sulfate, filtered and concentrated in vacuo to obtain 2-bromo-5-methanesulfinyl-1,3-thiazole (0.35 g crude) as a viscous colorless liquid: MS (ES) m/z 226.0; 228.0 (1:1; M+H).

Step 4: Preparation of tert-butyl (3R)-3-((5-(5-(methylsulfinyl)thiazol-2-yl)-1-((2-(trimethylsilyl)ethoxy)methyl)-1H-pyrrolo[2,3-b]pyridin-4-yl)amino)piperidine-1-carboxylate

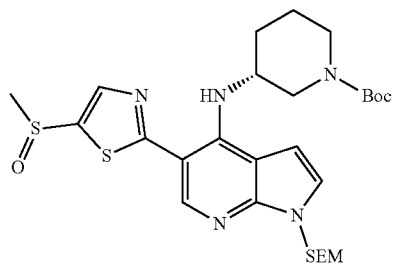 [SMILES: CS(=O)c1cnc(-c2cnc3c(ccn3COCC[Si](C)(C)C)c2N[C@@H]2CCCN(C(=O)OC(C)(C)C)C2)s1]

A solution of 5-bromothiazol-2-amine (4.5 g, 25.14 mmol) and sodium thiomethoxide (3.52 g, 50.28 mmol) in N,N-dimethylformamide (30 mL) was stirred at 50° C. for 5 hours. The reaction mixture was cooled to ambient temperature, diluted with ethyl acetate, washed with water and brine. The organic layer was dried over anhydrous sodium sulfate, filtered and concentrated in vacuo. The crude was purified using flash chromatography (30% ethyl acetate/hexane) to To a stirred solution of (3R)-1-methyl-N-[5-(4,4,5,5-tetramethyl-1,3,2-dioxaborolan-2-yl)-1-{[2-(trimethyl silyl)ethoxy]methyl}-1H-pyrrolo[2,3-b]pyridin-4-yl]piperidin-3-amine (1.5 g, 2.62 mmol) and 2-bromo-5-methanesulfinyl-1,3-thiazole (0.39 g, 1.75 mmol) in N,N-dimethylformamide (4.00 mL) was added 1,1'-bis(diphenylphosphino)ferrocene-palladium(II)dichloride dichloromethane complex (0.28 g, 0.35 mmol) and cesium fluoride (1.06 g, 6.99 mmol) and the resulting mixture heated at 80° C. for 5 hours. The reaction mixture was cooled to ambient temperature, diluted with ethyl acetate, washed with water and brine. The organic layer was dried over anhydrous sodium sulfate, filtered and concentrated in vacuo. The crude was purified using flash chromatography (50% ethyl acetate/hexane) to provide tert-butyl (3R)-3-{[5-(5-methanesulfinyl-1,3-thiazol-2-yl)-1-{[2-(trimethylsilyl)ethoxy]methyl}-1H-pyrrolo[2,3-b]pyridin-4-yl]amino}piperidine-1-carboxylate as a brown colored liquid (0.12 g, 11%, yield): MS (ES) m/z 593.4 (M+H).

Step 5: Preparation of 5-(5-(methylsulfinyl)thiazol-2-yl)-N-((R)-piperidin-3-yl)-1H-pyrrolo[2,3-b]pyridin-4-amine

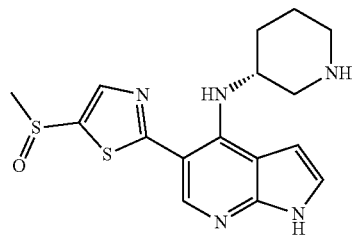 [SMILES: CS(=O)c1cnc(-c2cnc3[nH]ccc3c2N[C@@H]2CCCNC2)s1]

A solution of tert-butyl (3R)-3-{[5-(5-methanesulfinyl-1,3-thiazol-2-yl)-1-{[2-(trimethylsilyl)ethoxy]methyl}-1H-pyrrolo[2,3-b]pyridin-4-yl]amino}piperidine-1-carboxylate (0.12 g, 0.20 mmol) in dichloromethane:trifluoroacetic acid (2 mL:2 mL) was stirred at ambient temperature for 3 hours. The reaction mixture was concentrated in vacuo, the obtained residue was dissolved in 1,4-dioxane:aqueous ammonia (3 mL:3 mL, 23% in water) and then stirred at ambient temperature for 16 hours. The reaction mixture was concentrated in vacuo to provide (3R)-N-[5-(5-methanesulfinyl-1,3-thiazol-2-yl)-1H-pyrrolo[2,3-b]pyridin-4-yl]piperidin-3-amine as a gummy solid (0.2 g, crude): MS (ES) m/z 362.1 (M+H).

Step 6: Preparation of 3-((3R)-3-((5-(5-(methylsulfinyl)thiazol-2-yl)-1H-pyrrolo[2,3-b]pyridin-4-yl)amino)piperidin-1-yl)-3-oxopropanenitrile

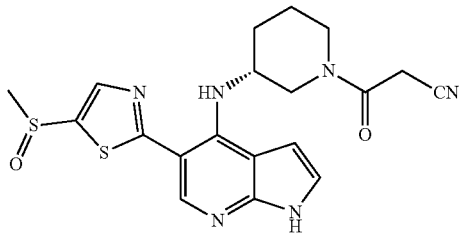 [SMILES: CS(=O)c1cnc(-c2cnc3[nH]ccc3c2N[C@@H]2CCCN(C(=O)CC#N)C2)s1]

A solution of 2-cyanoacetic acid (0.04 g, 0.45 mmol) and 1-hydroxybenzotriazole (0.05 g, 0.30 mmol) in dichloromethane (5 mL) was stirred for 2 minutes. Then (3R)-N-[5-(5-methanesulfinyl-1,3-thiazol-2-yl)-1H-pyrrolo[2,3-b]pyridin-4-yl]piperidin-3-amine (0.1 g, 0.3 mmol), N-(3-dimethylaminopropyl)-N'-ethylcarbodiimide hydrochloride (0.08 g, 0.41 mmol) and triethylamine (0.11 g, 1.11 mmol) were added and the mixture stirred at ambient temperature for 16 hours. The reaction mixture was quenched with water and extracted with ethyl acetate. The organic layer was washed with water, brine, dried over anhydrous sodium sulfate, filtered and concentrated in vacuo. The crude material was purified by reverse phase chromatography to provide 3-((3R)-3-((5-(5-(methylsulfinyl)thiazol-2-yl)-1H-pyrrolo[2,3-b]pyridin-4-yl)amino)piperidin-1-yl)-3-oxopropanenitrile as a pale yellow solid (5 mg, 4% yield): $^1$H NMR (400 MHz, DMSO-$d_6$) δ 11.73 (br s, 1H), 9.65 (br s, 1H), 8.44 (s, 1H), 8.17 (s, 1H), 8.07 (s, 1H), 7.24 (s, 1H), 6.71 (s, 1H), 5.91-6.11 (m, 1H), 5.31 (s, 1H), 4.12-4.50 (m, 1H), 3.75-4.22 (m, 2H), 3.42-3.72 (m, 2H), 2.95-3.12 (m, 3H), 1.95-2.10 (m, 1H), 1.45-1.82 (m, 2H); MS (ES) m/z 429.2 (M+H).

Analytical Conditions:
Flow rate: 0.3 mL/min
Column Ascentis Express C18 (50 mm×2.1 mm×2.73 μm)
Mobile Phase (A): 0.1% Formic acid in water
Mobile Phase (B): MeCN Example 46: Preparation of (R)-3-(3-((5-(5-(methylsulfonyl)thiazol-2-yl)-1H-pyrrolo[2,3-b]pyridin-4-yl)amino)piperidin-1-yl)-3-oxopropanenitrile

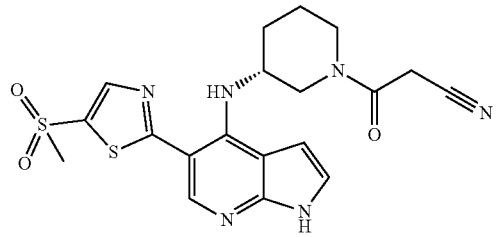 [SMILES: CS(=O)(=O)c1cnc(-c2cnc3[nH]ccc3c2N[C@@H]2CCCN(C(=O)CC#N)C2)s1]

Scheme 44. Preparation of (R)-3-(3-((5-(5-(methylsulfonyl)thiazol-2-yl)-1H-pyrrolo[2,3-b]pyridin-4-yl)amino) piperidin-1-yl)-3-oxopropanenitrile

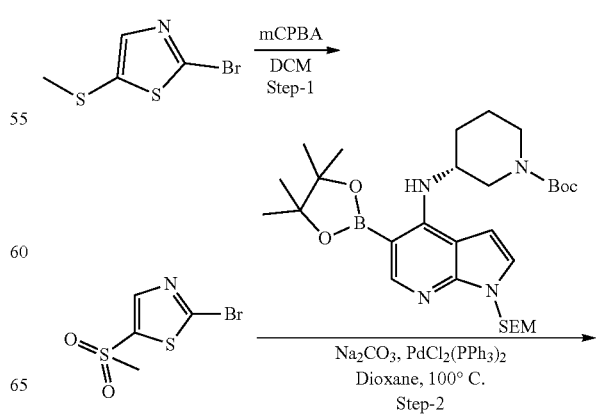

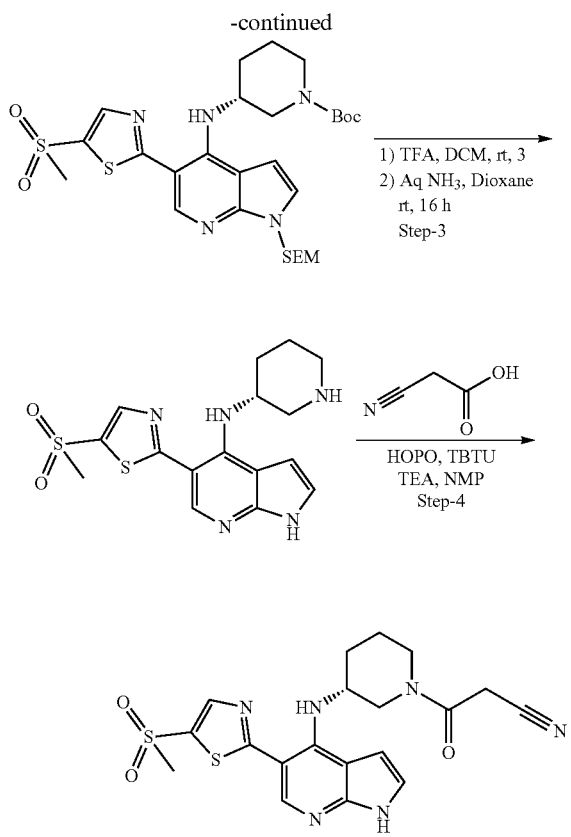

Step 1: Preparation of 2-bromo-5-(methylsulfonyl)thiazole

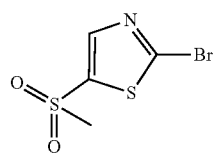

A solution of 2-bromo-5-(methylthio)-1,3-thiazole (0.59 g, 2.81 mmol) and meta-chloroperoxybenzoic acid (1.2 g, 7.02 mmol) in dichloromethane (20 mL) was stirred at ambient temperature for 3 hours. The reaction mixture was quenched with saturated bicarbonate solution and stirred for 30 minutes. The organic layer was separated, washed with water, brine, dried over sodium sulfate, filtered and concentrated in vacuo to obtain 2-bromo-5-methanesulfonyl-1,3-thiazole (0.35 g crude) as an off-white solid (0.45 g, 70% yield): $^1$H NMR (400 MHz, DMSO-$d_6$) δ 8.30 (s, 1H), 3.45 (s, 3H).

Step 2: Preparation of tert-butyl (R)-3-((5-(5-(methylsulfonyl)thiazol-2-yl)-1-((2-(trimethylsilyl)ethoxy)methyl)-1H-pyrrolo[2,3-b]pyridin-4-yl)amino)piperidine-1-carboxylate

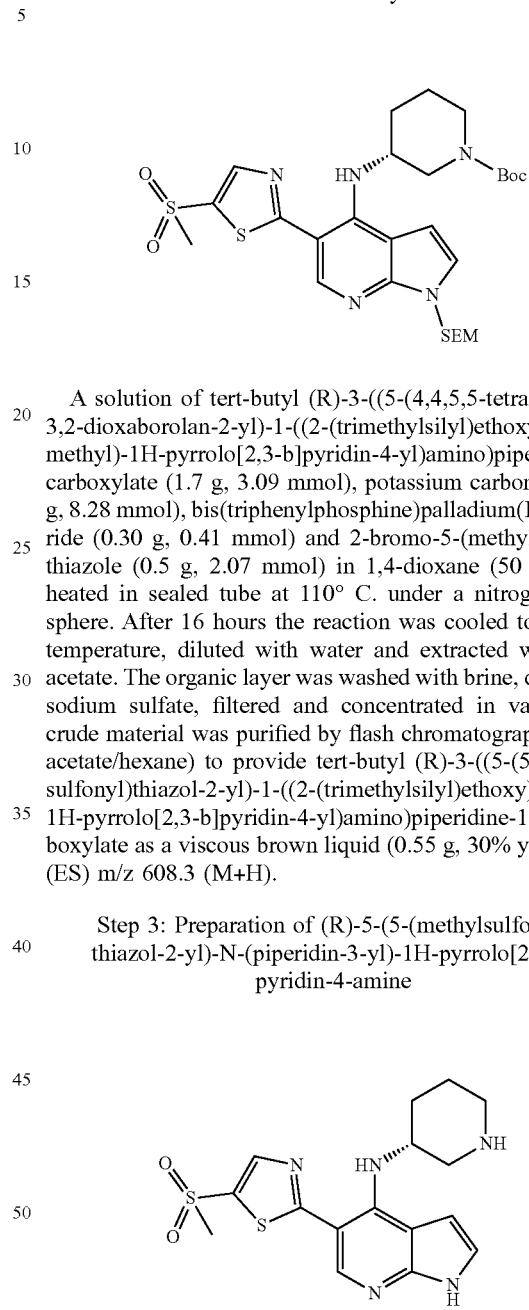

A solution of tert-butyl (R)-3-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate (1.7 g, 3.09 mmol), potassium carbonate (1.14 g, 8.28 mmol), bis(triphenylphosphine)palladium(II) dichloride (0.30 g, 0.41 mmol) and 2-bromo-5-(methylsulfonyl)thiazole (0.5 g, 2.07 mmol) in 1,4-dioxane (50 mL) was heated in sealed tube at 110° C. under a nitrogen atmosphere. After 16 hours the reaction was cooled to ambient temperature, diluted with water and extracted with ethyl acetate. The organic layer was washed with brine, dried over sodium sulfate, filtered and concentrated in vacuo. The crude material was purified by flash chromatography (ethyl acetate/hexane) to provide tert-butyl (R)-3-((5-(5-(methylsulfonyl)thiazol-2-yl)-1-((2-(trimethylsilyl)ethoxy)methyl)-1H-pyrrolo[2,3-b]pyridin-4-yl)amino)piperidine-1-carboxylate as a viscous brown liquid (0.55 g, 30% yield): MS (ES) m/z 608.3 (M+H).

Step 3: Preparation of (R)-5-(5-(methylsulfonyl)thiazol-2-yl)-N-(piperidin-3-yl)-1H-pyrrolo[2,3-b]pyridin-4-amine A solution of tert-butyl (R)-3-((5-(5-(methylsulfonyl)thiazol-2-yl)-1-((2-(trimethylsilyl)ethoxy)methyl)-1H-pyrrolo[2,3-b]pyridin-4-yl)amino)piperidine-1-carboxylate (0.55 g, 0.91 mmol) in dichloromethane:trifluoroacetic acid (5.0 mL:5.0 mL) was stirred at ambient temperature for 3 hours. The reaction mixture was concentrated in vacuo, the residue was dissolved in 1,4-dioxane:aqueous ammonia (5 mL:5 mL) and stirred at ambient temperature for 16 hours. The reaction mixture was concentrated in vacuo to provide (R)-5-(5-(methylsulfonyl)thiazol-2-yl)-N-(piperidin-3-yl)-1H-pyrrolo[2,3-b]pyridin-4-amine as a gummy brown solid (0.6 g, crude): MS (ES) m/z 378.1 (M+H).

Step 4: Preparation of (R)-3-(3-((5-(5-(methylsulfonyl)thiazol-2-yl)-1H-pyrrolo[2,3-b]pyridin-4-yl)amino) piperidin-1-yl)-3-oxopropanenitrile

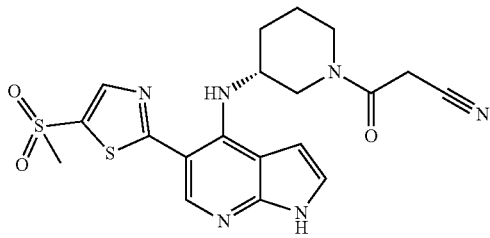 [SMILES: CS(=O)(=O)c1cnc(-c2cnc3[nH]ccc3c2N[C@@H]2CCCN(C(=O)CC#N)C2)s1]

To a stirred solution of cyanoacetic acid (0.03 g, 0.39 mmol), 1-hydroxy-2-pyridone (0.03 g, 0.31 mmol) and 2-(1H-benzotriazole-1-yl)-1,1,3,3-tetramethylamonium tetrafluoroborate (0.10 g, 0.31 mmol) in N-methylpyrrolidone (5 mL) was added (R)-5-(5-(methylsulfonyl)thiazol-2-yl)-N-(piperidin-3-yl)-1H-pyrrolo[2,3-b]pyridin-4-amine (0.1 g, 0.26 mmol) followed by triethylamine (0.11 mL, 0.79 mmol) and the resulting mixture stirred at ambient temperature for 2 hours. The reaction mixture was diluted with water and extracted with ethyl acetate. The organic layer was washed with brine, dried over sodium sulfate, filtered and concentrated in vacuo. The crude was purified by column chromatography to provide (R)-3-(3-((5-(5-(methylsulfonyl)thiazol-2-yl)-1H-pyrrolo[2,3-b]pyridin-4-yl)amino)piperidin-1-yl)-3-oxopropanenitrile as a yellow solid (0.01 g, 10% yield): $^1$H NMR (400 MHz, DMSO-$d_6$, VT at 100° C.) 11.58 (br s, 1H), 9.65 (br s, 1H), 8.42 (s, 1H), 8.24 (s, 1H), 7.21 (s, 1H), 6.71 (s, 1H), 3.54-4.44 (m, 6H), 3.42 (s, 3H), 1.21-2.04 (m, 5H); MS (ES) m/z 445.1 (M+H).

Example 47: Preparation of (R)-3-(3-((5-(5-(methylsulfonyl)thiazol-2-yl)-1H-pyrrolo[2,3-b]pyridin-4-yl)amino)piperidin-1-yl)propanenitrile

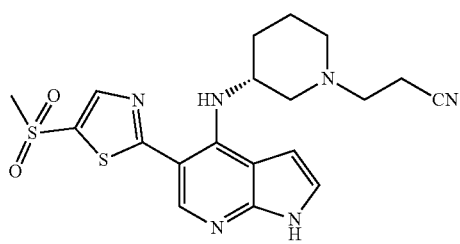 [SMILES: CS(=O)(=O)c1cnc(-c2cnc3[nH]ccc3c2N[C@@H]2CCCN(CCC#N)C2)s1]

Scheme 45. Preparation of (R)-3-(3-((5-(5-(methylsuflonyl)thiazol-2-yl)-1H-pyrrolo[2,3-b]pyridin-4-yl)amino)piperidin-1-yl)propanenitrile

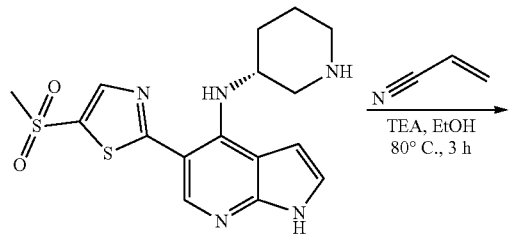

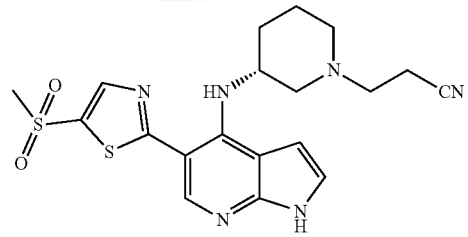

Preparation of (R)-3-(3-((5-(5-(methylsulfonyl)thiazol-2-yl)-1H-pyrrolo[2,3-b]pyridin-4-yl)amino) piperidin-1-yl)propanenitrile

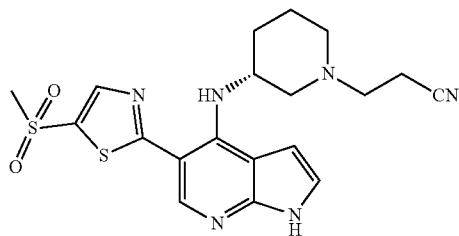 [SMILES: CS(=O)(=O)c1cnc(-c2cnc3[nH]ccc3c2N[C@@H]2CCCN(CCC#N)C2)s1]

To a solution of (R)-5-(5-(methylsulfonyl)thiazol-2-yl)-N-(piperidin-3-yl)-1H-pyrrolo[2,3-b]pyridin-4-amine (0.1 g, 0.26 mmol, Example 46, step 3) in ethanol (3 mL) was added acrylonitrile (0.14 g, 2.65 mmol) and triethylamine (0.06 ml, 0.79 mmol) and the solution stirred at 80° C. for 3 hours. The reaction was cooled to ambient temperature and concentrated in vacuo. The crude material was purified by reverse phase chromatography to provide (R)-3-(3-((5-(5-(methylsulfonyl)thiazol-2-yl)-1H-pyrrolo[2,3-b]pyridin-4-yl)amino)piperidin-1-yl)propanenitrile as an off-white solid (0.03 g, 25%): $^1$H NMR (400 MHz, DMSO-$d_6$) δ 9.83 (br s, 1H), 9.12 (br s, 1H), 8.45 (s, 1H), 8.24 (s, 1H), 7.10 (s, 1H), 6.69 (s, 1H), 4.32 (s, 1H), 3.24 (s, 3H), 2.95-3.07 (m, 1H), 2.65-2.85 (m, 2H), 2.37-2.67 (m, 4H), 1.80-2.04 (m, 2H), 1.16-1.30 (s, 3H); MS (ES) m/z 431.2 (M+H).

Analytical Conditions:
Flow rate: 20.0 ml/min
Column: Ascentis Express C18 (50 mm×2.1 mm×2.7 μm)
Mobile Phase (A): 1% Ammonia in water
Mobile Phase (B): MeCN Example 48: Preparation of (R)-3-(3-((5-(5-(methylsulfonyl)oxazol-2-yl)-1H-pyrrolo[2,3-b]pyridin-4-yl) amino)piperidin-1-yl)-3-oxopropanenitrile

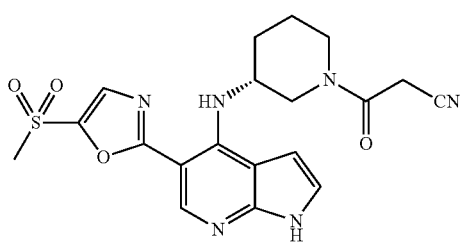 [SMILES: CS(=O)(=O)c1cnc(-c2cnc3[nH]ccc3c2N[C@@H]2CCCN(C(=O)CC#N)C2)o1]

Scheme 46. Preparation of (R)-3-((5-(5-(methylsulfonyl)oxazol-2-yl)-1H-pyrrolo[2,3-b]pyridin-4-yl) amino)piperidin-1-yl)-3-oxopropanenitrile
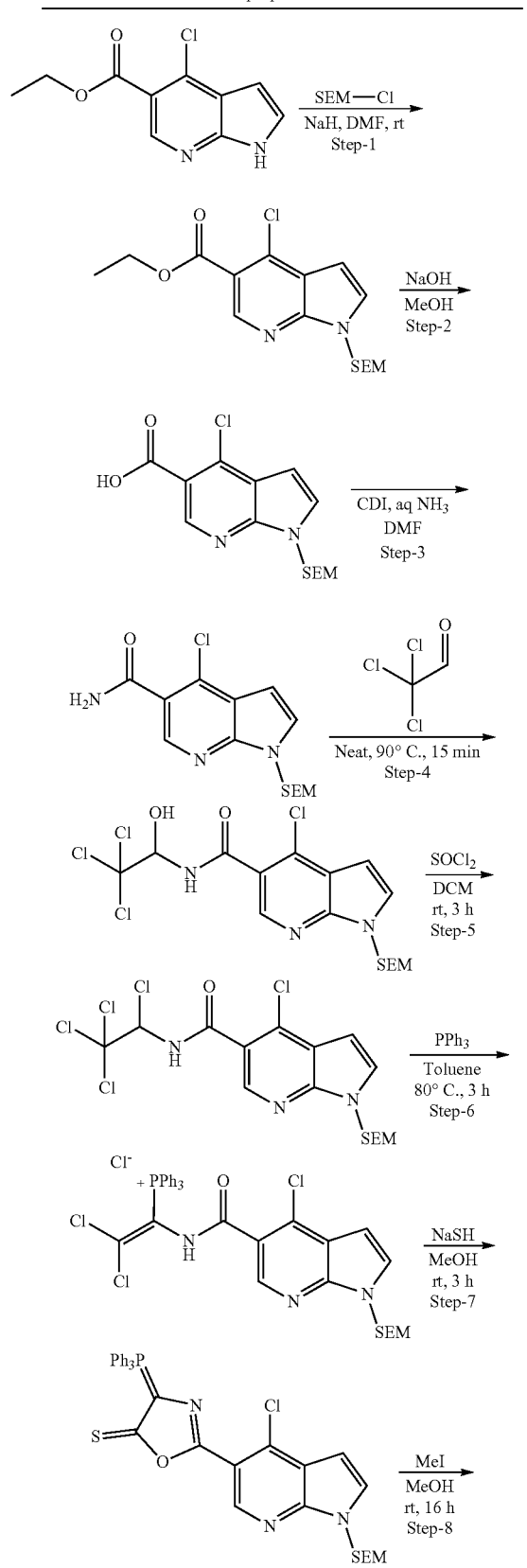
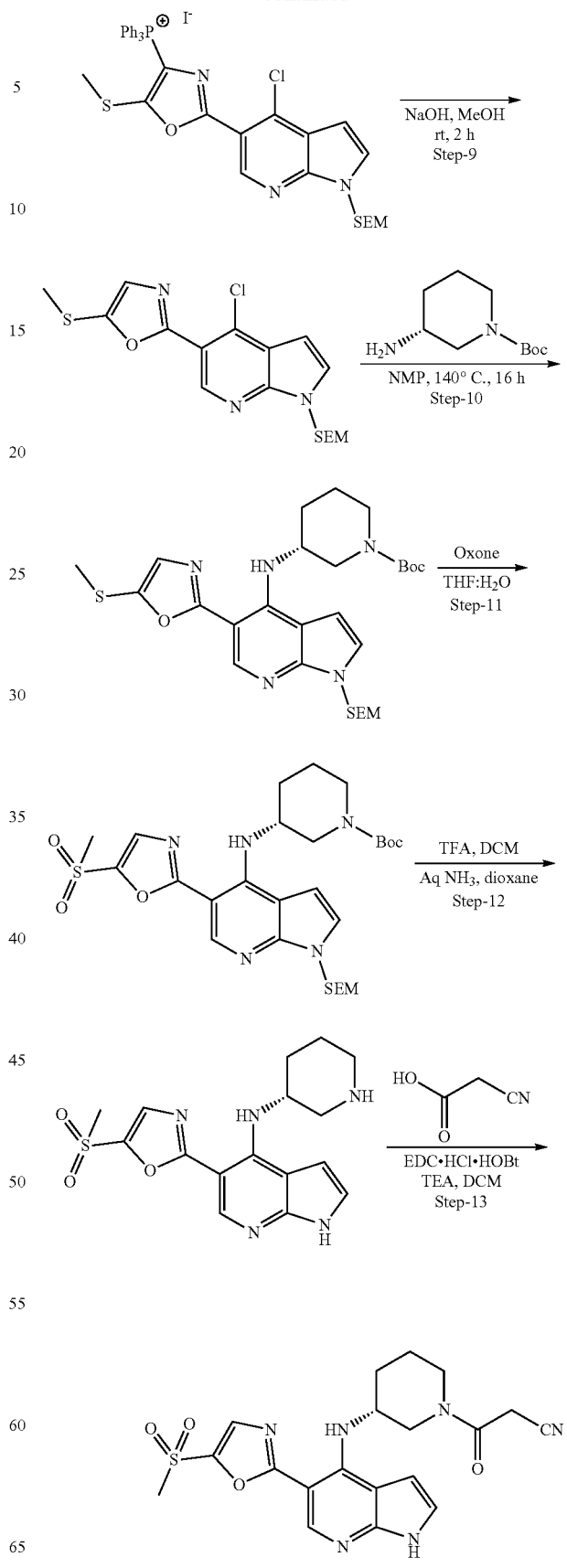

Step 1: Preparation of ethyl 4-chloro-1-((2-(trimethylsilyl)ethoxy)methyl)-1H-pyrrolo[2,3-b]pyridine-5-carboxylate

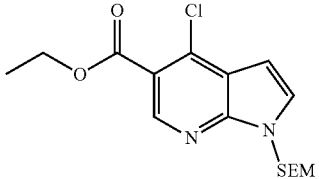 [SMILES: CCOC(=O)c1cnc2c(ccn2COCC[Si](C)(C)C)c1Cl]

To a stirred suspension of sodium hydride (2.14 g, 89.28 mmol, 60% in mineral oil) in N,N-dimethylformamide (75 mL) was added ethyl 4-chloro-1H-pyrrolo[2, 3-b]pyridine-5-carboxylate (10 g, 44.64 mmol) at 0° C. After stirring for 0.5 hour, 2-(trimethylsilyl)ethoxymethyl chloride (8.7 mL, 55.34 mmol) was added at 0° C. and the reaction stirred for 2 hours. The reaction was quenched with ice water and extracted with ethyl acetate. The organic layer was dried over anhydrous sodium sulfate, filtered and concentrated. The crude was purified using flash chromatography (15% ethyl acetate/hexane) to provide ethyl 4-chloro-1-((2-(trimethyl silyl)ethoxy)methyl)-1H-pyrrolo[2,3-b]pyridine-5-carboxylate as a colorless liquid (7.8 g, 49% yield): MS (ES) m/z 355.1 (M+H).

Step 2: Preparation of 4-chloro-1-((2-(trimethylsilyl)ethoxy)methyl)-1H-pyrrolo[2,3-b]pyridine-5-carboxylic acid

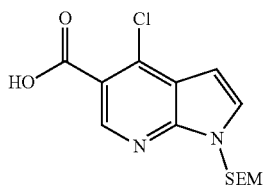 [SMILES: C[Si](C)(C)CCOCn1ccc2c(Cl)c(C(=O)O)cnc21]

To a solution of ethyl 4-chloro-1-((2-(trimethylsilyl)ethoxy)methyl)-1H-pyrrolo[2,3-b]pyridine-5-carboxylate (7.8, 21.91 mmol) in methanol (80 mL) was added 2M aqueous solution of sodium hydroxide (4.38 g, 109.55 mmol) and the mixture stirred at ambient temperature for 5 hours. The reaction was concentrated to remove volatiles to obtain a residue which was dissolved in water and acidified with 1N hydrochloric acid to adjust pH3. The aqueous layer was extracted with ethyl acetate, dried over anhydrous sodium sulfate, filtered and concentrated in vacuo to provide 4-chloro-1-((2-(trimethylsilyl)ethoxy)methyl)-1H-pyrrolo[2,3-b]pyridine-5-carboxylic acid as an off-white solid (6.3 g, 88% yield): MS (ES) m/z: 327.1 (M+H).

Step 3: Preparation of 4-chloro-1-((2-(trimethylsilyl)ethoxy)methyl)-1H-pyrrolo[2,3-b]pyridine-5-carboxamide

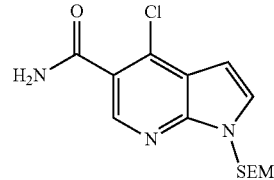 [SMILES: C[Si](C)(C)CCOCn1ccc2c(Cl)c(C(N)=O)cnc21]

A solution of 4-chloro-1-((2-(trimethylsilyl)ethoxy)methyl)-1H-pyrrolo[2,3-b]pyridine-5-carboxylic acid (6.3 g, 19.32 mmol) and carbonyldiimidazole (4.7 g, 28.98 mmol) in dimethylformamide (30 mL) was stirred at ambient temperature for 1 hour. Ammonia (10 mL, 23% in water) was added followed by N,N-diisopropylethylamine (5.0 mL, 28.98 mmol) and the solution stirred for 3 hours. The reaction was quenched with ice water and extracted with ethyl acetate. The organic layer was dried over anhydrous sodium sulfate, filtered and concentrated. The crude was purified using flash chromatography (30% ethyl acetate/hexane) to provide an off-white solid (4.56 g, 72%, yield): MS (ES) m/z: 326.1 (M+H).

Step 4: Preparation of 4-chloro-N-(2,2,2-trichloro-1-hydroxyethyl)-1-((2-(trimethylsilyl)ethoxy)methyl)-1H-pyrrolo[2,3-b]pyridine-5-carboxamide

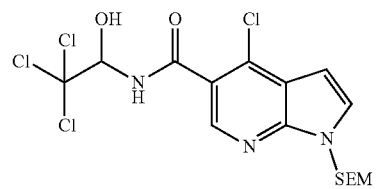 [SMILES: C[Si](C)(C)CCOCn1ccc2c(Cl)c(C(=O)NC(O)C(Cl)(Cl)Cl)cnc21]

A solid mixture of 4-chloro-1-((2-(trimethylsilyl)ethoxy)methyl)-1H-pyrrolo[2,3-b]pyridine-5-carboxamide (3.0 g, 9.21 mmol) and 2,2,2-trichloroacetaldehyde (1.36 g, 9.21 mmol) was heated to 90° C. until complete melting. The reaction mixture was cooled to ambient temperature and the crude product was purified using flash chromatography (30% ethyl acetate/hexane) to provide 4-chloro-N-(2,2,2-trichloro-1-hydroxyethyl)-1-((2-(trimethylsilyl)ethoxy)methyl)-1H-pyrrolo[2,3-b]pyridine-5-carboxamide as an off-white solid (2 g, 47% yield): MS (ES) m/z: 474.2 (M+H).

Step 5: Preparation of 4-chloro-N-(1,2,2,2-tetrachloroethyl)-1-((2-(trimethylsilyl)ethoxy)methyl)-1H-pyrrolo[2,3-b]pyridine-5-carboxamide

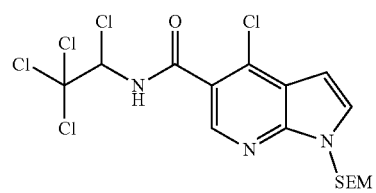 [SMILES: C[Si](C)(C)CCOCn1ccc2c(Cl)c(C(=O)NC(Cl)C(Cl)(Cl)Cl)cnc21]

To a solution of 4-chloro-N-(2,2,2-trichloro-1-hydroxyethyl)-1-{[2-(trimethylsilyl)ethoxy]methyl}-1H-pyrrolo[2,3-b]pyridine-5-carboxamide (1.30 g, 2.75 mmol) in dichloromethane (30 mL) was added thionyl chloride (0.24 mL, 3.30 mmol) and the solution stirred at ambient temperature. After 3 hours the reaction was concentrated in vacuo under a nitrogen atmosphere to provide 4-chloro-N-(1,2,2,2-tetrachloroethyl)-1-{[2-(trimethylsilyl)ethoxy]methyl}-1H-pyrrolo[2,3-b]pyridine-5-carboxamide as a colorless gum (1.35 g, crude). The crude product was taken to next step without further purification.

Step 6: Preparation of (2,2-dichloro-1-(4-chloro-1-((2-(trimethylsilyl)ethoxy)methyl)-1H-pyrrolo[2,3-b]pyridine-5-carboxamido)vinyl)triphenylphosphoniumchloride

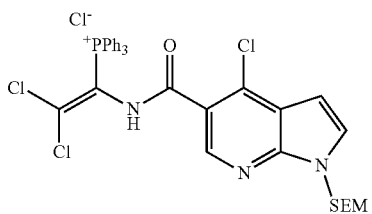

To a stirred solution of 4-chloro-N-(1,2,2,2-tetrachloroethyl)-1-{[2-(trimethylsilyl)ethoxy]methyl}-1H-pyrrolo[2,3-b]pyridine-5-carboxamide (1.35 g, 2.75 mmol) in toluene (30 mL) was added triphenylphosphine (0.72 g, 2.75 mmol) and the solution was heated to 80° C. After 3 hours the reaction was cooled to ambient temperature and concentrated in vacuo to provide (2,2-dichloro-1-(4-chloro-1-((2-(trimethylsilyl)ethoxy) methyl)-1H-pyrrolo[2,3-b]pyridine-5-carboxamido)vinyl)triphenylphosphonium chloride as a colorless gum (2.07 g, crude): MS (ES) m/z: 682.4 (M-Cl).

Step 7: Preparation of 2-(4-chloro-1-{[2-(trimethylsilyl)ethoxy]methyl}-1H-pyrrolo[2,3-b]pyridin-5-yl)-4-(triphenyl-λ⁵-phosphanylidene)-4,5-dihydro-1,3-oxazole-5-thione

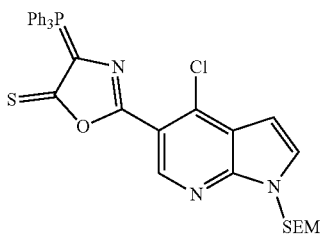

To a stirred solution of (2,2-dichloro-1-(4-chloro-1-((2-(trimethylsilyl)ethoxy)methyl)-1H-pyrrolo[2,3-b]pyridine-5-carboxamido)vinyl)triphenylphosphonium chloride (2.0 g, 2.78 mmol) in methanol (45 mL) was added sodium hydrosulfide (0.5 g, 8.80 mmol) and the mixture stirred at ambient temperature. After 3 hours the reaction mixture was diluted with ethyl acetate and washed with water and brine. The organic layer was dried over anhydrous sodium sulfate, filtered and concentrated. The crude was purified using flash chromatography (50% ethyl acetate/hexane) to provide 2-(4-chloro-1-{[2-(trimethylsilyl)ethoxy]methyl}-1H-pyrrolo[2, 3-b]pyridin-5-yl)-4-(triphenyl-λ⁵-phosphanylidene)-4,5-dihydro-1,3-oxazole-5-thione as a pale yellow thick liquid (1.23 g, 65% yield): MS (ES) m/z: 642.2 (M+H).

Step 8: Preparation of (2-(4-chloro-1-((2-(trimethylsilyl)ethoxy)methyl)-1H-pyrrolo[2,3-b]pyridin-5-yl)-5-(methylthio)oxazol-4-yl)triphenylphosphoniumiodide

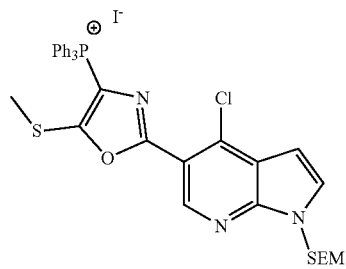

To a stirred solution of 2-(4-chloro-1-{[2-(trimethylsilyl)ethoxy]methyl}-1H-pyrrolo[2,3-b]pyridin-5-yl)-4-(triphenyl-λ⁵-phosphanylidene)-4,5-dihydro-1,3-oxazole-5-thione (1.35 g, 2.10 mmol) in methanol (30 mL) was added iodomethane (0.9 g, 6.31 mmol) and the mixture stirred at ambient temperature for 16 hours. The reaction mixture was concentrated in vacuo to dryness to provide [2-(4-chloro-1-{[2-(trimethylsilyl)ethoxy]methyl}-1H-pyrrolo[2,3-b]pyridin-5-yl)-5-(methylsulfanyl)-1,3-oxazol-4-yl]triphenylphosphanium iodide as a viscous pale yellow liquid (1.50 g, crude): MS (ES) m/z: 656.2 (M-I).

Step 9: Preparation of 2-(4-chloro-1-((2-(trimethylsilyl)ethoxy)methyl)-1H-pyrrolo[2,3-b]pyridin-5-yl)-5-(methylthio)oxazole

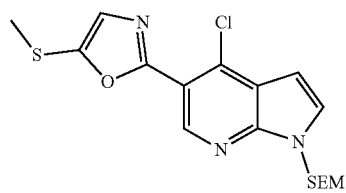 [SMILES: CSc1cnc(-c2cnc3c(ccn3COCC[Si](C)(C)C)c2Cl)o1]

To a stirred solution of 2-(4-chloro-1-{[2-(trimethylsilyl)ethoxy]methyl}-1H-pyrrolo[2,3-b]pyridin-5-yl)-5-(methylsulfanyl)-1,3-oxazol-4-yl]triphenylphosphanium iodide (1.50 g, 2.28 mmol) in methanol (2 mL) was added 2 M aqueous solution of sodium hydroxide (0.36 g, 9.13 mmol) and the solution stirred at ambient temperature for 2 hours. The reaction mixture was diluted with ethyl acetate, washed with water, brine, dried over anhydrous sodium sulfate, filtered and concentrated in vacuo. The crude material was purified by flash chromatography (10% ethyl acetate/hexane) to provide 2-(4-chloro-1-((2-(trimethylsilyl)ethoxy)methyl)-1H-pyrrolo[2,3-b]pyridin-5-yl)-5-(methylthio)oxazole as a pale yellow liquid (0.22 g, 24% yield): MS (ES) m/z: 396.1 (M+H).

Step 10: Preparation of tert-butyl (R)-3-((5-(5-(methylthio)oxazol-2-yl)-1-((2-(trimethylsilyl)ethoxy)methyl)-1H-pyrrolo[2,3-b]pyridin-4-yl)amino)piperidine-1-carboxylate

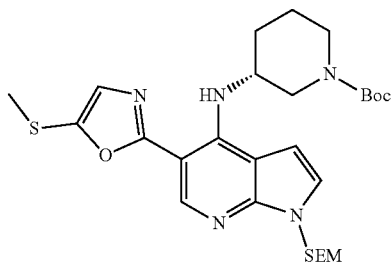 [SMILES: CSc1cnc(-c2cnc3c(ccn3COCC[Si](C)(C)C)c2N[C@@H]2CCCN(C(=O)OC(C)(C)C)C2)o1]

In a 10 mL vial, a solution of 2-(4-chloro-1-{[2-(trimethylsilyl)ethoxy]methyl}-1H-pyrrolo[2,3-b]pyridin-5-yl)-5-(methylsulfanyl)-1,3-oxazole (0.4 g, 1.01 mmol), tert-butyl (3R)-3-aminopiperidine-1-carboxylate (0.4 g, 2.02 mmol) and N,N-diisopropylethylamine (0.39 g, 3.03 mmol) in N-methyl-2-pyrrolidone (10 mL) was heated to 140° C. for 16 hours. The reaction mixture was cooled to ambient temperature, diluted with ethyl acetate and washed with water and brine. The organic layer was dried over anhydrous sodium sulfate, filtered and concentrated in vacuo. The crude material was purified using flash chromatography (30% ethyl acetate/hexane) to provide tert-butyl (3R)-3-({5-[5-(methylsulfanyl)-1,3-oxazol-2-yl]-1-{[2-(trimethylsilyl)ethoxy]methyl}-1H-pyrrolo[2,3-b]pyridin-4-yl}amino)piperidine-1-carboxylate as a viscous brown liquid (0.41 g, 72% yield): MS (ES) m/z: 560.5 (M+H).

Step 11: Preparation of tert-butyl (R)-3-((5-(5-(methylsulfonyl)oxazol-2-yl)-1-((2-(trimethylsilyl)ethoxy)methyl)-1H-pyrrolo[2,3-b]pyridin-4-yl)amino)piperidine-1-carboxylate

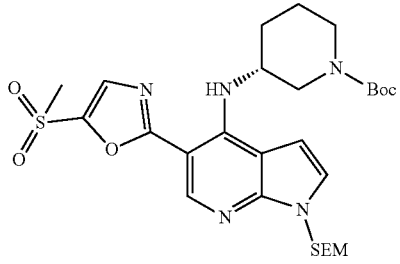 [SMILES: CC(C)(C)OC(=O)N1CCC[C@@H](Nc2c(-c3ncc(S(C)(=O)=O)o3)cnc3c2ccn3COCC[Si](C)(C)C)C1]

To a stirred solution of tert-butyl (3R)-3-({5-[5-(methylsulfanyl)-1,3-oxazol-2-yl]-1-{[2-(trimethylsilyl)ethoxy]methyl}-1H-pyrrolo[2,3-b]pyridin-4-yl}amino)piperidine-1-carboxylate (0.38 g, 0.68 mmol) in tetrahydrofuran:water (10 mL:3 mL) was added oxone (1.68 g, 2.72 mmol) and the mixture stirred at ambient temperature for 16 hours. The reaction mixture was diluted with ethyl acetate, washed with water and brine. The organic layer was dried over anhydrous sodium sulfate, filtered and concentrated in vacuo. The crude was purified using flash chromatography (40% ethyl acetate/hexane) to provide tert-butyl (3R)-3-{[5-(5-methanesulfonyl-1,3-oxazol-2-yl)-1-{[2-(trimethylsilyl)ethoxy]methyl}-1H-pyrrolo[2,3-b]pyridin-4-yl]amino}piperidine-1-carboxylate as a pale yellow gummy solid (0.32 g, 80% yield): MS (ES) m/z: 592.5 (M+H).

Step 12: Preparation of (R)-5-(5-(methylsulfonyl)oxazol-2-yl)-N-(piperidin-3-yl)-1H-pyrrolo[2,3-b]pyridin-4-amine

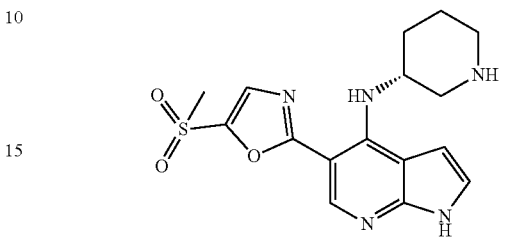

A solution of tert-butyl (3R)-3-{[5-(5-methanesulfonyl-1,3-oxazol-2-yl)-1-{[2-(trimethylsilyl)ethoxy]methyl}-1H-pyrrolo[2,3-b]pyridin-4-yl]amino}piperidine-1-carboxylate (0.26 g, 439 μmol) in dichloromethane:trifluoroacetic acid (5 mL:5 mL) was stirred at ambient temperature for 3 hours. The mixture was concentrated in vacuo, the residue was dissolved in 1,4-dioxane:aqueous ammonia (5 mL:5 mL (23% in water) and the solution stirred at ambient temperature for 16 hours. The reaction mixture was concentrated in vacuo to dryness to provide (3R)-N-[5-(5-methanesulfonyl-1,3-oxazol-2-yl)-1H-pyrrolo[2,3-b]pyridin-4-yl]piperidin-3-amine as a colorless gummy solid (0.32 g, 80% yield): MS (ES) m/z: 362.2 (M+H).

Step 13: Preparation of (R)-3-(3-((5-(5-(methylsulfonyl)oxazol-2-yl)-1H-pyrrolo[2,3-b]pyridin-4-yl)amino)piperidin-1-yl)-3-oxopropanenitrile

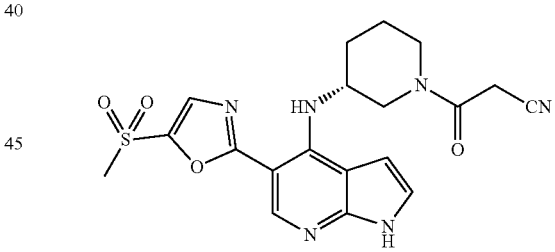

A solution of 2-cyanoacetic acid (0.04 g, 0.45 mmol) and 1-hydroxybenzotriazole (0.06 g, 0.4 mmol) in dichloromethane (10 mL) was stirred for 2 minutes. Then (3R)-N-[5-(5-methanesulfonyl-1,3-oxazol-2-yl)-1H-pyrrolo[2,3-b]pyridin-4-yl]piperidin-3-amine (0.11 g, 0.30 mmol), N-(3-dimethylaminopropyl)-N'-ethylcarbodiimide hydrochloride (0.09 g, 0.46 mmol) and triethylamine (0.18 mL, 1.12 mmol) were added and the mixture stirred at ambient temperature for 16 hours. The reaction mixture was quenched with water and extracted with ethyl acetate. The organic layer was washed with water, brine, dried over anhydrous sodium sulfate, filtered and concentrated in vacuo. The crude material was purified by reverse phase chromatography to provide 3-[(3R)-3-{[5-(5-methanesulfonyl-1,3-oxazol-2-yl)-1H-pyrrolo[2,3-b]pyridin-4-yl]amino}piperidin-1-yl]-3-oxopropanenitrile as an off-white solid (0.03 g, 60% yield): $^1$H NMR (400 MHz, DMSO-$d_6$, VT at 80° C.) δ 11.58 (br s, 1H), 8.74 (d, J=5.6 Hz, 1H), 8.62 (s, 1H), 7.93 (s, 1H), 7.23 (s, 1H), 6.71 (s, 1H), 4.24-4.43 (m, 1H), 3.71-4.05 (m, 3H), 3.41-3.55 (m, 6H), 2.80-2.11 (m, 1H), 1.55-1.85 (m, 3H); MS (ES) m/z 429.1 (M+H).

Analytical Conditions:

Flow rate: 0.3 mL/min

Column: Ascentis Express C18 (50 mm×2.1 mm×2.7 μm)

Mobile Phase (A): 0.1% Formic acid in water

Mobile Phase (B): MeCN

Example 49: Preparation of (R)-3-(3-((5-(2-(methylthio)pyrimidin-4-yl)-1H-pyrrolo[2,3-b]pyridin-4-yl)amino)piperidin-1-yl)-3-oxopropanenitrile

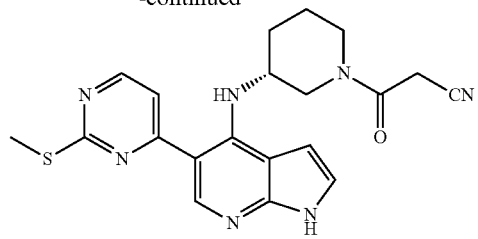

Step 1: Preparation of tert-butyl (R)-3-((5-(2-(methylthio)pyrimidin-4-yl)-1-((2-(trimethylsilyl)ethoxy)methyl)-1H-pyrrolo[2,3-b]pyridin-4-yl)amino)piperidine-1-carboxylate

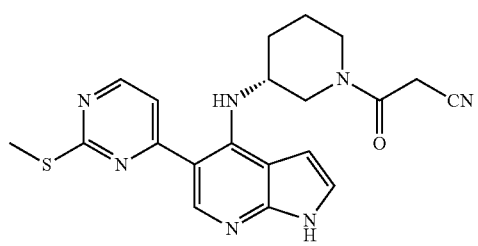 [SMILES: CSc1nccc(-c2cnc3[nH]ccc3c2N[C@@H]2CCCN(C(=O)CC#N)C2)n1]

Scheme 47. Preparation of (R)-3-(3-((5-(2-(methylthio)pyrimidin-4-yl)-1H-pyrrolo[2,3-b]pyridin-4-yl)amino)piperidin-1-yl)-3-oxopropanenitrile

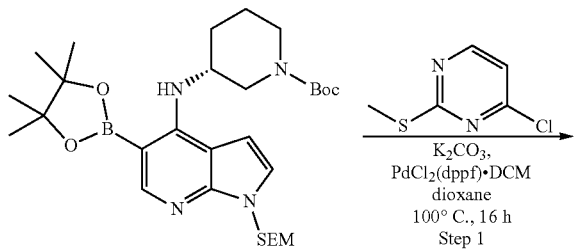

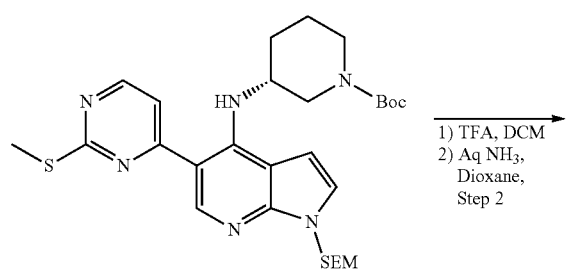

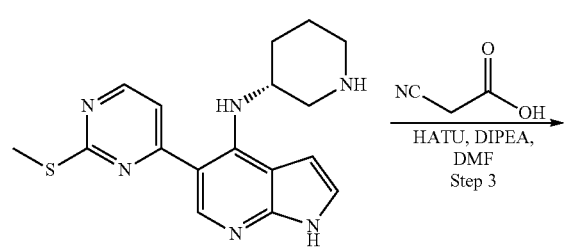

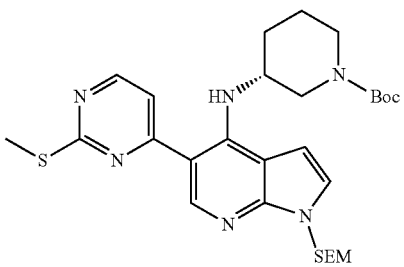 [SMILES: CSc1nccc(-c2cnc3c(ccn3COCC[Si](C)(C)C)c2N[C@@H]2CCCN(C(=O)OC(C)(C)C)C2)n1]

To a stirred solution of 4-chloro-2-(methylthio)pyrimidine (0.30 g, 1.87 mmol) and tert-butyl (R)-3-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate (1.07 g, 1.87 mmol) in 1,4-dioxane (40 mL) was added [1,1'-bis(diphenylphosphino) ferrocene]dichloropalladium(II) complex with dichloromethane (0.08 g, 0.09 mmol) and potassium carbonate (0.64 g, 4.68 mmol) and the mixture heated to 100° C. for 16 hours. The reaction was cooled to ambient temperature and diluted with ethyl acetate and water. The organic layer was separated, dried over sodium sulfate, filtered and concentrated in vacuo. The crude residue was purified using flash chromatography (40% ethyl acetate/hexane) to provide tert-butyl (R)-3-((5-(2-(methylthio)pyrimidin-4-yl)-1-((2-(trimethylsilyl) ethoxy)methyl)-1H-pyrrolo[2,3-b]pyridin-4-yl)amino)piperidine-1-carboxylate as a yellow liquid (0.5 g, 50% yield): MS (ES) m/z 571.4 (M+H).

Step 2: Preparation of (R)-5-(2-(methylthio)pyrimidin-4-yl)-N-(piperidin-3-yl)-1H-pyrrolo[2,3-b]pyridin-4-amine

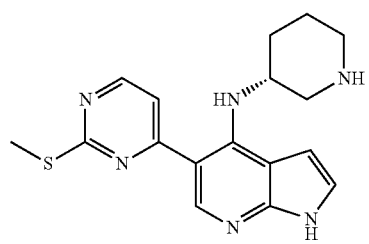

A solution of tert-butyl (R)-3-((5-(2-(methylthio)pyrimidin-4-yl)-1-((2-(trimethylsilyl)ethoxy)methyl)-1H-pyrrolo[2,3-b]pyridin-4-yl)amino)piperidine-1-carboxylate (0.35 g, 0.61 mmol) in dichloromethane:trifluoroacetic acid (3 mL:6 mL) was stirred at ambient temperature for 3 hours. The reaction mixture was concentrated in vacuo and the residue was dissolved in 1,4-dioxane:aqueous ammonia (3 mL:5 mL, 23% in water) and the reaction mixture stirred at ambient temperature for 16 hours. The reaction was concentrated in vacuo to provide (R)-5-(2-(methylthio)pyrimidin-4-yl)-N-(piperidin-3-yl)-1H-pyrrolo[2,3-b]pyridin-4-amine as a yellow solid (0.3 g, crude): MS (ES) m/z 341.1 (M+H).

Step 3: (R)-3-(3-((5-(2-(methylthio)pyrimidin-4-yl)-1H-pyrrolo[2,3-b]pyridin-4-yl)amino)piperidin-1-yl)-3-oxopropanenitrile

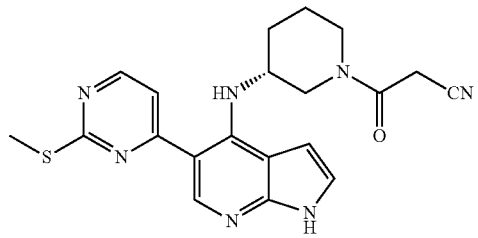 [SMILES: CSc1nccc(-c2cnc3[nH]ccc3c2N[C@@H]2CCCN(C(=O)CC#N)C2)n1]

A solution of cyanoacetic acid (0.11 g, 1.32 mmol) and (1-[bis(dimethylamino)methylene]-1H-1,2,3-triazolo[4,5-b]pyridinium 3-oxide hexafluorophosphate (0.40 g, 1.05 mmol) in N,N-dimethylformamide (60 mL) was stirred for 3 minutes. Then (R)-5-(2-(methylthio)pyrimidin-4-yl)-N-(piperidin-3-yl)-1H-pyrrolo[2,3-b]pyridin-4-amine (0.30 g, 0.88 mmol) was added followed by N,N-diisopropylethylamine (0.48 mL, 2.64 mmol). The reaction mixture was stirred at ambient temperature for 16 hours. The reaction mixture was diluted with ethyl acetate and washed with water and brine. The organic layer was dried over anhydrous sodium sulfate, filtered and concentrated in vacuo. The crude residue was purified by reverse phase chromatography to provide (R)-3-(3-((5-(2-(methylthio)pyrimidin-4-yl)-1H-pyrrolo[2,3-b]pyridin-4-yl)amino)piperidin-1-yl)-3-oxopropanenitrile as a pale yellow solid (0.03 g, 2% yield): $^1$HNMR (400 MHz, DMSO-$d_6$,) δ 11.61 (s, 1H), 9.90-9.92 (m, 1H), 8.50-8.54 (m, 2H), 7.70 (d, J=5.6 Hz, 1H), 7.20-7.21 (m, 1H), 6.70 (s, 1H), 4.30-4.33 (m, 1H), 4.05-4.11 (m, 1H), 3.68-3.93 (m, 2H), 3.48-3.52 (m, 1H), 3.11-3.23 (m, 1H), 2.98-3.03 (m, 1H), 2.56 (s, 3H), 2.15-2.20 (m, 1H), 1.80-1.90 (m, 1H), 1.61-1.70 (m, 2H); MS (ES) m/z 408.1 (M+H).

Analytical Conditions:

Flow rate: 0.3 mL/min

Column: BEH C18 (100 mm×2.1 mm×1.7 μm)

Mobile Phase (A): 0.1% Formic acid in water

Mobile Phase (B): MeCN

Example 50: Preparation of 2-cyano-N-(1-(4-(4-(((R)-1-(2-cyanoacetyl)piperidin-3-yl)amino)-1H-pyrrolo[2,3-b]pyridin-5-yl)pyrimidin-2-yl)pyrrolidin-3-yl)-N-methylacetamide

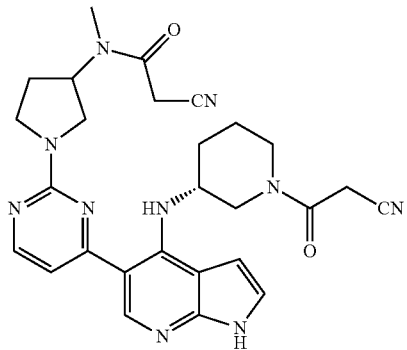 [SMILES: CN(C(=O)CC#N)C1CCN(c2nccc(-c3cnc4[nH]ccc4c3N[C@@H]3CCCN(C(=O)CC#N)C3)n2)C1]

Scheme 48. Preparation of 2-cyano-N-(1-(4-(4-(((R)-1-(2-cyanoacetyl)piperidin-3-yl)amino)-1H-pyrrolo[2,3-b]pyridin-5-yl)pyrimidin-2-yl)pyrrolidin-3-yl)-N-methylacetamide

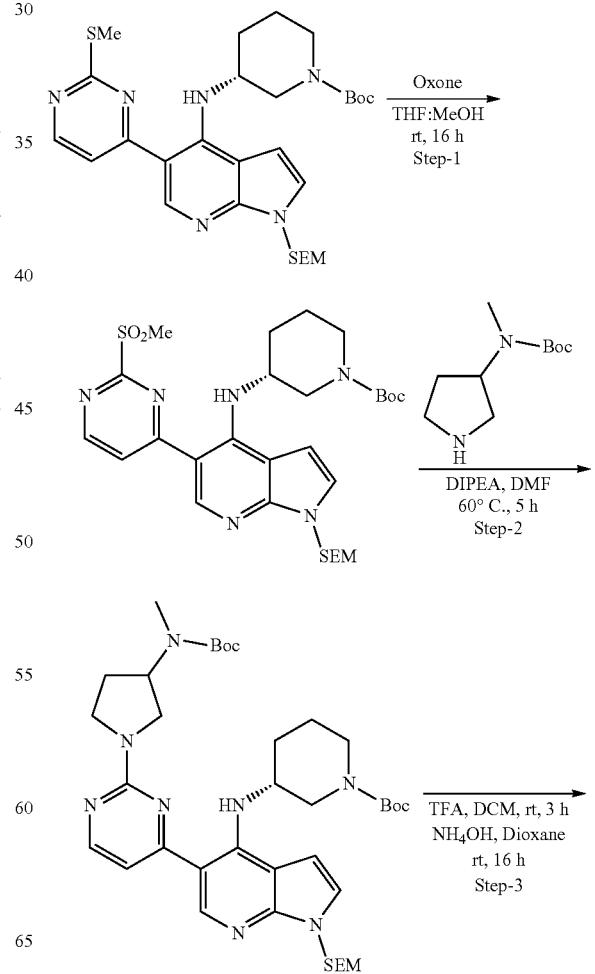

251

-continued

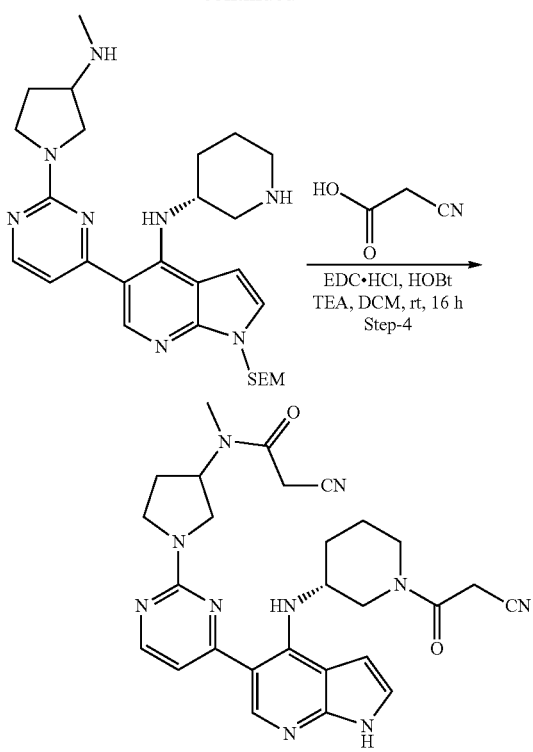

Step 1: Preparation of tert-butyl (R)-3-((5-(2-(methylsulfonyl)pyrimidin-4-yl)-1-((2-(trimethylsilyl)ethoxy)methyl)-1H-pyrrolo[2,3-b]pyridin-4-yl)amino)piperidine-1-carboxylate

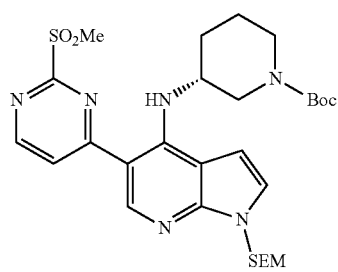 [SMILES: CC(C)(C)OC(=O)N1CCC[C@@H](Nc2c(-c3ccnc(S(C)(=O)=O)n3)cnc3c2ccn3COCC[Si](C)(C)C)C1]

To a solution of tert-butyl (R)-3-((5-(2-(methylthio)pyrimidin-4-yl)-1-((2-(trimethylsilyl)ethoxy)methyl)-1H-pyrrolo[2,3-b]pyridin-4-yl)amino)piperidine-1-carboxylate (0.6 g, 1.05 mmol, Example 43, step 1) in tetrahydrofuran:water (6 mL:3 mL) was added oxone (0.64 g, 4.21 mmol) and the mixture stirred at ambient temperature for 16 hours. The reaction mixture was diluted with ethyl acetate, washed with water and brine. The organic layer was dried over anhydrous sodium sulfate, filtered and concentrated in vacuo. The crude was purified using flash chromatography (60% ethyl acetate/hexane) to provide tert-butyl (R)-3-((5-(2-(methylsulfonyl)pyrimidin-4-yl)-1-((2-(trimethylsilyl)ethoxy)methyl)-1H-pyrrolo[2,3-b]pyridin-4-yl)amino)piperidine-1-carboxylate as a brown oil (0.25 g, 39% yield): MS (ES) m/z 603.6 (M+1).

252

Step 2: Preparation of tert-butyl (3R)-3-((5-(2-(3-((tert-butoxycarbonyl)(methyl)amino)pyrrolidin-1-yl)pyrimidin-4-yl)-1-((2-(trimethylsilyl)ethoxy)methyl)-1H-pyrrolo[2,3-b]pyridin-4-yl)amino)piperidine-1-carboxylate

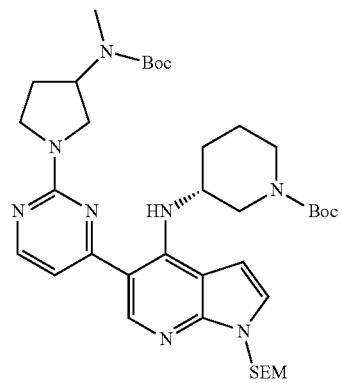 [SMILES: CN(C(=O)OC(C)(C)C)C1CCN(c2nccc(-c3cnc4c(ccn4COCC[Si](C)(C)C)c3N[C@@H]3CCCN(C(=O)OC(C)(C)C)C3)n2)C1]

A solution of (R)-3-((5-(2-(methylsulfonyl)pyrimidin-4-yl)-1-((2-(trimethylsilyl)ethoxy)methyl)-1H-pyrrolo[2,3-b]pyridin-4-yl)amino)piperidine-1-carboxylate (0.1 g, 0.17 mmol), tert-butyl methyl(pyrrolidin-3-yl)carbamate (0.04 g, 0.20 mmol) and N,N-diisopropylethylamine (0.06 mL, 0.34 mmol) in N,N-dimethylformamide (2 mL) was stirred at 60° C. for 5 hours. The reaction mixture was cooled to ambient temperature, diluted with ethyl acetate, washed with water and brine. The organic layer was dried over anhydrous sodium sulfate, filtered and concentrated in vacuo. The crude was purified using flash chromatography (20% ethyl acetate/hexane) to provide tert-butyl (3R)-3-((5-(2-(3-((tert-butoxycarbonyl)(methyl)amino)pyrrolidin-1-yl)pyrimidin-4-yl)-1-((2-(trimethylsilyl)ethoxy)methyl)-1H-pyrrolo[2,3-b]pyridin-4-yl)amino)piperidine-1-carboxylate as a brown gummy solid (0.07 g, 58% yield): MS (ES) m/z 723.4 (M+1).

Step 3: Preparation of 5-(2-(3-(methylamino)pyrrolidin-1-yl)pyrimidin-4-yl)-N-((R)-piperidin-3-yl)-1H-pyrrolo[2,3-b]pyridin-4-amine

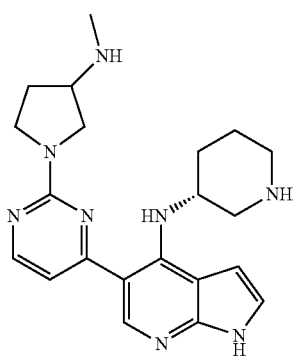 [SMILES: CNC1CCN(c2nccc(-c3cnc4[nH]ccc4c3N[C@@H]3CCCNC3)n2)C1]

A solution of tert-butyl (3R)-3-((5-(2-(3-((tert-butoxycarbonyl)(methyl)amino)pyrrolidin-1-yl)pyrimidin-4-yl)-1-((2-(trimethylsilyl)ethoxy)methyl)-1H-pyrrolo[2,3-b]pyridin-4-yl)amino)piperidine-1-carboxylate (0.15 g mg, 0.21 mmol) in dichloromethane:trifluoroacetic acid (2 mL:2 mL)

was stirred at ambient temperature for 3 hours. The reaction mixture was concentrated in vacuo, the obtained residue was dissolved in 1,4-dioxane:aqueous ammonia (3 mL:3 mL, 23% in water) and was then stirred at ambient temperature for 16 hours. The reaction mixture was concentrated in vacuo to provide 5-(2-(3-(methylamino)pyrrolidin-1-yl)pyrimidin-4-yl)-N-((R)-piperidin-3-yl)-1H-pyrrolo[2,3-b]pyridin-4-amine as a pale yellow thick liquid (0.07 g, crude): MS (ES) m/z 393.3 (M+H).

Step 4: Preparation of 2-cyano-N-(1-(4-(4-(((R)-1-(2-cyanoacetyl)piperidin-3-yl)amino)-1H-pyrrolo[2,3-b]pyridin-5-yl)pyrimidin-2-yl)pyrrolidin-3-yl)-N-methylacetamide

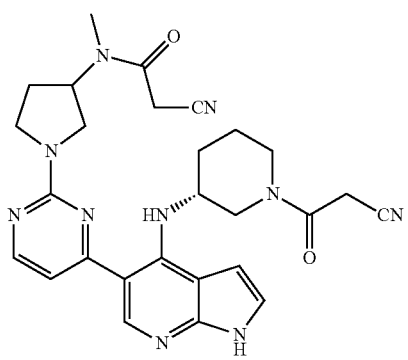 [SMILES: CN(C(=O)CC#N)C1CCN(c2nccc(-c3cnc4[nH]ccc4c3N[C@@H]3CCCN(C(=O)CC#N)C3)n2)C1]

A solution of 2-cyanoacetic acid (0.02 g, 0.23 mmol), 1-hydroxybenzotriazole (0.03 g, 0.20 mmol) and N-(3-dimethylaminopropyl)-N'-ethylcarbodiimide hydrochloride (0.08 g, 0.41 mmol) in dichloromethane (5 mL) was stirred at room temperature for 3 minutes. Then 5-(2-(3-(methylamino)pyrrolidin-1-yl)pyrimidin-4-yl)-N-((R)-piperidin-3-yl)-1H-pyrrolo[2,3-b]pyridin-4-amine (0.07 g, 0.17 mmol) and triethylamine (0.07 mL, 0.51 mmol) were added and the mixture stirred at ambient temperature for 16 hours. The reaction mixture was quenched with water and extracted with ethyl acetate. The organic layer was washed with water, brine, dried over anhydrous sodium sulfate, filtered and concentrated in vacuo. The crude material was purified by reverse phase chromatography to provide 2-cyano-N-(1-(4-(4-(((R)-1-(2-cyanoacetyl)piperidin-3-yl)amino)-1H-pyrrolo[2,3-b]pyridin-5-yl)pyrimidin-2-yl)pyrrolidin-3-yl)-N-methylacetamide as a pale yellow solid (0.02 g, 21% yield): $^1$H NMR (400 MHz, DMSO-$d_6$, VT at 100° C.) δ 11.23 (br s, 1H), 9.49 (br s, 1H), 8.38 (s, 1H), 8.29 (d, J=5.2 Hz, 1H), 7.14 (s, 1H), 7.04 (d, J=5.2 Hz, 1H), 6.65 (s, 1H), 4.50-5.00 (m, 2H), 3.72-4.20 (m, 7H), 3.40-3.60 (m, 2H), 2.88 (s, 3H), 2.12-2.27 (m, 4H), 1.45-1.80 (m, 5H); MS (ES) m/z 527.5 (M+H).

Analytical Conditions:

Flow rate: 0.8 mL min

Column: XB C18 (100 mm×4.6 mm×3.5 μm)

Mobile Phase (A): 0.1% Ammonia in water

Mobile Phase (B): MeCN

Example 51: Preparation of (R)-3-(3-((5-(2-amino-pyrimidin-4-yl)-1H-pyrrolo[2,3-b]pyridin-4-yl)amino) piperidin-1-yl)-3-oxopropanenitrile

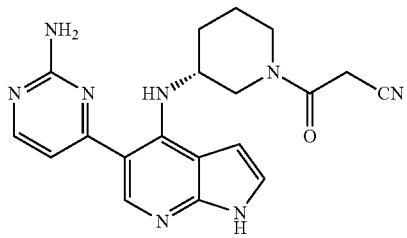 [SMILES: N#CCC(=O)N1CCC[C@@H](Nc2c(-c3ccnc(N)n3)cnc3[nH]ccc23)C1]

Scheme 49. Preparation of (R)-3-(3-((5-(2-aminopyrimidin-4-yl)-1H-pyrrolo[2,3-b]pyridin-4-yl)amino) piperidin-1-yl)-3-oxopropanenitrile

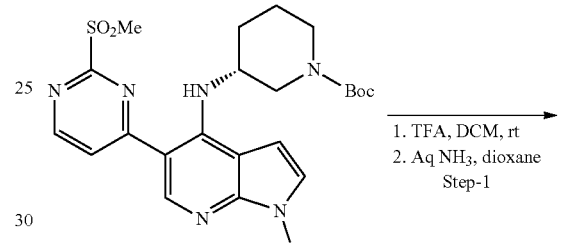

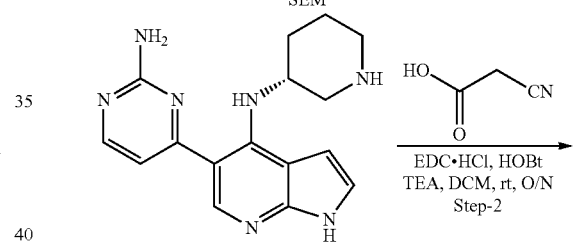

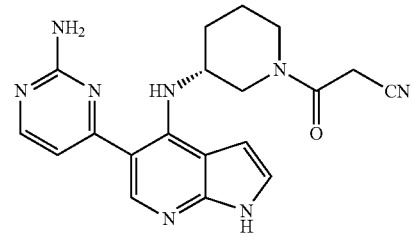

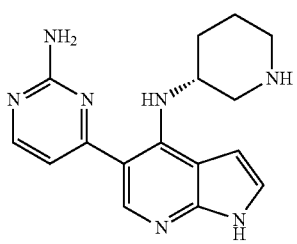 [SMILES: Nc1nccc(-c2cnc3[nH]ccc3c2N[C@@H]2CCCNC2)n1]

A solution of tert-butyl (R)-3-((5-(2-(methylsulfonyl)pyrimidin-4-yl)-1-((2-(trimethylsilyl)ethoxy)methyl)-1H-pyrrolo[2,3-b]pyridin-4-yl)amino)piperidine-1-carboxylate (0.25 g, 0.41 mmol, Example 50, step 1) in dichloromethane: trifluoroacetic acid (3 mL:3 mL) was stirred at ambient temperature for 3 hours. The reaction mixture was concentrated in vacuo, the residue was dissolved in 1,4-dioxane: aqueous ammonia (5 mL:5 mL, 23% in water) and stirred at ambient temperature for 16 hours. The reaction mixture was concentrated in vacuo to provide (R)-5-(2-aminopyrimidin-4-yl)-N-(piperidin-3-yl)-1H-pyrrolo[2,3-b]pyridin-4-amine as a viscous brown liquid (0.3 g, crude): MS (ES) m/z 310.2 (M+H).

Step 2: Preparation of (R)-3-(3-((5-(2-aminopyrimidin-4-yl)-1H-pyrrolo[2,3-b]pyridin-4-yl)amino) piperidin-1-yl)-3-oxopropanenitrile

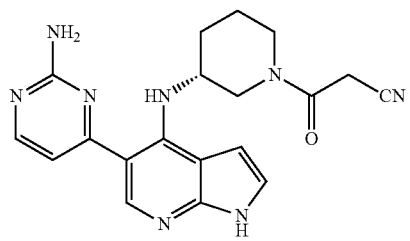 [SMILES: N#CCC(=O)N1CCC[C@@H](Nc2c(-c3ccnc(N)n3)cnc3[nH]ccc23)C1]

A solution of 2-cyanoacetic acid (0.04 g, 0.5 mmol), 1-hydroxybenzotriazole (0.06 g, 0.45 mmol) and N-(3-dimethylaminopropyl)-N'-ethylcarbodiimide hydrochloride (0.11 g, 0.58 mmol) in dichloromethane (5 mL) was stirred at rt for 3 minutes. Then (R)-5-(2-aminopyrimidin-4-yl)-N-(piperidin-3-yl)-1H-pyrrolo[2,3-b]pyridin-4-amine (0.12 g, 0.39 mmol) was added followed by triethylamine (0.27 mL, 1.95 mmol) and the mixture stirred at ambient temperature for 16 hours. The reaction mixture was quenched with water and extracted with ethyl acetate. The organic layer was washed with water, brine, dried over anhydrous sodium sulfate, filtered and concentrated in vacuo. The crude material was purified by reverse phase chromatography to provide (R)-3-(3-((5-(2-aminopyrimidin-4-yl)-1H-pyrrolo[2,3-b]pyridin-4-yl)amino)piperidin-1-yl)-3-oxopropanenitrile as an off-white solid (0.02 g, 13% yield): $^1$H NMR (400 MHz, DMSO-$d_6$, VT at 100° C.) 11.11 (br s, 1H), 9.95 (br s, 1H), 8.37 (s, 1H), 8.17 (s, 1H), 7.12 (s, 1H), 7.00 (s, 1H), 6.26 (s, 1H), 6.22 (s, 2H), 4.20-4.42 (m, 2H), 3.20-3.80 (m, 5H), 2.00-2.07 (m, 1H), 1.45-1.80 (m, 3H); MS (ES) m/z 377.4 (M+H).

Analytical Conditions:

Flow rate: 0.8 mL/min

Column: X-Bridge C18 (100 mm×4.6 mm×3.5 μm)

Mobile Phase (A): 0.1% Ammonia in water

Mobile Phase (B): MeCN

Example 52: Preparation of 3-((3S,5R)-3-methyl-5-((5-(2-methylpyrimidin-4-yl)-1H-pyrrolo[2,3-b]pyridin-4-yl)amino)piperidin-1-yl)-3-oxopropanenitrile

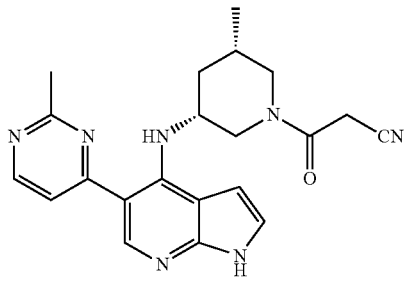 [SMILES: Cc1nccc(-c2cnc3[nH]ccc3c2N[C@@H]2C[C@H](C)CN(C(=O)CC#N)C2)n1]

Scheme 50. Preparation of 3-((3S,5R)-3-methyl-5-((5-(2-methylpyrimidin-4-yl)-1H-pyrrolo[2,3-b]pyridin-4-yl)amino)piperidin-1-yl)-3-oxopropanenitirile

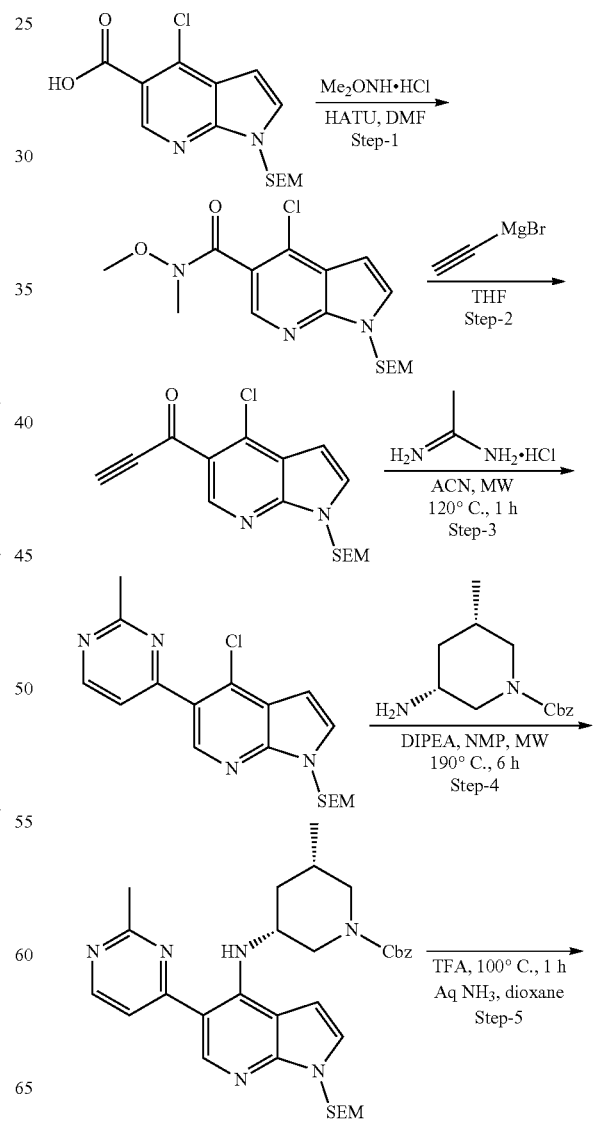

-continued

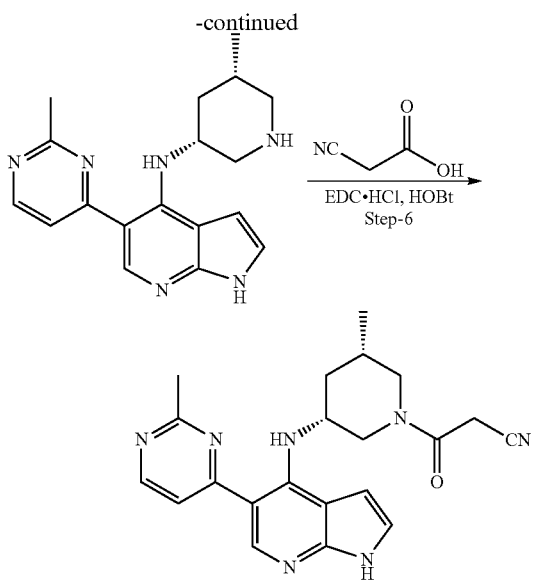

Step 1: Preparation of 4-chloro-N-methoxy-N-methyl-1-((2-(trimethylsilyl)ethoxy)methyl)-1H-pyrrolo[2,3-b]pyridine-5-carboxamide

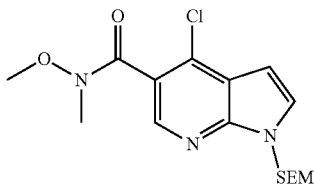 [SMILES: CON(C)C(=O)c1cnc2c(ccn2COCC[Si](C)(C)C)c1Cl]

A solution of 4-chloro-1-{[2-(trimethylsilyl)ethoxy]methyl}-1H-pyrrolo[2,3-b]pyridine-5-carboxylic acid (2.00 g, 6.12 mmol) and (1-[bis(dimethylamino)methylene]-1H-1,2,3-triazolo[4,5-b]pyridinium 3-oxide hexafluorophosphate (3.49 g, 9.18 mmol) in N,N-dimethylformamide (25.0 mL) was stirred at ambient temperature for 3 minutes. Then N,O-dimethylhydroxylamine hydrochloride (1.49 g, 15.3 mmol) was added followed by triethylamine (4.28 mL, 30.6 mmol) and the mixture was stirred at ambient temperature for 16 hours. The reaction mixture was diluted with ethyl acetate and water. The organic layer was separated, washed with water, brine, dried over anhydrous sodium sulfate, filtered and concentrated in vacuo. The crude material was purified using flash chromatography (40% ethyl acetate/hexane) to provide 4-chloro-N-methoxy-N-methyl-1-{[2-(trimethylsilyl)ethoxy]methyl}-1H-pyrrolo[2,3-b]pyridine-5-carboxamide as a pale yellow liquid (1.82 g, 80% yield): MS (ES) m/z 370.2 (M+H).

Step 2: Preparation of 1-(4-chloro-1-((2-(trimethylsilyl)ethoxy)methyl)-1H-pyrrolo[2,3-b]pyridin-5-yl)prop-2-yn-1-one

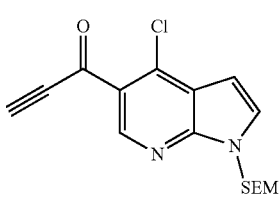 [SMILES: C#CC(=O)c1cnc2c(ccn2COCC[Si](C)(C)C)c1Cl]

To a solution of 4-chloro-N-methoxy-N-methyl-1-{[2-(trimethylsilyl)ethoxy]methyl}-1H-pyrrolo[2,3-b] pyridine-5-carboxamide (2.20 g, 5.95 mmol) in tetrahydrofuran (25 mL), was added bromo(ethynyl)magnesium (18 mL, 8.92 mmol, 3M solution in THF) at 0° C. The reaction mixture was warmed to ambient temperature and stirred for 16 hours. The reaction mixture was quenched with saturated aqueous ammonium chloride and extracted with ethyl acetate. The organic layer was washed with water, brine, dried over anhydrous sodium sulfate, filtered and concentrated in vacuo. The crude material was purified using flash chromatography (40% ethyl acetate/hexane) to provide 1-(4-chloro-1-{[2-(trimethylsilyl)ethoxy]methyl}-1H-pyrrolo[2,3-b]pyridin-5-yl)prop-2-yn-1-one as a pale yellow semi-solid (1.25 g, 63% yield): MS (ES) m/z 335.1 (M+H).

Step 3: Preparation of 4-chloro-5-(2-methylpyrimidin-4-yl)-1-((2-(trimethylsilyl)ethoxy)methyl)-1H-pyrrolo[2,3-b]pyridine

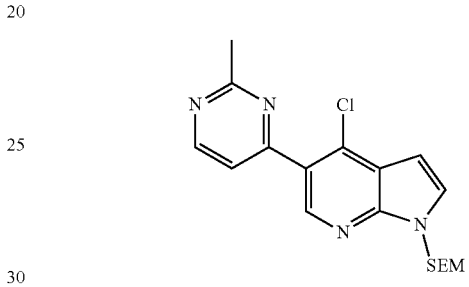

To a stirred suspension of 1-(4-chloro-1-{[2-(trimethylsilyl)ethoxy]methyl}-1H-pyrrolo[2,3-b]pyridin-5-yl)prop-2-yn-1-one (1.20 g, 3.58 mmol), was added N-chloroethanimidamide (0.5 mg, 5.38 mmol) and sodium carbonate (1.14 g, 10.8 mmol) in acetonitrile (10 mL) and the mixture subjected to MW irradiation at 120° C. for 1 hour. The reaction was cooled to ambient temperature and diluted with ethyl acetate and water. The organic layer was separated, washed with water, brine, dried over anhydrous sodium sulfate, filtered and concentrated to obtain a thick gum. The crude material was purified using flash chromatography (40% ethyl acetate/hexane) to provide 4-(4-chloro-1-{[2-(trimethylsilyl)ethoxy]methyl}-1H-pyrrolo[2,3-b]pyridin-5-yl)-2-methylpyrimidine as a brown liquid (0.72 g, 54% yield): MS (ES) m/z 375.1 (M+H).

Step 4: Preparation of benzyl (3S,5R)-3-methyl-5-((5-(2-methylpyrimidin-4-yl)-1-((2-(trimethylsilyl)ethoxy)methyl)-1H-pyrrolo[2,3-b]pyridin-4-yl)amino)piperidine-1-carboxylate

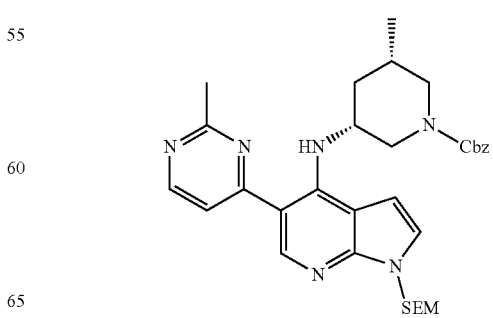

In a 20 mL MW vial a solution of 4-(4-chloro-1-{[2-(trimethylsilyl)ethoxy]methyl}-1H-pyrrolo[2,3-b]pyridin-5-yl)-2-methylpyrimidine (0.6 g, 1.60 mmol), benzyl (3R,5S)-3-amino-5-methylpiperidine-1-carboxylate (0.6 g, 2.40 mmol) and N,N-diisopropylethylamine (0.6 mL 3.20 mmol) in N-methylpyrrolidin-2-one (7 mL) was subjected to microwave irradiation at 190° C. for 6 hours. The reaction was cooled to ambient temperature, diluted with ethyl acetate and water. The organic layer was separated, washed with water, brine, dried over anhydrous sodium sulfate, filtered and concentrated. The crude material was purified using flash chromatography (40% ethyl acetate/hexane) to provide benzyl (3S,5R)-3-methyl-5-{[5-(2-methylpyrimidin-4-yl)-1-{[2-(trimethylsilyl)ethoxy]methyl}-1H-pyrrolo[2,3-b]pyridin-4-yl]amino}piperidine-1-carboxylate as a brown thick liquid (0.34 g, 36% yield): MS (ES) m/z 587.6 (M+H).

Step 5: Preparation of N-((3R,5S)-5-methylpiperidin-3-yl)-5-(2-methylpyrimidin-4-yl)-1H-pyrrolo[2,3-b]pyridin-4-amine

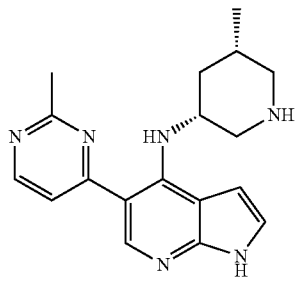 [SMILES: Cc1nccc(-c2cnc3[nH]ccc3c2N[C@H]2CNC[C@@H](C)C2)n1]

A solution of benzyl (3S,5R)-3-methyl-5-{[5-(2-methylpyrimidin-4-yl)-1-{[2-(trimethylsilyl)ethoxy]methyl}-1H-pyrrolo[2,3-b]pyridin-4-yl]amino}piperidine-1-carboxylate (0.33 g, 0.56 mmol) in trifluoroacetic acid (5 mL) was stirred for 1 hour at 100° C. in a sealed tube. After 1 hour the reaction mixture was cooled to ambient temperature and concentrated in vacuo to dryness. The residue was dissolved in 1,4-dioxane:aqueous ammonia (5 mL:5 mL) and stirred at ambient temperature for 16 hours. The reaction mixture was concentrated to dryness to obtain (3R,5S)-5-methyl-N-[5-(2-methylpyrimidin-4-yl)-1H-pyrrolo[2,3-b]pyridin-4-yl]piperidin-3-amine as a colorless gummy solid (0.35 g, crude): MS (ES) m/z 323.2 (M+H).

Step 6: Preparation of 3-((3S,5R)-3-methyl-5-((5-(2-methylpyrimidin-4-yl)-1H-pyrrolo[2,3-b]pyridin-4-yl)amino)piperidin-1-yl)-3-oxopropanenitrile

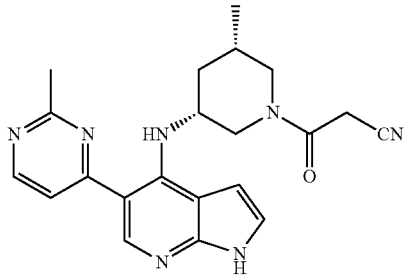 [SMILES: Cc1nccc(-c2cnc3[nH]ccc3c2N[C@@H]2C[C@H](C)CN(C(=O)CC#N)C2)n1]

A solution of 2-cyanoacetic acid (0.03 g, 0.32 mol), 1-hydroxy-1,2-dihydropyridin-2-one (0.31 g, 0.28 mmol) and O-(benzotriazol-1-yl)-N,N,N',N'-tetramethyluronium tetrafluoroborate (0.1 g, 0.32 mol) in N-methylpyrrolidin-2-one (2 mL) was stirred at ambient temperature for 3 minutes. Then (3R,5S)-5-methyl-N-[5-(2-methylpyrimidin-4-yl)-1H-pyrrolo[2,3-b]pyridin-4-yl]piperidin-3-amine (0.07 g, 0.22 mmol) was added followed by triethylamine (0.1 mL, 0.70 mmol) and the mixture stirred at ambient temperature for 16 hours. The reaction mixture was diluted with ethyl acetate, washed with water and brine. The organic layer was dried over anhydrous sodium sulfate, filtered and concentrated in vacuo. The crude material was purified using reverse phase chromatography to obtain 3-[(3S,5R)-3-methyl-5-{[5-(2-methylpyrimidin-4-yl)-1H-pyrrolo[2,3-b]pyridin-4-yl]amino}piperidin-1-yl]-3-oxopropanenitrile as a white solid (0.02 g, 20% yield): $^1$H NMR (400 MHz, DMSO-d$_6$, VT at 80° C.) δ 11.29 (br s, 1H), 10.38 (br s, 1H), 8.54-8.56 (m, 2H), 7.75-7.76 (m, 1H), 7.15 (s, 1H), 6.70 (s, 1H), 4.81-4.84 (m, 1H), 3.93-4.33 (m, 5H), 2.65 (s, 4H), 2.27-2.30 (m, 1H), 1.65-1.95 (m, 1H), 1.17-1.30 (m, 1H), 0.95 (d, J=6.4 Hz, 3H); MS (ES) m/z 390.4 (M+H).

Analytical Conditions:
Column: X-Bridge, C18 19*100*5 micron
Mobile phase (A): 0.1% Ammonia in H$_2$O
Mobile phase (B): MeCN
Flow rate: 20.0 mL/min Example 53: Preparation of (R)-2-(4-((1-(2-cyanoacetyl)piperidin-3-yl)amino)-1H-pyrrolo[2,3-b]pyridin-5-yl)-N-methylthiazole-5-carboxamide

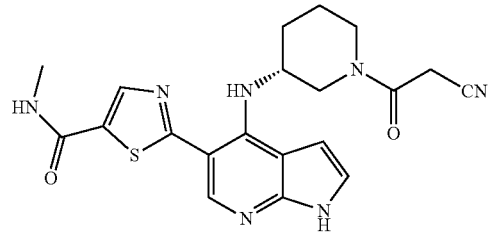 [SMILES: CNC(=O)c1cnc(-c2cnc3[nH]ccc3c2N[C@@H]2CCCN(C(=O)CC#N)C2)s1]

Scheme 51. Preparation of (R)-2-(4-((1-(2-cyanoacetyl)piperidin-3-yl)amino)-1H-pyrrolo[2,3-b]pyridin-5-yl)-N-methylthiazole-5-carboxamide

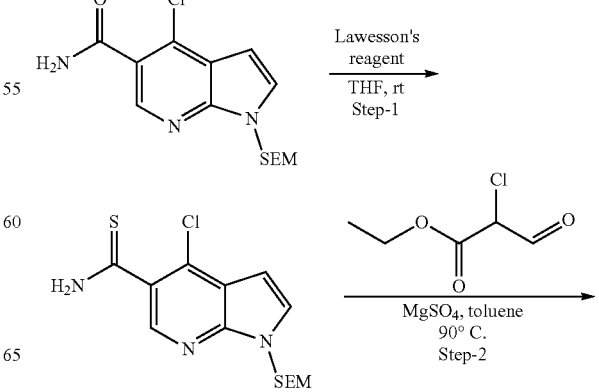

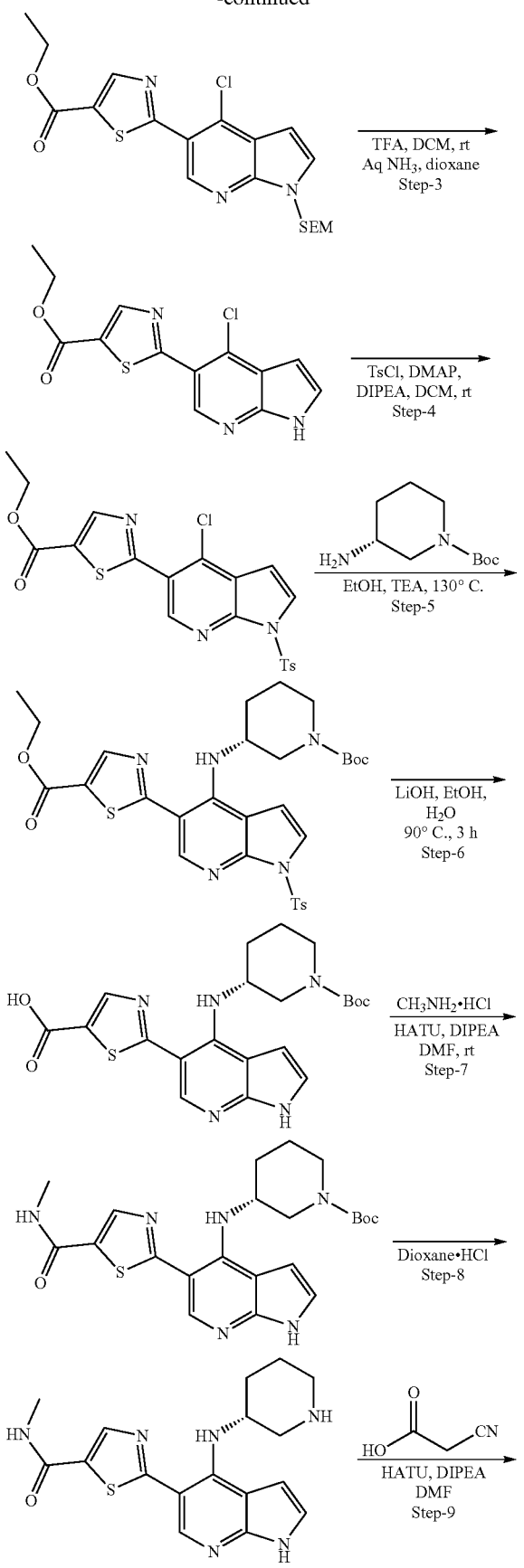

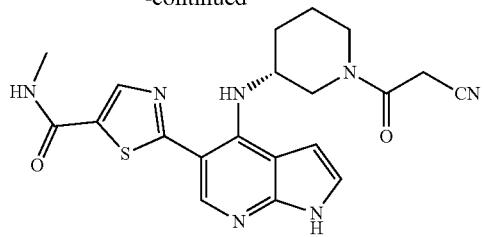

Step 1: Preparation of 4-chloro-1-((2-(trimethylsilyl)ethoxy)methyl)-1H-pyrrolo[2,3-b]pyridine-5-carbothioamide

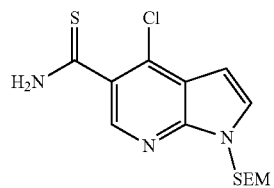 [SMILES: C[Si](C)(C)CCOCn1ccc2c(Cl)c(C(N)=S)cnc21]

To a solution of 4-chloro-1-((2-(trimethylsilyl)ethoxy)methyl)-1H-pyrrolo[2,3-b]pyridine-5-carboxylic acid (7.0 g, 21.5 mmol, Example 48, step 3) in tetrahydrofuran (30 mL) was added Lawesson's reagent (8.70 g, 21.5 mmol) and the mixture stirred at ambient temperature for 3 hours. The reaction mixture was quenched with ice cold saturated sodium bicarbonate solution, extracted with ethyl acetate and washed with brine. The organic layer was dried over anhydrous sodium sulfate, filtered and concentrated in vacuo to provide 4-chloro-1-((2-(trimethylsilyl)ethoxy)methyl)-1H-pyrrolo[2,3-b]pyridine-5-carbothioamide as a pale yellow thick liquid (1.5 g, 47% yield): MS (ES) m/z 342.0 (M+H).

Step 2: Preparation of ethyl 2-(4-chloro-1-((2-(trimethylsilyl)ethoxy)methyl)-1H-pyrrolo[2,3-b]pyridin-5-yl)thiazole-5-carboxylate

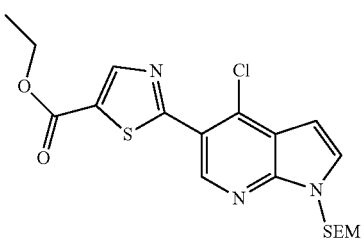 [SMILES: CCOC(=O)c1cnc(-c2cnc3c(ccn3COCC[Si](C)(C)C)c2Cl)s1]

To a solution of 4-chloro-1-((2-(trimethylsilyl)ethoxy)methyl)-1H-pyrrolo[2,3-b]pyridine-5-carbothioamide (6.0 g, 17.5 mmol) in toluene (60 mL) was added ethyl 2-chloro-3-oxopropaonate (7.93 g, 52.6 mmol) and magnesium sulfate (4.22 g, 35.1 mmol) and the mixture heated to 90° C. for 12 hours. The reaction was cooled to ambient temperature, quenched with water and extracted with ethyl acetate and washed with brine. The organic layer was dried over anhydrous sodium sulfate, filtered and concentrated in vacuo to provide ethyl 2-(4-chloro-1-((2-(trimethylsilyl)ethoxy)

methyl)-1H-pyrrolo[2,3-b]pyridin-5-yl)thiazole-5-carboxylate as a viscous brown liquid (0.6 g, 7.81% yield): MS (ES) m/z 438.1 (M+H).

Step 3: Preparation of ethyl 2-(4-chloro-1H-pyrrolo [2,3-b]pyridin-5-yl)thiazole-5-carboxylate

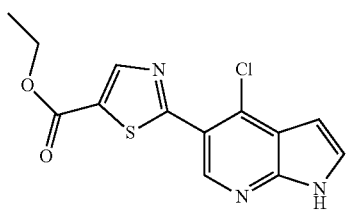 [SMILES: CCOC(=O)c1cnc(-c2cnc3[nH]ccc3c2Cl)s1]

A solution of ethyl 2-(4-chloro-1-((2-(trimethylsilyl) ethoxy)methyl)-1H-pyrrolo[2,3-b]pyridin-5-yl)thiazole-5-carboxylate (0.50 g, 0.22 mmol) in dichloromethane:trifluoroacetic acid (5 mL:5 mL) was stirred at ambient temperature for 3 hours. The reaction mixture was concentrated in vacuo. The residue was dissolved in 1,4-dioxane: aqueous ammonia (5 mL:5 mL 23% in water) and the mixture stirred at ambient temperature for 16 hours. The reaction mixture was concentrated in vacuo to provide ethyl 2-(4-chloro-1H-pyrrolo[2,3-b]pyridin-5-yl)thiazole-5-carboxylate as an off-white solid (0.52 g, crude): MS (ES) m/z 308.0 (M+H).

Step 4: Preparation of ethyl 2-(4-chloro-1-tosyl-1H-pyrrolo[2,3-b]pyridin-5-yl)thiazole-5-carboxylate

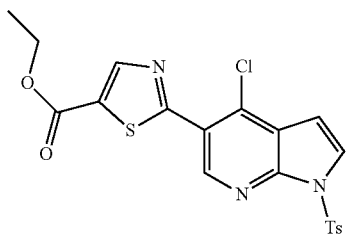 [SMILES: CCOC(=O)c1cnc(-c2cnc3c(ccn3S(=O)(=O)c3ccc(C)cc3)c2Cl)s1]

To a stirred solution of ethyl 2-(4-chloro-1H-pyrrolo[2,3-b]pyridin-5-yl)thiazole-5-carboxylate (0.20 g, 0.65 mmol), 4-dimethylaminopyridine (0.02 g, 0.13 mmol) and triethylamine (0.09 mL, 0.65 mmol) in dichloromethane (3 mL) was added 4-methyl-benzenesulfonyl chloride (0.15 g, 0.78 mmol) and the reaction mixture stirred at ambient temperature for 3 hours. The reaction mixture was quenched with saturated sodium bicarbonate solution, extracted with dichloromethane and washed with brine. The organic layer was dried over sodium sulfate, filtered and concentrated in vacuo to afford ethyl 2-(4-chloro-1-tosyl-H-pyrrolo[2,3-b] pyridin-5-yl)thiazole-5-carboxylate as a brown solid (0.2 g, 34% yield): MS (ES) m/z 462.1 (M+H).

Step 5: Preparation of ethyl (R)-2-(4-((1-(tert-butoxycarbonyl)piperidin-3-yl)amino)-1-tosyl-1H-pyrrolo[2,3-b]pyridin-5-yl)thiazole-5-carboxylate

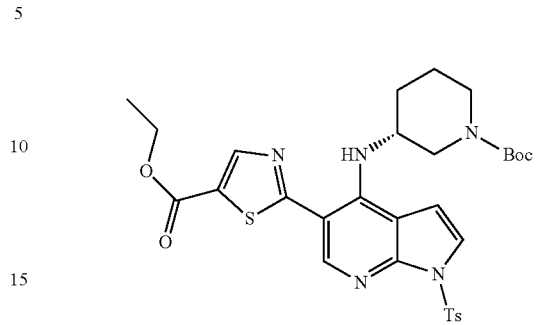

To a solution of ethyl 4-chloro-1H-pyrrolo[2,3-b]pyridine-5-carboxylate (0.2 g, 0.75 mmol) in ethanol (0.5 mL) was added tert-butyl (R)-3-aminopiperidine-1-carboxylate (0.35 g, 1.73 mmol) and triethylamine (0.5 mL, 3.6 mmol) and the mixture subjected to microwave irradiation at 130° C. for 15 minutes. The reaction was cooled to ambient temperature, quenched with water and extracted with ethyl acetate. The organic layer was washed with brine, dried over anhydrous sodium sulfate, filtered and concentrated in vacuo. The crude material was purified using flash chromatography (50% ethyl acetate/hexane) to provide ethyl (R)-2-(4-((1-(tert-butoxycarbonyl)piperidin-3-yl)amino)-1-tosyl-1H-pyrrolo[2,3-b]pyridin-5-yl)thiazole-5-carboxylate as a viscous colorless liquid (0.17 g, 62% yield): MS (ES) m/z 626.2 (M+H).

Step 6: Preparation of (R)-2-(4-((1-(tert-butoxycarbonyl)piperidin-3-yl)amino)-1H-pyrrolo[2,3-b]pyridin-5-yl)thiazole-5-carboxylic acid

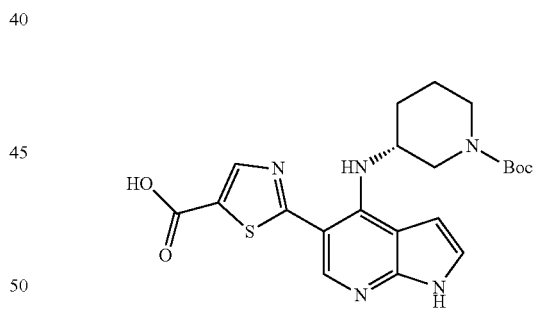

To a stirred solution of ethyl (R)-2-(4-((1-(tert-butoxycarbonyl)piperidin-3-yl)amino)-1-tosyl-1H-pyrrolo[2,3-b]pyridin-5-yl)thiazole-5-carboxylate (0.35 g, 0.55 mmol) in ethanol (1 mL) was added a 2M aqueous solution of lithium hydroxide (0.07 g, 2.8 mmol) and the mixture was subjected to heating at 90° C. for 3 hours. The reaction was cooled to ambient temperature and concentrated in vacuo to remove volatiles. The residual material was dissolved in water and acidified with 1N hydrochloric acid to adjust pH to 3. The precipitated solid was filtered, washed with water and dried in high vacuo to provide (R)-2-(4-((1-(tert-butoxycarbonyl) piperidin-3-yl)amino)-1H-pyrrolo[2,3-b]pyridin-5-yl)thiazole-5-carboxylic acid as an off-white solid (0.2 g, 83% yield): MS (ES) m/z 444.2 (M+H).

Step 7: Preparation of tert-butyl (R)-3-((5-(5-(methylcarbamoyl)thiazol-2-yl)-1H-pyrrolo[2,3-b]pyridin-4-yl)amino)piperidine-1-carboxylate

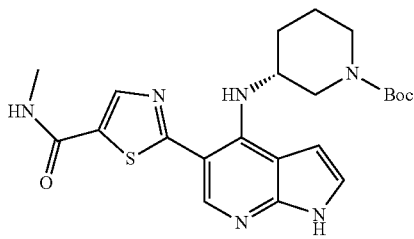 [SMILES: CNC(=O)c1cnc(-c2cnc3[nH]ccc3c2N[C@@H]2CCCN(C(=O)OC(C)(C)C)C2)s1]

A solution of (R)-2-(4-((1-(tert-butoxycarbonyl)piperidin-3-yl)amino)-1H-pyrrolo[2,3-b]pyridin-5-yl)thiazole-5-carboxylic acid (0.25 g, 0.56 mmol) and 1-[bis(dimethylamino)methylene]-1H-1,2,3-triazolo[4,5-b]pyridinium-3-oxide hexafluorophosphate (0.43 g, 1.12 mmol) in N,N-dimethylformamide (5 mL) was stirred at ambient temperature for 5 minutes. Methylamine hydrochloride (0.07 g, 0.68 mmol) was added followed by triethylamine (0.4 mL, 2.77 mmol) and the mixture stirred for 12 hours. The reaction was quenched with water and extracted with ethyl acetate. The organic layer was washed with brine, dried over anhydrous sodium sulfate, filtered and concentrated in vacuo. The crude material was purified using flash chromatography (80% ethyl acetate/hexane) to provide tert-butyl (R)-3-((5-(5-(methylcarbamoyl)thiazol-2-yl)-1H-pyrrolo[2,3-b]pyridin-4-yl)amino)piperidine-1-carboxylate as a viscous colorless liquid (0.25 g, 97% yield): MS (ES) m/z 457.2 (M+H).

Step 8: Preparation of (R)-N-methyl-2-(4-(piperidin-3-ylamino)-1H-pyrrolo[2,3-b]pyridin-5-yl)thiazole-5-carboxamide hydrochloride

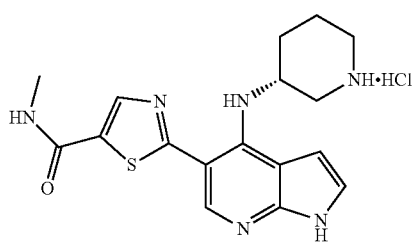

(R)-3-((5-(5-(Methylcarbamoyl)thiazol-2-yl)-1H-pyrrolo[2,3-b]pyridin-4-yl)amino)piperidine-1-carboxylate (0.25 g, 0.54 mmol) was added to 4N hydrochloric acid and 1,4-dioxane (5 mL) and the mixture stirred at ambient temperature for 4 hours. The reaction mixture was concentrated in vacuo and dried to provide (R)-N-methyl-2-(4-(piperidin-3-ylamino)-1H-pyrrolo[2,3-b]pyridin-5-yl)thiazole-5-carboxamide hydrochloride as an off-white solid (0.16 g, 77% yield): MS (ES) m/z 357.3 (M+H)$^+$.

Step 9: Preparation of (R)-2-(4-((1-(2-cyanoacetyl)piperidin-3-yl)amino)-1H-pyrrolo[2,3-b]pyridin-5-yl)-N-methylthiazole-5-carboxamide

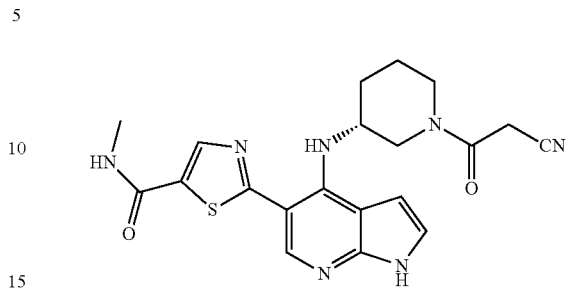

A solution of cyanoacetic acid (0.04 g, 0.64 mmol) and 1-[bis(dimethylamino)methylene]-1H-1,2,3-triazolo[4,5-b]pyridinium 3-oxide hexafluorophosphate (0.24 g, 0.63 mmol) in N,N-dimethylformamide (4 mL) was stirred at ambient temperature for 3 minutes. Then (R)-N-methyl-2-(4-(piperidin-3-ylamino)-1H-pyrrolo[2,3-b]pyridin-5-yl)thiazole-5-carboxamide hydrochloride (0.15 g, 0.42 mmol) was added followed by N,N-diisopropylethylamine (0.5 mL, 1.42 mmol) and the mixture stirred at ambient temperature for 16 hours. The reaction was quenched with water and extracted with ethyl acetate. The organic layer was washed with brine, dried over anhydrous sodium sulfate, filtered and concentrated in vacuo. The crude material was purified by reverse phase chromatography to provide (R)-N-(2-(4-((1-(2-cyanoacetyl)piperidin-3-yl)amino)-1H-pyrrolo[2,3-b]pyridin-5-yl)pyridin-4-yl)methanesulfonamide as an off-white solid (0.01 g, 6% yield): $^1$H NMR (400 MHz, DMSO-$d_6$, VT at 80° C.) δ 11.45 (s, 1H), 9.65 (br s, 1H), 8.20-8.31 (m, 3H), 7.19 (s, 1H), 6.68 (s, 1H), 3.89-4.50 (m, 4H), 3.68 (m, 2H), 3.43 (m, 2H), 2.79 (s, 2H), 2.07 (s, 1H), 1.64-1.75 (m, 3H); MS (ES) m/z 424.2 (M+H).

Analytical Conditions:
Column: Ascentis Express C18 (50 mm×2.1 mm×2.7 μm)
Mobile phase (A): 0.1% % Formic acid in water
Mobile phase (B): MeCN
Flow rate: 1.0 mL/min

Example 54: Preparation of (R)-N-(2-(4-((1-(2-cyanoacetyl)piperidin-3-yl)amino)-1H-pyrrolo[2,3-b]pyridin-5-yl)pyridin-4-yl)N,N-dimethyl sulfuric diamide

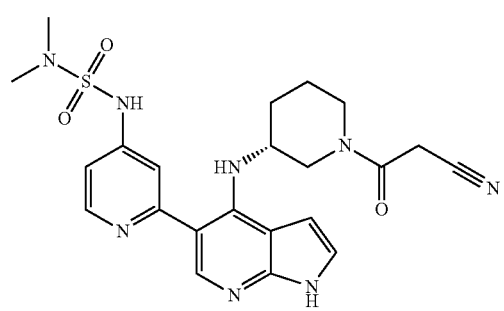 [SMILES: CN(C)S(=O)(=O)Nc1ccnc(-c2cnc3[nH]ccc3c2N[C@@H]2CCCN(C(=O)CC#N)C2)c1]

Scheme 52. Preparation of (R)-N-(2-(4-((1-(2-cyanoacetyl)piperidin-3-yl)amino)-1H-pyrrolo[2,3-b]pyridin-5-yl)N,N-dimethyl sulfuric diamide

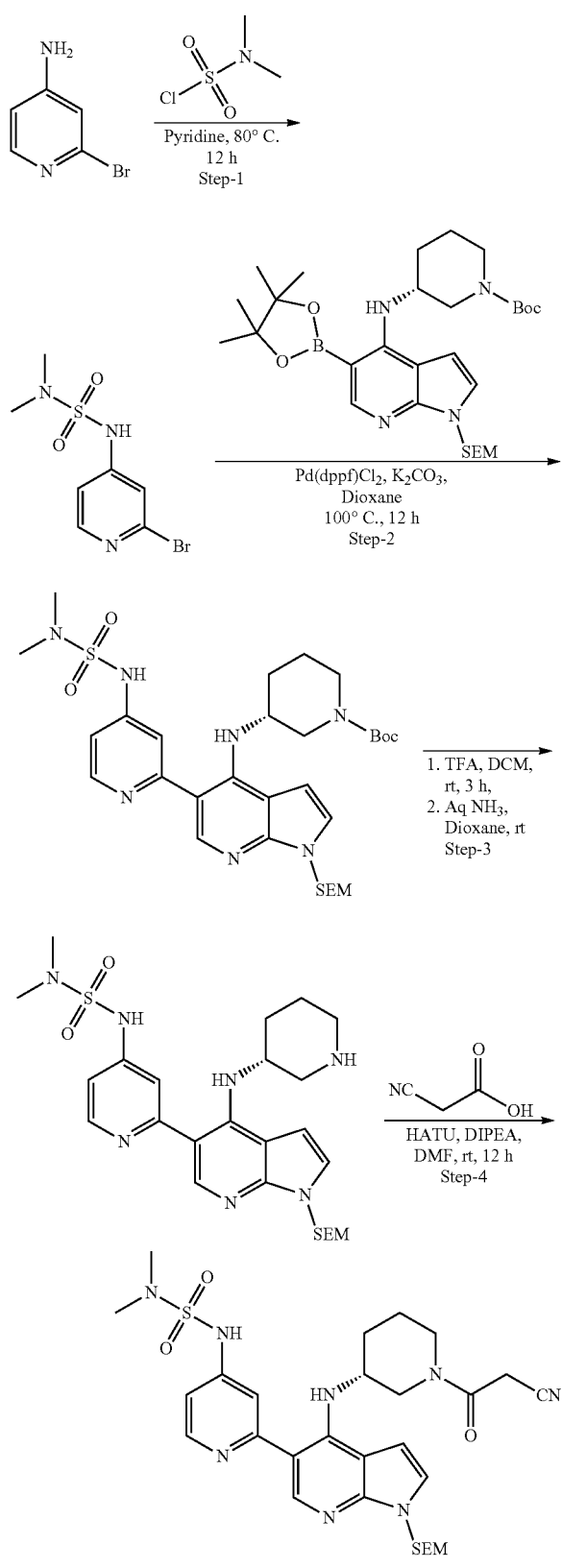

Step 1: Preparation of [(2-bromopyridin-4-yl)sulfamoyl]dimethylamine

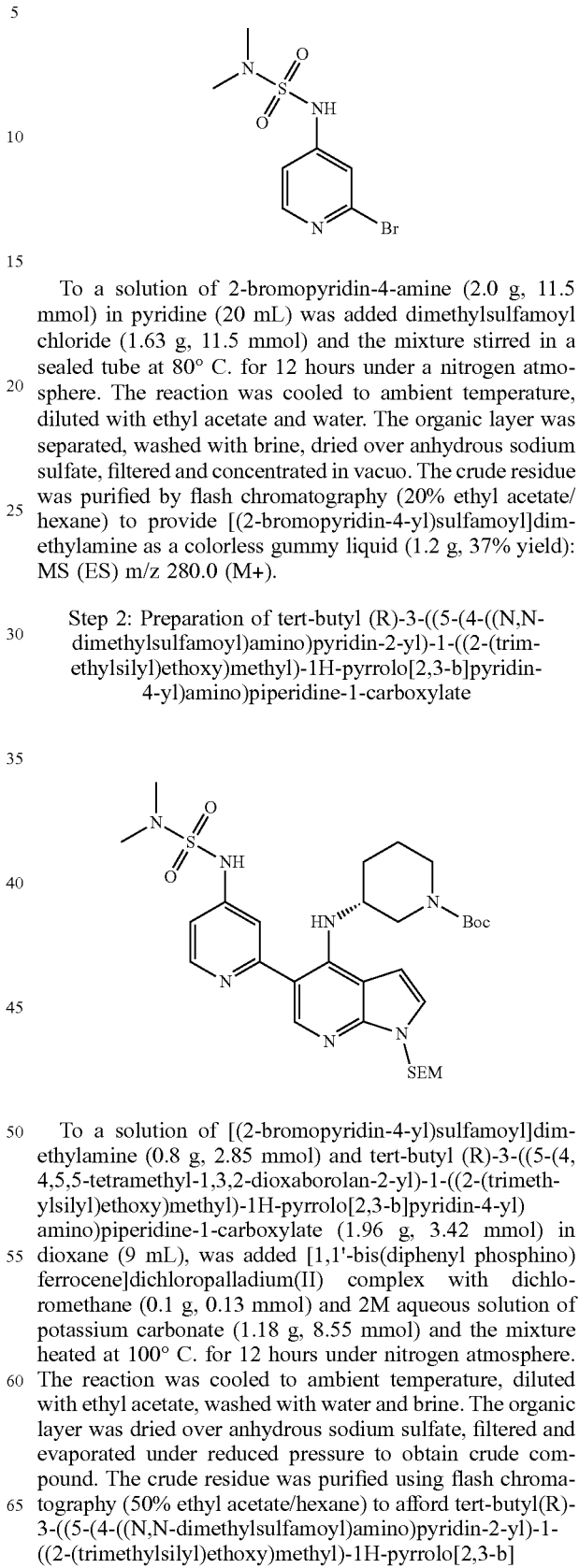

To a solution of 2-bromopyridin-4-amine (2.0 g, 11.5 mmol) in pyridine (20 mL) was added dimethylsulfamoyl chloride (1.63 g, 11.5 mmol) and the mixture stirred in a sealed tube at 80° C. for 12 hours under a nitrogen atmosphere. The reaction was cooled to ambient temperature, diluted with ethyl acetate and water. The organic layer was separated, washed with brine, dried over anhydrous sodium sulfate, filtered and concentrated in vacuo. The crude residue was purified by flash chromatography (20% ethyl acetate/hexane) to provide [(2-bromopyridin-4-yl)sulfamoyl]dimethylamine as a colorless gummy liquid (1.2 g, 37% yield): MS (ES) m/z 280.0 (M+).

Step 2: Preparation of tert-butyl (R)-3-((5-(4-((N,N-dimethylsulfamoyl)amino)pyridin-2-yl)-1-((2-(trimethylsilyl)ethoxy)methyl)-1H-pyrrolo[2,3-b]pyridin-4-yl)amino)piperidine-1-carboxylate To a solution of [(2-bromopyridin-4-yl)sulfamoyl]dimethylamine (0.8 g, 2.85 mmol) and tert-butyl (R)-3-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate (1.96 g, 3.42 mmol) in dioxane (9 mL), was added [1,1'-bis(diphenyl phosphino)ferrocene]dichloropalladium(II) complex with dichloromethane (0.1 g, 0.13 mmol) and 2M aqueous solution of potassium carbonate (1.18 g, 8.55 mmol) and the mixture heated at 100° C. for 12 hours under nitrogen atmosphere. The reaction was cooled to ambient temperature, diluted with ethyl acetate, washed with water and brine. The organic layer was dried over anhydrous sodium sulfate, filtered and evaporated under reduced pressure to obtain crude compound. The crude residue was purified using flash chromatography (50% ethyl acetate/hexane) to afford tert-butyl(R)-3-((5-(4-((N,N-dimethylsulfamoyl)amino)pyridin-2-yl)-1-((2-(trimethylsilyl)ethoxy)methyl)-1H-pyrrolo[2,3-b]

pyridin-4-yl)amino)piperidine-1-carboxylate as a gummy brown solid (0.25 g, 54% yield): MS (ES) m/z 645.9 (M+H).

Step 3: Preparation of (3R)-N-(5-{4-[(dimethylsulfamoyl)amino]pyridin-2-yl}-1H-pyrrolo[2,3-b]pyridin-4-yl)piperidin-3-amine

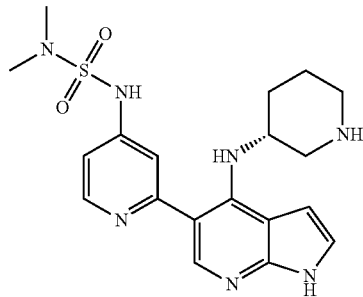 [SMILES: CN(C)S(=O)(=O)Nc1ccnc(-c2cnc3[nH]ccc3c2N[C@@H]2CCCNC2)c1]

A solution of tert-butyl (R)-3-((5-(4-((N,N-dimethylsulfamoyl)amino)pyridin-2-yl)-1-((2-(trimethylsilyl) ethoxy) methyl)-1H-pyrrolo[2,3-b]pyridin-4-yl)amino)piperidine-1-carboxylate (0.25 g, 0.38 mmol) in dichloromethane: trifluoroacetic acid (5 mL:5 mL) was stirred at ambient temperature for 3 hours. The reaction mixture was concentrated in vacuo and the residue was dissolved in 1,4-dioxane: aqueous ammonia (5 mL:5 mL 23% in water) and stirred at ambient temperature for 16 hours. The reaction mixture was diluted with ethyl acetate, washed with water and brine. The organic layer was dried over anhydrous sodium sulfate, filtered and concentrated in vacuo to provide (R)-5-(5-methyloxazol-2-yl)-N-(piperidin-3-yl)-1H-pyrrolo[2,3-b] pyridin-4-amine as a gummy yellow solid (0.15 g, crude): MS (ES) m/z 413.9 (M−H).

Step 4: Preparation of (R)-N-(2-(4-((1-(2-cyanoacetyl)piperidin-3-yl)amino)-1H-pyrrolo[2,3-b]pyridin-5-yl)pyridin-4-yl)N,N-dimethyl sulfuric diamide

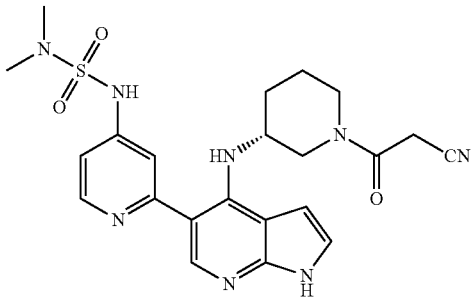 [SMILES: CN(C)S(=O)(=O)Nc1ccnc(-c2cnc3[nH]ccc3c2N[C@@H]2CCCN(C(=O)CC#N)C2)c1]

A solution of cyanoacetic acid (0.036 g, 0.43 mmol) and (1-[bis(dimethylamino)methylene]-1H-1,2,3-triazolo[4,5-b]pyridinium 3-oxid hexafluorophosphate (0.22 g, 0.43 mmol) in N,N-dimethylformamide (5 mL) was stirred for 5 minutes. Then (R)-5-(5-methyloxazol-2-yl)-N-(piperidin-3-yl)-1H-pyrrolo[2,3-b]pyridin-4-amine (0.15 g, 0.36 mmol) was added followed by N,N-diisopropylethylamine (0.19 mL, 1.08 mmol), and the reaction mixture stirred at ambient temperature for 12 hours. The reaction mixture was diluted with ethyl acetate, washed with water and brine. The organic layer was dried over anhydrous sodium sulfate, filtered and concentrated in vacuo. The crude material was purified by reverse phase chromatography to provide 3-[(3R)-3-{[5-(4-{[(5-bromo-3-formyl-1H-indol-7-yl)(methyl)sulfamoyl] amino}pyridin-2-yl)-1H-pyrrolo[2,3-b]pyridin-4-yl] amino}piperidin-1-yl]-3-oxopropanenitrile as an off-white solid (0.01 g, 6% yield): $^1$H NMR (400 MHz, DMSO-d$_6$) δ 12.37 (s, 1H), 10.81 (s, 2H), 8.45-8.46 (m, 1H), 8.24-8.26 (m, 1H), 7.41-7.48 (m, 2H) 7.16-7.17 (m, 1H), 6.91 (s, 1H), 4.08 (s, 1H), 3.60-3.76 (m, 4H), 2.80 (s, 6H), 2.04-21.30 (m, 6H); MS (ES) m/z 483.2 (M+H).

Analytical Conditions:
Flow rate: 0.3 mL/min
Column: BEH C18 (50 mm×2.1 mm×1.7 μm)
Mobile Phase (A): 0.1% TFA in water
Mobile Phase (B): MeCN Example 55: Preparation of (R)-3-(3-((5-(5-(methylsulfonyl)pyridin-2-yl)-1H-pyrrolo[2,3-b]pyridin-4-yl)amino)piperidin-1-yl)-3-oxopropanenitrile

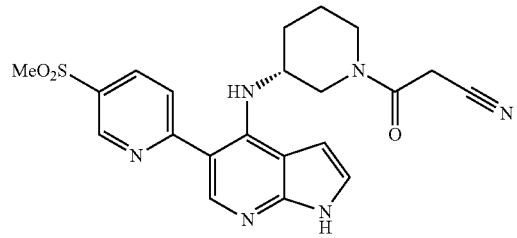 [SMILES: CS(=O)(=O)c1ccc(-c2cnc3[nH]ccc3c2N[C@@H]2CCCN(C(=O)CC#N)C2)nc1]

Scheme 53. Preparation of (R)-3-(3-((5-(5-(methylsulfonyl)pyridin-2-yl)-1H-pyrrolo[2,3-b]pyridin-4-yl)amino) piperidin-1-yl)-3-oxopropanenitrile

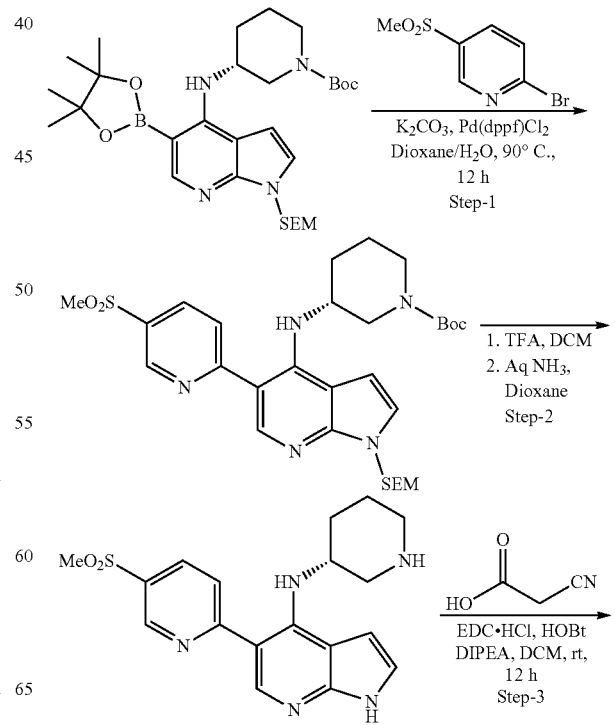

-continued

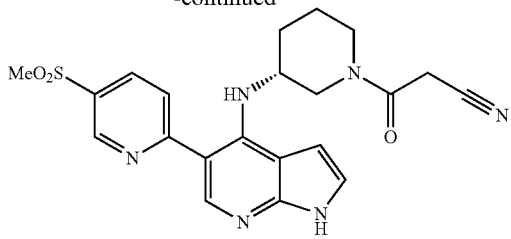

Step 1: Preparation of tert-butyl (R)-3-((5-(5-(methylsulfonyl)pyridin-2-yl)-1-((2-(trimethylsilyl)ethoxy)methyl)-1H-pyrrolo[2,3-b]pyridin-4-yl)amino)piperidine-1-carboxylate

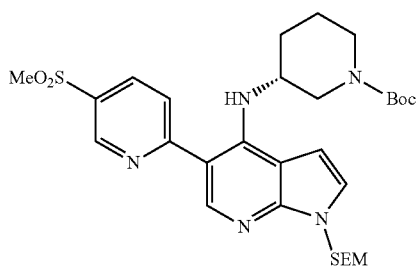 [SMILES: CC(C)(C)OC(=O)N1CCC[C@@H](Nc2c(-c3ccc(S(C)(=O)=O)cn3)cnc3c2ccn3COCC[Si](C)(C)C)C1]

To a stirred solution of tert-butyl (R)-3-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate (1.0 g, 1.75 mmol) and 2-bromo-5-(methylsulfonyl)pyridine (0.62 g, 2.6 mmol) in 1,4-dioxane (10 mL) was added dichlorobis (triphenylphosphine)palladium(II) (0.07 g, 0.09 mmol) followed by a 2M aqueous solution of potassium carbonate (0.72 g, 5.25 mmol) and the mixture was heated at 90° C. for 12 hours under nitrogen in a sealed tube. The reaction was cooled to ambient temperature, diluted with ethyl acetate and water. The organic layer was separated, washed with brine, dried over anhydrous sodium sulfate, filtered and concentrated in vacuo. The crude material was purified by flash chromatography (40% ethyl acetate/hexane) to provide tert-butyl (R)-3-((5-(5-(methylsulfonyl)pyridin-2-yl)-1-((2-(trimethylsilyl)ethoxy)methyl)-1H-pyrrolo[2,3-b]pyridin-4-yl)amino)piperidine-1-carboxylate as a sticky pale yellow solid (0.19 g, 18% yield): MS (ES) m/z 602.3 (M+H).

Step 2: Preparation of (R)-5-(5-(methylsulfonyl)pyridin-2-yl)-N-(piperidin-3-yl)-1H-pyrrolo[2,3-b]pyridin-4-amine

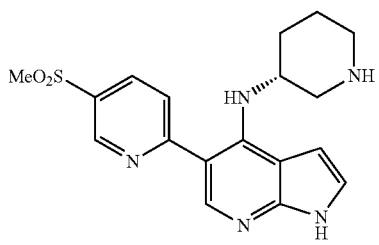 [SMILES: CS(=O)(=O)c1ccc(-c2cnc3[nH]ccc3c2N[C@@H]2CCCNC2)nc1]

A solution of tert-butyl (R)-3-((5-(5-(methylsulfonyl)pyridin-2-yl)-1-((2-(trimethylsilyl)ethoxy)methyl)-1H-pyrrolo[2,3-b]pyridin-4-yl)amino)piperidine-1-carboxylate (0.19 g, 0.32 mmol) in dichloromethane:trifluoroacetic acid (3 mL:3 mL) was stirred at ambient temperature for 3 hours. The reaction mixture was concentrated in vacuo, the residue was dissolved in 1,4-dioxane:aqueous ammonia (3 mL:3 mL 23% in water) and the solution stirred at ambient temperature for 16 hours. The reaction mixture was concentrated in vacuo to provide (R)-5-(5-(methylsulfonyl)pyridin-2-yl)-N-(piperidin-3-yl)-1H-pyrrolo [2,3-b]pyridin-4-amine as an off-white solid (0.15 g, crude); MS (ES) m/z 372.2 (M+H).

Step 3: Preparation of (R)-3-(3-((5-(5-(methylsulfonyl)pyridin-2-yl)-1H-pyrrolo[2,3-b]pyridin-4-yl)amino)piperidin-1-yl)-3-oxopropanenitrile

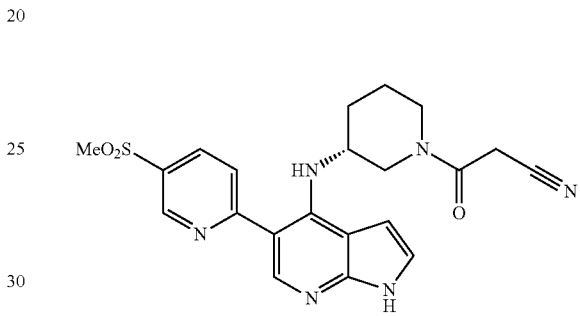

A solution of cyanoacetic acid (0.051 g, 0.6 mmol), N-(3-dimethylaminopropyl)-N'-ethylcarbodiimide hydrochloride (0.085 g, 0.6 mmol), 1-hydroxybenzotriazole (0.82 g, 0.6 mmol) and N,N-diisopropylethylamine (0.2 mL, 1.2 mmol) in dichloromethane (15 mL) was stirred at ambient temperature for 5 minutes. Then (R)-5-(5-(methylsulfonyl)pyridin-2-yl)-N-(piperidin-3-yl)-1H-pyrrolo[2,3-b]pyridin-4-amine (0.15 g, 0.4 mmol) was added and the resulting mixture stirred at ambient temperature for 12 hours. The reaction mixture was quenched with water and extracted with dichloromethane. The organic layer was washed with water, brine, dried over anhydrous sodium sulfate, filtered and concentrated in vacuo. The crude material was purified by reverse phase chromatography to provide (R)-3-(3-((5-(5-(methylsulfonyl)pyridin-2-yl)-1H-pyrrolo[2,3-b]pyridin-4-yl)amino)piperidin-1-yl)-3-oxopropanenitrile as an off-white solid (0.03 g, 16% yield): $^1$H NMR (400 MHz, DMSO-$d_6$ VT at 100° C.) δ 11.27 (br s, 1H), 9.96 (br s, 1H), 8.98 (s, 1H), 8.51 (s, 1H), 8.24 (d, J=2.2 Hz, 1H), 8.13 (d, J=2.2 Hz, 1H), 7.16 (s, 1H), 6.66 (s, 1H), 4.29 (br s, 1H), 3.89 (br s, 2H), 3.40-3.45 (m, 3H), 3.27 (s, 3H), 2.08 (br s, 1H), 1.64-1.77 (m, 3H), 1.25 (s, 1H); MS (ES) m/z 439.1 (M+H).

Analytical Conditions:
Column: X bridge (250 mm×4.6 mm×5 micron)
Mobile phase (A): 0.1% Ammonia in water
Mobile phase (B): Methanol
Flow rate: 1.0 mL/min Example 56: Preparation of (R)-N-(2-(4-((1-(2-cyanoacetyl)piperidin-3-yl)amino)-1H-pyrrolo[2,3-b]pyridin-5-yl)pyridin-4-yl)methanesulfonamide

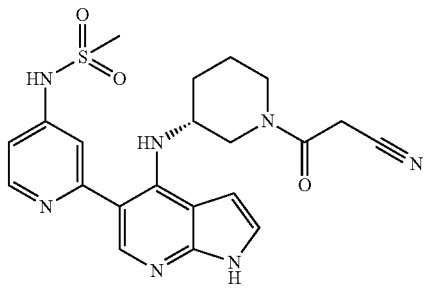 [SMILES: CS(=O)(=O)Nc1ccnc(-c2cnc3[nH]ccc3c2N[C@@H]2CCCN(C(=O)CC#N)C2)c1]

Scheme 54. Preparation of (R)-N-(2-(4-((1-(2-cyanoacetyl)piperidin-3-yl)amino)-1H-pyrrolo[2,3-b] pyridin-5-yl)pyridin-4-yl)methanesulfonamide

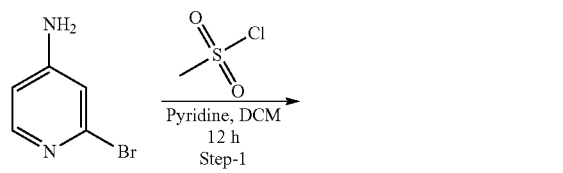

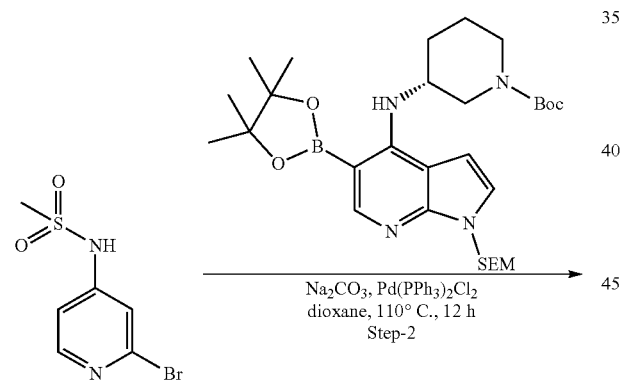

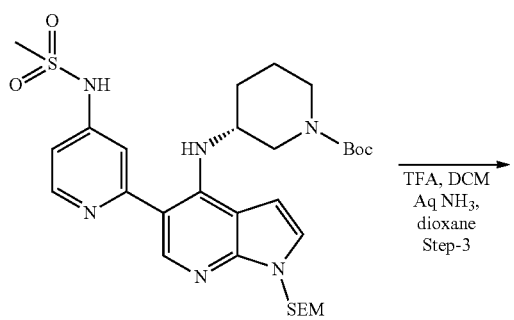

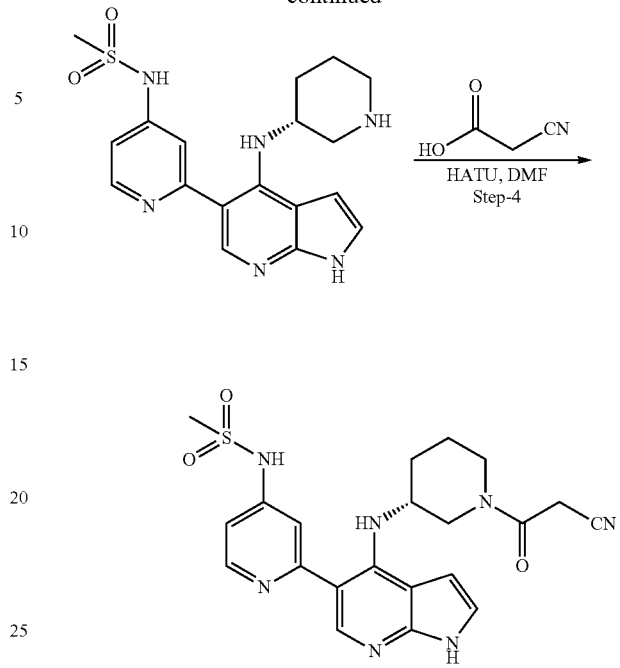

Step 1: Preparation of N-(2-bromopyridin-4-yl)methanesulfonamide

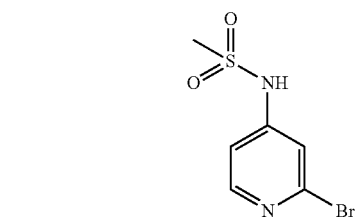

Methanesulfonyl chloride (0.79 ml, 6.97 mmol) was added to a stirred solution of 2-bromopyridin-4-amine (1.0 g, 5.81 mmol) and pyridine (1 mL) in dichloromethane (5 mL) at 0° C. and the solution warmed to ambient temperature and stirred for 12 hours. The reaction mixture was quenched with ice cold water and extracted with ethyl acetate. The organic layer was washed with water, brine and dried over anhydrous sodium sulfate. The solution was filtered and concentrated in vacuo. The crude material was purified by using flash chromatography (20% ethyl acetate/hexane) to provide N-(2-bromopyridin-4-yl)methanesulfonamide as a brown solid (0.4 g, 28% yield): MS (ES) m/z 252.8 (M+H).

Step 2: Preparation of tert-butyl (R)-3-((5-(4-(methylsulfonamido)pyridin-2-yl)-1-((2-(trimethylsilyl)ethoxy)methyl)-1H-pyrrolo[2,3-b]pyridin-4-yl)amino)piperidine-1-carboxylate

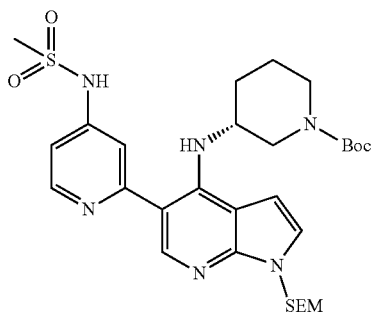 [SMILES: CC(C)(C)OC(=O)N1CCC[C@@H](Nc2c(-c3cc(NS(C)(=O)=O)ccn3)cnc3c2ccn3COCC[Si](C)(C)C)C1]

To a solution of tert-butyl (R)-3-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate (0.80 g, 1.39 mmol) and N-(2-bromopyridin-4-yl)methanesulfonamide (0.28 g, 1.58 mmol) in 1,4-dioxane (8 mL) was added bis(triphenylphosphine) palladium(II) dichloride (0.09 g, 0.02 mmol) followed by a 2M aqueous solution of sodium carbonate (0.45 g, 4.17 mmol) and the mixture stirred at 100° C. for 12 hours under a nitrogen atmosphere. The reaction mixture was cooled to ambient temperature, diluted with ethyl acetate, washed with water, brine, dried over anhydrous sodium sulfate, filtered and concentrated in vacuo. The crude material was purified by flash chromatography (30% ethyl acetate/hexane) to provide tert-butyl (R)-3-((5-(4-(methylsulfonamido)pyridin-2-yl)-1-((2-(trimethylsilyl)ethoxy)methyl)-1H-pyrrolo[2,3-b]pyridin-4-yl)amino)piperidine-1-carboxylate as a colorless thick liquid (0.12 g, 12% yield): MS (ES) m/z 616.9 (M+H).

Step 3: Preparation of (R)-N-(2-(4-(piperidin-3-ylamino)-1H-pyrrolo[2,3-b]pyridin-5-yl)pyridin-4-yl)methanesulfonamide

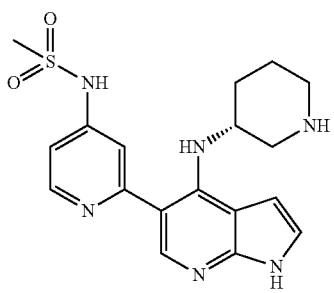 [SMILES: CS(=O)(=O)Nc1ccnc(-c2cnc3[nH]ccc3c2N[C@@H]2CCCNC2)c1]

A solution of (R)-3-((5-(4-(methylsulfonamido)pyridin-2-yl)-1-((2-(trimethylsilyl)ethoxy)methyl)-1H-pyrrolo[2,3-b]pyridin-4-yl)amino)piperidine-1-carboxylate (0.140 g, 0.22 mmol) in dichloromethane:trifluoroacetic acid (2 mL:2 mL) was stirred at ambient temperature for 3 hours. The reaction mixture was concentrated in vacuo, the obtained residue dissolved in 1,4-dioxane:aqueous ammonia (2 mL:4 mL 23% in water) and stirred at ambient temperature for 16 hours. The reaction mixture was concentrated in vacuo to provide (R)-N-(2-(4-(piperidin-3-ylamino)-1H-pyrrolo[2,3-b]pyridin-5-yl)pyridin-4-yl)methanesulfonamide as an off-white solid (0.11 g, crude): MS (ES) m/z 385.1 (M−H)⁺.

Step 4: Preparation of (R)-N-(2-(4-((1-(2-cyanoacetyl)piperidin-3-yl)amino)-1H-pyrrolo[2,3-b]pyridin-5-yl)pyridin-4-yl)methanesulfonamide

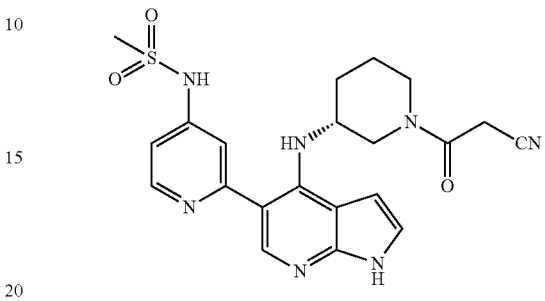

To a stirred solution of cyanoacetic acid (0.036 g, 0.426 mmol) and 1-[bis(dimethylamino)methylene]-1H-1,2,3-triazolo[4,5-b]pyridinium 3-oxide hexafluorophosphate (0.140 g, 0.37 mmol) in N,N-dimethylformamide (5 mL) was added (R)-N-(2-(4-(piperidin-3-ylamino)-1H-pyrrolo[2,3-b]pyridin-5-yl)pyridin-4-yl)methanesulfonamide (0.11 g, 0.284 mmol) followed by N,N-diisopropylethylamine (0.45 mL, 1.42 mmol) and the mixture stirred at ambient temperature for 16 hours. The reaction was quenched with water and extracted with ethyl acetate. The organic layer was washed with water, brine and dried over anhydrous sodium sulfate. The solution was filtered and concentrated in vacuo. The crude material was purified by reverse phase chromatography to provide (R)-N-(2-(4-((1-(2-cyanoacetyl)piperidin-3-yl)amino)-1H-pyrrolo[2,3-b]pyridin-5-yl)pyridin-4-yl)methanesulfonamide as an off-white solid (0.02 g, 15% yield): ¹H NMR (400 MHz, DMSO-d$_6$) δ 11.37-11.41 (m, 1H), 9.90 (br s, 1H), 8.17-8.31 (m, 3H), 7.40-7.42 (s, 1H), 7.15 (s, 1H) 6.94 (s, 1H), 6.61 (s, 1H), 4.04 (m, 1H), 3.92-3.99 (m, 3H), 3.55-3.67 (m, 2H), 3.55 (m, 2H), 3.11 (s, 2H), 2.87 (s, 1H), 1.97 (s, 2H), 1.60-1.69 (s, 1H); MS (ES) m/z 454.1 (M+H).

Analytical Conditions:
Column: X-BridgeC-18 (250 mm×4.6 mm×5 mic)
Mobile phase (A): 0.1% Ammonia in water
Mobile phase (B): MeCN
Flow rate: 1.0 mL/min Example 57: Preparation of 3-((3R,5S)-3-methyl-5-((5-(pyrimidin-4-yl)-1H-pyrrolo[2,3-b]pyridin-4-yl)amino)piperidin-1-yl)-3-oxopropanenitrile

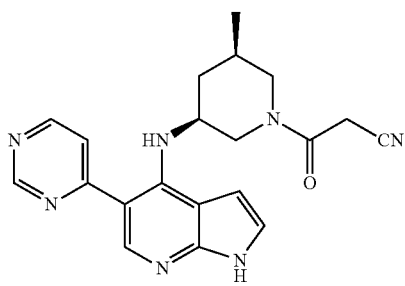 [SMILES: C[C@@H]1C[C@H](Nc2c(-c3ccncn3)cnc3[nH]ccc23)CN(C(=O)CC#N)C1]

277

Scheme 55. Preparation of 3-((3R,5S)-3-methyl-5-((5-(pyrimidin-4-yl)-1H-pyrrolo[2,3-b]pyridin-4-yl)amino)piperidin-1-yl)-3-oxopropanenitrile

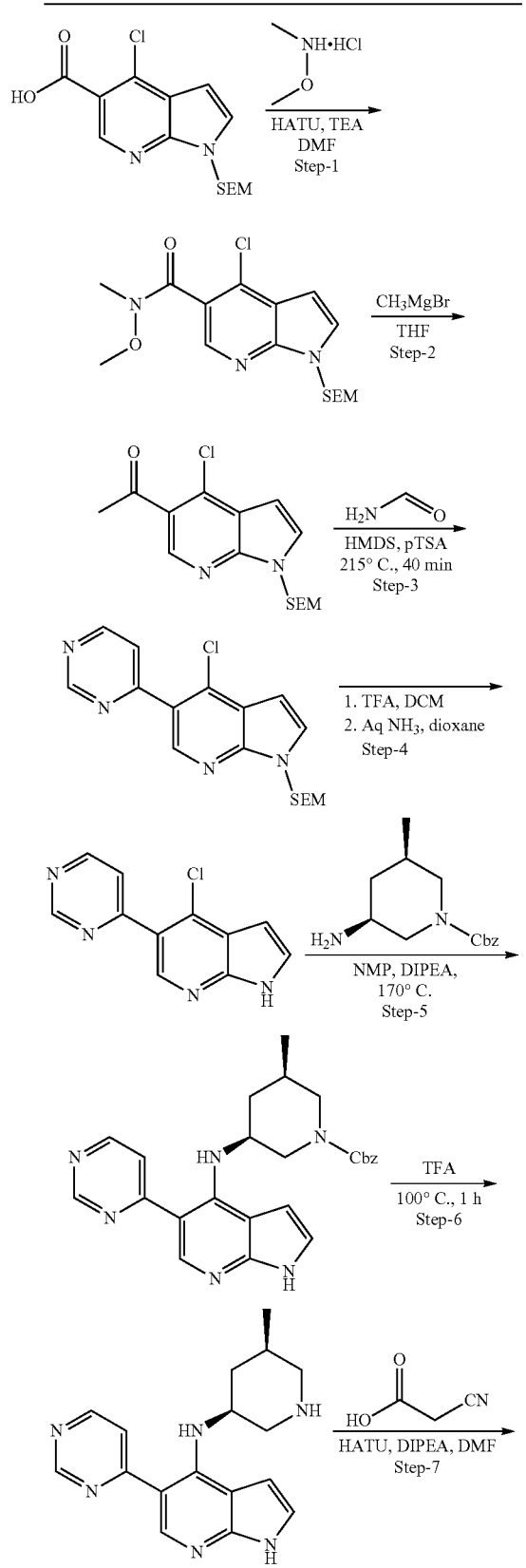

278

-continued

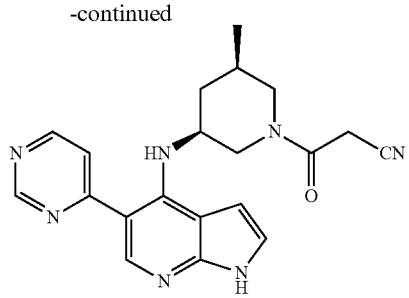

Step 1: Preparation of 4-chloro-N-methoxy-N-methyl-1-((2-(trimethylsilyl)ethoxy)methyl)-1H-pyrrolo[2,3-b]pyridine-5-carboxamide

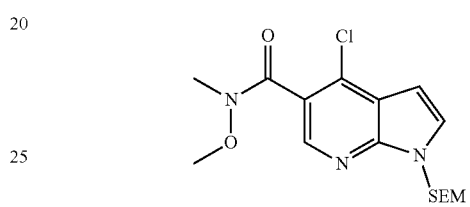

A solution of compound 4-chloro-1-{[2-(trimethylsilyl)ethoxy]methyl}-1H-pyrrolo[2,3-b]pyridine-5-carboxylic acid (5.0 g, 15.3 mmol) and [(dimethylamino)-1H-1,2,3-triazolo-[4,5-b]pyridin-1-ylmethylene]-N-methylmethanaminium hexafluorophosphate N-oxide (11.6 g, 30.6 mmol) in dichloromethane (50 mL) was stirred for 5 minutes. Methoxy(methyl)amine (1.40 g, 22.9 mmol) and N,N-diisopropylethylamine (7.99 mL, 45.9 mmol) were added and the mixture was stirred at ambient temperature. After 5 hours the reaction mixture was diluted with ethyl acetate, washed with water and brine. The organic layer was dried over anhydrous sodium sulfate, filtered and concentrated. The crude material was purified by flash chromatography (20% ethyl acetate/hexane) to provide 4-chloro-N-methoxy-N-methyl-1-{[2-(trimethylsilyl)ethoxy]methyl}-1H-pyrrolo[2,3-b]pyridine-5-carboxamide as a gummy brown solid (4 g, 71% yield): MS (ES) m/z 370.2 (M+H).

Step 2: Preparation of 1-(4-chloro-1-((2-(trimethylsilyl)ethoxy)methyl)-1H-pyrrolo[2,3-b]pyridine-5-yl)ethan-1-one

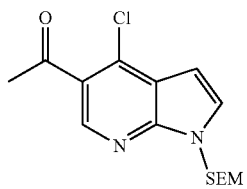 [SMILES: CC(=O)c1cnc2c(ccn2COCC[Si](C)(C)C)c1Cl]

To a stirred solution of 4-chloro-N-methoxy-N-methyl-1-{[2-(trimethylsilyl)ethoxy]methyl}-1H-pyrrolo[2,3-b]pyridine-5-carboxamide (10 g, 27 mmol) in tetrahydrofuran (100 mL) was added bromo(methyl)magnesium (27 mL 81.1 mmol) at 0° C. and the solution allowed to stir at ambient temperature for 2 hours. The reaction was quenched with saturated ammonium chloride solution and extracted with ethyl acetate. The organic layer was washed with brine, dried over sodium sulfate, filtered and concentrated to provide 1-(4-chloro-1-{[2-(trimethylsilyl) ethoxy]methyl}-1H-pyrrolo[2,3-b]pyridin-5-yl)ethan-1-one as a pale yellow thick liquid (6.5 g, 68% yield): MS (ES) m/z 325.2 (M+H).

Step 3: Preparation of 4-chloro-5-(pyrimidin-4-yl)-1-((2-(trimethylsilyl)ethoxy)methyl)-1H-pyrrolo[2,3-b]pyridine

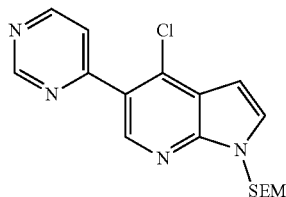 [SMILES: C[Si](C)(C)CCOCn1ccc2c(Cl)c(-c3ccncn3)cnc21]

A mixture of 1-(4-chloro-1-{[2-(trimethylsilyl)ethoxy]methyl}-1H-pyrrolo[2,3-b]pyridin-5-yl)ethan-1-one (2.0 g, 6.16 mmol), formamide (6 mL), p-toluenesulfonic acid (0.30 g, 1.54 mmol) and bis(trimethylsilyl)amine (1.61 mL, 7.70 mmol) was subjected to microwave irradiation at 215° C. for 40 minutes. The reaction mixture was cooled to room temperature and quenched with crushed ice and extracted with ethyl acetate. The organic layer was washed with brine, dried over sodium sulfate, filtered and concentrated in vacuo. The crude material was purified by flash chromatography (30% ethyl acetate/hexane to provide 4-(4-chloro-1-{[2-(trimethylsilyl)ethoxy]methyl}-1H-pyrrolo [2,3-b]pyridin-5-yl)pyrimidine as a brown solid (0.4 g, 18% yield): MS (ES) m/z 361.1 (M+H).

Step 4: Preparation of 4-chloro-5-(pyrimidin-4-yl)-1H-pyrrolo[2,3-b]pyridine

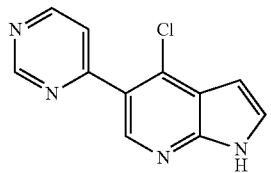 [SMILES: Clc1c(-c2ccncn2)cnc2[nH]ccc12]

A solution of 4-(4-chloro-1-{[2-(trimethylsilyl)ethoxy] methyl}-1H-pyrrolo[2,3-b]pyridin-5-yl)pyrimidine (0.80 g, 0.29 mmol) in dichloromethane:trifluoroacetic acid (0.5 mL:2 mL) was stirred at ambient temperature for 3 hours. The reaction mixture was concentrated in vacuo and the residue was dissolved in 1,4-dioxane:aqueous ammonia (0.2 mL:2 mL, 23% in water) and the mixture stirred at ambient temperature for 16 hours. The reaction mixture was concentrated in vacuo to provide 4-chloro-5-(pyrimidin-4-yl)-1H-pyrrolo[2,3-b]pyridine as a brown solid (0.5 g, crude): MS (ES) m/z 231.1 (M+H).

Step 5: Preparation of benzyl (3R,5S)-3-methyl-5-((5-(pyrimidin-4-yl)-1H-pyrrolo[2,3-b]pyridin-4-yl)amino)piperidine-1-carboxylate

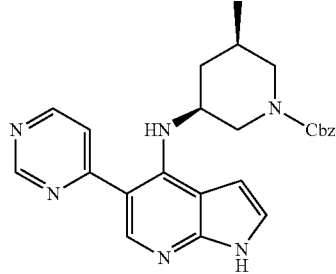 [SMILES: C[C@@H]1C[C@H](Nc2c(-c3ccncn3)cnc3[nH]ccc23)CN(C(=O)OCc2ccccc2)C1]

A stirred solution of 4-{4-chloro-1H-pyrrolo[2,3-b]pyridin-5-yl}pyrimidine (0.10 g, 0.43 mmol), 1-methylpyrrolidin-2-one (2 mL), benzyl (3S,5R)-3-amino-5-methylpiperidine-1-carboxylate (118 mg, 1.48 mmol) and N,N-diisopropylethylamine (0.1 mL, 0.58 mmol) was heated at 170° C. for 32 hours in a 10 mL sealed tube. The reaction mixture was cooled to ambient temperature and quenched with water and extracted with ethyl acetate. The organic layer was washed with brine, dried over sodium sulfate, filtered and concentrated in vacuo to provide benzyl (3R,5S)-3-methyl-5-{[5-(pyrimidin-4-yl)-1H-pyrrolo[2,3-b]pyridin-4-yl]amino}piperidine-1-carboxylate as a brown liquid (0.15 g, 44.57% yield): MS (ES) m/z 443.2 (M+H).

Step 6: Preparation of N-((3S,5R)-5-methylpiperidin-3-yl)-5-(pyrimidin-4-yl)-1H-pyrrolo[2,3-b]pyridin-4-amine

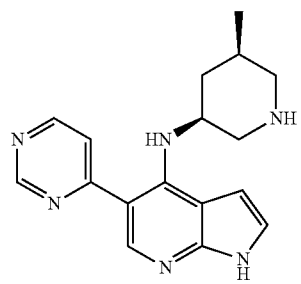 [SMILES: C[C@H]1CNC[C@@H](Nc2c(-c3ccncn3)cnc3[nH]ccc23)C1]

A stirred solution of benzyl (3R,5S)-3-methyl-5-{[5-(pyrimidin-4-yl)-1H-pyrrolo[2,3-b]pyridin-4-yl]amino}piperidine-1-carboxylate (0.25 g, 0.56 mmol) in trifluoroacetic acid (1 mL) was heated to 100° C. for 1 hour in a sealed tube. The reaction mixture was cooled to ambient temperature and concentrated in vacuo to provide N-((3S,5R)-5-methylpiperidin-3-yl)-5-(pyrimidin-4-yl)-1H-pyrrolo[2,3-b]pyridin-4-amine as a colorless gummy solid (0.17 g, 99% yield): MS (ES) m/z 309.2 (M+H).

Step 7: Preparation of 3-((3R,5S)-3-methyl-5-((5-(pyrimidin-4-yl)-1H-pyrrolo[2,3-b]pyridin-4-yl)amino)piperidin-1-yl)-3-oxopropanenitrile

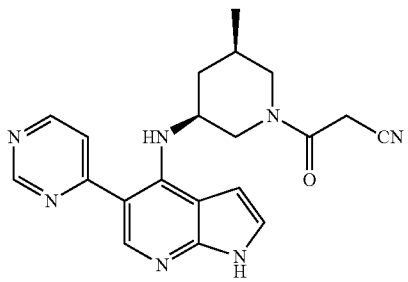 [SMILES: C[C@@H]1C[C@H](Nc2c(-c3ccncn3)cnc3[nH]ccc23)CN(C(=O)CC#N)C1]

A solution of cyanoacetic acid (0.06 g, 0.71 mmol) and 1-[bis(dimethylamino)methylene]-1H-1,2,3-triazolo[4,5-b]pyridinium 3-oxide hexafluorophosphate (0.252 g, 1.07 mmol) in N,N-dimethylformamide (1 mL) was stirred at ambient temperature for 3 minutes. Then (3S,5R)-5-methyl-N-[5-(pyrimidin-4-yl)-1H-pyrrolo[2,3-b]pyridin-4-yl]piperidin-3-amine (0.22 g, 0.71 mmol) was added followed by N,N-diisopropylethylamine (0.5 mL, 2.14 mmol) and the mixture stirred at ambient temperature for 16 hours. The reaction mixture was diluted with ethyl acetate, washed with water and brine. The organic layer was dried over anhydrous sodium sulfate, filtered and concentrated in vacuo. The crude material was purified by reverse phase chromatography to provide 3-((3R,5S)-3-methyl-5-((5-(pyrimidin-4-yl)-1H-pyrrolo[2,3-b]pyridin-4-yl) amino) piperidin-1-yl)-3-oxopropanenitrile as an off-white solid (0.012 g, 4.5% yield): $^1$H NMR (400 MHz, DMSO-$d_6$, VT at 80° C.) δ 11.36 (s, 1H), 10.06 (br s, 1H), 9.08 (s, 1H), 8.65-8.66 (s, 1H), 8.54 (s, 1H), 7.96-7.97 (m, 1H), 7.16 (s, 1H), 6.71 (s, 1H), 4.77 (s, 1H), 3.98 (m, 4H), 3.65 (m, 1H), 2.70 (m, 1H), 2.30 (m, 1H), 1.85 (m, 1H), 1.29 (m, 1H), 0.93-0.94 (m, 3H); MS (ES) m/z 376.2 (M+H).

Analytical Conditions:

Column: BEH C18 (50 mm×2.1 mm×1.7 μm)

Mobile phase (A): 0.1% Formic acid in water

Mobile phase (B): MeCN

Flow rate: 0.3 mL/min

Example 58: Preparation of (R)-3-(3-((5-(1H-pyrazol-5-yl)-1H-pyrrolo[2,3-b]pyridin-4-yl)amino)piperidin-1-yl)-3-oxopropanenitrile

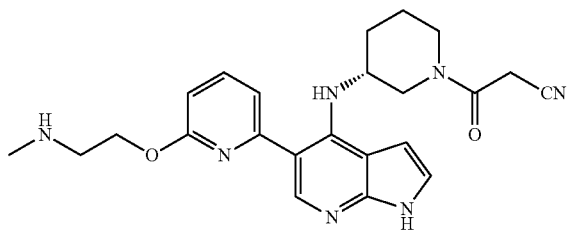 [SMILES: CNCCOc1cccc(-c2cnc3[nH]ccc3c2N[C@@H]2CCCN(C(=O)CC#N)C2)n1]

Scheme 56. Preparation of (R)-3-(3-((5-(1H-pyrazol-5-yl)-1H-pyrrolo[2,3-b]pyridin-4-yl)amino)piperidin-1-yl)-3-oxopropanenitrile

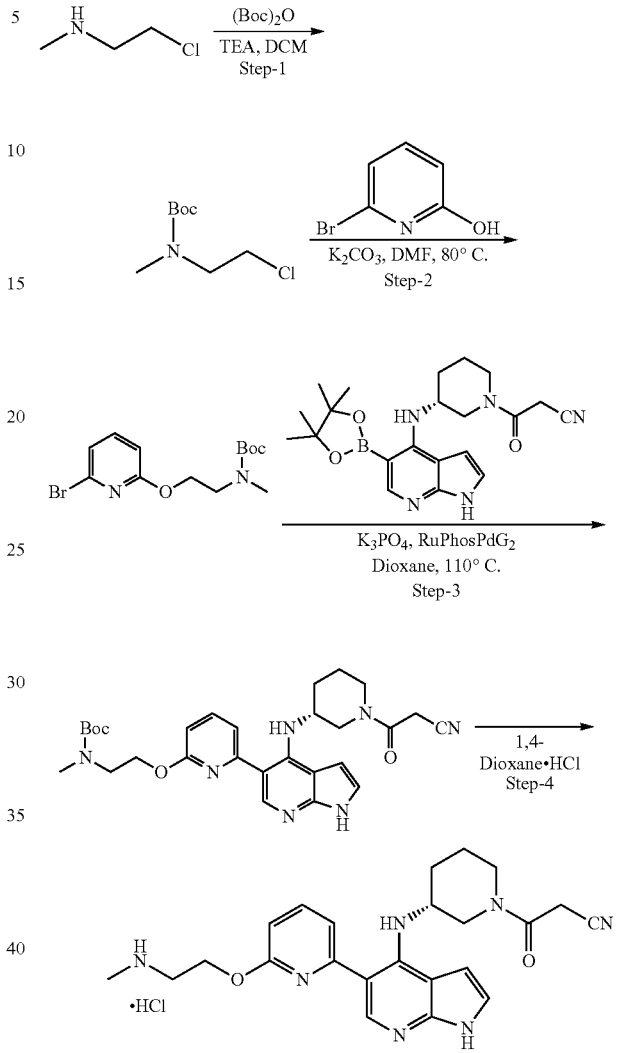

Step 1: Preparation of tert-butyl (2-chloroethyl)(methyl)carbamate

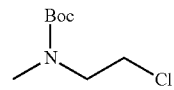

To a stirred solution of 2-chloro-N-methylethan-1-amine (4.0 g, 42.9 mmol) and triethylamine (17.99 mL, 128.7) in dichloromethane (30 mL) was added di-tert-butyl dicarbonate (12.8 mL, 55.8 mmol) and the solution stirred at ambient temperature for 12 hours. The reaction was quenched with water and extracted with ethyl acetate. The organic layer was washed with water, brine and dried over anhydrous sodium sulfate. The solution was filtered and concentrated in vacuo to provide tert-butyl (2-chloroethyl)(methyl)carbamate as a semi solid (3 g, crude).

Step 2: Preparation of tert-butyl (2-((6-bromopyridin-2-yl)oxy)ethyl)(methyl)carbamate

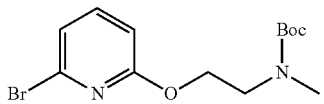

A suspension of 6-bromopyridin-2-ol (2.0 g, 10.4 mmol) and potassium carbonate (2.3 g, 17.2 mmol) in N,N-dimethylformamide (15 mL) was added to tert-butyl (2-chloroethyl)(methyl)carbamate (1.5 g, 8.6 mmol) and the mixture was heated to 80° C. for 12 hours. The reaction was cooled to ambient temperature, quenched with water and extracted with ethyl acetate. The organic layer was washed with water, brine and dried over anhydrous sodium sulfate, filtered and concentrated in vacuo. The crude material was purified using flash chromatography (10% ethyl acetate/hexane) to provide tert-butyl (2-((6-bromopyridin-2-yl)oxy)ethyl)(methyl)carbamate as a colorless gummy solid (0.65 g, 26% yield): MS (ES) m/z 330.1; 333.1 (1:1; M+H).

Step 3: Preparation of tert-butyl (R)-(2-((6-(4-((1-(2-cyanoacetyl)piperidin-3-yl)amino)-1H-pyrrolo[2,3-b]pyridin-5-yl)pyridin-2-yl)oxy)ethyl)(methyl)carbamate

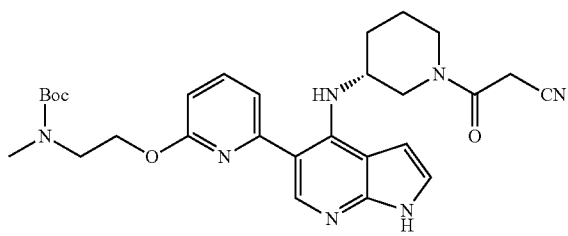 [SMILES: CN(CCOc1cccc(-c2cnc3[nH]ccc3c2N[C@@H]2CCCN(C(=O)CC#N)C2)n1)C(=O)OC(C)(C)C]

To a stirred solution of (R)-3-oxo-3-(3-((5-(4,4,5,5-tetramethyl-1,3,2-dioxaborolan-2-yl)-1H-pyrrolo[2,3-b]pyridin-4-yl)amino)piperidin-1-yl)propanenitrile (0.2 g, 0.49 mmol, Example 61, step 1), and tert-butyl (2-((6-bromopyridin-2-yl)oxy)ethyl)(methyl)carbamate (0.16 g, 0.49 mmol) in 1,4-dioxane (8 mL) was added chloro(2-dicyclohexylphosphino-2',4',6'-triisopropyl-1,1'-biphenyl)[2-(2'-amino-1,1'-biphenyl)]palladium(I) (0.04 g, 0.05 mmol) followed by 2M aqueous solution of potassium phosphate (0.31 g, 1.46 mmol) and the mixture stirred at 110° C. for 12 hours under a nitrogen atmosphere. The reaction mixture was cooled to ambient temperature, filtered and concentrated in vacuo. The crude material was purified by flash chromatography (5% methanol/chloromethane) to provide tert-butyl (R)-(2-((6-(4-((1-(2-cyanoacetyl)piperidin-3-yl)amino)-1H-pyrrolo[2,3-b]pyridin-5-yl)pyridin-2-yl)oxy)ethyl)(methyl)carbamate as a viscous brown liquid (0.06 g, 23% yield): MS (ES) m/z 534.2 (M+H).

Step 4: Preparation of (R)-3-(3-((5-(6-(2-(methylamino)ethoxy)pyridin-2-yl)-1H-pyrrolo[2,3-b]pyridin-4-yl)amino)piperidin-1-yl)-3-oxopropanenitrile hydrochloride

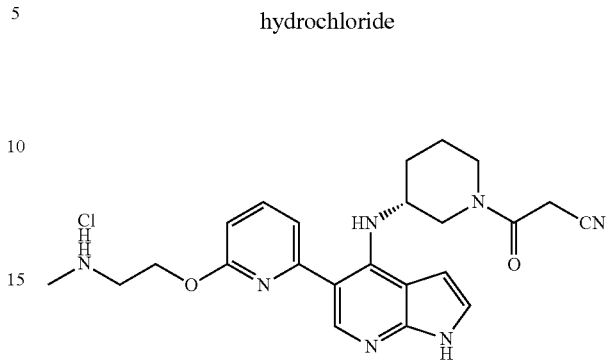

A solution of tert-butyl (R)-(2-((6-(4-((1-(2-cyanoacetyl)piperidin-3-yl)amino)-1H-pyrrolo[2,3-b]pyridin-5-yl)pyridin-2-yl)oxy)ethyl)(methyl)carbamate (0.05 g, 0.09 mmol) in dioxane (1 mL): 4N hydrochloride in dioxane (0.5 mL) was stirred at ambient temperature for 40 minutes. The reaction mixture was concentrated in vacuo and purified by reverse phase chromatography to provide (R)-3-(3-((5-(6-(2-(methylamino)ethoxy)pyridin-2-yl)-1H-pyrrolo[2,3-b]pyridin-4-yl)amino)piperidin-1-yl)-3-oxopropanenitrile hydrogen chloride as an off-white solid (0.01 g, 23% yield): $^1$H NMR (400 MHz, DMSO-$d_6$) δ 12.14 (br s, 1H), 8.70 (br s, 2H), 8.25-8.27 (m, 1H), 7.90-7.93 (m, 1H), 7.37-7.43 (m, 2H), 6.87-6.89 (m, 2H), 4.49-4.52 (m, 3H), 4.30 (m, 1H), 3.99-4.10 (m, 3H), 3.75-3.80 (m, 1H), 3.60 (m, 2H), 2.79-2.85 (m, 1H), 2.64 (s, 3H), 2.13 (s, 1H), 1.68 (br s, 3H); MS (ES) m/z 434.6 (M+H).

Analytical Conditions:
Kinetex EVO C18 (100 mm×2.1 mm×2.6 μm)
Mobile phase (A): 0.1% trifluoroacetic acid in water
Mobile phase (B): MeCN
Flow rate: 0.75 mL/min

Example 59. Preparation of (R)-3-(3-((5-(3-(methylsulfonyl)phenyl)-1H-pyrrolo[2,3-b]pyridin-4-yl)amino)piperidin-1-yl)-3-oxopropanenitrile

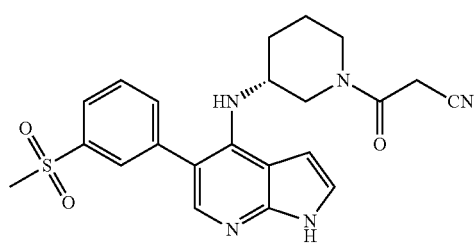 [SMILES: CS(=O)(=O)c1cccc(-c2cnc3[nH]ccc3c2N[C@@H]2CCCN(C(=O)CC#N)C2)c1]

285

Scheme 57. Preparation of (R)-3-(3-((5-(3-(methylsulfonyl)phenyl)-1H-pyrrolo[2,3-b]pyridin-4-yl)amino)piperidin-1-yl)-3-oxopropanenitrile

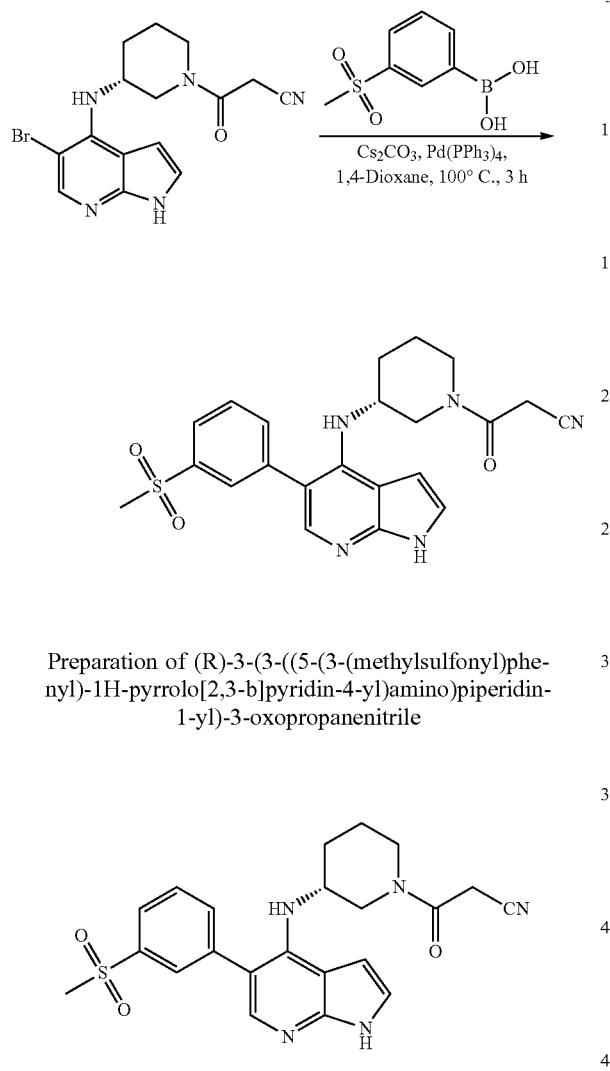

Preparation of (R)-3-(3-((5-(3-(methylsulfonyl)phenyl)-1H-pyrrolo[2,3-b]pyridin-4-yl)amino)piperidin-1-yl)-3-oxopropanenitrile To a stirred solution of (R)-3-(3-((5-bromo-1H-pyrrolo[2,3-b]pyridin-4-yl)amino)piperidin-1-yl)-3-oxopropanenitrile (0.05 g, 0.14 mmol) in 1,4-dioxane (4 mL) was added 3-(methylsulfonyl)phenylboronic acid (0.04 g, 0.21 mmol) and 2M aqueous solution of cesium carbonate (0.13 g, 0.41 mmol) and the mixture degassed with argon for 15 minutes. Tetrakistriphenylphosphine palladium (0) (0.01 g, 0.07 mmol) was added and the resulting mixture was heated in a sealed tube at 100° C. for 3 hours. The reaction mixture was cooled to room temperature, filtered through celite and the filtrate was collected and concentrated in vacuo. The crude was purified by column chromatography (5% methanol/dichloromethane) to provide (R)-3-(3-((5-(3-(methylsulfonyl)phenyl)-1H-pyrrolo[2,3-b]pyridin-4-yl)amino)piperidin-1-yl)-3-oxopropanenitrile as an off-white solid (0.05 g, 42% yield): $^1$H NMR (400 MHz, DMSO-$d_6$, VT at 70° C.) δ 11.23 (s, 1H), 7.81-7.87 (m, 2H), 7.73 (d, J=6.8 Hz, 3H), 7.22 (s, 1H), 6.61 (s, 1H), 4.90 (br s, 1H), 4.11 (br s, 1H), 3.84 (br s, 5H), 3.42 (br s, 1H), 3.21 (s, 3H), 1.93 (br s, 1H), 1.51-1.58 (m, 3H); MS (ES) m/z 437.9 (M+H).

286

Example 60: Preparation of (R)-3-(3-((5-(4-methylpyridin-2-yl)-1H-pyrrolo[2,3-b]pyridin-4-yl)amino)piperidin-1-yl)-3-oxopropanenitrile

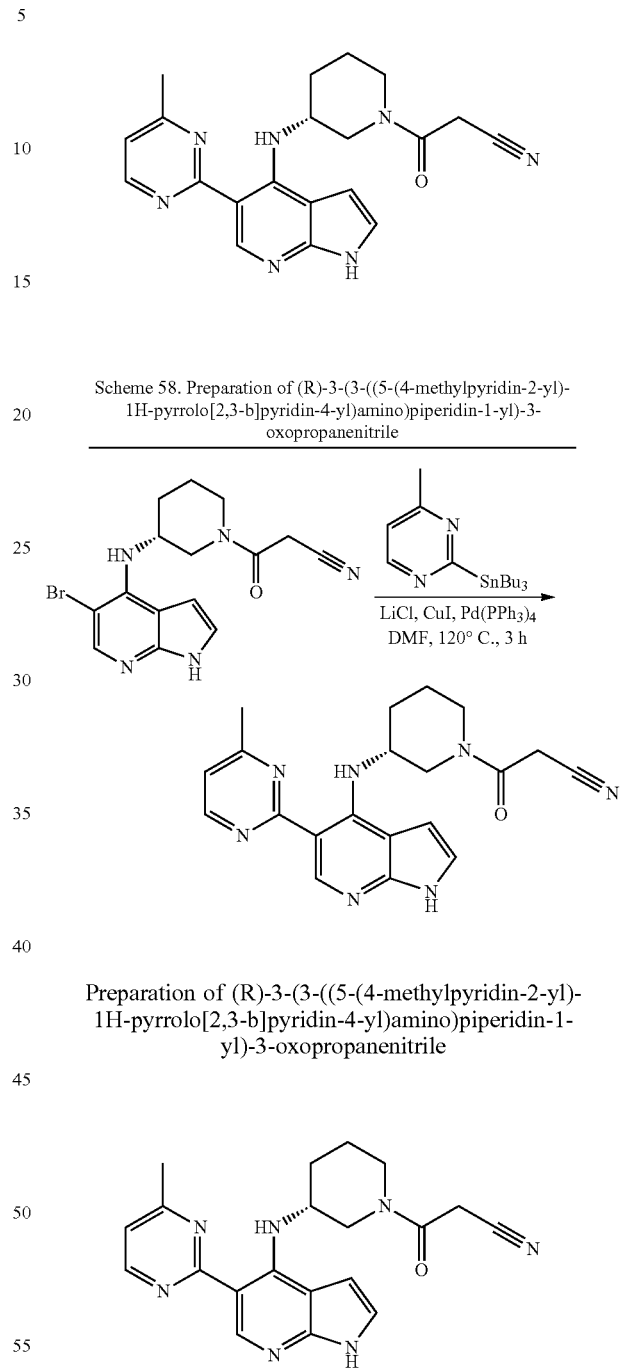

Scheme 58. Preparation of (R)-3-(3-((5-(4-methylpyridin-2-yl)-1H-pyrrolo[2,3-b]pyridin-4-yl)amino)piperidin-1-yl)-3-oxopropanenitrile Preparation of (R)-3-(3-((5-(4-methylpyridin-2-yl)-1H-pyrrolo[2,3-b]pyridin-4-yl)amino)piperidin-1-yl)-3-oxopropanenitrile To a solution of (R)-3-(3-((5-bromo-1H-pyrrolo[2,3-b]pyridin-4-yl)amino)piperidin-1-yl)-3-oxopropanenitrile (0.4 g, 1.1 mmol) in N,N-dimethylformamide (10 mL) was added lithium chloride (0.095 g, 1.1 mmol), 4-methyl-2-(tributylstannyl)pyrimidine (0.50 g, 1.3 mmol), copper iodide (0.021 g, 0.05 mmol), and tetrakis(triphenyl-phosphine)palladium (0) (0.07 g, 0.05 mmol) and the resulting mixture stirred at 120° C. for 3 hours in sealed tube under a nitrogen atmosphere. The reaction was cooled to ambient temperature, diluted with ethyl acetate and water. The organic layer was separated, washed with brine, dried over anhydrous sodium sulfate, filtered and concentrated in vacuo. The crude material was purified by reverse phase chromatography to provide ((R)-3-(3-((5-(4-methylpyridin-2-yl)-1H-pyrrolo[2,3-b]pyridin-4-yl)amino)piperidin-1-yl)-3-oxopropanenitrile as an off-white solid (0.01 g, 7% yield): $^1$H NMR (400 MHz, DMSO-$d_6$) δ 12.09 (br s, 1H), 8.43 (br s, 1H), 8.21 (s, 1H), 7.49 (s, 1H), 7.35 (s, 1H), 7.16 (d, J=4.8 Hz, 1H), 6.87 (s, 1H), 4.30-4.55 (m, 1H), 3.55-4.05 (m, 3H), 3.30-3.45 (m, 2H), 2.82 (s, 3H), 1.95-2.10 (m, 2H), 1.60-1.85 (m, 3H); MS (ES) m/z 376.1 (M+H).

Analytical Conditions:
Column: X-BridgeC-18 (250 mm×4.6 mm×5 mic)
Mobile phase (A): 0.1% Ammonia in water
Mobile phase (B): MeCN
Flow rate: 1.0 mL/min Example 61: Preparation of (R)-2-(4-((1-(2-cyanoacetyl)piperidin-3-yl)amino)-1H-pyrrolo[2,3-b]pyridin-5-yl)-N-methylisonicotinamide

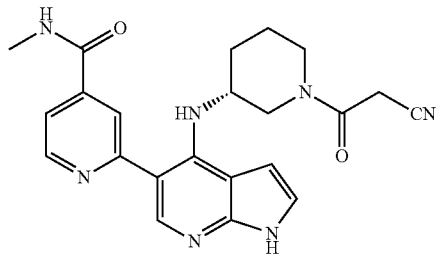 [SMILES: CNC(=O)c1ccnc(-c2cnc3[nH]ccc3c2N[C@@H]2CCCN(C(=O)CC#N)C2)c1]

Scheme 59. Preparation of (R)-2-(4-((1-(2-cyanoacetyl)piperidin-3-yl)amino)-1H-pyrrolo[2,3-b][pyridin-5-yl)-N-methylisonicotinamide

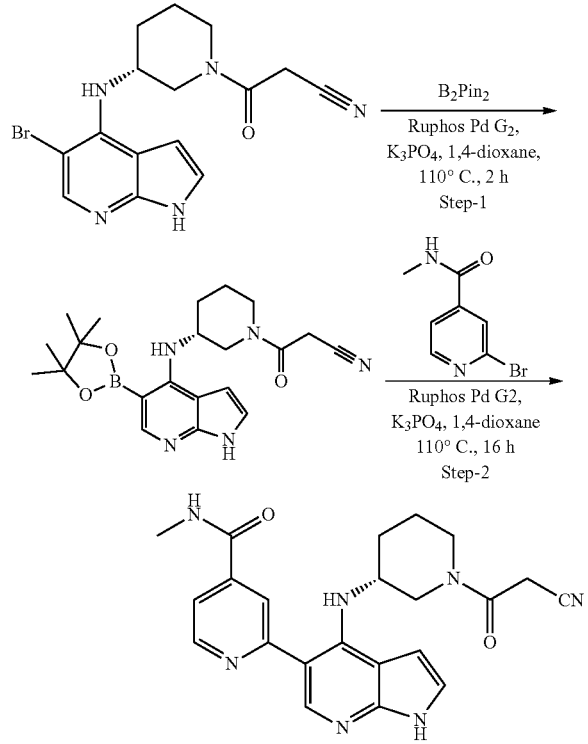

Step 1: Preparation of (R)-3-oxo-3-(3-((5-(4,4,5,5-tetramethyl-1,3,2-dioxaborolan-2-yl)-1H-pyrrolo[2,3-b]pyridin-4-yl)amino)piperidin-1-yl)propanenitrile

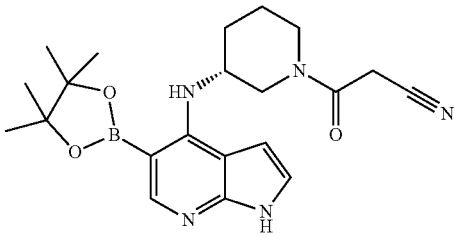 [SMILES: CC1(C)OB(c2cnc3[nH]ccc3c2N[C@@H]2CCCN(C(=O)CC#N)C2)OC1(C)C]

To a stirred solution of (R)-3-(3-((5-bromo-1H-pyrrolo[2,3-b]pyridin-4-yl)amino)piperidin-1-yl)-3-oxopropanenitrile (0.20 g, 0.55 mmol) in 1,4-dioxane (6 ml) was added 4,4,5,5-tetramethyl-2-(4,4,5,5-tetramethyl-1,3,2-dioxaborolan-2-yl)-1,3,2-dioxaborolane (0.14 g, 0.57 mmol), potassium phosphate (0.35 g, 1.66 mmol) and chloro(2-dicyclohexylphosphino-2',6'-diisopropoxy-1,1'-biphenyl)[2-(2'-amino-1,1'-biphenyl)]palladium(II) (0.09 g, 0.11 mmol) and the reaction mixture stirred at 110° C. for 2 hours under a nitrogen atmosphere. The reaction was cooled to ambient temperature, diluted with ethyl acetate and washed with water. The organic layer was washed with brine, dried over anhydrous sodium sulfate, filtered and concentrated in vacuo. The crude material was purified by reverse phase chromatography to provide (R)-3-oxo-3-(3-((5-(4,4,5,5-tetramethyl-1,3,2-dioxaborolan-2-yl)-1H-pyrrolo[2,3-b]pyridin-4-yl)amino)piperidin-1-yl)propanenitrile as a sticky brown solid (0.45 g, crude).

Step 2: Preparation of (R)-2-(4-((1-(2-cyanoacetyl)piperidin-3-yl)amino)-1H-pyrrolo[2,3-b]pyridin-5-yl)-N-methylisonicotinamide

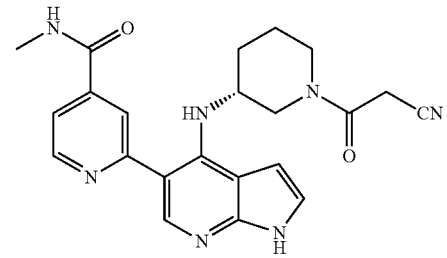 [SMILES: CNC(=O)c1ccnc(-c2cnc3[nH]ccc3c2N[C@@H]2CCCN(C(=O)CC#N)C2)c1]

To a stirred solution of (R)-3-oxo-3-(3-((5-(4,4,5,5-tetramethyl-1,3,2-dioxaborolan-2-yl)-1H-pyrrolo[2,3-b]pyridin-4-yl)amino)piperidin-1-yl)propanenitrile (0.20 g, 0.49 mmol) in 1,4-dioxane:water (10 mL), was added 2-bromo-N-methylisonicotinamide (0.13 g, 0.58 mmol), chloro(2-dicyclohexylphosphino-2',6'-diisopropoxy-1,1'-biphenyl)[2-(2'-amino-1,1'-biphenyl)]palladium(II) (0.04 g, 4.89 mmol) and 2M aqueous solution of potassium phosphate (0.31 g, 0.15 mmol) and the reaction mixture stirred at 110° C. under a nitrogen atmosphere. After 16 hours, the reaction mixture was cooled to ambient temperature, diluted with DCM, and filtered through celite. The filtrate was concentrated in vacuo and the crude material purified by reverse phase chromatography to provide (R)-2-(4-((1-(2-cyanoacetyl)piperidin- 3-yl)amino)-1H-pyrrolo[2,3-b]pyridin-5-yl)-N-methyl isonicotinamide as a pale yellow solid (0.08 g, 7% yield): $^1$H NMR (400 MHz, DMSO-$d_6$, VT at 80° C.) 11.23 (br s, 1H), 9.83 (br s, 1H), 8.51-8.62 (m, 3H), 8.20 (s, 1H), 7.56-7.57 (m, 1H), 7.15 (s, 1H), 6.63 (s, 1H), 4.19-4.38 (m, 2H), 3.94 (m, 2H), 3.64 (m, 2H), 3.40-3.45 (m, 2H), 2.84-2.85 (m, 2H), 2.02 (br s, 2H), 1.60 (m, 2H); MS (ES) m/z 418.3 (M+H)$^+$.

Analytical Conditions:
Column: X-Bridge, C18 (19 mm×100 mm×5 mic)
Mobile phase (A): 0.1% Ammonia in water
Mobile phase (B): MeCN
Flow rate: 20.0 mL/min Preparation of 2-bromo-N-methylpyridine-4-carboxamide

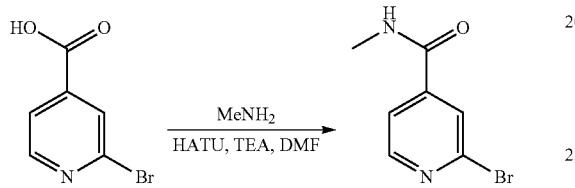

A solution of 2-bromoisonicotinic acid (1.0 g, 4.95 mmol) and (1-[bis(dimethylamino)methylene]-1H-1,2,3-triazolo[4,5-b]pyridinium 3-oxide hexafluorophosphate (2.45 g, 6.44 mmol) in N,N-dimethylformamide (10 mL) was stirred at ambient temperature for 3 minutes. Methylamine (12.4 mL, 24.8 mmol) was added followed by triethylamine (1.04 mL, 7.43 mmol) and the mixture stirred at ambient temperature. After 5 hours the reaction mixture was diluted with ethyl acetate, washed with water and brine. The organic layer was dried over anhydrous sodium sulfate, filtered and concentrated. The crude material was purified by flash chromatography (30% ethyl acetate/hexane) to provide 2-bromo-N-methylpyridine-4-carboxamide as a viscous colorless liquid (0.85 g, 3.95 mmol): MS (ES) m/z 214.9 (M+1).

Example 62: Preparation of (R)-3-(3-((5-(1-(2-hydroxyethyl)-1H-pyrazol-3-yl)-1H-pyrrolo[2,3-b]pyridin-4-yl)amino)piperidin-1-yl)-3-oxopropanenitrile

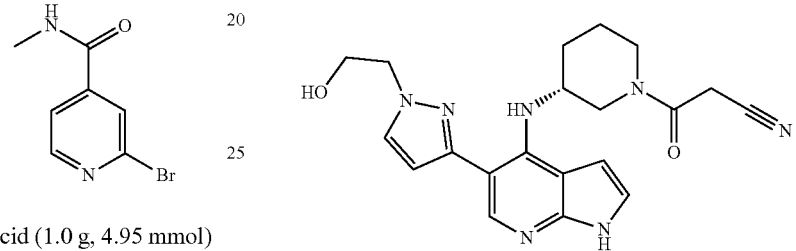

Scheme 60. Preparation of (R)-3-(3-((5-(1-(2-hydroxyethyl)-1H-pyrazol-3-yl)-1H-pyrrolo[2,3-b]pyridin-4-yl)amino)piperidin-1-yl)-3-oxopropanenitrile

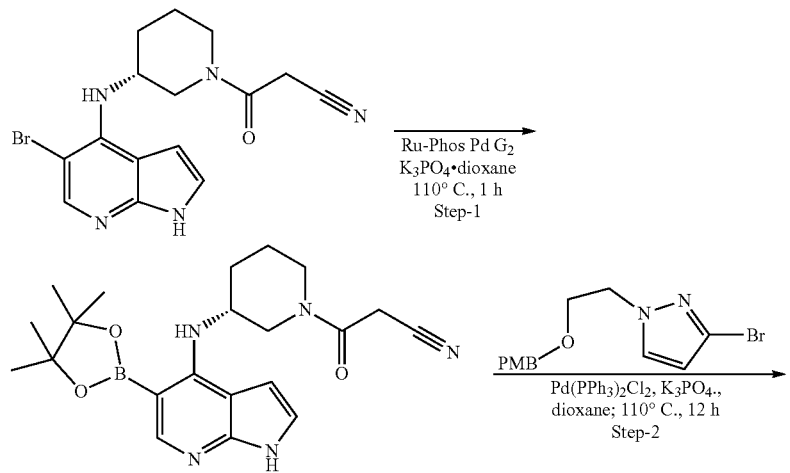

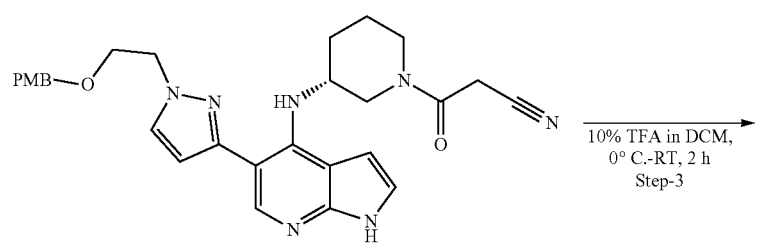

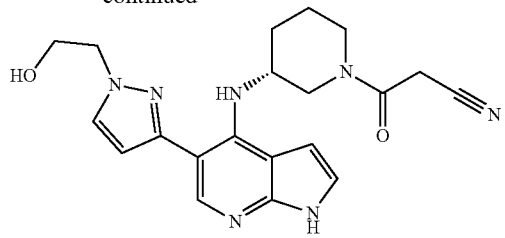

Step 1: Preparation of (R)-3-oxo-3-(3-((5-(4,4,5,5-tetramethyl-1,3,2-dioxaborolan-2-yl)-1H-pyrrolo[2,3-b]pyridin-4-yl)amino)piperidin-1-yl)propanenitrile

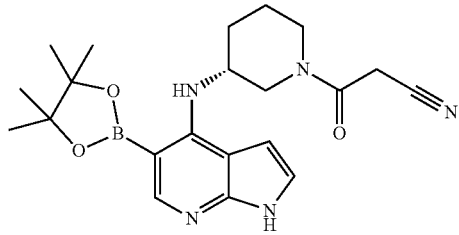 [SMILES: CC1(C)OB(c2cnc3[nH]ccc3c2N[C@@H]2CCCN(C(=O)CC#N)C2)OC1(C)C]

To a suspension of (R)-3-(3-((5-bromo-1H-pyrrolo[2,3-b]pyridin-4-yl)amino)piperidin-1-yl)-3-oxopropanenitrile (0.35 g, 0.96 mmol), 4,4,4',4',5,5,5',5'-octamethyl-2,2'-bi(1,3,2-dioxaborolane) (0.36 g, 1.45 mmol), potassium phosphate (0.60 g, 2.89 mmol) in 1,4-dioxane (10 mL) was added chloro(2-dicyclohexylphosphino-2',6'-diisopropoxy-1,1'-biphenyl) [2-(2'-amino-1,1'-biphenyl)]palladium(II) (0.07 g, 0.09 mmol) and the mixture heated at 110° C. for 1 hour. The reaction was cooled to ambient temperature and the mixture was used for next step without work up.

Step 2: Preparation of (R)-3-(3-((5-(1-(2-((4-methoxybenzyl)oxy)ethyl)-1H-pyrazol-3-yl)-1H-pyrrolo[2,3-b]pyridin-4-yl)amino)piperidin-1-yl)-3-oxopropanenitrile

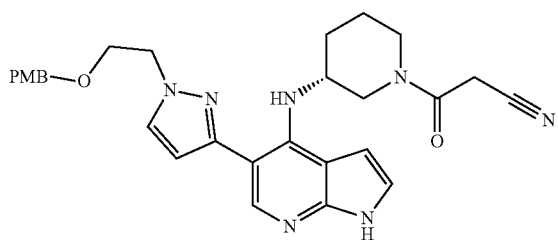

To a stirred mixture of (R)-3-oxo-3-(3-((5-(4,4,5,5-tetramethyl-1,3,2-dioxaborolan-2-yl)-1H-pyrrolo[2,3-b]pyridin-4-yl)amino)piperidin-1-yl)propanenitrile (~0.35 g), 3-bromo-1-(2-((4-methoxybenzyl)oxy)ethyl)-1H-pyrazole (0.39 g, 1.283 mmol) in dioxane (10 mL) was added bis(triphenylphosphine)palladium(I) dichloride (0.03 g, 0.04 mmol) followed by a 2M aqueous solution of potassium phosphate (0.54 g, 2.56 mmol) and the reaction mixture heated at 110° C. for 12 hours. The reaction mixture was cooled to ambient temperature, filtered through celite and the filtrate concentrated in vacuo. The crude material was purified using flash chromatography (5% methanol/dichloromethane) to provide 2(R)-3-(3-((5-(1-(2-((4-methoxybenzyl)oxy)ethyl)-1H-pyrazol-3-yl)-1H-pyrrolo[2,3-b]pyridin-4-yl)amino)piperidin-1-yl)-3-oxopropanenitrile as a brown semi-solid (0.2 g, 46% yield): MS (ES) m/z 514.3 (M+H).

Step 3: Preparation of (R)-3-(3-((5-(1-(2-hydroxyethyl)-1H-pyrazol-3-yl)-1H-pyrrolo[2,3-b]pyridin-4-yl)amino)piperidin-1-yl)-3-oxopropanenitrile

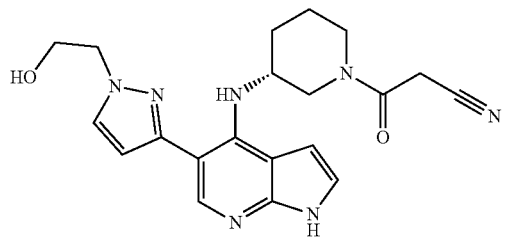 [SMILES: N#CCC(=O)N1CCC[C@@H](Nc2c(-c3ccn(CCO)n3)cnc3[nH]ccc23)C1]

To a solution of 2(R)-3-(3-((5-(1-(2-((4-methoxybenzyl)oxy)ethyl)-1H-pyrazol-3-yl)-1H-pyrrolo[2,3-b] pyridin-4-yl)amino)piperidin-1-yl)-3-oxopropanenitrile (0.18 g, 0.35 mmol) in dichloromethane (5 mL) was added trifluoroacetic acid (0.5 mL) at 0° C. and the mixture stirred at ambient temperature for 3 hours. The reaction was diluted with dichloromethane, washed with saturated sodium bicarbonate solution and brine. The organic layer was dried over anhydrous sodium sulfate, filtered and concentrated in vacuo. The crude material was purified by reverse phase chromatography to provide (R)-3-(3-((5-(1-(2-hydroxyethyl)-1H-pyrazol-3-yl)-1H-pyrrolo[2,3-b]pyridin-4-yl)amino)piperidin-1-yl)-3-oxopropanenitrile as an off white solid (0.01 g, 7% yield): $^1$H NMR (400 MHz, DMSO-d$_6$) δ 12.22 (s, 1H), 10.1 (s, 1H), 8.43 (d, J=6.0 Hz, 1H), 7.88 (s, 1H), 7.40 (s, 1H), 6.91 (d, J=14.8 Hz, 2H), 4.60 (br s, 1H), 4.32 (br s, 1H), 4.22-4.23 (m, 2H), 3.97-4.07 (m, 2H), 3.66-3.79 (m, 4H), 2.11-2.30 (m, 2H), 1.77 (m, 4H); MS (ES) m/z 394.4 (M+H).

Analytical Conditions:

Column: X-BridgeC-18 (250 mm×4.6 mm×5 mic)

Mobile phase (A): 0.1% Ammonia in water

Mobile phase (B): MeCN

Flow rate: 1.0 mL/min

Preparation of 3-bromo-1-(2-((4-methoxybenzyl)oxy)ethyl)-1H-pyrazole

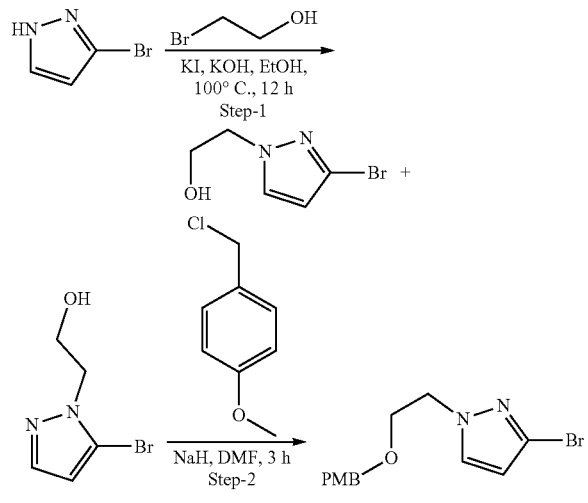

Step 1: Preparation of 2-(3-bromo-1H-pyrazol-1-yl)ethan-1-ol and 2-(5-bromo-1H-pyrazol-1-yl)ethan-1-ol

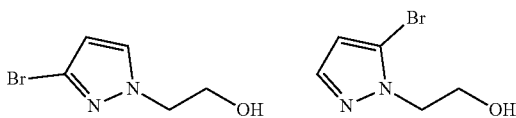 [SMILES: OCCn1ccc(Br)n1 ; OCCn1nccc1Br]

A mixture of 3-bromo-1H-pyrazole (2.5 g, 17.123 mmol), 2-bromoethan-1-ol (3.95 g, 31.67 mmol), potassium iodide (4.26 g, 25.68 mmol) and potassium hydroxide (1.91 g, 34.24 mmol) in ethanol (30 mL) was heated at 100° C. for 12 hours. The reaction was cooled to ambient temperature, filtered to remove the solid and the filtrate was concentrated in vacuo. The residue was dissolved in ethyl acetate and washed with water, brine, dried over sodium sulfate, filtered and concentrated in vacuo. The crude was purified by column chromatography (n-hexane:ethanol with 0.1% DEA) to provide 2-(3-bromo-1H-pyrazol-1-yl)ethan-1-ol as a liquid (1.2 g, 37% yield) and 2-(5-bromo-1H-pyrazol-1-yl)ethan-1-ol as a colorless gummy solid (0.8 g, 24%): MS (ES) m/z: 191.0 (M+H).

Step 2: Preparation of 3-bromo-1-(2-((4-methoxybenzyl)oxy)ethyl)-1H-pyrazole

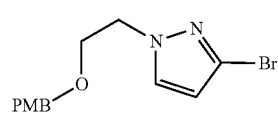

To a stirred solution of 2-(3-bromo-1H-pyrazol-1-yl)ethan-1-ol (1.2 g, 6.34 mmol) in N,N-dimethylformamide (10 mL) was added sodium hydride (0.4 g, 9.53 mmol, 60% mineral oil dispersion) at 0° C. After 20 minutes 1-(chloromethyl)-4-methoxybenzene (1.48 g, 9.52 mmol) was added at 0° C. and the reaction warmed to ambient temperature for 3 hours. The reaction was quenched with ice cold water and extracted with ethyl acetate. The organic layer was washed with brine, dried over anhydrous sodium sulfate, filtered and concentrated in vacuo. The crude material was purified by using flash chromatography (30% ethyl acetate/hexane) to provide bromo-1-(2-((4-methoxy benzyl)oxy)ethyl)-1H-pyrazole as a pale yellow oil (1.45 g, 73%): MS (ES) m/z 313.3 (M+H).

Example 63: Preparation of (R)-3-(3-((5-(3-(hydroxymethyl)phenyl)-1H-pyrrolo[2,3-b]pyridin-4-yl)amino)piperidin-1-yl)-3-oxopropanenitrile

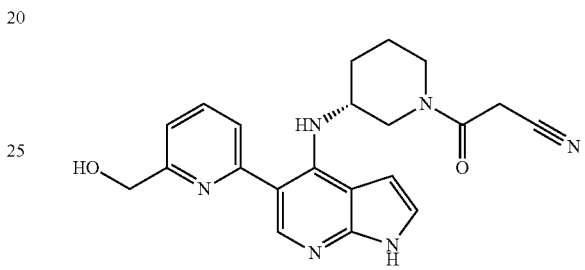

Scheme 61. Preparation of (R)-3-(3-((5-(3-(hydroxymethyl)phenyl)-1H-pyrrolo[2,3-b]pyridin-4-yl)amino)piperidin-1-yl)-3-oxopropanenitrile

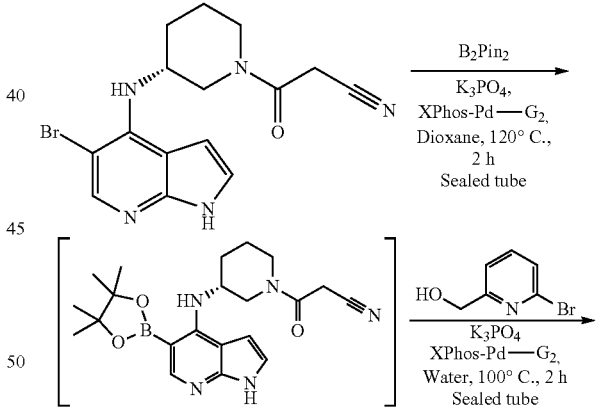

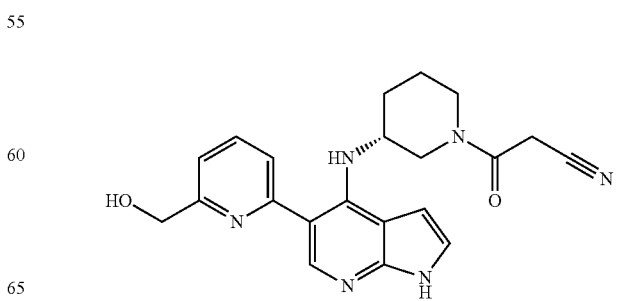

Preparation of (R)-3-(3-((5-(3-(hydroxymethyl)phenyl)-1H-pyrrolo[2,3-b]pyridin-4-yl)amino)piperidin-1-yl)-3-oxopropanenitrile

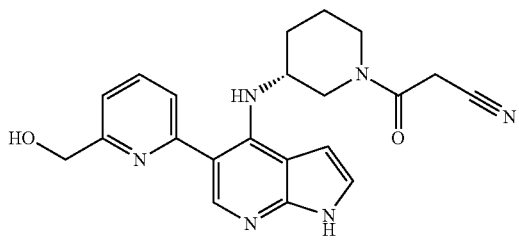 [SMILES: N#CCC(=O)N1CCC[C@@H](Nc2c(-c3cccc(CO)n3)cnc3[nH]ccc23)C1]

To a stirred solution of (R)-3-(3-((5-bromo-1H-pyrrolo[2,3-b]pyridin-4-yl)amino)piperidin-1-yl)-3-oxopropanenitrile (0.35 g, 0.96 mml) in dioxane (8 mL) was added bis(pinacolato)diboron (0.37 g, 1.45 mmol) and potassium phosphate (0.61 g, 2.9 mmol) followed by XPhos-Pd-G2 (0.08 g, 0.1 mmol). The resulting suspension was heated to 120° C. for 2 hours. The reaction mixture was cooled to ambient temperature and then (6-bromopyridin-2-yl)methanol (0.28 g, 1.45 mmol), 2M aqueous solution of potassium phosphate (0.41 g, 1.93 mmol) and XPhos-Pd-G2 (0.08 g, 0.1 mmol) were added and the mixture was heated at 100° C. for 2 hours. The reaction mass was cooled to ambient temperature, filtered through celite and washed with ethyl acetate. The filtrate was washed with water and brine. The organic layer was dried over anhydrous sodium sulfate, filtered and concentrated in vacuo. The crude material was purified by reverse phase chromatography to provide (R)-3-(3-((5-(3-(hydroxymethyl)phenyl)-1H-pyrrolo[2,3-b]pyridin-4-yl)amino)piperidin-1-yl)-3-oxopropanenitrile as an off-white solid (16 mg, 19% yield): $^1$H NMR (400 MHz, DMSO-d$_6$ at 70° C.) δ 11.20 (s, 1H), 9.93-10.08 (m, 1H), 8.38 (s, 1H), 7.82 (m, 1H), 7.70 (d, J=8.0 Hz, 1H), 7.29 (d, J=7.23 Hz, 1H), 7.14 (s, 1H), 6.63 (s, 1H), 5.25 (s, 1H), 4.63 (d, J=6.0 Hz, 2H), 4.28-4.49 (m, 1H), 3.94-4.02 (m, 2H), 3.68-3.75 (m, 1H), 3.54-3.62 (m, 1H), 2.80-2.96 (m, 1H), 1.92-2.20 (m, 2H), 1.52-1.86 (m, 3H); MS (ES) m/z: 391.1 (M+H).

Analytical Conditions:
Zorbax-Eclipse XDB C18 (150 mm×4.6 mm×5 μm)
Mobile phase (A): 0.1% ammonia in water
Mobile phase (B): MeCN
Flow rate: 1.0 mL/min Example 64. Preparation of 3-((3R,5S)-3-((5-(6-(hydroxymethyl)pyridin-2-yl)-1H-pyrrolo[2,3-b]pyridin-4-yl)amino)-5-methylpiperidin-1-yl)-3-oxopropanenitrile

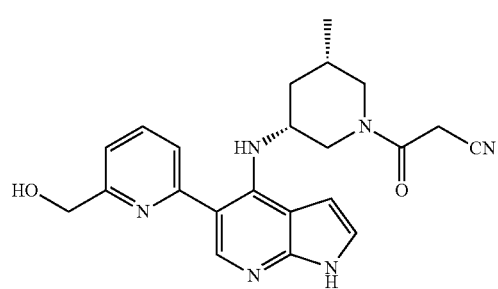 [SMILES: C[C@H]1C[C@@H](Nc2c(-c3cccc(CO)n3)cnc3[nH]ccc23)CN(C(=O)CC#N)C1]

Scheme 62. Preparation of 3-((3R,5S)-3-((5-(6-(hydroxymethyl)pyridin-2-yl)-1H-pyrrolo[2,3-b]pyridin-4-yl)amino)-5-methylpiperidin-1-yl)-3-oxopropanenitrile

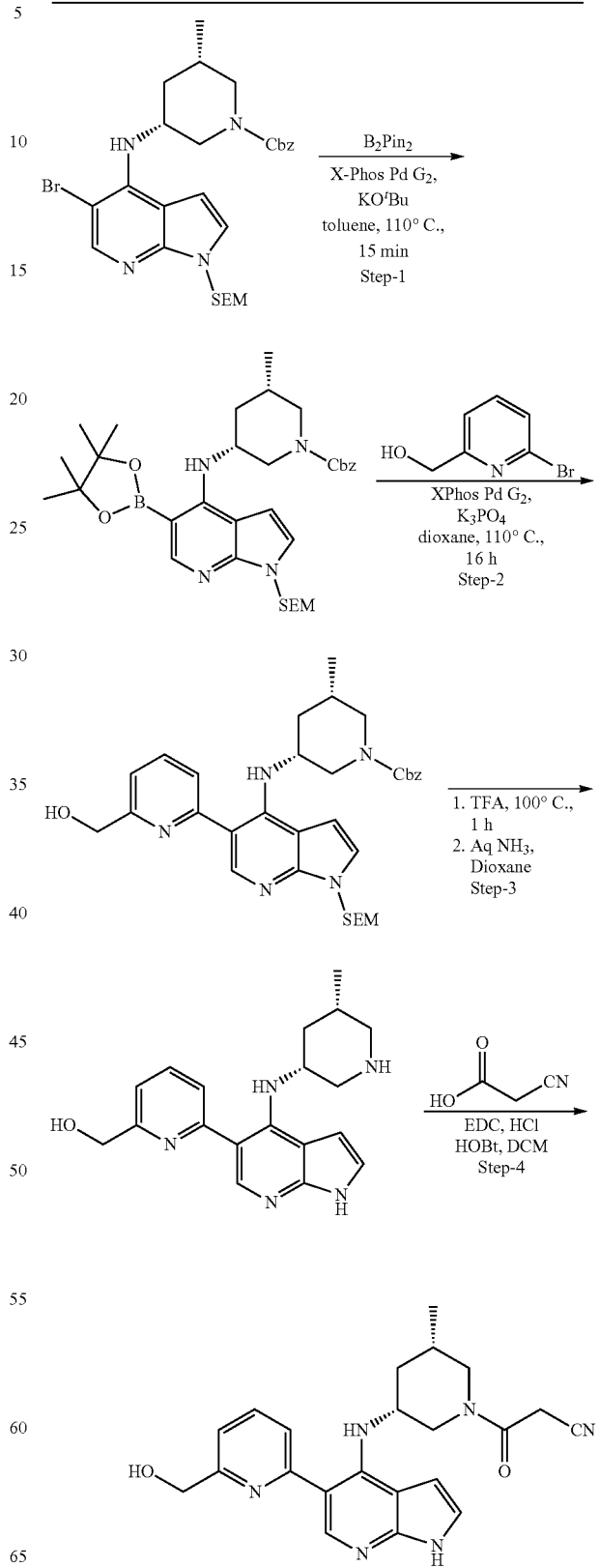

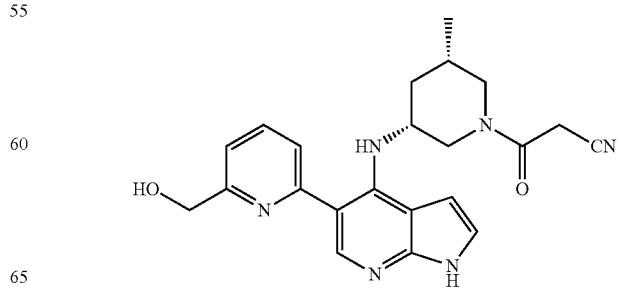

Step 1: Preparation of benzyl (3S,5R)-3-methyl-5-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate

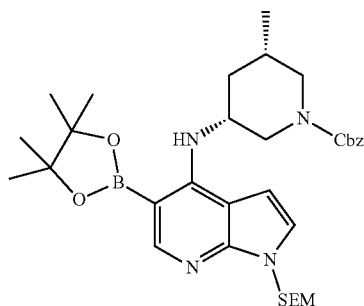 [SMILES: C[C@H]1C[C@@H](Nc2c(B3OC(C)(C)C(C)(C)O3)cnc3c2ccn3COCC[Si](C)(C)C)CN(C(=O)OCc2ccccc2)C1]

To a stirred solution of benzyl (3R,5S)-3-((5-bromo-1-((2-(trimethylsilyl)ethoxy)methyl)-1H-pyrrolo[2,3-b]pyridin-4-yl)amino)-5-methylpiperidine-1-carboxylate (0.70 g, 1.22 mmol) in toluene (30.0 mL) was added chloro(2-dicyclohexylphosphino-2',4',6'-triisopropyl-1,1'-biphenyl)[2-(2'-amino-1,1'-biphenyl)]palladium(II) (0.19 g, 0.24 mmol), 4,4,5,5-tetramethyl-2-(4,4,5,5-tetramethyl-1,3,2-dioxaborolan-2-yl)-1,3,2-dioxaborolane (0.68 g, 2.68 mmol) and potassium tert-butoxide (0.34 g, 3.05 mmol) and the mixture stirred on a pre-heated oil bath at 110° C. for 15 minutes. The reaction was cooled to ambient temperature, diluted with ethyl acetate, washed with water and brine. The organic layer was dried over anhydrous sodium sulfate, filtered and concentrated to obtain benzyl (3S,5R)-3-methyl-5-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate as viscous brown liquid (1.24 g, crude): MS (ES) m/z 621.4 (M+H).

Step 2: Preparation of benzyl (3R,5S)-3-((5-(6-(hydroxymethyl)pyridin-2-yl)-1-((2-(trimethylsilyl)ethoxy)methyl)-1H-pyrrolo[2,3-b]pyridin-4-yl)amino)-5-methylpiperidine-1-carboxylate

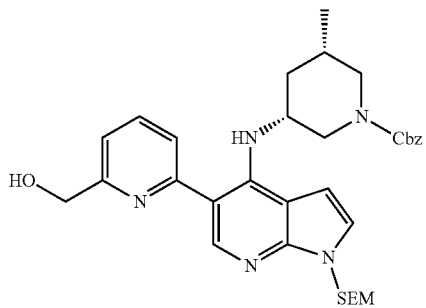 [SMILES: C[C@H]1C[C@@H](Nc2c(-c3cccc(CO)n3)cnc3c2ccn3COCC[Si](C)(C)C)CN(C(=O)OCc2ccccc2)C1]

A stirred mixture of benzyl (3S,5R)-3-methyl-5-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate (1.20 g, 1.93 mmol), (6-bromopyridin-2-yl)methanol (0.24 mg, 1.29 mmol), chloro(2-dicyclohexylphosphino-2',4',6'-triisopropyl-1,1'-biphenyl)[2-(2'-amino-1,1'-biphenyl)]palladium(II) (0.20 g, 0.26 mmol) and 2M aqueous solution of tripotassium phosphate (1.09 g, 5.16 mmol) in 1,4-dioxane (35 mL) was heated at 110° C. for 16 hours. The reaction was cooled to ambient temperature and diluted with ethyl acetate and water. The organic layer was separated, dried over anhydrous sodium sulfate, filtered and concentrated in vacuo. The crude was purified by combi-flash eluting with 0-50% ethyl acetate/hexane to obtain benzyl (3R,5S)-3-((5-(6-(hydroxymethyl)pyridin-2-yl)-1-((2-(trimethylsilyl)ethoxy)methyl)-1H-pyrrolo[2,3-b]pyridin-4-yl)amino)-5-methylpiperidine-1-carboxylate as a viscous brown liquid (0.51 g, 66% yield):MS (ES) m/z 602.4 (M+H).

Step 3: Preparation of (6-(4-(((3R,5S)-5-methylpiperidin-3-yl)amino)-1H-pyrrolo[2,3-b]pyridin-5-yl)pyridin-2-yl)methanol

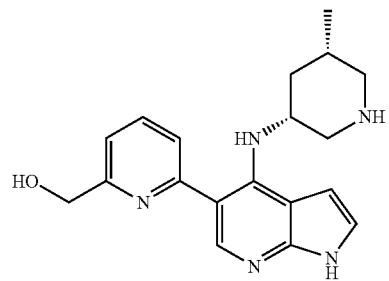 [SMILES: C[C@@H]1CNC[C@H](Nc2c(-c3cccc(CO)n3)cnc3[nH]ccc23)C1]

A stirred solution of benzyl (3R,5S)-3-((5-(6-(hydroxymethyl)pyridin-2-yl)-1-((2-(trimethylsilyl) ethoxy)methyl)-1H-pyrrolo[2,3-b]pyridin-4-yl)amino)-5-methylpiperidine-1-carboxylate (0.56 g, 0.85 mmol) in trifluoroacetic acid (5.0 mL) was heated to 100° C. for 1 hour. The reaction mixture was cooled to ambient temperature and then concentrated in vacuo, the residue was dissolved in 1,4-dioxane:aqueous ammonia (5 mL:5 mL) and stirred at ambient temperature for 16 hours. The reaction mixture was concentrated in vacuo to provide (6-(4-(((3R,5S)-5-methylpiperidin-3-yl)amino)-1H-pyrrolo[2,3-b]pyridin-5-yl)pyridin-2-yl)methanol as a viscous brown liquid (0.52 g, crude); MS (ES) m/z 338.2 (M+H).

Step 4: Preparation of 3-((3R,5S)-3-((5-(6-(hydroxymethyl)pyridin-2-yl)-1H-pyrrolo[2,3-b]pyridin-4-yl)amino)-5-methylpiperidin-1-yl)-3-oxopropanenitrile

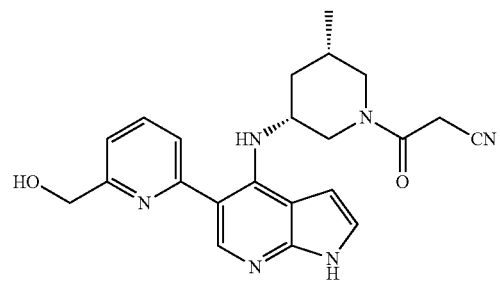 [SMILES: C[C@H]1C[C@@H](Nc2c(-c3cccc(CO)n3)cnc3[nH]ccc23)CN(C(=O)CC#N)C1]

A solution of 2-cyanoacetic acid (0.14 g, 1.69 mmol), 1-hydroxybenzotriazole (0.21 mg, 1.35 mmol) and N-(3-dimethylaminopropyl)-N'-ethylcarbodiimide hydrochloride (0.32 g, 1.69 mmol) in dichloromethane (4.0 mL) was stirred at ambient temperature for 3 minutes. Then (6-(4-(((3R,5S)-5-methylpiperidin-3-yl)amino)-1H-pyrrolo[2,3-b]pyridin-5-yl)pyridin-2-yl)methanol (0.38 g, 1.13 mmol) was added followed by triethylamine (1.08 mL, 5.63 mmol) and the mixture stirred at ambient temperature for 16 hours. The reaction mixture was diluted with ethyl acetate, washed with water and brine. The organic layer was dried over anhydrous sodium sulfate, filtered and concentrated in vacuo. The crude was purified using reverse phase chromatography to provide 3-((3R,5S)-3-((5-(6-(hydroxymethyl)pyridin-2-yl)-1H-pyrrolo[2,3-b]pyridin-4-yl)amino)-5-methylpiperidin-1-yl)-3-oxopropanenitrile as an off-white solid (0.03 g, 7% yield): $^1$H NMR (400 MHz, DMSO-d$_6$, VT at 80° C.) δ 11.16 (br s, 1H), 10.05 (br s, 1H), 8.39 (s, 1H), 7.79-7.83 (m, 1H), 7.70-7.72 (m, 1H), 7.28 (d, J=7.6 Hz, 1H), 7.12 (s, 1H), 6.65 (s, 1H), 4.15-4.30 (m, 1H), 4.75-4.85 (m, 1H), 4.60-4.67 (m, 1H), 3.87-4.07 (m, 1H), 3.60-3.67 (m, 1H), 3.55 (s, 2H), 2.80-2.90 (m, 1H), 2.15-2.25 (m, 2H), 1.65-1.80 (m, 2H), 1.10-1.30 (m, 1H), 0.92 (d, J=6.0 Hz, 3H); MS (ES) m/z 405.2 (M+H).

Analytical Conditions:

Flow rate: 0.3 mL/min

Column: Ascentis Express C18 (50 mm×2.1 mm×2.73 μm)

Mobile Phase (A): 0.1% Formic acid in water

Mobile Phase (B): MeCN

Example 65. Preparation of 3-((3S,5R)-3-methyl-5-((5-(5-(methylsulfonyl)thiazol-2-yl)-1H-pyrrolo[2,3-b]pyridin-4-yl)amino)piperidin-1-yl)-3-oxopropanenitrile

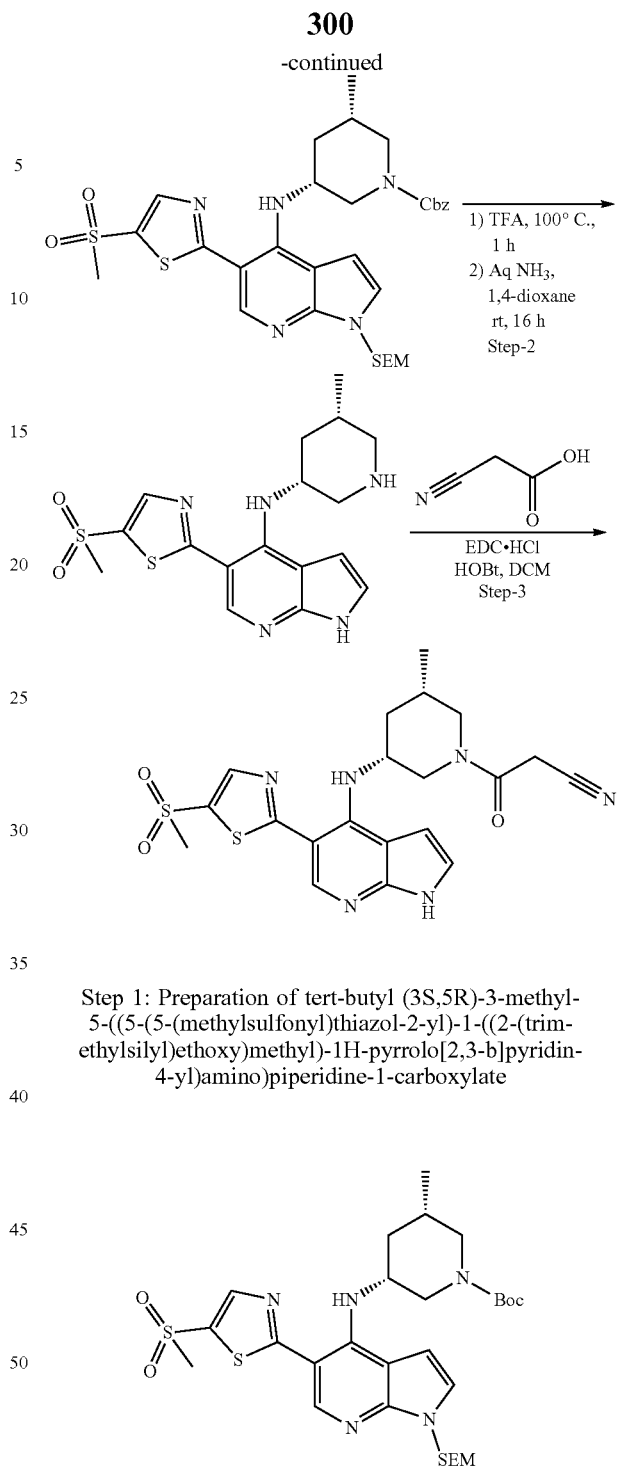

Scheme 63. Preparation of 3-((3S,5R)-3-methyl-5-((5-(5-(methylsulfonyl)thiazol-2-yl)-1H-pyrrolo[2,3-b]pyridin-4-yl)amino)piperidin-1-yl)-3-oxopropanenitrile

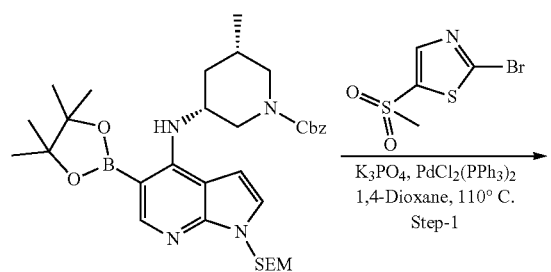

Step 1: Preparation of tert-butyl (3S,5R)-3-methyl-5-((5-(5-(methylsulfonyl)thiazol-2-yl)-1-((2-(trimethylsilyl)ethoxy)methyl)-1H-pyrrolo[2,3-b]pyridin-4-yl)amino)piperidine-1-carboxylate To a stirred solution of benzyl (3S,5R)-3-methyl-5-{[5-(4,4,5,5-tetramethyl-1,3,2-dioxaborolan-2-yl)-1-{[2-(trimethylsilyl)ethoxy]methyl}-1H-pyrrolo[2,3-b]pyridin-4-yl]amino}piperidine-1-carboxylate (1.0 g, 1.61 mmol) and 2-bromo-5-methanesulfonyl-1,3-thiazole (0.28 g, 1.18 mmol) in 1,4-dioxane (30 mL) was added palladium(II)bis(triphenylphosphine) dichloride (0.15 g, 0.21 mmol) and 2M aqueous solution of tripotassium phosphate (0.91 g, 4.30 mmol) and the mixture heated to 110° C. for 16 hours. The reaction was cooled to ambient temperature and diluted with ethyl acetate and water. The organic layer was separated, dried over anhydrous sodium sulfate and concentrated in vacuo. The crude was purified by flash chromatography (20% ethyl acetate/hexane) to provide tert-butyl (3S,5R)-3-methyl-5-((5-(5-(methylsulfonyl)thiazol-2-yl)-1-((2-(trimethylsilyl)ethoxy)methyl)-1H-pyrrolo[2,3-b]pyridin-4-yl)amino)piperidine-1-carboxylate as a viscous brown liquid (0.32, 45% yield): MS (ES) m/z 622.8 (M+H).

Step 2: Preparation of N-((3R,5S)-5-methylpiperidin-3-yl)-5-(5-(methylsulfonyl)thiazol-2-yl)-1H-pyrrolo[2,3-b]pyridin-4-amine

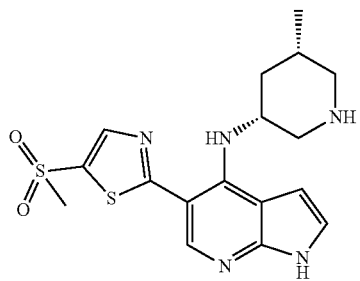 [SMILES: C[C@@H]1CNC[C@H](Nc2c(-c3ncc(S(C)(=O)=O)s3)cnc3[nH]ccc23)C1]

A stirred solution of tert-butyl (3S,5R)-3-methyl-5-((5-(5-(methylsulfonyl)thiazol-2-yl)-1-((2-(trimethylsilyl)ethoxy)methyl)-1H-pyrrolo[2,3-b]pyridin-4-yl)amino)piperidine-1-carboxylate (0.52 g, 1.00 mmol) in trifluoroacetic acid (5.0 mL) was heated at 100° C. for 1 hour in a sealed tube. The reaction mixture was cooled to ambient temperature and then concentrated in vacuo, the residue was dissolved in 1,4-dioxane:aqueous ammonia (5 mL:5 mL) and stirred at ambient temperature for 16 hours. The reaction mixture was concentrated in vacuo to provide N-((3R,5S)-5-methylpiperidin-3-yl)-5-(5-(methylsulfonyl)thiazol-2-yl)-1H-pyrrolo[2,3-b]pyridin-4-amine as a brown gummy solid (0.45 g, crude): MS (ES) m/z 392.1 (M+H).

Step 3: Preparation of 3-((3S,5R)-3-methyl-5-((5-(5-(methylsulfonyl)thiazol-2-yl)-1H-pyrrolo[2,3-b]pyridin-4-yl)amino)piperidin-1-yl)-3-oxopropanenitrile

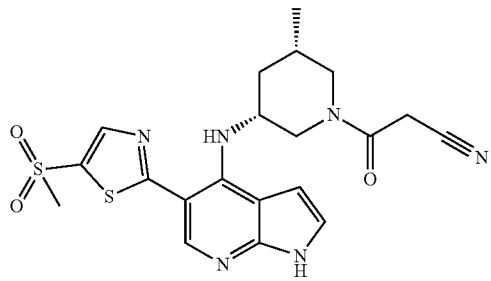 [SMILES: C[C@H]1C[C@@H](Nc2c(-c3ncc(S(C)(=O)=O)s3)cnc3[nH]ccc23)CN(C(=O)CC#N)C1]

A solution of 2-cyanoacetic acid (0.13 g, 1.53 mmol), 1-hydroxybenzotriazole (0.19 mg, 1.23 mmol) and N-(3-dimethylaminopropyl)-N'-ethylcarbodiimide hydrochloride (0.29 g, 1.53 mmol) in dichloromethane (4.0 mL) was stirred at ambient temperature for 3 minutes. Then N-((3R,5S)-5-methylpiperidin-3-yl)-5-(5-(methylsulfonyl)thiazol-2-yl)-1H-pyrrolo[2,3-b]pyridin-4-amine (0.40 g, 1.02 mmol) was added followed by triethylamine (0.70 mL, 5.11 mmol) and the mixture stirred at ambient temperature overnight. The reaction mixture was diluted with ethyl acetate, washed with water and brine. The organic layer was dried over anhydrous sodium sulfate, filtered and concentrated in vacuo. The crude was purified by reverse phase chromatography to provide 3-((3S,5R)-3-methyl-5-((5-(5-(methylsulfonyl)thiazol-2-yl)-1H-pyrrolo[2,3-b]pyridin-4-yl)amino)piperidin-1-yl)-3-oxopropanenitrile as an off-white solid (0.05 g, 11% yield): $^1$H NMR (400 MHz, DMSO-d$_6$, VT at 80° C.) δ 11.56 (br s, 1H), 9.33 (br s, 1H), 8.41 (s, 1H), 8.30 (s, 1H), 7.21 (s, 1H), 6.76 (s, 1H), 4.79 (br s, 1H), 3.84-4.44 (m, 3H), 3.60-3.74 (m, 1H), 3.56 (s, 1H), 3.39 (s, 3H), 2.60-2.80 (m, 1H), 2.20-2.40 (m, 1H), 1.75-1.85 (m, 1H), 1.15-1.27 (m, 1H), 0.94 (d, J=6.4 Hz, 3H); MS (ES) m/z 459.1 (M+H).

Analytical Conditions:

Mobile Phase A: 0.1% NH$_4$OH in H$_2$O

Mobile Phase B: MeCN

Column: X-Bridge, C18 19*100*5 micron

Flow rate: 20 mL/min

Example 66. Preparation of (R)-3-(3-((5-(5-acetyloxazol-2-yl)-1H-pyrrolo[2,3-b]pyridin-4-yl)amino)piperidin-1-yl)-3-oxopropanenitrile

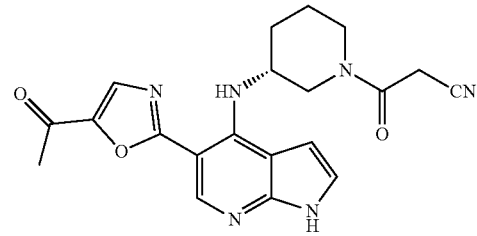 [SMILES: CC(=O)c1cnc(-c2cnc3[nH]ccc3c2N[C@@H]2CCCN(C(=O)CC#N)C2)o1]

Scheme 64. Preparation of (R)-3-(3-((5-(5-acetyloxazol-2-yl)-1H-pyrrolo[2,3-b]pyridin-4-yl)amino)piperidin-1-yl)-3-oxopropanenitrile

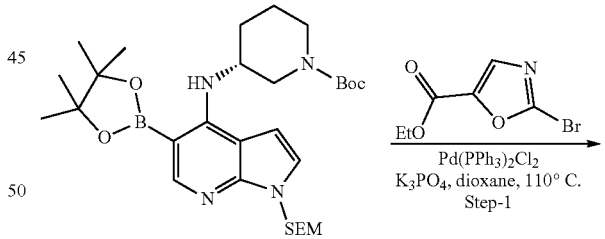

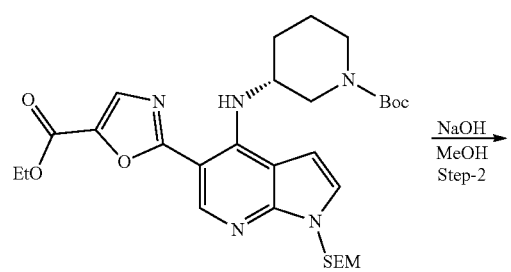

303

-continued

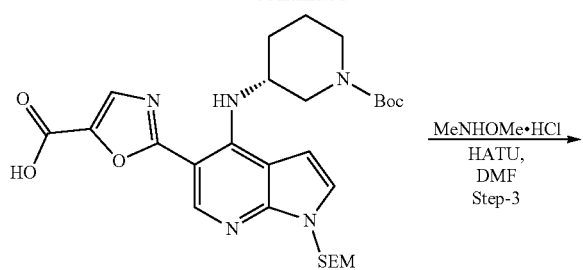

MeNHOMe•HCl
HATU,
DMF
Step-3

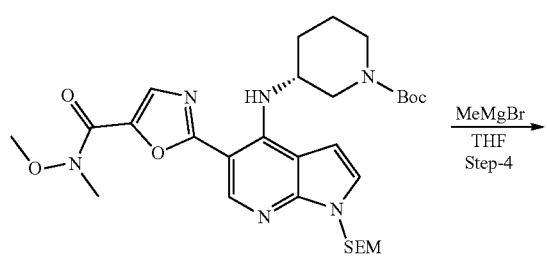

MeMgBr
THF
Step-4

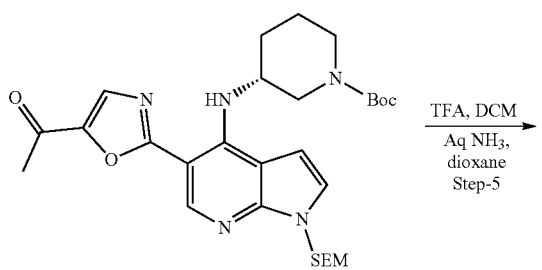

TFA, DCM
Aq NH₃,
dioxane
Step-5

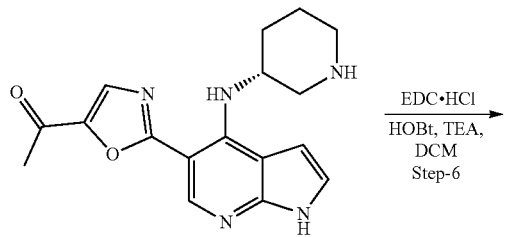

EDC•HCl
HOBt, TEA,
DCM
Step-6

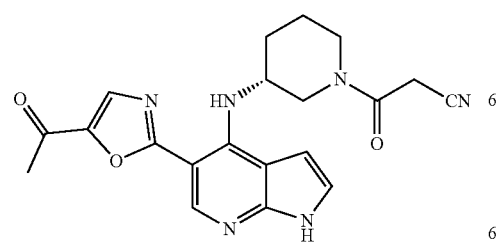

304

Step 1: Preparation of ethyl (R)-2-(4-((1-(tert-butoxycarbonyl)piperidin-3-yl)amino)-1-((2-(trimethylsilyl)ethoxy)methyl)-1H-pyrrolo[2,3-b]pyridin-5-yl)oxazole-5-carboxylate

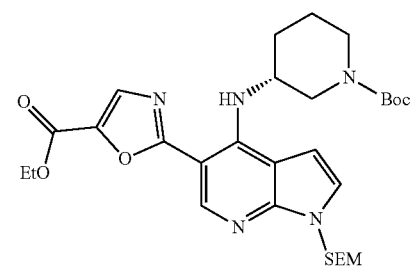 [SMILES: CCOC(=O)c1cnc(-c2cnc3c(ccn3COCC[Si](C)(C)C)c2N[C@@H]2CCCN(C(=O)OC(C)(C)C)C2)o1]

To a stirred solution of tert-butyl (3R)-3-{[5-(4,4,5,5-tetramethyl-1,3,2-dioxaborolan-2-yl)-1-{[2-(trimethylsilyl)ethoxy]methyl}-1H-pyrrolo[2,3-b]pyridin-4-yl]amino}piperidine-1-carboxylate (1.50 g, 2.62 mmol) and ethyl 2-bromo-1,3-oxazole-5-carboxylate (0.38 g, 1.74 mmol) in 1,4-dioxane (40 mL) was added bis(triphenylphosphine)palladium(II) dichloride (0.25 g, 0.35 mol) and 2M aqueous solution of tripotassium phosphate (1.48 g, 6.97 mmol) and the mixture stirred at 110° C. for 16 hours. The reaction was cooled to ambient temperature, diluted with ethyl acetate, washed with water and brine. The organic layer was dried over anhydrous sodium sulfate, filtered and concentrated in vacuo. The crude was purified using flash chromatography (20% ethyl acetate/hexane) to provide ethyl (R)-2-(4-((1-(tert-butoxycarbonyl)piperidin-3-yl)amino)-1-((2-(trimethylsilyl)ethoxy)methyl)-1H-pyrrolo[2,3-b]pyridin-5-yl)oxazole-5-carboxylate as a viscous brown liquid (0.65 g, 63% yield): MS (ES) m/z 586.3 (M+H).

Step 2: Preparation of (R)-2-(4-((1-(tert-butoxycarbonyl)piperidin-3-yl)amino)-1-((2-(trimethylsilyl)ethoxy)methyl)-1H-pyrrolo[2,3-b]pyridin-5-yl)oxazole-5-carboxylic acid To a stirred solution of ethyl (R)-2-(4-((1-(tert-butoxycarbonyl)piperidin-3-yl)amino)-1-((2-(trimethylsilyl) ethoxy) methyl)-1H-pyrrolo[2,3-b]pyridin-5-yl)oxazole-5-carboxylate (0.50 g, 0.85 mmol) in methanol (20 mL) was added 2M aqueous solution of sodium hydroxide (0.17 g, 4.27 mmol) and the solution stirred at ambient temperature for 4 hours. The reaction was concentrated to remove volatiles, the obtained residue was dissolved in water and acidified with 1N hydrochloric acid and adjusted to pH ~3. The aqueous layer was extracted with ethyl acetate, dried over anhydrous sodium sulfate, filtered and concentrated to provide (R)-2-

(4-((1-(tert-butoxycarbonyl)piperidin-3-yl)amino)-1-((2-(trimethylsilyl)ethoxy)methyl)-1H-pyrrolo[2,3-b]pyridin-5-yl)oxazole-5-carboxylic acid as a colorless gum (0.22 g, 46% yield): MS (ES) m/z 558.3 (M+H).

Step 3: Preparation of tert-butyl (R)-3-((5-(5-(methoxy(methyl)carbamoyl)oxazol-2-yl)-1-((2-(trimethylsilyl)ethoxy)methyl)-1H-pyrrolo[2,3-b]pyridin-4-yl)amino)piperidine-1-carboxylate

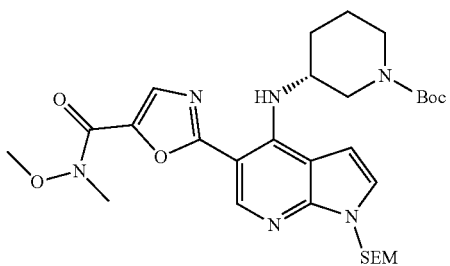 [SMILES: CON(C)C(=O)c1cnc(-c2cnc3c(ccn3COCC[Si](C)(C)C)c2N[C@@H]2CCCN(C(=O)OC(C)(C)C)C2)o1]

A solution of (R)-2-(4-((1-(tert-butoxycarbonyl)piperidin-3-yl)amino)-1-((2-(trimethylsilyl)ethoxy)methyl)-1H-pyrrolo[2,3-b]pyridin-5-yl)oxazole-5-carboxylicacid (0.22 g, 0.40 mmol) and 1-[bis (dimethylamino)methylene]-1H-1,2,3-triazolo[4,5-b]pyridinium 3-oxide hexafluorophosphate (HATU) (0.23 g, 0.60 mmol) in N,N-dimethylformamide (5 mL) was stirred at ambient temperature for 3 minutes. Then N,O-dimethylhydroxylamine hydrochloride (0.2 g, 1.2 mmol) was added followed by triethylamine (0.38 mL, 2.76 mmol) and the mixture stirred at ambient temperature for 5 hours. The reaction mixture was quenched with water and extracted with ethyl acetate. The organic layer was washed with water, brine, dried over anhydrous sodium sulfate, filtered and concentrated in vacuo. The crude material was purified by flash chromatography (30% ethyl acetate/hexane) to provide tert-butyl (R)-3-((5-(5-(methoxy(methyl)carbamoyl)oxazol-2-yl)-1-((2-(trimethylsilyl)ethoxy)methyl)-1H-pyrrolo[2,3-b]pyridin-4-yl)amino)piperidine-1-carboxylate as a viscous liquid (0.2 g, 84% yield): MS (ES) m/z 601.6 (M+H).

Step 4: Preparation of tert-butyl (R)-3-((5-(5-acetyloxazol-2-yl)-1-((2-(trimethylsilyl)ethoxy)methyl)-1H-pyrrolo[2,3-b]pyridin-4-yl)amino)piperidine-1-carboxylate

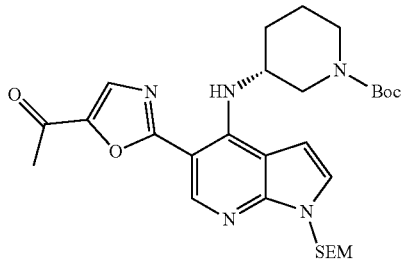 [SMILES: CC(=O)c1cnc(-c2cnc3c(ccn3COCC[Si](C)(C)C)c2N[C@@H]2CCCN(C(=O)OC(C)(C)C)C2)o1]

To a solution of tert-butyl (R)-3-((5-(5-(methoxy(methyl)carbamoyl)oxazol-2-yl)-1-((2-(trimethylsilyl)ethoxy)methyl)-1H-pyrrolo[2,3-b]pyridin-4-yl)amino)piperidine-1-carboxylate (0.20 g, 0.33 mmol) in tetrahydrofuran (4.0 mL) at 0° C. was added methyl magnesium bromide (0.34 mL, 1.00 mmol). The reaction mixture was warmed to ambient temperature and stirred for overnight. The reaction mixture was quenched with saturated ammonium chloride solution and extracted with ethyl acetate. The organic layer was washed with water, brine, dried over anhydrous sodium sulfate, filtered and concentrated in vacuo. The crude material was purified using flash chromatography (40% ethyl acetate/hexane) to provide tert-butyl (R)-3-((5-(5-acetyloxazol-2-yl)-1-((2-(trimethylsilyl)ethoxy)methyl)-1H-pyrrolo[2,3-b]pyridin-4-yl)amino)piperidine-1-carboxylate as a pale yellow semi solid (0.12 g, 65% yield): MS (ES) m/z 556.3 (M+H).

Step 5: Preparation of (R)-1-(2-(4-(piperidin-3-ylamino)-1H-pyrrolo[2,3-b]pyridin-5-yl)oxazol-5-yl)ethan-1-one

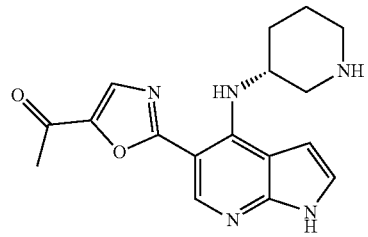 [SMILES: CC(=O)c1cnc(-c2cnc3[nH]ccc3c2N[C@@H]2CCCNC2)o1]

A solution of tert-butyl(R)-3-((5-(5-acetyloxazol-2-yl)-1-((2-(trimethylsilyl)ethoxy)methyl)-1H-pyrrolo[2,3-b]pyridin-4-yl)amino)piperidine-1-carboxylate (0.12 g, 0.22 mmol) in dichloromethane:trifluoroacetic acid (2.0 mL:2.0 mL) was stirred at ambient temperature. After 3 hours the reaction was concentrated to dryness, the residue was dissolved in 1,4-dioxane:aqueous ammonia (2 mL:2 mL) and stirred at ambient temperature for 16 hours. The reaction mixture was concentrated in vacuo to provide (R)-1-(2-(4-(piperidin-3-ylamino)-1H-pyrrolo[2,3-b]pyridin-5-yl)oxazol-5-yl)ethan-1-one as a colorless gum (0.12 g, crude): MS (ES) m/z 326.3 (M+H).

Step 6: Preparation of (R)-3-(3-((5-(5-acetyloxazol-2-yl)-1H-pyrrolo[2,3-b]pyridin-4-yl)amino)piperidin-1-yl)-3-oxopropanenitrile

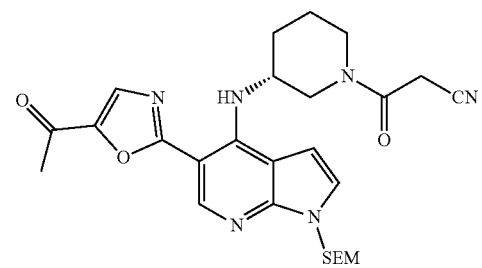 [SMILES: CC(=O)c1cnc(-c2cnc3c(ccn3COCC[Si](C)(C)C)c2N[C@@H]2CCCN(C(=O)CC#N)C2)o1]

To a stirred solution of 2-cyanoacetic acid (0.04 g, 0.42 mmol) and 1-hydroxybenzotriazole (0.51 g, 0.33 mmol) in dichloromethane (5 mL) was added N-(3-dimethylaminopropyl)-N'-ethylcarbodiimide hydrochloride (0.8 g, 0.42 mmol) and the mixture stirred at ambient temperature for 5 minutes. Then (R)-1-(2-(4-(piperidin-3-ylamino)-1H-pyrrolo[2,3-b]pyridin-5-yl)oxazol-5-yl)ethan-1-one (0.09 g, 0.28 mmol) was added followed by triethylamine (0.2 mL, 0.38 mmol) and the resulting mixture stirred at ambient temperature for 18 hours. The reaction mixture was quenched with water and extracted with dichloromethane. The organic layer was washed with water, brine, dried over anhydrous sodium sulfate, filtered and concentrated in vacuo. The crude material was purified by reverse phase chromatography to provide (R)-3-(3-((5-(5-acetyloxazol-2-yl)-1H-pyrrolo[2,3-b]pyridin-4-yl)amino)piperidin-1-yl)-3-oxopropanenitrile as a pale yellow solid (7.0 mg, 7% yield): $^1$H NMR (400 MHz, DMSO-d$_6$, VT at 80° C.) 11.53 (br s, 1H), 9.45 (br s, 1H), 8.61 (s, 1H), 8.11 (s, 1H), 7.21 (s, 1H), 6.70 (s, 1H), 4.20-4.40 (m, 1H), 3.80-4.00 (m, 3H), 3.50-3.65 (m, 1H), 3.40-3.50 (m, 3H), 2.00-2.15 (m, 2H), 1.55-1.84 (m, 4H); MS (ES) m/z 393.1 (M+H).

Analytical Conditions:

Mobile Phase A: 0.1% NH$_4$OH in H$_2$O

Mobile Phase B: MeCN

Column: Phenomenex, C18, 21.2 mm*250 mm*5 micron,

Flow rate: 20 mL/min

Example 67. Preparation of N-((3R,5S)-1-((2,2-difluorocyclopropyl)methyl)-5-methylpiperidin-3-yl)-5-(thiazol-2-yl)-1H-pyrrolo[2,3-b]pyridin-4-amine

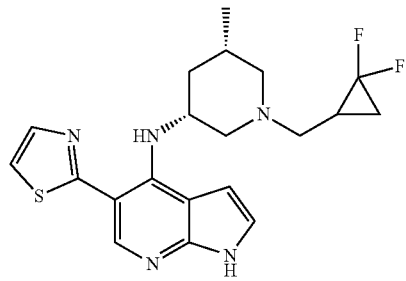

Scheme 65. Preparation of N-((3R,5S)-1-((2,2-difluorocyclpropyl)methyl)-5-methylpiperidin-3-yl)-5-(thiazol-2-yl)-1H-pyrrolo[2,3-b]pyridin-4-amine

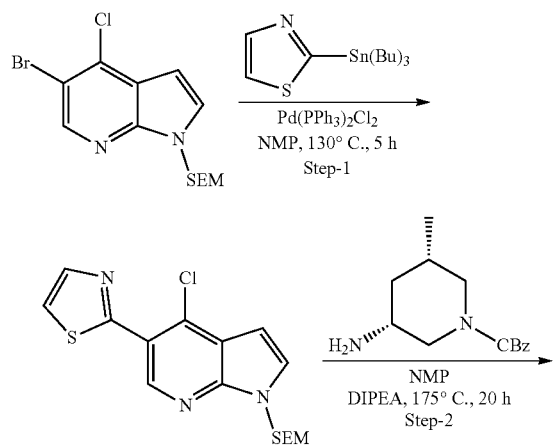

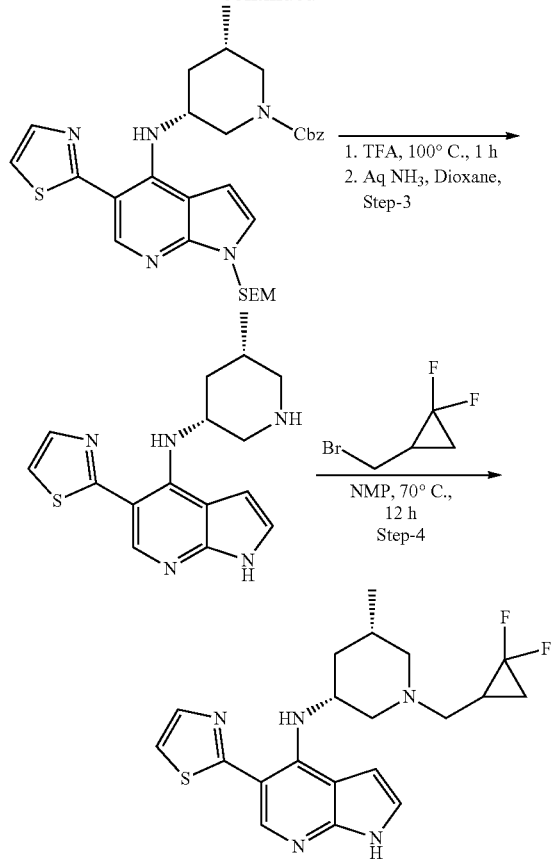

Step 1: Preparation of 2-(4-chloro-1-((2-(trimethylsilyl)ethoxy)methyl)-1H-pyrrolo[2,3-b]pyridin-5-yl)thiazole

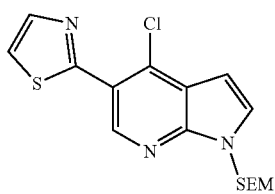 [SMILES: C[Si](C)(C)CCOCn1ccc2c(Cl)c(-c3nccs3)cnc21]

A stirred solution of 5-bromo-4-chloro-1-((2-(trimethylsilyl)ethoxy)methyl)-1H-pyrrolo[2,3-b]pyridine (1.5 g, 4.15 mmol), 2-(tributylstannyl)thiazole (1.7 g, 4.57 mmol) and bis(triphenylphosphine)palladium(II) dichloride (0.58 g, 0.83 mmol) in N-methyl-2-pyrrolidone (15 mL) was heated at 130° C. in a sealed tube under a nitrogen atmosphere. After 5 hours the reaction mixture was cooled to ambient temperature, diluted with ethyl acetate and filtered through celite. The filtrate was washed with water, brine, dried over anhydrous sodium sulfate, filtered and concentrated in vacuo. The crude material was purified by using flash chromatography (10% ethyl acetate in hexane) to provide 2-(4-chloro-1-((2-(trimethylsilyl)ethoxy)methyl)-1H-pyrrolo[2,3-b]pyridin-5-yl)thiazole as a colorless oil (0.75 g, 49% yield): MS (ES) m/z 365.8 (M+H).

Step 2: Preparation of benzyl (3S,5R)-3-methyl-5-((5-(thiazol-2-yl)-1-((2-(trimethylsilyl)ethoxy)methyl)-1H-pyrrolo[2,3-b]pyridin-4-yl)amino)piperidine-1-carboxylate

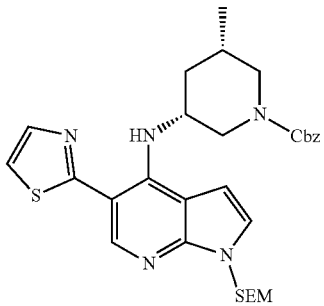 [SMILES: C[C@H]1C[C@@H](Nc2c(-c3nccs3)cnc3c2ccn3COCC[Si](C)(C)C)CN(C(=O)OCc2ccccc2)C1]

A stirred solution of 2-(4-chloro-1-((2-(trimethylsilyl)ethoxy)methyl)-1H-pyrrolo[2,3-b]pyridin-5-yl)thiazole (1.0 g, 2.73 mmol), benzyl (3R,5S)-3-amino-5-methylpiperidine-1-carboxylate (0.74 g, 3.0 mmol) and N,N-diisopropylethylamine (2.0 mL, 13.6 mmol) in N-methyl-2-pyrrolidone (20 mL) was heated at 175° C. for 20 hours. The reaction was cooled to ambient temperature, diluted with ethyl acetate, washed with water, brine, dried over anhydrous sodium sulfate, filtered and concentrated in vacuo. The crude material was purified by using flash chromatography (20% ethyl acetate in hexane) to provide benzyl (3S,5R)-3-methyl-5-((5-(thiazol-2-yl)-1-((2-(trimethylsilyl)ethoxy)methyl)-1H-pyrrolo[2,3-b]pyridin-4-yl)amino)piperidine-1-carboxylate as a yellow liquid (0.5 g, 32% yield): MS (ES) m/z 578.9 (M+H).

Step 3: Preparation of N-((3R,5S)-5-methylpiperidin-3-yl)-5-(thiazol-2-yl)-1H-pyrrolo[2,3-b]pyridin-4-amine

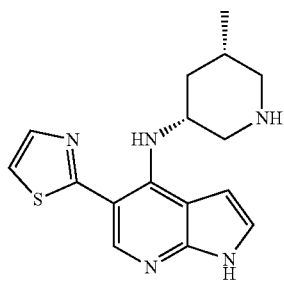 [SMILES: C[C@@H]1CNC[C@H](Nc2c(-c3nccs3)cnc3[nH]ccc23)C1]

A solution of benzyl (3S,5R)-3-methyl-5-((5-(thiazol-2-yl)-1-((2-(trimethylsilyl)ethoxy)methyl)-1H-pyrrolo[2,3-b]pyridin-4-yl)amino)piperidine-1-carboxylate (0.5 g, 0.39 mmol) and trifluoroacetic acid (5.0 mL) was stirred at 100° C. for 1 hour in a sealed tube. After cooling the reaction mixture was concentrated in vacuo, the obtained residue was dissolved in 1,4-dioxane:aqueous ammonia (5.0 mL:5.0 mL) and stirred at ambient temperature overnight. The reaction mixture was concentrated in vacuo to provide N-((3R,5S)-5-methylpiperidin-3-yl)-5-(thiazol-2-yl)-1H-pyrrolo[2,3-b]pyridin-4-amine as an off-white solid (0.2 g, crude): MS (ES) m/z 314.0 (M+H).

Step 4: Preparation of N-((3R,5S)-1-((2,2-difluorocyclopropyl)methyl)-5-methylpiperidin-3-yl)-5-(thiazol-2-yl)-1H-pyrrolo[2,3-b]pyridin-4-amine

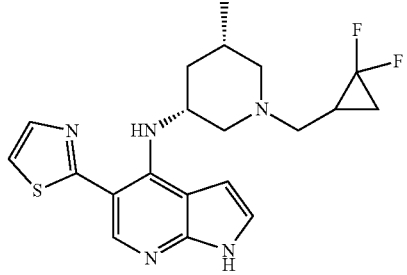 [SMILES: C[C@H]1C[C@@H](Nc2c(-c3nccs3)cnc3[nH]ccc23)CN(CC2CC2(F)F)C1]

To a stirred solution of (3R,5S)-5-methyl-N-[5-(1,3-thiazol-2-yl)-1H-pyrrolo[2,3-b]pyridin-4-yl]piperidin-3-amine (0.1 g, 0.32 mmol) in N-methylpyrrolidin-2-one (1.5 mL) was added 2-(bromomethyl)-1,1-difluorocyclopropane (0.87 g, 0.51 mmol) and the solution heated at 70° C. for 12 hours in a sealed tube. After cooling, the reaction was quenched with ice cold water, extracted with ethyl acetate, washed with brine, dried over anhydrous sodium sulfate, filtered and concentrated in vacuo. The crude material was purified using reverse phase to chromatography provide N-((3R,5S)-1-((2,2-difluorocyclopropyl)methyl)-5-methylpiperidin-3-yl)-5-(thiazol-2-yl)-1H-pyrrolo[2,3-b]pyridin-4-amine (0.003 g, 3% yield) as an off-white solid: $^1$H NMR (400 MHz, DMSO-$d_6$, VT at 80° C.) δ 11.35 (m, 1H), 9.53 (m, 1H), 8.37 (m, 1H), 7.80 (s, 1H), 7.50 (s, 1H), 7.15 (m, 1H), 6.55 (m, 1H), 4.21 (m, 1H), 3.3 (m, 1H), 2.80-2.92 (m, 1H), 2.17-2.31 (m, 1H), 1.73-1.92 (m, 3H), 1.42-1.59 (m, 1H), 1.35 (m, 1H), 1.24 (s, 3H), 0.90-1.11 (m, 4H); MS (ES) m/z 404.3 (M+H).

Analytical Conditions:
Column: Sunfire C18 19*150*5 micron
Mobile phase (A): 0.1% TFA in H$_2$O
Mobile phase (B): MeCN
Flow rate: 20 mL/min

Example 68. Preparation of 3-((3R,5S)-3-((5-(1,3,4-thiadiazol-2-yl)-1H-pyrrolo[2,3-b]pyridin-4-yl)amino)-5-methylpiperidin-1-yl)-3-oxopropanenitrile

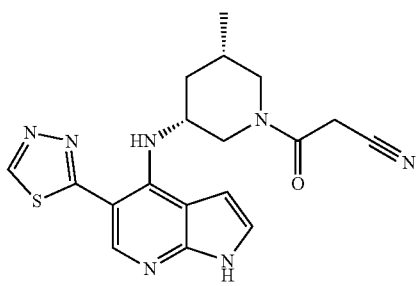

311

Scheme 66. Preparation of 3-((3R,5S)-3-((5-(1,3,4-thiadiazol-2-yl)-1H-pyrrolo[2,3-b]pyridin-4-yl)amino)-5-methylpiperidin-1-yl)-3-oxopropanenitrile

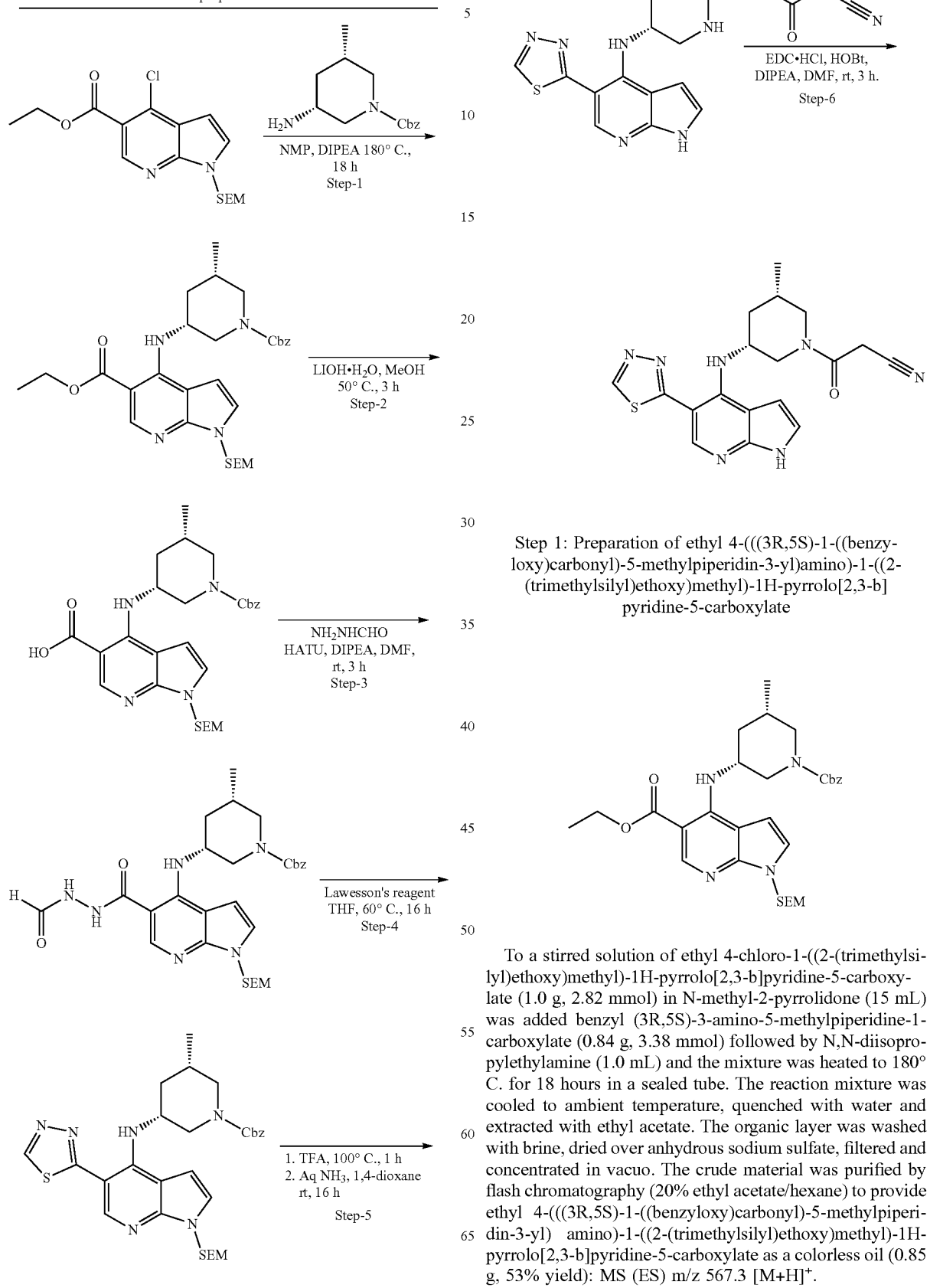

Step 1: Preparation of ethyl 4-(((3R,5S)-1-((benzyloxy)carbonyl)-5-methylpiperidin-3-yl)amino)-1-((2-(trimethylsilyl)ethoxy)methyl)-1H-pyrrolo[2,3-b]pyridine-5-carboxylate To a stirred solution of ethyl 4-chloro-1-((2-(trimethylsilyl)ethoxy)methyl)-1H-pyrrolo[2,3-b]pyridine-5-carboxylate (1.0 g, 2.82 mmol) in N-methyl-2-pyrrolidone (15 mL) was added benzyl (3R,5S)-3-amino-5-methylpiperidine-1-carboxylate (0.84 g, 3.38 mmol) followed by N,N-diisopropylethylamine (1.0 mL) and the mixture was heated to 180° C. for 18 hours in a sealed tube. The reaction mixture was cooled to ambient temperature, quenched with water and extracted with ethyl acetate. The organic layer was washed with brine, dried over anhydrous sodium sulfate, filtered and concentrated in vacuo. The crude material was purified by flash chromatography (20% ethyl acetate/hexane) to provide ethyl 4-(((3R,5S)-1-((benzyloxy)carbonyl)-5-methylpiperidin-3-yl) amino)-1-((2-(trimethylsilyl)ethoxy)methyl)-1H-pyrrolo[2,3-b]pyridine-5-carboxylate as a colorless oil (0.85 g, 53% yield): MS (ES) m/z 567.3 [M+H]⁺.

Step 2: Preparation of 4-(((3R,5S)-1-((benzyloxy)carbonyl)-5-methylpiperidin-3-yl)amino)-1-((2-(trimethylsilyl)ethoxy)methyl)-1H-pyrrolo[2,3-b]pyridine-5-carboxylic acid

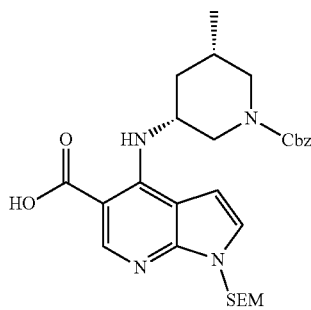 [SMILES: C[C@H]1C[C@@H](Nc2c(C(=O)O)cnc3c2ccn3COCC[Si](C)(C)C)CN(C(=O)OCc2ccccc2)C1]

To a stirred solution of ethyl 4-(((3R,5S)-1-((benzyloxy)carbonyl)-5-methylpiperidin-3-yl)amino)-1-((2-(trimethylsilyl)ethoxy)methyl)-1H-pyrrolo[2,3-b]pyridine-5-carboxylate (0.85 g, 1.50 mmol) in methanol (10 mL) was added 2M aqueous solution of lithium hydroxide-monohydrate (0.126 g, 3.0 mmol) and the solution stirred at room temperature for 6 hours at 50° C. for 2 hours. The reaction was cooled to ambient temperature and concentrated in vacuo to remove volatiles. The residue was dissolved in water and acidified with 1N hydrochloric acid to adjust pH3. The aqueous layer was extracted with ethyl acetate. The organic layer was washed with brine, dried over anhydrous sodium sulfate, filtered and concentrated in vacuo. The crude material was triturated with n-pentane to provide 4-(((3R,5S)-1-((benzyloxy)carbonyl)-5-methylpiperidin-3-yl)amino)-1-((2-(trimethylsilyl)ethoxy)methyl)-1H-pyrrolo[2,3-b]pyridine-5-carboxylic acid as a sticky solid (0.7 g, crude): MS (ES) m/z 539.3 [M+H]$^+$.

Step 3: Preparation of benzyl (3R,5S)-3-((5-(2-formylhydrazine-1-carbonyl)-1-((2-(trimethylsilyl)ethoxy)methyl)-1H-pyrrolo[2,3-b]pyridin-4-yl)amino)-5-methylpiperidine-1-carboxylate

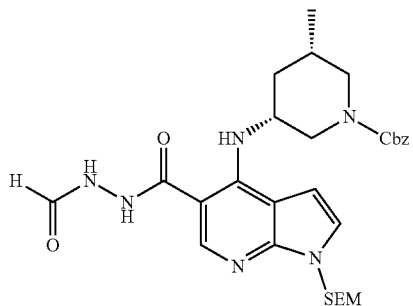 [SMILES: C[C@H]1C[C@@H](Nc2c(C(=O)NNC=O)cnc3c2ccn3COCC[Si](C)(C)C)CN(C(=O)OCc2ccccc2)C1]

A solution of 4-(((3R,5S)-1-((benzyloxy)carbonyl)-5-methylpiperidin-3-yl)amino)-1-((2-(trimethylsilyl) ethoxy)methyl)-1H-pyrrolo[2,3-b]pyridine-5-carboxylic acid (0.6 g, 1.11 mmol) and 1-[bis(dimethylamino) methylene]-1H-1,2,3-triazolo[4,5-b]pyridinium 3-oxide hexafluorophosphate (0.50 g, 1.34 mmol) in dimethylformamide (10 mL) was stirred at ambient temperature for 3 minutes. Formylhydrazide (0.13 g, 2.23 mmol) was added followed by N,N-diisopropylethylamine (0.6 mL, 3.34 mmol) and the mixture stirred at ambient temperature for 3 hours. The reaction was quenched with water and extracted with ethyl acetate. The organic layer was washed with brine and dried over anhydrous sodium sulfate. The solution was filtered and concentrated in vacuo to provide benzyl (3R,5S)-3-((5-(2-formylhydrazine-1-carbonyl)-1-((2-(trimethylsilyl) ethoxy)methyl)-1H-pyrrolo[2,3-b]pyridin-4-yl)amino)-5-methylpiperidine-1-carboxylate as an off-white solid (0.45 g, 69% yield): MS (ES) m/z 581.3 [M+H]$^+$.

Step 4: Preparation of benzyl (3R,5S)-3-((5-(1,3,4-thiadiazol-2-yl)-1-((2-(trimethylsilyl)ethoxy)methyl)-1H-pyrrolo[2,3-b]pyridin-4-yl)amino)-5-methylpiperidine-1-carboxylate

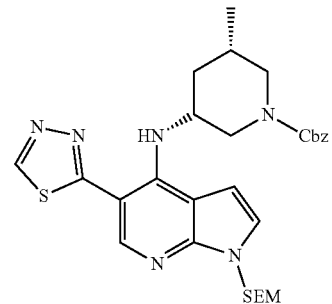

To a solution of benzyl (3R,5S)-3-((5-(2-formylhydrazine-1-carbonyl)-1-((2-(trimethylsilyl)ethoxy)methyl)-1H-pyrrolo[2,3-b]pyridin-4-yl)amino)-5-methylpiperidine-1-carboxylate (0.45 g, 0.77 mmol) in tetrahydrofuran (20 mL) was added Lawesson's reagent (0.47 g, 1.16 mmol) at ambient temperature and the mixture stirred at 70° C. for 16 hours. The reaction was cooled to ambient temperature and quenched with saturated sodium bicarbonate solution. The product was extracted with ethyl acetate, the organic layer washed with water and brine, dried over anhydrous sodium sulfate, filtered and concentrated in vacuo. The crude material was purified by flash chromatography (30% ethyl acetate/hexane) to provide benzyl (3R,5S)-3-((5-(1,3,4-thiadiazol-2-yl)-1-((2-(trimethylsilyl) ethoxy)methyl)-1H-pyrrolo[2,3-b]pyridin-4-yl)amino)-5-methylpiperidine-1-carboxylate as an off white solid (0.35 g, 78% yield): MS (ES) m/z 579.3 [M+H]$^+$.

Step 5: Preparation of N-((3R,5S)-5-methylpiperidin-3-yl)-5-(1,3,4-thiadiazol-2-yl)-1H-pyrrolo[2,3-b]pyridin-4-amine

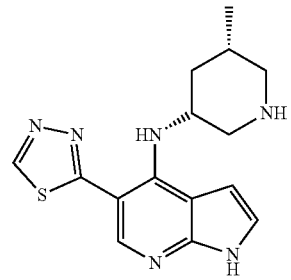

A solution of benzyl (3R,5S)-3-((5-(1,3,4-thiadiazol-2-yl)-1-((2-(trimethylsilyl)ethoxy)methyl)-1H-pyrrolo[2,3-b]pyridin-4-yl)amino)-5-methylpiperidine-1-carboxylate (0.35 g, 1.02 mmol) and trifluoroacetic acid (5.0 mL) was stirred at 100° C. for 1 hour in a sealed tube. After cooling the reaction mixture was concentrated in vacuo, the obtained residue was dissolved in 1,4-dioxane:aqueous ammonia (5.0 mL:5.0 mL) and stirred at ambient temperature overnight. The reaction mixture was concentrated in vacuo to provide N-((3R,5S)-5-methylpiperidin-3-yl)-5-(1,3,4-thiadiazol-2-yl)-1H-pyrrolo[2,3-b]pyridin-4-amine as an off-white solid (0.3 g, crude): MS (ES) m/z 315.2 (M+H).

Step 6: Preparation of 3-((3R,5S)-3-((5-(1,3,4-thiadiazol-2-yl)-1H-pyrrolo[2,3-b]pyridin-4-yl)amino)-5-methylpiperidin-1-yl)-3-oxopropanenitrile

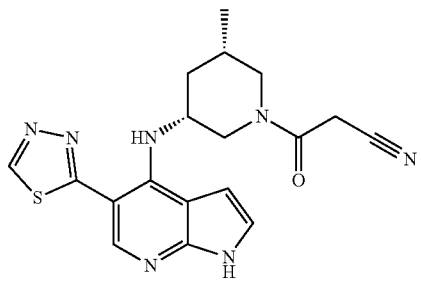 [SMILES: C[C@H]1C[C@@H](Nc2c(-c3nncs3)cnc3[nH]ccc23)CN(C(=O)CC#N)C1]

A solution of 2-cyanoacetic acid (0.16 g, 1.91 mmol), 1-hydroxybenzotriazole (0.22 g, 1.43 mmol) and 1-ethyl-3-(3-dimethylaminopropyl) carbodiimide hydrochloride (0.27 g, 1.43 mmol) in N,N-dimethylformamide (6 mL) was stirred at ambient temperature for 3 minutes, Then N-((3R,5S)-5-methylpiperidin-3-yl)-5-(1,3,4-thiadiazol-2-yl)-1H-pyrrolo[2,3-b]pyridin-4-amine (0.3 g, 0.95 mmol) was added followed by N,N-diisopropylethylamine (0.5 mL, 2.86 mmol) and the resulting mixture stirred at ambient temperature for 3 hours. The reaction mixture was quenched with ice cold water and the product extracted with ethyl acetate. The organic layer was washed with sodium bicarbonate solution, brine, dried over anhydrous sodium sulfate, filtered and concentrated in vacuo. The crude material was purified using reverse phase chromatography to provide 3-((3R,5S)-3-((5-(1,3,4-thiadiazol-2-yl)-1H-pyrrolo[2,3-b]pyridin-4-yl)amino)-5-methylpiperidin-1-yl)-3-oxopropanenitrile as an off white solid (0.02 g, 5% yield): $^1$H NMR (400 MHz, DMSO-$d_6$) δ 11.71 (br s, 1H), 9.36-9.46 (m, 2H), 8.34 (s, 1H), 7.25 (s, 1H), 6.79 (s, 1H), 4.82-4.84 (m, 1H), 4.30 (m, 1H), 3.93-4.09 (m, 3H), 3.58-3.61 (m, 1H), 2.64-2.74 (m, 1H), 2.19-2.30 (m, 1H), 1.87 (m, 1H), 1.32-1.35 (m, 1H), 0.91 (br s, 3H); MS (ES) m/z 382.4 (M+H).

Analytical Conditions:

Column: X-Bridge, C18 19*100*5 micron

Mobile phase (A): 0.1% Ammonium hydroxide in water

Mobile phase (B): MeCN

Flow rate: 20 mL/min

Preparation of tert-butyl(R)-3-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate

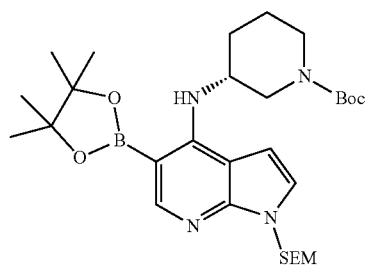 [SMILES: CC(C)(C)OC(=O)N1CCC[C@@H](Nc2c(B3OC(C)(C)C(C)(C)O3)cnc3c2ccn3COCC[Si](C)(C)C)C1]

Scheme 67. Preparation of tert-butyl (R)-3-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate

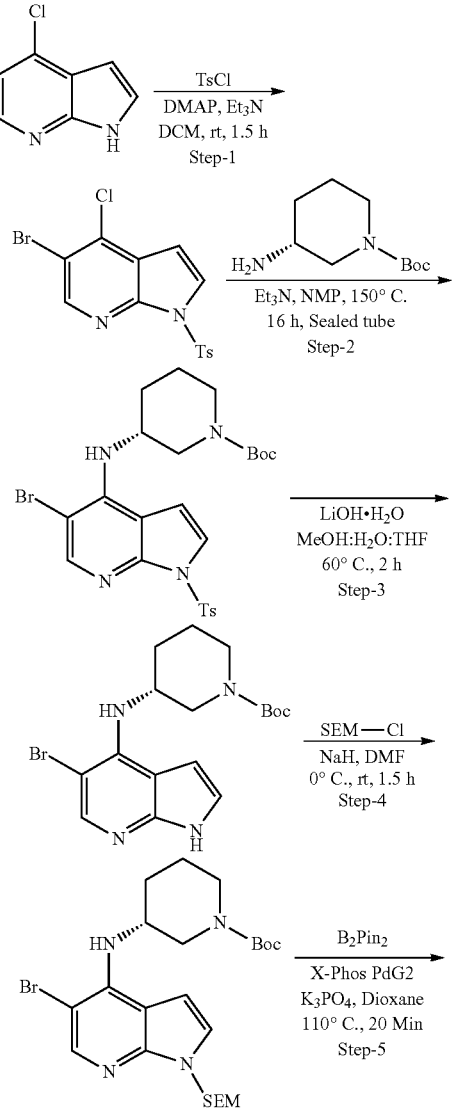

-continued

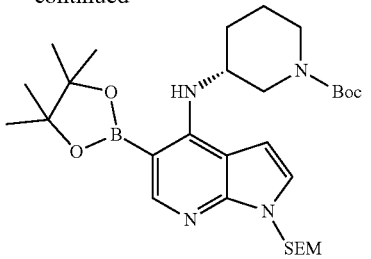

Step 1: Preparation of 5-bromo-4-chloro-1-tosyl-1H-pyrrolo[2,3-b]pyridine

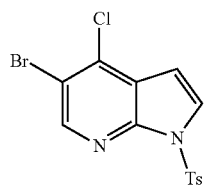

To a stirred solution of 5-bromo-4-chloro-1H-pyrrolo[2,3-b]pyridine (20 g, 87.3 mmol), triethylamine (36.4 mL, 262.0 mmol) and 4-dimethylaminopyridine (1.06 g, 8.73 mmol) in dichloromethane (40 mL) was added p-toulenesufonyl chloride (24.9 g, 131.0 mmol) at 0° C. and the mixture stirred at room temperature for 1 hour. The reaction was quenched with water and extracted with ethyl acetate. The organic layer was washed with water, brine, dried over anhydrous sodium sulfate, filtered and concentrated in vacuo. The crude product was washed with n-hexane to provide 5-bromo-4-chloro-1-tosyl-1H-pyrrolo[2,3-b]pyridine as an off-white solid (32.5 g, 97% yield): MS (ES) m/z 387.0 (M+2).

Step 2: Preparation of tert-butyl (R)-3-((5-bromo-1-tosyl-1H-pyrrolo[2,3-b]pyridin-4-yl)amino)piperidine-1-carboxylate

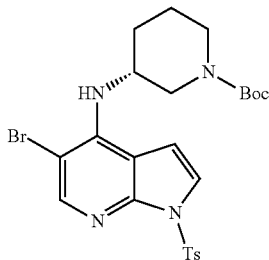 [SMILES: Cc1ccc(S(=O)(=O)n2ccc3c(N[C@@H]4CCCN(C(=O)OC(C)(C)C)C4)c(Br)cnc32)cc1]

In a sealed tube a stirred solution of 5-bromo-4-chloro-1-tosyl-1H-pyrrolo[2,3-b]pyridine (5 g, 13.0 mmol), tert-butyl (R)-3-aminopiperidine-1-carboxylate (3.9 g, 19.5 mmol) and triethylamine (0.9 mL, 6.5 mmol) in N-methylpyrrolidone (25 mL) was heated at 150° C. for 16 h. The reaction was cooled to ambient temperature and the reaction was quenched with water and extracted with ethyl acetate. The organic layer was washed with water, brine, dried over anhydrous sodium sulfate, filtered and concentrated in vacuo. The crude material was purified using flash chromatography (15% ethyl acetate/hexane) to provide tert-butyl (R)-3-((5-bromo-1-tosyl-1H-pyrrolo[2,3-b]pyridin-4-yl)amino)piperidine-1-carboxylate as a brown liquid (4.0 g, 56% yield): MS (ES) m/z 549 (M+).

Step 3: Preparation of tert-butyl (R)-3-((5-bromo-1H-pyrrolo[2,3-b]pyridin-4-yl)amino)piperidine-1-carboxylate

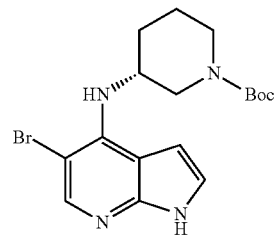 [SMILES: CC(C)(C)OC(=O)N1CCC[C@@H](Nc2c(Br)cnc3[nH]ccc23)C1]

A stirred solution of tert-butyl (R)-3-((5-bromo-1-tosyl-1H-pyrrolo[2,3-b]pyridin-4-yl)amino)piperidine-1-carboxylate (18.4 g, 33.5 mmol) and lithium hydroxide monohydrate (4.93 g, 117.5 mmol) in THF:MeOH:water (25 mL:100 mL:25 mL) was heated to 60° C. for 2 hours. The reaction was cooled to ambient temperature and then concentrated in vacuo. The crude was dissolved in ethyl acetate and washed with water, brine, dried over anhydrous sodium sulfate, filtered and concentrated in vacuo to provide tert-butyl (R)-3-((5-bromo-1H-pyrrolo[2,3-b]pyridin-4-yl)amino)piperidine-1-carboxylate as a brown liquid (12.4 g, crude): MS (ES) m/z 395.1 (M+).

Step 4: Preparation of tert-butyl (R)-3-((5-bromo-1-((2-(trimethylsilyl)ethoxy)methyl)-1H-pyrrolo[2,3-b]pyridin-4-yl)amino)piperidine-1-carboxylate

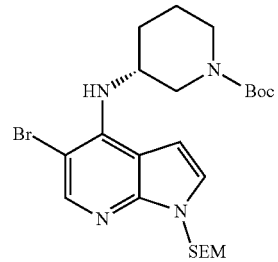 [SMILES: CC(C)(C)OC(=O)N1CCC[C@@H](Nc2c(Br)cnc3c2ccn3COCC[Si](C)(C)C)C1]

To a suspension of sodium hydride (1.29 g, 32.4 mmol, 60% suspension in mineral oil) in dry dimethylformamide (80 mL) was slowly added tert-butyl (R)-3-((5-bromo-1H-pyrrolo[2,3-b]pyridin-4-yl)amino)piperidine-1-carboxylate (8.0 g, 20.2 mmol) at 0° C. and the mixture stirred for 30 minutes. Then 2-(trimethylsilyl)ethoxymethyl chloride (6.45 mL, 36.4 mmol) was added at 0° C. and the mixture stirred at ambient temperature for 1.5 hours. The reaction mixture was quenched with saturated ammonium chloride solution and extracted with ethyl acetate. The organic extract was washed with water, brine, and dried over anhydrous sodium sulfate. The solution was filtered and concentrated in vacuo to provide a crude material which was purified by column chromatography (5% ethyl acetate/hexane) to provide tert-butyl (R)-3-((5-bromo-1-((2-(trimethylsilyl)ethoxy)methyl)-1H-pyrrolo[2,3-b]pyridin-4-yl)amino)piperidine-1-carboxylate as a yellow oil (7.0 g, 66% yield): MS (ES) m/z 525.0 (M+).

Step 5: Preparation of tert-butyl (R)-3-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate

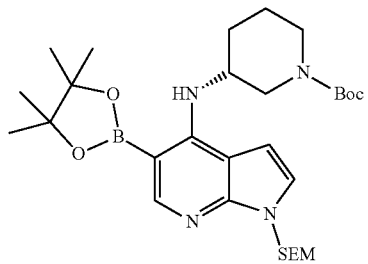

To a solution of tert-butyl (R)-3-((5-bromo-1-((2-(trimethylsilyl)ethoxy)methyl)-1H-pyrrolo[2,3-b]pyridin-4-yl)amino)piperidine-1-carboxylate (2 g, 3.80 mmol) in 1,4-dioxane:toluene (4:1) was added 4,4,4',4',5,5,5',5'-octamethyl-2,2'-bi(1,3,2-dioxaborolane) (1.25 g, 4.95 mmol) and potassium phosphate tribasic (2.42 g, 11.4 mmol). The mixture was purged with nitrogen for 15 minutes. X-Phos Pd G2 (0.60 g, 0.76 mmol) was added and the resulting mixture stirred at 110° C. for 15 minutes on pre-heated oil bath. The reaction was cooled to ambient temperature, diluted with ethyl acetate and filtered through celite. The filtrate was washed with water, brine, dried over anhydrous sodium sulfate, filtered and concentrated in vacuo to provide tert-butyl (R)-3-((5-(4,4,5,5-tetramethyl-1,3,2-dioxaborolan-2-yl)-1-((2-(trimethylsilyl)ethoxy)methyl)-1H-pyrrolo[2,3-b]pyridin-4-yl)amino)piperidine-1-carboxylate as a crude (3 g, crude): MS (ES) m/z 573.0 (M+H)+.

Biological Activity Assay
JAK1, JAK2, JAK3, and Tyk-2 Enzyme Activity Assays

The activity of JAK3 (a.a. 781-1124, ThermoFisher) was quantified by measuring the phosphorylation of SRCtide (FAM-GEEPLYWSFPAKKK-NH$_2$). Kinase reactions were run in a 384-well Greiner plate with 2% final DMSO concentration under the buffer conditions of 20 mM HEPES, pH 7.5, 10 mM MgCl$_2$, 0.01% BSA, and 0.0005% Tween-20. The kinase reaction components were 2.5 nM JAK3, 1 µM SRCtide peptide and 1 uM ATP. Examples were tested in dose-response starting at 2 M (11 concentrations, 3-fold serial dilution, duplicate reactions). The reactions were incubated at room temperature for 40 minutes, then stopped by adding a 1:1 volume of 30 mM EDTA in 20 mM HEPES, pH 7.5 (15 mM EDTA final). After the reaction was stopped, the phosphorylated and unphosphorylated peptides were separated and quantified using a Caliper LC3000/EZ-Reader system and HTS Well Analyzer Software (Caliper, A PerkinElmer Company, Hopkinton, Mass.). GraFit (Erithacus Software Ltd., Horley, U.K.) was used to calculate inhibitor potency by fitting dose-response data to the 4-parameter logistical IC$_{50}$ equation.

The inhibitory potency of candidate compounds of JAK1, JAK2, and Tyk-2 was done at Thermo Fisher Scientific in their Selectscreen using a Z-lyte assay. Following are the assay details for each enzyme.

JAK: The 2×JAK-enzyme/Tyr 06 mixture is prepared in 50 mM HEPES pH 6.5, 0.01% BRIJ-35, 10 mM MgCl$_2$, 1 mM EGTA, 0.02% NaN$_3$. The final 10 µL of the Kinase Reaction consists of 21.2-91.5 ng JAK and 2 M Tyr 06 in 50 mM HEPES pH 7.0, 0.01% BRIJ-35, 10 mM MgCl$_2$, 1 mM EGTA, 0.01% NaN$_3$. After the one hour Kinase Reaction incubation, 5 µL of a 1:128 dilution of Development Reagent is added.

JAK2: The 2×JAK2/Tyr 06 mixture is prepared in 50 mM HEPES pH 7.5, 0.01% BRIJ-35, 10 mM MgCl$_2$, 1 mM EGTA. The final 10 µL Kinase Reaction consists of 0.12-0.5 ng JAK2 and 2 M Tyr 06 in 50 mM HEPES pH 7.5, 0.01% BRIJ-35, 10 mM MgCl$_2$, 1 mM EGTA. After the one hour Kinase Reaction incubation, 5 µL of a 1:128 dilution of Development Reagent A is added.

TYK2: The 2×TYK2/Tyr 03 mixture is prepared in 50 mM HEPES pH 6.5, 0.01% BRIJ-35, 10 mM MgCl$_2$, 1 mM EGTA, 0.02% NaN$_3$. The final 10 µL Kinase Reaction consists of 3.75-15 ng TYK2 and 2 M Tyr 03 in 50 mM HEPES pH 7.0, 0.01% BRIJ-35, 10 mM MgCl$_2$, 1 mM EGTA, 0.01% NaN$_3$. After the one hour KinaseReaction incubation, 5 µL of a 1:4096 dilution of Development Reagent A is added.

Data reduction for JAK1, JAK2 and TYK2 is done the same, independent of the enzyme run. In summary, background signal is defined in the absence of enzyme and uninhibited signal is defined in the presence of vehicle (2% DMSO) alone. Compounds were evaluated in an 11 point dose-response ranging from 20 mM to 0.34 nM. IC$_{50}$ values of compounds are determined using a 4 parameter logistical fit of emission ratio as a function of the concentration of compound. The results are shown in Table 3.

TABLE 3

| Example No | JAK1 Inhibition IC$_{50}$<br>+++ indicates ≤0.01 µM<br>++ indicates 0.01-0.1 µM<br>+ indicates 0.1-1 µM<br>− indicates >1 µM | JAK2 Inhibition IC$_{50}$<br>+++ indicates ≤0.01 µM<br>++ indicates 0.01-0.1 µM<br>+ indicates 0.1-1 µM<br>− indicates >1 µM | JAK3 Inhibition IC$_{50}$<br>+++ indicates ≤0.01 µM<br>++ indicates 0.01-0.1 µM<br>+ indicates 0.1-1 µM<br>− indicates >1 µM | Tyk-2 Inhibition IC$_{50}$<br>+++ indicates ≤0.01 µM<br>++ indicates 0.01-0.1 µM<br>+ indicates 0.1-1 µM<br>− indicates >1 µM |
|---|---|---|---|---|
| 1 | ++ | ++ | ++ | ++ |
| 2 | +++ | ++ | +++ | ++ |
| 3 | ++ | + | ++ | + |
| 4 | +++ | +++ | +++ | +++ |
| 5 | +++ | +++ | +++ | +++ |
| 6 | +++ | ++ | +++ | ++ |
| 7 | ++ | ++ | ++ | ++ |
| 8 | +++ | ++ | +++ | ++ |
| 9 | + | + | ++ | + |
| 10 | +++ | +++ | +++ | +++ |
| 11 | ++ | ++ | ++ | + |

TABLE 3-continued

| Example No | JAK1 Inhibition IC$_{50}$ +++ indicates ≤0.01 μM ++ indicates 0.01-0.1 μM + indicates 0.1-1 μM − indicates >1 μM | JAK2 Inhibition IC$_{50}$ +++ indicates ≤0.01 μM ++ indicates 0.01-0.1 μM + indicates 0.1-1 μM − indicates >1 μM | JAK3 Inhibition IC$_{50}$ +++ indicates ≤0.01 μM ++ indicates 0.01-0.1 μM + indicates 0.1-1 μM − indicates >1 μM | Tyk-2 Inhibition IC$_{50}$ +++ indicates ≤0.01 μM ++ indicates 0.01-0.1 μM + indicates 0.1-1 μM − indicates >1 μM |
|---|---|---|---|---|
| 12 | + | + | ++ | + |
| 13 | ++ | ++ | ++ | + |
| 14 | +++ | ++ | +++ | ++ |
| 15 | +++ | ++ | +++ | ++ |
| 16 | ++ | + | ++ | + |
| 17 | − | − | − | − |
| 18 | +++ | ++ | +++ | ++ |
| 19 | ++ | + | ++ | + |
| 20 | +++ | ++ | ++ | + |
| 21 | +++ | ++ | ++ | ++ |
| 22 | ++ | ++ | ++ | ++ |
| 23 | ++ | + | ++ | + |
| 24 | +++ | ++ | +++ | +++ |
| 25 | +++ | ++ | ++ | ++ |
| 26 | +++ | ++ | ++ | ++ |
| 27 | ++ | ++ | +++ | + |
| 28 | +++ | +++ | +++ | +++ |
| 29 | ++ | ++ | +++ | + |
| 30 | +++ | +++ | + | +++ |
| 31 | +++ | +++ | +++ | +++ |
| 32 | + | + | ++ | + |
| 33 | +++ | ++ | +++ | ++ |
| 34 | +++ | ++ | +++ | ++ |
| 35 | +++ | ++ | +++ | ++ |
| 36 | +++ | +++ | +++ | +++ |
| 37 | +++ | ++ | +++ | ++ |
| 38 | ++ | ++ | ++ | + |
| 39 | ++ | +++ | +++ | ++ |
| 40 | +++ | +++ | +++ | +++ |
| 41 | +++ | +++ | +++ | +++ |
| 42 | +++ | +++ | +++ | +++ |
| 43 | +++ | ++ | ++ | ++ |
| 44 | +++ | ++ | ++ | ++ |
| 45 | +++ | +++ | +++ | +++ |
| 46 | +++ | +++ | +++ | +++ |
| 47 | ++ | ++ | ++ | ++ |
| 48 | +++ | ++ | ++ | ++ |
| 49 | +++ | ++ | +++ | ++ |
| 50 | +++ | ++ | +++ | ++ |
| 51 | +++ | +++ | +++ | ++ |
| 52 | +++ | +++ | +++ | +++ |
| 53 | +++ | +++ | +++ | +++ |
| 54 | ++ | ++ | + | + |
| 55 | +++ | ++ | +++ | +++ |
| 56 | ++ | + | + | + |
| 57 | + | + | ++ | + |
| 58 | +++ | + | ++ | + |
| 59 | +++ | + | + | − |
| 60 | +++ | ++ | ++ | ++ |
| 61 | ++ | ++ | ++ | + |
| 62 | +++ | +++ | +++ | ++ |
| 63 | +++ | +++ | +++ | ++ |
| 64 | +++ | +++ | +++ | +++ |
| 65 | +++ | +++ | +++ | +++ |
| 66 | +++ | ++ | +++ | ++ |
| 67 | ++ | ++ | +++ | ++ |
| 68 | +++ | +++ | +++ | +++ |

JAK Cellular Target Modulation Assays

Target modulation was based upon the ability of a compound to inhibit JAK isoform specific phosphorylation of selected substrates. IL-2 stimulated STAT5 phosphorylation on Tyr694 was used to assess JAK1/3 compound selectivity. GM-CSF stimulated STAT5 phosphorylation on Tyr694 was used to assess JAK2 compound selectivity. IFNγ stimulated STAT1 phosphorylation on Tyr701 was used to assess JAK1/2 compound selectivity. IL-12 stimulated STAT4 phosphorylation on Tyr693 was used to assess JAK2/TYK2 compound selectivity. For all four assays, human PBMC from frozen stocks were thawed, pelleted, resuspended in complete media (90% RPMI, 10% heat inactivated FBS, 10 mM HEPES, 47 μM 2-ME, pen/strep) and placed in wells of a 96 well V-bottom plate at 200,000 per well in 120 μl complete media. Compounds were added as 15 μl per well of 10× working stock solutions in complete media with 1% DMSO (or medium with 1% DMSO for controls) and placed on a plate shaker in a 37° C. incubator with 5% CO$_2$ for 1 hour with gentle shaking (setting of 3). Stimulation used the addition of soluble cytokines. For the JAK1/3 phospho-STAT5 assay, 15 μl of 10× working stock recombinant human IL-2 was added to a final concentration of 25 ng/ml. For the JAK2 phospho-STAT5 assay, 15 μl of 10× working stock recombinant human GM-CSF was added to a final concentration of 5 ng/ml. For the JAK1/2 phospho-STAT1 assay, 15 μl of 10× working stock of recombinant human IFNγ was added to a final concentration of 10 ng/ml. For the JAK2/TYK2 phospho-STAT4 assay, 15 μl of 10× working stock of recombinant human IL-12 was added to a final concentration of 1.7 ng/ml. Plates were then placed back on the plate shaker in the incubator for an additional 5, 5, 10, and 25 minutes respectively upon which the plates were removed from the incubator, sealed with a plate sealer and the cells pelleted at 400×g for 5 minutes. After pelleting, the media was removed by aspiration and the cells were lysed in assay specific cell lysis buffer. The levels of phospho-STAT5 were determined using a Phospho (Tyr694) STAT5a,b Whole Cell Lysate kit from Meso Scale Discovery. Levels of phospho-STAT1 were determined using a CST-PathScan Phospho-STAT1 (Tyr701) Sandwich ELISA kit. Levels of phospho-STAT4 were determined using a Phospho-STAT4 (Tyr693) Whole Cell Lysate kit from Meso Scale Discovery. The results are shown in Table 4.

TABLE 4

| Example No | IL2-STAT5 $IC_{50}$ ++ indicates ≤0.1 μM + indicates 0.1-1 μM − indicates >1 μM | Infγ-STAT1 $IC_{50}$ ++ indicates ≤0.1 μM + indicates 0.1-1 μM − indicates >1 μM | IL12-STAT4 $IC_{50}$ ++ indicates ≤0.1 μM + indicates 0.1-1 μM − indicates >1 μM |
|---|---|---|---|
| 1 | + | + | |
| 2 | ++ | + | + |
| 3 | + | − | |
| 4 | ++ | ++ | + |
| 5 | ++ | ++ | + |
| 6 | ++ | + | − |
| 7 | + | + | − |
| 8 | ++ | + | + |
| 9 | − | | |
| 10 | ++ | ++ | ++ |
| 11 | − | − | |
| 12 | + | − | |
| 13 | + | − | − |
| 14 | + | − | |
| 15 | ++ | + | − |
| 16 | + | − | |
| 17 | − | | |
| 18 | ++ | + | − |
| 19 | + | − | − |
| 20 | ++ | + | − |
| 21 | ++ | + | + |
| 22 | + | + | − |
| 23 | + | − | − |
| 24 | ++ | + | + |
| 25 | ++ | + | |
| 26 | ++ | + | − |
| 27 | + | − | − |
| 28 | ++ | ++ | + |
| 29 | ++ | + | − |
| 30 | + | + | − |
| 31 | ++ | ++ | − |
| 32 | − | | |
| 33 | ++ | + | − |
| 34 | + | + | − |
| 35 | + | | − |
| 36 | ++ | ++ | + |
| 37 | ++ | + | − |
| 38 | + | − | − |
| 39 | − | − | |
| 40 | ++ | ++ | ++ |
| 41 | ++ | + | + |
| 42 | ++ | + | + |
| 43 | ++ | + | − |
| 44 | + | + | − |
| 45 | + | + | − |
| 46 | ++ | ++ | + |
| 47 | + | − | − |
| 48 | ++ | + | − |
| 49 | ++ | ++ | − |
| 50 | − | | |
| 51 | + | + | − |
| 52 | ++ | ++ | + |
| 53 | ++ | ++ | |
| 54 | − | | |
| 55 | ++ | + | − |
| 56 | − | | |
| 57 | − | | |
| 58 | + | − | |
| 59 | + | − | |
| 60 | ++ | + | − |
| 61 | − | | |

TABLE 4-continued

| Example No | IL2-STAT5 IC$_{50}$ ++ indicates ≤0.1 µM + indicates 0.1-1 µM − indicates >1 µM | Infγ-STAT1 IC$_{50}$ ++ indicates ≤0.1 µM + indicates 0.1-1 µM − indicates >1 µM | IL12-STAT4 IC$_{50}$ ++ indicates ≤0.1 µM + indicates 0.1-1 µM − indicates >1 µM |
|---|---|---|---|
| 62 | ++ | + | − |
| 63 | ++ | + | − |
| 64 | ++ | ++ | − |
| 65 | ++ | ++ | ++ |
| 66 | ++ | + | |
| 67 | + | + | − |
| 68 | ++ | ++ | ++ |

GI Exposure PK in Mice

The test compound was wetted with ~0.025% of Tween-20 and triturated in a mortar and pestle, then slowly 0.5% of methyl cellulose was added to make up the final volume to 7.25 mL. The BalbC test animals were subjected to anesthesia induced with a mixture of 5% isoflurane and 0.8-1.5 L/min 02 gas flow. The formulated test compound was then dosed via oral gavage. At various time points (0.5, 1, 2, 4, 6 and 8 h) blood samples (~100 µL) were collected from portal vein (pre-hepatic) followed by cardiac puncture (circulating) into tubes containing 2% w/v aqueous $K_2$ EDTA solution as per time points. Post blood sampling, the gastro intestine (GI) tissues were collected from the mice at the same time points. The GI tissue was dissected into different parts as duodenum, jejunum, ileum and colon. The separated tissues were washed by flushing with PBS via oral gavage needle to remove GI content. Post collection all the tissues were blotted, weighed and homogenized with PBS buffer (pH 7.4). The blood samples were immediately placed on ice and centrifuged within 30 min at 4° C. for 5 min at 8,000 rpm to obtain plasma. Plasma was transferred by pipettes to pre-labelled centrifuge tubes and immediately transferred to −80° C. until bioanalysis. Tissue samples were placed in pre-labelled container and all samples were kept in −80° C. until homogenized. The homogenate was stored immediately in −80° C. until bioanalysis was conducted. Study samples were thawed to room temperature and 50 µL of sample was aliquoted into pre-labeled vials. To these was added 400 µL of 100% acetonitrile containing an IS (100 ng/mL; warfarin, tolbutamide and loperamide). The vials were mixed well, vortexed for 5 min, followed by centrifugation for 5 min at 14000 rpm at 4° C. The supernatant was separated and same was injected on LC-MS/MS. Plasma and GI tissue levels of test compound were determined by LC-MS analysis using a standard curve in the text matrix. Individual concentration-time data were analyzed using Phoenix WinNonlin (Version 8.1) by the non-compartmental analysis (NCA) method. The results are shown in Table 5.

TABLE 5

Cmax, Tmax, and AUC calculations for Example 31 in male BalbC mice after an oral dose of 5 mg/kg.

| Tissue | Cmax (ng/mL or ng/g) | Tmax (h) | AUC h*ng/mL |
|---|---|---|---|
| Circulating plasma | 9.2[1] | 4 | NRV[2] |
| Portal plasma | 11.3 | 0.5 | 17.2 |
| Duodenum | 2881 | 0.5 | 4658 |
| Jejunum | 37007 | 0.5 | 57391 |

TABLE 5-continued

Cmax, Tmax, and AUC calculations for Example 31 in male BalbC mice after an oral dose of 5 mg/kg.

| Tissue | Cmax (ng/mL or ng/g) | Tmax (h) | AUC h*ng/mL |
|---|---|---|---|
| Ileum | 43840 | 2 | 82490 |
| Colon | 1286 | 4 | 6815 |

[1]For two of three subjects, below limit of quatification (BLQ) for third animal. Other time points are BLQ except at 8 h for one animal with 13.5 ng/mL.
[2]NRV (No reported value) - Insufficient data points to calculate the PK parameter.

Acute DSS Colitis Model in Mice

Oral administration of the sulfated polysaccharide dextran sulfate sodium (DSS) to mice via drinking water induces severe colitis characterized by weight loss, bloody diarrhea, ulcer formation, loss of epithelial cells and infiltrations with neutrophils, macrophages and lymphocytes, resembling some features of human inflammatory bowel disease (IBD). See Okayasu, I. et al. Gastroenterology, 98: 694-702 (1990) and Wirtz et al. *Nature Protocols.* 12(7):1295 (2017). Nine-twelve-week old female C57BL/6 mice from Charles River were given 4% DSS (Colitis grade DSS, molecular weight: 36,000-50,000; MP Biomedicals Cat. No. 160110) in sterile drinking water for 5 days. On day 6, the mice were switched to sterile drinking water, and drugs were dosed (PO, BID) from day 6 to 10 or day 10 to 14.

Body weight was monitored daily and reported as a percentage of initial body weight. Stool consistency and bloody diarrhea were also scored (0-4). At the end of each study, mice were sacrificed and the entire colon was removed and flushed with PBS. The colon weight and length were measured, and the ratio of colon weight to length was reported. A 0.5 cm segment of the distal colon was collected in a microfuge tube and frozen in dry ice. Lysates of this tissue were prepared for colonic cytokine determination using V-PLEX mouse cytokine 29-plex kit from MSD. A 3 cm segment of distal colon was collected to a cassette and fixed in 10% formalin for histology. Slides were prepared and stained with hematoxylin and eosin (H&E) and scored in a blinded fashion by a pathologist. Scoring of H&E slides included categories for inflammation, gland loss, erosion, submucosal edema, mucosal thickness, neutrophil score and lymphoid aggregate count and size.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

The invention claimed is:

1. A compound, or a derivative thereof, of Formula (I):

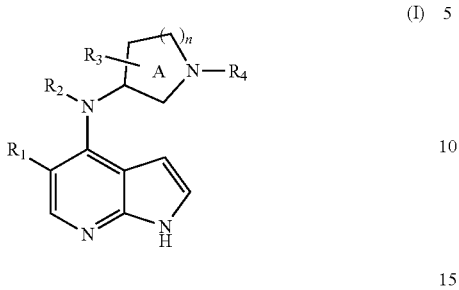

wherein:

$R_1$ is selected from CN or a heteroaryl group and is optionally substituted at the one or more available nitrogen atoms with a group independently selected from H or $C_1$-$C_5$alkyl and at one or more available carbon atoms with substituents wherein each substituent is independently selected from H, halogen, CN, —$C_1$—$C_4$alkyl, —$C_0$-$C_6$alkyl$C_3$—$C_6$cycloalkyl, —($C_0$-$C_6$alkyl)$C_3$-$C_6$heterocycle, —OH, —$SO_2R_9$, —$SOR_9$, —$SR_9$, —$NHSO_2R_9$, —$OSO_2R_9$, —$C_0$-$C_6$alkyl$SO_2R_9$, $C_0$-$C_6$alkylCO$R_9$, $C_0$-$C_6$alkyl$NR_7C(O)NR_7R_8$, $C_0$-$C_6$alkylOC(O)$NR_7R_8$, $C_0$-$C_6$alkyl$NR_7SO_2R_9$, —$C_0$-$C_6$alkyl$NR_7COR_9$, -$OC_1$-$C_5$alkyl, —$OC_0$-$C_6$alkyl$C_3$-$C_6$cycloalkyl, —$OC_0$-$C_6$alkyl$C_3$-$C_6$heterocycle, —$OC_0$-$C_6$alkyl$NR_7C(O)NR_7R_8$, —O-$C_0$-$C_6$alkylOC(O)$NR_7R_8$, —$OC_0$-$C_6$alkyl$NR_7SO_2R_9$, —$OC_0$-$C_6$alkyl$NR_7COR_9$, —$NR_7R_8$, —$NR_7C_0$-$C_6$alkyl$C_1$-$C_6$alkyl, -$NR_7C_0$-$C_6$alkyl$C_3$-$C_6$cycloalkyl, —$NR_7C_0$-$C_6$alkyl$NR_7C(O)NR_7R_8$, —$NR_7C_0$-$C_6$alkylOC(O)$NR_7R_8$, —$NR_7C_0$-$C_6$alkyl$NR_7SO_2R_9$, —$NR_7C_0$-$C_6$alkyl$NR_7COR_9$, —$NR_7C_0$-$C_6$alkyl$C_3$-$C_6$heterocycle, aryl and heteroaryl wherein each alkyl, cycloalkyl, aryl, heterocyclyl, or heteroaryl group is optionally substituted with one or more groups selected from: halogen, —OH, —$C_0$-$C_6$alkyl$NR_7R_8$, —$C_0$-$C_6$alkylOH, —$SO_2R_9$, —$SOR_9$, —$NHSO_2R_9$, —$C_0$-$C_6$alkyl$NR_7R_4$, CN, —$C_1$-$C_5$alkylalkoxy, $C_1$-$C_5$alkoxy or —O-$C_1$-$C_5$alkyl;

$R_2$ is selected from H, —$C_1C_4$alkyl, —$C_3$-$C_6$cycloalkyl, or —$C_1$-$C_2$alkyl-$C_3$-$C_6$cycloalkyl, wherein the alkyl or cycloalkyl groups are optionally substituted with one or more groups selected from halogen, —OH, or —O-$_1$-$C_5$alkyl;

n is 2;

Ring A is substituted at one or more carbons with one, two, or three $R_3$ substituents wherein each $R_3$ substituent is independently selected from H, halogen, —$C_1$-$C_4$alkyl, —$C_3$-$C_6$cycloalkyl, —OH, or —O-$C_1$-$C_5$alkyl wherein each alkyl or cycloalkyl group is optionally substituted with one or more groups selected from: halogen, —OH, —$C_1$-$C_5$alkylalkoxy, or —O-$C_1$-$C_5$alkyl;

Two $R_3$ groups on the same or different carbon atoms of the ring A may be optionally joined to form a spirocyclic or bicyclic ring system with ring A;

$R_4$ is selected from —C(O)-$R_6$, —$CH_2R_6$, —C(O)-$C_1$-$C_5$alkyl, or —C(O)-$C_3$-$C_6$cycloalkyl, wherein the alkyl or cycloalkyl groups may be optionally substituted with one or more groups selected from —OH, halogen, alkyne, or —CN;

$R_5$ is selected from —$C_1$-$C_5$alkyl, or —$C_3$-$C_6$cycloalkyl wherein the alkyl or cycloalkyl groups may be optionally substituted by one or more groups selected from halogen, —OH, or —O-$C_1$-$C_5$alkyl;

$R_6$ is selected from —$C_1$-$C_5$alkyl, —$C_3$-$C_6$cycloalkyl, —$C_1$-$C_5$alkyl-$C_3$-$C_6$cycloalkyl, —$NR_7R_8$, —O-aryl, —O-heteroaryl, or heteroaryl wherein the alkyl, cycloalkyl, aryl or heteroaryl groups can be optionally substituted by one or more groups selected from halogen, —CN, alkyne, —OH, trifluoromethyl, —O-$C_1$-$C_5$alkyl, or —O-$C_3$-$C_6$cycloalkyl;

$R_7$ and $R_8$ are independently selected from H, —$C_1$-$C_5$ alkyl, —$C_1$-$C_5$ alkoxy, or —$C_3$-$C_5$ cycloalkyl wherein the alkyl groups may be optionally substituted by one or more groups selected from halogen, —OH, or —CN;

$R_7$ and $R_8$ may be optionally joined to form a ring to form a heterocycle such as piperidine, pyrrolidine, or with another heteroatom to form a ring such as morpholine wherein the heterocyclic ring may be optionally substituted by one or more groups selected from halogen, —OH, $NH_2$, NHMe, $NMe_2$, or —CN; and $R_9$ is selected from H, —$C_1C_5$alkyl, —$OC_1C_5$alkyl, —$C_3$-$C_6$cycloalkyl, and $NR_7R_8$ wherein the alkyl, heterocycle, or cycloalkyl groups may be optionally substituted by one or more groups selected from halogen, —OH, $NH_2$, NHMe, $NMe_2$, or —CN.

2. The compound of claim 1, wherein the compound is selected from the group consisting of:

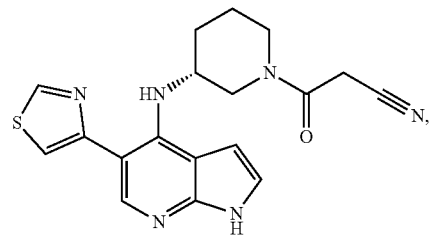

(R)-3-oxo-3-(3-((5-thiazol-4-yl)-1H-pyrrolo[2,3-b]pyridin-4-yl)amino)piperidin-1-yl)propanenitrile

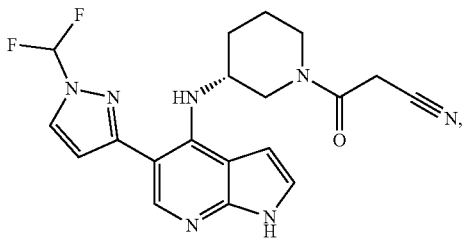

(R)-3-(3-((5-(1-(difluoromethyl)-1H-pyrazol-3-yl)-1H-pyrrolo[2,3-b]pyridin-4-yl)amino)piperidin-1-yl)-3-oxopropanenitrile

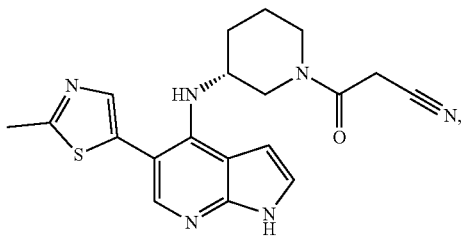

(R)-3-(3-((5-(2-methylthiazol-5-yl)-1H-pyrrolo[2,3-b]pyridin-4-yl)amino)piperidin-1-yl)-3-oxopropanenitrile

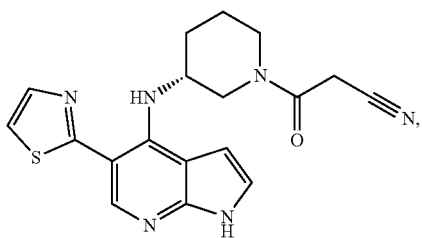

(R)-3-oxo-3-(3-((5-thiazol-2-yl)-1H-pyrrolo[2,3-b]pyridin-4-yl)amino)piperidin-1-yl)propanenitrile

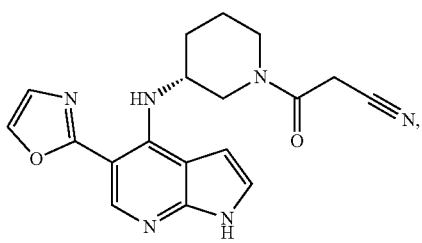

(R)-3-(3-((5-(oxazol-2-yl)-1H-pyrrolo[2,3-b]pyridin-4-yl)amino)piperidin-1-yl)-3-oxopropanenitrile

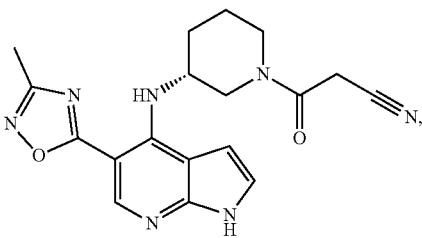

(R)-3-(3-((5-(3-methyl-1,2,4-oxadiazol-5-yl)-1H-pyrrolo[2,3-b]pyridin-4-yl)amino)piperidin-1-yl)-3-oxopropanenitrile

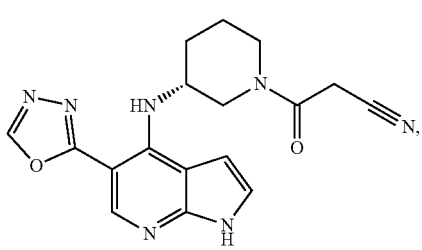

(R)-3-(3-((5-(1,3,4-oxadiazol-2-yl)-1H-pyrrolo[2,3-b]pyridin-4-yl)amino)piperidin-1-yl)-3-oxopropanenitrile

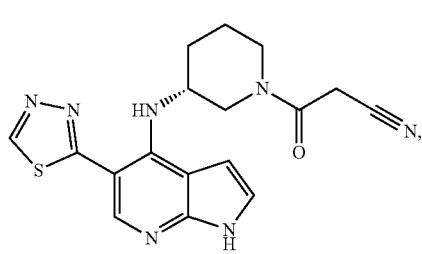

rac-(R)-3-(3-((5-(1,3,4-thiadiazol-2-yl)-1H-pyrrolo[2,3-b]pyridin-4-yl)amino)piperidin-1-yl)-3-oxopropanenitrile

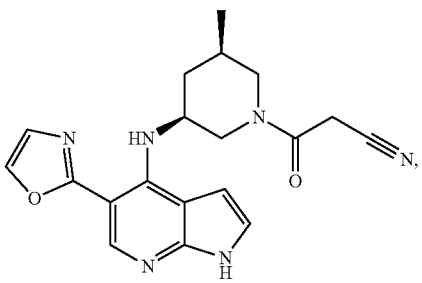

3-((3R,5S)-3-methyl-5-((5-(oxazol-2-yl)-1H-pyrrolo[2,3-b]pyridin-4-yl)amino)piperidin-1-yl)-3-oxopropanenitrile

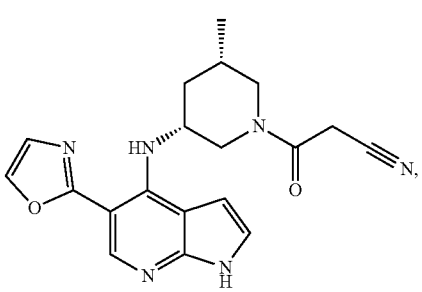

3-((3S,5R)-3-methyl-5-((5-(oxazol-2-yl)-1H-pyrrolo[2,3-b]pyridin-4-yl)amino)piperidin-1-yl)-3-oxopropanenitrile

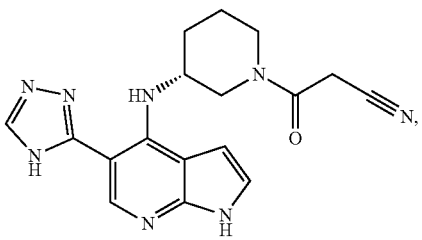

(R)-3-(3-((5-(4H-1,2,4-triazol-3-yl)-1H-pyrrolo[2,3-b]pyridin-4-yl)amino)piperidin-1-yl)-3-oxopropanenitrile

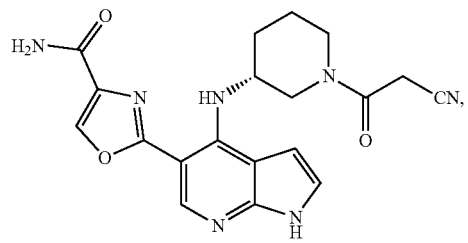

(R)-2-(4-(((1-(2-cyanoacetyl)piperidin-3-yl)amino)-1H-pyrrolo[2,3-b]pyridin-5-yl)oxazole-4-carboxamide

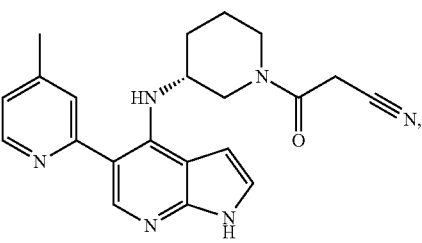

(R)-3-(3-((5-(4-methylpyridin-2-yl)-1H-pyrrolo[2,3-b]pyridin-4-yl)amino)piperidin-1-yl)-3-oxopropanenitrile

331
-continued

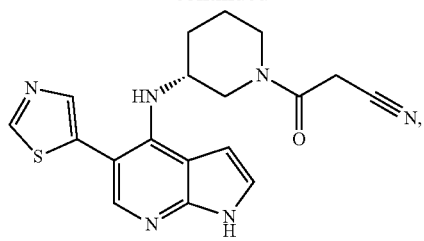

(R)-3-oxo-3-(3-((5-(thiazol-5-yl)-1H-pyrrolo[2,3-b]pyridin-4-yl)amino)piperidin-1-yl)propanenitrile

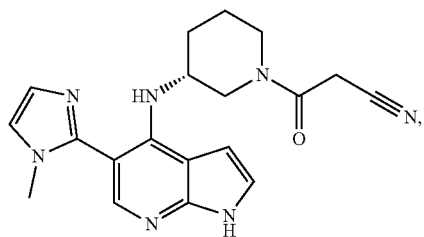

(R)-3-(3-((5-(1-methyl-1H-imidazol-2-yl)-1H-pyrrolo[2,3-b]pyridin-4-yl)amino)piperidin-1-yl)-3-oxopropanenitrile

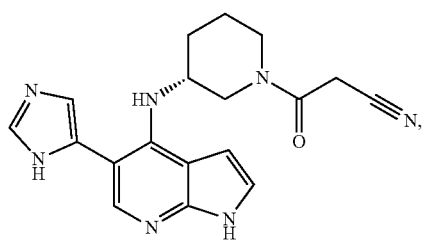

(R)-3-(3-((5-(1H-pyrazol-5-yl)-1H-pyrrolo[2,3-b]pyridin-4-yl)amino)piperidin-1-yl)-3-oxopropanenitrile

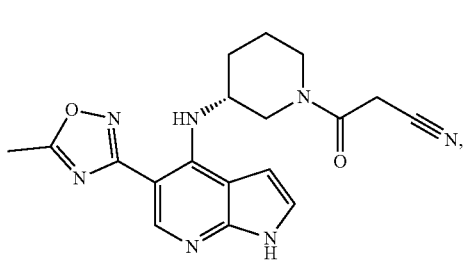

(R)-3-(3-((5-(5-methyl-1,2,4-oxadiazol-3-yl)-1H-pyrrolo[2,3-b]pyridin-4-yl)amino)piperidin-1-yl)-3-oxopropanenitrile

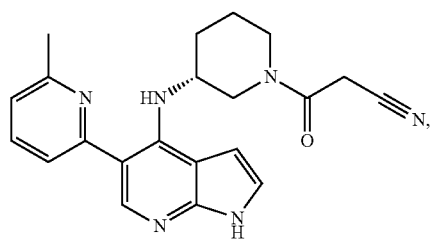

(R)-3-(3-((5-(6-methylpyridin-2-yl)-1H-pyrrolo[2,3-b]pyridin-4-yl)amino)piperidin-1-yl)-3-oxopropanenitrile

332
-continued

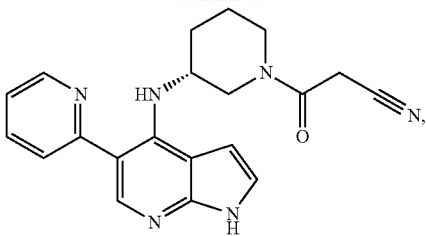

(R)-3-oxo-3-(3-((5-(pyridin-2-yl)-1H-pyrrolo[2,3-b]pyridin-4-yl)amino)piperidin-1-yl)propanenitrile

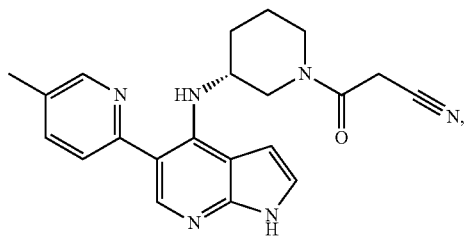

(R)-3-(3-((5-(5-methylpyridin-2-yl)-1H-pyrrolo[2,3-b]pyridin-4-yl)amino)piperidin-1-yl)-3-oxopropanenitrile

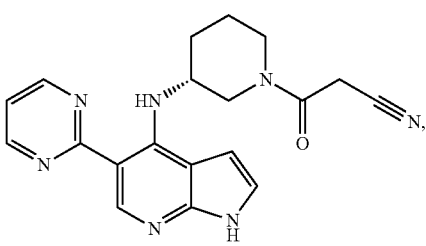

(R)-3-oxo-3-(3-((5-(pyrimidin-2-yl)-1H-pyrrolo[2,3-b]pyridin-4-yl)amino)piperidin-1-yl)propanenitrile

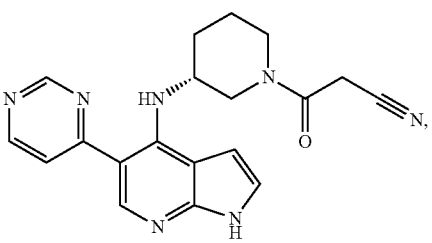

(R)-3-oxo-3-(3-((5-(pyrimidin-4-yl)-1H-pyrrolo[2,3-b]pyridin-4-yl)amino)piperidin-1-yl)propanenitrile

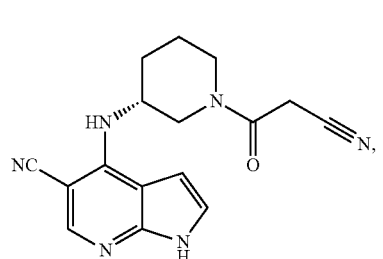

(R)-4-((1-(2-cyanoacetyl)piperidin-3-yl)amino)-1H-pyrrolo[2,3-b]pyridine-5-carbonitrile

333

-continued

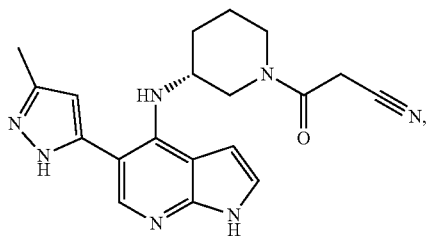

(R)-3-(3-((5-(3-methyl-1H-pyrazol-5-yl)-1H-pyrrolo[2,3-b]pyridin-4-yl)amino)piperidin-1-yl)-3-oxopropanenitrile

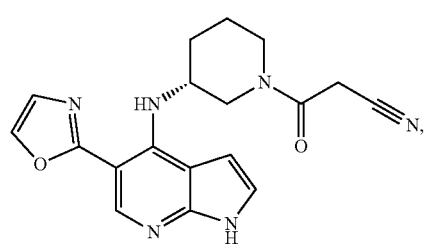

(R)-3-(3-((5-(oxazol-2-yl)-1H-pyrrolo[2,3-b]pyridin-4-yl)amino)piperidin-1-yl)propanenitrile

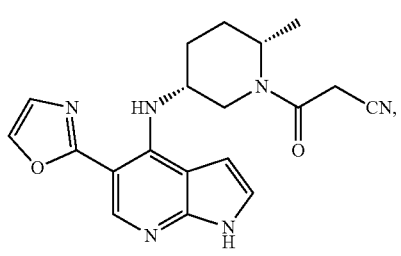

3-((2S,5R)-2-methyl-5-((5-(oxazol-2-yl)-1H-pyrrolo[2,3-b]pyridin-4-yl)amino)piperidin-1-yl)-3-oxopropanenitrile

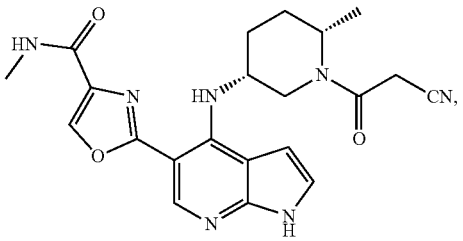

2-(4-(((3R,6S)-1-(2-cyanoacetyl)-6-methylpiperidin-3-yl)amino)-1H-pyrrolo[2,3-b]pyridin-5-yl)-N-methyloxazole-4-carboxamide

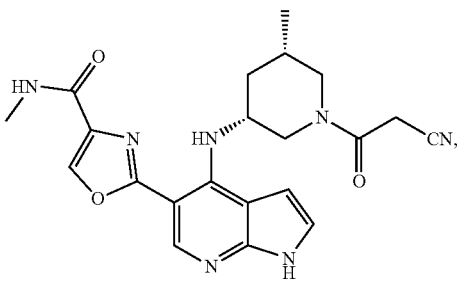

2-(4-(((3R,5S)-1-(2-cyanoacetyl)-5-methylpiperidin-3-yl)amino)-1H-pyrrolo[2,3-b]pyridin-5-yl)-N-methyloxazole-4-carboxamide

334

-continued

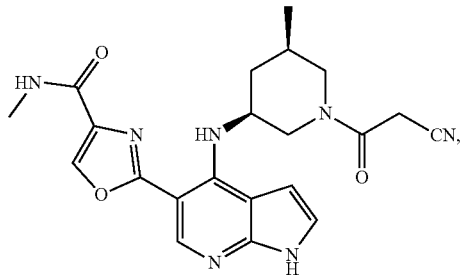

2-(4-(((3S,5R)-1-(2-cyanoacetyl)-5-methylpiperidin-3-yl)amino)-1H-pyrrolo[2,3-b]pyridin-5-yl)-N-methyloxazole-4-carboxamide

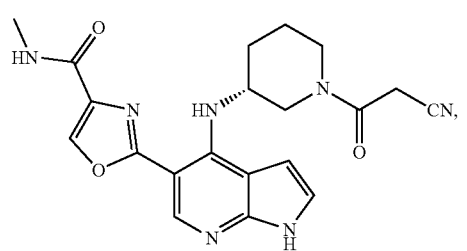

(R)-2-(4-(((1-(2-cyanoacetyl)piperidin-3-yl)amino)-1H-pyrrolo[2,3-b]pyridin-5-yl)-N-methyloxazole-4-carboxamide

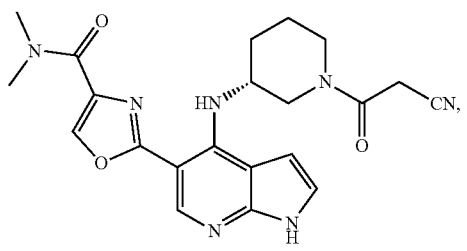

(R)2-(4-((1-(2-cyanoacetyl)piperidin-3-yl)amino)-1H-pyrrolo[2,3-b]pyridin-5-yl)-N-N-dimethyl-oxazole-4-carboxamide

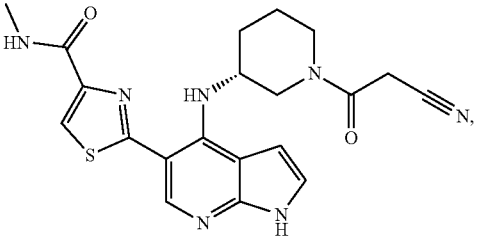

(R)-2-(4-((1-(2-cyanoacetyl)piperidin-3-yl)amino)-1H-pyrrolo[2,3-b]pyridin-5-yl)-N-methylthiazole-4-carboxamide

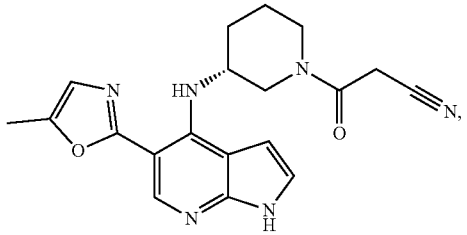

(R)-3-(3-((5-(5-methyloxazol-2-yl)-1H-pyrrolo[2,3-b]pyridin-4-yl)amino)piperidin-1-yl)-3-oxopropanenitrile

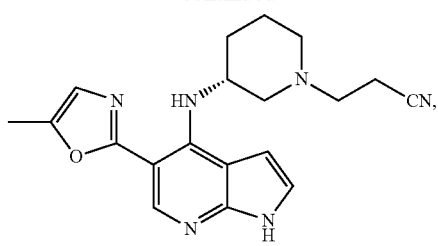

(R)-3-(3-((5-(5-methyloxazol-2-yl)-1H-pyrrolo[2,3-b]pyridin-4-yl)amino)piperidin-1-yl)propanenitrile

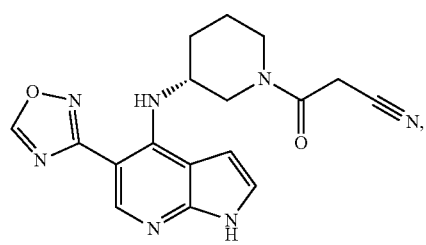

(R)-3-(3-((5-(1,2,4-oxadiazol-3-yl)-1H-pyrrolo[2,3-b]pyridin-4-yl)amino)piperidin-1-yl)-3-oxopropanenitrile

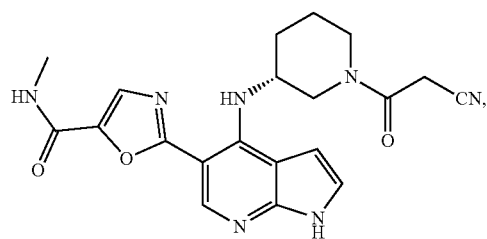

(R)-2-(4-((1-(2-cyanoacetyl)piperidin-3-yl)amino)-1H-pyrrolo[2,3-b]pyridin-5-yl)-N-methyloxazole-5-carboxamide

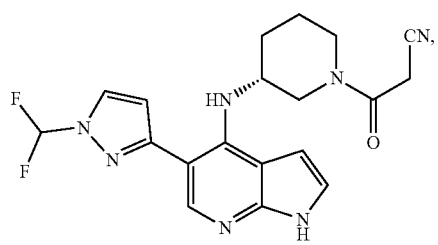

3-((3R,5S)-3-((5-(1-(difluoromethyl)-1H-pyrazol-3-yl)-1H-pyrrolo[2,3-b]pyridin-4-yl)-amino)-5-methylpiperidin-1-yl)-3-oxopropanenitrile

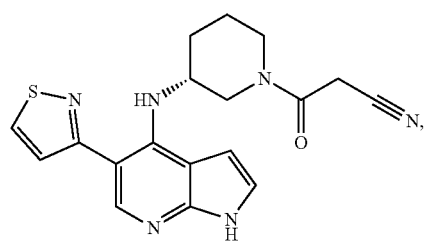

(R)-3-(3-((5-(isothiazol-3-yl)-1H-pyrrolo[2,3-b]pyridin-4-yl)amino)piperidin-1-yl)-3-oxopropanenitrile

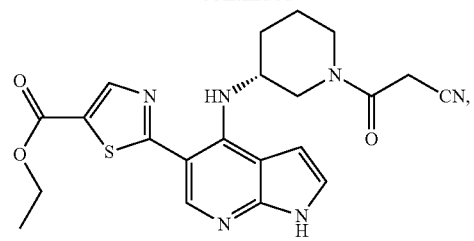

(R)-2-(4-((1-(2-cyanoacetyl)piperidin-3-yl)amino)-1H-pyrrolo[2,3-b]pyridin-5-yl)thiazole-5-carboxylate

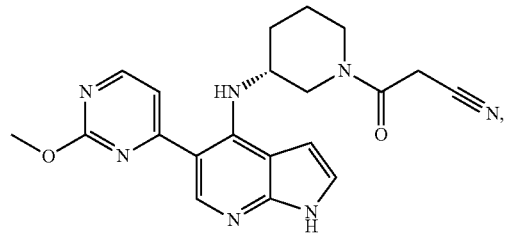

(R)-3-(3-((5-(2-methoxypyridin-4-yl)-1H-pyrrolo[2,3-b]pyridin-4-yl)amino)piperidin-1-yl)-3-oxopropanenitrile

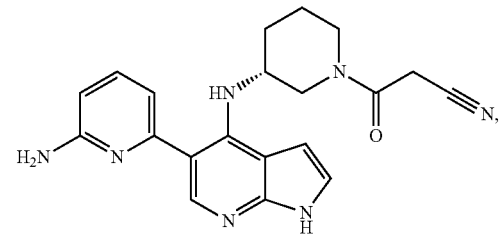

(R)-3-(3-((5-(6-aminopyridin-2-yl)-1H-pyrrolo[2,3-b]pyridin-4-yl)amino)piperidin-1-yl)-3-oxopropanenitrile

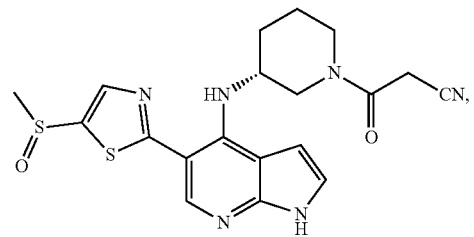

3-((3R)-3-((5-(5-(methylsulfonyl)thiazol-2-yl)-1H-pyrrolo[2,3-b]pyridin-4-yl)amino)piperidin-1-yl)-3-oxopropanenitrile

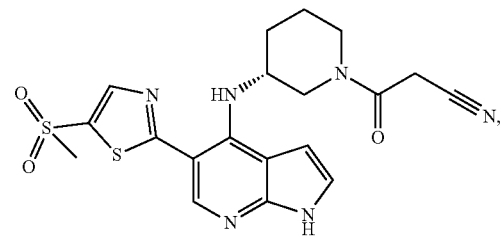

(R)-3-(3-((5-(5-(methylsulfonyl)thiazol-2-yl)-1H-pyrrolo[2,3-b]pyridin-4-yl)amino)piperidin-1-yl)-3-oxopropanenitrile

337

-continued

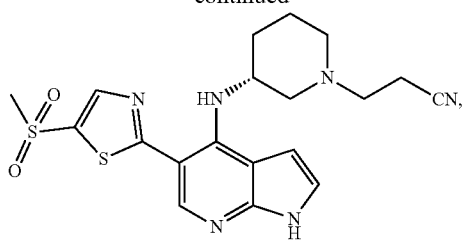

(R)-3-(3-((5-(5-(methylsulfonyl)thiazol-2-yl)-1H-pyrrolo[2,3-b]pyridin-4-yl)amino)piperidin-1-yl)propanenitrile

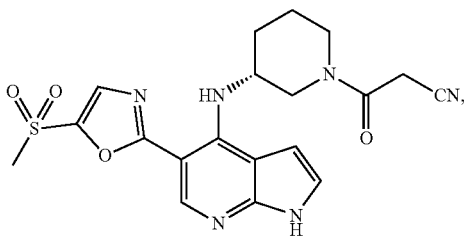

(R)-3-(3-((5-(5-(methylsulfonyl)oxazol-2-yl)-1H-pyrrolo[2,3-b]pyridin-4-yl)amino)piperidin-1-yl)-3-oxopropanenitrile

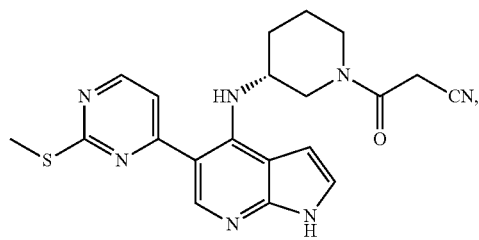

(R)-3-(3-((5-(5-(methylthio)pyrimidin-4-yl)-1H-pyrrolo[2,3-b]pyridin-4-yl)amino)piperidin-1-yl)-3-oxopropanenitrile

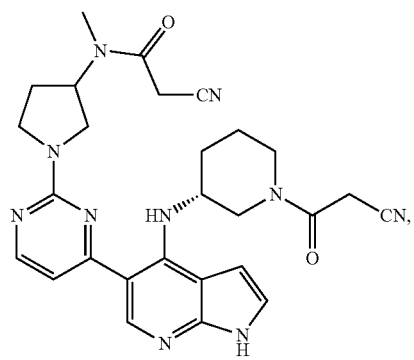

2-cyano-N-(1-(4-(4-(((R)-1-(2-cyanoacetyl)piperidin-3-yl)amino)-1H-pyrrolo[2,3-b]pyridin-5-yl)pyrimidin-2-yl)pyrrolidin-3-yl)-N-methylacetamide

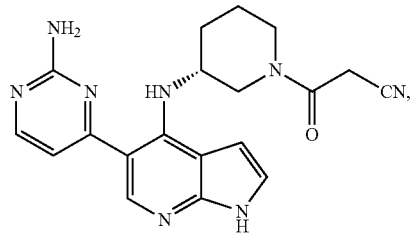

(R)-3-(3-((5-(2-aminopyrimidin-4-yl)-1H-pyrrolo[2,3-b]pyridin-4-yl)amino)piperidin-1-yl)-3-oxopropanenitrile

338

-continued

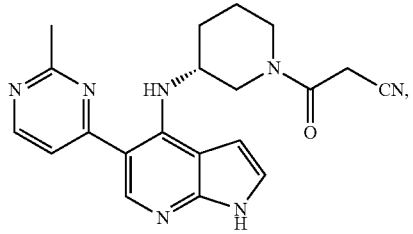

3-((3S,5R)-3-methyl-5-((5-(2-methylpyrimidin-4-yl)-1H-pyrrolo[2,3-b]pyridin-4-yl)amino)piperidin-1-yl)-3-oxopropanenitrile

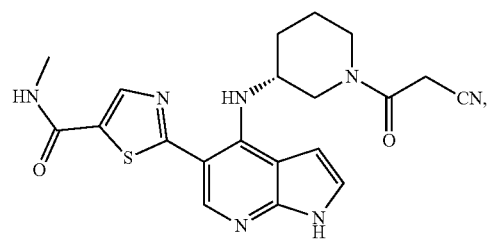

(R)-2-(4-((1-(2-cyanoacetyl)piperidin-3-yl)amino)-1H-pyrrolo[2,3-b]pyridin-5-yl)-N-methylthiazole-5-carboxamide

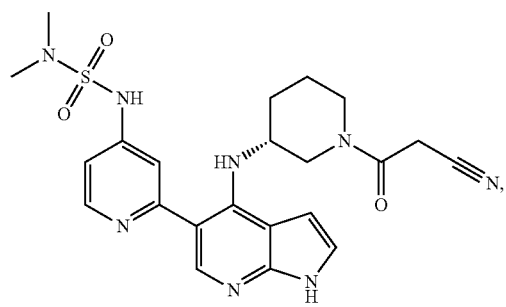

(R)-N-(2-(4-((1-(2-cyanoacetyl)piperidin-3-yl)amino)-1H-pyrrolo[2,3-b]pyridin-5-yl)pyridin-4-yl)N,N-dimethyl sulfuric diamide

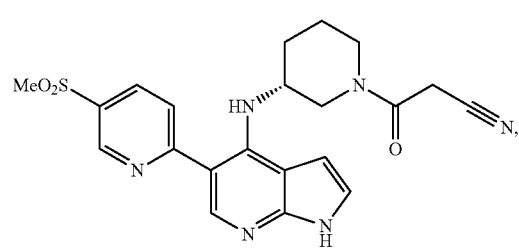

(R)-3-(3-((5-(5-(methylsulfonyl)pyridin-2-yl)-1H-pyrrolo[2,3-b]pyridin-4-yl)amino)piperidin-1-yl)-3-oxopropanenitrile -continued

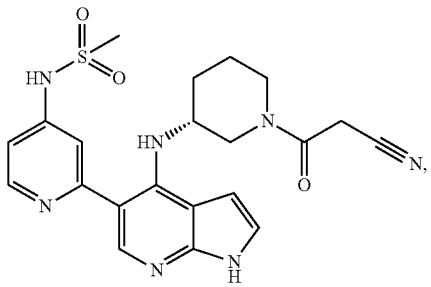

(R)-N-(2-(4-(((1-(2-(cyanoacetyl)piperidin-3-yl)amino)-1H-pyrrolo[2,3-b]pyridin-5-yl)pyridin-4-yl)methanesulfonamide

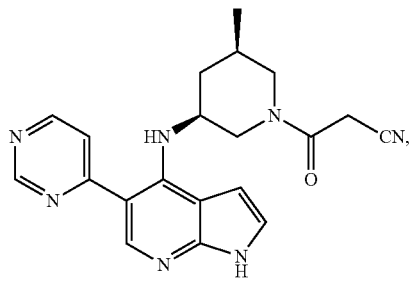

3-((3R,5S)-3-methyl-5-((5-(pyrimidin-4-yl)-1H-pyrrolo[2,3-b]pyridin-4-yl)amino)piperidin-1-yl)-3-oxopropanenitrile

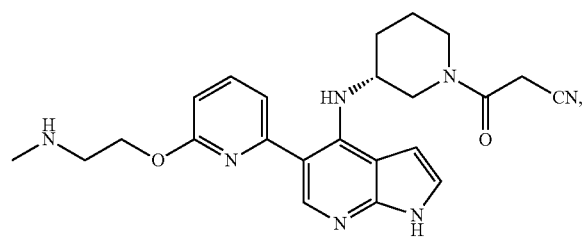

(R)-3-(3-((5-(1H-pyrazol-5-yl)-1H-pyrrolo[2,3-b]pyridin-4-yl)amino)piperidin-1-yl)-3-oxopropanenitrile

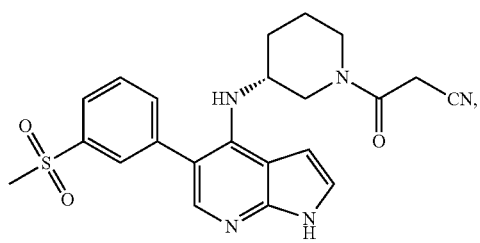

(R)-3-(3-((5-(3-(methylsulfonyl)phenyl)-1H-pyrrolo[2,3-b]pyridin-4-yl)amino)piperidin-1-yl)-3-oxopropanenitrile

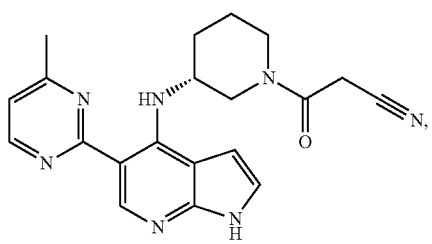

(R)-3-(3-((5-(4-methylpyridin-2-yl)-1H-pyrrolo[2,3-b]pyridin-4-yl)amino)piperidin-1-yl)-3-oxopropanenitrile -continued

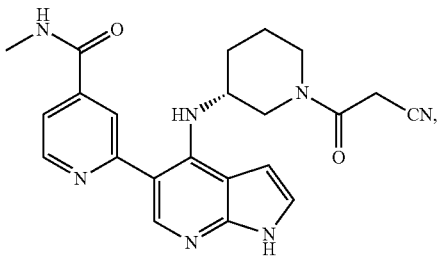

(R)-2-(4-((1-(2-cyanoacetyl)piperidin-3-yl)amino)-1H-pyrrolo[2,3-b]pyridin-5-yl)-N-methylisonicotinamide

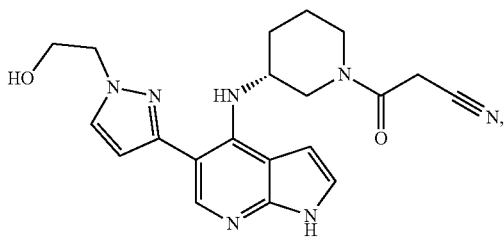

(R)-3-(3-((5-(1-(2-hydroxyethyl)-1H-pyrazol-3-yl)-1H-pyrrolo[2,3-b]pyridin-4-yl)amino)piperidin-1-yl)-3-oxopropanenitrile

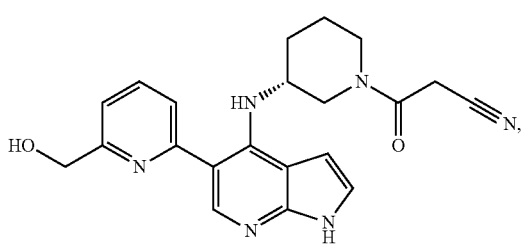

(R)-3-(3-((5-(3-(hydroxymethyl)phenyl)-1H-pyrrolo[2,3-b]pyridin-4-yl)amino)piperidin-1-yl)-3-oxopropanenitrile

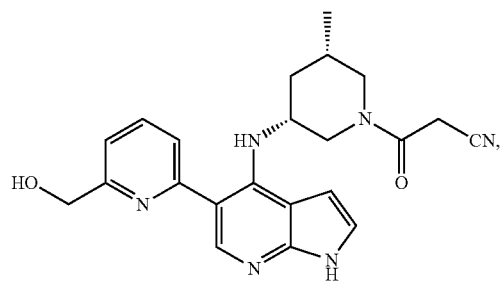

3-((3R,5S)-3-((5-(6-(hydroxymethyl)pyridin-2-yl)-1H-pyrrolo[2,3-b]pyridin-4-yl)amino)-5-methylpiperidin-1-yl)-3-oxopropanenitrile

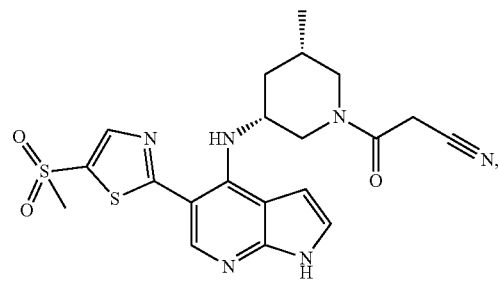

3-((3S,5R)-3-methyl-5-((5-(5-(methylsulfonyl)thiazol-2-yl)-1H-pyrrolo[2,3-b]pyridin-4-yl)amino)piperidin-1-yl)-3-oxopropanenitrile -continued

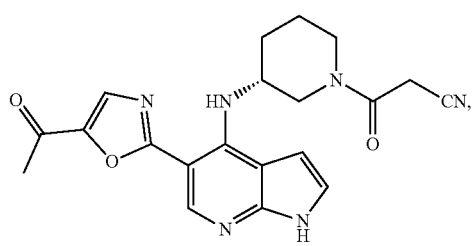

(R)-3-(3-((5-(5-acetyloxazol-2-yl)-1H-pyrrolo[2,3-b]pyridin-4-yl)amino)piperidin-1-yl)-3-oxopropanenitrile

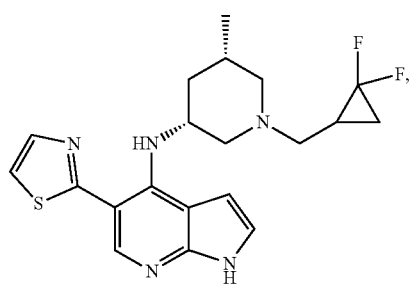

N-((3R,5S)-1-((2,2-difluorocyclopropyl)methyl)-5-methylpiperidin-3-yl)-5-(thiazol-2-yl)-1H-pyrrolo[2,3-b]pyridin-4-amine

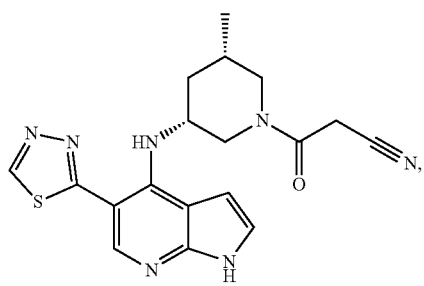

3-((3R,5S)-3-((5-(1,3,4-thiadiazol-2-yl)-1H-pyrrolo[2,3-b]pyridin-4-yl)amino)-5-methylpiperidin-1-yl)-3-oxopropanenitrile

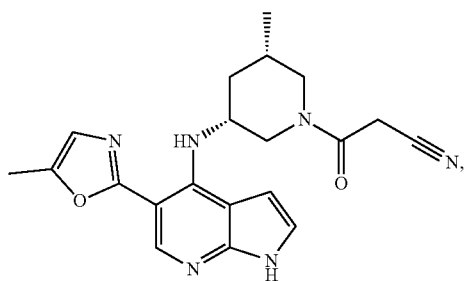

3-((3S,5R)-3-methyl-5-((5-(5-methyloxazol-2-yl)-1H-pyrrolo[2,3-b]pyridin-4-yl)amino)piperidin-1-yl)-3-oxopropanenitrile -continued

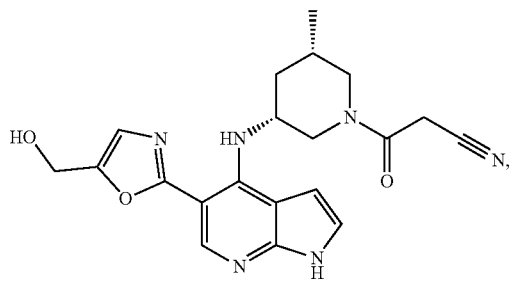

3-((3R,5S)-3-((5-(5-(hydroxymethyl)oxazol-2-yl)-1H-pyrrolo[2,3-b]pyridin-4-yl)amino)-5-methylpiperidin-1-yl)-3-oxopropanenitrile

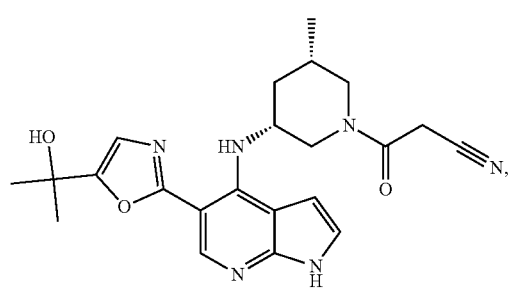

3-((3R,5S)-3-((5-(5-(2-hydroxypropan-2-yl)oxazol-2-yl)-1H-pyrrolo[2,3-b]pyridin-4-yl)amino)-5-methylpiperidin-1-yl)-3-oxopropanenitrile

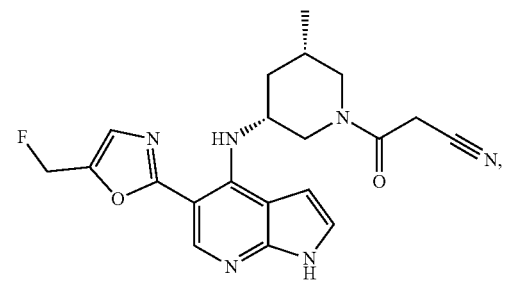

3-((3R,5S)-3-((5-(5-(fluoromethyl)oxazol-2-yl)-1H-pyrrolo[2,3-b]pyridin-4-yl)amino)-5-methylpiperidin-1-yl)-3-oxopropanenitrile

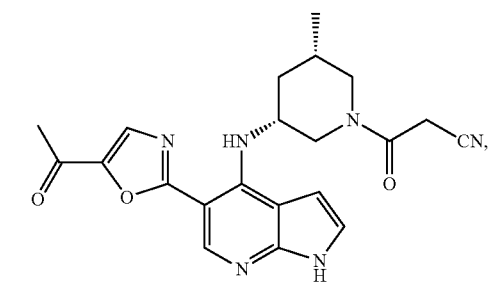

3-((3R,5S)-3-((5-(5-acetyloxazol-2-yl)-1H-pyrrolo[2,3-b]pyridin-4-yl)amino)-5-methylpiperidin-1-yl)-3-oxopropanenitrile

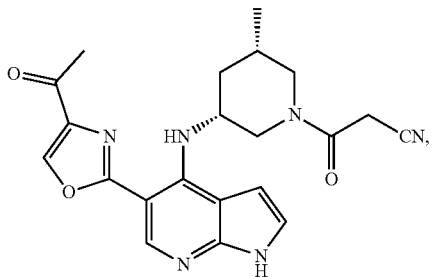

3-((3R,5S)-3-((5-(5-acetyloxazol-2-yl)-1H-pyrrolo[2,3-b]pyridin-4-yl)amino)-5-methylpiperidin-1-yl)-3-oxopropanenitrile

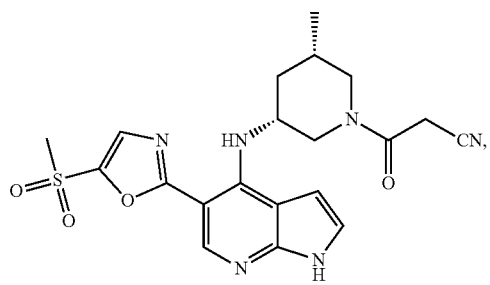

3-((3S,5R)-3-methyl-5-((5-(5-(methylsulfonyl)oxazol-2-yl)-1H-pyrrolo[2,3-b]pyridin-4-yl)amino)piperidin-1-yl)-3-oxopropanenitrile

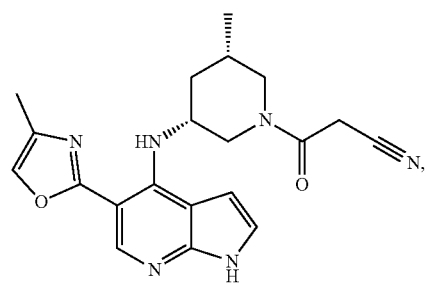

3-((3S,5R)-3-methyl-5-((5-(4-methyloxazol-2-yl)-1H-pyrrolo[2,3-b]pyridin-4-yl)amino)piperidin-1-yl)-3-oxopropanenitrile

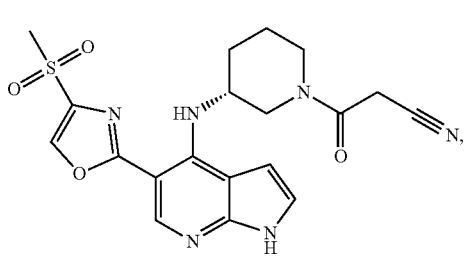

(R)-3-(3-((5-(4-(methylsulfonyl)oxazol-2-yl)-1H-pyrrolo[2,3-b]pyridin-4-yl)amino)piperidin-1-yl)-3-oxopropanenitrile

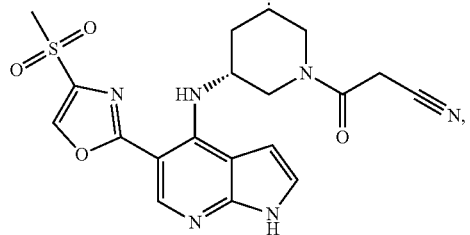

3-((3S,5R)-3-methyl-5-((5-(4-(methylsulfonyl)oxazol-2-yl)-1H-pyrrolo[2,3-b]pyridin-4-yl)amino)piperidin-1-yl)-3-oxopropanenitrile

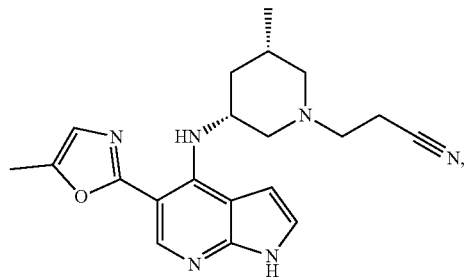

3-((3S,5R)-3-methyl-5-((5-(5-methyloxazol-2-yl)-1H-pyrrolo[2,3-b]pyridin-4-yl)amino)piperidin-1-yl)propanenitrile

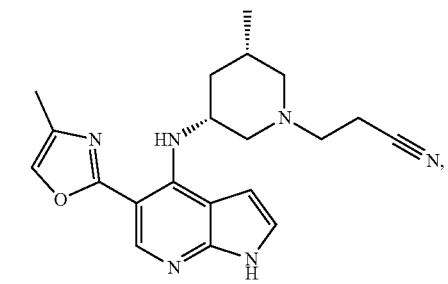

3-((3S,5R)-3-methyl-5-((5-(4-methyloxazol-2-yl)-1H-pyrrolo[2,3-b]pyridin-4-yl)amino)piperidin-1-yl)propanenitrile

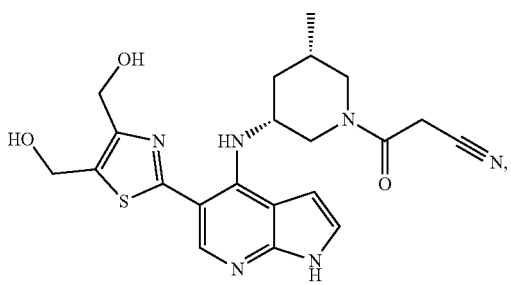

3-((3R,5S)-3-((5-(4,5-bis(hydroxymethyl)thiazol-2-yl)-1H-pyrrolo[2,3-b]pyridin-4-yl)amino)-5-methylpiperidin-1-yl)-3-oxopropanenitrile

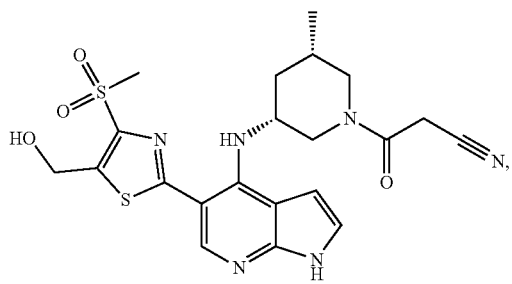

3-((3R,5S)-3-((5-(5-(hydroxymethyl)-4-(methylsulfonyl)thiazol-2-yl)-1H-pyrrolo[2,3-b]pyridin-4-yl)amino)-5-methylpiperidin-1-yl)-3-oxopropanenitrile

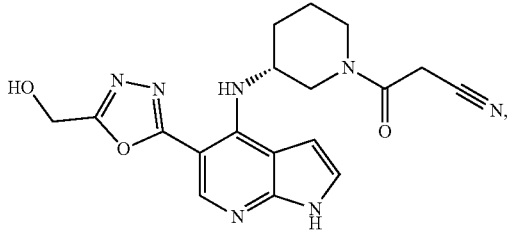

3-((3R,5S)-3-((5-(5-(hydroxymethyl)-1,3,4-oxadiazol-2-yl)-1H-pyrrolo[2,3-b]pyridin-4-yl)amino)-5-methylpiperidin-1-yl)-3-oxopropanenitrile

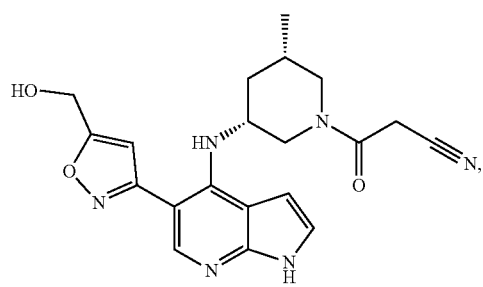

3-((3R,5S)-3-((5-(5-(hydroxymethyl)isoxazol-3-yl)-1H-pyrrolo[2,3-b]pyridin-4-yl)amino)-5-methylpiperidin-1-yl)-3-oxopropanenitrile

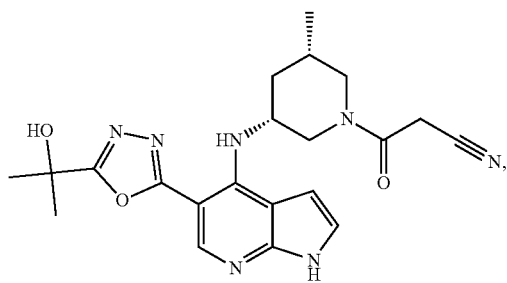

3-((3R,5S)-3-((5-(5-(2-hydroxypropan-2-yl)-1,3,4-oxadiazol-2-yl)-1H-pyrrolo[2,3-b]pyridin-4-yl)amino)-5-methylpiperidin-1-yl)-3-oxopropanenitrile

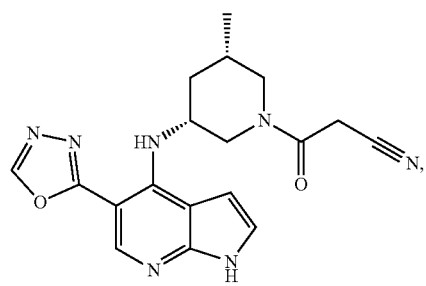

3-((3R,5S)-3-((5-(1,3,4-oxadiazol-2-yl)-1H-pyrrolo[2,3-b]pyridin-4-yl)amino)-5-methylpiperidin-1-yl)-3-oxopropanenitrile

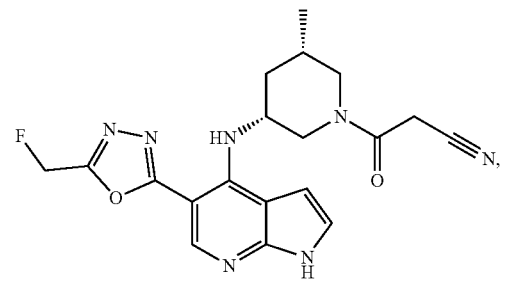

3-((3R,5S)-3-((5-(5-(fluoromethyl)-1,3,4-oxadiazol-2-yl)-1H-pyrrolo[2,3-b]pyridin-4-yl)amino)-5-methylpiperidin-1-yl)-3-oxopropanenitrile

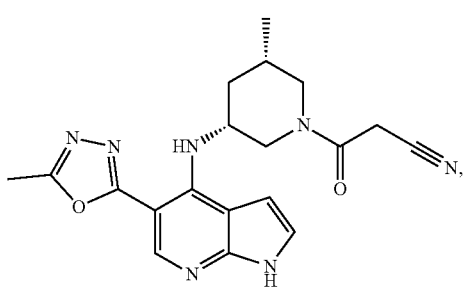

3-((3S,5R)-3-methyl-5-((5-(5-methyl-1,3,4-oxadiazol-2-yl)-1H-pyrrolo[2,3-b]pyridin-4-yl)amino)piperidin-1-yl)-3-oxopropanenitrile

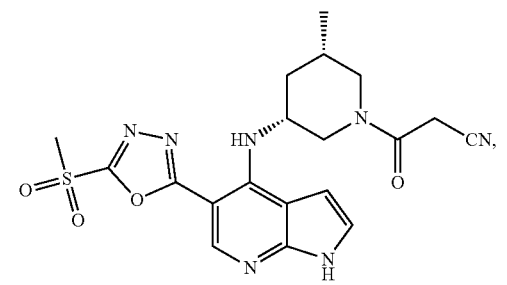

3-((3S,5R)-3-methyl-5-((5-(5-(methylsulfonyl)-1,3,4-oxadiazol-2-yl)-1H-pyrrolo[2,3-b]pyridin-4-yl)amino)piperidin-1-yl)-3-oxopropanenitrile

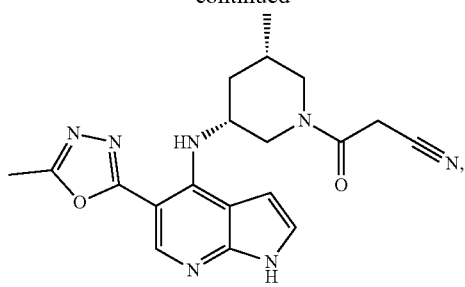

3-((3S,5R)-3-methyl-5-((5-(5-methyl-1,3,4-oxadiazol-2-yl)-1H-pyrrolo[2,3-b]pyridin-4-yl)amino)piperidin-1-yl)propanenitrile

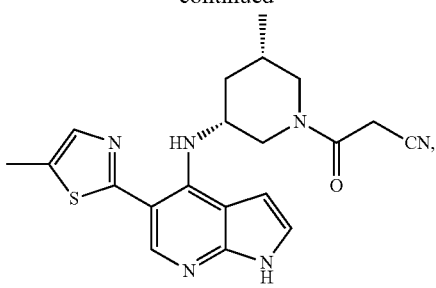

3-((3S,5R)-3-methyl-5-((5-(5-methylthiazol-2-yl)-1H-pyrrolo[2,3-b]pyridin-4-yl)amino)piperidin-1-yl)-3-oxopropanenitrile

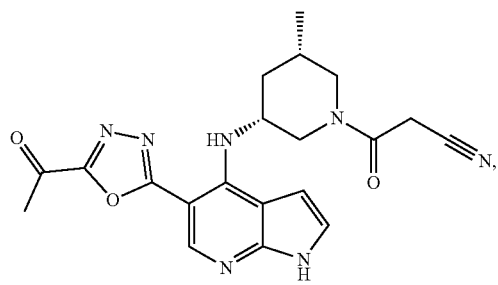

3-((3R,5S)-3-((5-(5-acetyl-1,3,4-oxadiazol-2-yl)-1H-pyrrolo[2,3-b]pyridin-4-yl)amino)-5-methylpiperidin-1-yl)-3-oxopropanenitrile

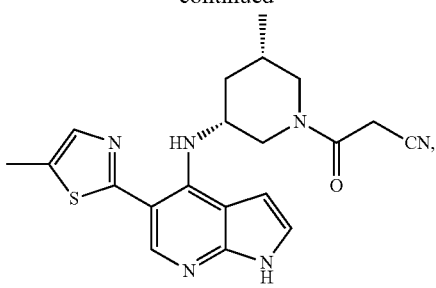

3-((3R,5S)-3-((5-(5-(hydroxymethyl)thiazol-2-yl)-1H-pyrrolo[2,3-b]pyridin-4-yl)amino)-5-methylpiperidin-1-yl)-3-oxopropanenitrile

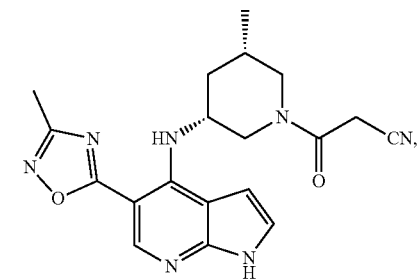

3-((3S,5R)-3-methyl-5-((5-(5-methyl-1,2,4-oxadiazol-5-yl)-1H-pyrrolo[2,3-b]pyridin-4-yl)amino)piperidin-1-yl)-3-oxopropanenitrile

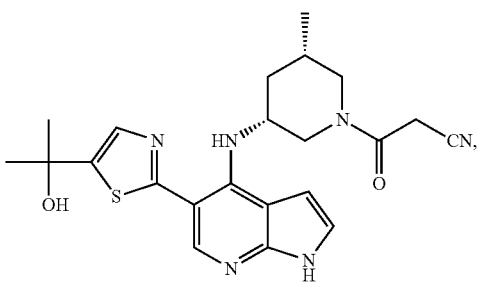

3-((3R,5S)-3-((5-(5-(hydroxypropan-2-yl)thiazol-2-yl)-1H-pyrrolo[2,3-b]pyridin-4-yl)amino)-5-methylpiperidin-1-yl)-3-oxopropanenitrile

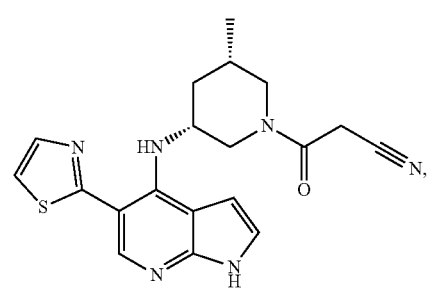

3-((3S,5R)-3-methyl-5-((5-(thiazol-2-yl)-1H-pyrrolo[2,3-b]pyridin-4-yl)amino)piperidin-1-yl)-3-oxopropanenitrile

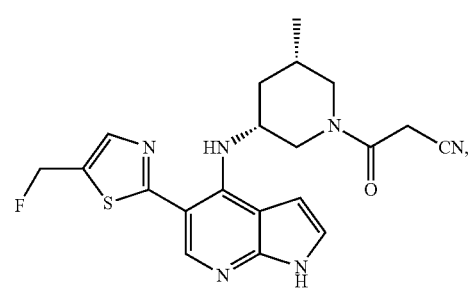

3-((3R,5S)-3-((5-(5-(fluoromethyl)thiazol-2-yl)-1H-pyrrolo[2,3-b]pyridin-4-yl)amino)-5-methylpiperidin-1-yl)-3-oxopropanenitrile

349

-continued

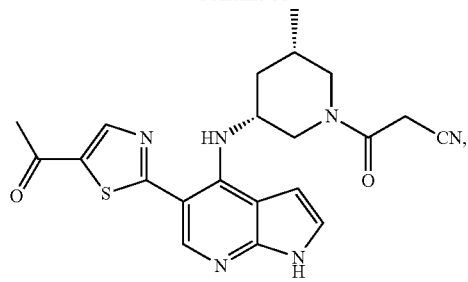

3-((3R,5S)-3-((5-(5-acetylthiazol-2-yl)-1H-pyrrolo[2,3-b]pyridin-4-yl)amino)-5-methylpiperidin-1-yl)-3-oxopropanenitrile

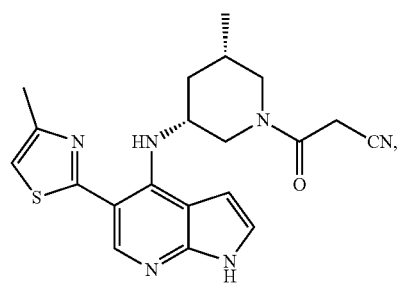

3-((3S,5R)-3-methyl-5-((5-(5-methylthiazol-2-yl)-1H-pyrrolo[2,3-b]pyridin-4-yl)amino)piperidin-1-yl)-3-oxopropanenitrile

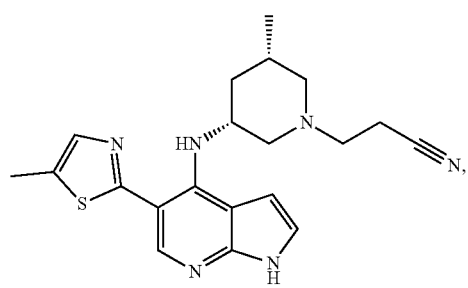

3-((3S,5R)-3-methyl-5-((5-(5-methylthiazol-2-yl)-1H-pyrrolo[2,3-b]pyridin-4-yl)amino)piperidin-1-yl)propanenitrile

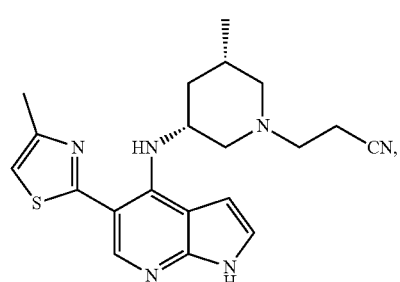

3-((3S,5R)-3-methyl-5-((5-(4-methylthiazol-2-yl)-1H-pyrrolo[2,3-b]pyridin-4-yl)amino)piperidin-1-yl)propanenitrile

350

-continued

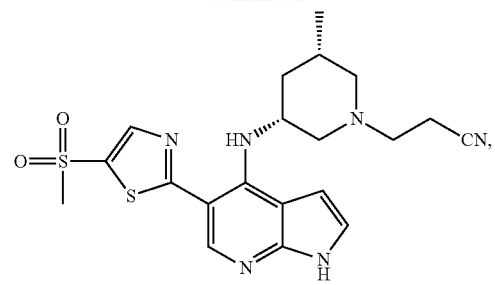

3-((3S,5R)-3-methyl-5-((5-(5-(methylsulfonyl)thiazol-2-yl)-1H-pyrrolo[2,3-b]pyridin-4-yl)amino)piperidin-1-yl)propanenitrile

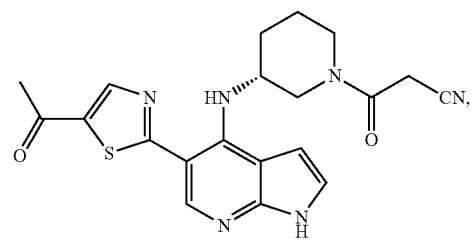

(R)-3-(3-((5-(5-acetylthiazol-2-yl)-1H-pyrrolo[2,3-b]pyridin-4-yl)amino)piperidin-1-yl)-3-oxopropanenitrile

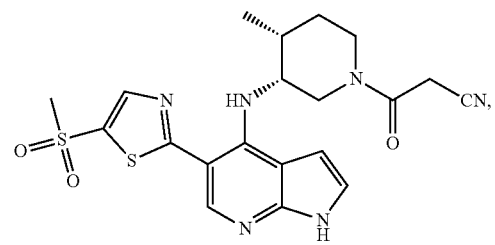

3-((3R,4R)-4-methyl-5-((5-(5-(methylsulfonyl)thiazol-2-yl)-1H-pyrrolo[2,3-b]pyridin-4-yl)amino)piperidin-1-yl)-3-oxopropanenitrile

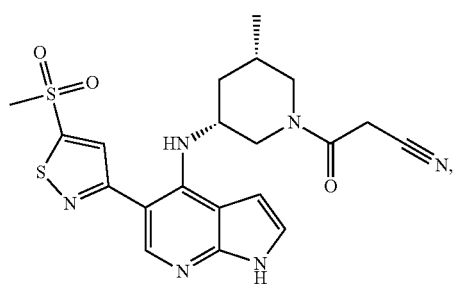

3-((3S,5R)-3-methyl-5-((5-(5-(methylsulfonyl)isothiazol-3-yl)-1H-pyrrolo[2,3-b]pyridin-4-yl)amino)piperidin-1-yl)-3-oxopropanenitrile

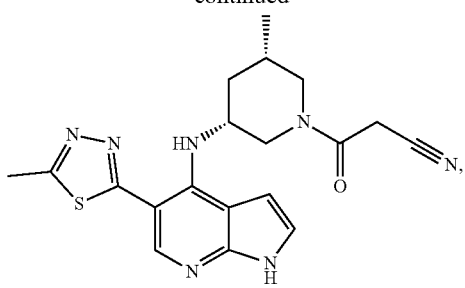

3-((3S,5R)-3-methyl-5-((5-(5-methyl-1,3-thiadiazol-2-yl)-1H-pyrrolo[2,3-b]pyridin-4-yl)amino)piperidin-1-yl)-3-oxopropanenitrile

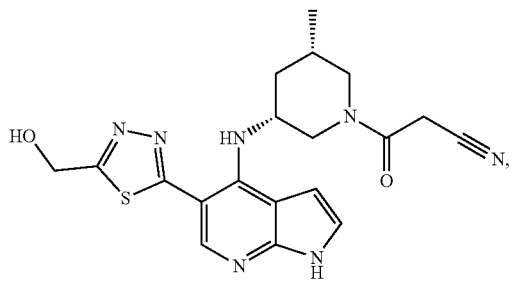

3-((3R,5S)-3-((5-(5-(hydroxymethyl)-1,3,4-thiadiazol-2-yl)-1H-pyrrolo[2,3-b]pyridin-4-yl)amino)-5-methylpiperidin-1-yl)-3-oxopropanenitrile

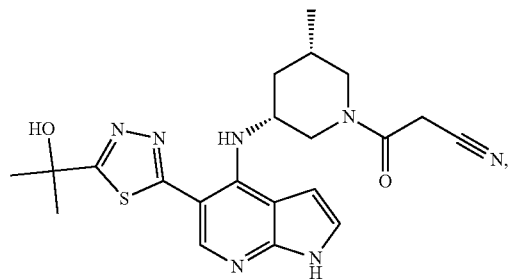

3-((3R,5S)-3-((5-(5-(2-hydroxypropan-2-yl)-1,3,4-thiadiazol-2-yl)-1H-pyrrolo[2,3-b]pyridin-4-yl)amino)-5-methylpiperidin-1-yl)-3-oxopropanenitrile

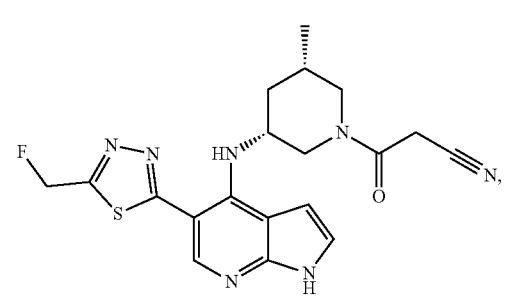

3-((3R,5S)-3-((5-(5-(fluoromethyl)-1,3,4-thiadiazol-2-yl)-1H-pyrrolo[2,3-b]pyridin-4-yl)amino)-5-methylpiperidin-1-yl)-3-oxopropanenitrile

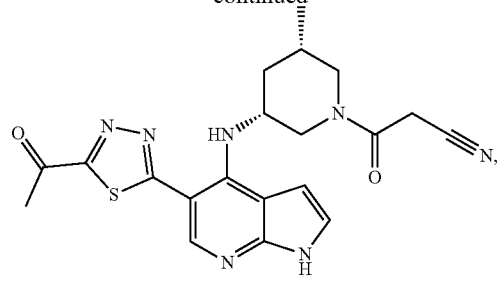

3-((3R,5S)-3-((5-(5-(5-acetyl-1,3,4-thiadiazol-2-yl)-1H-pyrrolo[2,3-b]pyridin-4-yl)amino)-5-methylpiperidin-1-yl)-3-oxopropanenitrile

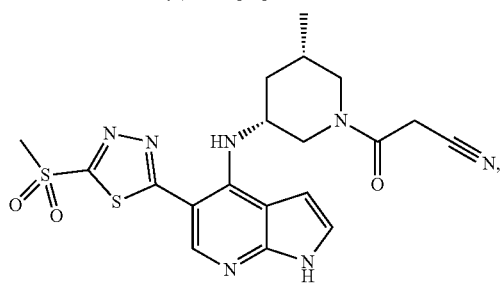

3-((3S,5R)-3-methyl-5-((5-(5-methylsulfonyl)-1,3,4-thiadiazol-2-yl)-1H-pyrrolo[2,3-b]pyridin-4-yl)amino)piperidin-1-yl)-3-oxopropanenitrile

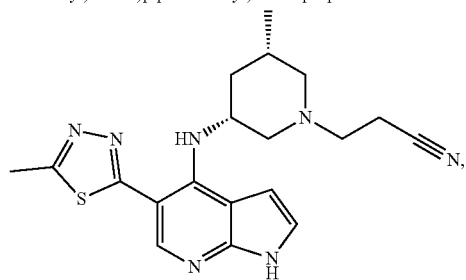

3-((3S,5R)-3-methyl-5-((5-(5-methyl-1,3,4-thiadiazol-2-yl)-1H-pyrrolo[2,3-b]pyridin-4-yl)amino)piperidin-1-yl)propanenitrile

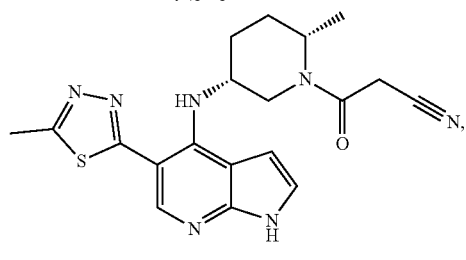

3-((2S,5R)-2-methyl-5-((5-(5-methyl-1,3,4-thiadiazol-2-yl)-1H-pyrrolo[2,3-b]pyridin-4-yl)amino)piperidin-1-yl)-3-oxopropanenitrile

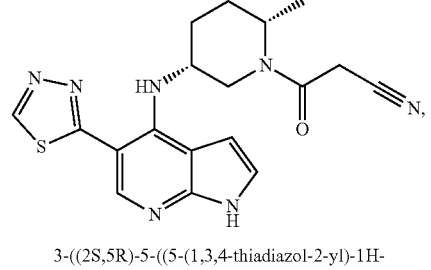

3-((2S,5R)-5-((5-(1,3,4-thiadiazol-2-yl)-1H-pyrrolo[2,3-b]pyridin-4-yl)amino)-2-methylpiperidin-1-yl)-3-oxopropanenitrile

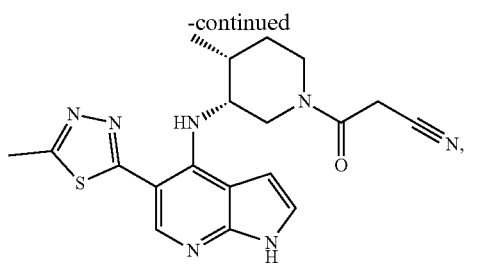

3-((3R,4R)-4-methyl-3-((5-(5-methyl-1,3,4-thiadiazol-2-yl)-1H-pyrrolo[2,3-b]pyridin-4-yl)amino)piperidin-1-yl)-3-oxopropanenitrile

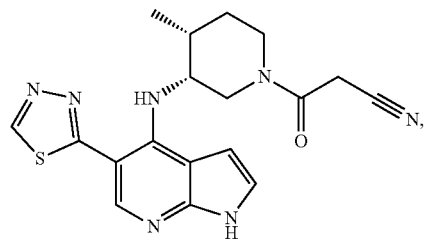

3-((3R,4R)-3-((5-(1,3,4-thiadiazol-2-yl)-1H-pyrrolo[2,3-b]pyridin-4-yl)amino)-4-methylpiperidin-1-yl)-3-oxopropanenitrile

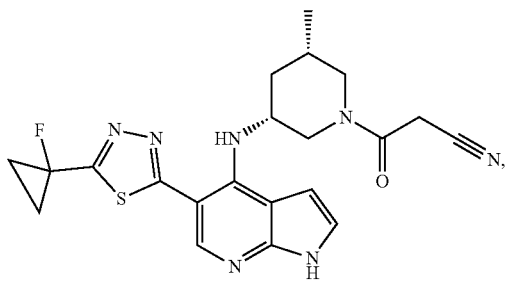

3-((3R,5S)-3-((5-(5-(1-fluorocyclopropyl)-1,3,4-thiadiazol-2-yl)-1H-pyrrolo[2,3-b]pyridin-4-yl)amino)-5-methylpiperidin-1-yl)-3-oxopropanenitrile

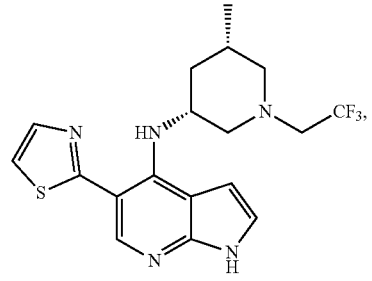

N-((3R,5S)-5-methyl-1-(2,2,2-trifluoroethyl)piperidin-3-yl)-5-(thiazol-2-yl)-1H-pyrrolo[2,3-b]pyridin-4-amine

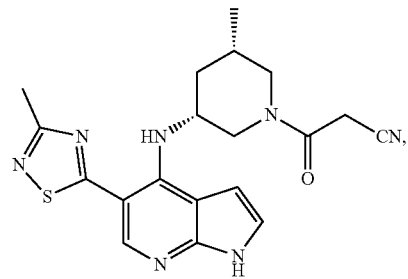

3-((3S,5R)-3-methyl-5-((5-(3-methyl-1,2,4-thiadiazol-5-yl)-1H-pyrrolo[2,3-b]pyridin-4-yl)amino)piperidin-1-yl)-3-oxopropanenitrile

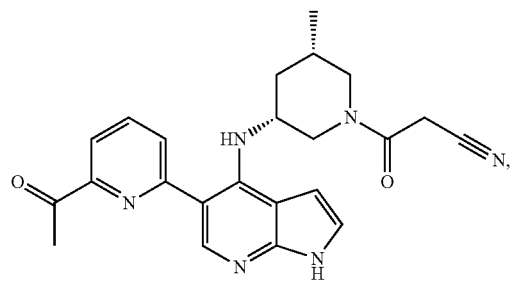

3-((3R,5S)-3-((5-(6-(acetylpyridin-2-yl)-1H-pyrrolo[2,3-b]pyridin-4-yl)amino)-5-methylpiperidin-1-yl)-3-oxopropanenitrile

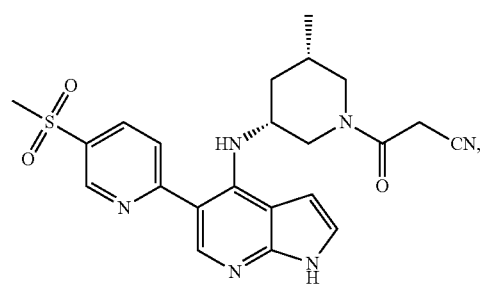

3-((3S,5R)-3-methyl-5-((5-(5-methylsulfonyl)pyridin-2-yl)-1H-pyrrolo[2,3-b]pyridin-4-yl)amino)piperidin-1-yl)-3-oxopropanenitrile

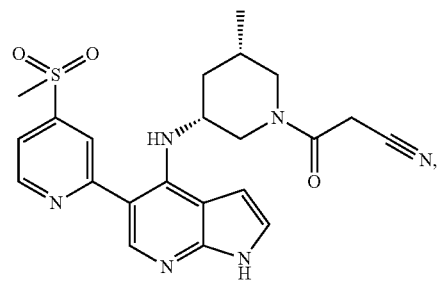

3-((3S,5R)-3-methyl-5-((5-(4-(methylsulfonyl)pyridin-2-yl)-1H-pyrrolo[2,3-b]pyridin-4-yl)amino)piperidin-1-yl)-3-oxopropanenitrile

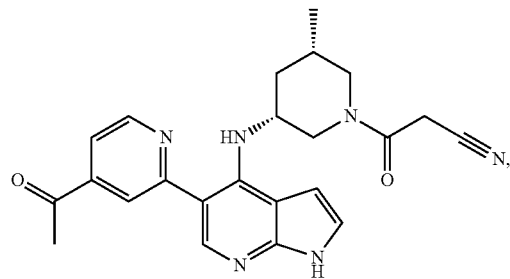

3-((3R,5S)-3-((5-(4-(acetylpyridin-2-yl)-1H-pyrrolo[2,3-b]pyridin-4-yl)amino)-5-methylpiperidin-1-yl)-3-oxopropanenitrile

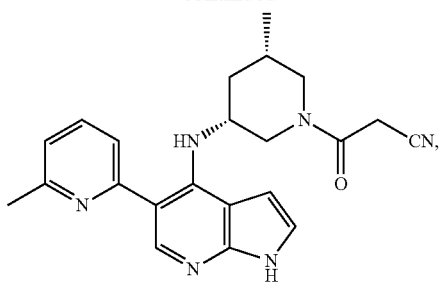

3-((3S,5R)-3-methyl-5-((5-(6-methylpyridin-2-yl)-1H-pyrrolo[2,3-b]pyridin-4-yl)amino)piperidin-1-yl)-3-oxopropanenitrile

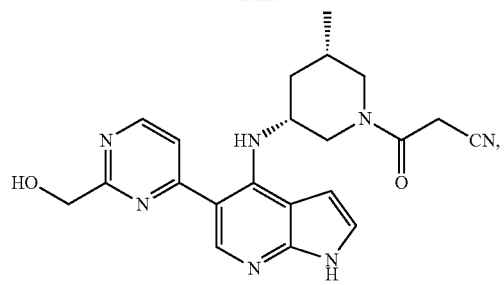

3-((3R,5S)-3-((5-(2-hydroxymethyl)pyrimidin-4-yl)-1H-pyrrolo[2,3-b]pyridin-4-yl)amino)-5-methylpiperidin-1-yl)-3-oxopropanenitrile

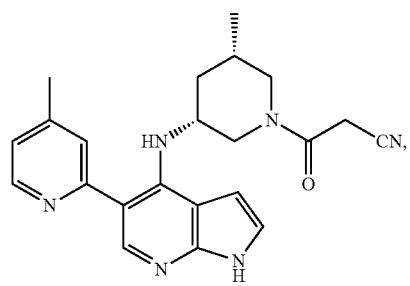

3-((3S,5R)-3-methyl-5-((5-(4-methylpyridin-2-yl)-1H-pyrrolo[2,3-b]pyridin-4-yl)amino)piperidin-1-yl)-3-oxopropanenitrile

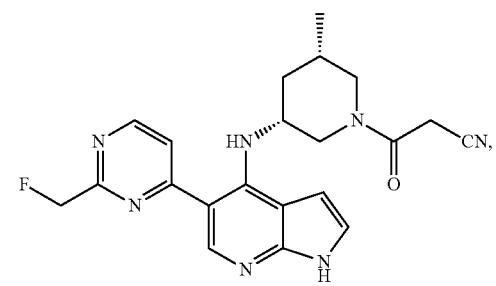

3-((3R,5S)-3-((5-(2-fluoromethyl)pyrimidin-4-yl)-1H-pyrrolo[2,3-b]pyridin-4-yl)amino)-5-methylpiperidin-1-yl)-3-oxopropanenitrile

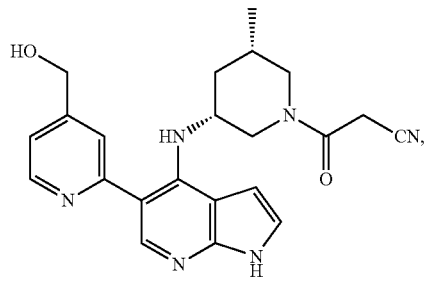

3-((3R,5S)-3-((5-(4-hydroxymethyl)pyridin-2-yl)-1H-pyrrolo[2,3-b]pyridin-4-yl)amino)-5-methylpiperidin-1-yl)-3-oxopropanenitrile

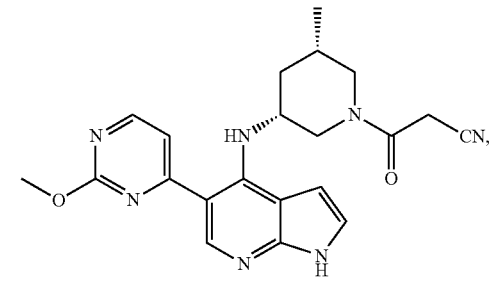

3-((3R,5S)-3-((5-(2-methoxypyrimidin-4-yl)-1H-pyrrolo[2,3-b]pyridin-4-yl)amino)-5-methylpiperidin-1-yl)-3-oxopropanenitrile

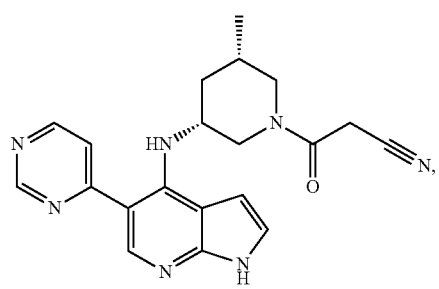

3-((3S,5R)-3-methyl-5-((5-(5-(pyrimidin-4-yl)-1H-pyrrolo[2,3-b]pyridin-4-yl)amino)piperidin-1-yl)-3-oxopropanenitrile

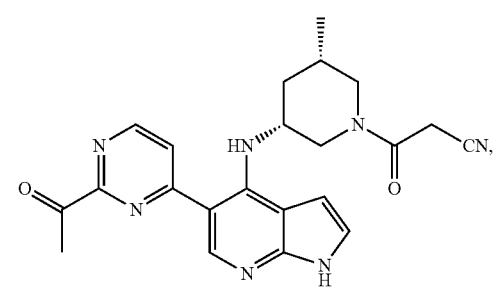

3-((3R,5S)-3-((5-(2-acetylpyrimidin-4-yl)-1H-pyrrolo[2,3-b]pyridin-4-yl)amino)-5-methylpiperidin-1-yl)-3-oxopropanenitrile

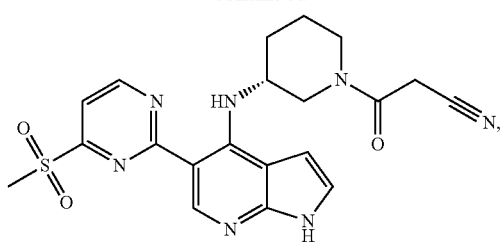

(R)-3-(3-((5-(4-(methylsulfonyl)pyrimidin-2-yl)-1H-
pyrrolo[2,3-b]pyridin-4-yl)amino)piperidin-1-yl)-3-
oxopropanenitrile

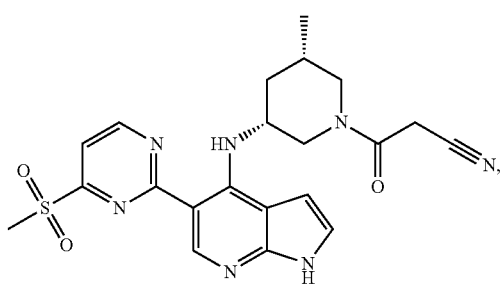

3-((3R,5S)-3-methyl-5-((5-(4-
methylsulfonyl)pyrimidin-2-yl)-1H-pyrrolo[2,3-
b]pyridin-4-yl)amino)piperidin-1-yl)-3-
oxopropanenitrile

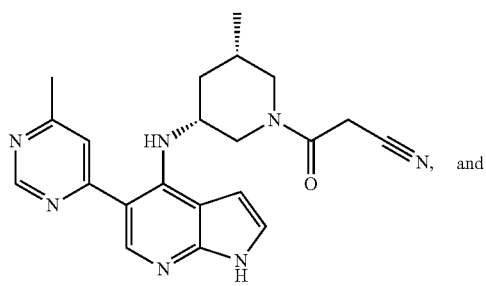

3-((3S,5R)-3-methyl-5-((5-(6-methylpyridin-4-yl)-
1H-pyrrolo[2,3-b]pyridin-4-yl)amino)piperidin-1-yl)-3-
oxopropanenitrile

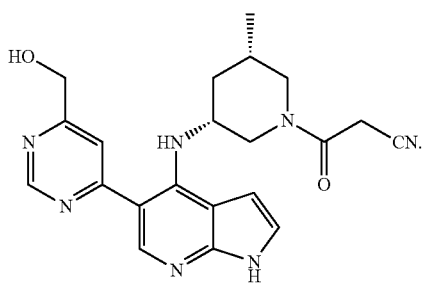

3-((3R,5S)-3-((5-(6-hydroxymethyl)pyrimidin-4-yl)-
1H-pyrrolo[2,3-b]pyridin-4-yl)amino)-5-
methylpiperidin-1-yl)-3-oxopropanenitrile 3. A pharmaceutical composition comprising: a compound of claims 1 or 2, a derivative thereof, or a combination thereof; and a pharmaceutically acceptable excipient.

4. The compound of claim 2, wherein the compound, is

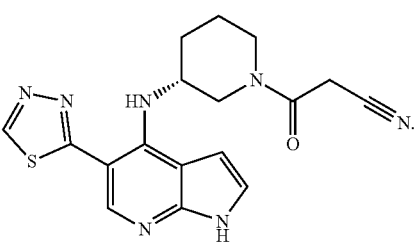

rac-(R)-3-(3-((5-(1,3,4-thiadiazol-2-yl)-1H-pyrrolo[2,3-b]pyridin-4-
yl)amino)piperidin-1-yl)-3-oxopropanenitrile 5. A pharmaceutical composition comprising: a compound of claim 4, a derivative thereof, or a combination thereof; and a pharmaceutically acceptable excipient.

6. The compound of claim 2, wherein the compound, is

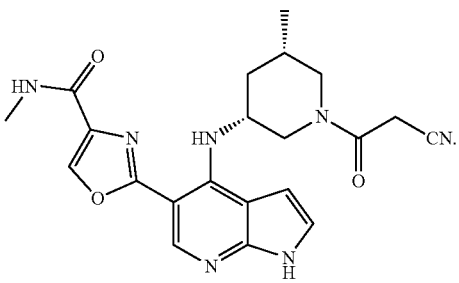

2-(4-(((3R,5S)-1-(2-cyanoacetyl)-5-methylpiperidin-3-yl)amino)-1H-
pyrrolo[2,3-b]pyridin-5-yl)-N-methyloxazole-4-carboxamide 7. A pharmaceutical composition comprising: a compound of claim 6, a derivative thereof, or a combination thereof; and a pharmaceutically acceptable excipient.

8. The compound of claim 2, wherein the compound, is

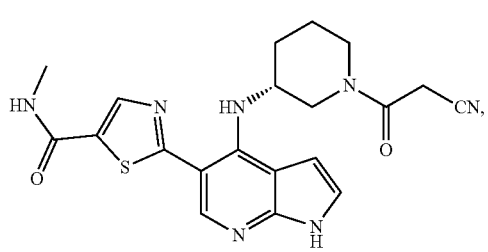

(R)-2-(4-((1-(2-cyanoacetyl)piperidin-3-yl)amino)-1H-pyrrolo[2,3-
b]pyridin-5-yl)piperidin-5-yl)-N-methylthiazole-5-carboxamide 9. A pharmaceutical composition comprising: a compound of claim 8, a derivative thereof, or a combination thereof; and a pharmaceutically acceptable excipient.

10. The compound of claim 2, wherein the compound, is

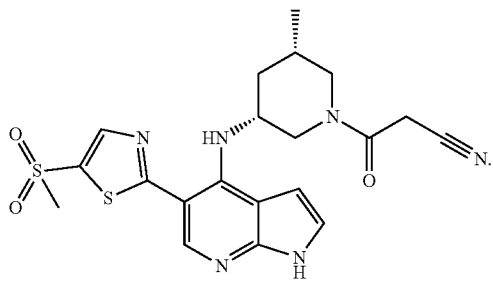

3-((3S,5R)-3-methyl-5-((5-(5-(methylsulfonyl)thiazol-2-yl)-1H-pyrrolo[2,3-b]pyridin-4-yl)amino)piperidin-1-yl)-3-oxopropanenitrile 11. A pharmaceutical composition comprising: a compound of claim 10, a derivative thereof, or a combination thereof; and a pharmaceutically acceptable excipient.

12. The compound of claim 2, wherein the compound, is

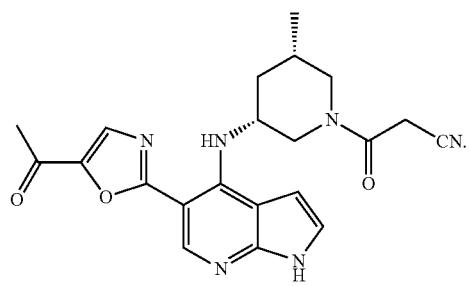

3-((3R,5S)-3-((5-(5-acetyloxazol-2-yl)-1H-pyrrolo[2,3-b]pyridin-4-yl)amino)-5-methylpiperidin-1-yl)-3-oxopropanenitrile 13. A pharmaceutical composition comprising: a compound of claim 12, a derivative thereof, or a combination thereof; and a pharmaceutically acceptable excipient.

14. The compound of claim 2, wherein the compound, is

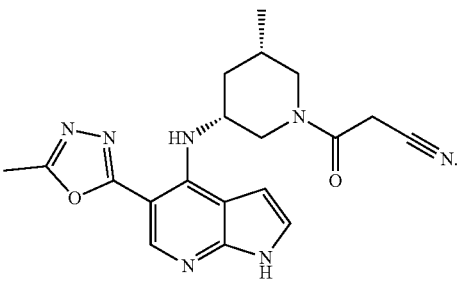

3-((3S,5R)-3-methyl-5-((5-(5-methyl-1,3,4-oxadiazol-2-yl)-1H-pyrrolo[2,3-b]pyridin-4-yl)amino)piperidin-1-yl)-3-oxopropanenitrile 15. A pharmaceutical composition comprising: a compound of claim 14, a derivative thereof, or a combination thereof; and a pharmaceutically acceptable excipient.

16. The compound of claim 2, wherein the compound, is

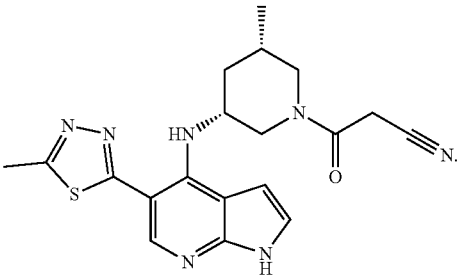

3-((3S,5R)-3-methyl-5-((5-(5-methyl-1,3,4-thiadiazol-2-yl)-1H-pyrrolo[2,3-b]pyridin-4-yl)amino)piperidin-1-yl)-3-oxopropanenitrile 17. A pharmaceutical composition comprising: a compound of claim 16, a derivative thereof, or a combination thereof; and a pharmaceutically acceptable excipient.

* * * * *